US005977336A

United States Patent [19]
Barenkamp

[11] Patent Number: 5,977,336
[45] Date of Patent: Nov. 2, 1999

[54] HIGH MOLECULAR WEIGHT SURFACE PROTEINS OF NON-TYPEABLE HAEMOPHILUS

[75] Inventor: Stephen J. Barenkamp, Webster Grove, Mo.

[73] Assignees: St. Louis University; Washington University, both of St. Louis, Mo.

[21] Appl. No.: 08/617,697

[22] Filed: Apr. 1, 1996

Related U.S. Application Data

[63] Continuation-in-part of application No. 08/302,832, Oct. 5, 1994, Pat. No. 5,603,938, which is a continuation of application No. PCT/US93/02166, Mar. 16, 1993.

[51] Int. Cl.⁶ .................................................. C07H 21/04
[52] U.S. Cl. .................... 536/23.7; 424/256.1; 536/23.1; 435/320.1; 530/350
[58] Field of Search ........................ 424/256.1; 536/23.1, 536/23.7; 435/320.1; 530/350

[56] References Cited

U.S. PATENT DOCUMENTS

| 4,258,029 | 3/1981 | Moloney et al. | 424/88 |
| 4,855,283 | 8/1989 | Lockhoff et al. | 424/278 |
| 4,952,496 | 8/1990 | Studier et al. | 435/91 |
| 5,194,254 | 3/1993 | Barber et al. | 424/70 |

FOREIGN PATENT DOCUMENTS

WO 92/17167  10/1992  WIPO .

OTHER PUBLICATIONS

Nixon–George et al. (Jun. 15, 1990) The Adjuvant Effect of Stearyl Tyrosine on a Recombinant Subunit Hepatitis B Surface Antigen, J. Immunol. vol. 144:4798–4802.
Weismuller K–H, et al. (1989) Novel low molecular weight synthetic vaccine against foot–and–mouth disease containing a potent B–cell and macrophage activator, Vaccine vol. 7, Feb. 1989, pp. 29–33.
Chang et al., (1978) Nature 275:617–624.
Itakura et al., (1977) Science 198:1056–1063.
Goeddel et al., (1979) Nature 281:544–548.
Goeddel et al., (1980) Nucl. Acids Res. 8:4057–4074.
Pediatric Infectious Disease Journal, vol. 9, No. 5, issued May 1990, S.J. Barenkamp et al., "Development of Serum Bactericidal Activity Following Nontypable *Haemophilus influenzae* Acute Otitis Media", pp. 333–339, see entire document.
Journal of Clinical Microbiology, vol. 29, No. 11, issued Nov. 1991, A.C. Caputa et al., "110 Kilodalton Recombinant Protein which is immunoreactive with Sera from Humans, Dogs, and Horses with Lyme Borreliosis", pp. 2418–2423, see entire document.
Joint Meeting of the American Pediatric Society and the Society for Pediatric Research, May 7–10, 1990, S.J. Barenkamp, "Cloning and Expression of Genes for Nontypable *Haemophilus influenzae* (NTH) High Molecular Weight (HMW) Outer Membrane Proteins which are Targets of Bactericidal Antibody", Abstract 983, Pediatric Research, vol. 27, (4 part 2).

The Journal of Infectious Diseases, vol. 165 (Suppl.), issued Aug. 1992, S.J. Barenkamp, "Outer Membrane Protein and Lipopolysaccharides of Nontypeable *Haemophilus influenzae* ", pp. S181–S184, see entire document.
Infection and Immunity, vol. 60(4), issued Apr. 1992, S.J. Barenkamp et al, Cloning, Expression and DNA Sequence Analysis of Genes Encoding Nontypable *Haemophilus influenzae* High–Molecular–Weight Surface–Exposed Proteins Related to Filamentous Hemagglutinin of *Bordetella pertussis* pp. 1302–1313, see entire document.
Infection and Immunity, vol. 56(1), issued Jan. 1988, E.J. Hansen, Immune Enhancement of Pulmonary Clearance on Nontypable *Haemophilus influenzae*, pp. 182–190, see entire document, especially Figures 3 and 4.
Infection and Immunity, vol. 52(2), issued May 1986, S.J. Barenkamp, "Protection by Serum Antibodies in Experimental Nontypable *Haemophilus influenzae* Otitis Media", pp. 572–578, see Figures 1 and 2.
Proceedings of the National Academy of Sciences USA, vol. 80, issued Mar. 1983, R.A. Young et al, "Efficient Isolation of Genes by Using Antibody Probes", pp. 1194–1198, see entire document.
Infection and Immunity, vol. 45(3), issued Sep. 1984, R. Schneerson et al, "Serum Antibody Responses of Juvenile and Infant Rhesus Monkeys Injected with *Haemophilus influenzae* Type b and Pneumococcus Type 6A Capsular Polysaccharide–Protein Conjugates", pp. 582–591, see entire document.
Journal of Molecular Biology, vol. 157, issued 1982, J. Kyte et al, "A Simple Method for Displaying the Hydropathic Character of a Protein", pp. 105–132, see entire document.
Proceedings of the National Academy of Sciences, vol. 78(6), issued Jun. 1981, T.P. Hopp et al, "Prediction of Protein Antigenic Determinants from Amino Acid Sequences", pp. 3824–3828, see entire document.
Pediatr. Infect. Dis. J., 9:333–339, 1990, Stephen J. Barenkamp and Frank F. Bodor, Development of Serum Bacterial Activity Following Nontypable *Haemophilus influenzae* Acute Otitis Media.
Shakin R.D. et al. Mucosal Immunization with filametous hemagglutinin protects against *Bordetella pertussis* respiratory Infection, Infect. Immun. 60: 1482–1488, 1992.
Giebink G.S. et al. Pneumococcal Capsular Polysaccharide — meningoccocal outer membrane protein complex conjugate vaccines: Immunogenicity and efficacy in experimental pnuemococcal otitis media. J. Infect. Dis. 167:347–355, 1993.

(List continued on next page.)

*Primary Examiner*—James C. Housel
*Assistant Examiner*—Jennifer Shaver
*Attorney, Agent, or Firm*—Shoemaker and Mattare, Ltd

[57] ABSTRACT

High molecular weight surface proteins of non-typeable *Haemophilus influenzae* which exhibit immunogenic properties and genes encoding the same are described. Specifically, genes coding for two immunodominant high molecular weight proteins, HMW1 and HMW2, have been cloned, expressed and sequenced, while genes coding for high molecular proteins HMW3 and HMW4 have also been cloned, expressed and sequenced.

4 Claims, 81 Drawing Sheets

OTHER PUBLICATIONS

Selected Abstracts from 1993 Interscience Conference on Antimicrobial Agents and Chemotherapy (Annual American Society for Microbiology ICAAC Meeting) in New OrleansO.

Green B.A. et al., Evaluation of mixtures of purified *Haemophilus Influenzae* outer membrane proteins in the chinchilla otitis media model. Infect. Immun. 61: 1950–1957, 1993.

Murphy, T.F. et al., Somatic Antigens of *Haemophilus influenzae* as vaccine components. Pedia. Infect. Dis. J. 8:S66–S68, 1989.

Consensus. Pediatr. Infect. Dis. J.8: S94–S97, 1989.

Makela et al. Pneumococcal Vaccine and Otitis Media, Lancet 2: 547–551, 1990.

Giebink et al. J. Infect. Dis. 140:716–723, 1979.

Giebink, Rev. Infect. Dis. 3:342–352, 1981.

Van Regenmortel, M.H.V., Immunology Today 10(8): 266–272, 1989.

Dick, W.E. et al., Microbiol. Immunol. 10: 48–114, 1989.

Roitt, I.M. et al., Immunology, C.V. Mosby Co. St. Louis, Gower Medical Publishing, London, 1989, pp. 8.3–8.4, 1985.

Boslego, J.W., et al. Vaccine 9: 154–162, Mar. 1991.

Beachey J. Infect. Dis. 143:325–345, 1981.

Barenkamp S.J., St Geme JW III. Genes encoding high molecular weight adhesion proteins of nontypable *Haemophilis influenzae* are part of gene clusters. Infect Immun 62:3320–3328, 1994.

Brunham, R.C., F.A. Plummer, and R.S. Stephens. 1993. Bacterial antigenic variation, host immune response, and pathogen–host coevolution. Infect. Immun. 61:2273–2276.

Green, B.A., T. Quinn–Dey, and G.W. Zlotnick. 1987. Biologic activities of antibody to peptidoglycan–associated lipoprotein of *Haemophilus influenzae* against multiple clinical isolates of *H. influenzae* type b. Infect. Immun. 55:2878–2883.

Green, B.A., B.J. Metcalf, T. Quinn Dey, D.H. Kirkley, S.A. Quataert, and R.A. Deich, 1990. A recombinant non–fatty acylated form of the Hi–PAL (P6) protein of *Haemophilus influenzae* elicits biologically active antibody against both nontypeable and type b.*H. influenzae*. Infect. Immun. 58:3272–3278.

Gnehm, H.E., S.I. Pelton, S. Galati, and P.A. Rice. 1985. Characterization of antigens from nontypable *Haemophilus influenzae* recognized by human bactercidal antibodies: Role of Haemophilus outer membrane proteins. J. Clin. Invest. 75:1645–1658.

Groeneveld, K., L. van Alphen, C, Voorter, P.P. Eijk, H.M. Jansen, and H.C. Zanen. 1989. Antigenic drift of *Haemophilus influenzae* in patients with chronic obstructive pulmonary disease. Infect. Immunol. 57:3038–3044.

Groeneveld, K., L. van Alphen, P.P. Eijk, H.M. Jansen, and H.C. Zanen. 1988. Changes in outer membrane proteins of nontypable *Haemophilus influenzae* in patients with chronic obstructive pulmonary disease. J. Infect. Dis. 1 58:360–365.

Goding, J.W. 1986. Monoclonal antibodies: Principles and practice, p. 59–141. Academic Press Limited, London England.

Hansen, E.J., D.A. Hart, J.L. McGehee, and G.B. Toews. 1988. Immune enhancement of pulmonary clearance of nontypable *Haemophilus influenzae*. Infect. Immun. 56:182–190.

Karasic, R.B., C.E. Trumpp, H. Gnehm, P.A. Rice, and S.I. Pelton. 1985. Modification of otitis media in chinchillas rechallenged with nontypable *Haemophilus influenzae* and serologic response to outer membrane antigens. J. Infect. Dis. 151:273–279.

Kilian, M. 1985. Haemophilus, p. 387–393. In E.H. Lennette, A. Balows, W.J. Hausler, Jr., and H.J. Shadomy (ed.), Manual of clinical microbiology, 4th ed. American Society for Microbiology, Washington, D.C.

Kuklinska, D., and M. Kilian. 1984 Relative proportions of Haemophilus species in the throat of healthy children and adults. Eur. J. Clin. Microbiol. 3:249–252.

Murphy, T.F., L.C. Bartos, P.A. Rice, M.B. Nelson, K.C. Dudas, and M.A. Apicelia. 1986. Identification of a 16,600 dalton outer membrane protein of nontypable *Haemophilus influenzae* as a target for human serum bactericidal antibody. J. Clin. Invest. 78:1020–1027.

Murphy, T.F., and M.A. Apicelia, 1987. Nontypable *Haemophilus influenzae:* A review of clinical aspects, surface antigens, and the human immune response to infection. Rev. Infect. Dis. 9:1–15.

Murphy, T.F., and L.C. Bartos. 1988. Purification and analysis with monoclonal antibodies of P2, the major outer membrane protein of nontypable *Haemophilus influenzae*. Infect. Immun. 56:1084–1089.

Murphy, T.F., and L.C. Bartos. 1988. Human bactericidal antibody response to outer membrane protein P2 of nontypable *Haemophilus influenzae*. Infect. Immun. 56:2673–2679.

Rabinovich, N.R., P. McInnes, D.L. Klein, and B.F. Hall. 1994. Vaccine technologies: View to the future. Science 265:1401–1404.

St. Geme, J.W. III, S. Falkow, and S.J. Barenkamp. 1993. High–molecular–weight proteins of nontypable *Haemophilus influenzae* mediate attachment to human epithelial cells. Proc. Natl . Acad. Sci. USA 90:2875–2879.

Tabor, S., and C.C. Richardson. 1985. A bacteriophage T7 RNA polymerase/promoter system for controlled exclusive expression of specific genes. Proc. Natl. Acad. Sci. USA 82:1074–1078.

Wallace, R.J., Jr., D.M. Musher, E.J. Septimus, J.E. McGowan, Jr., F.J. Quinones, K. Wiss, P.H. Vance, and P.A. Trier. 1981. *Haemophilus influenzae* infection in adults: characterization of strains by serotypes, biotypes, and beta––lactamase production. J. Infect. Dis. 144:101–106.

Yamanaka, N., and H. Faden. 1993. Antibody response to outer membrane proteins of nontypeable *Haemophilus influenzae* in otis–prone children. J. Pediatr. 122:212–218.

Erwin et al Can. Journ.of Microbiology 34: 723–729, 1988.

Thomas et al Infection & Immunity 58: 1909–1913, 1990.

Barenkamp, Pediatric Research vol. 29, 167A, Abstract 985, 1991.

Barenkamp, Abstract 983, Pediatric Research vol.27.

Young et al, PNAS 80: 1194–1198, 1983.

Houghten et al. Vaccine 86, pp. 21–25.

Abstracts of the 31st Inter science Conferende on Antimicrobial Agents and Chemotherapy, vol.31, Oct. 1991, p. 286 Stem/phen J. Barenkamp Abstract No. 1126.

Thomas et al. Infect & Immun. Jun. 1990. 58(6): 1909–1913.

Barenkanp et al. Apr. 1992. Infect & Immun. 60(4) : 1302–1313.

Barenkanp. Ped. Res. Apr. 29–May 2, 1991, 29(4 pt2.) Abstract 985.

Barenkanp. Ped. Res. May 1990. 27(4 Pt 2). Abstract 983.

FIG. 1A. DNA SEQUENCE OF HIGH MOLECULAR WEIGHT PROTEIN I (HMW1)

```
  1  ACAGCGTTCT CTTAATACTA GTACAAACCC ACAATAAAAT ATGACAAACA
 51  ACAATTACAA CACCTTTTTT GCAGTCTATA TGCAAATATT TTAAAAAATA
101  GTATAAATCC GCCATATAAA ATGGTATAAT CTTTCATCTT TCATCTTTCA
151  TCTTTCATCT TTCATCTTTC ATCTTTCATC TTTCATCTTT CATCTTTCAT
201  CTTTCATCTT TCATCTTTCA TCTTTCATCT TTCATCTTTC ACATGCCCTG
251  ATGAACCGAG GGAAGGGAGG GAGGGGCAAG AATGAAGAGG GAGCTGAACG
301  AACGCAAATG ATAAAGTAAT TTAATTGTTC AACTAACCTT AGGAGAAAAT
351  ATGAACAAGC TATATCGTCT CAAATTCAGC AAACGCCTGA ATGCTTTGGT
401  TGCTGTGTCT GAATTGGCAC GGGGTTGTGA CCATTCCACA GAAAAAGGCA
451  GCGAAAAACC TGCTCGCATG AAAGTGCGTC ACTTAGCGTT AAAGCCACTT
501  TCCGCTATGT TACTATCTTT AGGTGTAACA TCTATTCCAC AATCTGTTTT
551  AGCAAGCGGC TTACAAGGAA TGGATGTAGT ACACGGCACA GCCACTATGC
601  AAGTAGATGG TAATAAAACC ATTATCCGCA ACAGTGTTGA CGATATCATT
651  AATTGGAAAC AATTTAACAT CGACCAAAAT GAAATGGTGC AGTTTTTACA
701  AGAAAACAAC AACTCCGCCG TATTCAACCG TGTTACATCT AACCAAATCT
```

FIG. 1B.

```
 751  CCCAATTAAA AGGGATTTTA GATTCTAACG GACAAGTCTT TTTAATCAAC
 801  CCAAATGGTA TCACAATAGG TAAAGACGCA ATTATTAACA CTAATGGCTT
 851  TACGGCTTCT ACGCTAGACA TTTCTAACGA AAACATCAAG GCGCGTAATT
 901  TCACCTTCGA GCAAACCAAA GATAAAGCGC TCGCTGAAAT TGTGAATCAC
 951  GGTTTAATTA CTGTCGGTAA AGACGGCAGT GTAAATCTTA TTGGTGGCAA
1001  AGTGAAAAAC GAGGGTGTGA TTAGCGTAAA TGGTGGCAGC ATTTCTTTAC
1051  TCGCAGGGCA AAAAATCACC ATCAGCGATA TAATAAACCC AACCATTACT
1101  TACAGCATTG CCGCGCCTGA AAATGAAGCG GTCAATCTGG GCGATATTTT
1151  TGCCAAAGGC GGTAACATTA ATGTCCCGTGC TGCCACTATT CGAAACCAAG
1201  GTAAACTTTC TGCTGATTCT GTAAGCAAAG ATAAAAGCGG CAATATTGTT
1251  CTTTCCGCCA AAGAGGGTGA AGCGGAAATT GGCGGTGTAA TTTCCGCTCA
1301  AAATCAGCAA GCTAAAGGCG GCAAGCTGAT GATTACAGGC GATAAAGTCA
1351  CATTAAAAAC AGGTGCAGTT ATCGACCTTT CAGGTAAAGA AGGGGAGAA
1401  ACTTACCTTG GCGGTGACGA GCGCGGGCAA GGTAAAAAGG GCATTCAATT
1451  AGCAAAGAAA ACCTCTTTAG AAAAAGGCTC AACCATCAAT GTATCAGGCA
1501  AAGAAAAAGG CGGACGCGCT ATTGTGTGGG GCGATATTGC GTTAATTGAC
```

FIG. 1C.

```
1551  GGCAATATTA ACGCTCAAGG TAGTGGTGAT ATCGCTAAAA CCGGTGGTTT
1601  TGTGGAGACG TCGGGGCATG ATTTATTCAT CAAAGACAAT GCAATTGTTG
1651  ACGCCAAAGA GTGGTTGTTA GACCCGGATA ATGTATCTAT TAATGCAGAA
1701  ACAGCAGGAC GCAGCAATAC TTCAGAAGAC GATGAATACA CGGGATCCGG
1751  GAATAGTGCC AGCACCCCAA AACGAAAACAA AGAAAAGACA ACATTAACAA
1801  ACACAACTCT TGAGAGTATA CTAAAAAAAG GTACCTTTGT TAACATCACT
1851  GCTAATCAAC GCATCTATGT CAATAGCTCC ATTAATTTAT CCAATGGCAG
1901  CTTAACTCTT TGGAGTGAGG GTCGGAGCGG TGGCGGCGTT GAGATTAACA
1951  ACGATATTAC CACCGGTGAT GATACCAGAG GTGCAAACTT AACAATTTAC
2001  TCAGGCGGCT GGGTTGATGT TCATAAAAAT ATCTCACTCG GGGCGCAAGG
2051  TAACATAAAC ATTACAGCTA AACAAGATAT CGCCTTTGAG AAAGGAAGCA
2101  ACCAAGTCAT TACAGGTCAA GGGACTATTA CCTCAGGCAA TCAAAAAGGT
2151  TTTAGATTTA ATAATGTCTC TCTAAACGGC ACTGGCAGCG GACTGCAATT
2201  CACCACTAAA AGAACCAATA AATACGCTAT CACAAATAAA TTTGAAGGGA
2251  CTTTAAATAT TTCAGGGAAA GTGAACATCT CAATGGTTTT ACCTAAAAAT
2301  GAAAGTGGAT ATGATAAATT CAAAGGACGC ACTTACTGGA ATTTAACCTC
```

FIG. 1D.

```
2351  CTTAAATGTT  TCCGAGAGTG  GCGAGTTTAA  CCTCACTATT  GACTCCAGAG
2401  GAAGCGATAG  TGCAGGCACA  CTTACCCAGC  CTTATAATTT  AAACGGTATA
2451  TCATTCAACA  AAGACACTAC  CTTTAATGTT  GAACGAAATG  CAAGAGTCAA
2501  CTTTGACATC  AAGGCACCAA  TAGGGATAAA  TAAGTATTCT  AGTTTGAATT
2551  ACGCATCATT  TAATGGAAAC  ATTTCAGTTT  CGGGAGGGGG  GAGTGTTGAT
2601  TTCACACTTC  TCGCCTCATC  CTCTAACGTC  CAAACCCCCG  GTGTAGTTAT
2651  AAATTCTAAA  TACTTTAATG  TTTCAACAGG  GTCAAGTTTA  AGATTAAAA
2701  CTTCAGGCTC  AACAAAAACT  GGCTTCTCAA  TAGAGAAAGA  TTTAACTTTA
2751  AATGCCACCG  GAGGCAACAT  AACACTTTTG  CAAGTTGAAG  GCACCGATGG
2801  AATGATTGGT  AAAGGCATTG  TAGCCAAAAA  AAACATAACC  TTTGAAGGAG
2851  GTAACATCAC  CTTTGGCTCC  AGGAAAGCCG  TAACAGAAAT  CGAAGGCAAT
2901  GTTACTATCA  ATAACAACGC  TAACGTCACT  CTTATCGGTT  CGGATTTTGA
2951  CAACCATCAA  AAACCTTTAA  CTATTAAAAA  AGATGTCATC  ATTAATAGCG
3001  GCAACCTTAC  CGCTGGAGGC  AATATTGTCA  ATATAGCCGG  AAATCTTACC
3051  GTTGAAAGTA  ACGCTAATTT  CAAAGCTATC  ACAAATTTCA  CTTTTAATGT
3101  AGGCGGCTTG  TTTGACAACA  AAGGCAATTC  AAATATTTCC  ATTGCCAAAG
3151  GAGGGGCTCG  CTTTAAAGAC  ATTGATAATT  CCAAGAATTT  AAGCATCACC
```

FIG. 1E.

```
3201 ACCAACTCCA GCTCCACTTA CCGCACTATT ATAAGCGGCA ATATAACCAA
3251 TAAAAACGGT GATTTAAATA TTACGAACGA AGGTAGTGAT ACTGAAATGC
3301 AAATTGGCGG CGATGTCTCG CAAAAAGAAG GTAATCTCAC GATTCTTCT
3351 GACAAAATCA ATATTACCAA ACAGATAACA ATCAAGGCAG GTGTTGATGG
3401 GGAGAATTCC GATTCAGACG CGACAAACAA TGCCAATCTA ACCATTAAAA
3451 CCAAAGAATT GAAATTAACG CAAGACCTAA ATATTTCAGG TTTCAATAAA
3501 GCAGAGATTA CAGCTAAAGA TGGTAGTGAT TTAACTATTG GTAACACCAA
3551 TAGTGCTGAT GGTACTAATG CCAAAAAAGT AACCTTTAAC CAGGTTAAAG
3601 ATTCAAAAAT CTCTGCTGAC GGTCACAAGG TGACACTACA CAGCAAAGTG
3651 GAAACATCCG GTAGTAATAA CAACACTGAA GATAGCAGTG ACAATAATGC
3701 CGGCTTAACT ATCGATGCAA AAAATGTAAC AGTAAACAAC AATATTACTT
3751 CTCACAAAGC AGTGAGCATC TCTGCGACAA GTGGAGAAAT TACCACTAAA
3801 ACAGGTACAA CCATTAACGC AACCACTGGT AACGTGGAGA TAACCGCTCA
3851 AACAGGTAGT ATCCTAGGTG GAATTGAGTC CAGCTCTGGC TCTGTAACAC
3901 TTACTGCAAC CGAGGGCGCT CTTGCTGTAA GCAATATTTC GGGCAACACC
3951 GTTACTGTTA CTGCAAATAG CGGTGCATTA ACCACTTTGG CAGGCTCTAC
```

FIG. 1F.

```
4001 AATTAAAGGA ACCGAGAGTG TAACCACTTC AAGTCAATCA GGCGATATCG
4051 GCGGTACGAT TTCTGGTGGC ACAGTAGAGG TTAAAGCAAC CGAAAGTTTA
4101 ACCACTCAAT CCAATTCAAA AATTAAAGCA ACAACAGGCG AGGCTAACGT
4151 AACAAGTGCA ACAGGTACAA TTGGTGGTAC GATTTCCGGT AATACGGTAA
4201 ATGTTACGGC AAACGCTGGC GATTTAACAG TTGGGAATGG CGCAGAAATT
4251 AATGCGACAG AAGGAGCTGC AACCTTAACT ACATCATCGG GCAAATTAAC
4301 TACCGAAGCT AGTTCACACA TTACTTCAGC CAAGGGTCAG GTAAATCTTT
4351 CAGCTCAGGA TGGTAGCGTT GCAGGAAGTA TTAATGCCGC CAATGTGACA
4401 CTAAATACTA CAGGCACTTT AACTACCGTG AAGGGTTCAA ACATTAATGC
4451 AACCAGCGGT ACCTTGGTTA TTAACGCAAA AGACGCTGAG CTAAATGGCG
4501 CAGCATTGGG TAACCACACA GTGGTAAATG CAACCAACGC AAATGGCTCC
4551 GGCAGCGTAA TCGCGACAAC CTCAAGCAGA GTGAACATCA CTGGGGATTT
4601 AATCACAATA AATGGATTAA ATATCATTTC AAAAAACGGT ATAAACACCG
4651 TACTGTTAAA AGGCGTTAAA ATTGATGTGA AATACATTCA ACCGGGTATA
4701 GCAAGCGTAG ATGAAGTAAT TGAAGCGAAA CGCATCCTTG AGAAGGTAAA
4751 AGATTTATCT GATGAAGAAA GAGAAGCGTT AGCTAAACTT GGAGTAAGTG
4801 CTGTACGTTT TATTGAGCCA AATAATACAA TTACAGTCGA TACACAAAAT
```

FIG. 1G.

```
4851  GAATTTGCAA  CCAGACCATT  AAGTCGAATA  GTGATTTCTG  AAGGCAGGGC
4901  GTGTTTCTCA  AACAGTGATG  GCGCGACGGT  GTGCGTTAAT  ATCGCTGATA
4951  ACGGGCGGTA  GCGGTCAGTA  ATTGACAAGG  TAGATTTCAT  CCTGCAATGA
5001  AGTCATTTTA  TTTTCGTATT  ATTTACTGTG  TGGGTTAAAG  TTCAGTACGG
5051  GCTTTACCCA  TCTTGTAAAA  AATTACGGAG  AATACAATAA  AGTATTTTTA
5101  ACAGGTTATT  ATTATG
```

FIG. 2A. AMINO ACID SEQUENCE OF HIGH MOLECULAR WEIGHT PROTEIN I

```
  1  MNKIYRLKFS KRLNALVAVS ELARGCDHST EKGSEKPARM KVRHLALKPL
 51  SAMLLSLGVT SIPQSVLASG LQGMDVVHGT ATMQVDGNKT IIRNSVDAII
101  NWKQFNIDQN EMVQFLQENN NSAVFNRVTS NQISQLKGIL DSNGQVFLIN
151  PNGITIGKDA IINTNGFTAS TLDISNENIK ARNFTFEQTK DKALAEIVNH
201  GLITVGKDGS VNLIGGKVKN EGVISVNGGS ISLLAGQKIT ISDIINPTIT
251  YSIAAPENEA VNLGDIFAKG GNINVRAATI RNQGKLSADS VSKDKSGNIV
301  LSAKEGEAEI GGVISAQNQQ AKGGKLMITG DKVTLKTGAV IDLSGKEGGE
351  TYLGGDERGE GKNGIQLAKK TSLEKGSTIN VSGKEKGGRA IVWGDIALID
401  GNINAQGSGD IAKTGGFVET SGHDLFIKDN AIVDAKEWLL DFDNVSINAE
451  TAGRSNTSED DEYTGSGNSA STPKRNKEKT TLTNTTLESI LKKGTFVNIT
501  ANQRIYVNSS INLSNGSLTL WSEGRSGGGV EINNDITTGD DTRGANLTIY
551  SGGWVDVHKN ISLGAQNIN ITAKQDIAFE KGSNQVITGQ GTITSGNQKG
601  FRFNNVSLNG TGSGLQFTTK RTNKYAITNK FEGTLNISGK VNISMVLPKN
651  ESGYDKFKGR TYWNLTSLNV SESGEFNLTI DSRGSDSAGT LTQPYNLNGI
701  SFNKDTTFNV ERNARVNFDI KAPIGINKYS SLNYASFNGN ISVSGGGSVD
```

FIG. 2B.

```
 751  FTLLASSSNV  QTPGVVINSK  YFNVSTGSSL  RFKTSGSTKT  GFSIEKDLTL
 801  NATGGNITLL  QVEGTDGMIG  KGIVAKKNIT  FEGGNITFGS  RKAVTEIEGN
 851  VTINNNANVT  LIGSDFDNHQ  KPLTIKKDVI  INSGNLTAGG  NIVNIAGNLT
 901  VESNANFKAI  TNFTFNVGGL  FDNKGNSNIS  IAKGGARFKD  IDNSKNLSIT
 951  TNSSSTYRTI  ISGNITNKNG  DLNITNEGSD  TEMQIGGDVS  QKEGNLTISS
1001  DKINITKQIT  IKAGVDGENS  DSDATNNANL  TIKTKELKLT  QDLNISGFNK
1051  AEITAKDGSD  LTIGNTNSAD  GTNAKKVTFN  QVKDSKISAD  GHKVTLHSKV
1101  ETSGSNNNTE  DSSDNNAGLT  IDAKNVTVNN  NITSHKAVSI  SATSGEITTK
1151  TGTTINATTG  NVEITAQTGS  ILGGIESSSG  SVTLTATEGA  LAVSNISGNT
1201  VTVTANSGAL  TTLAGSTIKG  TESVTTSSQS  GDIGGTISGG  TVEVKATESL
1251  TTQSNSKIKA  TGTIGGTISG  SSHITSAKGQ  NTVNVTANAG  DLTVGNGAEI
1301  NATEGAATLT  TSSGKLTTEA  SSHITSAKGQ  VNLSAQDGSV  AGSINAANVT
1351  LNTTGTLTTV  KGSNINATSG  TLVINAKDAE  LNGAALGNHT  VVNATNANGS
1401  GSVIATTSSR  VNITGDLITI  NGLNIISKNG  INTVLLKGVK  IDVKYIQPGI
1451  ASVDEVIEAK  RILEKVKDLS  DEEREALAKL  GVSAVRFIEP  NNTITVDTQN
1501  EFATRPLSRI  VISEGRACFS  NSDGATVCVN  IADNGR
```

FIG. 3A. AMINO ACID SEQUENCE OF HIGH MOLECULAR WEIGHT PROTEIN II (HMW2)

```
  1  TAAATATACA AGATAATAAA AATAAATCAA GATTTTGTG  ATGACAAACA
 51  ACAATTACAA CACCTTTTTT GCAGTCTATA TGCAAATATT TTAAAAAAAT
101  AGTATAAATC CGCCATATAA AATGGTATAA TCTTTCATCT TTCATCTTTA
151  ATCTTTCATC TTTCATCTTT CATCTTTCAT CTTTCATCTT TCATCTTTCA
201  TCTTTCATCT TTCATCTTTC ATCTTTCATC TTTCATCTTT CACATGAAAT
251  GATGAACCGA GGGAAGGGAG GGAGGGGCAA GAATGAAGAG GGAGCTGAAC
301  GAACGCAAAT GATAAAGTAA TTTAATTGTT CAACTAACCT TAGGAGAAAA
351  TATGAACAAG ATATATCGTC TCAAATTCAG CAAACGCCTG AATGCTTTGG
401  TTGCTGTGTC TGAATTGGCA CGGGGTTGTG ACCATTCCAC AGAAAAAGGC
451  TTCCGCTATG TTACTATCTT TAGGTGTAAC CACTTAGCGT TAAAGCCACT
501  TTCCGCTATG TTACTATCTT TAGGTGTAAC ATCTATTCCA CAATCTGTTT
551  TAGCAAGCGG CTTACAAGGA ATGGATGTAG TACACGGCAC AGCCACTATG
601  CAAGTAGATG GTAATAAAAC CATTATCCGC AACAGTGTTG ACGCTATCAT
651  TAATTGGAAA CAATTTAACA TCGACCAAAA TGAAATGGTG CAGTTTTTAC
701  AAGAAAACAA CAACTCCGCC GTATTCAACC GTGTTACATC TAACCAAATC
```

FIG. 3B.

```
 751  TCCCAATTAA AAGGGATTTT AGATTCTAAC GGACAAGTCT TTTTAATCAA
 801  CCCAAATGGT ATCACAATAG GTAAAGACGC AATTATTAAC ACTAATGGCT
 851  TTACGGCTTC TACGCTAGAC ATTTCTAACG AAAACATCAA GGCGCGTAAT
 901  TTCACCTTCG AGCAAACCAA AGATAAAGCG CTCGCTGAAA TTGTGAATCA
 951  CGGTTTAATT ACTGTCGGTA AAGACGGCAG TGTAAATCTT ATTGGTGGCA
1001  AAGTGAAAAA CGAGGGTGTG ATTAGCGTAA ATGGTGGCAG CATTTCTTTA
1051  CTCGCAGGGC AAAAAATCAC CATCAGCGAT ATAATAAACC CAACCATTAC
1101  TTACAGCATT GCCGCGCCTG AAAATGAAGC GGTCAATCTG GGCGATATTT
1151  TTGCCAAAGG CGGTAACATT AATGTCCGTG CTGCCACTAT TCGAAACCAA
1201  GGTAAACTTT CTGCTGATTC TGTAAGCAAA GATAAAAGCG GCAATATTGT
1251  TCTTTCCGCC AAAGAGGGTG AAGCGGAAAT TGGCGGTGTA ATTTCCGCTC
1301  AAAATCAGCA AGCTAAAGGC GGCAAGCTGA TGATTACAGG CGATAAAGTC
1351  ACATTAAAAA CAGGTGCAGT TATCGACCTT TCAGGTAAAG AAGGGGGAGA
1401  AACTTACCTT GGCGGTGACG AGCGCGGCGA AGGTAAAAAC GGCATTCAAT
1451  TAGCAAAGAA AACCTCTTTA GAAAAAGGCT CAACCATCAA TGTATCAGGC
1501  AAAGAAAAAG GCGGACGCGC TATTGTGTGG GGCGATATTG CGTTAATTGA
```

FIG. 3C.

```
1551  CGGCAATATT AACGCTCAAG GTAGTGGTGA TATCGCTAAA ACCGGTGGTT
1601  TTGTGGAGAC ATCGGGGCAT TATTTATCCA TTGACAGCAA TGCAATTGTT
1651  AAAACAAAAG AGTGGTTGCT AGACCCTGAT GATGTAACAA TTGAAGCCGA
1701  AGACCCCCTT CGCAATAATA CCGGTATAAA TGATGAATTC CCAACAGGCA
1751  CCGGTGAAGC AAGCGACCCT AAAAAAAATA GCGAACTCAA AACAACGCTA
1801  ACCAATACAA CTATTTCAAATTATCTGAAA AACGCCTGGA CAATGAATAT
1851  AACGGCATCA AGAAAACTTA CCGTTAATAG CTCAATCAAC ATCGGAAGCA
1901  ACTCCCACTT AATTCTCCAT AGTAAAGGTC AGCGTGGCGG AGGCGTTCAG
1951  ATTGATGGAG ATATTACTTC TAAAGGCGGA AATTTAACCA TTTATTCTGG
2001  CGGATGGGTT GATGTTCATA AAAATATTAC GCTTGATCAG GGTTTTTTAA
2051  ATATTACCGC CGCTTCCGTA GCTTTTTGAAG GTGGAAATAA CAAAGCACGC
2101  GACGCGGGCAA ATGCTAAAAT TGTCGCCCAG GGCACTGTAA CCATTACAGG
2151  AGAGGGAAAA GATTTCAGGG CTAACAACGT ATCTTTAAAC GGAACGGGTA
2201  AAGGTCTGAA TATCATTTCA TCAGTGAATA ATTTAACCCA CAATCTTAGT
2251  GGCACAATTA ACATATCTGG GAATATAACA ATTAACCAAA CTACGAGAAA
2301  GAACACCTCG TATTGGCAAA CCAGCCATGA TTCGCACTGG AACGTCAGTG
2351  CTCTTAATCT AGAGACAGGC GCAAATTTTA CCTTTATTAA ATACATTTCA
```

FIG. 3D.

```
2401 AGCAATAGCA AAGGCTTAAC AACACAGTAT AGAAGCTCTG CAGGGGTGAA
2451 TTTTAACGGC GTAAATGGCA ACATGTCATT CAATCTCAAA GAAGGAGCGA
2501 AAGTTAATTT CAAATTAAAA CCAAACGAGA ACATGAACAC AAGCAAACCT
2551 TTACCAATTC GGTTTTTAGC CAATATCACA GCCACTGGTG GGGGCTCTGT
2601 TTTTTTTGAT ATATATGCCA ACCATTCTGG CAGAGGGGCT GAGTTAAAAA
2651 TGAGTGAAAT TAATATCTCT AACGGCGCTA ATTTTACCTT AAATTCCCAT
2701 GTTCGCGGCG ATGACGCTTT TAAAATCAAC AAAGACTTAA CCATAAATGC
2751 AACCAATTCA AATTTCAGCC TCAGACAGAC GAAAGATGAT TTTTATGACG
2801 GGTACGCACG CAATGCCATC AATTCAACCT ACAACATATC CATTCTGGGC
2851 GGTAATGTCA CCCTTGGTGG ACAAAACTCA AGCAGCAGCA TTACGGGGAA
2901 TATTACTATC GAGAAAGCAG CAAATGTTAC GCTAGAAGCC AATAACGCCC
2951 CTAATCAGCA AAACATAAGG GATAGAGTTA TAAAACTTGG CAGCTTGCTC
3001 GTTAATGGGA GTTTAAGTTT AACTGGCGAA AATGCAGATA TTAAAGGCAA
3051 TCTCACTATT TCAGAAAGCG CCACTTTTAA AGGAAAGACT AGAGATACCC
3101 TAAATATCAC CGGCAATTTT ACCAATAATG GCACTGCCGA AATTAATATA
3151 ACACAAGGAG TGGTAAAACT TGGCAATGTT ACCAATGATG GTGATTTAAA
```

FIG. 3E.

```
3201  CATTACCACT  CACGCTAAAC  GCAACCAAAG  AAGCATCATC  GGCGGAGATA
3251  TAATCAACAA  AAAAGGAAGC  TTAAATATTA  CAGACAGTAA  TAATGATGCT
3301  GAAATCCAAA  TTGGCGGCAA  TATCTCGCAA  AAAGAAGGCA  ACCTCACGAT
3351  TTCTTCCGAT  AAAATTAATA  TCACCAAACA  GATAACAATC  AAAAAGGGTA
3401  TTGATGGAGA  GGACTCTAGT  TCAGATGCGA  CAAGTAATGC  CAACCTAACT
3451  ATTAAAACCA  AAGAATTGAA  ATTGACAGAA  GACCTAAGTA  TTTCAGGTTT
3501  CAATAAAGCA  GAGATTACAG  CCAAAGATGG  TAGAGATTTA  ACTATTGGCA
3551  ACAGTAATGA  CGGTAACAGC  GGTGCCGAAG  CCAAAACAGT  AACTTTTAAC
3601  AATGTTAAAG  ATTCAAAAAT  CTCTGCTGAC  GGTCACAATG  TGACACTAAA
3651  TAGCAAAGTG  AAAACATCTA  GCAGCAATGG  CGGACGTGAA  AGCAATAGCG
3701  ACAACGATAC  CGGCTTAACT  ATTACTGCAA  AAAATGTAGA  AGTAAACAAA
3751  GATATTACTT  CTCTCAAAAC  AGTAAATATC  ACCGCGTCGG  AAAAGGTTAC
3801  CACCACAGCA  GGCTCGACCA  TTAACGCAAC  AAATGGCAAA  GCAAGTATTA
3851  CAACCAAAAC  AGGTGATATC  AGCGGTACGA  TTTCCGGTAA  CACGGTAAGT
3901  GTTAGCGCGA  CTGGTGATTT  AACCACTAAA  TCCGCTCAA   AAATTGAAGC
3951  GAAATCGGGT  GAGGCTAATG  AACAGGTACA  TAACAAGTGC  ATTGGCGGTA
```

FIG. 3F.

```
4001 CAATTTCCGG TAATACGGTA AATGTTACGG CAAACGCTGG CGATTTAACA
4051 GTTGGGAATG GCGCAGAAAT TAATGCGACA GAAGGAGCTG CAACCTTAAC
4101 CGCAACAGGG AATACCTTGA CTACTGAAGC CGGTTCTAGC ATCACTTCAA
4151 CTAAGGGTCA GGTAGACCTC TTGGCTCAGA ATGGTAGCAT CGCAGGAAGC
4201 ATTAATGCTG CTAATGTGAC ATTAAATACT ACAGGCACCT TAACCACCGT
4251 GGCAGGCTCG GATATTAAAG CAACCAGCGG CACCTTGGTT ATTAACGCAA
4301 AAGATGCTAA GCTAAATGGT GATGCATCAG GTGATAGTAC AGAAGTGAAT
4351 GCAGTCAACG CAAGCGGCTC TGGTAGTGTG ACTGCGGCAA CCTCAAGCAG
4401 TGTGAATATC ACTGGGGATT TAAACACAGT AAATGGGTTA AATATCATTT
4451 CGAAAGATGG TAGAAACACT GTGCGCTTAA GAGGCAAGGA AATTGAGGTG
4501 AAATATATCC AGCCAGGTGT AGCAAGTGTA GAAGAAGTAA TTGAAGCGAA
4551 ACGCGTCCTT GAAAAAGTAA AAGATTTATC TGATGAAGAA AGAGAAACAT
4601 TAGCTAAACT TGGTGTAAGT GCTGTACGTT TTGTTGAGCC AAATAATACA
4651 ATTACAGTCA ATACACAAAA TGAATTTACA ACCAGACCGT CAAGTCAAGT
4701 GATAATTTCT GAAGGTAAGG CGTGTTTCTC AAGTGGTAAT GGCGCACGAG
4751 TATGTACCAA TGTTGCTGAC GATGGACAGC CGTAGTCAGT AATTGACAAG
4801 GTAGATTTCA TCCTGCAATG AAGTCATTTT ATTTCGTAT TATTTACTGT
```

FIG. 3G.

4851  GTGGGTAAAA GTTCAGTACG GGCTTTACCC ATCTTGTAAA AAATTACGGA
4901  GAATACAATA AAGTATTTTT AACAGGTTAT TATTATG

FIG. 4A. AMINO ACID SEQUENCE OF HIGH MOLECULAR WEIGHT PROTEIN 2

```
  1  MNKIYRLKFS KRLNALVAVS ELARGCDHST EKGSEKPARM KVRHLALKPL
 51  SAMLLSLGVT SIPQSVLASG LQGMDVVHGT ATMQVDGNKT IIRNSVDAII
101  NWKQFNIDQN EMVQFLQENN NSAVFNRVTS NQISQLKGIL DSNGQVFLIN
151  PNGITIGKDA IINTNGFTAS TLDISNENIK ARNFTFEQTK DKALAEIVNH
201  GLITVGKDGS VNLIGGKVKN EGVISVNGGS ISLLAGQKIT ISDIINPTIT
251  YSIAAPENEA VNLGDIFAKG GNINVRAATI RNQGKLSADS VSKDKSGNIV
301  LSAKEGEAEI GGVISAQNQQ AKGGKLMITG DKVTLKTGAV IDLSGKEGGE
351  TYLGGDERGE GKNGIQLAKK TSLEKGSTIN VSGKEKGGRA IVWGDIALID
401  GNINAQGSGD IAKTGGFVET SGHDLFIKDN AIVDAKEWLL DFDNVSINAE
451  DPLRNNTGIN DEFPTGTGEA SDPKKNSELK TTLTNTTISN YLKNAWTMNI
501  TASRKLTVNS SINIGSNSHL ILHSKGQRGG GVQIDGDITS KGGNLTIYSG
551  GWVDVHKNIT LDQGFLNITA ASVAFEGGNN KARDAANAKI VAQGTVTITG
601  EGKDFRANNV SLNGTGKGLN IISSVNNLTH NLSGTINISG NITINQTTRK
651  NTSYWQTSHD SHWNVSALNL ETGANFTFIK YISSNSKGLT TQYRSSAGVN
701  FNGVNGNMSF NLKEGAKVNF KLKPNENMNT SKPLPIRFLA NITATGGGSV
```

FIG. 4B.

```
 751  FFDIYANHSG  RGAELKMSEI  NISNGANFTL  NSHVRGDDAF  KINKDLTINA
 801  TNSNFSLRQT  KDDFYDGYAR  NAINSTYNIS  ILGGNVTLGG  QNSSSSITGN
 851  ITIEKAANVT  LEANNAPNQQ  NIRDRVIKLG  SLLVNGSLSL  TGENADIKGN
 901  LTISESATFK  GKTRDTLNIT  GNFTNNGTAE  INITQGVVKL  GNVTNDGDLN
 951  ITTHAKRNQR  SIGGDIINK   KGSLNITDSN  NDAEIQIGGN  ISQKEGNLTI
1001  SSDKINITKQ  ITIKKGIDGE  DSSSDATSNA  NLTIKTKELK  LTEDLSISGF
1051  NKAEITAKDG  RDLTIGNSND  GNSGAEAKTV  TFNNVKDSKI  SADGHNVTLN
1101  SKVKTSSSNG  GRESNSDNDT  GLTITAKNVE  VNKDITSLKT  VNITASEKVT
1151  TTAGSTINAT  NGKASITTKT  GDISGTISGN  TVSVSATVDL  TTKSGSKIEA
1201  KSGEANVTSA  TGTIGGTISG  NTVNVTANAG  DLTVGNGAEI  NATEGAATLT
1251  ATGNTLTTEA  GSSITSTKGQ  VDLLAQNGSI  AGSINAANVT  LNTTGTLTTV
1301  AGSDIKATSG  TLVINAKDAK  LNGDASGDST  EVNAVNASGS  GSVTAATSSS
1351  VNITGDLNTV  NGLNIISKDG  RNTVRLRGKE  IEVKYIQPGV  ASVEEVIEAK
1401  RVLEKVKDLS  DEERETLAKL  GVSAVRFVEP  NNTITVNTQN  EFTTRPSSQV
1451  IISEGKACFS  SGNGARVCTN  VADDGQP
```

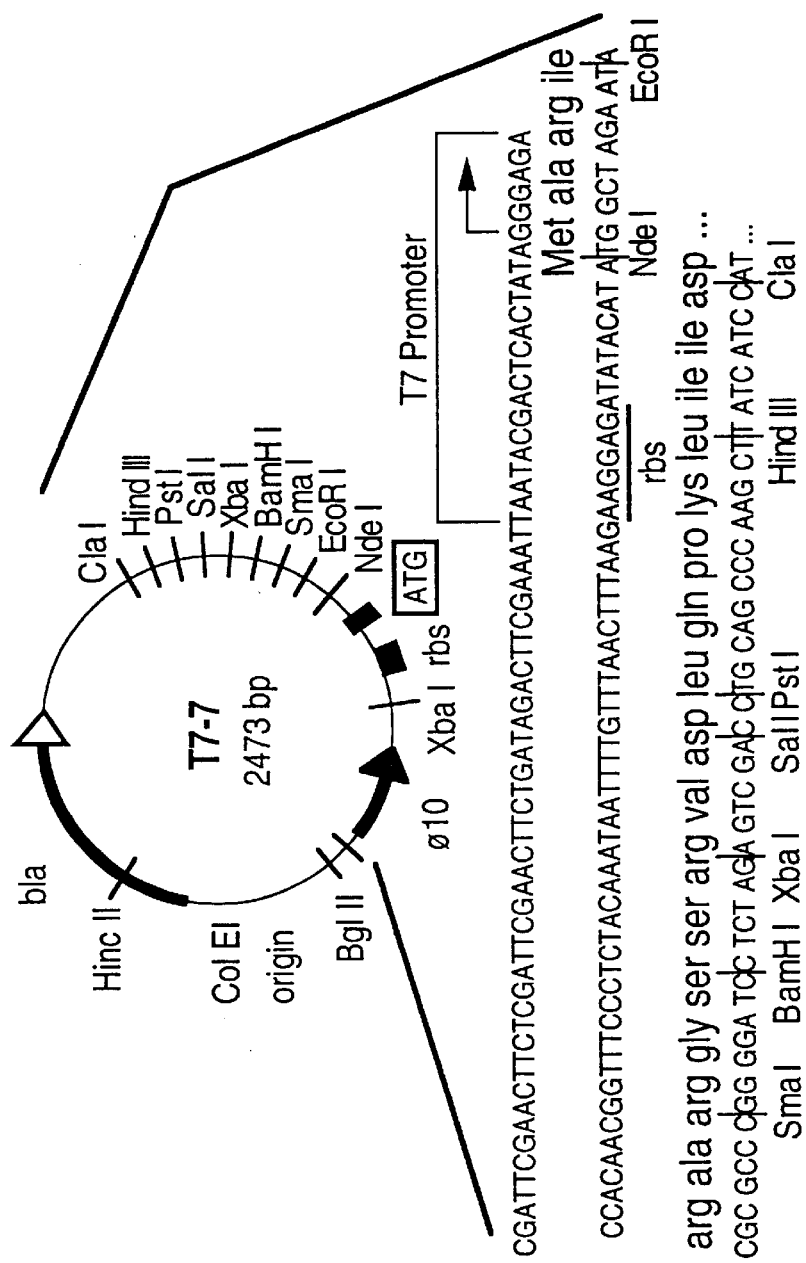

FIG. 5B.

(A) Partial restriction maps of representative HMW1 and HMW2 recombinant phage and of HMW1 plasmid subclones. The shaded boxes indicate the locations of the structural genes. In the recombinant phage, transcription proceeds from left to right for the HMW1 gene and from right to left for the HMW2 gene. The methods used for construction of the plasmids shown are described in the text. (B) Restriction map of the T7 expression vector pT7-7. This vector contains the T7 RNA polymerase promoter φ10, a ribosome - binding site (rbs), and the translational start site for the T7 gene 10 protein upstream from a multiple cloning site (37).

FIG. 6A.

```
  1 ACAGGCGTTCT CTTAATACTA GTACAAACCC ACAATAAAAT ATGACAAACA
 51 ACAATTACAA CACCTTTTTT GCAGTCTATA TGCAAATATT TTAAAAAATA
101 GTATAAATCC GCCATATAAA ATGGTATAAT CTTTCATCTT TCATCTTTCA
151 TCTTTCATCT TTCATCTTTC ATCTTTCATC TTTCATCTTT CATCTTTCAT
201 CTTTCATCTT TCATCTTTCA TCTTTCATCT TTCATCTTTC ACATGAAATG
251 ATGAACCGAG GGAAGGGAGG GAGGGGCAAG AATGAAGAGG GAGCTGAACG
301 AACGCAAATG ATAAAGTAAT TTAATTGTTC AACTAACCTT AGGAGAAAAT
351 ATGAACAAGA TATATCGTCT CAAATTCAGC AAACGCCTGA ATGCTTTGGT
401 TGCTGTGTCT GAATTGGCAC GGGGTTGTGA CCATTCCACA GAAAAGGCA
451 GCGAAAAACC TGCTCGCATG AAAGTGCGTC ACTTAGCGTT AAAGCCACTT
501 TCCGCTATGT TACTATCTTT AGGTGTAACA TCTATTCCAC AATCTGTTTT
551 AGCAAGCGGC TTACAAGGAA TGGATGTAGT ACACGGCACA GCCACTATGC
601 AAGTAGATGG TAATAAAACC ATTATCCGCA ACAGTGTTGA CGCTATCATT
651 AATTGGAAAC AATTTAACAT CGACCAAAAT GAAATGGTGC AGTTTTTACA
701 AGAAAACAAC AACTCCGCCG TATTCAACCG TGTTACATCT AACCAAATCT
751 CCCAATTAAA AGGGATTTTA GATTCTAACG GACAAGTCTT TTTAATCAAC
```

FIG. 6B.

```
801   CCAAATGGTA  TCACAATAGG  TAAAGACGCA  ATTATTAACA  CTAATGCTT
851   TACGGCTTCT  ACGCTAGACA  TTTCTAACGA  AAACATCAAG  GCGCGTAATT
901   TCACCCTTCGA GCAAACCAAA  GATAAAGCGC  TCGCTGAAAT  TGTGAATCAC
951   GGTTTAATTA  CTGTCGGTAA  AGACGGCAGT  GTAAATCTTA  TTGGTGGCAA
1001  AGTGAAAAAC  GAGGGTGTGA  TTAGCGTAAA  TGGTGGCAGC  ATTTCTTTAC
1051  TCGCAGGGCA  AAAAATCACC  ATCAGCGATA  TAATAAACCC  AACCATTACT
1101  TACAGCATTG  CCGCGCCTGA  AAATGAAGCG  GTCAATCTGG  GCGATATTTT
1151  TGCCAAAGGC  GGTAACATTA  ATGTCCGTGC  TGCCACTATT  CGAAACCAAG
1201  CTTTCCGCCA  AAGAGGGTGA  AGCGGAAATT  GGCGGTGTAA  TTTCCGCTCA
1301  AAATCAGCAA  GCTAAAGGCG  GCAAGCTGAT  GATTACAGGC  GATAAAGTCA
1351  CATTAAAAAC  AGGTGCAGTT  ATCGACCTTT  CAGGTAAAGA  AGGGGAGAA
1401  ACTTACCTTG  GCGGTGACGA  GCGCGGCGAA  GGTAAAAACG  GCATTCAATT
1451  AGCAAAGAAA  ACCTCTTTAG  AAAAAGGCTC  AACCATCAAT  GTATCAGGCA
1501  AAGAAAAAGG  CGGACGCGCT  ATTGTGTGGG  GCGATATTGC  GTTAATTGAC
1551  GGCAATATTA  ACGCTCAAGG  TAGTGGTGAT  ATCGCTAAAA  CCGGTGGTTT
1601  TGTGGAGACG  TCGGGGCATG  ATTTATTCAT  CAAAGACAAT  GCAATTGTTG
```

FIG. 6C.

```
1651  ACGCCAAAGA  GTGGTTGTTA  GACCCGGATA  ATGTATCTAT  TAATGCAGAA
1701  ACAGCAGGAC  GCAGCAATAC  TTCAGAAGAC  GATGAATACA  CGGGATCCGG
1751  GAATAGTGCC  AGCACCCCAA  AACGAAACAA  AGAAAAGACA  ACATTAACAA
1801  ACACAACTCT  TGAGAGTATA  CTAAAAAAAG  GTACCTTTGT  TAACATCACT
1851  GCTAATCAAC  GCATCTATGT  CAATAGCTCC  ATTAATTTAT  CCAATGGCAG
1901  CTTAACTCTT  TGGAGTGAGG  GTCGGAGCGG  TGGCGGCGTT  GAGATTAACA
1951  ACGATATTAC  CACCGGTGAT  GATACCAGAG  GTGCAAACTT  AACAATTAC
2001  TCAGGCGGCT  GGGTTGATGT  TCATAAAAAT  ATCTCACTCG  GGGCGCAAGG
2051  TAACATAAAC  ATTACAGCTA  AACAAGATAT  CGCCTTTGAG  AAAGGAAGCA
2101  ACCAAGTCAT  TACAGGTCAA  GGGACTATTA  CCTCAGGCAA  TCAAAAAGGT
2151  TTTAGATTTA  ATAATGTCTC  TCTAAACGGC  ACTGGCAGCG  GACTGCAATT
2201  CACCACTAAA  AGAACCAATA  AATACGCTAT  CACAAATAAA  TTTGAAGGGA
2251  CTTTAAATAT  TTCAGGGAAA  GTGAACATCT  CAATGGTTTT  ACCTAAAAAT
2301  GAAAGTGGAT  ATGATAAATT  CAAAGGACGC  ACTTACTGGA  ATTTAACCTC
2351  GAAAGTGGAT  ATGATAAATT  CAAAGGACGC  CCTCACTATT  GACTCCAGAG
2401  GAAGCGATAG  TGCAGGCACA  CTTACCCAGC  CTTATAATTT  AAACGGTATA
2451  TCATTCAACA  AAGACACTAC  CTTTAATGTT  GAACGAAATG  CAAGAGTCAA
```

FIG. 6D.

```
2501 CTTTGACATC AAGGCACCAA TAGGGATAAA TAAGTATTCT AGTTTGAATT
2551 ACGCATCATT TAATGGAAAC ATTTCAGTTT CGGGAGGGGG GAGTGTTGAT
2601 TTCACACTTC TCGCCTCATC CTCTAACGTC CAAACCCCCG GTGTAGTTAT
2651 AAATTCTAAA TACTTTAATG TTTCAACAGG GTCAAGTTTA AGATTAAAA
2701 CTTCAGGCTC AACAAAAACT GGCTTCTCAA TAGAGAAAGA TTTAACTTTA
2751 AATGCCACCG GAGGCAACAT AACACTTTTG CAAGTTGAAG GCACCGATGG
2801 AATGATTGGT AAAGGCATTG TAGCCAAAAA AAACATAACC TTTGAAGGAG
2851 GTAAGATGAG GTTGGCTCC AGGAAAGCCG TAACAGAAAT CGAAGGCAAT
2901 GTTACTATCA ATAACAACGC TAACGTCACT CTTATCGGTT CGGATTTTGA
2951 CAACCATCAA AAACCTTTAA CTATTAAAAA AGATGTCATC ATTAATAGCG
3001 GCAACCTTAC CGCTGGAGGC AATATTGTCA ATATAGCCGG AAATCTTACC
3051 GTTGAAAGTA ACGCTAATTC CAAAGCTATC ACAAATTTCA CTTTTAATGT
3101 AGGCGGCTTG TTTGACAACA AAGGCAATTC AAATATTTCC ATTGCCAAAG
3151 GAGGGGCTCG CTTTAAAGAC ATTGATAATT CCAAGAATTT AAGCATCACC
3201 ACCAACTCCA GCTCCACTTA CCGCACTATT ATAAGCGGCA ATATAACCAA
3251 TAAAAACGGT GATTTAAATA TTACGAACGA AGGTAGTGAT ACTGAAATGC
```

FIG. 6E.

```
3301  AAATTGGCGG CGATGTCTCG CAAAAGAAG GTAATCTCAC GATTCTTCT
3351  GACAAAATCA ATATTACCAA ACAGATAACA ATCAAGGCAG GTGTTGATGG
3401  GGAGAATTCC GATTCAGACG CGACAAACAA TGCCAATCTA ACCATTAAAA
3451  CCAAAGAATT GAAATTAACG CAAGACCTAA ATATTTCAGG TTTCAATAAA
3501  GCAGAGATTA CAGCTAAAGA TGGTAGTGAT TTAACTATTG GTAACACCAA
3551  TAGTGCTGAT GGTACTAATG CCAAAAAAGT AACCTTTAAC CAGGTTAAAG
3601  ATTCAAAAAT CTCTGCTGAC GGTCACAAGG TGACACTACA CAGCAAAGTG
3651  GAAACATCCG GTAGTAATAA CAACACTGAA GATAGCAGTG ACAATAATGC
3701  CGGCTTAACT ATCGATGCAA AAAATGTAAC AGTAAACAAC AATATTACTT
3751  CTCACAAAGC AGTGAGCATC TCTGCGACAA GTGGAGAAAT TACCACTAAA
3801  ACAGGTACAA CCATTAACGC AACCACTGGT AACGTGGAGA TAACCGCTCA
3851  AACAGGTAGT ATCCTAGGTG GAATTGAGTC CAGCTCTGGC TCTGTAACAC
3901  TTACTGCAAC CGAGGGCGCT CTTGCTGTAA GCAATATTTC GGGCAACACC
3951  GTTACTGTTA CTGCAAATAG CGGTGCATTA ACCACTTTGG CAGGCTCTAC
4001  AATTAAAGGA ACCGAGAGTG TAACCACTTC AAGTCAATCA GGCGATATCG
4051  GCGGTACGAT TTCTGGTGGC ACAGTAGAGG TTAAAGCAAC CGAAAGTTTA
```

FIG. 6F.

```
4101 ACCACTCAAT CCAATTCAAA AATTAAAGCA ACAACAGGCG AGGCTAACGT
4151 AACAAGTGCA ACAGGTACAA TTGGTGGTAC GATTCCGGT  AATACGGTAA
4201 ATGTTACGGC AAACGCTGGC GATTTAACAG TTGGGAATGG CGCAGAAATT
4251 AATGCGACAG AAGGAGCTGC AACCTTAACT ACATCATCGG GCAAATTAAC
4301 TACCGAAGCT AGTTCACACA TTACTTCAGC CAAGGGTCAG GTAAATCTTT
4351 CAGCTCAGGA TGGTAGCGTT GCAGGAAGTA TTAATGCCGC CAATGTGACA
4401 CTAAATACTA CAGGCACTTT AACTACCGTG AAGGGTTCAA ACATTAATGC
4451 AACCAGCGGT ACCTTGGTTA TTAACGCAAA AGACGCTGAG CTAAATGGCG
4501 CAGCATTGGG TAACCACACA GTGGTAAATG CAACCAACGC AAATGGCTCC
4551 GGCAGCGTAA TCGCGACAAC CTCAAGCAGA GTGAACATCA CTGGGGATTT
4601 AATCACAATA AATGGATTAA ATATCATTTC AAAAAAACGG ATAAACACCG
4651 TACTGTTAAA AGGCGTTAAA ATTGATGTGA AATACATTCA ACCGGGTATA
4701 GCAAGCGTAG ATGAAGTAAT TGAAGCGAAA CGCATCCTTG AGAAGGTAAA
4751 AGATTTATCT GATGAAGAAA GAGAAGCGTT AGCTAAACTT GGCGTAAGTG
4801 CTGTACGTTT TATTGAGCCA AATAATACAA TTACAGTCGA TACACAAAAT
4851 GAATTTGCAA CCAGACCATT AAGTCGAATA AGTGATTCTG AAGGCAGGGC
4901 GTGTTTCTCA AACAGTGATG GCGCGACGGT GTGCGTTAAT ATCGCTGATA
```

FIG. 6G.

```
4951  ACGGGCGGTA GCGGTCAGTA ATTGACAAGG TAGATTTCAT CCTGCAATGA
5001  AGTCATTTTA TTTTCGTATT ATTTACTGTG TGGGTTAAAG TTCAGTACGG
5051  GCTTTACCCA TCTTGTAAAA AATTACGGAG AATACAATAA AGTATTTTTA
5101  ACAGGTTATT ATTATGAAAA ATATAAAAAG CAGATTAAAA CTCAGTGCAA
5151  TATCAGTATT GCTTGGCCTG GCTTCTTCAT CATTGTATGC AGAAGAAGCG
5201  TTTTTAGTAA AAGGCTTTCA GTTATCTGGT GCACTTGAAA CTTTAAGTGA
5251  AGACGCCCAA CTGTCTGTAG CAAAATCTTT ATCTAAATAC CAAGGCTCGC
5301  AAACTTTAAC AAACCTAAAA ACAGCACAGC TTGAATTACA GGCTGTGCTA
5351  GATAAGATTG AGCCAAATAA GTTTGATGTG ATATTGCCAC AACAAACCAT
5401  TACGGATGGC AATATTATGT TTGAGCTAGT CTCGAAATCA GCCGCAGAAA
5451  GCCAAGTTTT TTATAAGGCG AGCCAGGGTT ATAGTGAAGA AAATATCGCT
5501  CGTAGCCTGC CATCTTTGAA ACAAGGAAAA GTGTATGAAG ATGGTCGTCA
5551  GTGGTTCGAT TGCCTGAAT TCAATATGGC AAAAGAAAAT CCACTTAAAG
5601  TCACTCGCGT GCATTACGAG TTAAACCCTA AAAACAAAAC CTCTGATTTG
5651  GTAGTTGCAG GTTTTCGCC TTTTGGCAAA ACGCGTAGCT TTGTTTCCTA
5701  TGATAATTTC GGCGCAAGGG AGTTTAACTA TCAACGTGTA AGTCTAGGTT
```

FIG. 6H.

```
5751  TTGTAAATGC  CAATTTGACC  GGACATGATG  ATGTATTAAA  TCTAAACGCA
5801  TTGACCAATG  TAAAAGCACC  ATCAAAATCT  TATGCGGTAG  GCATAGGATA
5851  TACTTATCCG  TTTTATGATA  AACACCAATC  CTTAAGTCTT  TATACCAGCA
5901  TGAGTTATGC  TGATTCTAAT  GATATCGACG  GCTTACCAAG  TGCGATTAAT
5951  CGTAAATTAT  CAAAAGGTCA  ATCTATCTCT  GCGAATCTGA  AATGGAGTTA
6001  TTATCTCCCG  ACATTTAACC  TTGGAATGGA  AGACCAGTTT  AAAATTAATT
6051  TAGGCTACAA  CTACCGCCAT  ATTAATCAAA  CATCCGAGTT  AAACACCCTG
6101  GGTGCAACGA  AGAAAAAATT  TGCAGTATCA  GGCGTAAGTG  CAGGCATTGA
6151  TGGACATATC  CAATTTACCC  CTAAAACAAT  CTTTAATATT  GATTTAACTC
6201  ATCATTATTA  CGCGAGTAAA  TTACCAGGCT  CTTTTGGAAT  GGAGCGCATT
6251  GGCGAAACAT  TTAATCGCAG  CTATCACATT  AGCACAGCCA  GTTTAGGGTT
6301  GAGTCAAGAG  TTTGCTCAAG  GTTGGCATTT  TAGCAGTCAA  TTATCGGGTC
6351  AGTTTACTCT  ACAAGATATA  AGTAGCATAG  ATTTATTCTC  TGTAACAGGT
6401  ACTTATGGCG  TCAGAGGCTT  TAAATACGGC  GGTGCAAGTG  GTGAGCGCGG
6451  TCTTGTATGG  CGTAATGAAT  TAAGTATGCC  AAAATACACC  CGCTTTCAAA
6501  TCAGCCCTTA  TGCGTTTTAT  GATGCAGGTC  AGTTCCGTTA  TAATAGCGAA
6551  AATGCTAAAA  CTTACGGCGA  AGATATGCAC  ACGGTATCCT  CTGCGGGTTT
```

FIG. 6I.

```
6601 AGGCATTAAA ACCTCTCCTA CACAAAACTT AAGCTTAGAT GCTTTTGTTG
6651 CTCGTCGCTT TGCAAATGCC AATAGTGACA ATTTGAATGG CAACAAAAAA
6701 CGCACAAGCT CACCTACAAC CTTCTGGGGT AGATTAACAT TCAGTTTCTA
6751 ACCCTGAAAT TTAATCAACT GGTAAGCGTT CCGCCTACCA GTTTATAACT
6801 ATATGCTTTA CCCGCCAATT TACAGTCTAT ACGCAACCCT GTTTTCATCC
6851 TTATATATCA AACAAACTAA GCAAACCAAG CAAACCAAGC AAACCAAGCA
6901 AACCAAGCAA ACCAAGCAAA CCAAGCAAAC CAAGCAAAAC AAGCAAACCA
6951 AGCAAACCAA GCAAACCAAG CAAACCAAGC AAACCAAGCA ATGCTAAAAA
7001 ACAATTTATA TGATAAACTA AAACATACTC AAAGTGTTCC CAATACAAGG
7051 GATTTAATAA TATGACAAAA GAAAATTTAC CAAACTTCCC ACAAAATACG
7101 ACCGCTTCAC TTGTAGAATC AAACAACGAC CCTGGAACAA TGCAAATACT
7151 TAAACAACCA CCCAAACCCA ACCTATTACG TAATGGCGAT CATGTCGCCA
7201 AAAAAGATTA TGAGCTTGCT TGCCGCGAAT ATTGAATTTG TTTGGAAAAA
7251 ATGGACGCTA ATTTTGGAGG CGTTCACGAT AATTCATTTT ACGCACCTGC
7301 TCAGCTGGCA TATCTACCCG AAAAACTACT AATTCATTTT GCCACTCGTC
7351 TCGCTAATGC AATTACAACA CTCTTTTCCG ACCCCGAATT GGCAATTTCC
```

FIG. 6J.

```
7401  GAAGAAGGGG  CATTAAAGAT  GATTAGCCCTG  CAACGCTGGT  TGACGCTGAT
7451  TTTGCCTCT   TCCCCCTACG  TTAACGCAGA  CCATATTCTC  AATAAATATA
7501  ATATCAACCC  AGATTCCGAA  GGTGGCTTTC  ATTTAGCAAC  AGACAACTCT
7551  TCTATTGCTA  AATTCTGTAT  TTTTTACTTA  CCCGAATCCA  ATGTCAATAT
7601  GAGTTTAGAT  GCGTTATGGG  CAGGGAATCA  ACAACTTTGT  GCTTCATTGT
7651  GTTTGCGTT   GCAGTCTTCA  CGTTTTATTG  GTACTGCATC  TGCGTTTCAT
7701  AAAAGAGCGG  TGGTTTTACA  GTGGTTTCCT  AAAAAACTCG  CCGAAATTGC
7751  TAATTTAGAT  GAATTGCCTG  CAAATATCCT  TCATGATGTA  TATATGCACT
7801  GCAGTTATGA  TTTAGCAAAA  AACAAGCACG  ATGTTAAGCG  TCCATTAAAC
7851  GAACTTGTCC  GCAAGCATAT  CCTCACGCAA  GGATGGCAAG  ACCGCTACCT
7901  TTACACCTTA  GGTAAAAAGG  ACGGCAAACC  TGTGATGATG  GTACTGCTTG
7951  AACATTTTAA  TTCGGGACAT  TCGATTTATC  GCACGCATTC  AACTTCAATG
8001  ATTGCTGCTC  GAGAAAAATT  CTATTTAGTC  GGCTTAGGCC  ATGAGGGCGT
8051  TGATAACATA  GGTCGAGAAG  TGTTTGACGA  GTTCTTTGAA  ATCAGTAGCA
8101  ATAATATAAT  GGAGAGACTG  TTTTTTATCC  GTAAACAGTG  CGAAACTTTC
8151  CAACCCCGCAG TGTTCTATAT  GCCAAGCATT  GGCATGGATA  TTACCACGAT
```

FIG. 6K.

```
8201 TTTGTGAGC AACACTCGGC TTGCCCCTAT TCAAGCTGTA GCCTTGGGTC
8251 ATCCTGCCAC TACGCATTCT GAATTTATTG ATTATGTCAT CGTAGAAGAT
8301 GATTATGTGG GCAGTGAAGA TTGTTTAGC  GAAACCCTTT TACGCTTACC
8351 CAAAGATGCC CTACCTTATG TACCATCTGC ACTCGCCCCA CAAAAAGTGG
8401 ATTATGTACT CAGGGAAAAC CCTGAAGTAG TCAATATCGG TATTGCCGCT
8451 ACCACAATGA AATTAAACCC TGAATTTTTG CTAACATTGC AAGAAATCAG
8501 AGATAAAGCT AAAGTCAAAA TACATTTTCA TTTCGCACTT GGACAATCAA
8551 CAGGCTTGAC ACACCCTTAT GTCAAATGGT TTATCGAAAG CTATTAGGT
8601 GACGATGCCA CTGCACATCC CCACGCACCT TATCACGATT ATCTGGCAAT
8651 ATTGCGTGAT TGCGATATGC TACTAAATCC GTTTCCTTTC GGTAATACTA
8701 ACGGCATAAT TGATATGGTT ACATTAGGTT TAGTTGGTGT ATGCAAACG
8751 GGGGATGAAG TACATGAACA TATTGATGAA GGTCTGTTTA AACGCTTAGG
8801 ACTACCAGAA TGGCTGATAG CCGACACACG AGAAACATAT ATTGAATGTG
8851 CTTTGCGTCT AGCAGAAAAC CATCAAGAAC GCCTTGAACT CCGTCGTTAC
8901 ATCATAGAAA ACAAACGCTT ACAAAAGCTT TTTACAGGCG ACCCTCGTCC
8951 ATTGGGCAAA ATACTGCTTA AGAAAACAAA TGAATGGAAG CGGAAGCACT
9001 TGAGTAAAAA ATAACGGTTT TTTAAAGTAA AAGTGCGGTT AATTTCAAA
```

FIG. 6L.

```
9051 GCGTTTAAAA AACCTCTCAA AAATCAACCG CACTTTTATC TTTATAACGC
9101 TCCCGGCCGC TGACAGTTTA TCTCTTTCTT AAAATACCCA TAAAATTGTG
9151 GCAATAGTTG GGTAATCAAA TTCAATTGTT GATACGGCAA ACTAAAGACG
9201 GCGCGTTCTT CGGCAGTCAT C
```

FIG. 7A.

```
  1  CGCCACTTCA ATTTTGGATT GTTGAAATTC AACTAACCAA AAAGTGCGGT
 51  TAAATCTGT  GGAGAAAATA GGTTGTAGTG AAGAACGAGG TAATTGTTCA
101  AAAGGATAAA GCTCTCTTAA TTGGGCATTG GTTGGCGTTT CTTTTCGGT
151  TAATAGTAAA TTATATTCTG GACGACTATG CAATCCACCA ACAACTTTAC
201  CGTTGGTTTT AAGCGTTAAT GTAAGTTCTT GCTCTTCTTG GCGAATACGT
251  AATCCCATTT TTTGTTTAGC AAGAAAAATGA TCGGGATAAT CATAATAGGT
301  GTTGCCCAAA AATAAATTTT GATGTTCTAA AATCATAAAT TTTGCAAGAT
351  ATTGTGGCAA TTCAATACCT ATTTGTGGCG AAATCGCCAA TTTTAATTCA
401  ATTTCTTGTA GCATAATATT TCCCACTCAA ATCAACTGGT TAAATATACA
451  AGATAATAAA AATAAATCAA GATTTTTGTG ATGACAAACA ACAATTACAA
501  CACCTTTTTT GCAGTCTATA TGCAAATATT TTAAAAAAT AGTATAAATC
551  CGCCATATAA AATGGTATAA TCTTTCATCT TTCATCTTTC ATCTTTCATC
601  TTTCATCTTT CATCTTTCAT CTTTCATCTT TCATCTTTCA TCTTTCATCT
651  TTCATCTTTC ATCTTTCATC TTTCATCTTT CACATGAAAT GATGAACCGA
701  GGGAAGGGAG GGAGGGGCAA GAATGAAGAG GGAGCTGAAC GAACGCAAAT
751  GATAAAGTAA TTTAATTGTT CAACTAACCT TAGGAGAAAA TATGAACAAG
```

FIG. 7B.

```
 801  ATATATCGTC TCAAATTCAG CAAACGCCTG AATGCTTTGG TTGCTGTGTC
 851  TGAATTGGCA CGGGGTTGTG ACCATTCCAC AGAAAAAGGC AGCGAAAAAC
 901  CTGCTCGCAT GAAAGTGCGT CACTTAGCGT TAAAGCCACT TTCCGCTATG
 951  TTACTATCTT TAGGTGTAAC ATCTATTCCA CAATCTGTTT TAGCAAGCGG
1001  CAATTTAACA TCGACCAAAA TGAAATGGTG CAGTTTTTAC AAGAAAACAA
1051  GTAATAAAAC CATTATCCGC AACAGTGTTG ACGCTATCAT TAATTGGAAA
1101  CAATTTAACA TCGACCAAAA TGAAATGGTG CAGTTTTTAC AAGAAAACAA
1151  CAACTCCGCC GTATTCAACC GTGTTACATC TAACCAAATC TCCCAATTAA
1201  AAGGGATTTT AGATTCTAAC GGACAAGTCT TTTTAATCAA CCCAAATGGT
1251  ATCACAATAG GTAAAGACGC AATTATTAAC ACTAATGGCT TTACGGCTTC
1301  TACGCTAGAC ATTTCTAACG AAAACATCAA GGCGCGTAAT TTCACCTTCG
1351  AGCAAACCAA AGATAAAGCG CTCGCTGAAA TTGTGAATCA CGGTTTAATT
1401  ACTGTCGGTA AAGACGGCAG TGTAAATCTT ATTGGTGGCA AAGTGAAAAA
1451  CGAGGGTGTG ATTAGCGTAA ATGGTGGCAG CATTTCTTTA CTCGCAGGGC
1501  AAAAAATCAC CATCAGCGAT ATAATAAACC CAACCATTAC TTACAGCATT
1551  GCCGCGCCTG AAAATGAAGC GGTCAATCTG GGCGATATTT TTGCCAAAGG
```

FIG. 7C.

```
1601 CGGTAACATT AATGTCCGTG CTGCCACTAT TCGAAACCAA GGTAAACTTT
1651 CTGCTGATTC TGTAAGCAAA GATAAAAGCG GCAATATTGT TCTTTCCGCC
1701 AAAGAGGGTG AAGCGGAAAT TGGCGGTGTA ATTTCCGCTC AAAATCAGCA
1751 AGCTAAAGGC GGCAAGCTGA TGATTACAGG CGATAAAGTC ACATTAAAAA
1801 CAGGTGCAGT TATCGACCTT TCAGGTAAAG AAGGGGGAGA AACTTACCTT
1851 GGCGGTGACG AGCGCGGCGA AGGTAAAAAC GGCATTCAAT TAGCAAAGAA
1901 AACCTCTTTA GAAAAAGGCT CAACCATCAA TGTATCAGGC AAAGAAAAAG
1951 GCGGACGCGC TATTGTGTGG GGCGATATTG CGTTAATTGA CGGCAATATT
2001 AACGCTCAAG GTAGTGGTGA TATCGCTAAA ACCGGTGGTT TTGTGGAGAC
2051 ATCGGGGCAT TATTTATCCA TTGACAGCAA TGCAATTGTT AAAACAAAAG
2101 AGTGGTTGCT AGACCCTGAT GATGTAAACA TTGAAGCCGA AGACCCCCTT
2151 CGCAATAATA CCGGTATAAA TGATGAATTC CCAACAGGCA CCGGTGAAGC
2201 AAGCGACCCT AAAAAAAATA GCGAACTCAA AACAACGCTA ACCAATACAA
2251 CTATTTCAAA TTATCTGAAA AACGCCTGGA CAATGAATAT AACGGCATCA
2301 AGAAAACTTA CCGTTAATAG CTCAATCAAC ATCGGAAGCA ACTCCCACTT
2351 AATTCTCCAT AGTAAAGGTC AGCGTGGCGG AGCGTTCAG ATTGATGGAG
2401 ATATTACTTC TAAAGGCGGA AATTTAACCA TTTATTCTGG CGGATGGGTT
```

FIG. 7D.

```
2451 GATGTTCATA AAAATATTAC GCTTGATCAG GGTTTTTTAA ATATTACCGC
2501 CGCTTCCGTA GCTTTTGAAG GTGGAAATAA CAAAGCACGC GACGCGGCAA
2551 ATGCTAAAAT TGTCGCCCAG GGCACTGTAA CCATTACAGG AGAGGGAAAA
2601 GATTTCAGGG CTAACAACGT ATCTTTAAAC GGAACGGGTA AAGGTCTGAA
2651 TATCATTTCA TCAGTGAATA ATTTAACCCA CAATCTTAGT GGCACAATTA
2701 ACATATCTGG GAATATAACA ATTAACCAAA CTACGAGAAA GAACACCTCG
2751 TATTGGCAAA CCAGCCATGA TTCGCACTGG AACGTCAGTG CTCTTAATCT
2801 AGAGACAGGC GCAAATTTTA CCTTTATTAA ATACATTTCA AGCAATAGCA
2851 AAGGCTTAAC AACACAGTAT AGAAGCTCTG CAGGGGTGAA TTTTAACGGC
2901 GTAAATGGCA ACATGTCATT CAATCTCAAA GAAGGAGCGA AAGTTAATTT
2951 CAAATTAAAA CCAAACGAGA ACATGAACAC AAGCAAACCT TTACCAATTC
3001 GGTTTTTAGC CAATATCACA GCCACTGGTG GGGCTCTGT TTTTTTTGAT
3051 ATATATGCCA ACCATTCTGG CAGAGGGGCT GAGTTAAAAA TGAGTGAAAT
3101 TAATATCTCT AACGGGCTA ATTTTACCTT AAATTCCCAT GTTCGCGGCG
3151 ATGACGCTTT TAAAATCAAC AAAGACTTAA CCATAAATGC AACCAATTCA
3201 AATTTCAGCC TCAGACAGAC GAAAGATGAT TTTTATGACG GGTACGCACG
```

FIG. 7E.

```
3251 CAATGCCATC AATTCAACCT ACAACATATC CATTCTGGGC GGTAATGTCA
3301 CCCTTGGTGG ACAAAACTCA AGCAGCAGCA TTACGGGAA TATTACTATC
3351 GAGAAAGCAG CAAATGTTAC GCTAGAAGCC AATAACGCCC CTAATCAGCA
3401 AAACATAAGG GATAGAGTTA TAAAACTTGG CAGCTTGCTC GTTAATGGGA
3451 GTTTAAGTTT AACTGGCGAA AATGCAGATA TTAAAGGCAA TCTCACTATT
3501 TCAGAAAGCG CCACTTTTAA AGGAAAGACT AGAGATACCC TAAATATCAC
3551 CGGCAATTTT ACCAATAAATG GCACTGCCGA AATTAATATA ACACAAGGAG
3601 TGGTAAAACT TGGCAATGTT ACCAATGATG GTGATTTAAA CATTACCACT
3651 CACGCTAAAC GCAACCAAAG AAGCATCATC GGCGGAGATA TAATCAACAA
3701 AAAAGGAAGC TTAAATATTA CAGACAGTAA TAATGATGCT GAAATCCAAA
3751 TTGGCGGCAA TATCTCGCAA AAAGAAGGCA ACCTCACGAT TTCTTCCGAT
3801 AAAATTAATA TCACCAAACA GATAACAATC AAAAAGGGTA TTGATGGAGA
3851 GGACTCTAGT TCAGATGCGA CAAGTAATGC CAACCTAACT ATTAAAACCA
3901 AAGAATTGAA ATTGACAGAA CAAGTAAGTA GACCTAAGTA TTTCAGGTTT CAATAAAGCA
3951 GAGATTACAG CCAAAGATGG TAGAGATTTA TAGAGATTA ACAGTAATGA
4001 CGGTAACAGC GGTGCCGAAG CCAAAACAGT AACTTTTAAC AATGTTAAAG
```

FIG. 7F.

```
4051  ATTCAAAAAT CTCTGCTGAC GGTCACAATG TGACACTAAA TAGCAAAGTG
4101  AAAACATCTA GCAGCAATGG CGGACGTGAA AGCAATAGCG ACAACGATAC
4151  CGGCTTAACT ATTACTGCAA AAAATGTAGA AGTAAACAAA GATATTACTT
4201  CTCTCAAAAC AGTAAATATC ACCGCGTCGG AAAAGGTTAC CACCACAGCA
4251  GGCTCGACCA TTAACGCAAC AAATGGCAAA GCAAGTATTA CAACCAAAAC
4301  AGGTGATATC AGCGGTACGA TTTCCGGTAA CACGGTAAGT GTTAGCGCGA
4351  CTGGTGATTT AACCACTAAA TCCGGCTCAA AAATTGAAGC GAAATCGGGT
4401  GAGGCTAATG TAACAAGTGC AACAGGTACA ATTGGCGGTA CAATTTCCGG
4451  TAATACGGTA AATGTTACGG CAAACGCTGG CGATTTAACA GTTGGGAATG
4501  GCGCAGAAAT TAATGCGACA GAAGGAGCTG CAACCTTAAC CGCAACAGGG
4551  AATACCTTGA CTACTGAAGC CGGTTCTAGC ATCACTTCAA CTAAGGGTCA
4601  GGTAGACCTC TTGGCTCAGA ATGGTAGCAT CGCAGGAAGC ATTAATGCTG
4651  CTAATGTGAC ATTAAATACT ACAGGCACCT TAACCACCGT GGCAGGCTCG
4701  GATATTAAAG CAACCAGCGG CACCTTGGTT ATTAACGCAA AAGATGCTAA
4751  GCTAAATGGT GATGCATCAG GTGATAGTAC AGAAGTGAAT GCAGTCAACG
4801  ACTGGGGATT TGGTAGTGTG ACTGCGGCAA CCTCAAGCAG TGTGAATATC
4851  ACTGGGGATT TAAACACAGT AAATGGGTTA AATATCATTT CGAAAGATGG
```

FIG. 7G.

```
4901 TAGAAACACT GTGCGCTTAA GAGGCAAGGA AATTGAGGTG AAATATATCC
4951 AGCCAGGTGT AGCAAGTGTA GAAGAAGTAA TTGAAGCGAA ACGGGTCCTT
5001 GAAAAAGTAA AAGATTTATC TGATGAAGAA AGAGAAACAT TAGCTAAACT
5051 TGGTGTAAGT GCTGTACGTT TTGTTGAGCC AGAGAAACAT ATTACAGTCA
5101 ATACACAAAA TGAATTTACA ACCAGACCGT AAATAATACA GATAATTTCT
5151 GAAGGTAAGG CGTGTTTCTC AAGTGGTAAT CAAGTCAAGT TATGTACCAA
5201 TGTTGCTGAC GATGGACAGC CGTAGTCAGT GGCGCACGAG GTAGATTTCA
5251 TCCTGCAATG AAGTCATTTT ATTTTCGTAT AATTGACAAG GTGGGTTAAA
5301 GTTCAGTACG GGCTTTACCC ATCTTGTAAA TATTTACTGT GAATACAATA
5351 AAGTATTTTT AACAGGTTAT TATTATGAAA AAATTACGGA GCAGATTAAA
5401 ACTCAGTGCA ATATCAGTAT TGCTTGGCCT AATATAAAAA TCATTGTATG
5451 CAGAAGAAGC GTTTTAGTA  AAAGGCTTTC GGCTTCTTCA TGCACTTGAA
5501 ACTTTAAGTG AAGACGCCCA ACTGTCTGTA AGTTATCTGG TATCTAAATA
5551 CCAAGGCTCG CAAACTTTAA CAAACCTAAA GCAAAATCTT CTTGAATTAC
5601 AGGCTGTGCT AGATAAGATT GAGCCAAATA AACAGCACAG GATATTGCCG
5651 CAACAAACCA TTACGGATGG CAATATCATG AATTTGATGT TCTCGAAATC
```

FIG. 7H.

```
5701 AGCCGCAGAA AGCCAAGTTT TTTATAAGGC GAGCCAGGGT TATAGTGAAG
5751 AAAATATCGC TCGTAGCCTG CCATCTTTGA AACAAGGAAA AGTGTATGAA
5801 GATGGTCGTC AGTGGTTCGA TTTGCGTGAA TTTAATATGG CAAAAGAAAA
5851 CCCGCTTAAG GTTACCCGTG TACATTACGA ACTAAACCCT AAAAACAAAA
5901 CCTCTAATTT GATAATTGCG GGCTTCTCGC CTTTTGGTAA AACGCGTAGC
5951 TTTATTTCTT ATGATAATTT CGGCGCGAGA GAGTTTAACT ACCAACGTGT
6001 AAGCTTGGGT TTTGTTAATG CCAATTTAAC TGGTCATGAT GATGTGTTAA
6151 TTATACCAGT ATGAGTTATG CTGATTCTAA TGATATCGAC GGCTTACCAA
6201 GTGCGATTAA TCGTAAATTA TCAAAAGGTC AATCTATCTC TGCGAATCTG
6251 AAATGGAGTT ATTATCTCCC AACATTTAAC CTTGGCATGG AAGACCAATT
6301 TAAAATTAAT TTAGGCTACA ACTACCGCCA TATTAATCAA ACCTCCCGT
6351 TAAATCGCTT GGGTGAAACG AAGAAAAAAT TTGCAGTATC AGGCGTAAGT
6401 GCAGGCATTG ATGGACATAT CCAAAAACAA TCTTTAATAT
6451 TGATTTAACT CATCATTATT ACGCGAGTAA ATTACCAGGC TCTTTTGGAA
6501 TGGAGCGCAT TGGCGAAACA TTTAATCGCA GCTATCACAT TAGCACAGCC
6551 AGTTTAGGGT TGAGTCAAGA GTTGCTCAA GGTTGGCATT TTAGCAGTCA
6601 ATTATCAGGT CAATTTACTC TACAAGATAT TAGCAGTATA GATTTATTCT
```

FIG. 7I.

```
6651  CTGTAACAGG  TACTTATGGC  GTCAGAGGCT  TTAAATACGG  CGGTGCAAGT
6701  GGTGAGCGCG  GTCTTGTATG  GCGTAATGAA  TTAAGTATGC  CAAAATACAC
6751  CCGCTTCCAA  ATCAGCCCTT  ATGCGTTTTA  TGATGCAGGT  CAGTTCCGTT
6801  ATAATAGCGA  AAATGCTAAA  ACTTACGGCG  AAGATATGCA  CACGGTATCC
6851  TCTGCGGGTT  TAGGCATTAA  AACCTCTCCT  ACACAAAACT  TAAGCCTAGA
6901  TGCTTTTGTT  GCTCGTCGCT  TTGCAAATGC  CAATAGTGAC  AATTTGAATG
6951  GCAACAAAAA  ACGCACAAGC  TCACCTACAA  CCTTCTGGGG  GAGATTAACA
7001  TTCAGTTTCT  AACCCTGAAA  TTTAATCAAC  TGGTAAGCGT  TCCGCCTACC
7051  AGTTTATAAC  TATATGCTTT  ACCCGCCAAT  TTACAGTCTA  TAGGCAACCC
7101  TGTTTTTACC  CTTATATATC  AAATAAACAA  GCTAAGCTGA  GCTAAGCAAA
7151  CCAAGCAAAC  TCAAGCAAGC  CAAGTAAATAC  TAAAAAAACA  ATTTATATGA
7201  TAAACTAAAG  TATACTCCAT  GCCATGGCGA  TACAAGGGAT  TTAATAATAT
7251  GACAAAAGAA  AATTTGCAAA  ACGCTCCTCA  AGATGCGACC  GCTTTACTTG
7301  CGGAATTAAG  CAACAATCAA  ACTCCCCTGC  GAATATTTAA  ACAACCACGC
7351  AAGCCCAGCC  TATTACGCTT  GGAACAACAT  ATCGCAAAAA  AAGATTATGA
7401  GTTTGCTTGT  CGTGAATTAA  TGGTGATTCT  GGAAAAAATG  GACGCTAATT
```

FIG. 7J.

```
7451  TTGGAGGCGT TCACGATATT GAATTTGACG CACCCGCTCA GCTGGCATAT
7501  CTACCCGAAA AATTACTAAT TTATTTTGCC ACTCGTCTCG CTAATGCAAT
7551  TACAACACTC TTTTCCGACC CCGAATTGGC AATTTCTGAA GAAGGGGCGT
7601  TAAAGATGAT TAGCCTGCAA CGCTGGTTGA CGCTGATTTT TGCCTCTTCC
7651  CCCTACGTTA ACGCAGACCA TATTCTCAAT AAATATAATA TCAACCCAGA
7701  TTCCGAAGGT GGCTTTCATT TAGCAACAGA CAACTCTTCT ATTGCTAAAT
7751  TCTGTATTTT TTACTTACCC GAATCCAATG TCAATATGAG TTTAGATGCG
7801  TTATGGGCAG GGAATCAACA ACTTTGTGCT TCATTGTGTT TTGCGTTGCA
7851  GTCTTCACGT TTTATTGGTA CCGCATCTGC GTTTCATAAA AGAGCGGTGG
7901  TTTTACAGTG GTTTCCTAAA AAACTCGCCG AAATTGCTAA TTTAGATGAA
7951  TTGCCTGCAA ATATCCTTCA TGATGTATAT ATGCACTGCA GTTATGATTT
8001  AGCAAAAAAC AAGCACGATG TTAAGCGTCC ATTAAACGAA CTTGTCCGCA
8051  AGCATATCCT CACGCAAGGA TGGCAAGACC GCTACCTTTA CACCTTAGGT
8101  AAAAGGACG GCAAACCTGT GATGATGGTA CTGCTTGAAC ATTTTAATTC
8151  GGGACATTCG ATTTATCGTA CACATTCAAC TTCAATGATT GCTGCTCGAG
8201  AAAAATTCTA TTTAGTCGGC TTAGGCCATG AGGGCGTTGA TAAAATAGGT
```

FIG. 7K.

| | | | | |
|---|---|---|---|---|
| 8251 | CGAGAAGTGT | TTGACGAGTT | CTTTGAAATC | AGTAGCAATA | ATATAATGGA |
| 8301 | GAGACTGTTT | TTTATCCGTA | AACAGTGCGA | AACTTTCCAA | CCCGCAGTGT |
| 8351 | TCTATATGCC | AAGCATTGGC | ATGGATATTA | CCACGATTTT | TGTGAGCAAC |
| 8401 | ACTCGGCTTG | CCCCTATTCA | AGCTGTAGCC | CTGGGTCATC | CTGCCACTAC |
| 8451 | GCATTCTGAA | TTTATTGATT | ATGTCATCGT | AGAAGATGAT | TATGTGGGCA |
| 8501 | GTGAAGATTG | TTTCAGCGAA | ACCCTTTTAC | GCTTACCCAA | AGATGCCCTA |
| 8551 | CCTTATGTAC | CTTCTGCACT | CGCCCCACAA | AAAGTGGATT | ATGTACTCAG |
| 8601 | GGAAAACCCT | GAAGTAGTCA | ATATCGGTAT | TGCCGCTACC | ACAATGAAAT |
| 8651 | TAAACCCTGA | ATTTTGCTA | ACATTGCAAG | AAATCAGAGA | TAAAGCTAAA |
| 8701 | GTCAAAATAC | ATTTTCATTT | CGCACTTGGA | CAATCAACAG | GCTTGACACA |
| 8751 | CCCTTATGTC | AAATGGTTTA | TCGAAAGCTA | TTTAGGTGAC | GATGCCACTG |
| 8801 | CACATCCCCA | CGCACCTTAT | CACGATTATC | TGGCAATATT | GCGTGATTGC |
| 8851 | GATATGCTAC | TAAATCCGTT | TCCTTTCGGT | AATACTAACG | GCATAATTGA |
| 8901 | TATGGTTACA | TTAGGTTTAG | TTGGTGTATG | CAAAACGGGG | GATGAAGTAC |
| 8951 | ATGAACATAT | TGATGAAGGT | CTGTTTAAAC | GCTTAGGACT | ACCAGAATGG |
| 9001 | CTGATAGCCG | ACACACGAGA | AACATATATT | GAATGTGCTT | TGCCGTCTAGC |
| 9051 | AGAAAACCAT | CAAGAACGCC | TTGAACTCCG | TCGTTACATC | ATAGAAAACA |

FIG. 7L.

```
9101 ACGGCTTACA AAAGCTTTTT ACAGGGCGACC CTCGTCCATT GGGCAAAATA
9151 CTGCTTAAGA AACAAATGA ATGGAAGCGG AAGCACTTGA GTAAAAAATA
9201 ACGGTTTTTT AAAGTAAAAG TGCGGTTAAT TTTCAAAGCG TTTTAAAAAC
9251 CTCTCAAAAA TCAACCGCAC TTTTATCTTT ATAACGATCC CGCACGCTGA
9301 CAGTTTATCA GCCTCCCGCC ATAAAACTCC GCCTTTCATG GCGGAGATTT
9351 TAGCCAAAAC TGGCAGAAAT TAAAGGCTAA AATCACCAAA TTGCACCACA
9401 AAATCACCAA TACCCACAAA AAA
```

FIG. 8A.

```
  1  GATCAATCTG GGCGATATTT TTGCCAAAGG TGGTAACATT AATGTCCGCG
 51  CTGCCACTAT TCGCAATAAA GGTAAACTTT CTGCCGACTC TGTAAGCAAA
101  GATAAAAGTG GTAACATTGT TCTCTCTGCC AAAGAAGGTG AAGCGGAAAT
151  TGGCGGTGTA ATTTCCGCTC AAAATCAGCA AGCCAAAGGT GGTAAGTTGA
201  TGATTACAGG CGATAAAGTT ACATTGAAAA CGGGTGCAGT TATCGACCTT
251  TCGGGTAAAG AAGGGGGAGA AACTTATCTT GGCGGTGACG AGCGTGGCGA
301  AGGTAAAAAC GGCATTCAAT TAGCAAAGAA AACCACTTTA GAAAAAGGCT
351  CAACAATTAA TGTGTCAGGT AAAGAAAAAG GTGGGCGCGC TATTGTATGG
401  GGCGATATTG CGTTAATTGA CGGCAATATT AATGCCCAAG GTAAAGATAT
451  CGCTAAAACT GGTGGTTTTG TGGAGACGTC GGGGCATTAC TTATCCATTG
501  ATGATAACGC AATTGTTAAA ACAAAAGAAT GGCTACTAGA CCCAGAGAAT
551  GTGACTATTG AAGCTCCTTC CGCTTCTCGC GTCGAGCTGG GTGCCGATAG
601  GAATTCCCAC TCGGCAGAGG TGATAAAAGT GACCCTAAAA AAAAATAACA
651  CCTCCCTTGA C AACACTAACC AATACAACCA TTTCAAATCT TCTGAAAAGT
701  GCCCACGTGG TGAACATAAC GGCAAGGAGA AAACTTACCG TTAATAGCTC
751  TATCAGTATA GAAAGAGGCT CCCACTTAAT TCTCCACAGT GAAGGTCAGG
```

FIG. 8B.

```
 801  GCGGTCAAGG TGTTCAGATT GATAAAGATA TTACTTCTGA AGGCGGAAAT
 851  TTAACCATTT ATTCTGGCGG ATGGGTTGAT GTTCATAAAA ATATTACGCT
 901  TGGTAGCGGC TTTTTAAACA TCACAACTAA AGAAGGAGAT ATCGCCTTCG
 951  AAGACAAGTC TGGACGGAAC AACCTAACCA TTACAGCCCA AGGGACCATC
1001  ACCTCAGGTA ATAGTAACGG CTTTAGATTT AACAACGTCT CTCTAAACAG
1051  CCTTGGCGGA AAGCTGAGCT TTACTGACAG CAGAGAGGAC AGAGGTAGAA
1101  GAACTAAGGG TAATATCTCA AACAAATTTG ACGGAACGTT AAACATTTCC
1151  GGAACTGTAG ATATCTCAAT GAAAGCACCC AAAGTCAGCT GGTTTTACAG
1201  AGACAAAGGA CGCACCTACT GGAACGTAAC CACTTTAAAT GTTACCTCGG
1251  GTAGTAAATT TAACCTCTCC ATTGACAGCA CAGGAAGTGG CTCAACAGGT
1301  CCAAGCATAC GCAATGCAGA ATTAAATGGC ATAACATTTA ATAAAGCCAC
1351  TTTTAATATC GCACAAGGCT CAACAGCTAA CTTTAGCATC AAGGCATCAA
1401  TAATGCCCTT TAAGAGTAAC GCTAACTACG CATTATTTAA TGAAGATATT
1451  TCAGTCTCAG GGGGGGGTAG CGTTAATTTC AAACTTAACG CCTCATCTAG
1501  CAACATACAA ACCCCTGGCG TAATTATAAA ATCTCAAAAC TTTAATGTCT
1551  CAGGAGGGTC AACTTTAAAT CTCAAGGCTG AAGGTTCAAC AGAAACCGCT
1601  TTTTCAATAG AAAATGATTT AAACTTAAAC GCCACCGGTG GCAATATAAC
```

FIG. 8C.

```
1651  AATCAGACAA GTCGAGGGTA CCGATTCACG CGTCAACAAA GGTGTCGCAG
1701  CCAAAAAAAA CATAACTTTT AAAGGGGGTA ATATCACCTT CGGCTCTCAA
1751  AAAGCCACAA CAGAAATCAA AGGCAATGTT ACCATCAATA AAAACACTAA
1801  CGCTACTCTT CGTGGTGCGA ATTTTGCCGA AAACAAATCG CCTTTAAATA
1851  TAGCAGGAAA TGTTATTAAT AATGGCAACC TTACCACTGC CGGCTCCATT
1901  ATCAATATAG CCGGAAATCT TACTGTTTCA AAAGGCGCTA ACCTTCAAGC
1951  TATAACAAAT TACACTTTTA ATGTAGCCGG AGAGGAGGGG CTCATTTGAC AACAATGGCG
2001  CTTCAAACAT TTCCATTGCC AGAGGAGGGG CTAAATTTAA AGATATCAAT
2051  AACACCAGTA GCTTAAATAT TACCACCAAC TCTGATACCA CTTACCGCAC
2101  CATTATAAAA GGCAATATAT CCAACAAATC AGGTGATTTG AATATTATTG
2151  ATAAAAAAAG CGACGCTGAA ATCCAAATTG GCGGCAATAT CTCACAAAAA
2201  GAAGGCAATC TCACAATTTC TTCTGATAAA GTAAATATTA CCAATCAGAT
2251  AACAATCAAA GCAGGCGTTG AAGGGGGGCG TTCTGATTCA AGTGAGGCAG
2301  AAAATGCTAA CCTAACTATT CAAACCAAAG AGTTAAAATT GGCAGGAGAC
2351  CTAAATATTT CAGGCTTTAA TAAAGCAGAA ATTACAGCTA AAATGGCAG
2401  TGATTTAACT ATTGGCAATG CTAGCGGTGG TAATGCTGAT GCTAAAAAAG
```

FIG. 8D.

```
2451  TGACTTTTGA  CAAGGTTAAA  GATTCAAAAA  TCTCGACTGA  CGGTCACAAT
2501  GTAACACTAA  ATAGCGAAGT  GAAAACGTCT  AATGGTAGTA  GCAATGCTGG
2551  TAATGATAAC  AGCACCGGTT  TAACCATTTC  CGCAAAAGAT  GTAACGGTAA
2601  ACAATAACGT  TACCTCCCAC  AAGACAATAA  ATATCTCTGC  CGCAGCAGGA
2651  AATGTAACAA  CCAAAGAAGG  CACAACTATC  AATGCAACCA  CAGGCAGCGT
2701  GGAAGTAACT  GCTCAAAATG  GTACAATTAA  AGGCAACATT  ACCTCGCAAA
2751  ATGTAACAGT  GACAGCAACA  GAAAATCTTG  TTACCACAGA  GAATGCTGTC
2801  ATTAATGCAA  CCAGCGGCAC  AGTAAACATT  AGTACAAAAA  CAGGGATAT
2851  TAAAGGTGGA  ATTGAATCAA  CTTCCGGTAA  TGTAAATATT  ACAGCGAGCG
2901  GCAATACACT  TAAGGTAAGT  AATATCACTG  GTCAAGATGT  AACAGTAACA
2951  GCGGATGCAG  GAGCCTTGAC  AACTACAGCA  GGCTCAACCA  TTAGTGCGAC
3001  AACAGGCAAT  GCAAATATTA  CAACCAAAAC  AGGTGATATC  AACGGTAAAG
3051  TTGAATCCAG  CTCCGGCTCT  GTAACACTTG  TTGCAACTGG  AGCAACTCTT
3101  GCTGTAGGTA  ATATTTCAGG  TAACACTGTT  ACTATTACTG  CGGATAGCGG
3151  TAAATTAACC  TCCACAGTAG  GTTCTACAAT  TAATGGGACT  AATAGTGTAA
3201  CCACCTCAAG  CCAATCAGGC  GATATTGAAG  GTACAATTTC  TGGTAATACA
3251  GTAAATGTTA  CAGCAAGCAC  TGGTGATTTA  ACTATTGGAA  ATAGTGCAAA
```

FIG. 8E.

```
3301  AGTTGAAGCG  AAAAATGGAG  CTGCAACCTT  AACTGCTGAA  TCAGGCAAAT
3351  TAACCACCCA  AACAGGCTCT  AGCATTACCT  CAAGCAATGG  TCAGACAACT
3401  CTTACAGCCA  AGGATAGCAG  TATCGCAGGA  AACATTAATG  CTGCTAATGT
3451  GACGTTAAAT  ACCACAGGCA  CTTTAACTAC  TACAGGGGAT  TCAAAGATTA
3501  ACGCAACCAG  TGGTACCTTA  ACAATCAATG  CAAAAGATGC  CAAATTAGAT
3551  GGTGCTGCAT  CAGGTGACCG  CACAGTAGTA  AATGCAACTA  ACGCAAGTGG
3601  CTCTGGTAAC  GTGACTGCCA  AAACCTCAAG  CAGCGTGAAT  ATCACCGGGG
3651  ATTTAAACAC  AATAAAATGGG  TTAAATATCA  TTTCGGAAAA  TGGTAGAAAC
3701  ACTGTGCGCT  TAAGAGGCAA  GGAAATTGAT  GTGAAATATA  TCCAACCAGG
3751  TGTAGCAAGC  GTAGAAGAGG  TAATTGAAGC  GAAACGCGTC  CTTGAGAAGG
3801  TAAAAGATTT  ATCTGATGAA  GAAAGAGAAA  CACTAGCCAA  ACTTGGTGTA
3851  AGTGCTGTAC  GTTTCGTTGA  GCCAAATAAT  GCCATTACGG  TTAATACACA
3901  AAACGAGTTT  ACAACCAAAC  CATCAAGTCA  AGTGACAATT  TCTGAAGGTA
3951  AGGCGTGTTT  CTCAAGTGGT  AATGGCGCAC  GAGTATGTAC  CAATGTTGCT
4001  GACGATGGAC  AGCAGTAGTC  AGTAATTGAC  AAGGTAGATT  TCATCCTGCA
4051  ATGAAGTCAT  TTTATTTTCG  TATTATTTAC  TGTGTGGGTT  AAAGTTCAGT
```

FIG. 8F.

```
4101 ACGGGCTTTA CCCACCTTGT AAAAAATTAC GAAAAATACA ATAAAGTATT
4151 TTTAACAGGT TATTATTATG AAAAACATAA AAAGCAGATT AAAACTCAGT
4201 GCAATATCAA TATTGCTTGG CTTGGCTTCT TCATCGACGT ATGCAGAAGA
4251 AGCGTTTTTA GTAAAAGGCT TTCAGTTATC TGGCGCG
```

FIG. 9A.

```
  1 GGGAATGAGC GTCGTACACG GTACAGCAAC CATGCAAGTA GACGGCAATA
 51 AAACCACTAT CCGTAATAGC GTCAATGCTA TCATCAATTG GAAACAATTT
101 AACATTGACC AAAATGAAAT GGAGCAGTTT TTACAAGAAA GCAGCAACTC
151 TGCCGTTTTC AACCGTGTTA CATCTGACCA AATCTCCCAA TTAAAGGGA
201 TTTTAGATTC TAACGGACAA GTCTTTTTAA TCAACCCAAA TGGTATCACA
251 ATAGGTAAAG ACGCAATTAT TAACACTAAT GGCTTTACTG CTTCTACGCT
301 AGACATTTCT AACGAAAACA TCAAGGCGCG TAATTTCACC CTTGAGCAAA
351 CCAAGGATAA AGCACTCGCT GAAATCGTGA ATCACGGTTT AATTACCGTT
401 GGTAAAGACG GTAGCCGTAA CCTTATTGGT GGCAAAGTGA AAAACGAGGG
451 CGTGATTAGC GTAAATGGCG GTAGTATTTC TTTACTTGCA GGGCAAAAAA
501 TCACCATCAG CGATATAATA AATCCAACCA TCACTTACAG CATTGCTGCA
551 CCTGAAAACG AAGCGATCAA TCTGGGCGAT ATTTTTGCCA AAGGTGGTAA
601 CATTAATGTC CGCGCTGCCA CTATTCGCAA TAAAGGTAAA CTTTCTGCCG
651 ACTCTGTAAG CAAAGATAAA AGTGGTAACA TTGTTCTCTC TGCCAAAGAA
701 GGTGAAGCGG AAATTGGCGG TGTAATTTCC GCTCAAAATC AGCAAGCCAA
751 AGGTGGTAAG TTGATGATTA CAGGTGATAA AGTCACATTA AAAACAGGTG
```

FIG. 9B.

```
 801  CAGTTATCGA CCTTTCAGGT AAAGAAGGGG GAGAGACTTA TCTTGGCGGT
 851  GATGAGCGTG GCGAAGGTAA AAATGGTATT CAATTAGCGA AGAAACCTC
 901  TTTAGAAAAA GGCTCGACAA TTAATGTATC AGGCAAAGAA AAAGGCGGGC
 951  GCGCTATTGT ATGGGGCGAT ATTGCATTAA TTAATGGTAA CATTAATGCT
1001  CAAGGTAGCG ATATTGCTAA AACTGGCGGC TTTGTGGAAA CATCAGGACA
1051  TGACTTATCC ATTGGTGATG ATGTGATTGT TGACGCTAAA GAGTGGTTAT
1101  TAGACCCAGA TGATGTGTCC ATTGAAACTC TTACATCTGG ACGCAATAAT
1151  ACCGGCGAAA ACCAAGGATA TACAACAGGA GATGGGACTA AAGAGTCACC
1201  TAAAGGTAAT AGTATTTCTA AACCTACATT AACAAACTCA ACTCTTGAGC
1251  AAATCCTAAG AAGAGGTTCT TATGTTAATA TCACTGCTAA TAATAGAATT
1301  TATGTTAATA GCTCCATCAA CTTATCTAAT GGCAGTTTAA CACTTCACAC
1351  TAAACGAGAT GGAGTTAAAA TTAACGGTGA TATTACCTCA AACGAAAATG
1401  GTAATTTAAC CATTAAAGCA GGCTCTTGGG TTGATGTTCA TAAAAACATC
1451  ACGCTTGGTA CGGGTTTTTT GAATATTGTC GCTGGGGATT CTGTAGCTTT
1501  TGAGAGAGAG GGCGATAAAG CACGTAACGC AACAGATGCT CAAATTACCG
1551  CACAAGGGAC GATAACCGTC AATAAAGATG ATAAACAATT TAGATTCAAT
1601  AATGTATCTA TTAACGGGAC GGGCAAGGGT TTAAAGTTTA TTGCAAATCA
```

FIG. 9C.

```
1651  AAATAAATTTC  ACTCATAAAT  TTGATGGCGA  AATTAACATA  TCTGGAATAG
1701  TAACAATTAA   CCAAACCACG  AAAAAGATG   TTAAATACTG  GAATGCATCA
1751  AAAGACTCTT   ACTGGAATGT  TTCTTCTCTT  ACTTTGAATA  CGGTGCAAAA
1801  ATTTACCTTT   ATAAAATTCG  TTGATAGCGG  CTCAAATTCC  CAAGATTTGA
1851  GGTCATCACG   TAGAAGTTTT  GCAGGCGTAC  ATTTTAACGG  CATCGGAGGC
1901  AAAACAAACT   TCAACATCGG  AGCTAACGCA  AAAGCCTTAT  TTAAATTAAA
1951  ACCAAACGCC   GCTACAGACC  CAAAAAAAGA  ATTACCTATT  ACTTTTAACG
2001  CCAACATTAC   AGCTACCGGT  AACAGTGATA  GCTCTGTGAT  GTTTGACATA
2051  CACGCCAATC   TTACCTCTAG  AGCTGCCGGC  ATAAACATGG  ATTCAATTAA
2101  CATTACCGGC   GGGCTTGACT  TTTCCATAAC  ATCCCATAAT  CGCAATAGTA
2151  ATGCTTTTGA   AATCAAAAAA  GACTTAACTA  TAAATGCAAC  TGGCTCGAAT
2201  TTTAGTCTTA   AGCAAAACGAA AGATTCTTTT  TATAATGAAT  ACAGCAAACA
2251  CGCCATTAAC   TCAAGTCATA  ATCTAACCAT  TCTTGGCGGC  AATGTCACTC
2301  TAGGTGGGGA   AAATTCAAGC  AGTAGCATTA  CGGGCAATAT  CAATATCACC
2351  AATAAAGCAA   ATGTTACATT  ACAAGCTGAC  ACCAGCAACA  GCAACACAGG
2401  CTTGAAGAAA   AGAACTCTAA  CTCTTGGCAA  TATATCTGTT  GAGGGAATT
```

FIG. 9D.

```
2451  TAAGCCTAAC  TGGTGCAAAT  GCAAACATTG  TCGGCAATCT  TTCTATTGCA
2501  GAAGATTCCA  CATTTAAAGG  AGAAGCCAGT  GACAACCTAA  ACATCACCGG
2551  CACCTTTACC  AACAACGGTA  CCGCCAACAT  TAATATAAAA  CAAGGAGTGG
2601  TAAAACTCCA  AGGCGATATT  ATCAATAAAG  GTGGTTTAAA  TATCACTACT
2651  AACGCCTCAG  GCACTCAAAA  AACCATTATT  AACGGAAATA  TAACTAACGA
2701  AAAAGGCGAC  TTAAACATCA  AGAATATTAA  AGCCGACGCC  GAAATCCAAA
2751  TTGGCGGCAA  TATCTCACAA  AAAGAAGGCA  ATCTCACAAT  TTCTTCTGAT
2801  AAAGTAAATA  TTACCAATCA  GATAACAATC  AAAGCAGGCG  TTGAAGGGGG
2851  GCGTTCTGAT  TCAAGTGAGG  CAGAAAATGC  TAACCTAACT  ATTCAAACCA
2901  AAGAGTTAAA  ATTGGCAGGA  GACCTAAATA  TTTCAGGCTT  TAATAAAGCA
2951  GAAATTACAG  CTAAAAAATGG  CAGTGATTTA  ACTATTGGCA  ATGCTAGCGG
3001  TGGTAATGCT  GATGCTAAAA  AAGTGACTTT  TGACAAGGTT  AAAGATTCAA
3051  AAATCTCGAC  TGACGGTCAC  AATGTAACAC  TAAATAGCGA  AGTGAAAACG
3101  TCTAATGGTA  GTAGCAATGC  TGGTAATGAT  AACAGCACCG  GTTTAACCAT
3151  TTCCGCAAAA  GATGTAACGG  TAAACAATAA  CGTTACCTCC  CACAAGACAA
3201  TAAATATCTC  TGCCGCAGCA  GGAAATGTAA  CAACCAAAGA  AGGCACAACT
3251  ATCAATGCAA  CCACAGGCAG  CGTGGAAGTA  ACTGCTCAAA  ATGGTACAAT
```

FIG. 9E.

```
3301  TAAAGGCAAC  ATTACCTCGC  AAAATGTAAC  AGTGACAGCA  ACAGAAAATC
3351  TTGTTACCAC  AGAGAATGCT  GTCATTAATG  CAACCAGCGG  CACAGTAAAC
3401  ATTAGTACAA  AAACAGGGGA  TATTAAAGGT  GGAATTGAAT  CAACTTCCGG
3451  TAATGTAAAT  ATTACAGCGA  GCGGCAATAC  ACTTAAGGTA  AGTAATATCA
3501  CTGGTCAAGA  TGTAACAGTA  ACAGCGGATG  CAGGAGCCTT  GACAACTACA
3551  GCAGGCTCAA  CCATTAGTGC  GACAACAGGC  AATGCAAATA  TTACAACCAA
3601  AACAGGTGAT  ATCAACGGTA  AAGTTGAATC  CAGCTCCGGC  TCTGTAACAC
3651  TTGTTGCAAC  TGGAGCAACT  CTTGCTGTAG  GTAATATTTC  AGGTAACACT
3701  GTTACTATTA  CTGCGGATAG  CGGTAAATTA  ACCTCCACAG  TAGGTTCTAC
3751  AATTAATGGG  ACTAATAGTG  TAACCACCTC  AAGCCAATCA  GGCGATATTG
3801  AAGGTACAAT  TTCTGGTAAT  ACAGTAAATG  TTACAGCAAG  CACTGGTGAT
3851  TTAACTATTG  GAAATAGTGC  AAAAGTTGAA  GCGAAAAATG  GAGCTGCAAC
3901  CTTAACTGCT  GAATCAGGCA  AATTAACCAC  CCAAACAGGC  TCTAGCATTA
3951  CCTCAAGCAA  TGGTCAGACA  ACTCTTACAG  CCAAGGATAG  CAGTATCGCA
4001  GGAAACATTA  ATGCTGCTAA  TGTGACGTTA  AATACCACAG  GCACTTTAAC
4051  TACTACAGGG  GATTCAAAGA  TTAACGCAAC  CAGTGGTACC  TTAACAATCA
```

FIG. 9F.

```
4101 ATGCAAAAGA TGCCAAATTA GATGGTGCTG CATCAGGTGA CCGCACAGTA
4151 GTAAATGCAA CTAACGCAAG TGGCTCTGGT AACGTGACTG CGAAACCTC
4201 AAGCAGCGTG AATATCACCG GGGATTTAAA CACAATAAAT GGGTAAAATA
4251 TCATTTCGGA AAATGGTAGA AACACTGTGC GCTTAAGAGG CAAGGAAATT
4301 GATGTGAAAT ATATCCAACC AGGTGTAGCA AGCGTAGAAG AGGTAATTGA
4351 AGCGAAACGC GTCCTTGAGA AGGTAAAAGA TTTATCTGAT GAAGAAAGAG
4401 AAACACTAGC CAAACTTGGT GTAAGTGCTG TACGTTTCGT TGAGCCAAAT
4451 AATGCCATTA CGGTTAATAC ACAAAACGAG TTTACAACCA AACCATCAAG
4501 TCAAGTGACA ATTTCTGAAG GTAAGGCGTG TTTCTCAAGT GGTAATGGCG
4551 CACGAGTATG TACCAATGTT GCTGACGATG GACAGCAGTA GTCAGTAATT
4601 GACAAGGTAG ATTTCATCCT GCAATGAAGT CATTTTATTT TCGTATTATT
4651 TACTGTGTGG GTTAAAGTTC AGTACGGGCT TTACCCACCT TGTAAAAAAT
4701 TA
```

FIG. 10A. COMPARISON OF DERIVED AMINO ACID SEQUENCE

```
                1                                                    50
Hmw3com         ..........  ..........  ..........  ..........  ..........
Hmw4com         ..........  ..........  ..........  ..........  ..........
Hmw1com         MNKIYRLKFS  KRLNALVAVS  ELARGCDHST  EKGSEKPARM  KVRHLALKPL
Hmw2com         MNKIYRLKFS  KRLNALVAVS  ELARGCDHST  EKGSEKPARM  KVRHLALKPL 51                                                   100
Hmw3com         ..........  ..........  ..........  ..........  ..........
Hmw4com         ..........  ..........  ..GMSVVHGT  ATMQVDGNKT  TIRNSVNAII
Hmw1com         SAMLLSLGVT  SIPQSVLASG  LQGMSVVHGT  ATMQVDGNKT  TIRNSVNAII
Hmw2com         SAMLLSLGVT  SIPQSVLASG  LQGMSVVHGT  ATMQVDGNKT  TIRNSVNAII 101                                                  150
Hmw3com         ..........  ..........  ..........  ..........  ..........
Hmw4com         NWKQFNIDQN  EMEQFLQESS  NSAVFNRVTS  DQISQLKGIL  DSNGQVFLIN
```

FIG. 10B.

```
Hmw1com  NWKQFNIDQN  EMVQFLQENN  NSAVFNRVTS  NQISQLKGIL  DSNGQVFLIN
Hmw2com  NWKQFNIDQN  EMVQFLQENN  NSAVFNRVTS  NQISQLKGIL  DSNGQVFLIN
                                                                200
Hmw3com  ..........  ..........  ..........  ..........  ..........
         151
Hmw4com  PNGITIGKDA  IINTNGFTAS  TLDISNENIK  ARNFTLEQTK  DKALAEIVNH
Hmw1com  PNGITIGKDA  IINTNGFTAS  TLDISNENIK  ARNFTLEQTK  DKALAEIVNH
Hmw2com  PNGITIGKDA  IINTNGFTAS  TLDISNENIK  ARNFTLEQTK  DKALAEIVNH
                                                                250
Hmw3com  ..........  ..........  ..........  ..........  ..........
         201
Hmw4com  GLITVGKDGS  VNLIGGKVKN  EGVISVNGGS  ISLLAGQKIT  ISDIINPTIT
Hmw1com  GLITVGKDGS  VNLIGGKVKN  EGVISVNGGS  ISLLAGQKIT  ISDIINPTIT
Hmw2com  GLITVGKDGS  VNLIGGKVKN  EGVISVNGGS  ISLLAGQKIT  ISDIINPTIT
                                                                300
Hmw3com  ..........  INLGDIFAKG  GNINVRAATI  RNKGKLSADS  VSKDKSGNIV
         251
```

FIG. 10C.

```
        301                                                            350
Hmw4com YSIAAPENEA INLGDIFAKG GNINVRAATI RNKGKLSADS VSKDKSGNIV
Hmw1com YSIAAPENEA VNLGDIFAKG GNINVRAATI RNKGKLSADS VSKDKSGNIV
Hmw2com YSIAAPENEA VNLGDIFAKG GNINVRAATI RNKGKLSADS VSKDKSGNIV Hmw3com LSAKEGEAEI GGVISAQNQQ AKGGKLMITG DKVTLKTGAV IDLSGKEGGE
Hmw4com LSAKEGEAEI GGVISAQNQQ AKGGKLMITG DKVTLKTGAV IDLSGKEGGE
Hmw1com LSAKEGEAEI GGVISAQNQQ AKGGKLMITG DKVTLKTGAV IDLSGKEGGE
Hmw2com LSAKEGEAEI GGVISAQNQQ AKGGKLMITG DKVTLKTGAV IDLSGKEGGE 351                                                            400
Hmw3com TYLGGDERGE GKNGIQLAKK TTLEKGSTIN VSGKEKGGRA IVWGDIALID
Hmw4com TYLGGDERGE GKNGIQLAKK TTLEKGSTIN VSGKEKGGRA IVWGDIALID
Hmw1com TYLGGDERGE GKNGIQLAKK TTLEKGSTIN VSGKEKGGRA IVWGDIALID
Hmw2com TYLGGDERGE GKNGIQLAKK TTLEKGSTIN VSGKEKGGRA IVWGDIALID
```

FIG. 10D.

```
         401                                                          450
Hmw3com  GNINAQGK.D  IAKTGGFVET  SGHYLSIDDN  AIVKTKEWLL  DPENVTIEAP
Hmw4com  GNINAQGS..D IAKTGGFVET  SGHDLSIGDD  VIVDAKEWLL  DPDDVSIETL
Hmw1com  GNINAQGSGD  IAKTGGFVET  SGHDLFIKDN  AIVDAKEWLL  DPDNVTINAE
Hmw2com  GNINAQGSGD  IAKTGGFVET  SGHYLSIESN  AIVKTKEWLL  DPDDVTIEAE 451                                                          500
Hmw3com  SASRVELGAD  RNSHSAEVIK  VTLKKNNTSL  TTLTNTTISN  LLKSAHVVNI
Hmw4com  TSGRNNTGEN  QGYTTGDGTK  ESPKGNSISK  PTLTNSTLEQ  ILRRGSYVNI
Hmw1com  TAGRSNTSED  DEYTGSGNSA  STPKRNKE.K  TTLTNTTLES  ILKKGTFVNI
Hmw2com  DPLRNNTGIN  DEFPTGTGEA  SDPKKNSELK  TTLTNTTISN  YLKNAWTMNI 501                                                          550
Hmw3com  TARRKLTVNS  SISIERGSHL  ILHSEGQGGQ  GVQIDKDITS  .E...GGNLT
Hmw4com  TANNRIYVNS  SINLSNGS.L  TLHTK...RD  GVKINGDITS  NE...NGNLT
Hmw1com  TANQRIYVNS  SINL.SNGSL  TLWSEGRSGG  GVEINNDITT  GDDTRGANLT
Hmw2com  TASRKLTVNS  SINGSNGSHL  ILHSKGQRGG  GVQIDGDIT.  ...SKGGNLT
```

FIG. 10E.

```
        551                                                          600
Hmw3com IYSGGWVDVH KNITLGS.GF LNITTKEGDI AFEDKSGR.. ..NNLTITAQ
Hmw4com IKAGSWVDVH KNITLGT.GF LNIVAGDS.V AFEREGDKAR NATDAQITAQ
Hmw1com IYSGGWVDVH KNISLGAQGN INITAKQD.I AFEKGSNQV. ......ITGQ
Hmw2com IYSGGWVDVH KNITLD.QGF LNITA.AS.V AFEGGNNKAR DANNLTITAQ 601                                                          650
Hmw3com GTITSG.NSN GFRFNNVSLN SLGGKLSFTD SREDRGRRTK GNISNKFDGT
Hmw4com GTITVNKDDK QFRFNNVSIN GTGKGLKFIA NQN....... .NFTHKFDGE
Hmw1com GTIT.SGNQK GFRFNNVSLN GTGSGLQFTT KRTN......K YAITNKFEGT
Hmw2com GTVTITGEGK DFRANNVSLN GTGKGLNIIS SVNN...... ..LTHNLSGT 651                                                          700
Hmw3com LNISGTVDIS MKAPKVSWFY RD.KGRTYWN VTTLNVTSGS KFNLSIDSTG
Hmw4com INISGIVTIN QTTKKDVKYW NA.SKDSYWN VSSLTLNTVQ KFTF.IKFVD
Hmw1com LNISGKVNIS MVLPKNESGY DKFKGRTYWN LTSLNVSESG EFNLTIDSRG
```

FIG. 10F.

```
Hmw2com  INISGNITIN QTTRKNTSYW QTSHD.SHWN VSALNLETGA NFTF.IKYIS
                                                             750
         701

Hmw3com  SGSTG...PS IRNA..ELNG ITFN....KA TFNIAQGSTA NFSIKASIMP
Hmw4com  SGSNS...QD LRSSRRSFAG VHFNGIGGKT NFNIGANAKA LFKLKPNAAT
Hmw1com  SDSAGTLTQ. ....PYNLNG ISFN...KDT TFNVERNARV NFDIKAPIGI
Hmw2com  SNSKGLTTQY RSSAGVNFNG V..N...GNM SFNLKEGAKV NFKLKPNENM
                                                             800
         751

Hmw3com  FKSNANYAL. FNEDISVSG. .GGSVNFKLN ASSSNIQTPG VIIKSQNFNV
Hmw4com  DPKKELPIT. FNANITATGN SDSSVMFDIH A...NLTSRA AGINMDSINI
Hmw1com  NKYSSLNYAS FNGNISVSG. .GGSVDFTLL ASSSNVQTPG VVINSKYFNV
Hmw2com  NTSKPLPI.R FLANITATG. .GGSVFFDIY ANHS...GRG AELKMSEINI
                                                             850
         801

Hmw3com  SGGSTLNLKA EGSTETAFSI ENDLNLNATG GNITIRQVEG T..DSRVNKG
Hmw4com  TGGLDFSITS HNRNSNAFEI KKDLTINATG SNFSLKQTKD SFYNEYSKHA
```

FIG. 10G.

```
Hmw1com  STGSSLRFKT  SGSTKTGFSI  EKDLTLNATG  GNITLLQVEG  T..DGMIGKG
Hmw2com  SNGANFTLNS  HVRGDDAFKI  NKDLTINATN  SNFSLRQTKD  DFYDGYARNA
                                                                 900

Hmw3com  VAAKKNITFK  GGNITFGSQK  ATTEIKGNVT  INKNTNATLR  GANFAEN...
Hmw4com  INSSHNLTIL  GGNVTLGGEN  SSSSITGNIN  ITNKANVTLQ  ADTSNSNTGL
Hmw1com  IVAKKNITFE  GGNITFGSRK  AVTEIEGNVT  INNNANVTLI  GSDFDNHQ..
Hmw2com  INSTYNISIL  GGNVTLGGQN  SSSSITGNIT  IEKAANVTLE  ANNAPNQQNI
                                                                 950

Hmw3com  KSPLNIAGNV  INNGNLTTAG  SIINIAGNLT  VSKGANLQAI  TNYTFNVAGS
Hmw4com  KKRTLTLGNI  SVEGNLSLTG  ANANIVGNLS  IAEDSTFKGE  ASDNLNITGT
Hmw1com  KPLTIKKDVI  INSGNLTAGG  NIVNIAGNLT  VESNANFKAI  TNFTFNVGGL
Hmw2com  RDRVIKLGSL  LVNGSLSLTG  ENADIKGNLT  ISESATFKGK  TRDTLNITGN
                                                                1000
```

FIG. 10H.

```
Hmw3com  FDNNGASNIS  IARGGAKFK.  DINNTSSLNI  TTNSDTTYRT  IIKGNISNKS
Hmw4com  FTNNGTANIN  IKQGVVKLQG  DINNKGGLNI  TTNASGTQKT  IINGNITNEK
Hmw1com  FDNKGNSNIS  IAKGGARFK.  DIDNSKNLSI  TTNSSSTYRT  IISGNITNKN
Hmw2com  FTNNGTAEIN  ITQGVVKLG.  NVTNDGDLNI  TTHAKRNQRS  IIGGDIINNK
                    1001                                    1050
Hmw3com  GDLNIIDKKS  DAEIQIGGNI  SQKEGNLTIS  SDKVNITNQI  TIKAGVEGGR
Hmw4com  GDLNIKNIKA  DAEIQIGGNI  SQKEGNLTIS  SDKVNITNQI  TIKAGVEGGR
Hmw1com  GDLNITNEGS  DTEMQIGGDI  SQKEGNLTIS  SDKINITKQI  TIKAGVDGEN
Hmw2com  GSLNITDSNN  DAEIQIGGNI  SQKEGNLTIS  SDKINITKQI  TIKKGIDGED
                    1051                                    1100
Hmw3com  SDSSEAENAN  LTIQTKELKL  AGDLNISGFN  KAEITAKNGS  DLTIGNASGG
Hmw4com  SDSSEAENAN  LTIQTKELKL  AGDLNISGFN  KAEITAKNGS  DLTIGNASGG
Hmw1com  SDSDATNNAN  LTIKTKELKL  TQDLNISGFN  KAEITAKDGS  DLTIGNTNSA
Hmw2com  SSSDATSNAN  LTIKTKELKL  TEDLSISGFN  KAEITAKDGR  DLTIGNSNDG
```

FIG. 10I.

|  | 1101 |  |  |  |  | 1150 |
|---|---|---|---|---|---|---|
| Hmw3com | N..ADAKKVT | FDKVKDSKIS | TDGHNVTLNS | EVKT..SNGS | SNAGNDNSTG |
| Hmw4com | N..ADAKKVT | FDKVKDSKIS | TDGHNVTLNS | EVKT..SNGS | SNAGNDNSTG |
| Hmw1com | D.GTNAKKVT | FNQVKDSKIS | ADGHKVTLHS | KVETSGSNNN | TEDSSDNNAG |
| Hmw2com | NSGAEAKKVT | FNNVKDSKIS | ADGHNVTLNS | KVKTSSSNGG | RESNSDNDTG |

|  | 1151 |  |  |  |  | 1200 |
|---|---|---|---|---|---|---|
| Hmw3com | LTISAKDVTV | NNNVTSHKTI | NISAAAGNVT | TKEGTTINAT | TGSVEVTAQN |
| Hmw4com | LTISAKDVTV | NNNVTSHKTI | NISAAAGNVT | TKEGTTINAT | TGSVEVTAQN |
| Hmw1com | LTIDAKNVTV | NNNITSHKAV | SISATSGEIT | TKTGTTINAT | TGNVEIT... |
| Hmw2com | LTITAKNVEV | NKDVTSLKTV | NITA.SEKVT | TTAGSTINAT | NGKASIT... |

|  | 1201 |  |  |  |  | 1250 |
|---|---|---|---|---|---|---|
| Hmw3com | GTIKGNITSQ | NVTVTATENL | VTTENAVINA | TSGTVNISTK | TGDIKGGIES |
| Hmw4com | GTIKGNITSQ | NVTVTATENL | VTTENAVINA | TSGTVNISTK | TGDIKGGIES |
| Hmw1com | ......... | ......... | ......... | ........AQ | TGDIKGGIES |

FIG. 10J.

```
Hmw2com  ..........  ..........  ..........  ..........  .....TK T.........

1251                                                          1300
Hmw3com  TSGNVNITAS  GNTLKVSNIT  GQDVTVTADA  GALTTTAGST  ISATTGNANI
Hmw4com  TSGNVNITAS  GNTLKVSNIT  GQDVTVTADA  GALTTTAGST  ISATTGNANI
Hmw1com  SSGSVTLTAT  EGALAVSNIS  GNTVTVTANS  GALTTLAGST  IKG.TESVTT
Hmw2com  ..........  ..........  ..........  ..........  ..........

1301                                                          1350
Hmw3com  TTKTGDINGK  VESSSGSVTL  VATGATLAVG  NISGNTVTIT  ADSGKLTSTV
Hmw4com  TTKTGDINGK  VESSSGSVTL  VATGATLAVG  NISGNTVTIT  ADSGKLTSTV
Hmw1com  SSQSGDIG..  ..........  ........G  TISGGTVEVK  ATESLTTQSN
Hmw2com  ....GDIS..  ..........  ........G  TISGNTVSVS  ATVDLTTKSG 1351                                                          1400
Hmw3com  GSTINGTNSV  TTSSQSGDIE  GTISGNTVNV  TASTGDLTIG  NSAKVEAKNG
Hmw4com  GSTINGTNSV  TTSSQSGDIE  GTISGNTVNV  TASTGDLTIG  NSAKVEAKNG
```

FIG. 10K.

```
Hmw1com  SKIKATTGEA NVTSATGTIG GTISGNTVNV TANAGDLTVG NGAEINATEG
Hmw2com  SKIEAKSGEA NVTSATGTIG GTISGNTVNV TANAGDLTVG NGAEINATEG
                                                            1450

1401
Hmw3com  AATLTAESGK LTTQTGSSIT SSNGQTTLTA KDSSIAGNIN AANVTLNTTG
Hmw4com  AATLTAESGK LTTQTGSSIT SSNGQTTLTA KDSSIAGNIN AANVTLNTTG
Hmw1com  AATLTTSSGK LTTEASSHIT SAKGQVNLSA QDSSVAGSIN AANVTLNTTG
Hmw2com  AATLTATGNT LTTEAGSSIT STKGQVDLLA QNSSIAGNIN AANVTLNTTG
                 1451                                       1500

Hmw3com  TLTTTGDSKI NATSGTLTIN AKDAKLDGAA SGDRTVVNAT NASGSGNVTA
Hmw4com  TLTTTGDSKI NATSGTLTIN AKDAKLDGAA SGDRTVVNAT NASGSGNVTA
Hmw1com  TLTTVKGSNI NATSGTLTIN AKDAELNGAA LGNHTVVNAT NANGSGSVIA
Hmw2com  TLTTVAGSDI KATSGTLTIN AKDAKLNGDA SGDSTEVNAV NASGSGSVTA
                                                            1550
         1501
```

FIG. 10L.

```
Hmw3com  KTSSSVNITG  DLNTINGLNI  ISENGRNTVR  LRGKEIDVKY  IQPGVASVEE
Hmw4com  KTSSSVNITG  DLNTINGLNI  ISENGRNTVR  LRGKEIDVKY  IQPGVASVEE
Hmw1com  TTSSRVNITG  DLITINGLNI  ISKNGINTVL  LKGVKIDVKY  IQPGIASVDE
Hmw2com  ATSSSVNITG  DLNTVNGLNI  ISKDGRNTVR  LRGKEIEVKY  IQPGVASVEE
              1551                                                1600

Hmw3com  VIEAKRVLEK  VKDLSDEERE  TLAKLGVSAV  RFVEPNNAIT  VNTQNEFTTK
Hmw4com  VIEAKRVLEK  VKDLSDEERE  TLAKLGVSAV  RFVEPNNAIT  VNTQNEFTTK
Hmw1com  VIEAKRILEK  VKDLSDEERE  ALAKLGVSAV  RFIEPNNTIT  VDTQNEFATR
Hmw2com  VIEAKRVLEK  VKDLSDEERE  TLAKLGVSAV  RFVEPNNTIT  VNTQNEFTTR
              1601                                                1632

Hmw3com  PSSQVTISEG  KACFSSGNGA  RVCTNVADDG  QQ
Hmw4com  PSSQVTISEG  KACFSSGNGA  RVCTNVADDG  QQ
Hmw1com  PLSRIVISEG  RACFSNSDGA  TVCVNIADNG  R.
Hmw2com  PSSQVIISEG  KACFSSGNGA  RVCTNVADDG  QP
```

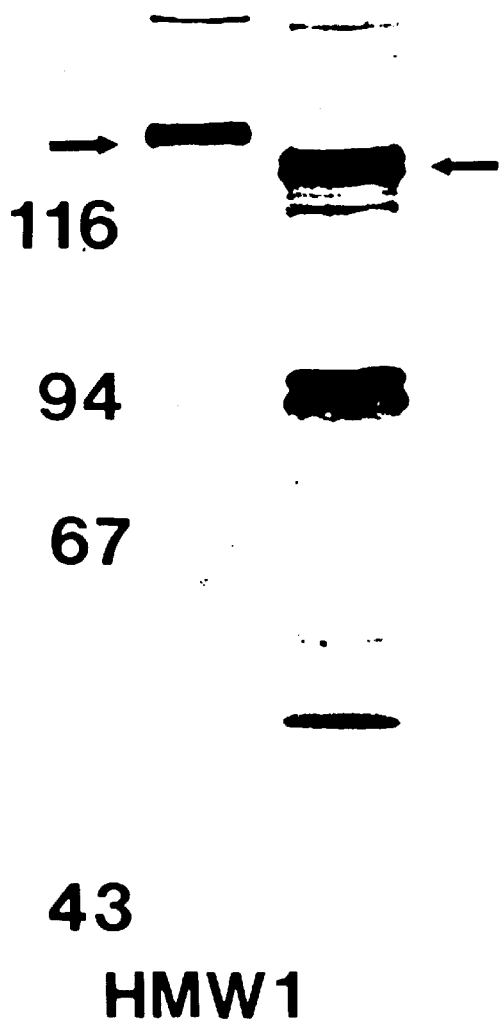
FIG. 11 HMW1 HMW2
WESTERN IMMUNOBLOT ASSAY OF PHAGE LYSATES CONTAINING EITHER THE HMW1 OR HMW2 RECOMBINANT PROTEINS. LYSATES WERE PROBED WITH AN *E. COLI*-ABSORBED ADULT SERUM SAMPLE WITH HIGH-TITER ANTIBODY AGAINST HIGH-MOLECULAR-WEIGHT PROTEINS. THE ARROWS INDICATE THE MAJOR IMMUNOREACTIVE PROTEIN BANDS OF 125 AND 120 kDa IN THE HMW1 AND HMW2 LYSATES, RESPECTIVELY.

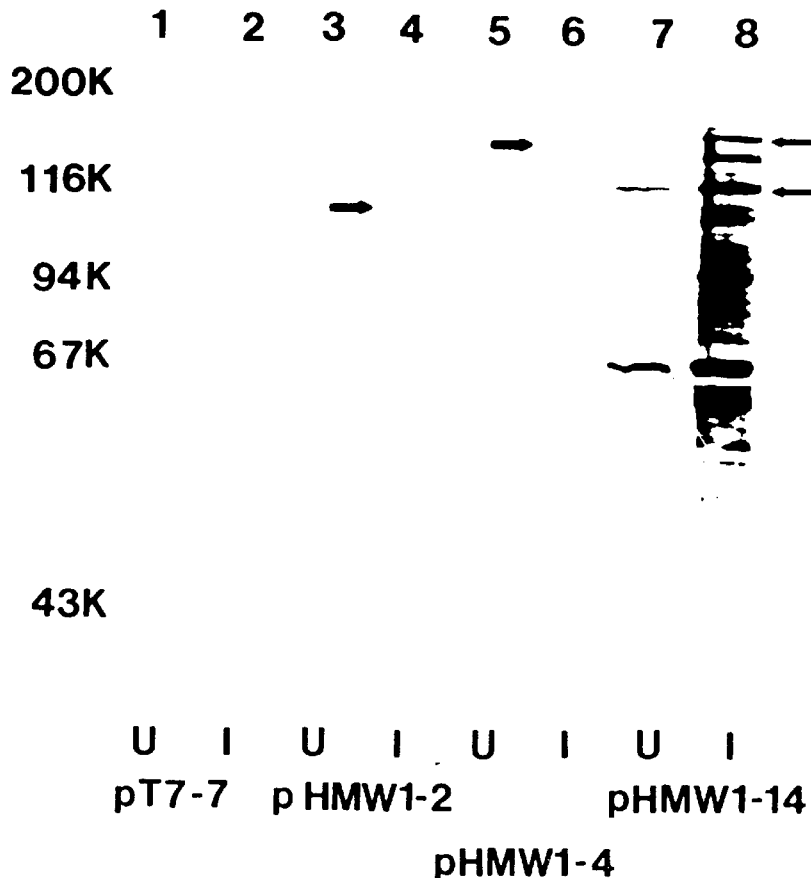

FIG. 12

WESTERN IMMUNOBLOT ASSAY OF CELL SONICATES PREPARED FROM E. COLI TRANSFORMED WITH PLASMID pT7-7 ( LANES 1 AND 2 ) pHMW1-2 (LANES 3 AND 4), pHMW1-4 ( LANES 5 AND 6), OR pHMW1-14 ( LANES 7 AND 8 ). THE SONICATES WERE PROBED WITH AN E. COLI-ABSORBED ADULT SERUM SAMPLE WITH HIGH -TITER ANTIBODY AGAINST HIGH - MOLECULAR -WEIGHT PROTEINS. LANES LABELED U AND I REPRESENT SONICATES PREPARED BEFORE AND AFTER INDUCTION OF THE GROWING SAMPLES WITH IPTG, RESPECTIVELY. THE ARROWS INDICATE PROTEIN BANDS OF INTEREST AS DESCRIBED IN THE TEXT.

FIG. 13

ELISA WITH rHMW1 ANTISERUM ASSAYED AGAINST PURIFIED FILAMENTOUS HEMAGLUTININ OF B. *PERTUSSIS*. Ab, ANTIBODY.

WESTERN IMMUNOBLOT ASSAY OF CELL SONICATES FROM A PANEL OF EPIDEMIOLOGICALLY UNRELATED NONTYPEABLE *H. INFLUENZAE* STRAINS. THE SONICATES WERE PROBED WITH RABBIT ANTISERUM PREPARED AGAINST HMW1-4 RECOMBINANT PROTEIN. THE STRAIN DESIGNATIONS ARE INDICATED BY THE NUMBERS BELOW EACH LANE.

200K

116K

94K

67K

43K
   5    7   12   14   15   16   17   18

WESTERN IMMUNOBLOT ASSAY OF CELL SONICATES FROM A PANEL OF EPIDEMIOLOGICALLY UNRELATED NONTYPEABLE H. INFLUENZAE STRAINS. THE SONICATES WERE PROBED WITH MONOCLONAL ANTIBODY X3C, A MURINE IgG ANTIBODY WHICH RECOGNIZES THE FILAMENTOUS HEMAGGLUTININ OF B. PERTUSSIS (13). THE STRAIN DESIGNATIONS ARE INDICATED BY THE NUMBERS BELOW EACH LANE.

IMMUNOBLOT ASSAY OF CELL SONICATES OF NONTYPABLE *H. INFLUENZAE* STRAIN 12 DERIVATIVES. THE SONICATES WERE PROBED WITH RABBIT ANTISERUM PREPARED AGAINST HMW-1 RECOMBINANT PROTEIN. LANES: 1, WILD-TYPE STRAIN; 2, HMW-2⁻ MUTANT; 3, HMW-1⁻ MUTANT; 4, HMW-1⁻ / HMW-2⁻ DOUBLE MUTANT.

IMMUNOELECTRON MICROSCOPY WITH Mab AD6

WESTERN IMMUNOBLOT ASSAY WITH Mab AD6 AND HMW1A OR HMW2A RECOMBINANT PROTEINS

WESTERN IMMUNOBLOT ASSAY WITH Mab 10C5 AND HMW1A OR HMW2A RECOMBINANT PROTEINS

WESTERN IMMUNOBLOT ASSAY WITH Mab AD6 AND TEN UNRELATED NONTYPABLE *HAEMOPHILUS INFLUENZAE*

HIGH MOLECULAR WEIGHT SURFACE PROTEINS OF NON-TYPEABLE HAEMOPHILUS

REFERENCE TO RELATED APPLICATION

This application is a continuation-in-part of U.S. patent application Ser. No. 08/302,832 filed Oct. 5, 1994, now U.S. Pat. No. 5,603,938, which is a continuation of PCT/US93/02166 filed Mar. 16, 1993.

FIELD OF INVENTION

This invention relates to high molecular weight proteins of non-typeable haemophilus.

BACKGROUND TO THE INVENTION

Non-typeable *Haemophilus influenzae* are non-encapsulated organisms that are defined by their lack of reactivity with antisera against known *H. influenzae* capsular antigens.

These organisms commonly inhabit the upper respiratory tract of humans and are frequently responsible for a variety of common mucosal surface infections, such as otitis media, sinusitis, conjunctivitis, chronic bronchitis and pneumonia. Otitis media remains an important health problem for children and most children have had at least one episode of otitis by their third birthday and approximately one-third of children have had three or more episodes. Non-typeable *Haemophilus influenzae* generally accounts for about 20 to 25% of acute otitis media and for a larger percentage of cases of chronic otitis media with effusion.

A critical first step in the pathogenesis of these infections is colonization of the respiratory tract mucosa. Bacterial surface molecules which mediate adherence, therefore, are of particular interest as possible vaccine candidates.

Since the non-typeable organisms do not have a polysaccharide capsule, they are not controlled by the present *Haemophilus influenzae* type b (Hib) vaccines, which are directed towards Hib bacterial capsular polysaccharides. The non-typeable strains, however, do produce surface antigens that can elicit bactericidal antibodies. Two of the major outer membrane proteins, P2 and P6, have been identified as targets of human serum bactericidal activity. However, it has been shown that the P2 protein sequence is variable, in particular in the non-typeable Haemophilus strains. Thus, a P2-based vaccine would not protect against all strains of the organism.

There have previously been identified by Barenkamp et al (*Pediatr. Infect. Dis. J.*, 9:333–339, 1990) a group of high-molecular-weight (HMW) proteins of non-typeable *Haemophilus influenzae* that appeared to be major targets of antibodies present in human convalescent sera. Examination of a series of middle ear isolates revealed the presence of one or two such proteins in most strains. However, prior to the present invention, the structures of these proteins and their encoding nucleic acid sequences were unknown as were pure isolates of such proteins. In addition, the identification of surface accessible epitopes of such proteins was unknown.

SUMMARY OF INVENTION

The inventor, in an effort to further characterize the high molecular weight (HMW) non-typeable Haemophilus proteins, has cloned, expressed and sequenced the genes coding for two immunodominant HMW proteins (designated HMW1 and HMW2) from a prototype non-typeable Haemophilus strain and has cloned, expressed and sequenced the genes coding for two additional immunodominant HMW proteins (designated HMW3 and HMW4) from another non-typeable Haemophilus strain.

In accordance with one aspect of the present invention, therefore, there is provided an isolated and purified nucleic acid molecule coding for a high molecular weight protein of a non-typeable Haemophilus strain, particularly a nucleic acid molecule coding for protein HMW1, HMW2, HMW3 or HMW4, as well as any variant or fragment of such protein which retains the immunological ability to protect against disease caused by a non-typeable Haemophilus strain.

The nucleic acid molecule may have a DNA sequence shown in FIG. 1 (SEQ ID No: 1) and encoding HMW1 for strain 12 having the derived amino acid sequence of FIG. 2 (SEQ ID No: 2). The nucleic acid molecule may have the DNA sequence shown in FIG. 3 (SEQ ID No: 3) and encoding protein HMW2 for strain 12 having the derived amino acid sequence of FIG. 4 (SEQ ID No: 4). The nucleic acid molecule may have the DNA sequence shown in FIG. 8 (SEQ ID No: 7) and encoding HMW3 for strain 5 having the derived amino acid sequence of FIG. 10 (SEQ ID No: 9). The nucleic acid molecule may have a DNA sequence shown in FIG. 9 (SEQ ID No: 8) and encoding protein HMW4 for strain 5 having the derived amino acid sequence of FIG. 10 (SEQ ID No: 10).

In another aspect of the invention, there is provided an isolated and purified nucleic acid molecule encoding a high molecular weight protein of a non-typeable Haemophilus strain, which is selected from the group consisting of:

(a) a DNA sequence as shown in any one of FIGS. 1, 3, 8 and 9 (SEQ ID Nos: 1, 3, 7 and 8);

(b) a DNA sequence encoding an amino acid sequence as shown in any one of FIGS. 2, 4 and 10 (SEQ ID Nos: 2, 4, 9 and 10); and (c) a DNA sequence which hybridizes under stringent conditions to any one of the sequences of (a) and (b).

A DNA sequence according to (c) may be one having at least about 90% identity of sequence to the DNA sequences (a) or (b).

The inventor has further found correct processing of the HMW protein requires the presence of additional downstream nucleic acid sequences. Accordingly, a further aspect of the present invention provides an isolated and purified gene cluster comprising a first nucleotide sequence encoding a high molecular weight protein of a non-typeable Haemophilus strain and at least one downstream nucleotide sequence for effecting expression of a gene product of the first nucleotide sequence fully encoded by the structural gene.

The gene cluster may comprise a DNA sequence encoding high molecular weight protein HMW1 or HMW2 and two downstream accessory genes. The gene cluster may have the DNA sequence shown in FIG. 6 (SEQ ID No: 5) or FIG. 7 (SEQ ID No. 6).

In an additional aspect, the present invention includes a vector adapted for transformation of a host, comprising a nucleic acid molecule as provided herein, particularly the gene cluster provided herein. The vector may be an expression vector or a plasmid adapted for expression of the encoded high molecular weight protein, fragments or analogs thereof, in a heterologous or homologous host and comprising expression means operatively coupled to the nucleic acid molecule. The expression means may include a nucleic acid portion encoding a leader sequence for secretion from the host of the high molecular weight protein. The expression means may include a nucleic acid portion encoding a lipidation signal for expression from the host of a lipidated form of the high molecular weight protein. The host may be selected from, for example, *E. coli*, Bacillus, Haemophilus, fungi, yeast, baculovirus and Semliki Forest Virus expression systems. The invention further includes a recombinant high molecular weight protein of non-typeable Haemophilus or fragment or analog thereof producible by the transformed host.

In another aspect, the invention provides an isolated and purified high molecular weight protein of non-typeable *Haemophilus influenzae* which is encoded by a nucleic acid molecule as provided herein. Such high molecular weight proteins may be produced recombinantly to be devoid of non-high molecular weight proteins of non-typeable *Haemophilus influenzae* or from natural sources.

Such protein may be characterized by at least one surface-exposed B-cell epitope which is recognized by monoclonal antibody AD6. Such protein may be HMW1 encoded by the DNA sequence shown in FIG. 1 (SEQ ID No: 1) and having the derived amino acid sequence of FIG. 2 (SEQ ID No: 2) and having an apparent molecular weight of 125 kDa. Such protein may be HMW2 encoded by the DNA sequence shown in FIG. 3 (SEQ ID No: 3) and having the derived amino acid sequence of FIG. 4 (SEQ ID No: 4) and having an apparent molecular weight of 120 kDA. Such protein may be HMW3 encoded by the DNA sequence shown in FIG. 8 (SEQ ID No: 7) and having the derived amino acid sequence of FIG. 10 (SEQ ID No: 9) and having an apparent molecular weight of 125 kDa. Such protein may be HMW4 encoded by the DNA sequence shown in FIG. 9 (SEQ ID No: 8) and having the derived amino acid sequence shown in FIG. 10 (SEQ ID No: 10) and having the apparent molecular weight of 123 kDa.

A further aspect of the invention provides an isolated and purified high molecular weight protein of non-typeable *Haemophilus influenzae* which is antigenically related to the filamentous hemagglutinin surface protein of *Bordetella pertussis*, particularly HMW1, HMW2, HMW3 or HMW4.

The novel high molecular weight proteins of non-typeable Haemophilus may be used as carrier molecules by linking to an antigen, hapten or polysaccharide for eliciting an immune response to the antigen, hapten or polysaccharide. An example of such polysaccharide is a protective polysaccharide against *Haemophilus influenzae* type b.

In a further aspect of the invention, there is provided a synthetic peptide having an amino acid sequence containing at least six amino acids and no more than 150 amino acids and corresponding to at least one protective epitope of a high molecular weight protein of non-typeable *Haemophilus influenzae*, specifically HMW1, HMW2, HMW3 or HMW4. The epitope may be one recognized by at least one of the monoclonal antibodies AD6 (ATCC) and 10C5. Specifically, the epitope may be located within 75 amino acids of the carboxy terminus of the HMW1 or HMW2 protein and recognized by the monoclonal antibody AD6.

The present invention also provides an immunogenic composition comprising an immunoeffective amount of an active component, which may be the novel high molecular weight protein or synthetic peptide provided herein, which may be formulated along with a pharmaceutically acceptable carrier therefor. The immunogenic composition may be formulated as a vaccine for in vivo administration to a host.

The immunogenic composition may be formulated as a microparticle, capsule, ISCOM or liposome preparation. The immunogenic composition may be used in combination with a targeting molecule for delivery to specific cells of the immune system or to mucosal surfaces. Some targeting molecules include vitamin B12 and fragments of bacterial toxins, as described in WO 92/17167 (Biotech Australia Pty. Ltd.), and monoclonal antibodies, as described in U.S. Pat. No. 5,194,254 (Barber et al). The immunogenic compositions of the invention (including vaccines) may further comprise at least one other immunogenic or immunostimulating material and the immunostimulating material may be at least one adjuvant.

Suitable adjuvants for use in the present invention include, (but are not limited to) aluminum phosphate, aluminum hydroxide, QS21, Quil A, derivatives and components thereof, ISCOM matrix, calcium phosphate, calcium hydroxide, zinc hydroxide, a glycolipid analog, an octadecyl ester of an amino acid, a muramyl dipeptide polyphosphazare, ISCOPRP, DC-chol, DDBA and a lipoprotein and other adjuvants to induce a Th1 response. Advantageous combinations of adjuvants are described in copending U.S. patent application Ser. No. 08/261,194 filed Jun. 16, 1994, assigned to Connaught Laboratories Limited and the disclosure of which is incorporated herein by reference.

In a further aspect of the invention, there is provided a method of generating an immune response in a host, comprising administering thereto an immuno-effective amount of the immunogenic composition as provided herein. The immune response may be a humoral or a cell-mediated immune response. Hosts in which protection against disease may be conferred include primates including humans.

The present invention additionally provides a method of producing antibodies specific for a high molecular weight protein of non-typeable *Haemophilus influenzae*, comprising:

(a) administering the high molecular weight protein or epitope containing peptide provided herein to at least one mouse to produce at least one immunized mouse;

(b) removing B-lymphocytes from the at least one immunized mouse;

(c) fusing the B-lymphocytes from the at least one immunized mouse with myeloma cells, thereby producing hybridomas;

(d) cloning the hybridomas;

(e) selecting clones which produce anti-high molecular weight protein antibody;

(f) culturing the anti-high molecular weight protein antibody-producing clones; and then (g) isolating anti-high molecular weight protein antibodies from the cultures.

Additional aspects of the present invention include monoclonal antibody AD6 and monoclonal antibody 10C5.

The present invention provides, in an additional aspect thereof, a method for producing an immunogenic composition, comprising administering the immunogenic composition provided herein to a first test host to determine an amount and a frequency of administration thereof to elicit a selected immune response against a high molecular weight protein of non-typeable *Haemophilus influenzae;* and formulating the immunogenic composition in a form suitable for administration to a second host in accordance with the determined amount and frequency of administration. The second host may be a human.

The novel envelope protein provided herein is useful in diagnostic procedures and kits for detecting antibodies to high molecular weight proteins of non-typeable *Haemophilus influenzae*. Further monoclonal antibodies specific for the high molecular protein or epitopes thereof are useful in diagnostic procedure and kits for detecting the presence of the high molecular weight protein.

Accordingly, a further aspect of the invention provides a method of determining the presence in a sample, of antibodies specifically reactive with a high molecular weight protein of *Haemophilus influenzae* comprising the steps of:

(a) contacting the sample with the high molecular weight protein or epitope-containing peptide as provided herein to produce complexes comprising the protein and any said antibodies present in the sample specifically reactive therewith; and (b) determining production of the complexes.

In a further aspect of the invention, there is provided a method of determining the presence, in a sample, of a high molecular weight protein of *Haemophilus influenzae* or an epitope-containing peptide, comprising the steps of:

(a) immunizing a host with the protein or peptide as provided herein, to produce antibodies specific for the protein or peptide;

(b) contacting the sample with the antibodies to produce complexes comprising any high molecular weight protein or epitope-containing peptide present in the sample and said specific antibodies; and (c) determining production of the complexes.

A further aspect of the invention provides a diagnostic kit for determining the presence of antibodies in a sample specifically reactive with a high molecular weight protein of non-typeable *Haemophilus influenzae* or epitope-containing peptide, comprising:

(a) the high molecular weight protein or epitope-containing peptide as provided herein;

(b) means for contacting the protein or peptide with the sample to produce complexes comprising the protein or peptide and any said antibodies present in the sample; and (c) means for determining production of the complexes.

The invention also provides a diagnostic kit for detecting the presence, in a sample, of a high molecular weight protein of *Haemophilus influenzae* or epitope-containing peptide, comprising:

(a) an antibody specific for the novel envelope protein as provided herein;

(b) means for contacting the antibody with the sample to produce a complex comprising the protein or peptide and protein-specific antibody; and (c) means for determining production of the complex.

In this application, the term "high molecular weight protein" is used to define a family of high molecular weight proteins of *Haemophilus influenzae*, generally having an apparent molecular weight of from about 120 to about 130 kDa and includes proteins having variations in their amino acid sequences. In this application, a first protein or peptide is a "functional analog" of a second protein or peptide if the first protein or peptide is immunologically related to and/or has the same function as the second protein or peptide. The functional analog may be, for example, a fragment of the protein or a substitution, addition or deletion mutant thereof. The invention also extends to such functional analogs.

Advantages of the present invention include:

an isolated and purified envelope high molecular weight protein of *Haemophilus influenzae* produced recombinantly to be devoid of non-high molecular weight proteins of *Haemophilus influenzae* or from natural sources as well as nucleic acid molecules encoding the same;

high molecular weight protein specific human monoclonal antibodies which recognize conserved epitopes in such protein; and diagnostic kits and immunological reagents for specific identification of hosts infected by *Haemophilus influenzae*.

BRIEF DESCRIPTION OF DRAWINGS

FIGS. 1A to 1G contain the DNA sequence of a gene coding for protein HMW1 (SEQ ID No: 1). The hmw1A open reading frame extends from nucleotides 351 to 4958;

FIGS. 2A and 2B contain the derived amino acid sequence of protein HMW1 (SEQ ID No: 2);

FIGS. 3A to 3G contain the DNA sequence of a gene coding for protein HMW2 (SEQ ID No: 3). The open hmw2A open reading frame extends from nucleotides 382 to 4782;

FIGS. 4A and 4B contain the derived amino acid sequence of HMW2 (SEQ ID No: 4);

FIG. 5B shows the restriction map of the T7 expression vector pT7-7. This vector contains the T7 RNA polymerase promoter Φ10, a ribosomal binding site (rbs) and the translational start site for the T7 gene 10 protein upstream from a multiple cloning site;

FIGS. 6A to 6L contain the DNA sequence of a gene cluster for the hmw1 gene (SEQ ID NO: 5), comprising nucleotides 351 to 4958 (ORF a) (as in FIG. 1), as well as two additional downstream genes in the 3' flanking region, comprising ORFs b, nucleotides 5114 to 6748 and c nucleotides 7062 to 9011;

FIGS. 7A to 7L contain the DNA sequence of a gene cluster for the hmw2 gene (SEQ ID NO: 6), comprising nucleotides 792 to 5222 (ORF a) (as in FIG. 3), as well as two additional downstream genes in the 3' flanking region, comprising ORFs b, nucleotides 5375 to 7009, and c, nucleotides 7249 to 9198;

FIGS. 8A–8F contain the DNA sequence of a gene coding for protein HMW3 (SEQ ID NO: 7);

FIGS. 9A–9F contain the DNA sequence of a gene coding for protein HMW4 (SEQ ID NO: 8);

FIGS. 10A to 10L contain a comparison table for the derived amino acid sequence for proteins HMW1 (SEQ ID No: 2), HMW2 (SEQ ID No: 4), HMW3 (SEQ ID No: 9) and HMW4 (SEQ ID No: 10);

FIG. 12 is a Western immunoblot assay of cell sonicates prepared from *E. coli* transformed with plasmid pT7-7 (lanes 1 and 2), pHMW1-2 (lanes 3 and 4), pHMW1-4 (lanes 5 and 6) or pHMW1-14 (lanes 7 and 8). The sonicates were probed with an *E. coli*-absorbed adult serum sample with high-titer antibody against high-molecular weight proteins.

Figure 14:
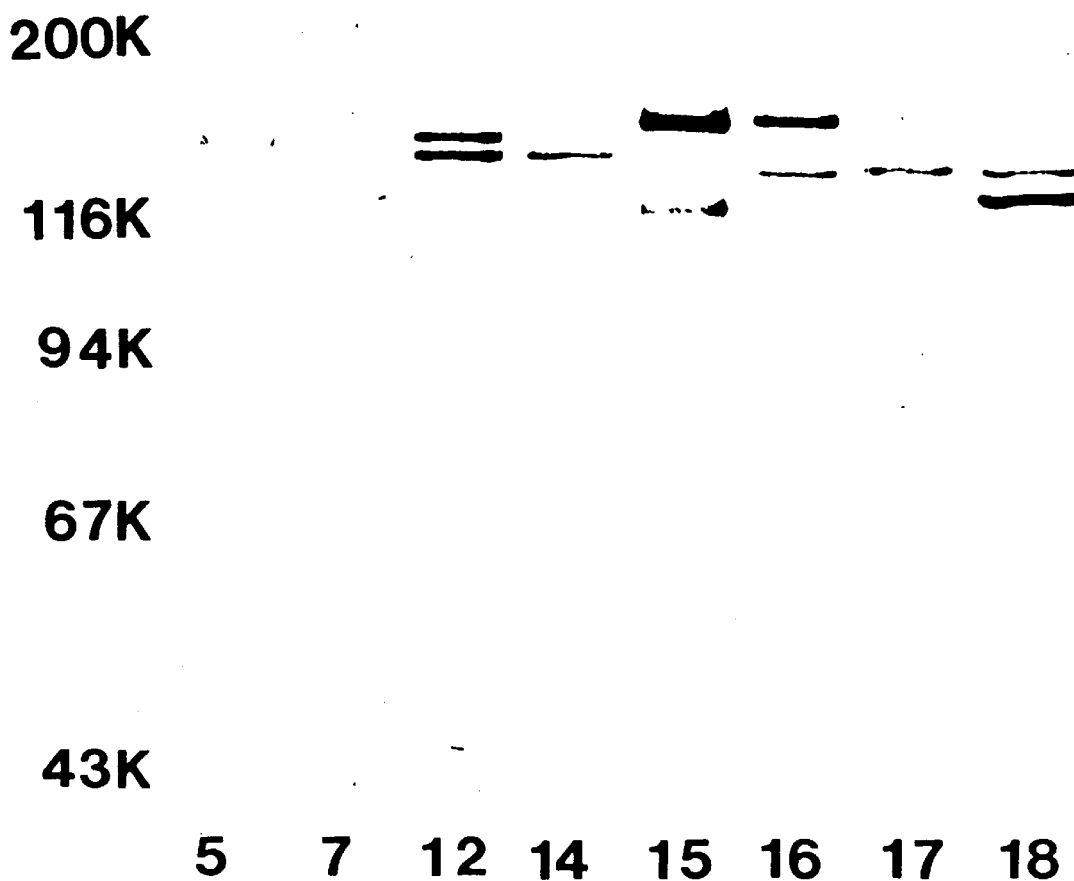
Figure 15:
Figure 16:
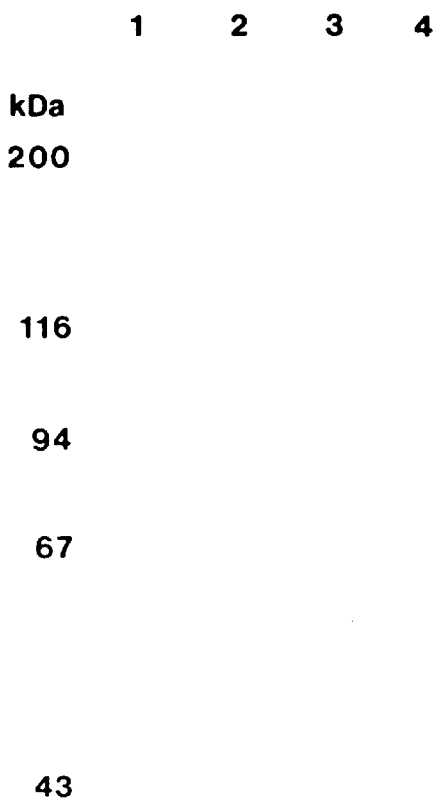
Figure 17:
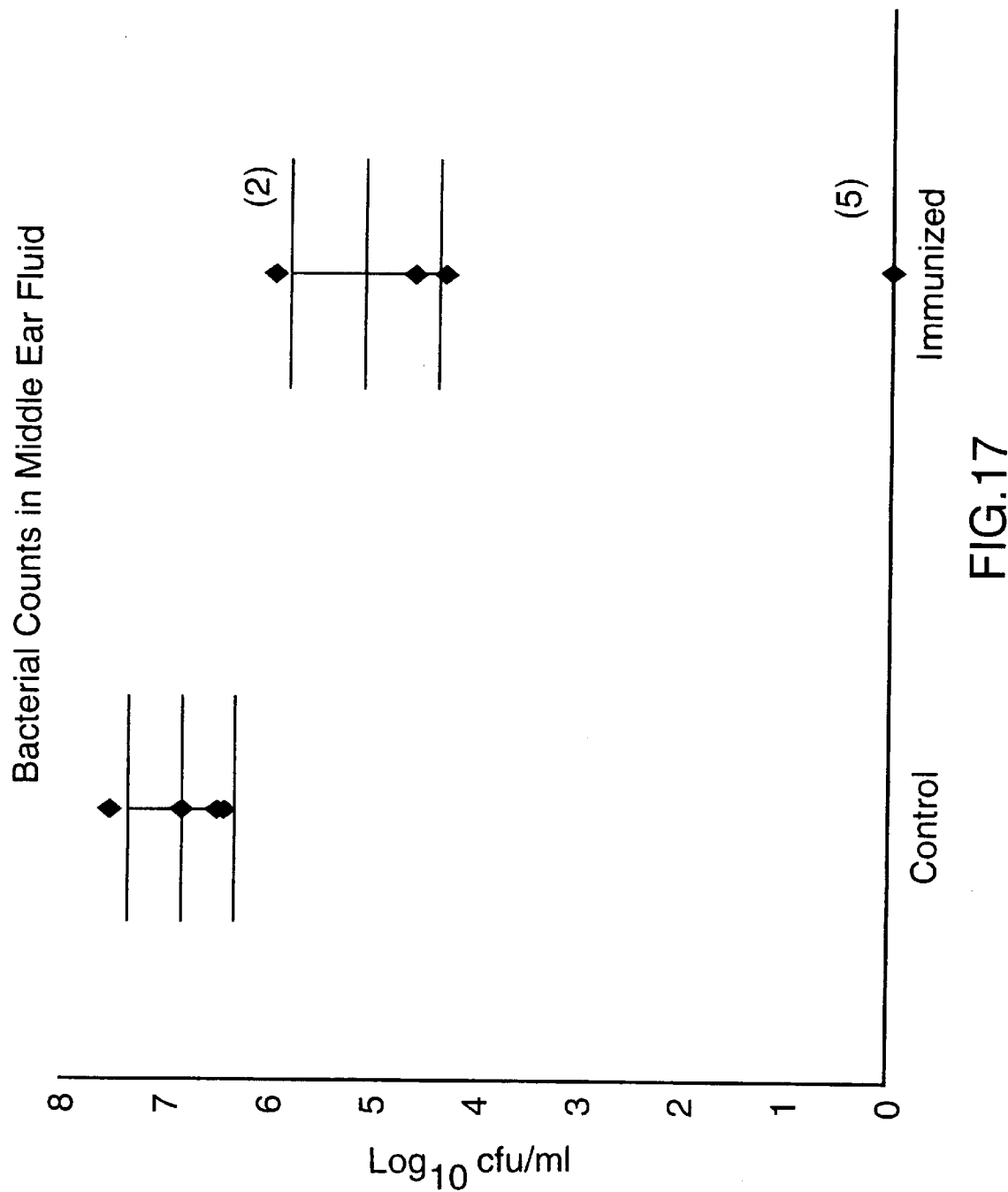
Figure 18:
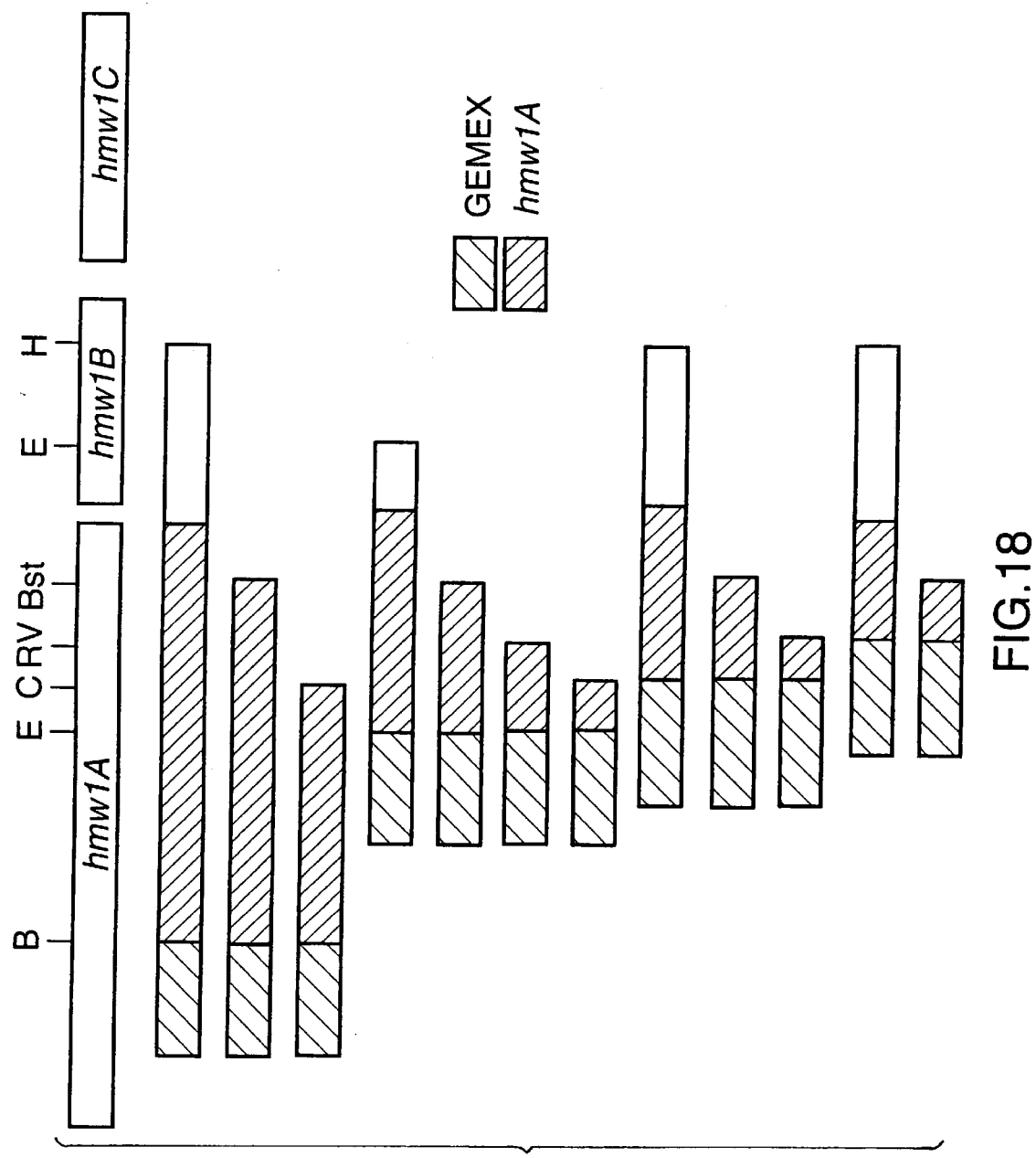
Figure 19:
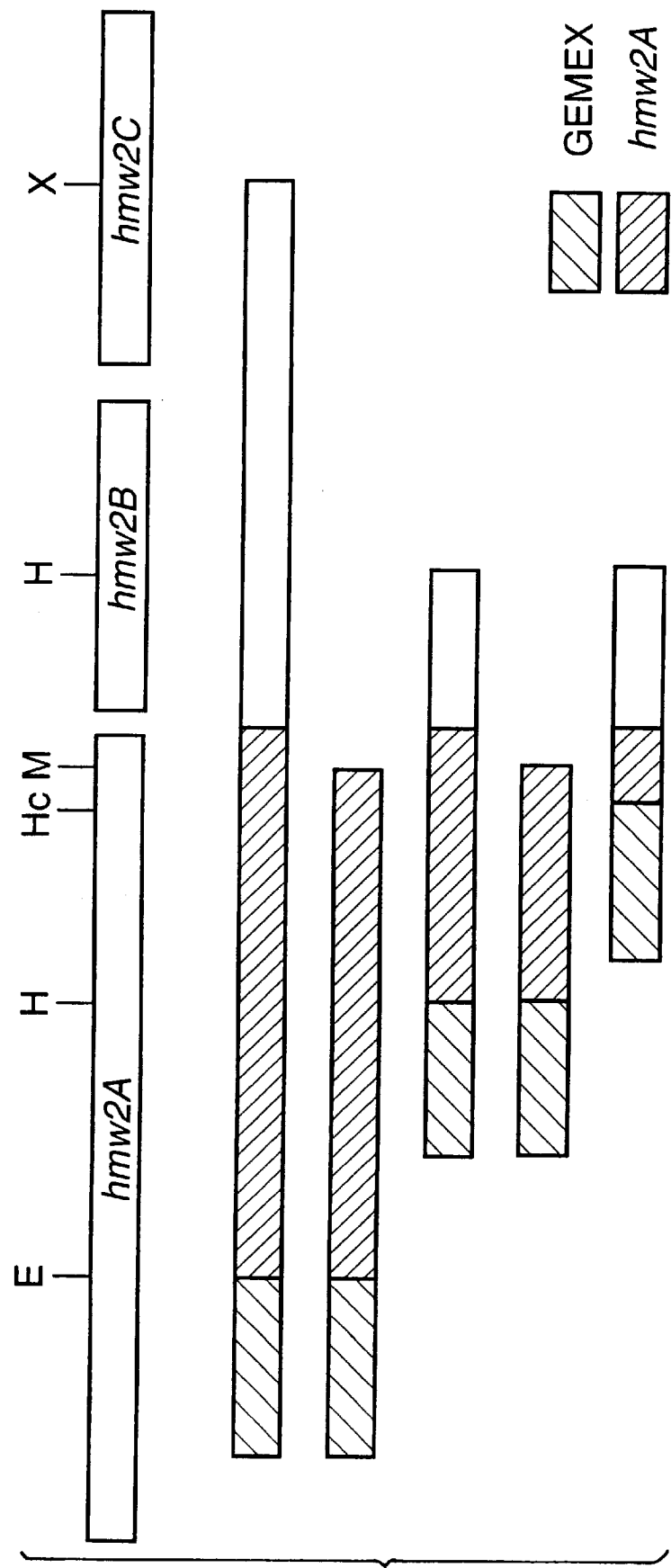
Figure 20:
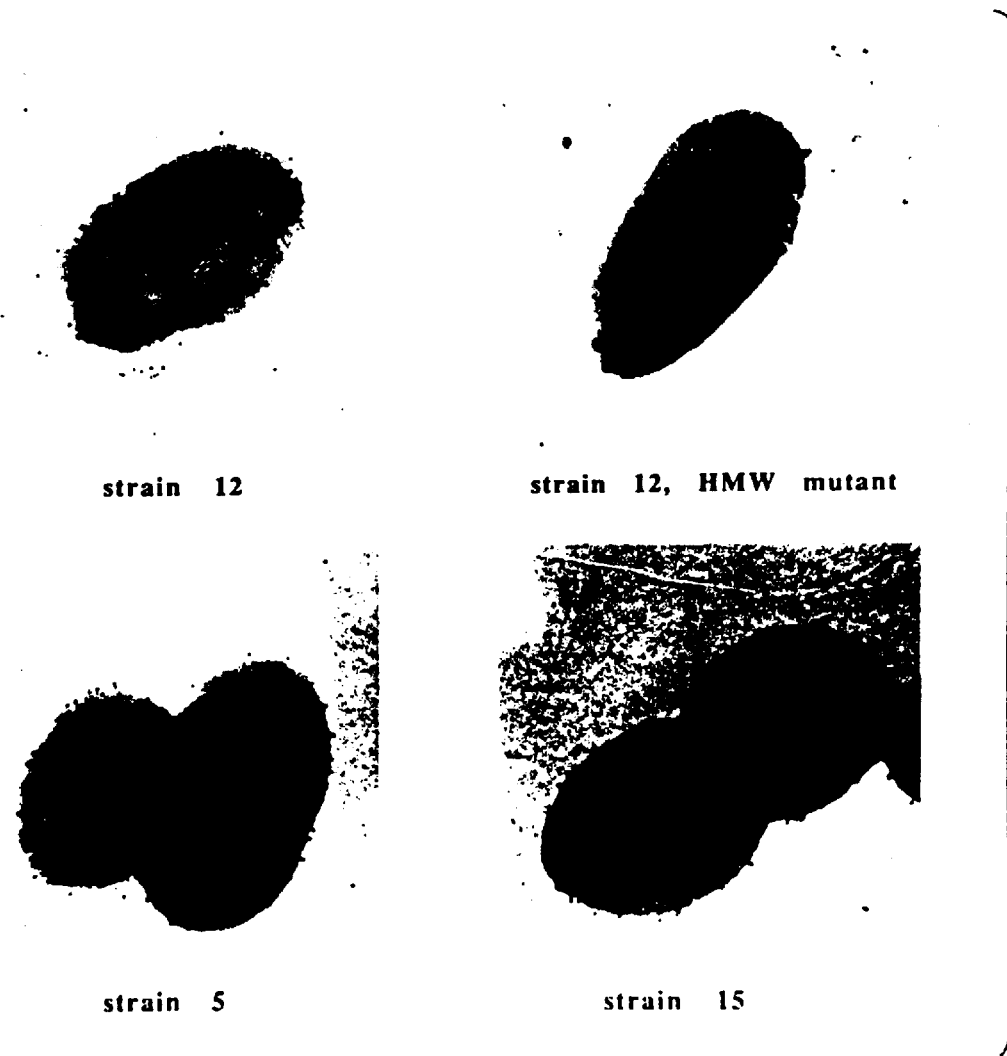
Figure 21:
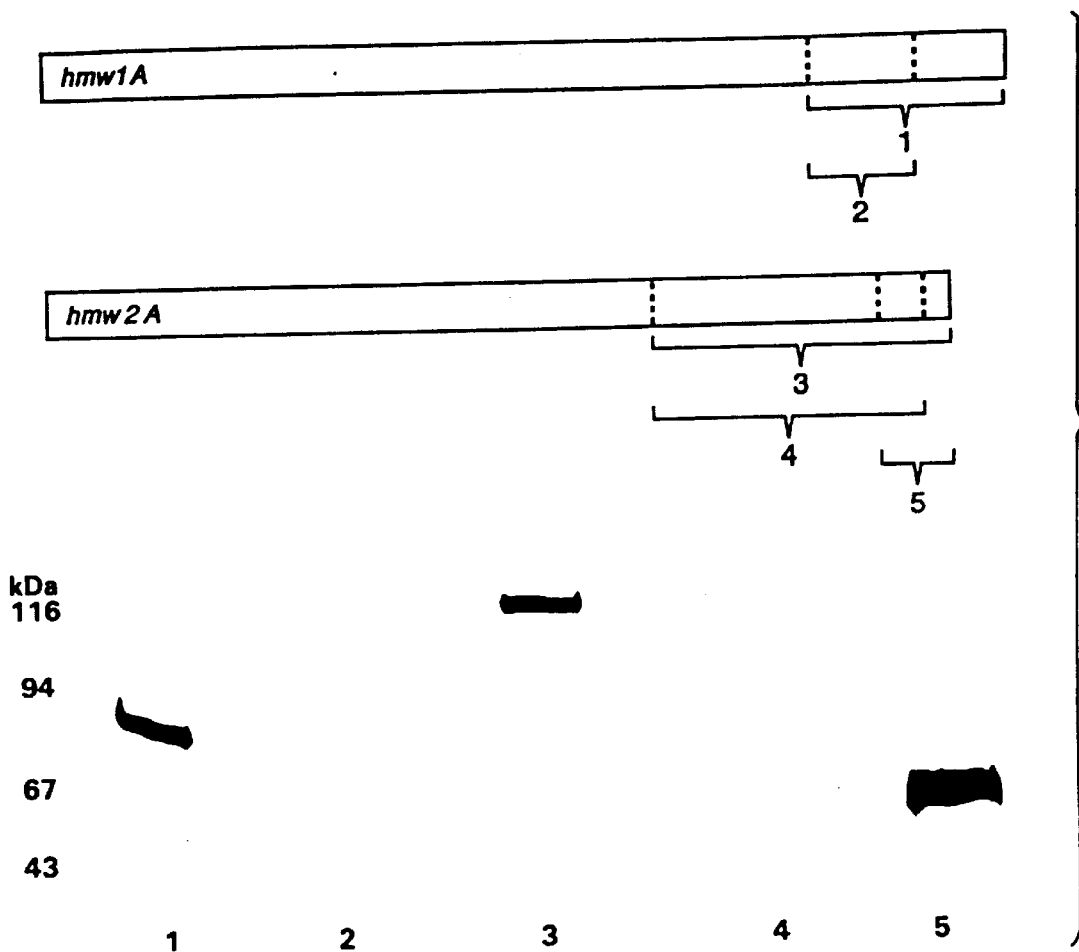
Figure 22:
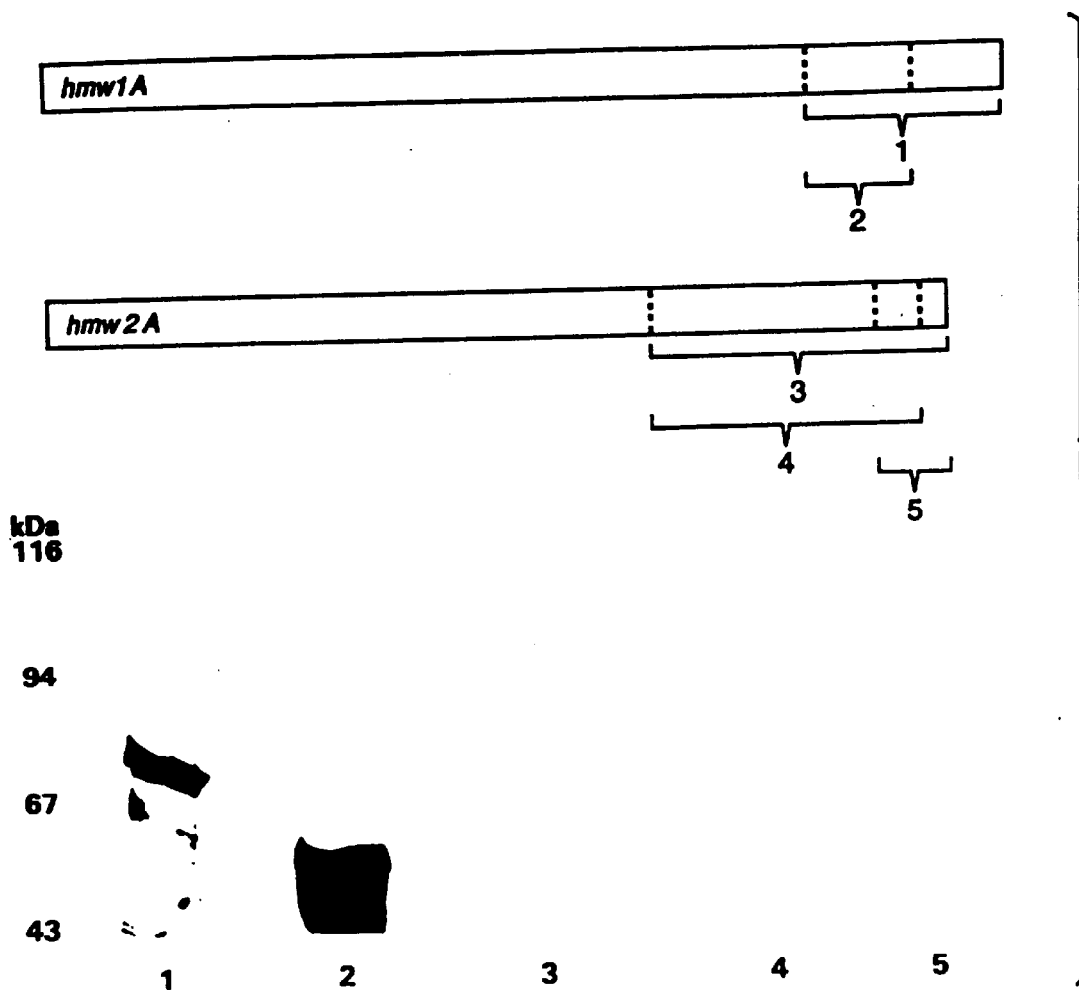
Figure 23:
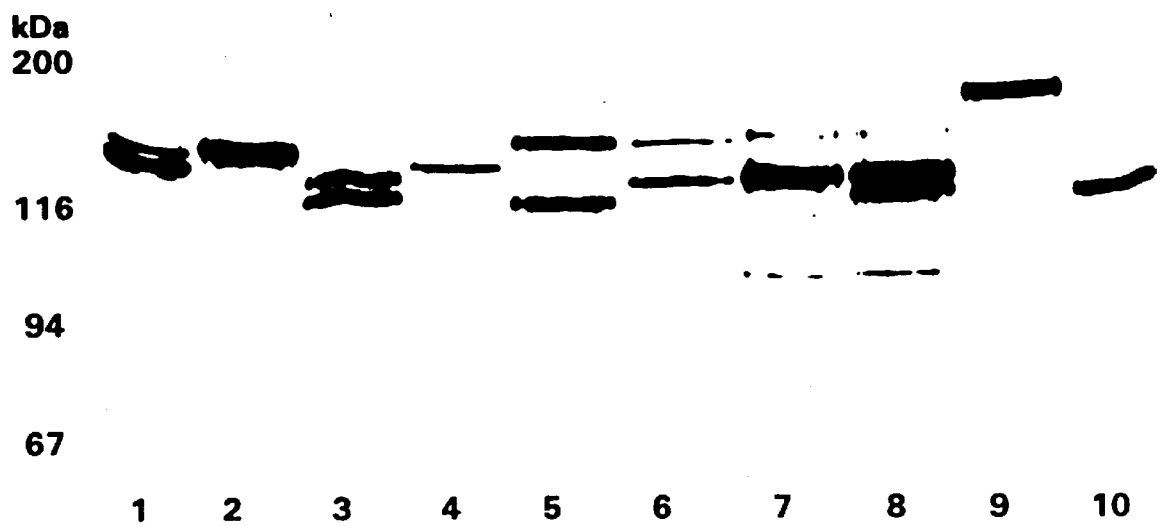
Figure 5A:
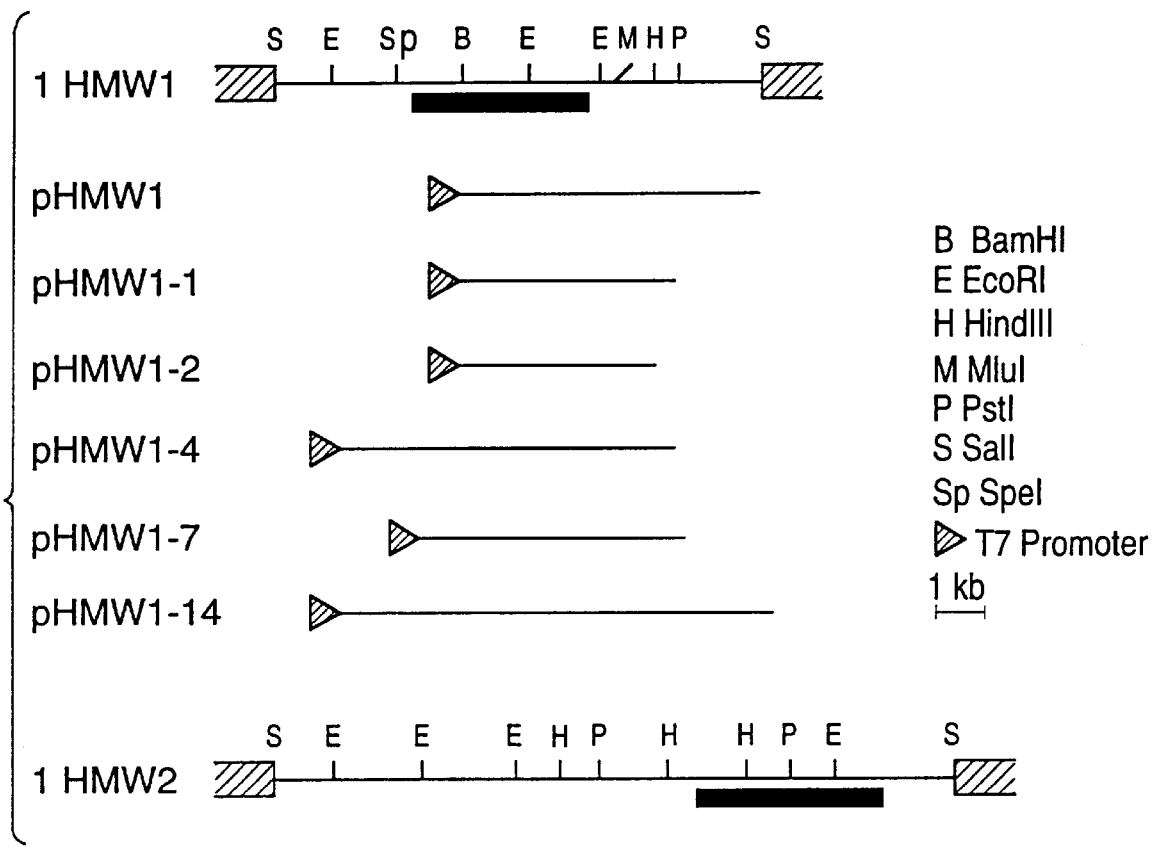

Lanes labelled U and I sequence sonicates prepared before and after indication of the growing samples with IPTG, respectively. The arrows indicate protein bands of interest as discussed below;

FIG. 13 is a graphical illustration of an ELISA with rHMW1 antiserum assayed against purified filamentous haemagglutinin of *B. pertussis*. Ab=antibody;

FIG. 14 is a Western immunoblot assay of cell sonicates from a panel of epidemiologically unrelated non-typeable *H. influenzae* strains. The sonicates were probed with rabbit antiserum prepared against HMW1-4 recombinant protein. The strain designations are indicated by the numbers below each line;

FIG. 15 is a Western immunoblot assay of cell sonicates from a panel of epidemiologically unrelated non-typeable *H. influenzae* strains. The sonicates were probed with monoclonal antibody X3C, a murine 1gG antibody which recognizes the filamentous hemagglutinin of *B. pertussis*. The strain designations are indicated by the numbers below each line;

FIG. 16 shows an immunoblot assay of cell sonicates of non-typeable *H. influenzae* strain 12 derivatives. The sonicates were probed with rabbit antiserum prepared against HMW-1 recombinant protein. Lanes: 1, wild-type strain; 2, HMW2$^-$ mutant; 3, HMW1$^-$ mutant; 4. HMW1$^-$ HMW2$^-$ double mutant;

FIG. 17 shows middle ear bacterial counts in PBS-immunized control animals (left panel) and HMW1/HMW2-immunized animals (right panel) seven days after middle ear inoculation with non-typeable *Haemophilus influenzae* strain 12. Data are log-transformed and the horizontal lanes indicate the means and standard deviations of middle ear fluid bacterial counts for only the infected animals in each group;

FIG. 18 is a schematic diagram of pGEMEX®-hmw1 recombinant plasmids. The restriction enzymes are B-BamHI, E-EcoRI, C-ClaI, RV-EcoRV, Bst-BstEII and H-HindIII;

FIG. 19 is a schematic diagram of pGEMEX®-hmw2 recombinant plasmids. The restriction enzymes are E-EcoRI, H-HindIII, Hc-HincII, M-MluI and X-XhoI;

FIG. 20 is an immunoelectron micrograph of representative non-typeable *Haemophilus influenzae* strains after incubation with monoclonal antibody AD6 followed by incubation with goat anti-mouse IgG conjugated with 10-nm colloidal gold particles. Strains are: upper left panel-strain 12; upper right panel-strain 12 mutant deficient in expression of the high molecular weight proteins; lower left panel-strain 5; lower right panel-strain 15;

FIG. 21 is a Western immunoblot assay with Mab AD6 and HMW1 or HMW2 recombinant proteins. The upper left panel indicates the segments of hmw1A or hmw2A structural genes which are being expressed in the recombinant proteins. The lane numbers correspond to the indicated segments;

FIG. 22 is a Western immunoblot assay with MAb 10C5 and HMW1 or HMW2 recombinant proteins. The upper panel indicates the segments of the hmw1A or hmw2A structural genes which are being expressed in the recombinant proteins. The lane numbers correspond to the indicated segments; and FIG. 23 is a Western immunoblot assay with MAb AD6 and a panel of unrelated non-typeable *Haemophilus influenzae* strains which express HMW1/HMW-2 like protein. Cell sonicates were prepared from freshly grown samples of each strain prior to analysis in the Western blot.

GENERAL DESCRIPTION OF INVENTION

The DNA sequences of the genes coding for the HMW1 and HMW2 proteins of non-typeable *Haemophilus influenzae* strain 12, shown in FIGS. 1 and 3 respectively, were shown to be about 80% identical, with the first 1259 base pairs of the genes being identical. The open reading frame extend from nucleotides 351 to 4958 and from nucleotide 382 to 4782 respectively. The derived amino acid sequences of the two HMW proteins, shown in FIGS. 2 and 4 respectively, are about 70% identical. Furthermore, the encoded proteins are antigenically related to the filamentous hemagglutinin surface protein of *Bordetella pertussis*. A monoclonal antibody prepared against filamentous hemagglutinin (FHA) of *Bordetella pertussis* was found to recognize both of the high molecular weight proteins. This data suggests that the HMW and FHA proteins may serve similar biological functions. The derived amino acid sequences of the HMW1 and HMW2 proteins show sequence similarity to that for the FHA protein. It has further been shown that these antigenically-related proteins are produced by the majority of the non-typeable strains of Haemophilus. Antisera raised against the protein expressed by the HMW1 gene recognizes both the HMW2 protein and the *B. pertussis* FHA. The present invention includes an isolated and purified high molecular weight protein of non-typeable haemophilus which is antigenically related to the *B. pertussis* FHA and which may be obtained from natural sources or produced recombinantly.

A phage genomic library of a known strain of non-typeable Haemophilus was prepared by standard methods and the library was screened for clones expressing high molecular weight proteins, using a high titre antiserum against HMW's. A number of strongly reactive DNA clones were plaque-purified and sub-cloned into a T7 expression plasmid. It was found that they all expressed either one or the other of the two high-molecular-weight proteins designated HMW1 and HMW2, with apparent molecular weights of 125 and 120 kDa, respectively, encoded by open reading frames of 4.6 kb and 4.4 kb, respectively.

Representative clones expressing either HMW1 or HMW2 were further characterized and the genes isolated, purified and sequenced. The DNA sequence of HMW1 is shown in FIG. 1 and the corresponding derived amino acid sequence in FIG. 2. Similarly, the DNA sequence of HMW2 is shown in FIG. 3 and the corresponding derived amino acid sequence in FIG. 4. Partial purification of the isolated proteins and N-terminal sequence analysis indicated that the expressed proteins are truncated since their sequence starts at residue number 442 of both full length HMW1 and HMW2 gene products.

Subcloning studies with respect to the hmw1 and hmw2 genes indicated that correct processing of the HMW proteins required the products of additional downstream genes. It has been found that both the hmw1 and hmw2 genes are flanked by two additional downstream open reading frames (ORFs), designated b and c, respectively, (see FIGS. 6 and 7).

The b ORFs are 1635 bp in length, extending from nucleotides 5114 to 6748 in the case of hmw1 and nucleotides 5375 to 7009 in the case of hmw2, with their derived amino acid sequences being 99% identical. The derived amino acid sequences demonstrate similarity with the derived amino acid sequences of two genes which encode proteins required for secretion and activation of hemolysins of *P. mirabilis* and *S. marcescens*.

The c ORFs are 1950 bp in length, extending from nucleotides 7062 to 9011 in the case of hmw1 and nucleotides 7249 to 9198 in the case of hmw2, with their derived amino acid sequences 96% identical. The hmw1c ORF is preceded by a series of 9 bp direct tandem repeats. In plasmid subclones, interruption of the hmw1 b or c ORF results in defective processing and secretion of the hmw1 structural gene product.

The two high molecular weight proteins HMW1 and HMW2 have been isolated and purified by the procedures described below in the Examples and shown to be protective against otitis media in chinchillas and to function as adhesins. These results indicate the potential for use of such high molecular proteins and structurally-related proteins of other non-typeable strains of *Haemophilus influenzae* as components in immunogenic compositions for protecting a susceptible host, such as a human infant, against disease caused by infection with non-typeable *Haemophilus influenzae*.

Since the proteins provided herein are good cross-reactive antigens and are present in the majority of non-typeable Haemophilus strains, it is evident that these HMW proteins may become integral constituents of a universal Haemophilus vaccine. Indeed, these proteins may be used not only as protective antigens against otitis, sinusitis and bronchitis caused by the non-typeable Haemophilus strains, but also may be used as carriers for the protective Hib polysaccharides in a conjugate vaccine against meningitis. The proteins also may be used as carriers for other antigens, haptens and polysaccharides from other organisms, so as to induce immunity to such antigens, haptens and polysaccharides.

The nucleotide sequences encoding two high molecular weight proteins of a different non-typeable Haemophilus strain (designated HMW3 and HMW4), namely strain 5 have been elucidated, and are presented in FIGS. 8 and 9 (SEQ ID Nos: 7 and 8). HMW3 has an apparent molecular weight of 125 kDa while HMW4 has an apparent molecular weight of 123 kDa. These high molecular weight proteins are antigenically related to the HMW1 and HMW2 proteins and to FHA. FIG. 10 contains a multiple sequence comparison of the derived amino acid sequences for the four high molecular weight proteins identified herein (HMW1, SEQ ID No: 2; HMW2, SEQ ID No: 4; HMW3, SEQ ID No: 9; HMW4, SEQ ID No. 10). As may be seen from this comparison, stretches of identical amino acid sequence may be found throughout the length of the comparison, with HMW3 more closely resembling HMW1 and HMW4 more closely resembling HMW2. This information is highly suggestive of a considerable sequence homology between high molecular weight proteins from various non-typeable Haemophilus strains. This information is also suggestive that the HMW3 and HMW4 proteins will have the same immunological properties as the HMW1 and HMW2 proteins and that corresponding HMW proteins from other non-typeable Haemophilus strains will have the same immunological properties as the HMW1 and HMW2 proteins.

In addition, mutants of non-typeable *H. influenzae* strains that are deficient in expression of HMW1 or HMW2 or both have been constructed and examined for their capacity to adhere to cultured human epithelial cells. The hmw1 and hmw2 gene clusters have been expressed in *E. coli* and have been examined for in vitro adherence. The results of such experimentation, described below, demonstrate that both HMW1 and HMW2 mediate attachment and hence are adhesins and that this function is present even in the absence of other *H. influenzae* surface structures. The ability of a bacterial surface protein to function as an adhesin provides strong in vitro evidence for its potential role as a protective antigen. In view of the considerable sequence homology between the HMW3 and HMW4 proteins and the HMW1 and HMW2 proteins, these results indicate that HMW3 and HMW4 also are likely to function as adhesins and that other HMW proteins of other strains of non-typeable *Haemophilus influenzae* similarly are likely to function as adhesins. This expectation is borne out by the results described in the Examples below.

With the isolation and purification of the high molecular weight proteins, the inventor is able to determine the major protective epitopes of the proteins by conventional epitope mapping and synthesizing peptides corresponding to these determinants for incorporation into fully synthetic or recombinant vaccines. Accordingly, the invention also comprises a synthetic peptide having at least six and no more than 150 amino acids and having an amino acid sequence corresponding to at least one protective epitope of a high molecular weight protein of a non-typeable *Haemophilus influenzae*. Such peptides are of varying length that constitute portions of the high molecular weight proteins, that can be used to induce immunity, either directly or as part of a conjugate, against the respective organisms and thus constitute active components of immunogenic compositions for protection against the corresponding diseases.

In particular, the applicant has sought to identify regions of the high molecular weight proteins which are demonstrated experimentally to be surface-exposed B-cell epitopes and which are common to all or at least a large number of non-typeable strains of *Haemophilus influenzae*. The strategy which has been adopted by the inventor has been to:

(a) generate a panel of monoclonal antibodies reactive with the high molecular weight proteins;

(b) screen those monoclonal antibodies for reactivity with surface epitopes of intact bacteria using immunoelectron microscopy or other suitable screening technique;

(c) map the epitopes recognized by the monoclonal antibody by determining the reactivity of the monoclonals with a panel of recombinant fusion proteins; and (d) determining the reactivity of the monoclonal antibodies with heterologous non-typable *Haemophilus influenzae* strains using standard Western blot assays.

Using this approach, the inventor has identified one monoclonal antibody, designated AD6, which recognized a surface-exposed B-cell epitope common to all non-typeable *H. influenzae* which express the HMW1 and HMW2 proteins. The epitope recognized by this antibody was mapped to a 75 amino acid sequence at the carboxy termini of both HMW1 and HMW2 proteins. The ability to identify shared surface-exposed epitopes on the high molecular weight adhesion proteins suggests that it would be possible to develop recombinant or synthetic peptide based vaccines which would be protective against disease caused by the majority of non-typeable *Haemophilus influenzae*.

The present invention also provides any variant or fragment of the proteins that retains the potential immunological ability to protect against disease caused by non-typeable Haemophilus strains. The variants may be constructed by partial deletions or mutations of the genes and expression of the resulting modified genes to give the protein variants.

It is clearly apparent to one skilled in the art, that the various embodiments of the present invention have many applications in the fields of vaccination, diagnosis, treatment of bacterial infections and the generation of immunological reagents. A further non-limiting discussion of such uses is further presented below.

1. Vaccine Preparation and Use

Immunogenic compositions, suitable to be used as vaccines, may be prepared from the high molecular weight proteins of *Haemophilus influenzae*, as well as analogs and fragments thereof, and synthetic peptides containing epitopes of the protein, as disclosed herein. The immunogenic composition elicits an immune response which produces antibodies, including anti-high molecular weight protein antibodies and antibodies that are opsonizing or bactericidal.

Immunogenic compositions, including vaccines, may be prepared as injectables, as liquid solutions or emulsions. The active component may be mixed with pharmaceutically acceptable excipients which are compatible therewith. Such excipients may include, water, saline, dextrose, glycerol, ethanol, and combinations thereof. The immunogenic compositions and vaccines may further contain auxiliary substances, such as wetting or emulsifying agents, pH buffering agents, or adjuvants to enhance the effectiveness thereof. Immunogenic compositions and vaccines may be administered parenterally, by injection subcutaneously or intramuscularly. Alternatively, the immunogenic compositions formed according to the present invention, may be formulated and delivered in a manner to evoke an immune response at mucosal surfaces. Thus, the immunogenic composition may be administered to mucosal surfaces by, for example, the nasal or oral (intragastric) routes. Alternatively, other modes of administration including suppositories and oral formulations may be desirable. For suppositories, binders and carriers may include, for example, polyalkalene glycols or triglycerides. Oral formulations may include normally employed incipients such as, for example, pharmaceutical grades of saccharine, cellulose and magnesium carbonate. These compositions can take the form of solutions, suspensions, tablets, pills, capsules, sustained release formulations or powders and contain about 1 to 95% of the active component. The immunogenic preparations and vaccines are administered in a manner compatible with the dosage formulation, and in such amount as will be therapeutically effective, protective and immunogenic. The quantity to be administered depends on the subject to be treated, including, for example, the capacity of the individual's immune system to synthesize antibodies, and if needed, to produce a cell-mediated immune response. Precise amounts of active ingredient required to be administered depend on the judgment of the practitioner. However, suitable dosage ranges are readily determinable by one skilled in the art and may be of the order of micrograms of the HMW proteins. Suitable regimes for initial administration and booster doses are also variable, but may include an initial administration followed by subsequent administrations. The dosage may also depend on the route of administration and will vary according to the size of the host.

The concentration of the active component in an immunogenic composition according to the invention is in general about 1 to 95%. A vaccine which contains antigenic material of only one pathogen is a monovalent vaccine. Vaccines which contain antigenic material of several pathogens are combined vaccines and also belong to the present invention. Such combined vaccines contain, for example, material from various pathogens or from various strains of the same pathogen, or from combinations of various pathogens.

Immunogenicity can be significantly improved if the antigens are co-administered with adjuvants, commonly used as 0.05 to 0.1 percent solution in phosphate-buffered saline. Adjuvants enhance the immunogenicity of an antigen but are not necessarily immunogenic themselves. Adjuvants may act by retaining the antigen locally near the site of administration to produce a depot effect facilitating a slow, sustained release of antigen to cells of the immune system. Adjuvants can also attract cells of the immune system to an antigen depot and stimulate such cells to elicit immune responses.

Immunostimulatory agents or adjuvants have been used for many years to improve the host immune responses to, for example, vaccines. Intrinsic adjuvants, such as lipopolysaccharides, normally are the components of the killed or attenuated bacteria used as vaccines. Extrinsic adjuvants are immunomodulators which are typically non-covalently linked to antigens and are formulated to enhance the host immune responses. Thus, adjuvants have been identified that enhance the immune response to antigens delivered parenterally. Some of these adjuvants are toxic, however, and can cause undesirable side-effects, making them unsuitable for use in humans and many animals. Indeed, only aluminum hydroxide and aluminum phosphate (collectively commonly referred to as alum) are routinely used as adjuvants in human and veterinary vaccines. The efficacy of alum in increasing antibody responses to diphtheria and tetanus toxoids is well established and a HBsAg vaccine has been adjuvanted with alum. While the usefulness of alum is well established for some applications, it has limitations. For example, alum is ineffective for influenza vaccination and inconsistently elicits a cell mediated immune response. The antibodies elicited by alum-adjuvanted antigens are mainly of the IgG1 isotype in the mouse, which may not be optimal for protection by some vaccinal agents.

A wide range of extrinsic adjuvants can provoke potent immune responses to antigens. These include saponins complexed to membrane protein antigens (immune stimulating complexes), pluronic polymers with mineral oil, killed mycobacteria in mineral oil, Freund's complete adjuvant, bacterial products, such as muramyl dipeptide (MDP) and lipopolysaccharide (LPS), as well as lipid A, and liposomes.

To efficiently induce humoral immune responses (HIR) and cell-mediated immunity (CMI), immunogens are often emulsified in adjuvants. Many adjuvants are toxic, inducing granulomas, acute and chronic inflammations (Freund's complete adjuvant, FCA), cytolysis (saponins and Pluronic polymers) and pyrogenicity, arthritis and anterior uveitis (LPS and MDP). Although FCA is an excellent adjuvant and widely used in research, it is not licensed for use in human or veterinary vaccines because of its toxicity.

Desirable characteristics of ideal adjuvants include:
(1) lack of toxicity;
(2) ability to stimulate a long-lasting immune response;
(3) simplicity of manufacture and stability in long-term storage;
(4) ability to elicit both CMI and HIR to antigens administered by various routes, if required;
(5) synergy with other adjuvants;
(6) capability of selectively interacting with populations of antigen presenting cells (APC);
(7) ability to specifically elicit appropriate $T_H1$ or $T_H2$ cell-specific immune responses; and
(8) ability to selectively increase appropriate antibody isotype levels (for example, IgA) against antigens.

U.S. Pat. No. 4,855,283 granted to Lockhoff et al on Aug. 8, 1989 which is incorporated herein by reference thereto teaches glycolipid analogues including N-glycosylamides, N-glycosylureas and N-glycosylcarbamates, each of which is substituted in the sugar residue by an amino acid, as immuno-modulators or adjuvants. Thus, Lockhoff et al. (U.S. Pat. No. 4,855,283 and ref. 29) reported that N-glycolipid analogs displaying structural similarities to the naturally-occurring glycolipids, such as glycosphingolipids and glycoglycerolipids, are capable of eliciting strong immune responses in both herpes simplex virus vaccine and pseudorabies virus vaccine. Some glycolipids have been synthesized from long chain-alkylamines and fatty acids that are linked directly with the sugars through the anomeric carbon atom, to mimic the functions of the naturally occurring lipid residues.

U.S. Pat. No. 4,258,029 granted to Moloney, incorporated herein by reference thereto, teaches that octadecyl tyrosine hydrochloride (OTH) functioned as an adjuvant when complexed with tetanus toxoid and formalin inactivated type I, II and III poliomyelitis virus vaccine. Also, Nixon-George et al. (ref. 30), reported that octadecyl esters of aromatic amino acids complexed with a recombinant hepatitis B surface antigen, enhanced the host immune responses against hepatitis B virus.

Lipidation of synthetic peptides has also been used to increase their immunogenicity. Thus, Wiesmuller 1989, describes a peptide with a sequence homologous to a foot-and-mouth disease viral protein coupled to an adjuvant tripalmityl-s-glyceryl-cysteinylserylserine, being a synthetic analogue of the N-terminal part of the lipoprotein from Gram negative bacteria. Furthermore, Deres et al. 1989, reported in vivo priming of virus-specific cytotoxic T lymphocytes with synthetic lipopeptide vaccine which comprised of modified synthetic peptides derived from influenza virus nucleoprotein by linkage to a lipopeptide, N-palmityl-s-[2,3-bis(palmitylxy)-(2RS)-propyl-[R]-cysteine (TPC).

2. Immunoassays

The high molecular weight protein of *Haemophilus influenzae* of the present invention is useful as an immunogen for the generation of anti-protein antibodies, as an antigen in immunoassays including enzyme-linked immunosorbent assays (ELISA), RIAs and other non-enzyme linked antibody binding assays or procedures known in the art for the detection of antibodies. In ELISA assays, the protein is immobilized onto a selected surface, for example, a surface capable of binding proteins, such as the wells of a polystyrene microtiter plate. After washing to remove incompletely adsorbed protein, a nonspecific protein, such as a solution of bovine serum albumin (BSA) that is known to be antigenically neutral with regard to the test sample, may be bound to the selected surface. This allows for blocking of nonspecific adsorption sites on the immobilizing surface and thus reduces the background caused by nonspecific bindings of antisera onto the surface.

The immobilizing surface is then contacted with a sample, such as clinical or biological materials, to be tested in a manner conducive to immune complex (antigen/antibody) formation. This may include diluting the sample with diluents, such as solutions of BSA, bovine gamma globulin (BGG) and/or phosphate buffered saline (PBS)/Tween. The sample is then allowed to incubate for from about 2 to 4 hours, at temperatures such as of the order of about 25° to 37° C. Following incubation, the sample-contacted surface is washed to remove non-immunocomplexed material. The washing procedure may include washing with a solution, such as PBS/Tween or a borate buffer. Following formation of specific immunocomplexes between the test sample and the bound protein, and subsequent washing, the occurrence, and even amount, of immunocomplex formation may be determined by subjecting the immunocomplex to a second antibody having specificity for the first antibody. If the test sample is of human origin, the second antibody is an antibody having specificity for human immunoglobulins and in general IgG. To provide detecting means, the second antibody may have an associated activity such as an enzymatic activity that will generate, for example, a colour development upon incubating with an appropriate chromogenic substrate. Quantification may then be achieved by measuring the degree of colour generation using, for example, a visible spectra spectrophotometer.

3. Use of sequences as Hybridization Probes

The nucleotide sequences of the present invention, comprising the sequences of the genes encoding the high molecular weight proteins of specific strains of non-typeable *Haemophilus influenzae*, now allow for the identification and cloning of the genes from any species of non-typeable Haemophilus and other strains of non-typeable *Haemophilus influenzae*.

The nucleotide sequences comprising the sequences of the genes of the present invention are useful for their ability to selectively form duplex molecules with complementary stretches of other genes of high molecular weight proteins of non-typeable Haemophilus. Depending on the application, a variety of hybridization conditions may be employed to achieve varying degrees of selectivity of the probe toward the other genes. For a high degree of selectivity, relatively stringent conditions are used to form the duplexes, such as low salt and/or high temperature conditions, such as provided by 0.02 M to 0.15 M NaCl at temperatures of between about 50° C. to 70C. For some applications, less stringent hybridization conditions are required such as 0.15 M to 0.9 M salt, at temperatures ranging from between about 20° C. to 55° C. Hybridization conditions can also be rendered more stringent by the addition of increasing amounts of formamide, to destabilize the hybrid duplex. Thus, particular hybridization conditions can be readily manipulated, and will generally be a method of choice depending on the desired results. In general, convenient hybridization temperatures in the presence of 50% formamide are: 42° C. for a probe which is 95 to 100% homologous to the target fragment, 37° C. for 90 to 95% homology and 32° C. for 85 to 90% homology.

In a clinical diagnostic embodiment, the nucleic acid sequences of the genes of the present invention may be used in combination with an appropriate means, such as a label, for determining hybridization. A wide variety of appropriate indicator means are known in the art, including radioactive, enzymatic or other ligands, such as avidin/biotin, which are capable of providing a detectable signal. In some diagnostic embodiments, an enzyme tag such as urease, alkaline phosphatase or peroxidase, instead of a radioactive tag may be used. In the case of enzyme tags, calorimetric indicator substrates are known which can be employed to provide a means visible to the human eye or spectrophotometrically, to identify specific hybridization with samples containing gene sequences encoding high molecular weight proteins of non-typeable Haemophilus.

The nucleic acid sequences of genes of the present invention are useful as hybridization probes in solution hybridizations and in embodiments employing solid-phase procedures. In embodiments involving solid-phase procedures, the test DNA (or RNA) from samples, such as clinical samples, including exudates, body fluids (e. g., serum, amniotic fluid, middle ear effusion, sputum, bronchoalveolar lavage fluid) or even tissues, is adsorbed or otherwise affixed to a selected matrix or surface. The fixed, single-stranded nucleic acid is then subjected to specific hybridization with selected probes comprising the nucleic acid sequences of the genes or fragments thereof of the present invention under desired conditions. The selected conditions will depend on the particular circumstances based on the particular criteria required depending on, for example, the G+C contents, type of target nucleic acid, source of nucleic acid, size of hybridization probe etc. Following washing of the hybridization surface so as to remove non-specifically bound probe molecules, specific hybridization is detected, or even quantified, by means of the label. As with the selection of peptides, it is preferred to select nucleic acid sequence portions which are conserved among species of non-typeable Haemophilus. The selected probe may be at least about 18 bp and may be in the range of about 30 bp to about 90 bp long.

4. Expression of the High Molecular Weight Protein Genes

Plasmid vectors containing replicon and control sequences which are derived from species compatible with the host cell may be used for the expression of the genes encoding high molecular weight proteins of non-typeable Haemophilus in expression systems. The vector ordinarily carries a replication site, as well as marking sequences which are capable of providing phenotypic selection in transformed cells. For example, *E. coli* may be transformed using pBR322 which contains genes for ampicillin and tetracycline resistance and thus provides easy means for identifying transformed cells. The pBR322 plasmid, or other microbial plasmid or phage must also contain, or be modified to contain, promoters which can be used by the host cell for expression of its own proteins.

In addition, phage vectors containing replicon and control sequences that are compatible with the host can be used as a transforming vector in connection with these hosts. For example, the phage in lambda GEM™-11 may be utilized in making recombinant phage vectors which can be used to transform host cells, such as *E. coli* LE392.

Promoters commonly used in recombinant DNA construction include the β-lactamase (penicillinase) and lactose promoter systems (Chang et al., 1978: Itakura et al., 1977 Goeddel et al., 1979; Goeddel et al., 1980) and other microbial promoters such as the T7 promoter system (U.S. Pat. No. 4,952,496). Details concerning the nucleotide sequences of promoters are known, enabling a skilled worker to ligate them functionally with genes. The particular promoter used will generally be a matter of choice depending upon the desired results. Hosts that are appropriate for expression of the genes encoding the high molecular weight proteins, fragment analogs or variants thereof, include *E. coli*, Bacillus species, Haemophilus, fungi, yeast or the baculovirus expression system may be used.

In accordance with this invention, it is preferred to make the high molecular weight proteins by recombinant methods, particularly since the naturally occurring high molecular weight protein as purified from a culture of a species of non-typeable Haemophilus may include trace amounts of toxic materials or other contaminants. This problem can be avoided by using recombinantly produced proteins in heterologous systems which can be isolated from the host in a manner to minimize comtaminants in the purified material. Particularly desirable hosts for expression in this regard include Gram positive bacteria which do not have LPS and are, therefore, endotoxin free. Such hosts include species of Bacillus and may be particularly useful for the production of non-pyrogenic high molecular weight protein, fragments or analogs thereof. Furthermore, recombinant methods of production permit the manufacture of HMW1, HMW2, HMW3 or HMW4, and corresponding HMW proteins from other non-typeable *Haemophilus influenzae* strains, or fragments thereof, separate from one another and devoid of non-HMW protein of non-typeable *Haemophilus influenzae*.

Biological Deposits

Certain hybridomas producing monoclonal antibodies specific for high molecular weight protein of *Haemophilus influenzae* according to aspects of the present invention that are described and referred to herein have been deposited with the American Type Culture Collection (ATCC) located at 12301 Parklawn Drive, Rockville, Md., USA, 20852, pursuant to the Budapest Treaty and prior to the filing of this application. Samples of the deposited hybridomas will become available to the public upon grant of a patent based upon this United States patent application. The invention described and claimed herein is not to be limited in scope by the hybridomas deposited, since the deposited embodiment is intended only as an illustration of the invention. Any equivalent or similar hybridomas that produce similar or equivalent antibodies as described in this application are within the scope of the invention.

EXAMPLES

The above disclosure generally describes the present invention. A more complete understanding can be obtained by reference to the following specific Examples. These Examples are described solely for purposes of illustration and are not intended to limit the scope of the invention. Changes in form and substitution of equivalents are contemplated as circumstances may suggest or render expedient. Although specific terms have been employed herein, such terms are intended in a descriptive sense and not for purposes of limitations.

Methods of molecular genetics, protein biochemistry, and immunology used but not explicitly described in this disclosure and these Examples are amply reported in the scientific literature and are well within the ability of those skilled in the art.

Example 1

This Example describes the isolation of DNA encoding HMW1 and HMW2 proteins, cloning and expression of such proteins, and sequencing and sequence analysis of the DNA molecules encoding the HMW1 and HMW2 proteins.

Non-typeable *H.influenzae* strains 5 and 12 were isolated in pure culture from the middle ear fluid of children with acute otitis media. Chromosomal DNA from strain 12, providing genes encoding proteins HMW1 and HMW2, was prepared by preparing Sau3A partial restriction digests of chromosomal DNA and fractionating on sucrose gradients. Fractions containing DNA fragments in the 9 to 20 kbp range were pooled and a library was prepared by ligation into λEMBL3 arms. Ligation mixtures were packaged in vitro and plate-amplified in a P2 lysogen of *E. coli* LE392.

For plasmid subcloning studies, DNA from a representative recombinant phage was subcloned into the T7 expression plasmid pT7-7, containing the T7 RNA polymerase promoter Φ10, a ribosome-binding site and the translational start site for the T7 gene 10 protein upstream from a multiple cloning site (see FIG. 5B).

DNA sequence analysis was performed by the dideoxy method and both strands of the HMW1 gene and a single strand of the HMW2 gene were sequenced.

Figure 11:
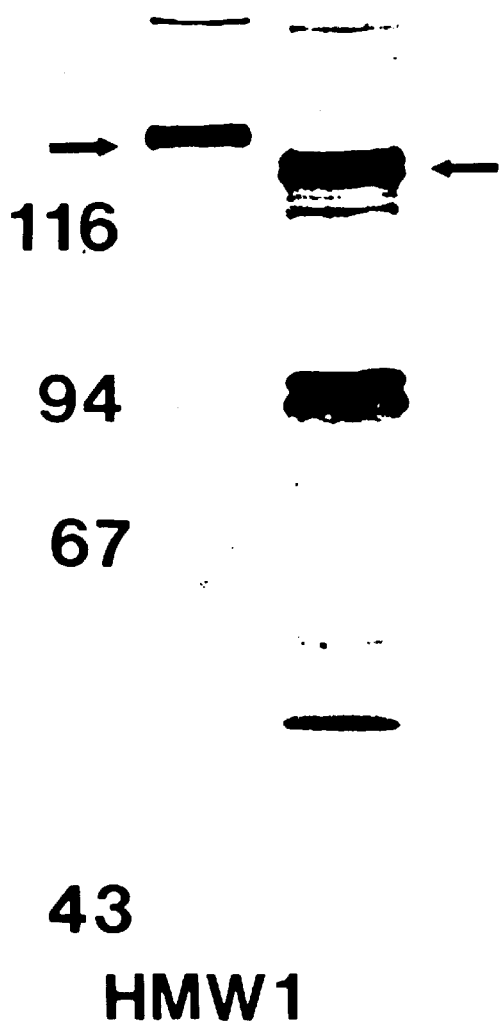
FIG. 11 illustrates a Western immunoblot assay of phage lysates containing either the HMW1 or HMW2 recombinant proteins. Lysates were probed with an *E. coli*-absorbed adult serum sample with high-titer antibody against high molecular weight proteins. The arrows indicate the major immunoreactive bands of 125 and 120 kDa in the HMW1 and HMW2 lysates respectively.
Figure 14:
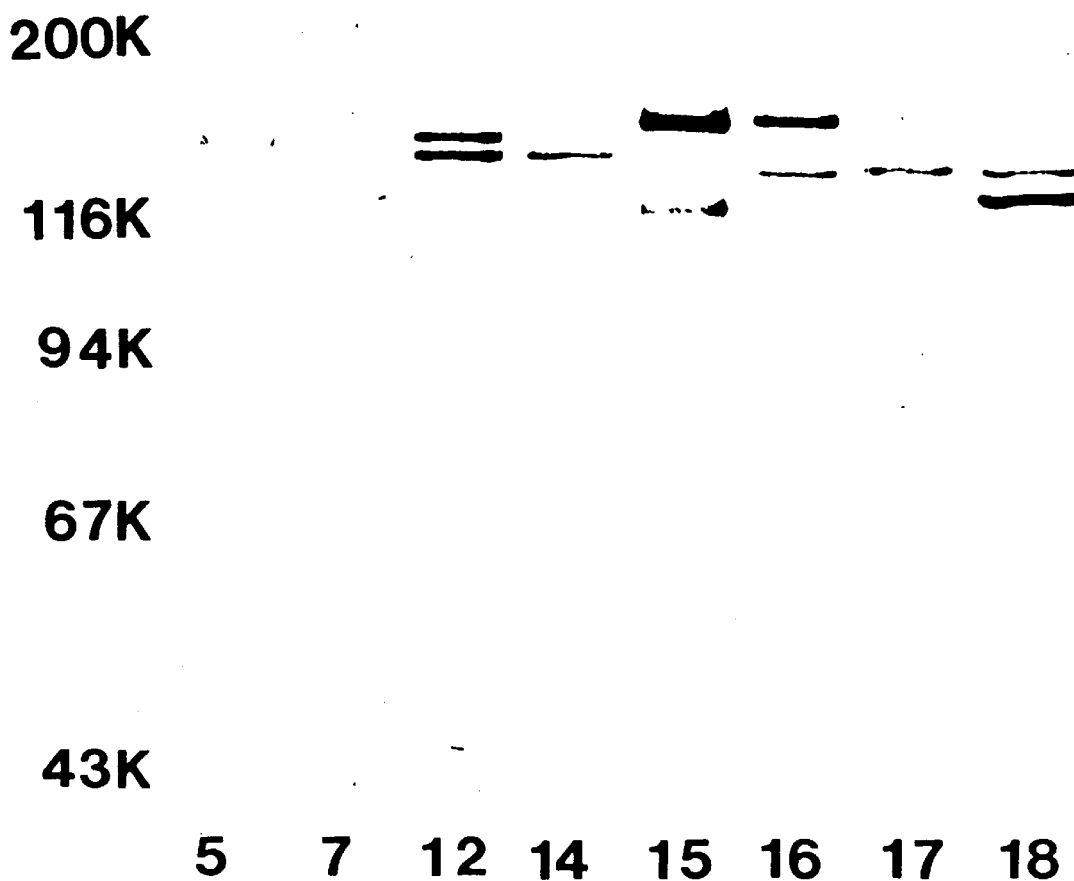
Figure 15:
Figure 16:
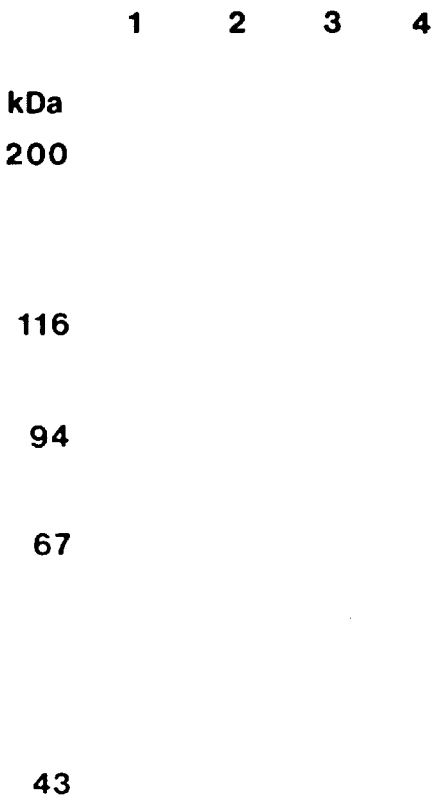
Figure 17:
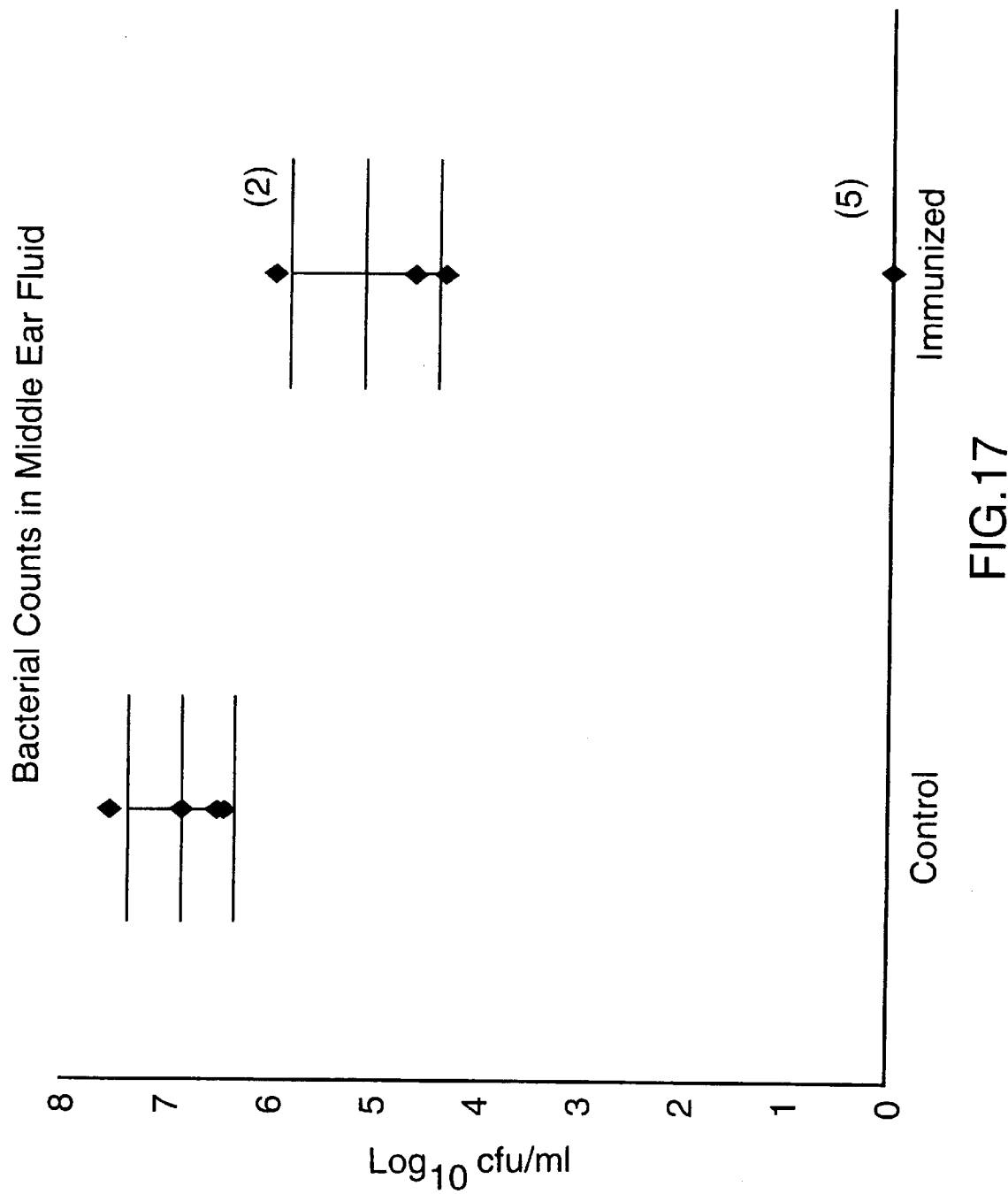
Figure 18:
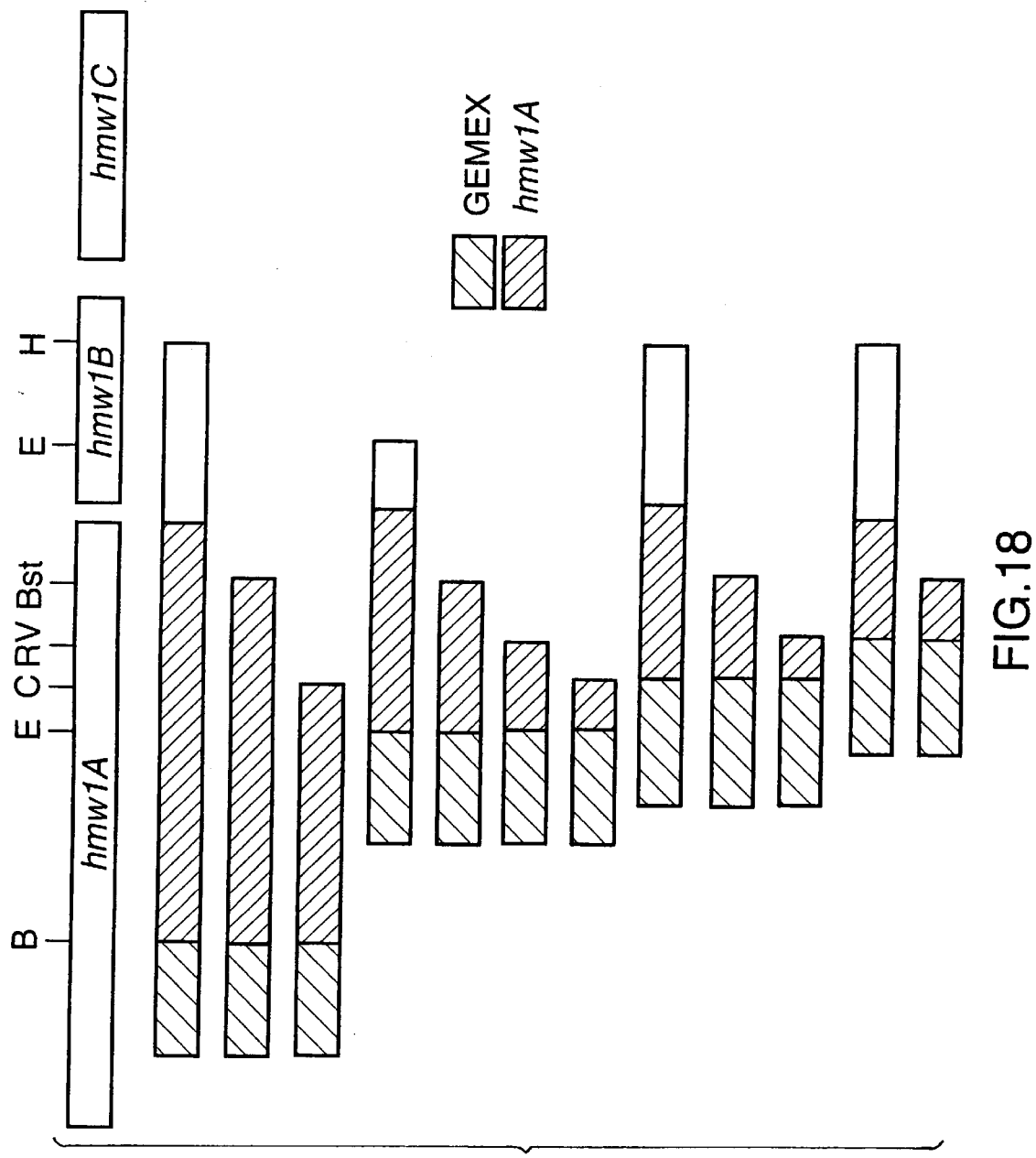
Figure 19:
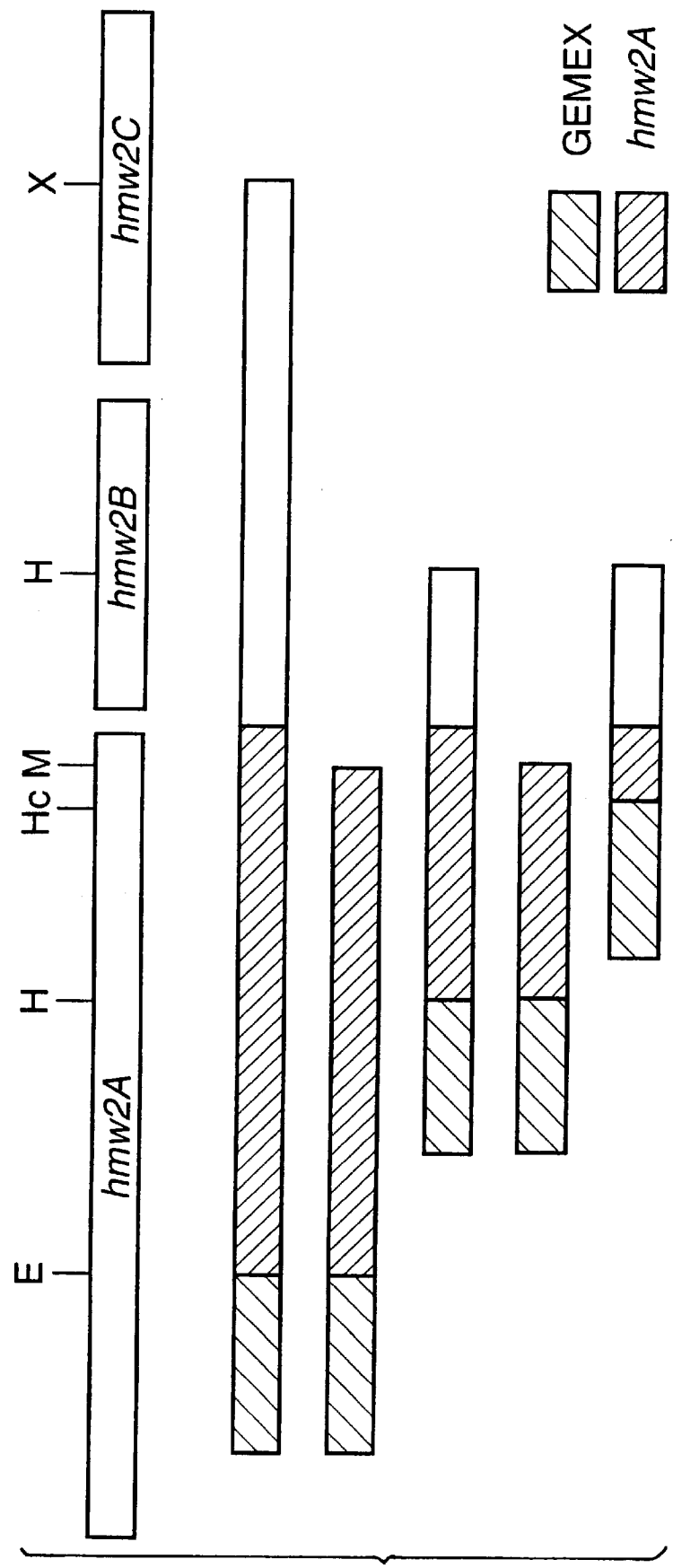
Figure 20:
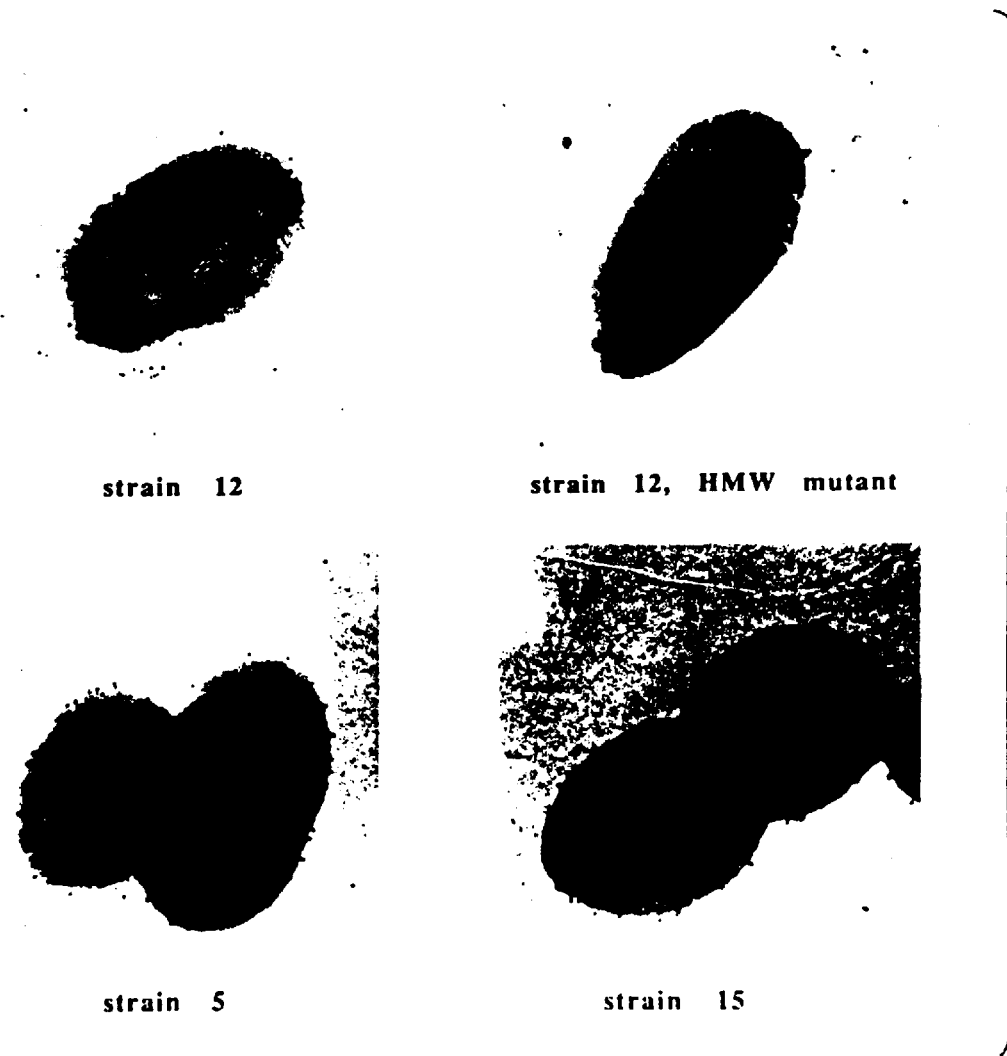
Figure 21:
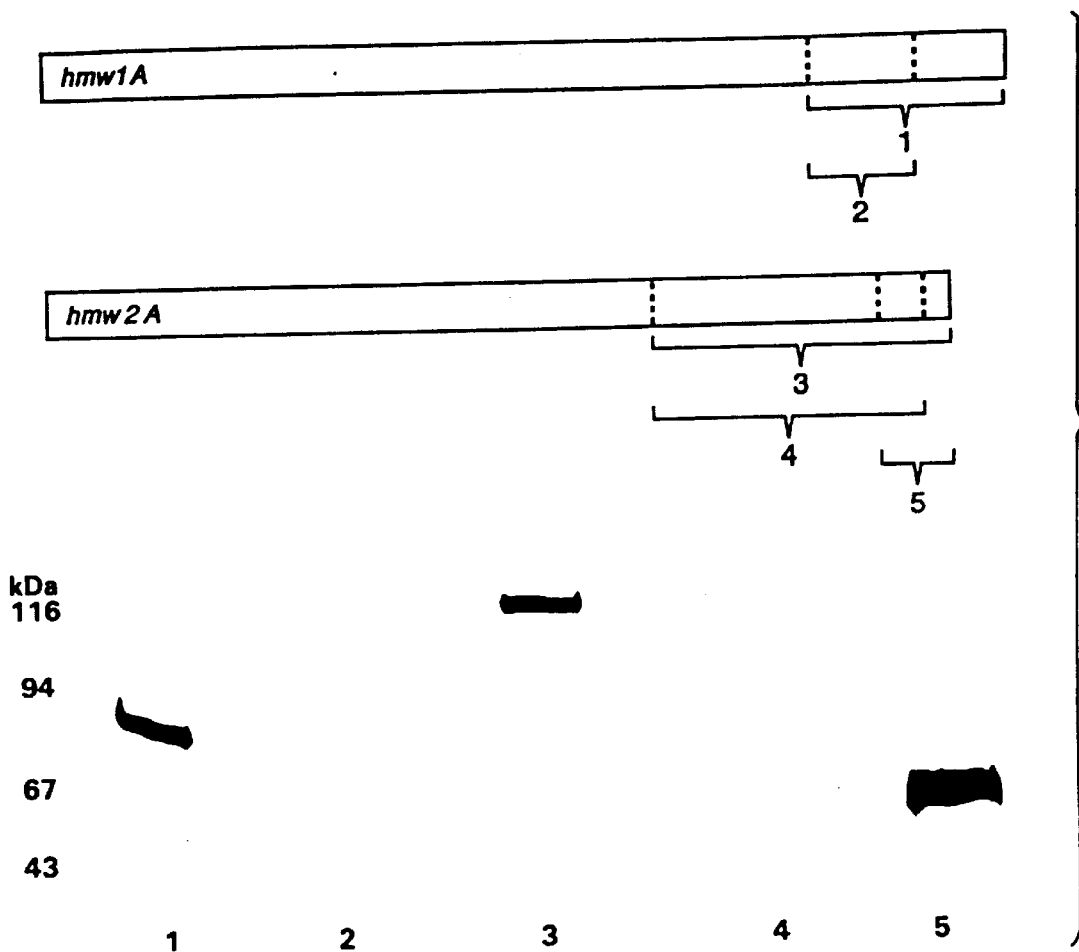
Figure 22:
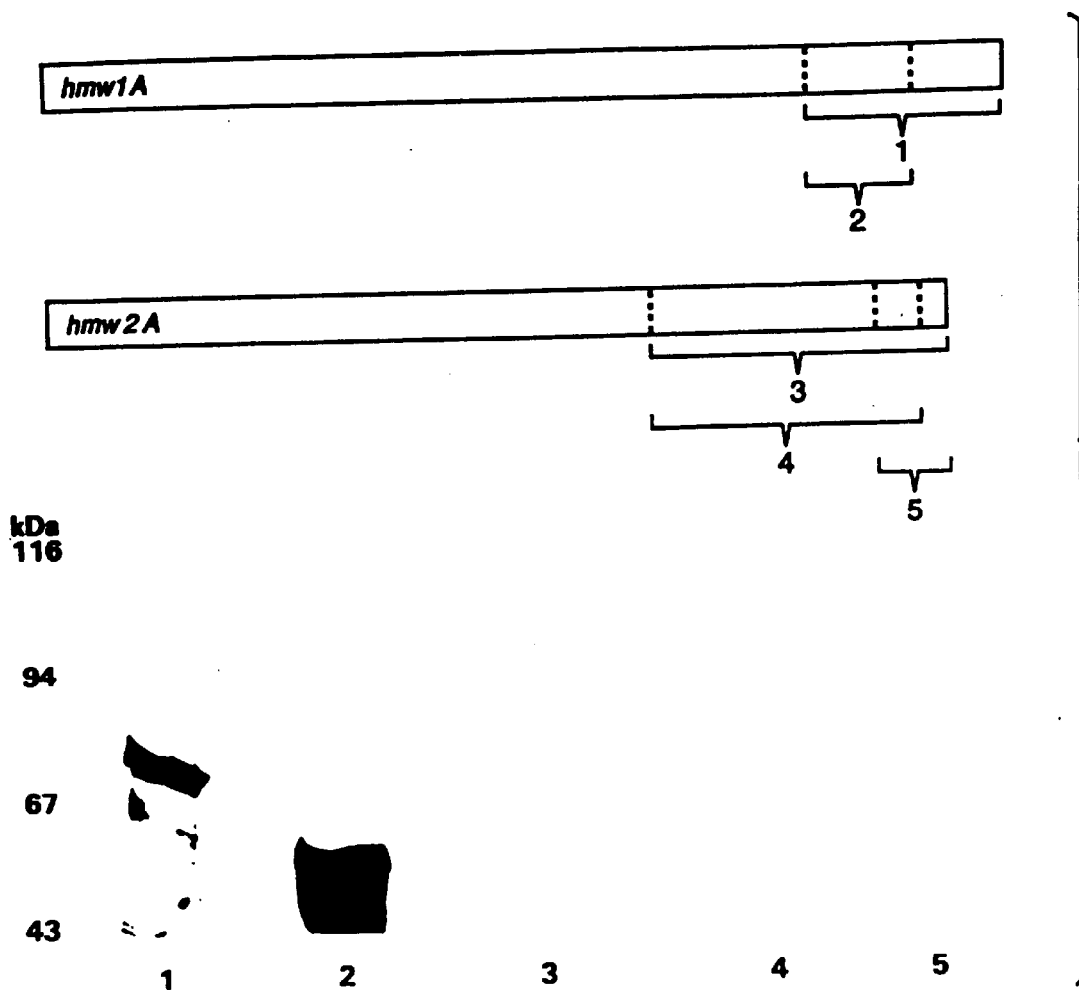
Figure 23:
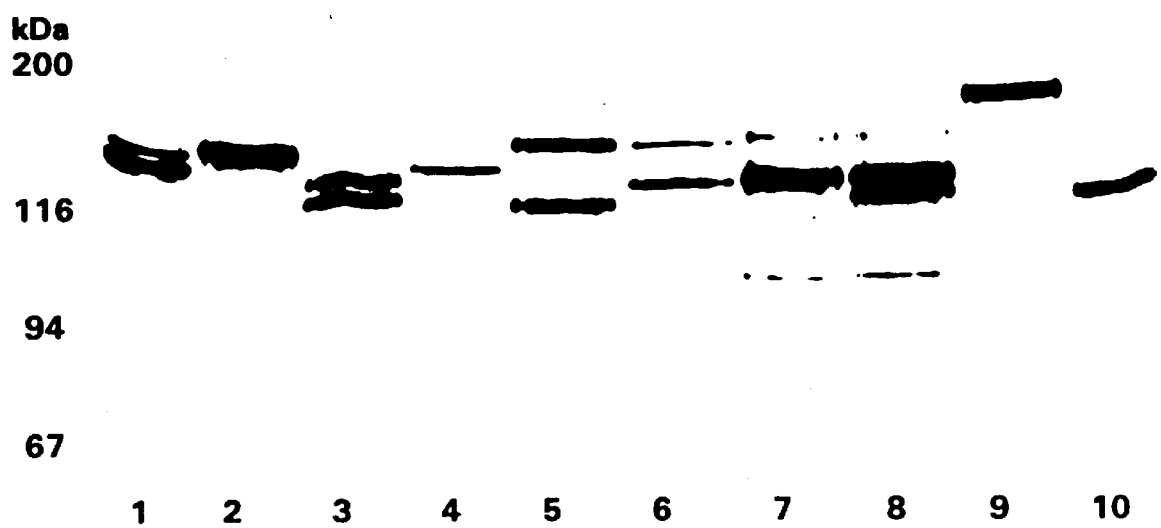

Western immunoblot analysis was performed to identify the recombinant proteins being produced by reactive phage clones (FIG. 11). Phage lysates grown in LE392 cells or plaques picked directly from a lawn of LE392 cells on YT plates were solubilized in gel electrophoresis sample buffer prior to electrophoresis. Sodium dodecyl sulfate polyacrylamide gel electrophoresis (SDS-PAGE) was performed on 7.5% or 11% polyacrylamide modified Laemmli gels. After transfer of the proteins to nitrocellulose sheets, the sheets were probed sequentially with an *E. coli*-absorbed human serum sample containing high-titer antibody to the high-molecular-weight proteins and then with alkaline phosphatase-conjugated goat anti-human immunoglobulin G (IgG) second antibody. Sera from healthy adults contains high-titer antibody directed against surface-exposed high-molecular-weight proteins of non-typeable *H. influenzae*. One such serum sample was used as the screening antiserum after having been extensively absorbed with LE392 cells.

To identify recombinant proteins being produced by *E. coli* transformed with recombinant plasmids, the plasmids of interest were used to transform *E. coli* BL21 (DE3)/pLysS. The transformed strains were grown to an $A_{600}$ of 0.5 in L broth containing 50 µg of ampicillin per ml. IPTG was then added to 1 mM. One hour later, cells were harvested, and a sonicate of the cells was prepared. The protein concentrations of the samples were determined by the bicinchoninic acid method. Cell sonicates containing 100 µg of total protein were solubilized in electrophoresis sample buffer, subjected to SDS-polyacrylamide gel electrophoresis, and transferred to nitrocellulose. The nitrocellulose was then probed sequentially with the *E. coli*-absorbed adult serum sample and then with alkaline phosphatase-conjugated goat anti-human IgG second antibody.

Western immunoblot analysis also was performed to determine whether homologous and heterologous non-typeable *H. influenzae* strains expressed high-molecular-weight proteins antigenically related to the protein encoded by the cloned HMW1 gene (rHMW1). Cell sonicates of bacterial cells were solubilized in electrophoresis sample buffer, subjected to SDS-polyacrylamide gel electrophoresis, and transferred to nitrocellulose. Nitrocellulose was probed sequentially with polyclonal rabbit rHMW1 antiserum and then with alkaline phosphatase-conjugated goat anti-rabbit IgG second antibody.

Finally, Western immunoblot analysis was performed to determine whether non-typeable Haemophilus strains expressed proteins antigenically related to the filamentous hemagglutinin protein of *Bordetella pertussis*. Monoclonal antibody X3C, a murine immunoglobulin G (IgG) antibody which recognizes filamentous hemagglutinin, was used to probe cell sonicates by Western blot. An alkaline phosphatase-conjugated goat anti-mouse IgG second antibody was used for detection.

To generate recombinant protein antiserum, *E. coli* BL21 (DE3)/pLysS was transformed with pHMW1-4, and expression of recombinant protein was induced with IPTG, as described above. A cell sonicate of the bacterial cells was prepared and separated into a supernatant and pellet fraction by centrifugation at 10,000×g for 30 min. The recombinant protein fractionated with the pellet fraction. A rabbit was subcutaneously immunized on biweekly schedule with 1 mg of protein from the pellet fraction, the first dose given with Freund's complete adjuvant and subsequent doses with Freund's incomplete adjuvant. Following the fourth injection, the rabbit was bled. Prior to use in the Western blot assay, the antiserum was absorbed extensively with sonicates of the host *E. coli* strain transformed with cloning vector alone.

To assess the sharing of antigenic determinants between HMW1 and filamentous hemagglutinin, enzyme-linked immunosorbent assay (ELISA) plates (Costar, Cambridge, Mass.) were coated with 60 µl of a 4-µg/ml solution of filamentous hemagglutinin in Dulbecco's phosphate-buffered saline per well for 2 h at room temperature. Wells were blocked for 1 h with 1% bovine serum albumin in Dulbecco's phosphate-buffered saline prior to addition of serum dilutions. rHMW1 antiserum was serially diluted in 0.1% Brij (Sigma, St. Louis, Mo.) in Dulbecco's phosphate-buffered saline and incubated for 3 h at room temperature. After being washed, the plates were incubated with peroxidase-conjugated goat anti-rabbit IgG antibody (Bio-Rad) for 2 h at room temperature and subsequently developed with 2,2'-azino-bis(3-ethylbenzthiazoline-6-sulfonic acid) (Sigma) at a concentration of 0.54 in mg/ml in 0.1 M sodium citrate buffer, pH 4.2, containing 0.03% $H_2O_2$. Absorbances were read on an automated ELISA reader.

Recombinant phage expressing HMW1 or HMW2 were recovered as follows. The non-typeable *H. influenzae* strain 12 genomic library was screened for clones expressing high-molecular-weight proteins with an *E. coli*-absorbed human serum sample containing a high titer of antibodies directed against the high-molecular-weight proteins.

Numerous strongly reactive clones were identified along with more weakly reactive ones. Twenty strongly reactive clones were plaque-purified and examined by Western blot for expression of recombinant proteins. Each of the strongly reactive clones expressed one of two types of high-molecular-weight proteins, designated HMW1 and HMW2. The major immunoreactive protein bands in the HMW1 and HMW2 lysates migrated with apparent molecular masses of 125 and 120 kDa, respectively. In addition to the major bands, each lysate contained minor protein bands of higher apparent molecular weight. Protein bands seen in the HMW2 lysates at molecular masses of less than 120 kDa were not regularly observed and presumably represent proteolytic degradation products. Lysates of LE392 infected with the XEMBL3 cloning vector alone were non-reactive when immunologically screened with the same serum sample. Thus, the observed activity was not due to cross-reactive *E. coli* proteins or XEMBL3-encoded proteins. Furthermore, the recombinant proteins were not simply binding immunoglobulin nonspecifically, since the proteins were not reactive with the goat anti-human IgG conjugate alone, with normal rabbit sera, or with serum from a number of healthy young infants.

Figure 5A:
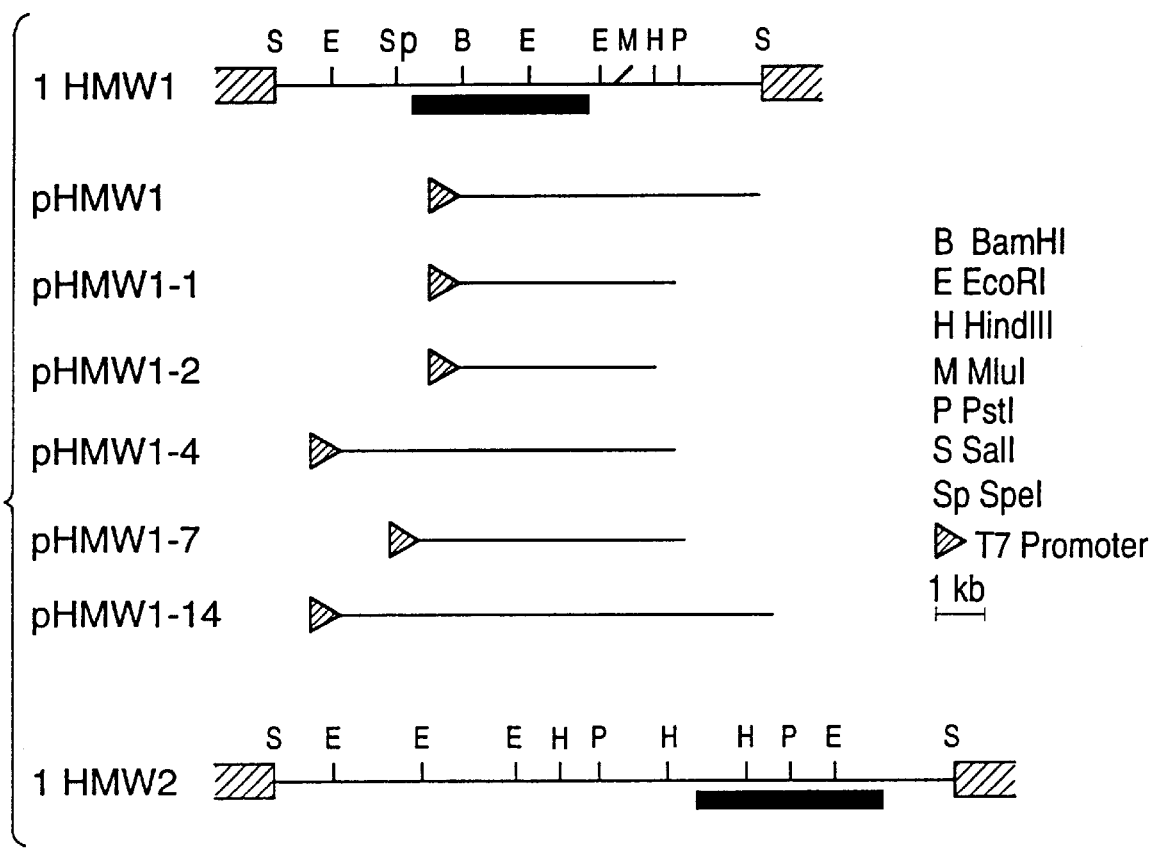
FIG. 5A shows restriction maps of representative recombinant phages which contained the HMW1 or HMW2 structural genes and of HMW1 plasmid subclones. The shaded boxes indicate the location of the structural genes. In the recombinant phage, transcription proceeds from left to right for the HMW1 gene and from right to left for the HMW2 gene.

Representative clones expressing either the HMW1 or HMW2 recombinant proteins were characterized further. The restriction maps of the two phage types were different from each other, including the regions encoding the HMW1 and HMW2 structural genes. FIG. 5A shows restriction maps of representative recombinant phage which contained the HMW1 or HMW2 structural genes. The locations of the structural genes are indicated by the shaded bars.

HMW1 plasmid subclones were constructed by using the T7 expression plasmid T7-7 (FIG. 5A and B). HMW2 plasmid subclones also were constructed, and the results with these latter subclones were similar to those observed with the HMW1 constructs.

The approximate location and direction of transcription of the HMW1 structure gene were initially determined by using plasmid pHMW1 (FIG. 5A). This plasmid was constructed by inserting the 8.5-kb BamHI-SalI fragment from λHMW1 into BamHI- and SalI-cut pT7-7. *E. coli* transformed with pHMW1 expressed an immunoreactive recombinant protein with an apparent molecular mass of 115 kDa, which was strongly inducible with IPTG. This protein was significantly smaller than the 125-kDa major protein expressed by the parent phage, indicating that it either was being expressed as a fusion protein or was truncated at the carboxy terminus.

To more precisely localize the 3' end of the structural gene, additional plasmids were constructed with progressive deletions from the 3' end of the pHMW1 construct. Plasmid pHMW1-1 was constructed by digestion of pHMW1 with PstI, isolation of the resulting 8.8-kb fragment, and religation. Plasmid pHMW1-2 was constructed by digestion of pHMW1 with HindIII, isolation of the resulting 7.5-kb fragment, and religation. E. coli transformed with either plasmid pHMW1-1 or pHMW1-2 also expressed an immunoreactive recombinant protein with an apparent molecular mass of 115 kDa. These results indicated that the 3' end of the structural gene was 5' of the HindIII site. FIG. 12 demonstrates the Western blot results with pHMW1-2 transformed cells before and after IPTG indicates (lanes 3 and 4, respectively). The 115 kDa recombinant protein is indicated by the arrow. Transformants also demonstrated cross-reactive bands of lower apparent molecular weight, and probably represent partial degradation products. Shown for comparison and the results for E. coli transformed with the pT7-7 cloning vector alone (FIG. 12, lanes 1 and 2).

To more precisely localize the 5' end of the gene, plasmids pHMW1-4 and pHMW1-7 were constructed. Plasmid pHMW1-4 was constructed by cloning the 5.1-kb BamHI-HindIII fragment from λHMW1 into a pT7-7-derived plasmid containing the upstream 3.8-kb EcoRI-BamHI fragment. E. coli transformed with pHMW1-4 expressed an immunoreactive protein with an apparent molecular mass of approximately 160 kDa (FIG. 12, lane 6). Although protein production was inducible with IPTG, the levels of protein production in these transformants were substantially lower than those with the pHMW1-2 transformants described above. Plasmid pHMW1-7 was constructed by digesting pHMW1-4 with NdeI and SpeI. The 9.0-kbp fragment generated by this double digestion was isolated, blunt ended, and religated. E. coli transformed with pHMW1-7 also expressed an immunoreactive protein with an apparent molecular mass of 160 kDa, a protein identical in size to that expressed by the pHMW1-4 transformants. The result indicated that the initiation codon for the HMW1 structural gene was 3' of the SpeI site. DNA sequence analysis (described below) confirmed this conclusion.

As noted above, the λHMW1 phage clones expressed a major immunoreactive band of 125 kDa, whereas the HMW1 plasmid clones pHMW1-4 and pHMW1-7, which contained what was believed to be the full-length gene, expressed an immunoreactive protein of approximately 160 kDa. This size discrepancy was disconcerting. One possible explanation was that an additional gene or genes necessary for correct processing of the HMW1 gene product were deleted in the process of subcloning. To address this possibility, plasmid pHMW1-14 was constructed. This construct was generated by digesting pHMW1 with NdeI and MluI and inserting the 7.6-kbp NdeI-MluI fragment isolated from pHMW1-4. Such a construct would contain the full-length HMW1 gene as well as the DNA 3' of the HMW1 gene which was present in the original HMW1 phage. E. coli transformed with this plasmid expressed major immunoreactive proteins with apparent molecular masses of 125 and 160 kDa as well as additional degradation products (FIG. 12, lanes 7 and 8). The 125- and 160-kDa bands were identical to the major and minor immunoreactive bands detected in the HMW1 phage lysates. Interestingly, the pHMW1-14 construct also expressed significant amounts of protein in the uninduced condition, a situation not observed with the earlier constructs.

The relationship between the 125- and 160-kDa proteins remains somewhat unclear. Sequence analysis, described below, reveals that the HMW1 gene would be predicted to encode a protein of 159 kDa. It is believed that the 160-kDa protein is a precursor form of the mature 125-kDa protein, with the conversion from one protein to the other being dependent on the products of the two downstream genes.

Sequence analysis of the HMW1 gene (FIG. 1) revealed a 4,608-bp open reading frame (ORF), beginning with an ATG codon at nucleotide 351 and ending with a TAG stop codon at nucleotide 4959. A putative ribosome-binding site with the sequence AGGAG begins 10 bp up-stream of the putative initiation codon. Five other in-frame ATG codons are located within 250 bp of the beginning of the ORF, but none of these is preceded by a typical ribosome-binding site. The 5'-flanking region of the ORF contains a series of direct tandem repeats, with the 7-bp sequence ATCTTTC repeated 16 times. These tandem repeats stop 100 bp 5' of the putative initiation codon. An 8-bp inverted repeat characteristic of a rho-independent transcriptional terminator is present, beginning at nucleotide 4983, 25 bp 3' of the presumed translational stop. Multiple termination codons are present in all three reading frames both upstream and downstream of the ORF. The derived amino acid sequence of the protein encoded by the HMW1 gene (FIG. 2) has a molecular weight of 159,000, in good agreement with the apparent molecular weights of the proteins expressed by the HMW1-4 and HMW1-7 transformants. The derived amino acid sequence of the amino terminus does not demonstrate the characteristics of a typical signal sequence. The BamHI site used in generation of pHMW1 comprises bp 1743 through 1748 of the nucleotide sequence. The ORF downstream of the BamHI site would be predicted to encode a protein of 111 kDa, in good agreement with the 115 kDa estimated for the apparent molecular mass of the pHMW1-encoded fusion protein.

The sequence of the HMW2 gene (FIG. 3) consists of a 4,431-bp ORF, beginning with an ATG codon at nucleotide 352 and ending with a TAG stop codon at nucleotide 4783. The first 1,259 bp of the ORF of the HMW2 gene are identical to those of the HMW1 gene. Thereafter, the sequences begin to diverge but are 80% identical overall. With the exception of a single base addition at nucleotide 93 of the HMW2 sequence, the 5'-flanking regions of the HMW1 and HMW2 genes are identical for 310 bp upstream from the respective initiation codons. Thus, the HMW2 gene is preceded by the same set of tandem repeats and the same putative ribosome-binding site which lies 5' of the HMW1 gene. A putative transcriptional terminator identical to that identified 3' of the HMW1 ORF is noted, beginning at nucleotide 4804. The discrepancy in the lengths of the two genes is principally accounted for by a 186-bp gap in the HMW2 sequence, beginning at nucleotide position 3839. The derived amino acid sequence of the protein encoded by the HMW2 gene (FIG. 4) has a molecular weight of 155,000 and is 71% identical with the derived amino acid sequence of the HMW1 gene.

The derived amino acid sequences of both the HMW1 and HMW2 genes (FIGS. 2 and 4) demonstrated sequence similarity with the derived amino acid sequence of filamentous hemagglutinin of Bordetella pertussis, a surface-associated protein of this organism. The initial and optimized TFASTA scores for the HMW1-filamentous hemagglutinin sequence comparison were 87 and 186, respectively, with a word size of 2. The z score for the comparison was 45.8. The initial and optimized TFASTA scores for the HMW2-filamentous hemagglutinin sequence comparison were 68 and 196, respectively. The z score for the latter comparison was 48.7. The magnitudes of the initial and optimized TFASTA scores and the z scores suggested that a biologically significant relationship existed between the HMW1 and HMW2 gene products and filamentous hemagglutinin. When the derived amino acid sequences of HMW1, HMW2, and filamentous hemagglutinin genes were aligned and compared, the similarities were most notable at the amino-terminal ends of the three sequences. Twelve of the first 22 amino acids in the predicted peptide sequences were identical. In addition, the sequences demonstrated a common five-amino-acid stretch, Asn-Pro-Asn-Gly-Ile, and several shorter stretches of sequence identity within the first 200 amino acids.

Example 2

This Example describes the relationship of filamentous hemagglutinin and the HMW1 protein.

To further explore the HMW1-filamentous hemagglutinin relationship, the ability of antiserum prepared against the HMW1-4 recombinant protein (rHMW1) to recognize purified filamentous hemagglutinin was assessed (FIG. 13). The rHMW1 antiserum demonstrated ELISA reactivity with filamentous hemagglutinin in a dose-dependent manner. Preimmune rabbit serum had minimal reactivity in this assay. The rHMW1 antiserum also was examined in a Western blot assay and demonstrated weak but positive reactivity with purified filamentous hemagglutinin in this system also.

To identify the native Haemophilus protein corresponding to the HMW1 gene product and to determine the extent to which proteins antigenically related to the HMW1 cloned gene product were common among other non-typeable *H. influenzae* strains, a panel of Haemophilus strains was screened by Western blot with the rHMW1 antiserum. The antiserum recognized both a 125- and a 120-kDa protein band in the homologous strain 12 (FIG. 14), the putative mature protein products of the HMW1 and HMW2 genes, respectively. The 120-kDa protein appears as a single band in FIG. 14, wherein it appeared as a doublet in the HMW2 phage lysates (FIG. 11).

When used to screen heterologous non-typeable *H. influenzae* strains, rHMW1 antiserum recognized high-molecular-weight proteins in 75% of 125 epidemiologically unrelated strains. In general, the antiserum reacted with one or two protein bands in the 100- to 150-kDa range in each of the heterologous strains in a pattern similar but not identical to that seen in the homologous strain (FIG. 14).

Monoclonal antibody X3C is a murine IgG antibody directed against the filamentous hemagglutinin protein of *B. pertussis*. This antibody can inhibit the binding of *B. pertussis* cells to Chinese hamster ovary cells and HeLa cells in culture and will inhibit hemagglutination of erythrocytes by purified filamentous hemagglutinin. A Western blot assay was performed in which this monoclonal antibody was screened against the same panel of non-typeable *H. influenzae* strains discussed above (FIG. 14). Monoclonal antibody X3C recognized both the high-molecular-weight proteins in non-typeable *H. influenzae* strain 12 which were recognized by the recombinant-protein antiserum (FIG. 15). In addition, the monoclonal antibody recognized protein bands in a subset of heterologous non-typeable *H. influenzae* strains which were identical to those recognized by the recombinant-protein antiserum, as may be seen by comparison of FIGS. 14 and 15. On occasion, the filamentous hemagglutinin monoclonal antibody appeared to recognize only one of the two bands which had been recognized by the recombinant-protein antiserum (compare strain lane 18 in FIGS. 14 and 15, for example). Overall, monoclonal antibody X3C recognized high-molecular-weight protein bands identical to those recognized by the rHMW1 antiserum in approximately 35% of our collection of non-typeable *H. influenzae* strains.

Example 3

This Example describes the adhesin properties of the HMW1 and HMW2 proteins.

Mutants deficient in expression of HMW1, HMW2 or both proteins were constructed to examine the role of these proteins in bacterial adherence. The following strategy was employed. pHMW1-14 (see Example 1, FIG. 5A) was digested with BamHI and then ligated to a kanamycin cassette isolated on a 1.3-kb BamHl fragment from pUC4K. The resultant plasmid (pHMW1-17) was linearized by digestion with XbaI and transformed into non-typeable *H. influenzae* strain 12, followed by selection for kanamycin resistant colonies. Southern analysis of a series of these colonies demonstrated two populations of transformants, one with an insertion in the HMW1 structural gene and the other with an insertion in the HMW2 structural gene. One mutant from each of these classes was selected for further studies.

Mutants deficient in expression of both proteins were recovered using the following protocol. After deletion of the 2.1-kb fragment of DNA between two EcoRI sites spanning the 3'-portion of the HMW1 structural gene and the 5'-portion of a downstream gene encoding an accessory processing protein in pHMW-15, the kanamycin cassette from pUC4K was inserted as a 1.3-kb EcoRl fragment. The resulting plasmid (pHMW1-16) was linearized by digestion with XbaI and transformed into strain 12, followed again by selection for kanamycin resistant colonies. Southern analysis of a representative sampling of these colonies demonstrated that in seven of eight cases, insertion into both the HMW1 and HMW2 loci had occurred. One such mutant was selected for further studies.

To confirm the intended phenotypes, the mutant strains were examined by Western blot analysis with a polyclonal antiserum against recombinant HMW1 protein. The parental strain expressed both the 125-kD HMW1 and the 120-kD HMW2 protein (FIG. 16). In contrast, the HMW2$^-$ mutant failed to express the 120-kD protein, and the HMW1 mutant failed to express the 125-kD protein. The double mutant lacked expression of either protein. On the basis of whole cell lysates, outer membrane profiles, and colony morphology, the wild type strain and the mutants were otherwise identical with one another. Transmission electron microscopy demonstrated that none of the four strains expressed pili.

The capacity of wild type strain 12 to adhere to Chang epithelial cells was examined. In such assays, bacteria were inoculated into broth and allowed to grow to a density of ~2×10$^9$ cfu/ml. Approximately 2×10$^7$ cfu were inoculated onto epithelial cell monolayers, and plates were gently centrifuged at 165×g for 5 minutes to facilitate contact between bacteria and the epithelial surface. After incubation for 30 minutes at 37° C. in 5% CO$_2$, monolayers were rinsed 5 times with PBS to remove nonadherent organisms and were treated with trypsin-EDTA (0.05% trypsin, 0.5% EDTA) in PBS to release them from the plastic support. Well contents were agitated, and dilutions were plated on solid medium to yield the number of adherent bacteria per monolayer. Percent adherence was calculated by dividing the number of adherent cfu per monolayer by the number of inoculated cfu.

As depicted in Table 1 below (the Tables appear at the end of the descriptive text), this strain adhered quite efficiently, with nearly 90% of the inoculum binding to the monolayer. Adherence by the mutant expressing HMW1 but not HMW2 (HMW2-) was also quite efficient and comparable to that by the wild type strain. In contrast, attachment by the strain expressing HMW2 but deficient in expression of HMW1 (HMW1⁻) was decreased about 15-fold relative to the wild type. Adherence by the double mutant (HMW1⁻/HMW2⁻) was decreased even further, approximately 50-fold compared with the wild type and approximately 3-fold compared with the HMW1 mutant. Considered together, these results suggest that both the HMW1 protein and the, HMW2 protein influence attachment to Chang epithelial cells. Interestingly, optimal adherence to this cell line appears to require HMW1 but not HMW2.

Example 4

This Example illustrates the preparation and expression of HMW3 and HMW4 proteins and their function as adhesins.

Using the plasmids pHMW1-16 and pHMW1-17 (see Example 3) and following a scheme similar to that employed with strain 12 as described in Example 3, three non-typeable Haemophilus strain 5 mutants were isolated, including one with the kanamycin gene inserted into the hmw1-like (designated hmw3) locus, a second with an insertion in the hmw2-like (designated hmw4) locus, and a third with insertions in both loci. As predicted, Western immunoblot analysis demonstrated that the mutant with insertion of the kanamycin cassette into the hmw1-like locus had lost expression of the HMW3 125-kD protein, while the mutant with insertion into the hmw2-like locus failed to express the HMW4 123-kD protein. The mutant with a double insertion was unable to express either of the high molecular weight proteins.

As shown in Table 1 below, wild type strain 5 demonstrated high level adherence, with almost 80% of the inoculum adhering per monolayer. Adherence by the mutant deficient in expression of the HMW2-like protein (i.e. HMW4 protein) was also quite high. In contrast, adherence by the mutant unable to express the HMW1-like protein (i.e. HMW3 protein) was reduced about 5-fold relative to the wild type, and attachment by the double mutant was diminished even further (approximately 25-fold). Examination of Giemsa-stained samples confirmed these observations (not shown). Thus, the results with strain 5 for proteins HMW3 and HMW4 corroborate the findings with strain 12 and the HMW1 and HMW2 proteins.

Example 5

This Example contains additional data concerning the adhesin properties of the HMW1 and HMW2 proteins.

To confirm an adherence function for the HMW1 and HMW2 proteins and to examine the effect of HMW1 and HMW2 independently of other *H. influenzae* surface structures, the hmw1 and the hmw2 gene clusters were introduced into *E. coli* DH5α, using plasmids pHMW1-14 and pHMW2-21, respectively. As a control, the cloning vector, pT7-7, was also transformed into *E. coli* DH5α. Western blot analysis demonstrated that *E. coli* DH5α containing the hmw1 genes expressed a 125 kDa protein, while the same strain harboring the hmw2 genes expressed a 120-kDa protein. *E. coli* DH5α containing pT7-7 failed to react with antiserum against recombinant HMW1. Transmission electron microscopy revealed no pili or other surface appendages on any of the *E. coli* strains.

Adherence by the *E. coli* strains was quantitated and compared with adherence by wild type non-typeable *H. influenzae* strain 12. As shown in Table 2 below, adherence by *E. coli* DH5α containing vector alone was less than 1% of that for strain 12. In contrast, *E. coli* DH5α harboring the hmw1 gene cluster demonstrated adherence levels comparable to those for strain 12. Adherence by *E. coli* DH5α containing the hmw2 genes was approximately 6-fold lower than attachment by strain 12 but was increased 20-fold over adherence by *E. coli* DH5α with pT7-7 alone. These results indicate that the HMW1 and HMW2 proteins are capable of independently mediating attachment to Chang conjunctival cells. These results are consistent with the results with the *H. influenzae* mutants reported in Examples 3 and 4, providing further evidence that, with Chang epithelial cells, HMW1 is a more efficient adhesin than is HMW2.

Experiments with *E. coli* HB101 harboring pT7-7, pHMW1-14, or pHMW2-21 confirmed the results obtained with the DH5α derivatives (see Table 2).

Example 6

This Example illustrates the copurification of HMW1 and HMW2 proteins from wild-type non-typeable *H. influenzae* strain.

HMW1 and HMW2 were isolated and purified from non-typeable *H. influenzae* (NTHI) strain 12 in the following manner. Non-typeable Haemophilus bacteria from frozen stock culture were streaked onto a chocolate plate and grown overnight at 37° C. in an incubator with 5% $CO_2$. 50 ml starter culture of brain heart infusion (BHI) broth, supplemented with 10 $\mu$g/ml each of hemin and NAD was inoculated with growth on chocolate plate. The starter culture was grown until the optical density (O.D.-600 nm) reached 0.6 to 0.8 and then the bacteria in the starter culture was used to inoculate six 500 ml flasks of supplemented BHI using 8 to 10 ml per flask. The bacteria were grown in 500 ml flasks for an additional 5 to 6 hours at which time the O.D. was 1.5 or greater. Cultures were centrifuged at 10,000 rpm for 10 minutes.

Bacterial pellets were resuspended in a total volume of 250 ml of an extraction solution comprising 0.5 M NaCl, 0.01 M $Na_2$EDTA, 0.01 M Tris 50 $\mu$M 1,10-phenanthroline, pH 7.5. The cells were not sonicated or otherwise disrupted. The resuspended cells were allowed to sit on ice at 0° C. for 60 minutes. The resuspended cells were centrifuged at 10,000 rpm for 10 minutes at 4° C. to remove the majority of intact cells and cellular debris. The supernatant was collected and centrifuged at 100,000×g for 60 minutes at 4° C. The supernatant again was collected and dialyzed overnight at 4° C. against 0.01 M sodium phosphate, pH 6.0.

The sample was centrifuged at 10,000 rpm for 10 minutes at 4° C. to remove insoluble debris precipitated from solution during dialysis. The supernatant was applied to a 10 ml CM Sepharose column which has been pre-equilibrated with 0.01 M sodium phosphate, pH 6. Following application to this column, the column was washed with 0.01 M sodium phosphate. Proteins were elevated from the column with a 0–0.5M KCl gradient in 0.01 M Na phosphate, pH 6 and fractions were collected for gel examination. Coomassie gels of column fractions were carried out to identify those fractions containing high molecular weight proteins. The fractions containing high molecular weight proteins were pooled and concentrated to a 1 to 3 ml volume in preparation for application of sample to gel filtration column.

A Sepharose CL-4B gel filtration column was equilibrated with phosphate-buffered saline, pH 7.5. The concentrated high molecular weight protein sample was applied to the gel filtration column and column fractions were collected. Coomassie gels were performed on the column fractions to identify those containing high molecular weight proteins. The column fractions containing high molecular weight proteins were pooled.

Example 7

This Example illustrates the use of specified HMW1 and HMW2 proteins in immunization studies.

The copurified HMW1 and HMW2 proteins prepared as described in Example 6 were tested to determine whether they would protect against experimental otitis media caused by the homologous strain.

Healthy adult chinchillas, 1 to 2 years of age with weights of 350 to 500 g, received three monthly subcutaneous injections with 40 μg of an HMW1-HMW2 protein mixture in Freund's adjuvant. Control animals received phosphate-buffered saline in Freunds' adjuvant. one month after the last injection, the animals were challenged by intrabullar inoculation with 300 cfu of NTHI strain 12.

Middle ear infection developed in 5 of 5 control animals versus 5 of 10 immunized animals. Although only 5 of 10 chinchillas were protected in this test, the test conditions are very stringent, requiring bacteria to be injected directly into the middle ear space and to proliferate in what is in essence a small abscess cavity. As seen from the additional data below, complete protection of chinchillas can be achieved.

The five HMW1/HMW2-immunized animals that did not develop otitis media demonstrated no signs of middle ear inflammation when examined by otoscopy nor were middle ear effusions detectable.

Among the five HMW1/HMW2-immunized animals that became infected, the total duration of middle ear infection as assessed by the persistence of culture-positive middle ear fluid was not different from controls. However, the degree of inflammation of the tympanic membranes was subjectively less than in the HMW1/HMW2-immunized animals. When quantitative bacterial counts were performed on the middle ear fluid specimens recovered from infected animals, notable differences were apparent between the HMW1/HMW2-immunized and PBS-immunized animals (FIG. 17). Shown in FIG. 17 are quantitative middle ear fluid bacterial counts from animals on day 7 post-challenge, a time point associated with the maximum colony counts in middle ear fluid. The data were log-transformed for purpose of statistical comparison. The data from the control animals are shown on the left and data from the high molecular weight protein immunized animals on the right. The two horizontal lines indicate the respective means and standard derivations of middle ear fluid colony counts for only the infected animals in each group. As can be seen from this Figure, the HMW1/HMW2-immunized animals had significantly lower middle ear fluid bacterial counts than the PBS-immunized controls, geometric means of $7.4 \times 10^6$ and $1.3 \times 10^5$, respectively (p=0.02, Students' t-test)

Serum antibody titres following immunization were comparable in uninfected and infected animals. However, infection in immunized animals was uniformly associated with the appearance of bacteria down-regulated in expression of the HMW proteins, suggesting bacterial selection in response to immunologic pressure.

Although this data shows that protection following immunization was not complete, this data suggests the HMW adhesin proteins are potentially important protective antigens which may comprise one component of a multi-component NTHI vaccine.

In addition, complete protection has been achieved in the chinchilla model at lower dosage challenge, as set forth in Table 3 below.

Groups of five animals were immunized with 20 μg of the HMW1-HMW2 mixture prepared as described in Example 6 on days 1, 28 and 42 in the presence of alum. Blood samples were collected on day 53 to monitor the antibody response. On day 56, the left ear of animals was challenged with about 10 cfu of *H. influenzae* strain 12. Ear infection was monitored on day 4. Four animals in Group 3 were infected previously by *H. influenzae* strain 12 and were recovered completely for at least one month before the second challenge.

Example 8

This Example illustrates the provision of synthetic peptides corresponding to a portion only of the HMW1 protein.

A number of synthetic peptides were derived from HMW1. Antisera then were raised to these peptides. The anti-peptide antisera to peptide HMW1-P5 was shown to recognize HMW1. Peptide HMW1-P5 covers amino acids 1453 to 1481 of HMW1, has the sequence VDEVIEAKRILEKVKDLSDEEREALAKLG (SEQ ID No: 11), and represents bases 1498 to 1576 in FIG. 10.

This finding demonstrates that the DNA sequence and the derived protein is being interpreted in the correct reading frame and that peptides derived from the sequence can be produced which will be immunogenic.

Example 9

This Example describes the generation of monoclonal antibodies to the high molecular weight proteins of non-typeable *H. influenzae*.

Monoclonal antibodies were generated using standard techniques. In brief, female BALB/c mice (4 to 6 weeks old) were immunized by intraperitoneal injection with high molecular weight proteins purified from nontypable Haemophilus strain 5 or strain 12, as described in Example 6. The first injection of 40 to 50 μg of protein was administered with Freund's complete adjuvant and the second dose, received four to five weeks after the first, was administered with phosphate-buffered saline. Three days following the second injection, the mice were sacrificed and splenic lymphocytes were fused with SP2/0-Agl4 plasmacytoma cells.

Two weeks following fusion, hybridoma supernatants were screened for the presence of high molecular weight protein specific antibodies by a dot-blot assay. Purified high molecular weight proteins at a concentration of 10 μg per ml in TRIS-buffered saline (TBS), were used to sensitize nitrocellulose sheets (Bio-Rad Laboratories, Richmond, Calif.) by soaking for 20 minutes. Following a blocking step with TBS-3% gelatin, the nitrocellulose was incubated for 60 minutes at room temperature with individual hybridoma supernatants, at a 1:5 dilution in TBS-0.1% Tween, using a 96-well Bio-Dot micro-filtration apparatus (Bio-Rad). After washing, the sheets were incubated for one hour with alkaline-phosphatase-conjugated affinity isolated goat-anti (mouse IgG+IgM) antibodies (Tago, Inc., Burlingame, Calif.). Following additional washes, positive supernatants were identified by incubation of the nitrocellulose sheet in alkaline phosphatase buffer (0.10 M TRIS, 0.10 M NaCl, 0.005 M $MgCl_2$) containing nitroblue tetrazolium (0.1 mg/ml) and 5-bromo-4-chloro-3-indoyl phosphate (BCIP) (0.05 mg/ml).

For the antibody isotyping and immunoelectron microscopy studies to be described below, the monoclonal antibodies were purified from hybridoma supernatants. The antibodies recovered in this work were all of the IgG class. To purify the monoclonal antibodies, the hybridoma supernatants were first subjected to ammonium sulfate precipitation (50% final concentration at 0° C.). Following overnight incubation, the precipitate was recovered by centrifugation and resolubilized in phosphate buffered saline. The solution was then dialyzed overnight against 0.01 M sodium phosphate buffer, pH 6.0. The following day the sample was applied to a DEAE-Sephacel column preequilibrated with the same phosphate buffer and the proteins were subsequently eluted with a KCl gradient. Column fractions containing the monoclonal antibodies were identified by examination of samples on Coomassie gels for protein bands typical of light and heavy chains.

The isotype of each monoclonal antibody was determined by immunodiffusion using the Ouchterlony method. Immunodiffusion plates were prepared on glass slides with 10 ml of 1% DNA-grade agarose (FMC Bioproducts, Rockland, Me.) in phospate-buffered saline. After the agarose solidified, 5-mm wells were punched into the agarose in a circular pattern. The center well contained a concentrated preparation of the monoclonal antibody being evaluated and the surrounding wells contained goat anti-mouse subclass-specific antibodies (Tago). The plates were incubated for 48 hours in a humid chamber at 4° C. and then examined for white lines of immunoprecipitation.

Hybridoma supernatants which were reactive in the dot-blot assay described above were examined by Western blot analysis, both to confirm the reactivity with the high molecular weight proteins of the homologous nontypable Haemophilus strain and to examine the cross-reactivity with similar proteins in heterologous strains. Nontypable *Haemophilus influenzae* cell sonicates containing 100 μg of total protein were solubilized in electrophoresis sample buffer, subjected to SDS-polyacrylamide gel electrophoresis on 7.5% acrylamide gels, and transferred to nitrocellulose using a Genie electrophoretic blotter (Idea Scientific Company, Corvallis, Oreg.) for 45 min at 24 V. After transfer, the nitrocellulose sheet was blocked and then probed sequentially with the hybridoma supernatant, with alkaline phosphatase-conjugated goat-anti(mouse IgG+IgM) second antibody, and finally bound antibodies were detected by incubation with nitroblue tetrazolium/BCIP solution. This same assay was employed to examine the reactivity of the monoclonals with recombinant fusion proteins expressed in *E. coli* (see below).

In preparation for immunoelectronmicroscopy, bacteria were grown overnight on supplemented chocolate agar and several colonies were suspended in phosphate-buffered-saline containing 1% albumin. A 20-μl drop of this bacterial suspension was then applied to a carbon-coated grid and incubated for 2 min. Excess fluid was removed and the specimen was then incubated for 5 min with the purified high molecular weight protein-specific monoclonal antibody being analyzed. Following removal of excess liquid and a wash with phosphatebuffered saline, the specimen was incubated with anti-mouse IgG conjugated to 10-nm colloidal gold particles. Following final washes with phosphate-buffered saline, the sample was rinsed with distilled water. Staining of the bacterial cells was performed with 0.5% uranyl acetate for 1 min. Samples were then examined in a Phillips 201c electron microscope.

Fourteen different hybridomas were recovered which produced monoclonal antibodies reactive with the purified HMW1 and HMW2 proteins of nontypable Haemophilus strain 12 in the immunoblot screening assay. Of the monoclonals screened by immunoelectron microscopy to date, as described below, two were demonstrated to bind surface epitopes on prototype strain 12. These two monoclonal antibodies, designated AD6 and 10C5 were both of the IgG1 subclass.

Example 10

This Example describes the identification of surface-exposed B-cell epitopes of high molecular weight proteins of non-typeable *H. influenzae*.

To map epitopes recognized by the monoclonal antibodies, their reactivity with a panel of recombinant fusion proteins expressed by pGEMEX® recombinant plasmids was examined. These plasmids were constructed by cloning various segments of the hmw1a or hmw2A structural genes into T7 expression vectors pGEMEX®-1 and GEMEX®-2 (Promega Corporation, Madison, Wis.). Shown in FIGS. 18 and 19 are the schematic diagrams depicting the segments derived from the hmw1 and hmw2 gene clusters cloned into the pGEMEX® expression plasmids. These segments were inserted such that in-frame fusions were created at each junction site. Thus, these plasmids encode recombinant fusion proteins containing pGEMEX®-encoded T7 gene 10 amino acids in the regions indicated by the hatched bars and hmw1a or hmw2A encoded amino acids in the regions indicated by the black bars in these Figures. A stop codon is present at the junction of the black and white segments of each bar.

Four discrete sites within the hmw1A structural gene were selected as the 5' ends of the hmw1 inserts. For each 5' end, a series of progressively smaller inserts was created by taking advantage of convenient downstream restriction sites. The first recombinant plasmid depicted in FIG. 18 was constructed by isolating a 4.9 kbp BamHI-HindIII fragment from pHMW1-14 (Example 1, FIG. 5A), which contains the entire hmw1 gene cluster and inserting it into BamHI-HindIII digested pGEMEX®-1. The second recombinant plasmid in this set was constructed by digesting the "parent" plasmid with BstEII-HindIII, recovering the 6.8 kbp larger fragment, blunt-ending with Klenow DNA polymerase, and religating. The third recombinant plasmid in this set was constructed by digesting the "parent" plasmid with ClaI-HindIII, recovering the 6.0 kbp larger fragment, blunt-ending, and religating. The next set of four hmw1 recombinant plasmids was derived from a "parent" plasmid constructed by ligating a 2.2 kbp EcoRI fragment from the hmw1 gene cluster into EcoRI-digested pGEMEX®-2. The other three recombinant plasmids in this second set were constructed by digesting at downstream BstEII, EcoRV, and ClaI sites, respectively, using techniques similar to those just described. The third set of three recombinant plasmids depicted was derived from a "parent" plasmid constructed by double-digesting the first recombinant plasmid described above (i.e. the one containing the 4.9 kbp BamHI-HindIII fragment) with BamHI and ClaI, blunt-ending, and religating. This resulted in a construct encoding a recombinant protein with an in-frame fusion at the ClaI site of the hmw1A gene. The remaining two plasmids in this third set were constructed by digesting at downstream BstEII and EcoRV sites, respectively. Finally, the fourth set of two recombinant plasmids was derived from a "parent" plasmid constructed by double-digesting the original BamHI-HindIII construct with HincII and EcoRV, then religating. This resulted in a construct encoding a recombinant protein with an in-frame fusion at the EcoRV site of the hmw1A gene. The remaining plasmid in this fourth set was constructed by digesting at the downstream BstEII site.

Three discrete sites with the hmw2A structural gene were selected as the 5' ends of the hmw2 inserts. The first recombinant plasmid depicted in FIG. 19 was constructed by isolating a 6.0 kbp EcoRI-XhoI fragment from pHMW2-21, which contains the entire hmw2 gene cluster, and inserting it into EcoRI-SalI digested pGEMEX®-1. The second recombinant plasmid in this set was constructed by digesting at an MluI site near the 3' end of the hmw2A gene. The second set of two hmw2 recombinant plasmids was derived from a "parent" plasmid constructed by isolating a 2.3 kbp HindIII fragment from pHMW2-21 and inserting it into HindIII-digested PGEMEX®-2. The remaining plasmid in this second set was constructed by digesting at the downstream MluI site. Finally, the last plasmid depicted was constructed by isolating a 1.2 kbp HincII-HindIII fragment from the indicated location in the hmw2 gene cluster and inserting it into HincII-HindIII digested pGEMEX®-1.

Each of the recombinant plasmids was used to transform *E. coli* strain JM101. The resulting transformants were used to generate the recombinant fusion proteins employed in the mapping studies. To prepare recombinant proteins, the transformed *E. coli* strains were grown to an A6 of 0.5 in L broth containing 50 µg of ampicillin per ml. IPTG was then added to 1 mM and mGP1-2, the M13 phage containing the T7 RNA polymerase gene, was added at multiplicity of infection of 10. One hour later, cells were harvested, and a sonicate of the cells was prepared. The protein concentrations of the samples were determined and cell sonicates containing 100 µg of total protein were solubilized in electrophoresis sample buffer, subjected to SDS-polyacrylamide gel electrophoresis, and examined on Coomassie gels to assess the expression level of recombinant fusion proteins. Once high levels of expression of the recombinant fusion proteins were confirmed, the cell sonicates were used in the Western blot analyses described above.

Shown in FIG. 20 is an electron micrograph demonstrating surface binding of Mab AD6 to representative nontypable *Haemophilus influenzae* strains. In the upper left panel of the Figure is nontypable Haemophilus strain 12 and in the upper right panel is a strain 12 derivative which no longer expressed the high molecular weight proteins. As can be seen, colloidal gold particles decorate the surface of strain 12, indicating bound AD6 antibody on the surface. In contrast, no gold particles are evident on the surface of the strain 12 mutant which no longer expresses the high molecular weight proteins. These results indicate that monoclonal antibody AD6 is recognizing a surface-exposed epitope on the high molecular weight proteins of strain 12. Analogous studies were performed with monoclonal antibody 10C5 demonstrating it too bound to surface-accessible epitopes on the high molecular weight HMW1 and HMW2 proteins of strain 12.

Having identified two surface-binding monoclonals, the epitope which each monoclonal recognized was mapped. To accomplish this task, the two sets of recombinant plasmids containing various portions of either the hmw1a or hmw2A structural genes (FIGS. 18 and 19) were employed. With these complementary sets of recombinant plasmids, the epitopes recognized by the monoclonal antibodies were mapped to relatively small regions of the very large HMW1 and HMW2 proteins.

To localize epitopes recognized by Mab AD6, the pattern of reactivity of this monoclonal antibody with a large set of recombinant fusion protein was examined. FIG. 21 is a Western blot which demonstrates the pattern of reactivity of Mab AD6 with five recombinant fusion proteins, a relevant subset of the larger number originally examined. From analysis of the pattern of reactivity of Mab AD6 with this set of proteins, one is able to map the epitope it recognizes to a very short segment of the HMW1 and HMW2 proteins. A brief summary of this analysis follows. For reference, the relevant portions of the hmw1A or hmw2A structural genes which were expressed in the recombinant proteins being examined are indicated in the diagram at the top of the figure. As shown in lane 1, Mab AD6 recognizes an epitope encoded by fragment 1, a fragment which encompasses the distal one-fourth of the hmw1A gene. Reactivity is lost when only the portion of the gene comprising fragment 2 is expressed. This observation localizes the AD6 epitope somewhere within the last 180 amino acids at the carboxy-terminal end of the HMW1 protein. Mab AD6 also recognizes an epitope encoded by fragment 3, derived from the hmw2A structural gene. This is a rather large fragment which encompasses nearly one-third of the gene. Reactivity is lost when fragment 4 is expressed. The only difference between fragments 3 and 4 is that the last 225 base pairs at the 3' end of the hmw2A structural gene were deleted in the latter construct. This observation indicates that the AD6 epitope is encoded by this short terminal segment of the hmw2A gene. Strong support for this idea is provided by the demonstrated binding of Mab AD6 to the recombinant protein encoded by fragment 5, a fragment encompassing the distal one-tenth of the hmw2A structural gene. Taken together, these data identify the AD6 epitope as common to both the HMW1 and HMW2 proteins and place its location with 75 amino acids of the carboxy termini of the two proteins.

FIG. 22 is a Western blot demonstrating the pattern of reactivity of Mab 10C5 with the same five recombinant fusion proteins examined in FIG. 21. As shown in lane 1, Mab 10C5 recognizes an epitope encoded by fragment 1. In contrast to Mab AD6, Mab 10C5 also recognizes an epitope encoded by fragment 2. Also in contrast to Mab AD6, Mab 10C5 does not recognize any of the hmw2A-derived recombinant fusion proteins. Thus, these data identify the 10C5 epitope as being unique to the HMW1 protein and as being encoded by the fragment designated as fragment 2 in this figure. This fragment corresponds to a 155-amino acid segment encoded by the EcoRV-BstEII segment of the hmw1A structural gene.

Having identified the approximate locations of the epitopes on HMW1 and HMW2 recognized by the two monoclonals, the extent to which these epitopes were shared by the high molecular weight proteins of heterologous nontypable Haemophilus strains was next determined. When examined in Western blot assays with bacterial cell sonicates, Mab AD6 was reactive with epitopes expressed on the high molecular weight proteins of 75% of the inventor's collection of more than 125 nontypable *Haemophilus influenzae* strains. In fact, this monoclonal appeared to recognize epitopes expressed on high molecular weight proteins in virtually all nontypable Haemophilus strains which we previously identified as expressing HMW1/HMW2-like proteins. FIG. 23 is an example of a Western blot demonstrating the reactivity of Mab AD6 with a representative panel of such heterologous strains. As can be seen, the monoclonal antibody recognizes one or two bands in the 100 to 150 kDa range in each of these strains. For reference, the strain shown in lane 1 is prototype strain 12 and the two bands visualized represent HMW1 and HMW2 as the upper and lower immunoreactive bands, respectively.

In contrast to the broad cross-reactivity observed with Mab AD6, Mab 10C5 was much more limited in its ability to recognize high molecular weight proteins in heterologous strains. Mab 10C5 recognized high molecular weight proteins in approximately 40% of the strains which expressed HMW1/HMW2-like proteins. As was the case with Mab AD6, Mab 10C5 did not recognize proteins in any the nontypable Haemophilus strains which did not express HMW1/HMW2-like proteins.

In a limited fashion, the reactivity of Mab AD6 with surface-exposed epitopes on the heterologous strains has been examined. In the bottom two panels of FIG. 20 are electron micrographs demonstrating the reactivity of Mab AD6 with surface-accessible epitopes on nontypable Haemophilus strains 5 and 15. As can be seen, abundant colloidal-gold particles are evident on the surfaces of each of these strains, confirming their surface expression of the AD6 epitope. Although limited in scope, these data suggest that the AD6 epitope may be a common surface-accessible epitope on the high molecular weight adhesion proteins of most nontypable *Haemophilus influenzae* which express HMW1/HMW2-like proteins.

SUMMARY OF DISCLOSURE

In summary of this disclosure, the present invention provides high molecular weight proteins of non-typeable Haemophilus, genes coding for the same and vaccines incorporating such proteins. Modifications are possible within the scope of this invention.

TABLE 1

Effect of mutation of high molecular weight proteins on adherence to change epithelial cells by nontypable *H. influenzae*.

| | ADHERENCE % * | |
|---|---|---|
| Strain | % Inoculation | Relative to wild Type† |
| Strain 12 derivatives wild type | 87.76 ± 5.9 | 100.0 ± 6.7 |
| HMW1 mutant | 6.0 ± 0.9 | 6.8 ± 1.0 |
| HMW2 mutant | 89.9 ± 10.8 | 102.5 ± 12.3 |
| HMW1/HMW2 mutant | 2.0 ± 0.3 | 2.3 ± 0.3 |
| Strain 5 derivatives wild type | 78.7 ± 3.2 | 100.0 ± 4.1 |
| HMW1-like mutant | 15.7 ± 2.6 | 19.9 ± 3.3 |
| HMW2-like mutant | 103.7 ± 14.0 | 131.7 ± 17.8 |
| double mutant | 3.5 ± 0.6 | 4.4 ± 0.8 |

TABLE 1-continued

Effect of mutation of high molecular weight proteins on adherence to change epithelial cells by nontypable *H. influenzae*.

| | ADHERENCE % * | |
|---|---|---|
| Strain | % Inoculation | Relative to wild Type† |

*Numbers represent mean (± standard error of the mean) of measurements in triplicate or quadruplicate from representative experiments.
†Adherence values for strain 12 derivatives are relative to strain 12 wild type; values for strain 5 derivatives are relative to strain 5 wild type.

TABLE 2

Adherence by *E. coli* DH5α and HB101 harboring *hmw1* or *hmw2* gene clusters.

| Strain* | Adherence relative to *H. influenzae* strain 12† |
|---|---|
| DH5α (pT7-7) | 0.7 ± 0.02 |
| DH5α (pHMW1-14) | 114.2 ± 15.9 |
| DH5α (pHMW2-21) | 14.0 ± 3.7 |
| HB101 (pT7-7) | 1.2 ± 0.5 |
| HB101 (pHMW1-14) | 93.6 ± 15.8 |
| HB101 (pHMW2-21) | 3.6 ± 0.9 |

*The plasmid PHMW1-14 contains the *hmw1* gene cluster,' while pHMW2-21 contains the *hmw2* gene cluster; pT7-7 is the cloning vector used in these constructs.
†Numbers represent the mean (± standard error of the mean) of measurements made in triplicate from representative experiments.

TABLE 3

Protective ability of HMW protein against non-typeable *H. influenzae* challenge in chinchilla model

| | | | Number of Animals Showed Positive Ear Infection | | |
|---|---|---|---|---|---|
| Group (#) | Antigens | Total Animals | Tympano-gram | Otoscopic Examination | cfu of Bacteria/10μL |
| 1 | HMW | 5 | 0 | 0 | 0 |
| 2 | None | 5 | 5 | 5 | 850–3200 (4/5) |
| 3 | Convalescent | 4 | 0 | 0 | 0 |

SEQUENCE LISTING (1) GENERAL INFORMATION:

(iii) NUMBER OF SEQUENCES: 11

(2) INFORMATION FOR SEQ ID NO:1:

(i) SEQUENCE CHARACTERISTICS:
      (A) LENGTH: 5116 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO:1:

```
ACAGCGTTCT CTTAATACTA GTACAAACCC ACAATAAAAT ATGACAAACA ACAATTACAA      60
CACCTTTTTT GCAGTCTATA TGCAAATATT TTAAAAAATA GTATAAATCC GCCATATAAA     120
ATGGTATAAT CTTTCATCTT TCATCTTTCA TCTTTCATCT TTCATCTTTC ATCTTTCATC     180
TTTCATCTTT CATCTTTCAT CTTTCATCTT TCATCTTTCA TCTTTCATCT TTCATCTTTC     240
ACATGCCCTG ATGAACCGAG GGAAGGGAGG GAGGGGCAAG AATGAAGAGG GAGCTGAACG     300
AACGCAAATG ATAAAGTAAT TTAATTGTTC AACTAACCTT AGGAGAAAAT ATGAACAAGC     360
TATATCGTCT CAAATTCAGC AAACGCCTGA ATGCTTTGGT TGCTGTGTCT GAATTGGCAC     420
GGGGTTGTGA CCATTCCACA GAAAAAGGCA GCGAAAAACC TGCTCGCATG AAAGTGCGTC     480
ACTTAGCGTT AAAGCCACTT TCCGCTATGT TACTATCTTT AGGTGTAACA TCTATTCCAC     540
AATCTGTTTT AGCAAGCGGC TTACAAGGAA TGGATGTAGT ACACGGCACA GCCACTATGC     600
AAGTAGATGG TAATAAAACC ATTATCCGCA ACAGTGTTGA CGATATCATT AATTGGAAAC     660
AATTTAACAT CGACCAAAAT GAAATGGTGC AGTTTTTACA AGAAAACAAC AACTCCGCCG     720
TATTCAACCG TGTTACATCT AACCAAATCT CCCAATTAAA AGGGATTTTA GATTCTAACG     780
GACAAGTCTT TTTAATCAAC CCAAATGGTA TCACAATAGG TAAAGACGCA ATTATTAACA     840
CTAATGGCTT TACGGCTTCT ACGCTAGACA TTTCTAACGA AAACATCAAG GCGCGTAATT     900
TCACCTTCGA GCAAACCAAA GATAAAGCGC TCGCTGAAAT TGTGAATCAC GGTTTAATTA     960
CTGTCGGTAA AGACGGCAGT GTAAATCTTA TTGGTGGCAA AGTGAAAAAC GAGGGTGTGA    1020
TTAGCGTAAA TGGTGGCAGC ATTTCTTTAC TCGCAGGGCA AAAAATCACC ATCAGCGATA    1080
TAATAAACCC AACCATTACT TACAGCATTG CCGCGCCTGA AAATGAAGCG GTCAATCTGG    1140
GCGATATTTT TGCCAAAGGC GGTAACATTA ATGTCCGTGC TGCCACTATT CGAAACCAAG    1200
GTAAACTTTC TGCTGATTCT GTAAGCAAAG ATAAAAGCGG CAATATTGTT CTTTCCGCCA    1260
AAGAGGGTGA AGCGGAAATT GGCGGTGTAA TTTCCGCTCA AAATCAGCAA GCTAAAGGCG    1320
GCAAGCTGAT GATTACAGGC GATAAAGTCA CATTAAAAAC AGGTGCAGTT ATCGACCTTT    1380
CAGGTAAAGA AGGGGGAGAA ACTTACCTTG GCGGTGACGA GCGCGGCGAA GGTAAAAAGG    1440
GCATTCAATT AGCAAAGAAA ACCTCTTTAG AAAAAGGCTC AACCATCAAT GTATCAGGCA    1500
AAGAAAAAGG CGGACGCGCT ATTGTGTGGG GCGATATTGC GTTAATTGAC GGCAATATTA    1560
ACGCTCAAGG TAGTGGTGAT ATCGCTAAAA CCGGTGGTTT TGTGGAGACG TCGGGGCATG    1620
ATTTATTCAT CAAAGACAAT GCAATTGTTG ACGCCAAAGA GTGGTTGTTA GACCCGGATA    1680
ATGTATCTAT TAATGCAGAA ACAGCAGGAC GCAGCAATAC TTCAGAAGAC GATGAATACA    1740
CGGGATCCGG GAATAGTGCC AGCACCCCAA AACGAAACAA AGAAAAGACA ACATTAACAA    1800
```

```
ACACAACTCT TGAGAGTATA CTAAAAAAAG GTACCTTTGT TAACATCACT GCTAATCAAC    1860

GCATCTATGT CAATAGCTCC ATTAATTTAT CCAATGGCAG CTTAACTCTT TGGAGTGAGG    1920

GTCGGAGCGG TGGCGGCGTT GAGATTAACA ACGATATTAC CACCGGTGAT GATACCAGAG    1980

GTGCAAACTT AACAATTTAC TCAGGCGGCT GGGTTGATGT TCATAAAAAT ATCTCACTCG    2040

GGGCGCAAGG TAACATAAAC ATTACAGCTA AACAAGATAT CGCCTTTGAG AAAGGAAGCA    2100

ACCAAGTCAT TACAGGTCAA GGGACTATTA CCTCAGGCAA TCAAAAAGGT TTTAGATTTA    2160

ATAATGTCTC TCTAAACGGC ACTGGCAGCG GACTGCAATT CACCACTAAA AGAACCAATA    2220

AATACGCTAT CACAAATAAA TTTGAAGGGA CTTTAAATAT TTCAGGGAAA GTGAACATCT    2280

CAATGGTTTT ACCTAAAAAT GAAAGTGGAT ATGATAAATT CAAAGGACGC ACTTACTGGA    2340

ATTTAACCTC CTTAAATGTT TCCGAGAGTG GCGAGTTTAA CCTCACTATT GACTCCAGAG    2400

GAAGCGATAG TGCAGGCACA CTTACCCAGC CTTATAATTT AAACGGTATA TCATTCAACA    2460

AAGACACTAC CTTTAATGTT GAACGAAATG CAAGAGTCAA CTTTGACATC AAGGCACCAA    2520

TAGGGATAAA TAAGTATTCT AGTTTGAATT ACGCATCATT TAATGGAAAC ATTTCAGTTT    2580

CGGGAGGGGG GAGTGTTGAT TTCACACTTC TCGCCTCATC CTCTAACGTC CAAACCCCCG    2640

GTGTAGTTAT AAATTCTAAA TACTTTAATG TTTCAACAGG GTCAAGTTTA AGATTTAAAA    2700

CTTCAGGCTC AACAAAAACT GGCTTCTCAA TAGAGAAAGA TTTAACTTTA AATGCCACCG    2760

GAGGCAACAT AACACTTTTG CAAGTTGAAG GCACCGATGG AATGATTGGT AAAGGCATTG    2820

TAGCCAAAAA AAACATAACC TTTGAAGGAG GTAACATCAC CTTTGGCTCC AGGAAAGCCG    2880

TAACAGAAAT CGAAGGCAAT GTTACTATCA ATAACAACGC TAACGTCACT CTTATCGGTT    2940

CGGATTTTGA CAACCATCAA AAACCTTTAA CTATTAAAAA AGATGTCATC ATTAATAGCG    3000

GCAACCTTAC CGCTGGAGGC AATATTGTCA ATATAGCCGG AAATCTTACC GTTGAAAGTA    3060

ACGCTAATTT CAAAGCTATC ACAAATTTCA CTTTTAATGT AGGCGGCTTG TTTGACAACA    3120

AAGGCAATTC AAATATTTCC ATTGCCAAAG GAGGGGCTCG CTTTAAAGAC ATTGATAATT    3180

CCAAGAATTT AAGCATCACC ACCAACTCCA GCTCCACTTA CCGCACTATT ATAAGCGGCA    3240

ATATAACCAA TAAAAACGGT GATTTAAATA TTACGAACGA AGGTAGTGAT ACTGAAATGC    3300

AAATTGGCGG CGATGTCTCG CAAAAAGAAG GTAATCTCAC GATTTCTTCT GACAAAATCA    3360

ATATTACCAA ACAGATAACA ATCAAGGCAG GTGTTGATGG GGAGAATTCC GATTCAGACG    3420

CGACAAACAA TGCCAATCTA ACCATTAAAA CCAAAGAATT GAAATTAACG CAAGACCTAA    3480

ATATTTCAGG TTTCAATAAA GCAGAGATTA CAGCTAAAGA TGGTAGTGAT TTAACTATTG    3540

GTAACACCAA TAGTGCTGAT GGTACTAATG CCAAAAAAGT AACCTTTAAC CAGGTTAAAG    3600

ATTCAAAAAT CTCTGCTGAC GGTCACAAGG TGACACTACA CAGCAAAGTG GAAACATCCG    3660

GTAGTAATAA CAACACTGAA GATAGCAGTG ACAATAATGC CGGCTTAACT ATCGATGCAA    3720

AAAATGTAAC AGTAAACAAC AATATTACTT CTCACAAAGC AGTGAGCATC TCTGCGACAA    3780

GTGGAGAAAT TACCACTAAA ACAGGTACAA CCATTAACGC AACCACTGGT AACGTGGAGA    3840

TAACCGCTCA AACAGGTAGT ATCCTAGGTG GAATTGAGTC CAGCTCTGGC TCTGTAACAC    3900

TTACTGCAAC CGAGGGCGCT CTTGCTGTAA GCAATATTTC GGGCAACACC GTTACTGTTA    3960

CTGCAAATAG CGGTGCATTA ACCACTTTGG CAGGCTCTAC AATTAAAGGA ACCGAGAGTG    4020

TAACCACTTC AAGTCAATCA GGCGATATCG GCGGTACGAT TTCTGGTGGC ACAGTAGAGG    4080

TTAAAGCAAC CGAAAGTTTA ACCACTCAAT CCAATTCAAA AATTAAAGCA ACAACAGGCG    4140

AGGCTAACGT AACAAGTGCA ACAGGTACAA TTGGTGGTAC GATTTCCGGT AATACGGTAA    4200
```

-continued

```
ATGTTACGGC AAACGCTGGC GATTTAACAG TTGGGAATGG CGCAGAAATT AATGCGACAG    4260

AAGGAGCTGC AACCTTAACT ACATCATCGG GCAAATTAAC TACCGAAGCT AGTTCACACA    4320

TTACTTCAGC CAAGGGTCAG GTAAATCTTT CAGCTCAGGA TGGTAGCGTT GCAGGAAGTA    4380

TTAATGCCGC CAATGTGACA CTAAATACTA CAGGCACTTT AACTACCGTG AAGGGTTCAA    4440

ACATTAATGC AACCAGCGGT ACCTTGGTTA TTAACGCAAA AGACGCTGAG CTAAATGGCG    4500

CAGCATTGGG TAACCACACA GTGGTAAATG CAACCAACGC AAATGGCTCC GGCAGCGTAA    4560

TCGCGACAAC CTCAAGCAGA GTGAACATCA CTGGGGATTT AATCACAATA AATGGATTAA    4620

ATATCATTTC AAAAAACGGT ATAAACACCG TACTGTTAAA AGGCGTTAAA ATTGATGTGA    4680

AATACATTCA ACCGGGTATA GCAAGCGTAG ATGAAGTAAT TGAAGCGAAA CGCATCCTTG    4740

AGAAGGTAAA AGATTTATCT GATGAAGAAA GAGAAGCGTT AGCTAAACTT GGAGTAAGTG    4800

CTGTACGTTT TATTGAGCCA AATAATACAA TTACAGTCGA TACACAAAAT GAATTTGCAA    4860

CCAGACCATT AAGTCGAATA GTGATTTCTG AAGGCAGGGC GTGTTTCTCA AACAGTGATG    4920

GCGCGACGGT GTGCGTTAAT ATCGCTGATA ACGGGCGGTA GCGGTCAGTA ATTGACAAGG    4980

TAGATTTCAT CCTGCAATGA AGTCATTTTA TTTTCGTATT ATTTACTGTG TGGGTTAAAG    5040

TTCAGTACGG GCTTTACCCA TCTTGTAAAA AATTACGGAG AATACAATAA AGTATTTTTA    5100

ACAGGTTATT ATTATG                                                   5116
```

(2) INFORMATION FOR SEQ ID NO:2:

(i) SEQUENCE CHARACTERISTICS:
        (A) LENGTH: 1536 amino acids
        (B) TYPE: amino acid
        (C) STRANDEDNESS: single
        (D) TOPOLOGY: linear (ii) MOLECULE TYPE: DNA (genomic)

(xi) SEQUENCE DESCRIPTION: SEQ ID NO:2:

```
Met Asn Lys Ile Tyr Arg Leu Lys Phe Ser Lys Arg Leu Asn Ala Leu
1               5                   10                  15

Val Ala Val Ser Glu Leu Ala Arg Gly Cys Asp His Ser Thr Glu Lys
            20                  25                  30

Gly Ser Glu Lys Pro Ala Arg Met Lys Val Arg His Leu Ala Leu Lys
        35                  40                  45

Pro Leu Ser Ala Met Leu Leu Ser Leu Gly Val Thr Ser Ile Pro Gln
    50                  55                  60

Ser Val Leu Ala Ser Gly Leu Gln Gly Met Asp Val Val His Gly Thr
65                  70                  75                  80

Ala Thr Met Gln Val Asp Gly Asn Lys Thr Ile Ile Arg Asn Ser Val
                85                  90                  95

Asp Ala Ile Ile Asn Trp Lys Gln Phe Asn Ile Asp Gln Asn Glu Met
            100                 105                 110

Val Gln Phe Leu Gln Glu Asn Asn Ser Ala Val Phe Asn Arg Val
            115                 120                 125

Thr Ser Asn Gln Ile Ser Gln Leu Lys Gly Ile Leu Asp Ser Asn Gly
    130                 135                 140

Gln Val Phe Leu Ile Asn Pro Asn Gly Ile Thr Ile Gly Lys Asp Ala
145                 150                 155                 160

Ile Ile Asn Thr Asn Gly Phe Thr Ala Ser Thr Leu Asp Ile Ser Asn
                165                 170                 175

Glu Asn Ile Lys Ala Arg Asn Phe Thr Phe Glu Gln Thr Lys Asp Lys
            180                 185                 190
```

-continued

Ala Leu Ala Glu Ile Val Asn His Gly Leu Ile Thr Val Gly Lys Asp
         195                 200                 205

Gly Ser Val Asn Leu Ile Gly Gly Lys Val Lys Asn Glu Gly Val Ile
210                 215                 220

Ser Val Asn Gly Gly Ser Ile Ser Leu Leu Ala Gly Gln Lys Ile Thr
225                 230                 235                 240

Ile Ser Asp Ile Ile Asn Pro Thr Ile Thr Tyr Ser Ile Ala Ala Pro
             245                 250                 255

Glu Asn Glu Ala Val Asn Leu Gly Asp Ile Phe Ala Lys Gly Gly Asn
         260                 265                 270

Ile Asn Val Arg Ala Ala Thr Ile Arg Asn Gln Gly Lys Leu Ser Ala
     275                 280                 285

Asp Ser Val Ser Lys Asp Lys Ser Gly Asn Ile Val Leu Ser Ala Lys
290                 295                 300

Glu Gly Glu Ala Glu Ile Gly Gly Val Ile Ser Ala Gln Asn Gln Gln
305                 310                 315                 320

Ala Lys Gly Gly Lys Leu Met Ile Thr Gly Asp Lys Val Thr Leu Lys
             325                 330                 335

Thr Gly Ala Val Ile Asp Leu Ser Gly Lys Glu Gly Glu Thr Tyr
         340                 345                 350

Leu Gly Gly Asp Glu Arg Gly Glu Gly Lys Asn Gly Ile Gln Leu Ala
     355                 360                 365

Lys Lys Thr Ser Leu Glu Lys Gly Ser Thr Ile Asn Val Ser Gly Lys
370                 375                 380

Glu Lys Gly Gly Arg Ala Ile Val Trp Gly Asp Ile Ala Leu Ile Asp
385                 390                 395                 400

Gly Asn Ile Asn Ala Gln Gly Ser Gly Asp Ile Ala Lys Thr Gly Gly
             405                 410                 415

Phe Val Glu Thr Ser Gly His Asp Leu Phe Ile Lys Asp Asn Ala Ile
         420                 425                 430

Val Asp Ala Lys Glu Trp Leu Leu Asp Phe Asp Asn Val Ser Ile Asn
     435                 440                 445

Ala Glu Thr Ala Gly Arg Ser Asn Thr Ser Glu Asp Asp Glu Tyr Thr
450                 455                 460

Gly Ser Gly Asn Ser Ala Ser Thr Pro Lys Arg Asn Lys Glu Lys Thr
465                 470                 475                 480

Thr Leu Thr Asn Thr Thr Leu Glu Ser Ile Leu Lys Lys Gly Thr Phe
             485                 490                 495

Val Asn Ile Thr Ala Asn Gln Arg Ile Tyr Val Asn Ser Ser Ile Asn
         500                 505                 510

Leu Ser Asn Gly Ser Leu Thr Leu Trp Ser Glu Gly Arg Ser Gly Gly
     515                 520                 525

Gly Val Glu Ile Asn Asn Asp Ile Thr Thr Gly Asp Asp Thr Arg Gly
530                 535                 540

Ala Asn Leu Thr Ile Tyr Ser Gly Gly Trp Val Asp Val His Lys Asn
545                 550                 555                 560

Ile Ser Leu Gly Ala Gln Gly Asn Ile Asn Ile Thr Ala Lys Gln Asp
             565                 570                 575

Ile Ala Phe Glu Lys Gly Ser Asn Gln Val Ile Thr Gly Gln Gly Thr
         580                 585                 590

Ile Thr Ser Gly Asn Gln Lys Gly Phe Arg Phe Asn Asn Val Ser Leu
     595                 600                 605

Asn Gly Thr Gly Ser Gly Leu Gln Phe Thr Thr Lys Arg Thr Asn Lys

```
            610                 615                 620
Tyr Ala Ile Thr Asn Lys Phe Glu Gly Thr Leu Asn Ile Ser Gly Lys
625                 630                 635                 640

Val Asn Ile Ser Met Val Leu Pro Lys Asn Glu Ser Gly Tyr Asp Lys
                645                 650                 655

Phe Lys Gly Arg Thr Tyr Trp Asn Leu Thr Ser Leu Asn Val Ser Glu
                660                 665                 670

Ser Gly Glu Phe Asn Leu Thr Ile Asp Ser Arg Gly Ser Asp Ser Ala
                675                 680                 685

Gly Thr Leu Thr Gln Pro Tyr Asn Leu Asn Gly Ile Ser Phe Asn Lys
                690                 695                 700

Asp Thr Thr Phe Asn Val Glu Arg Asn Ala Arg Val Asn Phe Asp Ile
705                 710                 715                 720

Lys Ala Pro Ile Gly Ile Asn Lys Tyr Ser Ser Leu Asn Tyr Ala Ser
                725                 730                 735

Phe Asn Gly Asn Ile Ser Val Ser Gly Gly Ser Val Asp Phe Thr
                740                 745                 750

Leu Leu Ala Ser Ser Asn Val Gln Thr Pro Gly Val Val Ile Asn
                755                 760                 765

Ser Lys Tyr Phe Asn Val Ser Thr Gly Ser Ser Leu Arg Phe Lys Thr
770                 775                 780

Ser Gly Ser Thr Lys Thr Gly Phe Ser Ile Glu Lys Asp Leu Thr Leu
785                 790                 795                 800

Asn Ala Thr Gly Gly Asn Ile Thr Leu Leu Gln Val Glu Gly Thr Asp
                805                 810                 815

Gly Met Ile Gly Lys Gly Ile Val Ala Lys Lys Asn Ile Thr Phe Glu
                820                 825                 830

Gly Gly Asn Ile Thr Phe Gly Ser Arg Lys Ala Val Thr Glu Ile Glu
                835                 840                 845

Gly Asn Val Thr Ile Asn Asn Asn Ala Asn Val Thr Leu Ile Gly Ser
                850                 855                 860

Asp Phe Asp Asn His Gln Lys Pro Leu Thr Ile Lys Lys Asp Val Ile
865                 870                 875                 880

Ile Asn Ser Gly Asn Leu Thr Ala Gly Gly Asn Ile Val Asn Ile Ala
                885                 890                 895

Gly Asn Leu Thr Val Glu Ser Asn Ala Asn Phe Lys Ala Ile Thr Asn
                900                 905                 910

Phe Thr Phe Asn Val Gly Gly Leu Phe Asp Asn Lys Gly Asn Ser Asn
                915                 920                 925

Ile Ser Ile Ala Lys Gly Gly Ala Arg Phe Lys Asp Ile Asp Asn Ser
930                 935                 940

Lys Asn Leu Ser Ile Thr Thr Asn Ser Ser Thr Tyr Arg Thr Ile
945                 950                 955                 960

Ile Ser Gly Asn Ile Thr Asn Lys Asn Gly Asp Leu Asn Ile Thr Asn
                965                 970                 975

Glu Gly Ser Asp Thr Glu Met Gln Ile Gly Gly Asp Val Ser Gln Lys
                980                 985                 990

Glu Gly Asn Leu Thr Ile Ser Ser Asp Lys Ile Asn Ile Thr Lys Gln
                995                 1000                1005

Ile Thr Ile Lys Ala Gly Val Asp Gly Glu Asn Ser Asp Ser Asp Ala
                1010                1015                1020

Thr Asn Asn Ala Asn Leu Thr Ile Lys Thr Lys Glu Leu Lys Leu Thr
1025                1030                1035                1040
```

```
Gln Asp Leu Asn Ile Ser Gly Phe Asn Lys Ala Glu Ile Thr Ala Lys
            1045                1050                1055

Asp Gly Ser Asp Leu Thr Ile Gly Asn Thr Asn Ser Ala Asp Gly Thr
            1060                1065                1070

Asn Ala Lys Lys Val Thr Phe Asn Gln Val Lys Asp Ser Lys Ile Ser
            1075                1080                1085

Ala Asp Gly His Lys Val Thr Leu His Ser Lys Val Glu Thr Ser Gly
            1090                1095                1100

Ser Asn Asn Asn Thr Glu Asp Ser Ser Asp Asn Asn Ala Gly Leu Thr
1105                1110                1115                1120

Ile Asp Ala Lys Asn Val Thr Asn Asn Ile Thr Ser His Lys
            1125                1130                1135

Ala Val Ser Ile Ser Ala Thr Ser Gly Glu Ile Thr Thr Lys Thr Gly
            1140                1145                1150

Thr Thr Ile Asn Ala Thr Thr Gly Asn Val Glu Ile Thr Ala Gln Thr
            1155                1160                1165

Gly Ser Ile Leu Gly Gly Ile Glu Ser Ser Ser Gly Ser Val Thr Leu
            1170                1175                1180

Thr Ala Thr Glu Gly Ala Leu Ala Val Ser Asn Ile Ser Gly Asn Thr
1185                1190                1195                1200

Val Thr Val Thr Ala Asn Ser Gly Ala Leu Thr Thr Leu Ala Gly Ser
            1205                1210                1215

Thr Ile Lys Gly Thr Glu Ser Val Thr Thr Ser Ser Gln Ser Gly Asp
            1220                1225                1230

Ile Gly Gly Thr Ile Ser Gly Gly Thr Val Glu Val Lys Ala Thr Glu
            1235                1240                1245

Ser Leu Thr Thr Gln Ser Asn Ser Lys Ile Lys Ala Thr Thr Gly Glu
            1250                1255                1260

Ala Asn Val Thr Ser Ala Thr Gly Thr Ile Gly Gly Thr Ile Ser Gly
1265                1270                1275                1280

Asn Thr Val Asn Val Thr Ala Asn Ala Gly Asp Leu Thr Val Gly Asn
            1285                1290                1295

Gly Ala Glu Ile Asn Ala Thr Glu Gly Ala Ala Thr Leu Thr Thr Ser
            1300                1305                1310

Ser Gly Lys Leu Thr Thr Glu Ala Ser Ser His Ile Thr Ser Ala Lys
            1315                1320                1325

Gly Gln Val Asn Leu Ser Ala Gln Asp Gly Ser Val Ala Gly Ser Ile
            1330                1335                1340

Asn Ala Ala Asn Val Thr Leu Asn Thr Thr Gly Thr Leu Thr Thr Val
1345                1350                1355                1360

Lys Gly Ser Asn Ile Asn Ala Thr Ser Gly Thr Leu Val Ile Asn Ala
            1365                1370                1375

Lys Asp Ala Glu Leu Asn Gly Ala Ala Leu Gly Asn His Thr Val Val
            1380                1385                1390

Asn Ala Thr Asn Ala Asn Gly Ser Gly Ser Val Ile Ala Thr Thr Ser
            1395                1400                1405

Ser Arg Val Asn Ile Thr Gly Asp Leu Ile Thr Ile Asn Gly Leu Asn
            1410                1415                1420

Ile Ile Ser Lys Asn Gly Ile Asn Thr Val Leu Leu Lys Gly Val Lys
1425                1430                1435                1440

Ile Asp Val Lys Tyr Ile Gln Pro Gly Ile Ala Ser Val Asp Glu Val
            1445                1450                1455

Ile Glu Ala Lys Arg Ile Leu Glu Lys Val Lys Asp Leu Ser Asp Glu
            1460                1465                1470
```

Glu Arg Glu Ala Leu Ala Lys Leu Gly Val Ser Ala Val Arg Phe Ile
         1475                1480                1485

Glu Pro Asn Asn Thr Ile Thr Val Asp Thr Gln Asn Glu Phe Ala Thr
    1490                1495                1500

Arg Pro Leu Ser Arg Ile Val Ile Ser Glu Gly Arg Ala Cys Phe Ser
1505                1510                1515                1520

Asn Ser Asp Gly Ala Thr Val Cys Val Asn Ile Ala Asp Asn Gly Arg
         1525                1530                1535

(2) INFORMATION FOR SEQ ID NO:3:

(i) SEQUENCE CHARACTERISTICS:
        (A) LENGTH: 4937 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:3:

| | | | | |
|---|---|---|---|---|
| TAAATATACA | AGATAATAAA | AATAAATCAA | GATTTTGTG | ATGACAAACA ACAATTACAA | 60 |
| CACCTTTTTT | GCAGTCTATA | TGCAAATATT | TTAAAAAAAT | AGTATAAATC CGCCATATAA | 120 |
| AATGGTATAA | TCTTTCATCT | TTCATCTTTA | ATCTTTCATC | TTTCATCTTT CATCTTTCAT | 180 |
| CTTTCATCTT | TCATCTTTCA | TCTTTCATCT | TTCATCTTTC | ATCTTTCATC TTTCATCTTT | 240 |
| CACATGAAAT | GATGAACCGA | GGGAAGGGAG | GGAGGGGCAA | GAATGAAGAG GGAGCTGAAC | 300 |
| GAACGCAAAT | GATAAAGTAA | TTTAATTGTT | CAACTAACCT | TAGGAGAAAA TATGAACAAG | 360 |
| ATATATCGTC | TCAAATTCAG | CAAACGCCTG | AATGCTTTGG | TTGCTGTGTC TGAATTGGCA | 420 |
| CGGGGTTGTG | ACCATTCCAC | AGAAAAAGGC | TTCCGCTATG | TTACTATCTT TAGGTGTAAC | 480 |
| CACTTAGCGT | TAAAGCCACT | TTCCGCTATG | TTACTATCTT | TAGGTGTAAC ATCTATTCCA | 540 |
| CAATCTGTTT | TAGCAAGCGG | CTTACAAGGA | ATGGATGTAG | TACACGGCAC AGCCACTATG | 600 |
| CAAGTAGATG | GTAATAAAAC | CATTATCCGC | AACAGTGTTG | ACGCTATCAT TAATTGGAAA | 660 |
| CAATTTAACA | TCGACCAAAA | TGAAATGGTG | CAGTTTTTAC | AAGAAAACAA CAACTCCGCC | 720 |
| GTATTCAACC | GTGTTACATC | TAACCAAATC | TCCCAATTAA | AAGGGATTTT AGATTCTAAC | 780 |
| GGACAAGTCT | TTTTAATCAA | CCCAAATGGT | ATCACAATAG | GTAAAGACGC AATTATTAAC | 840 |
| ACTAATGGCT | TTACGGCTTC | TACGCTAGAC | ATTTCTAACG | AAAACATCAA GGCGCGTAAT | 900 |
| TTCACCTTCG | AGCAAACCAA | AGATAAAGCG | CTCGCTGAAA | TTGTGAATCA CGGTTTAATT | 960 |
| ACTGTCGGTA | AAGACGGCAG | TGTAAATCTT | ATTGGTGGCA | AAGTGAAAAA CGAGGGTGTG | 1020 |
| ATTAGCGTAA | ATGGTGGCAG | CATTTCTTTA | CTCGCAGGGC | AAAAAATCAC CATCAGCGAT | 1080 |
| ATAATAAACC | CAACCATTAC | TTACAGCATT | GCCGCGCCTG | AAAATGAAGC GGTCAATCTG | 1140 |
| GGCGATATTT | TTGCCAAAGG | CGGTAACATT | AATGTCCGTG | CTGCCACTAT TCGAAACCAA | 1200 |
| GGTAAACTTT | CTGCTGATTC | TGTAAGCAAA | GATAAAAGCG | GCAATATTGT TCTTTCCGCC | 1260 |
| AAAGAGGGTG | AAGCGGAAAT | TGGCGGTGTA | ATTTCCGCTC | AAAATCAGCA AGCTAAAGGC | 1320 |
| GGCAAGCTGA | TGATTACAGG | CGATAAAGTC | ACATTAAAAA | CAGGTGCAGT TATCGACCTT | 1380 |
| TCAGGTAAAG | AAGGGGGAGA | AACTTACCTT | GGCGGTGACG | AGCGCGGCGA AGGTAAAAAC | 1440 |
| GGCATTCAAT | TAGCAAAGAA | AACCTCTTTA | GAAAAAGGCT | CAACCATCAA TGTATCAGGC | 1500 |
| AAAGAAAAAG | GCGGACGCGC | TATTGTGTGG | GGCGATATTG | CGTTAATTGA CGGCAATATT | 1560 |
| AACGCTCAAG | GTAGTGGTGA | TATCGCTAAA | ACCGGTGGTT | TTGTGGAGAC ATCGGGGCAT | 1620 |

```
TATTTATCCA TTGACAGCAA TGCAATTGTT AAAACAAAAG AGTGGTTGCT AGACCCTGAT    1680

GATGTAACAA TTGAAGCCGA AGACCCCCTT CGCAATAATA CCGGTATAAA TGATGAATTC    1740

CCAACAGGCA CCGGTGAAGC AAGCGACCCT AAAAAAAATA GCGAACTCAA AACAACGCTA    1800

ACCAATACAA CTATTTCAAA TTATCTGAAA AACGCCTGGA CAATGAATAT AACGGCATCA    1860

AGAAAACTTA CCGTTAATAG CTCAATCAAC ATCGGAAGCA ACTCCCACTT AATTCTCCAT    1920

AGTAAAGGTC AGCGTGGCGG AGGCGTTCAG ATTGATGGAG ATATTACTTC TAAAGGCGGA    1980

AATTTAACCA TTTATTCTGG CGGATGGGTT GATGTTCATA AAAATATTAC GCTTGATCAG    2040

GGTTTTTTAA ATATTACCGC CGCTTCCGTA GCTTTTGAAG GTGGAAATAA CAAAGCACGC    2100

GACGCGGCAA ATGCTAAAAT TGTCGCCCAG GGCACTGTAA CCATTACAGG AGAGGGAAAA    2160

GATTTCAGGG CTAACAACGT ATCTTTAAAC GGAACGGGTA AAGGTCTGAA TATCATTTCA    2220

TCAGTGAATA ATTTAACCCA CAATCTTAGT GGCACAATTA ACATATCTGG GAATATAACA    2280

ATTAACCAAA CTACGAGAAA GAACACCTCG TATTGGCAAA CCAGCCATGA TTCGCACTGG    2340

AACGTCAGTG CTCTTAATCT AGAGACAGGC GCAAATTTTA CCTTTATTAA ATACATTTCA    2400

AGCAATAGCA AAGGCTTAAC AACACAGTAT AGAAGCTCTG CAGGGGTGAA TTTTAACGGC    2460

GTAAATGGCA ACATGTCATT CAATCTCAAA GAAGGAGCGA AAGTTAATTT CAAATTAAAA    2520

CCAAACGAGA ACATGAACAC AAGCAAACCT TTACCAATTC GGTTTTTAGC CAATATCACA    2580

GCCACTGGTG GGGCTCTGT TTTTTTTGAT ATATATGCCA ACCATTCTGG CAGAGGGGCT    2640

GAGTTAAAAA TGAGTGAAAT TAATATCTCT AACGGCGCTA ATTTTACCTT AAATTCCCAT    2700

GTTCGCGGCG ATGACGCTTT TAAAATCAAC AAAGACTTAA CCATAAATGC AACCAATTCA    2760

AATTTCAGCC TCAGACAGAC GAAAGATGAT TTTTATGACG GGTACGCACG CAATGCCATC    2820

AATTCAACCT ACAACATATC CATTCTGGGC GGTAATGTCA CCCTTGGTGG ACAAAACTCA    2880

AGCAGCAGCA TTACGGGGAA TATTACTATC GAGAAAGCAG CAAATGTTAC GCTAGAAGCC    2940

AATAACGCCC CTAATCAGCA AAACATAAGG GATAGAGTTA TAAAACTTGG CAGCTTGCTC    3000

GTTAATGGGA GTTTAAGTTT AACTGGCGAA AATGCAGATA TTAAAGGCAA TCTCACTATT    3060

TCAGAAAGCG CCACTTTTAA AGGAAAGACT AGAGATACCC TAAATATCAC CGGCAATTTT    3120

ACCAATAATG GCACTGCCGA AATTAATATA ACACAAGGAG TGGTAAAACT TGGCAATGTT    3180

ACCAATGATG GTGATTTAAA CATTACCACT CACGCTAAAC GCAACCAAAG AAGCATCATC    3240

GGCGGAGATA TAATCAACAA AAAAGGAAGC TTAAATATTA CAGACAGTAA TAATGATGCT    3300

GAAATCCAAA TTGGCGGCAA TATCTCGCAA AAAGAAGGCA ACCTCACGAT TTCTTCCGAT    3360

AAAATTAATA TCACCAAACA GATAACAATC AAAAAGGGTA TTGATGGAGA GGACTCTAGT    3420

TCAGATGCGA CAAGTAATGC CAACCTAACT ATTAAAACCA AGAATTGAA ATTGACAGAA    3480

GACCTAAGTA TTTCAGGTTT CAATAAAGCA GAGATTACAG CCAAAGATGG TAGAGATTTA    3540

ACTATTGGCA ACAGTAATGA CGGTAACAGC GGTGCCGAAG CCAAAACAGT AACTTTTAAC    3600

AATGTTAAAG ATTCAAAAAT CTCTGCTGAC GGTCACAATG TGACACTAAA TAGCAAAGTG    3660

AAAACATCTA GCAGCAATGG CGGACGTGAA AGCAATAGCG ACAACGATAC CGGCTTAACT    3720

ATTACTGCAA AAAATGTAGA AGTAAACAAA GATATTACTT CTCTCAAAAC AGTAAATATC    3780

ACCGCGTCGG AAAAGGTTAC CACCCACAGCA GGCTCGACCA TTAACGCAAC AAATGGCAAA    3840

GCAAGTATTA CAACCAAAAC AGGTGATATC AGCGGTACGA TTTCCGGTAA CACGGTAAGT    3900

GTTAGCGCGA CTGGTGATTT AACCACTAAA TCCGGCTCAA AAATTGAAGC GAAATCGGGT    3960

GAGGCTAATG TAACAAGTGC AACAGGTACA ATTGGCGGTA CAATTTCCGG TAATACGGTA    4020
```

-continued

```
AATGTTACGG CAAACGCTGG CGATTTAACA GTTGGGAATG GCGCAGAAAT TAATGCGACA    4080

GAAGGAGCTG CAACCTTAAC CGCAACAGGG AATACCTTGA CTACTGAAGC CGGTTCTAGC    4140

ATCACTTCAA CTAAGGGTCA GGTAGACCTC TTGGCTCAGA ATGGTAGCAT CGCAGGAAGC    4200

ATTAATGCTG CTAATGTGAC ATTAAATACT ACAGGCACCT TAACCACCGT GGCAGGCTCG    4260

GATATTAAAG CAACCAGCGG CACCTTGGTT ATTAACGCAA AAGATGCTAA GCTAAATGGT    4320

GATGCATCAG GTGATAGTAC AGAAGTGAAT GCAGTCAACG CAAGCGGCTC TGGTAGTGTG    4380

ACTGCGGCAA CCTCAAGCAG TGTGAATATC ACTGGGGATT TAAACACAGT AAATGGGTTA    4440

AATATCATTT CGAAAGATGG TAGAAACACT GTGCGCTTAA GAGGCAAGGA AATTGAGGTG    4500

AAATATATCC AGCCAGGTGT AGCAAGTGTA AAGAAGTAA TTGAAGCGAA ACGCGTCCTT    4560

GAAAAAGTAA AAGATTTATC TGATGAAGAA AGAGAAACAT TAGCTAAACT TGGTGTAAGT    4620

GCTGTACGTT TTGTTGAGCC AAATAATACA ATTACAGTCA ATACACAAAA TGAATTTACA    4680

ACCAGACCGT CAAGTCAAGT GATAATTTCT GAAGGTAAGG CGTGTTTCTC AAGTGGTAAT    4740

GGCGCACGAG TATGTACCAA TGTTGCTGAC GATGGACAGC CGTAGTCAGT AATTGACAAG    4800

GTAGATTTCA TCCTGCAATG AAGTCATTTT ATTTTCGTAT TATTTACTGT GTGGGTTAAA    4860

GTTCAGTACG GGCTTTACCC ATCTTGTAAA AAATTACGGA GAATACAATA AAGTATTTTT    4920

AACAGGTTAT TATTATG                                                    4937
```

(2) INFORMATION FOR SEQ ID NO:4:

(i) SEQUENCE CHARACTERISTICS:
        (A) LENGTH: 1477 amino acids
        (B) TYPE: amino acid
        (C) STRANDEDNESS: single
        (D) TOPOLOGY: linear (xi) SEQUENCE DESCRIPTION: SEQ ID NO:4:

```
Met Asn Lys Ile Tyr Arg Leu Lys Phe Ser Lys Arg Leu Asn Ala Leu
1               5                   10                  15

Val Ala Val Ser Glu Leu Ala Arg Gly Cys Asp His Ser Thr Glu Lys
            20                  25                  30

Gly Ser Glu Lys Pro Ala Arg Met Lys Val Arg His Leu Ala Leu Lys
        35                  40                  45

Pro Leu Ser Ala Met Leu Leu Ser Leu Gly Val Thr Ser Ile Pro Gln
50                  55                  60

Ser Val Leu Ala Ser Gly Leu Gln Gly Met Asp Val Val His Gly Thr
65                  70                  75                  80

Ala Thr Met Gln Val Asp Gly Asn Lys Thr Ile Ile Arg Asn Ser Val
            85                  90                  95

Asp Ala Ile Ile Asn Trp Lys Gln Phe Asn Ile Asp Gln Asn Glu Met
            100                 105                 110

Val Gln Phe Leu Gln Glu Asn Asn Ser Ala Val Phe Asn Arg Val
        115                 120                 125

Thr Ser Asn Gln Ile Ser Gln Leu Lys Gly Ile Leu Asp Ser Asn Gly
130                 135                 140

Gln Val Phe Leu Ile Asn Pro Asn Gly Ile Thr Ile Gly Lys Asp Ala
145                 150                 155                 160

Ile Ile Asn Thr Asn Gly Phe Thr Ala Ser Thr Leu Asp Ile Ser Asn
            165                 170                 175

Glu Asn Ile Lys Ala Arg Asn Phe Thr Phe Glu Gln Thr Lys Asp Lys
            180                 185                 190

Ala Leu Ala Glu Ile Val Asn His Gly Leu Ile Thr Val Gly Lys Asp
```

-continued

```
                195                 200                 205
Gly Ser Val Asn Leu Ile Gly Gly Lys Val Lys Asn Glu Gly Val Ile
    210                 215                 220
Ser Val Asn Gly Gly Ser Ile Ser Leu Leu Ala Gly Gln Lys Ile Thr
225                 230                 235                 240
Ile Ser Asp Ile Ile Asn Pro Thr Ile Thr Tyr Ser Ile Ala Ala Pro
                245                 250                 255
Glu Asn Glu Ala Val Asn Leu Gly Asp Ile Phe Ala Lys Gly Gly Asn
                260                 265                 270
Ile Asn Val Arg Ala Ala Thr Ile Arg Asn Gln Gly Lys Leu Ser Ala
            275                 280                 285
Asp Ser Val Ser Lys Asp Lys Ser Gly Asn Ile Val Leu Ser Ala Lys
290                 295                 300
Glu Gly Glu Ala Glu Ile Gly Gly Val Ile Ser Ala Gln Asn Gln Gln
305                 310                 315                 320
Ala Lys Gly Gly Lys Leu Met Ile Thr Gly Asp Lys Val Thr Leu Lys
                325                 330                 335
Thr Gly Ala Val Ile Asp Leu Ser Gly Lys Glu Gly Glu Thr Tyr
            340                 345                 350
Leu Gly Gly Asp Glu Arg Gly Glu Gly Lys Asn Gly Ile Gln Leu Ala
            355                 360                 365
Lys Lys Thr Ser Leu Glu Lys Gly Ser Thr Ile Asn Val Ser Gly Lys
370                 375                 380
Glu Lys Gly Gly Phe Ala Ile Val Trp Gly Asp Ile Ala Leu Ile Asp
385                 390                 395                 400
Gly Asn Ile Asn Ala Gln Gly Ser Gly Asp Ile Ala Lys Thr Gly Gly
                405                 410                 415
Phe Val Glu Thr Ser Gly His Asp Leu Phe Ile Lys Asp Asn Ala Ile
                420                 425                 430
Val Asp Ala Lys Glu Trp Leu Leu Asp Phe Asp Asn Val Ser Ile Asn
            435                 440                 445
Ala Glu Asp Pro Leu Phe Asn Asn Thr Gly Ile Asn Asp Glu Phe Pro
        450                 455                 460
Thr Gly Thr Gly Glu Ala Ser Asp Pro Lys Lys Asn Ser Glu Leu Lys
465                 470                 475                 480
Thr Thr Leu Thr Asn Thr Thr Ile Ser Asn Tyr Leu Lys Asn Ala Trp
                485                 490                 495
Thr Met Asn Ile Thr Ala Ser Arg Lys Leu Thr Val Asn Ser Ser Ile
            500                 505                 510
Asn Ile Gly Ser Asn Ser His Leu Ile Leu His Ser Lys Gly Gln Arg
        515                 520                 525
Gly Gly Gly Val Gln Ile Asp Gly Asp Ile Thr Ser Lys Gly Gly Asn
    530                 535                 540
Leu Thr Ile Tyr Ser Gly Gly Trp Val Asp Val His Lys Asn Ile Thr
545                 550                 555                 560
Leu Asp Gln Gly Phe Leu Asn Ile Thr Ala Ala Ser Val Ala Phe Glu
                565                 570                 575
Gly Gly Asn Asn Lys Ala Arg Asp Ala Ala Asn Ala Lys Ile Val Ala
            580                 585                 590
Gln Gly Thr Val Thr Ile Thr Gly Glu Gly Lys Asp Phe Arg Ala Asn
        595                 600                 605
Asn Val Ser Leu Asn Gly Thr Gly Lys Gly Leu Asn Ile Ile Ser Ser
    610                 615                 620
```

-continued

```
Val Asn Asn Leu Thr His Asn Leu Ser Gly Thr Ile Asn Ile Ser Gly
625                 630                 635                 640

Asn Ile Thr Ile Asn Gln Thr Thr Arg Lys Asn Thr Ser Tyr Trp Gln
            645                 650                 655

Thr Ser His Asp Ser His Trp Asn Val Ser Ala Leu Asn Leu Glu Thr
        660                 665                 670

Gly Ala Asn Phe Thr Phe Ile Lys Tyr Ile Ser Ser Asn Ser Lys Gly
    675                 680                 685

Leu Thr Thr Gln Tyr Arg Ser Ser Ala Gly Val Asn Phe Asn Gly Val
690                 695                 700

Asn Gly Asn Met Ser Phe Asn Leu Lys Glu Gly Ala Lys Val Asn Phe
705                 710                 715                 720

Lys Leu Lys Pro Asn Glu Asn Met Asn Thr Ser Lys Pro Leu Pro Ile
            725                 730                 735

Arg Phe Leu Ala Asn Ile Thr Ala Thr Gly Gly Ser Val Phe Phe
        740                 745                 750

Asp Ile Tyr Ala Asn His Ser Gly Arg Gly Ala Glu Leu Lys Met Ser
    755                 760                 765

Glu Ile Asn Ile Ser Asn Gly Ala Asn Phe Thr Leu Asn Ser His Val
770                 775                 780

Arg Gly Asp Asp Ala Phe Lys Ile Asn Lys Asp Leu Thr Ile Asn Ala
785                 790                 795                 800

Thr Asn Ser Asn Phe Ser Leu Arg Gln Thr Lys Asp Asp Phe Tyr Asp
            805                 810                 815

Gly Tyr Ala Arg Asn Ala Ile Asn Ser Thr Tyr Asn Ile Ser Ile Leu
        820                 825                 830

Gly Gly Asn Val Thr Leu Gly Gly Gln Asn Ser Ser Ser Ile Thr
    835                 840                 845

Gly Asn Ile Thr Ile Glu Lys Ala Ala Asn Val Thr Leu Glu Ala Asn
850                 855                 860

Asn Ala Pro Asn Gln Gln Asn Ile Arg Asp Arg Val Ile Lys Leu Gly
865                 870                 875                 880

Ser Leu Leu Val Asn Gly Ser Leu Ser Leu Thr Gly Glu Asn Ala Asp
            885                 890                 895

Ile Lys Gly Asn Leu Thr Ile Ser Glu Ser Ala Thr Phe Lys Gly Lys
        900                 905                 910

Thr Arg Asp Thr Leu Asn Ile Thr Gly Asn Phe Thr Asn Asn Gly Thr
    915                 920                 925

Ala Glu Ile Asn Ile Thr Gln Gly Val Val Lys Leu Gly Asn Val Thr
930                 935                 940

Asn Asp Gly Asp Leu Asn Ile Thr His Ala Lys Arg Asn Gln Arg
945                 950                 955                 960

Ser Ile Ile Gly Gly Asp Ile Asn Lys Lys Gly Ser Leu Asn Ile
            965                 970                 975

Thr Asp Ser Asn Asn Asp Ala Glu Ile Gln Ile Gly Gly Asn Ile Ser
        980                 985                 990

Gln Lys Glu Gly Asn Leu Thr Ile Ser Ser Asp Lys Ile Asn Ile Thr
    995                 1000                1005

Lys Gln Ile Thr Ile Lys Lys Gly Ile Asp Gly Glu Asp Ser Ser Ser
    1010                1015                1020

Asp Ala Thr Ser Asn Ala Asn Leu Thr Ile Lys Thr Lys Glu Leu Lys
1025                1030                1035                1040

Leu Thr Glu Asp Leu Ser Ile Ser Gly Phe Asn Lys Ala Glu Ile Thr
            1045                1050                1055
```

-continued

Ala Lys Asp Gly Arg Asp Leu Thr Ile Gly Asn Ser Asn Asp Gly Asn
    1060                1065                1070

Ser Gly Ala Glu Ala Lys Thr Val Thr Phe Asn Asn Val Lys Asp Ser
    1075                1080                1085

Lys Ile Ser Ala Asp Gly His Asn Val Thr Leu Asn Ser Lys Val Lys
    1090                1095                1100

Thr Ser Ser Ser Asn Gly Gly Arg Glu Ser Asn Ser Asp Asn Asp Thr
1105                1110                1115                1120

Gly Leu Thr Ile Thr Ala Lys Asn Val Glu Val Asn Lys Asp Ile Thr
            1125                1130                1135

Ser Leu Lys Thr Val Asn Ile Thr Ala Ser Glu Lys Val Thr Thr Thr
            1140                1145                1150

Ala Gly Ser Thr Ile Asn Ala Thr Asn Gly Lys Ala Ser Ile Thr Thr
            1155                1160                1165

Lys Thr Gly Asp Ile Ser Gly Thr Ile Ser Gly Asn Thr Val Ser Val
    1170                1175                1180

Ser Ala Thr Val Asp Leu Thr Thr Lys Ser Gly Ser Lys Ile Glu Ala
1185                1190                1195                1200

Lys Ser Gly Glu Ala Asn Val Thr Ser Ala Thr Gly Thr Ile Gly Gly
            1205                1210                1215

Thr Ile Ser Gly Asn Thr Val Asn Val Thr Ala Asn Ala Gly Asp Leu
    1220                1225                1230

Thr Val Gly Asn Gly Ala Glu Ile Asn Ala Thr Glu Gly Ala Ala Thr
    1235                1240                1245

Leu Thr Ala Thr Gly Asn Thr Leu Thr Thr Glu Ala Gly Ser Ser Ile
    1250                1255                1260

Thr Ser Thr Lys Gly Gln Val Asp Leu Leu Ala Gln Asn Gly Ser Ile
1265                1270                1275                1280

Ala Gly Ser Ile Asn Ala Asn Val Thr Leu Asn Thr Thr Gly Thr
            1285                1290                1295

Leu Thr Thr Val Ala Gly Ser Asp Ile Lys Ala Thr Ser Gly Thr Leu
    1300                1305                1310

Val Ile Asn Ala Lys Asp Ala Lys Leu Asn Gly Asp Ala Ser Gly Asp
    1315                1320                1325

Ser Thr Glu Val Asn Ala Val Asn Ala Ser Gly Ser Gly Ser Val Thr
    1330                1335                1340

Ala Ala Thr Ser Ser Val Asn Ile Thr Gly Asp Leu Asn Thr Val
1345                1350                1355                1360

Asn Gly Leu Asn Ile Ile Ser Lys Asp Gly Arg Asn Thr Val Arg Leu
            1365                1370                1375

Arg Gly Lys Glu Ile Glu Val Lys Tyr Ile Gln Pro Gly Val Ala Ser
            1380                1385                1390

Val Glu Glu Val Ile Glu Ala Lys Arg Val Leu Glu Lys Val Lys Asp
    1395                1400                1405

Leu Ser Asp Glu Glu Arg Glu Thr Leu Ala Lys Leu Gly Val Ser Ala
    1410                1415                1420

Val Arg Phe Val Glu Pro Asn Asn Thr Ile Thr Val Asn Thr Gln Asn
1425                1430                1435                1440

Glu Phe Thr Thr Arg Pro Ser Ser Gln Val Ile Ile Ser Glu Gly Lys
            1445                1450                1455

Ala Cys Phe Ser Ser Gly Asn Gly Ala Arg Val Cys Thr Asn Val Ala
            1460                1465                1470

Asp Asp Gly Gln Pro

1475

(2) INFORMATION FOR SEQ ID NO:5:

(i) SEQUENCE CHARACTERISTICS:
        (A) LENGTH: 9171 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:5:

```
ACAGCGTTCT CTTAATACTA GTACAAACCC ACAATAAAAT ATGACAAACA ACAATTACAA      60

CACCTTTTTT GCAGTCTATA TGCAAATATT TTAAAAAATA GTATAAATCC GCCATATAAA     120

ATGGTATAAT CTTTCATCTT TCATCTTTCA TCTTTCATCT TTCATCTTTC ATCTTTCATC     180

TTTCATCTTT CATCTTTCAT CTTTCATCTT TCATCTTTCA TCTTTCATCT TTCATCTTTC     240

ACATGAAATG ATGAACCGAG GGAAGGGAGG GAGGGGCAAG AATGAAGAGG GAGCTGAACG     300

AACGCAAATG ATAAAGTAAT TTAATTGTTC AACTAACCTT AGGAGAAAAT ATGAACAAGA     360

TATATCGTCT CAAATTCAGC AAACGCCTGA ATGCTTTGGT TGCTGTGTCT GAATTGGCAC     420

GGGGTTGTGA CCATTCCACA GAAAAGGCA GCGAAAAACC TGCTCGCATG AAAGTGCGTC      480

ACTTAGCGTT AAAGCCACTT TCCGCTATGT TACTATCTTT AGGTGTAACA TCTATTCCAC     540

AATCTGTTTT AGCAAGCGGC TTACAAGGAA TGGATGTAGT ACACGGCACA GCCACTATGC     600

AAGTAGATGG TAATAAAACC ATTATCCGCA ACAGTGTTGA CGCTATCATT AATTGGAAAC     660

AATTTAACAT CGACCAAAAT GAAATGGTGC AGTTTTTACA AGAAACAAC AACTCCGCCG      720

TATTCAACCG TGTTACATCT AACCAAATCT CCCAATTAAA AGGGATTTTA GATTCTAACG     780

GACAAGTCTT TTTAATCAAC CCAAATGGTA TCACAATAGG TAAAGACGCA ATTATTAACA     840

CTAATGGCTT TACGGCTTCT ACGCTAGACA TTTCTAACGA AAACATCAAG GCGCGTAATT     900

TCACCTTCGA GCAAACCAAA GATAAAGCGC TCGCTGAAAT TGTGAATCAC GGTTTAATTA     960

CTGTCGGTAA AGACGGCAGT GTAAATCTTA TTGGTGGCAA AGTGAAAAAC GAGGGTGTGA    1020

TTAGCGTAAA TGGTGGCAGC ATTTCTTTAC TCGCAGGGCA AAAAATCACC ATCAGCGATA    1080

TAATAAACCC AACCATTACT TACAGCATTG CCGCGCCTGA AAATGAAGCG GTCAATCTGG    1140

GCGATATTTT TGCCAAAGGC GGTAACATTA ATGTCCGTGC TGCCACTATT CGAAACCAAG    1200

CTTTCCGCCA AAGAGGGTGA AGCGGAAATT GGCGGTGTAA TTTCCGCTCA AAATCAGCAA    1260

GCTAAAGGCG GCAAGCTGAT GATTACAGGC GATAAAGTCA CATTAAAAAC AGGTGCAGTT    1320

ATCGACCTTT CAGGTAAAGA AGGGGAGAA ACTTACCTTG GCGGTGACGA GCGCGGCGAA     1380

GGTAAAAACG GCATTCAATT AGCAAAGAAA ACCTCTTTAG AAAAAGGCTC AACCATCAAT    1440

GTATCAGGCA AGAAAAAGG CGGACGCGCT ATTGTGTGGG GCGATATTGC GTTAATTGAC     1500

GGCAATATTA ACGCTCAAGG TAGTGGTGAT ATCGCTAAAA CCGGTGGTTT TGTGGAGACG    1560

TCGGGGCATG ATTTATTCAT CAAAGACAAT GCAATTGTTG ACGCCAAAGA GTGGTTGTTA    1620

GACCCGGATA ATGTATCTAT TAATGCAGAA ACAGCAGGAC GCAGCAATAC TTCAGAAGAC    1680

GATGAATACA CGGGATCCGG GAATAGTGCC AGCACCCCAA AACGAAACAA AGAAAAGACA    1740

ACATTAACAA ACACAACTCT TGAGAGTATA CTAAAAAAAG GTACCTTTGT TAACATCACT    1800

GCTAATCAAC GCATCTATGT CAATAGCTCC ATTAATTTAT CCAATGGCAG CTTAACTCTT    1860

TGGAGTGAGG GTCGGAGCGG TGGCGGCGTT GAGATTAACA ACGATATTAC CACCGGTGAT    1920

GATACCAGAG GTGCAAACTT AACAATTTAC TCAGGCGGCT GGGTTGATGT TCATAAAAAT    1980
```

```
ATCTCACTCG GGGCGCAAGG TAACATAAAC ATTACAGCTA AACAAGATAT CGCCTTTGAG    2040

AAAGGAAGCA ACCAAGTCAT TACAGGTCAA GGGACTATTA CCTCAGGCAA TCAAAAAGGT    2100

TTTAGATTTA ATAATGTCTC TCTAAACGGC ACTGGCAGCG GACTGCAATT CACCACTAAA    2160

AGAACCAATA AATACGCTAT CACAAATAAA TTTGAAGGGA CTTTAAATAT TCAGGGAAA     2220

GTGAACATCT CAATGGTTTT ACCTAAAAAT GAAAGTGGAT ATGATAAATT CAAAGGACGC    2280

ACTTACTGGA ATTTAACCTC GAAAGTGGAT ATGATAAATT CAAAGGACGC CCTCACTATT    2340

GACTCCAGAG GAAGCGATAG TGCAGGCACA CTTACCCAGC CTTATAATTT AAACGGTATA    2400

TCATTCAACA AAGACACTAC CTTTAATGTT GAACGAAATG CAAGAGTCAA CTTTGACATC    2460

AAGGCACCAA TAGGGATAAA TAAGTATTCT AGTTTGAATT ACGCATCATT TAATGGAAAC    2520

ATTTCAGTTT CGGGAGGGGG GAGTGTTGAT TCACACTTC  TCGCCTCATC CTCTAACGTC    2580

CAAACCCCCG GTGTAGTTAT AAATTCTAAA TACTTTAATG TTTCAACAGG GTCAAGTTTA    2640

AGATTTAAAA CTTCAGGCTC AACAAAAACT GGCTTCTCAA TAGAGAAAGA TTTAACTTTA    2700

AATGCCACCG GAGGCAACAT AACACTTTTG CAAGTTGAAG GCACCGATGG AATGATTGGT    2760

AAAGGCATTG TAGCCAAAAA AAACATAACC TTTGAAGGAG GTAAGATGAG GTTTGGCTCC    2820

AGGAAAGCCG TAACAGAAAT CGAAGGCAAT GTTACTATCA ATAACAACGC TAACGTCACT    2880

CTTATCGGTT CGGATTTTGA CAACCATCAA AAACCTTTAA CTATTAAAAA AGATGTCATC    2940

ATTAATAGCG GCAACCTTAC CGCTGGAGGC AATATTGTCA ATATAGCCGG AAATCTTACC    3000

GTTGAAAGTA ACGCTAATTT CAAAGCTATC ACAAATTTCA CTTTTAATGT AGGCGGCTTG    3060

TTTGACAACA AAGGCAATTC AAATATTTCC ATTGCCAAAG GAGGGGCTCG CTTTAAAGAC    3120

ATTGATAATT CCAAGAATTT AAGCATCACC ACCAACTCCA GCTCCACTTA CCGCACTATT    3180

ATAAGCGGCA ATATAACCAA TAAAAACGGT GATTTAAATA TTACGAACGA AGGTAGTGAT    3240

ACTGAAATGC AAATTGGCGG CGATGTCTCG CAAAAAGAAG GTAATCTCAC GATTTCTTCT    3300

GACAAAATCA ATATTACCAA ACAGATAACA ATCAAGGCAG GTGTTGATGG GGAGAATTCC    3360

GATTCAGACG CGACAAACAA TGCCAATCTA ACCATTAAAA CCAAAGAATT GAAATTAACG    3420

CAAGACCTAA ATATTTCAGG TTTCAATAAA GCAGAGATTA CAGCTAAAGA TGGTAGTGAT    3480

TTAACTATTG GTAACACCAA TAGTGCTGAT GGTACTAATG CCAAAAAAGT AACCTTTAAC    3540

CAGGTTAAAG ATTCAAAAAT CTCTGCTGAC GGTCACAAGG TGACACTACA CAGCAAAGTG    3600

GAAACATCCG GTAGTAATAA CAACACTGAA GATAGCAGTG ACAATAATGC CGGCTTAACT    3660

ATCGATGCAA AAAATGTAAC AGTAAACAAC AATATTACTT CTCACAAAGC AGTGAGCATC    3720

TCTGCGACAA GTGGAGAAAT TACCACTAAA ACAGGTACAA CCATTAACGC AACCACTGGT    3780

AACGTGGAGA TAACCGCTCA AACAGGTAGT ATCCTAGGTG GAATTGAGTC CAGCTCTGGC    3840

TCTGTAACAC TTACTGCAAC CGAGGGCGCT CTTGCTGTAA GCAATATTTC GGGCAACACC    3900

GTTACTGTTA CTGCAAATAG CGGTGCATTA ACCACTTTGG CAGGCTCTAC AATTAAAGGA    3960

ACCGAGAGTG TAACCACTTC AAGTCAATCA GGCGATATCG GCGGTACGAT TTCTGGTGGC    4020

ACAGTAGAGG TTAAAGCAAC CGAAAGTTTA ACCACTCAAT CCAATTCAAA AATTAAAGCA    4080

ACAACAGGCG AGGCTAACGT AACAAGTGCA ACAGGTACAA TTGGTGGTAC GATTTCCGGT    4140

AATACGGTAA ATGTTACGGC AAACGCTGGC GATTTAACAG TTGGGAATGG CGCAGAAATT    4200

AATGCGACAG AAGGAGCTGC AACCTTAACT ACATCATCGG GCAAATTAAC TACCGAAGCT    4260

AGTTCACACA TTACTTCAGC CAAGGGTCAG GTAAATCTTT CAGCTCAGGA TGGTAGCGTT    4320

GCAGGAAGTA TTAATGCCGC CAATGTGACA CTAAATACTA CAGGCACTTT AACTACCGTG    4380
```

```
AAGGGTTCAA ACATTAATGC AACCAGCGGT ACCTTGGTTA TTAACGCAAA AGACGCTGAG      4440

CTAAATGGCG CAGCATTGGG TAACCACACA GTGGTAAATG CAACCAACGC AAATGGCTCC      4500

GGCAGCGTAA TCGCGACAAC CTCAAGCAGA GTGAACATCA CTGGGGATTT AATCACAATA      4560

AATGGATTAA ATATCATTTC AAAAAACGGT ATAAACACCG TACTGTTAAA AGGCGTTAAA      4620

ATTGATGTGA AATACATTCA ACCGGGTATA GCAAGCGTAG ATGAAGTAAT TGAAGCGAAA      4680

CGCATCCTTG AGAAGGTAAA AGATTTATCT GATGAAGAAA GAGAAGCGTT AGCTAAACTT      4740

GGCGTAAGTG CTGTACGTTT TATTGAGCCA AATAATACAA TTACAGTCGA TACACAAAAT      4800

GAATTTGCAA CCAGACCATT AAGTCGAATA GTGATTTCTG AAGGCAGGGC GTGTTTCTCA      4860

AACAGTGATG GCGCGACGGT GTGCGTTAAT ATCGCTGATA ACGGGCGGTA GCGGTCAGTA      4920

ATTGACAAGG TAGATTTCAT CCTGCAATGA AGTCATTTTA TTTTCGTATT ATTTACTGTG      4980

TGGGTTAAAG TTCAGTACGG GCTTTACCCA TCTTGTAAAA AATTACGGAG AATACAATAA      5040

AGTATTTTTA ACAGGTTATT ATTATGAAAA ATATAAAAAG CAGATTAAAA CTCAGTGCAA      5100

TATCAGTATT GCTTGGCCTG GCTTCTTCAT CATTGTATGC AGAAGAAGCG TTTTTAGTAA      5160

AAGGCTTTCA GTTATCTGGT GCACTTGAAA CTTAAGTGA AGACGCCCAA CTGTCTGTAG       5220

CAAAATCTTT ATCTAAATAC CAAGGCTCGC AAACTTTAAC AAACCTAAAA ACAGCACAGC      5280

TTGAATTACA GGCTGTGCTA GATAAGATTG AGCCAAATAA GTTGATGTG ATATTGCCAC       5340

AACAAACCAT TACGGATGGC AATATTATGT TTGAGCTAGT CTCGAAATCA GCCGCAGAAA      5400

GCCAAGTTTT TTATAAGGCG AGCCAGGGTT ATAGTGAAGA AAATATCGCT CGTAGCCTGC      5460

CATCTTTGAA ACAAGGAAAA GTGTATGAAG ATGGTCGTCA GTGGTTCGAT TTGCGTGAAT      5520

TCAATATGGC AAAAGAAAAT CCACTTAAAG TCACTCGCGT GCATTACGAG TTAAACCCTA      5580

AAAACAAAAC CTCTGATTTG GTAGTTGCAG GTTTTTCGCC TTTTGGCAAA ACGCGTAGCT      5640

TTGTTTCCTA TGATAATTTC GGCGCAAGGG AGTTTAACTA TCAACGTGTA AGTCTAGGTT      5700

TTGTAAATGC CAATTTGACC GGACATGATG ATGTATTAAA TCTAAACGCA TTGACCAATG      5760

TAAAAGCACC ATCAAAATCT TATGCGGTAG GCATAGGATA TACTTATCCG TTTTATGATA      5820

AACACCAATC CTTAAGTCTT TATACCAGCA TGAGTTATGC TGATTCTAAT GATATCGACG      5880

GCTTACCAAG TGCGATTAAT CGTAAATTAT CAAAAGGTCA ATCTATCTCT GCGAATCTGA      5940

AATGGAGTTA TTATCTCCCG ACATTTAACC TTGGAATGGA AGACCAGTTT AAAATTAATT      6000

TAGGCTACAA CTACCGCCAT ATTAATCAAA CATCCGAGTT AAACACCCTG GGTGCAACGA      6060

AGAAAAAATT TGCAGTATCA GGCGTAAGTG CAGGCATTGA TGGACATATC CAATTTACCC      6120

CTAAAACAAT CTTTAATATT GATTTAACTC ATCATTATTA CGCGAGTAAA TTACCAGGCT      6180

CTTTTGGAAT GGAGCGCATT GGCGAAACAT TTAATCGCAG CTATCACATT AGCACAGCCA      6240

GTTTAGGGTT GAGTCAAGAG TTTGCTCAAG GTTGGCATTT TAGCAGTCAA TTATCGGGTC      6300

AGTTTACTCT ACAAGATATA AGTAGCATAG ATTTATTCTC TGTAACAGGT ACTTATGGCG      6360

TCAGAGGCTT TAAATACGGC GGTGCAAGTG GTGAGCGCGG TCTTGTATGG CGTAATGAAT      6420

TAAGTATGCC AAAATACACC CGCTTTCAAA TCAGCCCTTA TGCGTTTTAT GATGCAGGTC      6480

AGTTCCGTTA TAATAGCGAA AATGCTAAAA CTTACGGCGA AGATATGCAC ACGGTATCCT      6540

CTGCGGGTTT AGGCATTAAA ACCTCTCCTA CACAAAACTT AAGCTTAGAT GCTTTTGTTG      6600

CTCGTCGCTT TGCAAATGCC AATAGTGACA ATTTGAATGG CAACAAAAAA CGCACAAGCT      6660

CACCTACAAC CTTCTGGGGT AGATTAACAT TCAGTTTCTA ACCCTGAAAT TTAATCAACT      6720

GGTAAGCGTT CCGCCTACCA GTTTATAACT ATATGCTTTA CCCGCCAATT TACAGTCTAT      6780
```

```
ACGCAACCCT GTTTTCATCC TTATATATCA AACAAACTAA GCAAACCAAG CAAACCAAGC     6840

AAACCAAGCA AACCAAGCAA ACCAAGCAAA CCAAGCAAAC CAAGCAAACC AAGCAAACCA     6900

AGCAAACCAA GCAAACCAAG CAAACCAAGC AAACCAAGCA ATGCTAAAAA ACAATTTATA     6960

TGATAAACTA AAACATACTC CATACCATGG CAATACAAGG GATTTAATAA TATGACAAAA     7020

GAAAATTTAC AAAGTGTTCC ACAAAATACG ACCGCTTCAC TTGTAGAATC AAACAACGAC     7080

CAAACTTCCC TGCAAATACT TAAACAACCA CCCAAACCCA ACCTATTACG CCTGGAACAA     7140

CATGTCGCCA AAAAAGATTA TGAGCTTGCT TGCCGCGAAT TAATGGCGAT TTTGAAAAA     7200

ATGGACGCTA ATTTTGGAGG CGTTCACGAT ATTGAATTTG ACGCACCTGC TCAGCTGGCA     7260

TATCTACCCG AAAAACTACT AATTCATTTT GCCACTCGTC TCGCTAATGC AATTACAACA     7320

CTCTTTTCCG ACCCCGAATT GGCAATTTCC GAAGAAGGGG CATTAAAGAT GATTAGCCTG     7380

CAACGCTGGT TGACGCTGAT TTTTGCCTCT TCCCCCTACG TTAACGCAGA CCATATTCTC     7440

AATAAATATA ATATCAACCC AGATTCCGAA GGTGGCTTTC ATTTAGCAAC AGACAACTCT     7500

TCTATTGCTA AATTCTGTAT TTTTTACTTA CCCGAATCCA ATGTCAATAT GAGTTTAGAT     7560

GCGTTATGGG CAGGGAATCA ACAACTTTGT GCTTCATTGT GTTTTGCGTT GCAGTCTTCA     7620

CGTTTTATTG GTACTGCATC TGCGTTTCAT AAAAGAGCGG TGGTTTTACA GTGGTTTCCT     7680

AAAAAACTCG CCGAAATTGC TAATTTAGAT GAATTGCCTG CAAATATCCT TCATGATGTA     7740

TATATGCACT GCAGTTATGA TTTAGCAAAA ACAAGCACG ATGTTAAGCG TCCATTAAAC     7800

GAACTTGTCC GCAAGCATAT CCTCACGCAA GGATGGCAAG ACCGCTACCT TTACACCTTA     7860

GGTAAAAAGG ACGGCAAACC TGTGATGATG GTACTGCTTG AACATTTTAA TTCGGGACAT     7920

TCGATTTATC GCACGCATTC AACTTCAATG ATTGCTGCTC GAGAAAAATT CTATTTAGTC     7980

GGCTTAGGCC ATGAGGGCGT TGATAACATA GGTCGAGAAG TGTTTGACGA GTTCTTTGAA     8040

ATCAGTAGCA ATAATATAAT GGAGAGACTG TTTTTTATCC GTAAACAGTG CGAAACTTTC     8100

CAACCCGCAG TGTTCTATAT GCCAAGCATT GGCATGGATA TTACCACGAT TTTTGTGAGC     8160

AACACTCGGC TTGCCCCTAT TCAAGCTGTA GCCTTGGGTC ATCCTGCCAC TACGCATTCT     8220

GAATTTATTG ATTATGTCAT CGTAGAAGAT GATTATGTGG GCAGTGAAGA TTGTTTTAGC     8280

GAAACCCTTT TACGCTTACC CAAAGATGCC CTACCTTATG TACCATCTGC ACTCGCCCCA     8340

CAAAAAGTGG ATTATGTACT CAGGGAAAAC CCTGAAGTAG TCAATATCGG TATTGCCGCT     8400

ACCACAATGA AATTAAACCC TGAATTTTTG CTAACATTGC AAGAAATCAG AGATAAAGCT     8460

AAAGTCAAAA TACATTTTCA TTTCGCACTT GGACAATCAA CAGGCTTGAC ACACCCTTAT     8520

GTCAAATGGT TTATCGAAAG CTATTTAGGT GACGATGCCA CTGCACATCC CCACGCACCT     8580

TATCACGATT ATCTGGCAAT ATTGCGTGAT TGCGATATGC TACTAAATCC GTTTCCTTTC     8640

GGTAATACTA ACGGCATAAT TGATATGGTT ACATTAGGTT TAGTTGGTGT ATGCAAAACG     8700

GGGGATGAAG TACATGAACA TATTGATGAA GGTCTGTTTA AACGCTTAGG ACTACCAGAA     8760

TGGCTGATAG CCGACACACG AGAAACATAT ATTGAATGTG CTTTGCGTCT AGCAGAAAAC     8820

CATCAAGAAC GCCTTGAACT CCGTCGTTAC ATCATAGAAA ACAACGGCTT ACAAAAGCTT     8880

TTTACAGGCG ACCCTCGTCC ATTGGGCAAA ATACTGCTTA AGAAAACAAA TGAATGGAAG     8940

CGGAAGCACT TGAGTAAAAA ATAACGGTTT TTTAAAGTAA AAGTGCGGTT AATTTTCAAA     9000

GCGTTTTAAA AACCTCTCAA AAATCAACCG CACTTTTATC TTTATAACGC TCCCGCGCGC     9060

TGACAGTTTA TCTCTTTCTT AAAATACCCA TAAAATTGTG GCAATAGTTG GGTAATCAAA     9120

TTCAATTGTT GATACGGCAA ACTAAAGACG GCGCGTTCTT CGGCAGTCAT C            9171
```

(2) INFORMATION FOR SEQ ID NO:6:

(i) SEQUENCE CHARACTERISTICS:
        (A) LENGTH: 9323 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:6:

```
CGCCACTTCA ATTTTGGATT GTTGAAATTC AACTAACCAA AAAGTGCGGT TAAAATCTGT      60

GGAGAAAATA GGTTGTAGTG AAGAACGAGG TAATTGTTCA AAAGGATAAA GCTCTCTTAA     120

TTGGGCATTG GTTGGCGTTT CTTTTTCGGT TAATAGTAAA TTATATTCTG GACGACTATG     180

CAATCCACCA ACAACTTTAC CGTTGGTTTT AAGCGTTAAT GTAAGTTCTT GCTCTTCTTG     240

GCGAATACGT AATCCCATTT TTTGTTTAGC AAGAAAATGA TCGGGATAAT CATAATAGGT     300

GTTGCCCAAA AATAAATTTT GATGTTCTAA AATCATAAAT TTTGCAAGAT ATTGTGGCAA     360

TTCAATACCT ATTTGTGGCG AAATCGCCAA TTTTAATTCA ATTTCTTGTA GCATAATATT     420

TCCCACTCAA ATCAACTGGT TAAATATACA AGATAATAAA AATAAATCAA GATTTTTGTG     480

ATGACAAACA ACAATTACAA CACCTTTTTT GCAGTCTATA TGCAAATATT TTAAAAAAAT     540

AGTATAAATC CGCCATATAA AATGGTATAA TCTTTCATCT TTCATCTTTC ATCTTTCATC     600

TTTCATCTTT CATCTTTCAT CTTTCATCTT TCATCTTTCA TCTTTCATCT TTCATCTTTC     660

ATCTTTCATC TTTCATCTTT CACATGAAAT GATGAACCGA GGGAAGGGAG GGAGGGGCAA     720

GAATGAAGAG GGAGCTGAAC GAACGCAAAT GATAAAGTAA TTTAATTGTT CAACTAACCT     780

TAGGAGAAAA TATGAACAAG ATATATCGTC TCAAATTCAG CAAACGCCTG AATGCTTTGG     840

TTGCTGTGTC TGAATTGGCA CGGGGTTGTG ACCATTCCAC AGAAAAGGC AGCGAAAAAC     900

CTGCTCGCAT GAAAGTGCGT CACTTAGCGT TAAAGCCACT TTCCGCTATG TTACTATCTT     960

TAGGTGTAAC ATCTATTCCA CAATCTGTTT TAGCAAGCGG CAATTTAACA TCGACCAAAA    1020

TGAAATGGTG CAGTTTTTAC AAGAAAACAA GTAATAAAAC CATTATCCGC AACAGTGTTG    1080

ACGCTATCAT TAATTGGAAA CAATTTAACA TCGACCAAAA TGAAATGGTG CAGTTTTTAC    1140

AAGAAAACAA CAACTCCGCC GTATTCAACC GTGTTACATC TAACCAAATC TCCCAATTAA    1200

AAGGGATTTT AGATTCTAAC GGACAAGTCT TTTTAATCAA CCCAAATGGT ATCACAATAG    1260

GTAAAGACGC AATTATTAAC ACTAATGGCT TTACGGCTTC TACGCTAGAC ATTTCTAACG    1320

AAAACATCAA GGCGCGTAAT TTCACCTTCG AGCAAACCAA AGATAAAGCG CTCGCTGAAA    1380

TTGTGAATCA CGGTTTAATT ACTGTCGGTA AAGACGGCAG TGTAAATCTT ATTGGTGGCA    1440

AAGTGAAAAA CGAGGGTGTG ATTAGCGTAA ATGGTGGCAG CATTTCTTTA CTCGCAGGGC    1500

AAAAAATCAC CATCAGCGAT ATAATAAACC CAACCATTAC TTACAGCATT GCCGCGCCTG    1560

AAAATGAAGC GGTCAATCTG GCGATATTT TTGCCAAAGG CGGTAACATT AATGTCCGTG    1620

CTGCCACTAT TCGAAACCAA GGTAAACTTT CTGCTGATTC TGTAAGCAAA GATAAAAGCG    1680

GCAATATTGT TCTTTCCGCC AAAGAGGGTG AAGCGGAAAT TGGCGGTGTA ATTTCCGCTC    1740

AAAATCAGCA AGCTAAAGGC GGCAAGCTGA TGATAAAGTC CGATAAAGTC ACATTAAAAA    1800

CAGGTGCAGT TATCGACCTT TCAGGTAAAG AAGGGGGAGA AACTTACCTT GGCGGTGACG    1860

AGCGCGGCGA AGGTAAAAAC GGCATTCAAT TAGCAAAGAA AACCTCTTTA GAAAAGGCT    1920

CAACCATCAA TGTATCAGGC AAAGAAAAAG GCGGACGCGC TATTGTGTGG GGCGATATTG    1980
```

```
CGTTAATTGA CGGCAATATT AACGCTCAAG GTAGTGGTGA TATCGCTAAA ACCGGTGGTT    2040

TTGTGGAGAC ATCGGGGCAT TATTTATCCA TTGACAGCAA TGCAATTGTT AAAACAAAAG    2100

AGTGGTTGCT AGACCCTGAT GATGTAACAA TTGAAGCCGA AGACCCCCTT CGCAATAATA    2160

CCGGTATAAA TGATGAATTC CCAACAGGCA CCGGTGAAGC AAGCGACCCT AAAAAAAATA    2220

GCGAACTCAA AACAACGCTA ACCAATACAA CTATTTCAAA TTATCTGAAA AACGCCTGGA    2280

CAATGAATAT AACGGCATCA AGAAAACTTA CCGTTAATAG CTCAATCAAC ATCGGAAGCA    2340

ACTCCCACTT AATTCTCCAT AGTAAAGGTC AGCGTGGCGG AGGCGTTCAG ATTGATGGAG    2400

ATATTACTTC TAAAGGCGGA AATTTAACCA TTTATTCTGG CGGATGGGTT GATGTTCATA    2460

AAAATATTAC GCTTGATCAG GGTTTTTTAA ATATTACCGC CGCTTCCGTA GCTTTTGAAG    2520

GTGGAAATAA CAAAGCACGC GACGCGGCAA ATGCTAAAAT TGTCGCCCAG GGCACTGTAA    2580

CCATTACAGG AGAGGGAAAA GATTTCAGGG CTAACAACGT ATCTTTAAAC GGAACGGGTA    2640

AAGGTCTGAA TATCATTTCA TCAGTGAATA ATTTAACCCA CAATCTTAGT GGCACAATTA    2700

ACATATCTGG GAATATAACA ATTAACCAAA CTACGAGAAA GAACACCTCG TATTGGCAAA    2760

CCAGCCATGA TTCGCACTGG AACGTCAGTG CTCTTAATCT AGAGACAGGC GCAAATTTTA    2820

CCTTTATTAA ATACATTTCA AGCAATAGCA AAGGCTTAAC AACACAGTAT AGAAGCTCTG    2880

CAGGGGTGAA TTTTAACGGC GTAAATGGCA ACATGTCATT CAATCTCAAA GAAGGAGCGA    2940

AAGTTAATTT CAAATTAAAA CCAAACGAGA ACATGAACAC AAGCAAACCT TTACCAATTC    3000

GGTTTTTAGC CAATATCACA GCCACTGGTG GGGGCTCTGT TTTTTTTGAT ATATATGCCA    3060

ACCATTCTGG CAGAGGGGCT GAGTTAAAAA TGAGTGAAAT TAATATCTCT AACGGCGCTA    3120

ATTTTACCTT AAATTCCCAT GTTCGCGGCG ATGACGCTTT TAAAATCAAC AAAGACTTAA    3180

CCATAAATGC AACCAATTCA AATTTCAGCC TCAGACAGAC GAAAGATGAT TTTTATGACG    3240

GGTACGCACG CAATGCCATC AATTCAACCT ACAACATATC CATTCTGGGC GGTAATGTCA    3300

CCCTTGGTGG ACAAAACTCA AGCAGCAGCA TTACGGGGAA TATTACTATC GAGAAAGCAG    3360

CAAATGTTAC GCTAGAAGCC AATAACGCCC CTAATCAGCA AAACATAAGG GATAGAGTTA    3420

TAAAACTTGG CAGCTTGCTC GTTAATGGGA GTTTAAGTTT AACTGGCGAA AATGCAGATA    3480

TTAAAGGCAA TCTCACTATT TCAGAAAGCG CCACTTTTAA AGGAAAGACT AGAGATACCC    3540

TAAATATCAC CGGCAATTTT ACCAATAATG GCACTGCCGA AATTAATATA ACACAAGGAG    3600

TGGTAAAACT TGGCAATGTT ACCAATGATG GTGATTTAAA CATTACCACT CACGCTAAAC    3660

GCAACCAAAG AAGCATCATC GGCGGAGATA TAATCAACAA AAAAGGAAGC TTAAATATTA    3720

CAGACAGTAA TAATGATGCT GAAATCCAAA TTGGCGGCAA TATCTCGCAA AAAGAAGGCA    3780

ACCTCACGAT TTCTTCCGAT AAAATTAATA TCACCAAACA GATAACAATC AAAAAGGGTA    3840

TTGATGGAGA GGACTCTAGT TCAGATGCGA CAAGTAATGC CAACCTAACT ATTAAAACCA    3900

AAGAATTGAA ATTGACAGAA GACCTAAGTA TTTCAGGTTT CAATAAAGCA GAGATTACAG    3960

CCAAAGATGG TAGAGATTTA ACTATTGGCA ACAGTAATGA CGGTAACAGC GGTGCCGAAG    4020

CCAAAACAGT AACTTTTAAC AATGTTAAAG ATTCAAAAAT CTCTGCTGAC GGTCACAATG    4080

TGACACTAAA TAGCAAAGTG AAAACATCTA GCAGCAATGG CGGACGTGAA AGCAATAGCG    4140

ACAACGATAC CGGCTTAACT ATTACTGCAA AAAATGTAGA AGTAAACAAA GATATTACTT    4200

CTCTCAAAAC AGTAAATATC ACCGCGTCGG AAAAGGTTAC CACCACAGCA GGCTCGACCA    4260

TTAACGCAAC AAATGGCAAA GCAAGTATTA CAACCAAAAC AGGTGATATC AGCGGTACGA    4320

TTTCCGGTAA CACGGTAAGT GTTAGCGCGA CTGGTGATTT AACCACTAAA TCCGGCTCAA    4380
```

```
AAATTGAAGC GAAATCGGGT GAGGCTAATG TAACAAGTGC AACAGGTACA ATTGGCGGTA    4440

CAATTTCCGG TAATACGGTA AATGTTACGG CAAACGCTGG CGATTTAACA GTTGGGAATG    4500

GCGCAGAAAT TAATGCGACA GAAGGAGCTG CAACCTTAAC CGCAACAGGG AATACCTTGA    4560

CTACTGAAGC CGGTTCTAGC ATCACTTCAA CTAAGGGTCA GGTAGACCTC TTGGCTCAGA    4620

ATGGTAGCAT CGCAGGAAGC ATTAATGCTG CTAATGTGAC ATTAAATACT ACAGGCACCT    4680

TAACCACCGT GGCAGGCTCG GATATTAAAG CAACCAGCGG CACCTTGGTT ATTAACGCAA    4740

AAGATGCTAA GCTAAATGGT GATGCATCAG GTGATAGTAC AGAAGTGAAT GCAGTCAACG    4800

ACTGGGGATT TGGTAGTGTG ACTGCGGCAA CCTCAAGCAG TGTGAATATC ACTGGGGATT    4860

TAAACACAGT AAATGGGTTA AATATCATTT CGAAAGATGG TAGAAACACT GTGCGCTTAA    4920

GAGGCAAGGA AATTGAGGTG AAATATATCC AGCCAGGTGT AGCAAGTGTA GAAGAAGTAA    4980

TTGAAGCGAA ACGCGTCCTT GAAAAAGTAA AAGATTTATC TGATGAAGAA AGAGAAACAT    5040

TAGCTAAACT TGGTGTAAGT GCTGTACGTT TTGTTGAGCC AAATAATACA ATTACAGTCA    5100

ATACACAAAA TGAATTTACA ACCAGACCGT CAAGTCAAGT GATAATTTCT GAAGGTAAGG    5160

CGTGTTTCTC AAGTGGTAAT GGCGCACGAG TATGTACCAA TGTTGCTGAC GATGGACAGC    5220

CGTAGTCAGT AATTGACAAG GTAGATTTCA TCCTGCAATG AAGTCATTTT ATTTTCGTAT    5280

TATTTACTGT GTGGGTTAAA GTTCAGTACG GGCTTTACCC ATCTTGTAAA AAATTACGGA    5340

GAATACAATA AAGTATTTTT AACAGGTTAT TATTATGAAA AATATAAAAA GCAGATTAAA    5400

ACTCAGTGCA ATATCAGTAT TGCTTGGCCT GGCTTCTTCA TCATTGTATG CAGAAGAAGC    5460

GTTTTTAGTA AAAGGCTTTC AGTTATCTGG TGCACTTGAA ACTTAAGTG AAGACGCCCA    5520

ACTGTCTGTA GCAAAATCTT TATCTAAATA CCAAGGCTCG CAAACTTTAA CAAACCTAAA    5580

AACAGCACAG CTTGAATTAC AGGCTGTGCT AGATAAGATT GAGCCAAATA AATTTGATGT    5640

GATATTGCCG CAACAAACCA TTACGGATGG CAATATCATG TTTGAGCTAG TCTCGAAATC    5700

AGCCGCAGAA AGCCAAGTTT TTTATAAGGC GAGCCAGGGT TATAGTGAAG AAAATATCGC    5760

TCGTAGCCTG CCATCTTTGA AACAAGGAAA AGTGTATGAA GATGGTCGTC AGTGGTTCGA    5820

TTTGCGTGAA TTTAATATGG CAAAAGAAAA CCCGCTTAAG GTTACCCGTG TACATTACGA    5880

ACTAAACCCT AAAAACAAAA CCTCTAATTT GATAATTGCG GGCTTCTCGC CTTTTGGTAA    5940

AACGCGTAGC TTTATTTCTT ATGATAATTT CGGCGCGAGA GAGTTTAACT ACCAACGTGT    6000

AAGCTTGGGT TTTGTTAATG CCAATTTAAC TGGTCATGAT GATGTGTTAA TTATACCAGT    6060

ATGAGTTATG CTGATTCTAA TGATATCGAC GGCTTACCAA GTGCGATTAA TCGTAAATTA    6120

TCAAAAGGTC AATCTATCTC TGCGAATCTG AAATGGAGTT ATTATCTCCC AACATTTAAC    6180

CTTGGCATGG AAGACCAATT TAAAATTAAT TTAGGCTACA ACTACCGCCA TATTAATCAA    6240

ACCTCCGCGT TAAATCGCTT GGGTGAAACG AAGAAAAAAT TGCAGTATC AGGCGTAAGT    6300

GCAGGCATTG ATGGACATAT CCAATTTACC CCTAAAACAA TCTTTAATAT TGATTTAACT    6360

CATCATTATT ACGCGAGTAA ATTACCAGGC TCTTTTGGAA TGGAGCGCAT TGGCGAAACA    6420

TTTAATCGCA GCTATCACAT TAGCACAGCC AGTTTAGGGT TGAGTCAAGA GTTTGCTCAA    6480

GGTTGGCATT TTAGCAGTCA ATTATCAGGT CAATTTACTC TACAAGATAT TAGCAGTATA    6540

GATTTATTCT CTGTAACAGG TACTTATGGC GTCAGAGGCT TTAAATACGG CGGTGCAAGT    6600

GGTGAGCGCG GTCTTGTATG GCGTAATGAA TTAAGTATGC CAAAATACAC CCGCTTCCAA    6660

ATCAGCCCTT ATGCGTTTTA TGATGCAGGT CAGTTCCGTT ATAATAGCGA AAATGCTAAA    6720

ACTTACGGCG AAGATATGCA CACGGTATCC TCTGCGGGTT TAGGCATTAA AACCTCTCCT    6780
```

```
ACACAAAACT TAAGCCTAGA TGCTTTTGTT GCTCGTCGCT TTGCAAATGC AATAGTGAC     6840

AATTTGAATG GCAACAAAAA ACGCACAAGC TCACCTACAA CCTTCTGGGG GAGATTAACA    6900

TTCAGTTTCT AACCCTGAAA TTTAATCAAC TGGTAAGCGT TCCGCCTACC AGTTTATAAC    6960

TATATGCTTT ACCCGCCAAT TTACAGTCTA TAGGCAACCC TGTTTTTACC CTTATATATC   7020

AAATAAACAA GCTAAGCTGA GCTAAGCAAA CCAAGCAAAC TCAAGCAAGC CAAGTAATAC   7080

TAAAAAAACA ATTTATATGA TAAACTAAAG TATACTCCAT GCCATGGCGA TACAAGGGAT   7140

TTAATAATAT GACAAAAGAA AATTTGCAAA ACGCTCCTCA AGATGCGACC GCTTTACTTG   7200

CGGAATTAAG CAACAATCAA ACTCCCCTGC GAATATTTAA ACAACCACGC AAGCCCAGCC   7260

TATTACGCTT GGAACAACAT ATCGCAAAAA AAGATTATGA GTTTGCTTGT CGTGAATTAA   7320

TGGTGATTCT GGAAAAAATG GACGCTAATT TTGGAGGCGT TCACGATATT GAATTTGACG   7380

CACCCGCTCA GCTGGCATAT CTACCCGAAA AATTACTAAT TTATTTTGCC ACTCGTCTCG   7440

CTAATGCAAT TACAACACTC TTTTCCGACC CCGAATTGGC AATTTCTGAA GAAGGGGCGT   7500

TAAAGATGAT TAGCCTGCAA CGCTGGTTGA CGCTGATTTT TGCCTCTTCC CCCTACGTTA   7560

ACGCAGACCA TATTCTCAAT AAATATAATA TCAACCCAGA TTCCGAAGGT GGCTTTCATT   7620

TAGCAACAGA CAACTCTTCT ATTGCTAAAT TCTGTATTTT TTACTTACCC GAATCCAATG   7680

TCAATATGAG TTTAGATGCG TTATGGGCAG GGAATCAACA ACTTTGTGCT TCATTGTGTT   7740

TTGCGTTGCA GTCTTCACGT TTTATTGGTA CCGCATCTGC GTTTCATAAA AGAGCGGTGG   7800

TTTTACAGTG GTTTCCTAAA AAACTCGCCG AAATTGCTAA TTTAGATGAA TTGCCTGCAA   7860

ATATCCTTCA TGATGTATAT ATGCACTGCA GTTATGATTT AGCAAAAAAC AAGCACGATG   7920

TTAAGCGTCC ATTAAACGAA CTTGTCCGCA AGCATATCCT CACGCAAGGA TGGCAAGACC   7980

GCTACCTTTA CACCTTAGGT AAAAAGGACG GCAAACCTGT GATGATGGTA CTGCTTGAAC   8040

ATTTTAATTC GGGACATTCG ATTTATCGTA CACATTCAAC TTCAATGATT GCTGCTCGAG   8100

AAAAATTCTA TTTAGTCGGC TTAGGCCATG AGGGCGTTGA TAAAATAGGT CGAGAAGTGT   8160

TTGACGAGTT CTTTGAAATC AGTAGCAATA ATATAATGGA GAGACTGTTT TTTATCCGTA   8220

AACAGTGCGA AACTTTCCAA CCCGCAGTGT TCTATATGCC AAGCATTGGC ATGGATATTA   8280

CCACGATTTT TGTGAGCAAC ACTCGGCTTG CCCCTATTCA AGCTGTAGCC CTGGGTCATC   8340

CTGCCACTAC GCATTCTGAA TTTATTGATT ATGTCATCGT AGAAGATGAT TATGTGGGCA   8400

GTGAAGATTG TTTCAGCGAA ACCCTTTTAC GCTTACCCAA AGATGCCCTA CCTTATGTAC   8460

CTTCTGCACT CGCCCCACAA AAAGTGGATT ATGTACTCAG GGAAAACCCT GAAGTAGTCA   8520

ATATCGGTAT TGCCGCTACC ACAATGAAAT TAAACCCTGA ATTTTTGCTA ACATTGCAAG   8580

AAATCAGAGA TAAAGCTAAA GTCAAAATAC ATTTTCATTT CGCACTTGGA CAATCAACAG   8640

GCTTGACACA CCCTTATGTC AAATGGTTTA TCGAAAGCTA TTTAGGTGAC GATGCCACTG   8700

CACATCCCCA CGCACCTTAT CACGATTATC TGGCAATATT GCGTGATTGC GATATGCTAC   8760

TAAATCCGTT TCCTTTCGGT AATACTAACG GCATAATTGA TATGGTTACA TTAGGTTTAG   8820

TTGGTGTATG CAAAACGGGG GATGAAGTAC ATGAACATAT TGATGAAGGT CTGTTTAAAC   8880

GCTTAGGACT ACCAGAATGG CTGATAGCCG ACACACGAGA AACATATATT GAATGTGCTT   8940

TGCGTCTAGC AGAAAACCAT CAAGAACGCC TTGAACTCCG TCGTTACATC ATAGAAAACA   9000

ACGGCTTACA AAAGCTTTTT ACAGGCGACC CTCGTCCATT GGGCAAAATA CTGCTTAAGA   9060

AAACAAATGA ATGGAAGCGG AAGCACTTGA GTAAAAAATA ACGTTTTTTT AAAGTAAAAG   9120

TGCGGTTAAT TTTCAAAGCG TTTTAAAAAC CTCTCAAAAA TCAACCGCAC TTTTATCTTT   9180
```

| ATAACGATCC CGCACGCTGA CAGTTTATCA GCCTCCCGCC ATAAAACTCC GCCTTTCATG | 9240 |
| GCGGAGATTT TAGCCAAAAC TGGCAGAAAT TAAAGGCTAA AATCACCAAA TTGCACCACA | 9300 |
| AAATCACCAA TACCCACAAA AAA | 9323 |

(2) INFORMATION FOR SEQ ID NO:7:

(i) SEQUENCE CHARACTERISTICS:
        (A) LENGTH: 4794 base pairs
        (B) TYPE: nucleic acid
        (C) STRANDEDNESS: single
        (D) TOPOLOGY: linear (xi) SEQUENCE DESCRIPTION: SEQ ID NO:7:

| ATGAACAAGA TATATCGTCT CAAATTCAGC AAACGCCTGA ATGCTTTGGT TGCTGTGTCT | 60 |
| GAATTGACAC GGGGTTGTGA CCATTCCACA GAAAAAGGCA GTGAAAAACC TGTTCGTACG | 120 |
| AAAGTACGCC ACTTGGCGTT AAAGCCACTT TCCGCTATAT TGCTATCTTT GGGCATGGCA | 180 |
| TCCATTCCGC AATCTGTTTT AGCGAGCGGT TTACAGGGAA TGAGCGTCGT ACACGGTACA | 240 |
| GCAACCATGC AAGTAGACGG CAATAAAACC ACTATCCGTA ATAGCGTCAA TGCTATCATC | 300 |
| AATTGGAAAC AATTTAACAT TGACCAAAAT GAAATGGTGC AGTTTTTACA AGAAAGCAGC | 360 |
| AACTCTGCCG TTTTCAACCG TGTTACATCT GACCAAATCT CCCAATTAAA AGGGATTTTA | 420 |
| GATTCTAACG GACAAGTCTT TTTAATCAAC CCAAATGGTA TCACAATAGG TAAAGACGCA | 480 |
| ATTATTAACA CTAATGGCTT TACTGCTTCT ACGCTAGACA TTTCTAACGA AAACATCAAG | 540 |
| GCGCGTAATT TCACCCTTGA GCAAACCAAG GATAAAGCAC TCGCTGAAAT CGTGAATCAC | 600 |
| GGTTTAATTA CCGTTGGTAA AGACGGTAGC GTAAACCTTA TTGGTGGCAA AGTGAAAAAC | 660 |
| GAGGGCGTGA TTAGCGTAAA TGGCGGTAGT ATTTCTTTAC TTGCAGGGCA AAAAATCACC | 720 |
| ATCAGCGATA TAATAAATCC AACCATCACT TACAGCATTG CTGCACCTGA AAACGAAGCG | 780 |
| ATCAATCTGG GCGATATTTT TGCCAAAGGT GGTAACATTA ATGTCCGCGC TGCCACTATT | 840 |
| CGCAATAAAG GTAAACTTTC TGCCGACTCT GTAAGCAAAG ATAAAAGTGG TAACATTGTT | 900 |
| CTCTCTGCCA AGAAGGTGA AGCGGAAATT GGCGGTGTAA TTTCCGCTCA AAATCAGCAA | 960 |
| GCCAAAGGTG GTAAGTTGAT GATTACAGGC GATAAAGTTA CATTGAAAAC GGGTGCAGTT | 1020 |
| ATCGACCTTT CGGGTAAAGA AGGGGGAGAA ACTTATCTTG GCGGTGACGA GCGTGGCGAA | 1080 |
| GGTAAAAACG GCATTCAATT AGCAAAGAAA ACCACTTTAG AAAAAGGCTC AACAATTAAT | 1140 |
| GTGTCAGGTA AAGAAAAAGG TGGGCGCGCT ATTGTATGGG GCGATATTGC GTTAATTGAC | 1200 |
| GGCAATATTA TGCCCAAGG TAAAGATATC GCTAAAACTG GTGGTTTTGT GGAGACGTCG | 1260 |
| GGGCATTACT TATCCATTGA TGATAACGCA ATTGTTAAAA CAAAGAATG GCTACTAGAC | 1320 |
| CCAGAGAATG TGACTATTGA AGCTCCTTCC GCTTCTCGCG TCGAGCTGGG TGCCGATAGG | 1380 |
| AATTCCCACT CGGCAGAGGT GATAAAAGTG ACCCTAAAAA AAAATAACAC CTCCTTGACA | 1440 |
| ACACTAACCA ATACAACCAT TTCAAATCTT CTGAAAAGTG CCCACGTGGT GAACATAACG | 1500 |
| GCAAGGAGAA AACTTACCGT TAATAGCTCT ATCAGTATAG AAAGAGGCTC CCACTTAATT | 1560 |
| CTCCACAGTG AAGGTCAGGG CGGTCAAGGT GTTCAGATTG ATAAAGATAT TACTTCTGAA | 1620 |
| GGCGGAAATT TAACCATTTA TTCTGGCGGA TGGGTTGATG TTCATAAAAA TATTACGCTT | 1680 |
| GGTAGCGGCT TTTTAAACAT CACAACTAAA GAAGGAGATA TCGCCTTCGA AGACAAGTCT | 1740 |
| GGACGGAACA ACCTAACCAT TACAGCCCAA GGGACCATCA CCTCAGGTAA TAGTAACGGC | 1800 |
| TTTAGATTTA ACAACGTCTC TCTAAACAGC CTTGGCGGAA AGCTGAGCTT TACTGACAGC | 1860 |
| AGAGAGGACA GAGGTAGAAG AACTAAGGGT AATATCTCAA ACAAATTTGA CGGAACGTTA | 1920 |

```
AACATTTCCG GAACTGTAGA TATCTCAATG AAAGCACCCA AAGTCAGCTG GTTTTACAGA    1980

GACAAAGGAC GCACCTACTG GAACGTAACC ACTTTAAATG TTACCTCGGG TAGTAAATTT    2040

AACCTCTCCA TTGACAGCAC AGGAAGTGGC TCAACAGGTC CAAGCATACG CAATGCAGAA    2100

TTAAATGGCA TAACATTTAA TAAAGCCACT TTTAATATCG CACAAGGCTC AACAGCTAAC    2160

TTTAGCATCA AGGCATCAAT AATGCCCTTT AAGAGTAACG CTAACTACGC ATTATTTAAT    2220

GAAGATATTT CAGTCTCAGG GGGGGTAGC CTTAATTTCA AACTTAACGC CTCATCTAGC     2280

AACATACAAA CCCCTGGCGT AATTATAAAA TCTCAAAACT TTAATGTCTC AGGAGGGTCA    2340

ACTTTAAATC TCAAGGCTGA AGGTTCAACA GAAACCGCTT TTTCAATAGA AAATGATTTA    2400

AACTTAAACG CCACCGGTGG CAATATAACA ATCAGACAAG TCGAGGGTAC CGATTCACGC    2460

GTCAACAAAG GTGTCGCAGC CAAAAAAAAC ATAACTTTTA AAGGGGGTAA TATCACCTTC    2520

GGCTCTCAAA AAGCCACAAC AGAAATCAAA GGCAATGTTA CCATCAATAA AAACACTAAC    2580

GCTACTCTTT GTGGTGCGAA TTTTGCCGAA AACAAATCGC CTTTAAATAT AGCAGGAAAT    2640

GTTATTAATA ATGGCAACCT TACCACTGCC GGCTCCATTA TCAATATAGC CGGAAATCTT    2700

ACTGTTTCAA AAGGCGCTAA CCTTCAAGCT ATAACAAATT ACACTTTTAA TGTAGCCGGC    2760

TCATTTGACA CAATGGCGC TTCAAACATT TCCATTGCCA GAGGAGGGGC TAAATTTAAA     2820

GATATCAATA ACACCAGTAG CTTAAATATT ACCACCAACT CTGATACCAC TTACCGCACC    2880

ATTATAAAAG GCAATATATC CAACAAATCA GGTGATTTGA ATATTATTGA TAAAAAAAGC    2940

GACGCTGAAA TCCAAATTGG CGGCAATATC TCACAAAAAG AAGGCAATCT CACAATTTCT    3000

TCTGATAAAG TAAATATTAC CAATCAGATA ACAATCAAAG CAGGCGTTGA AGGGGGGCGT    3060

TCTGATTCAA GTGAGGCAGA AAATGCTAAC CTAACTATTC AAACCAAAGA GTTAAAATTG    3120

GCAGGAGACC TAAATATTTC AGGCTTTAAT AAAGCAGAAA TTACAGCTAA AAATGGCAGT    3180

GATTTAACTA TTGGCAATGC TAGCGGTGGT AATGCTGATG CTAAAAAAGT GACTTTTGAC    3240

AAGGTTAAAG ATTCAAAAAT CTCGACTGAC GGTCACAATG TAACACTAAA TAGCGAAGTG    3300

AAAACGTCTA ATGGTAGTAG CAATGCTGGT AATGATAACA GCACCGGTTT AACCATTTCC    3360

GCAAAAGATG TAACGGTAAA CAATAACGTT ACCTCCCACA AGACAATAAA TATCTCTGCC    3420

GCAGCAGGAA ATGTAACAAC CAAAGAAGGC ACAACTATCA ATGCAACCAC AGGCAGCGTG    3480

GAAGTAACTG CTCAAAATGG TACAATTAAA GGCAACATTA CCTCGCAAAA TGTAACAGTG    3540

ACAGCAACAG AAAATCTTGT TACCACAGAG AATGCTGTCA TTAATGCAAC CAGCGGCACA    3600

GTAAACATTA GTACAAAAAC AGGGGATATT AAAGGTGGAA TTGAATCAAC TTCCGGTAAT    3660

GTAAATATTA CAGCGAGCGG CAATACACTT AAGGTAAGTA ATATCACTGG TCAAGATGTA    3720

ACAGTAACAG CGGATGCAGG AGCCTTGACA ACTACAGCAG GCTCAACCAT TAGTGCGACA    3780

ACAGGCAATG CAAATATTAC AACCAAAACA GGTGATATCA ACGGTAAAGT TGAATCCAGC    3840

TCCGGCTCTG TAACACTTGT TGCAACTGGA GCAACTCTTG CTGTAGGTAA TATTTCAGGT    3900

AACACTGTTA CTATTACTGC GGATAGCGGT AAATTAACCT CCACAGTAGG TTCTACAATT    3960

AATGGGACTA ATAGTGTAAC CACCTCAAGC CAATCAGGCG ATATTGAAGG TACAATTTCT    4020

GGTAATACAG TAAATGTTAC AGCAAGCACT GGTGATTTAA CTATTGGAAA TAGTGCAAAA    4080

GTTGAAGCGA AAAATGGAGC TGCAACCTTA ACTGCTGAAT CAGGCAAATT AACCACCCAA    4140

ACAGGCTCTA GCATTACCTC AAGCAATGGT CAGACAACTC TTACAGCCAA GGATAGCAGT    4200

ATCGCAGGAA ACATTAATGC TGCTAATGTG ACGTTAAATA CCACAGGCAC TTTAACTACT    4260

ACAGGGGATT CAAAGATTAA CGCAACCAGT GGTACCTTAA CAATCAATGC AAAAGATGCC    4320
```

```
AAATTAGATG GTGCTGCATC AGGTGACCGC ACAGTAGTAA ATGCAACTAA CGCAAGTGGC    4380

TCTGGTAACG TGACTGCGAA AACCTCAAGC AGCGTGAATA TCACCGGGGA TTTAAACACA    4440

ATAAATGGGT TAAATATCAT TTCGGAAAAT GGTAGAAACA CTGTGCGCTT AAGAGGCAAG    4500

GAAATTGATG TGAAATATAT CCAACCAGGT GTAGCAAGCG TAGAAGAGGT AATTGAAGCG    4560

AAACGCGTCC TTGAGAAGGT AAAAGATTTA TCTGATGAAG AAAGAGAAAC ACTAGCCAAA    4620

CTTGGTGTAA GTGCTGTACG TTTCGTTGAG CCAAATAATG CCATTACGGT TAATACACAA    4680

AACGAGTTTA CAACCAAACC ATCAAGTCAA GTGACAATTT CTGAAGGTAA GGCGTGTTTC    4740

TCAAGTGGTA ATGGCGCACG AGTATGTACC AATGTTGCTG ACGATGGACA GCAG         4794

(2) INFORMATION FOR SEQ ID NO:8:

(i) SEQUENCE CHARACTERISTICS:
         (A) LENGTH: 4803 base pairs
         (B) TYPE: nucleic acid
         (C) STRANDEDNESS: single
         (D) TOPOLOGY: linear (xi) SEQUENCE DESCRIPTION: SEQ ID NO:8:

ATGAACAAGA TATATCGTCT CAAATTCAGC AAACGCCTGA ATGCTTTGGT TGCTGTGTCT      60

GAATTGACAC GGGGTTGTGA CCATTCCACA GAAAAAGGCA GTGAAAAACC TGTTCGTACG     120

AAAGTACGCC ACTTGGCGTT AAAGCCACTT TCCGCTATAT TGCTATCTTT GGGCATGGCA     180

TCCATTCCGC AATCTGTTTT AGCGAGCGGT TTACAGGGAA TGAGCGTCGT ACACGGTACA     240

GCAACCATGC AAGTAGACGG CAATAAAACC ACTATCCGTA ATAGCGTCAA TGCTATCATC     300

AATTGGAAAC AATTTAACAT TGACCAAAAT GAAATGGTGC AGTTTTTACA AGAAAGCAGC     360

AACTCTGCCG TTTTCAACCG TGTTACATCT GACCAAATCT CCCAATTAAA AGGGATTTTA     420

GATTCTAACG GACAAGTCTT TTTAATCAAC CCAAATGGTA TCACAATAGG TAAAGACGCA     480

ATTATTAACA CTAATGGCTT TACTGCTTCT ACGCTAGACA TTTCTAACGA AAACATCAAG     540

GCGCGTAATT TCACCCTTGA GCAAACCAAG GATAAAGCAC TCGCTGAAAT CGTGAATCAC     600

GGTTTAATTA CCGTTGGTAA AGACGGTAGC GTAAACCTTA TTGGTGGCAA AGTGAAAAAC     660

GAGGGCGTGA TTAGCGTAAA TGGCGGTAGT ATTTCTTTAC TTGCAGGGCA AAAAATCACC     720

ATCAGCGATA TAATAAATCC AACCATCACT TACAGCATTG CTGCACCTGA AAACGAAGCG     780

ATCAATCTGG GCGATATTTT TGCCAAAGGT GGTAACATTA ATGTCCGCGC TGCCACTATT     840

CGCAATAAAG GTAAACTTTC TGCCGACTCT GTAAGCAAAG ATAAAAGTGG TAACATTGTT     900

CTCTCTGCCA AAGAAGGTGA AGCGGAAATT GGCGGTGTAA TTTCCGCTCA AAATCAGCAA     960

GCCAAAGGTG GTAAGTTGAT GATTACAGGT GATAAAGTCA CATTAAAAAC AGGTGCAGTT    1020

ATCGACCTTT CAGGTAAAGA AGGGGGAGAG ACTTATCTTG GCGGTGATGA GCGTGGCGAA    1080

GGTAAAAATG GTATTCAATT AGCGAAGAAA ACCTCTTTAG AAAAAGGCTC GACAATTAAT    1140

GTATCAGGCA AGAAAAAGG CGGGCGCGCT ATTGTATGGG GCGATATTGC ATTAATTAAT    1200

GGTAACATTA ATGCTCAAGG TAGCGATATT GCTAAAACTG GCGGCTTTGT GGAAACATCA    1260

GGACATGACT TATCCATTGG TGATGATGTG ATTGTTGACG CTAAAGAGTG GTTATTAGAC    1320

CCAGATGATG TGTCCATTGA AACTCTTACA TCTGGACGCA ATAATACCGG CGAAAACCAA    1380

GGATATACAA CAGGAGATGG GACTAAAGAG TCACCTAAAG GTAATAGTAT TTCTAAACCT    1440

ACATTAACAA ACTCAACTCT TGAGCAAATC CTAAGAAGAG GTTCTTATGT TAATATCACT    1500

GCTAATAATA GAATTTATGT TAATAGCTCC ATCAACTTAT CTAATGGCAG TTTAACACTT    1560
```

```
CACACTAAAC GAGATGGAGT TAAAATTAAC GGTGATATTA CCTCAAACGA AAATGGTAAT    1620

TTAACCATTA AAGCAGGCTC TTGGGTTGAT GTTCATAAAA ACATCACGCT TGGTACGGGT    1680

TTTTTGAATA TTGTCGCTGG GGATTCTGTA GCTTTTGAGA GAGAGGGCGA TAAAGCACGT    1740

AACGCAACAG ATGCTCAAAT TACCGCACAA GGGACGATAA CCGTCAATAA AGATGATAAA    1800

CAATTTAGAT TCAATAATGT ATCTATTAAC GGGACGGGCA AGGGTTTAAA GTTTATTGCA    1860

AATCAAAATA ATTTCACTCA TAAATTTGAT GGCGAAATTA ACATATCTGG AATAGTAACA    1920

ATTAACCAAA CCACGAAAAA AGATGTTAAA TACTGGAATG CATCAAAAGA CTCTTACTGG    1980

AATGTTTCTT CTCTTACTTT GAATACGGTG CAAAAATTTA CCTTTATAAA ATTCGTTGAT    2040

AGCGGCTCAA ATTCCCAAGA TTTGAGGTCA TCACGTAGAA GTTTTGCAGG CGTACATTTT    2100

AACGGCATCG GAGGCAAAAC AAACTTCAAC ATCGGAGCTA ACGCAAAAGC CTTATTTAAA    2160

TTAAAACCAA ACGCCGCTAC AGACCCAAAA AAAGAATTAC CTATTACTTT TAACGCCAAC    2220

ATTACAGCTA CCGGTAACAG TGATAGCTCT GTGATGTTTG ACATACACGC CAATCTTACC    2280

TCTAGAGCTG CCGGCATAAA CATGGATTCA ATTAACATTA CCGGCGGGCT TGACTTTTCC    2340

ATAACATCCC ATAATCGCAA TAGTAATGCT TTTGAAATCA AAAAGACTT AACTATAAAT    2400

GCAACTGGCT CGAATTTTAG TCTTAAGCAA ACGAAAGATT CTTTTTATAA TGAATACAGC    2460

AAACACGCCA TTAACTCAAG TCATAATCTA ACCATTCTTG GCGGCAATGT CACTCTAGGT    2520

GGGGAAAATT CAAGCAGTAG CATTACGGGC AATATCAATA TCACCAATAA AGCAAATGTT    2580

ACATTACAAG CTGACACCAG CAACAGCAAC ACAGGCTTGA AGAAAAGAAC TCTAACTCTT    2640

GGCAATATAT CTGTTGAGGG GAATTTAAGC CTAACTGGTG CAAATGCAAA CATTGTCGGC    2700

AATCTTTCTA TTGCAGAAGA TTCCACATTT AAAGGAGAAG CCAGTGACAA CCTAAACATC    2760

ACCGGCACCT TTACCAACAA CGGTACCGCC AACATTAATA TAAAACAAGG AGTGGTAAAA    2820

CTCCAAGGCG ATATTATCAA TAAAGGTGGT TTAAATATCA CTACTAACGC CTCAGGCACT    2880

CAAAAAACCA TTATTAACGG AAATATAACT AACGAAAAAG GCGACTTAAA CATCAAGAAT    2940

ATTAAAGCCG ACGCCGAAAT CCAAATTGGC GGCAATATCT CACAAAAAGA AGGCAATCTC    3000

ACAATTTCTT CTGATAAAGT AAATATTACC AATCAGATAA CAATCAAAGC AGGCGTTGAA    3060

GGGGGGCGTT CTGATTCAAG TGAGGCAGAA AATGCTAACC TAACTATTCA AACCAAAGAG    3120

TTAAAATTGG CAGGAGACCT AAATATTTCA GGCTTTAATA AAGCAGAAAT TACAGCTAAA    3180

AATGGCAGTG ATTTAACTAT TGGCAATGCT AGCGGTGGTA ATGCTGATGC TAAAAAAGTG    3240

ACTTTTGACA AGGTTAAAGA TTCAAAAATC TCGACTGACG GTCACAATGT AACACTAAAT    3300

AGCGAAGTGA AAACGTCTAA TGGTAGTAGC AATGCTGGTA ATGATAACAG CACCGGTTTA    3360

ACCATTTCCG CAAAAGATGT AACGGTAAAC AATAACGTTA CCTCCCACAA GACAATAAAT    3420

ATCTCTGCCG CAGCAGGAAA TGTAACAACC AAAGAAGGCA CAACTATCAA TGCAACCACA    3480

GGCAGCGTGG AAGTAACTGC TCAAAATGGT ACAATTAAAG GCAACATTAC CTCGCAAAAT    3540

GTAACAGTGA CAGCAACAGA AAATCTTGTT ACCACAGAGA ATGCTGTCAT TAATGCAACC    3600

AGCGGCACAG TAAACATTAG TACAAAAACA GGGGATATTA AAGGTGGAAT TGAATCAACT    3660

TCCGGTAATG TAAATATTAC AGCGAGCGGC AATACACTTA AGGTAAGTAA TATCACTGGT    3720

CAAGATGTAA CAGTAACAGC GGATGCAGGA GCCTTGACAA CTACAGCAGG CTCAACCATT    3780

AGTGCGACAA CAGGCAATGC AAATATTACA ACCAAAACAG GTGATATCAA CGGTAAAGTT    3840

GAATCCAGCT CCGGCTCTGT AACACTTGTT GCAACTGGAG CAACTCTTGC TGTAGGTAAT    3900

ATTTCAGGTA ACACTGTTAC TATTACTGCG GATAGCGGTA AATTAACCTC CACAGTAGGT    3960
```

```
TCTACAATTA ATGGGACTAA TAGTGTAACC ACCTCAAGCC AATCAGGCGA TATTGAAGGT     4020

ACAATTTCTG GTAATACAGT AAATGTTACA GCAAGCACTG GTGATTTAAC TATTGGAAAT     4080

AGTGCAAAAG TTGAAGCGAA AAATGGAGCT GCAACCTTAA CTGCTGAATC AGGCAAATTA     4140

ACCACCCAAA CAGGCTCTAG CATTACCTCA AGCAATGGTC AGACAACTCT TACAGCCAAG     4200

GATAGCAGTA TCGCAGGAAA CATTAATGCT GCTAATGTGA CGTTAAATAC CACAGGCACT     4260

TTAACTACTA CAGGGGATTC AAAGATTAAC GCAACCAGTG GTACCTTAAC AATCAATGCA     4320

AAAGATGCCA AATTAGATGG TGCTGCATCA GGTGACCGCA CAGTAGTAAA TGCAACTAAC     4380

GCAAGTGGCT CTGGTAACGT GACTGCGAAA ACCTCAAGCA GCGTGAATAT CACCGGGGAT     4440

TTAAACACAA TAAATGGGTT AAATATCATT TCGGAAAATG GTAGAAACAC TGTGCGCTTA     4500

AGAGGCAAGG AAATTGATGT GAAATATATC CAACCAGGTG TAGCAAGCGT AGAAGAGGTA     4560

ATTGAAGCGA AACGCGTCCT TGAGAAGGTA AAAGATTTAT CTGATGAAGA AAGAGAAACA     4620

CTAGCCAAAC TTGGTGTAAG TGCTGTACGT TTCGTTGAGC CAAATAATGC CATTACGGTT     4680

AATACACAAA ACGAGTTTAC AACCAAACCA TCAAGTCAAG TGACAATTTC TGAAGGTAAG     4740

GCGTGTTTCT CAAGTGGTAA TGGCGCACGA GTATGTACCA ATGTTGCTGA CGATGGACAG     4800

CAG                                                                  4803

(2) INFORMATION FOR SEQ ID NO:9:

(i) SEQUENCE CHARACTERISTICS:
        (A) LENGTH: 1599 amino acids
        (B) TYPE: amino acid
        (C) STRANDEDNESS: single
        (D) TOPOLOGY: linear (xi) SEQUENCE DESCRIPTION: SEQ ID NO:9:

Met Asn Lys Ile Tyr Arg Leu Lys Phe Ser Lys Arg Leu Asn Ala Leu
1               5                   10                  15

Val Ala Val Ser Glu Leu Thr Arg Gly Cys Asp His Ser Thr Glu Lys
                20                  25                  30

Gly Ser Glu Lys Pro Val Arg Thr Lys Val Arg His Leu Ala Leu Lys
            35                  40                  45

Pro Leu Ser Ala Ile Leu Leu Ser Leu Gly Met Ala Ser Ile Pro Gln
        50                  55                  60

Ser Val Leu Ala Ser Gly Leu Gln Gly Met Ser Val Val His Gly Thr
65                  70                  75                  80

Ala Thr Met Gln Val Asp Gly Asn Lys Thr Thr Ile Arg Asn Ser Val
                85                  90                  95

Asn Ala Ile Ile Asn Trp Lys Gln Phe Asn Ile Asp Gln Asn Glu Met
                100                 105                 110

Glu Gln Phe Leu Gln Glu Ser Ser Asn Ser Ala Val Phe Asn Arg Val
            115                 120                 125

Thr Ser Asp Gln Ile Ser Gln Leu Lys Gly Ile Leu Asp Ser Asn Gly
        130                 135                 140

Gln Val Phe Leu Ile Asn Pro Asn Gly Ile Thr Ile Gly Lys Asp Ala
145                 150                 155                 160

Ile Ile Asn Thr Asn Gly Phe Thr Ala Ser Thr Leu Asp Ile Ser Asn
                165                 170                 175

Glu Asn Ile Lys Ala Arg Asn Phe Thr Leu Glu Gln Thr Lys Asp Lys
                180                 185                 190

Ala Leu Ala Glu Ile Val Asn His Gly Leu Ile Thr Val Gly Lys Asp
            195                 200                 205
```

```
Gly Ser Val Asn Leu Ile Gly Gly Lys Val Lys Asn Glu Gly Val Ile
    210                 215                 220

Ser Val Asn Gly Gly Ser Ile Ser Leu Leu Ala Gly Gln Lys Ile Thr
225                 230                 235                 240

Ile Ser Asp Ile Ile Asn Pro Thr Ile Thr Tyr Ser Ile Ala Ala Pro
                245                 250                 255

Glu Asn Glu Ala Ile Asn Leu Gly Asp Ile Phe Ala Lys Gly Gly Asn
                260                 265                 270

Ile Asn Val Arg Ala Ala Thr Ile Arg Asn Lys Gly Lys Leu Ser Ala
                275                 280                 285

Asp Ser Val Ser Lys Asp Lys Ser Gly Asn Ile Val Leu Ser Ala Lys
                290                 295                 300

Glu Gly Glu Ala Glu Ile Gly Gly Val Ile Ser Ala Gln Asn Gln Gln
305                 310                 315                 320

Ala Lys Gly Gly Lys Leu Met Ile Thr Gly Asp Lys Val Thr Leu Lys
                325                 330                 335

Thr Gly Ala Val Ile Asp Leu Ser Gly Lys Glu Gly Gly Glu Thr Tyr
                340                 345                 350

Leu Gly Gly Asp Glu Arg Gly Glu Gly Lys Asn Gly Ile Gln Leu Ala
                355                 360                 365

Lys Lys Thr Thr Leu Glu Lys Gly Ser Thr Ile Asn Val Ser Gly Lys
370                 375                 380

Glu Lys Gly Gly Arg Ala Ile Val Trp Gly Asp Ile Ala Leu Ile Asp
385                 390                 395                 400

Gly Asn Ile Asn Ala Gln Gly Lys Asp Ile Ala Lys Thr Gly Gly Phe
                405                 410                 415

Val Glu Thr Ser Gly His Tyr Leu Ser Ile Asp Asp Asn Ala Ile Val
                420                 425                 430

Lys Thr Lys Glu Trp Leu Leu Asp Pro Glu Asn Val Thr Ile Glu Ala
                435                 440                 445

Pro Ser Ala Ser Arg Val Glu Leu Gly Ala Asp Arg Asn Ser His Ser
450                 455                 460

Ala Glu Val Ile Lys Val Thr Leu Lys Lys Asn Asn Thr Ser Leu Thr
465                 470                 475                 480

Thr Leu Thr Asn Thr Thr Ile Ser Asn Leu Leu Lys Ser Ala His Val
                485                 490                 495

Val Asn Ile Thr Ala Arg Arg Lys Leu Thr Val Asn Ser Ser Ile Ser
                500                 505                 510

Ile Glu Arg Gly Ser His Leu Ile Leu His Ser Glu Gly Gln Gly Gly
                515                 520                 525

Gln Gly Val Gln Ile Asp Lys Asp Ile Thr Ser Glu Gly Gly Asn Leu
                530                 535                 540

Thr Ile Tyr Ser Gly Gly Trp Val Asp Val His Lys Asn Ile Thr Leu
545                 550                 555                 560

Gly Ser Gly Phe Leu Asn Ile Thr Thr Lys Glu Gly Asp Ile Ala Phe
                565                 570                 575

Glu Asp Lys Ser Gly Arg Asn Asn Leu Thr Ile Thr Ala Gln Gly Thr
                580                 585                 590

Ile Thr Ser Gly Asn Ser Asn Gly Phe Arg Phe Asn Asn Val Ser Leu
                595                 600                 605

Asn Ser Leu Gly Gly Lys Leu Ser Phe Thr Asp Ser Arg Glu Asp Arg
                610                 615                 620

Gly Arg Arg Thr Lys Gly Asn Ile Ser Asn Lys Phe Asp Gly Thr Leu
625                 630                 635                 640
```

```
Asn Ile Ser Gly Thr Val Asp Ile Ser Met Lys Ala Pro Lys Val Ser
                645                 650                 655

Trp Phe Tyr Arg Asp Lys Gly Arg Thr Tyr Trp Asn Val Thr Thr Leu
            660                 665                 670

Asn Val Thr Ser Gly Ser Lys Phe Asn Leu Ser Ile Asp Ser Thr Gly
        675                 680                 685

Ser Gly Ser Thr Gly Pro Ser Ile Arg Asn Ala Glu Leu Asn Gly Ile
    690                 695                 700

Thr Phe Asn Lys Ala Thr Phe Asn Ile Ala Gln Gly Ser Thr Ala Asn
705                 710                 715                 720

Phe Ser Ile Lys Ala Ser Ile Met Pro Phe Lys Ser Asn Ala Asn Tyr
                725                 730                 735

Ala Leu Phe Asn Glu Asp Ile Ser Val Ser Gly Gly Ser Val Asn
                740                 745                 750

Phe Lys Leu Asn Ala Ser Ser Asn Ile Gln Thr Pro Gly Val Ile
            755                 760                 765

Ile Lys Ser Gln Asn Phe Asn Val Ser Gly Ser Thr Leu Asn Leu
    770                 775                 780

Lys Ala Glu Gly Ser Thr Glu Thr Ala Phe Ser Ile Glu Asn Asp Leu
785                 790                 795                 800

Asn Leu Asn Ala Thr Gly Gly Asn Ile Thr Ile Arg Gln Val Glu Gly
                805                 810                 815

Thr Asp Ser Arg Val Asn Lys Gly Val Ala Ala Lys Lys Asn Ile Thr
                820                 825                 830

Phe Lys Gly Gly Asn Ile Thr Phe Gly Ser Gln Lys Ala Thr Thr Glu
            835                 840                 845

Ile Lys Gly Asn Val Thr Ile Asn Lys Asn Thr Asn Ala Thr Leu Arg
    850                 855                 860

Gly Ala Asn Phe Ala Glu Asn Lys Ser Pro Leu Asn Ile Ala Gly Asn
865                 870                 875                 880

Val Ile Asn Asn Gly Asn Leu Thr Thr Ala Gly Ser Ile Ile Asn Ile
                885                 890                 895

Ala Gly Asn Leu Thr Val Ser Lys Gly Ala Asn Leu Gln Ala Ile Thr
                900                 905                 910

Asn Tyr Thr Phe Asn Val Ala Gly Ser Phe Asp Asn Asn Gly Ala Ser
            915                 920                 925

Asn Ile Ser Ile Ala Arg Gly Gly Ala Lys Phe Lys Asp Ile Asn Asn
    930                 935                 940

Thr Ser Ser Leu Asn Ile Thr Thr Asn Ser Asp Thr Thr Tyr Arg Thr
945                 950                 955                 960

Ile Ile Lys Gly Asn Ile Ser Asn Lys Ser Gly Asp Leu Asn Ile Ile
                965                 970                 975

Asp Lys Lys Ser Asp Ala Glu Ile Gln Ile Gly Asn Ile Ser Gln
                980                 985                 990

Lys Glu Gly Asn Leu Thr Ile Ser Ser Asp Lys Val Asn Ile Thr Asn
    995                 1000                1005

Gln Ile Thr Ile Lys Ala Gly Val Glu Gly Arg Ser Asp Ser Ser
    1010                1015                1020

Glu Ala Glu Asn Ala Asn Leu Thr Ile Gln Thr Lys Glu Leu Lys Leu
1025                1030                1035                1040

Ala Gly Asp Leu Asn Ile Ser Gly Phe Asn Lys Ala Glu Ile Thr Ala
                1045                1050                1055

Lys Asn Gly Ser Asp Leu Thr Ile Gly Asn Ala Ser Gly Gly Asn Ala
```

-continued

```
               1060                1065                1070
Asp Ala Lys Lys Val Thr Phe Asp Lys Val Lys Asp Ser Lys Ile Ser
           1075                1080            1085
Thr Asp Gly His Asn Val Thr Leu Asn Ser Glu Val Lys Thr Ser Asn
       1090                1095                1100
Gly Ser Ser Asn Ala Gly Asn Asp Asn Ser Thr Gly Leu Thr Ile Ser
1105                1110            1115                1120
Ala Lys Asp Val Thr Val Asn Asn Val Thr Ser His Lys Thr Ile
           1125                1130            1135
Asn Ile Ser Ala Ala Ala Gly Asn Val Thr Thr Lys Glu Gly Thr Thr
           1140                1145            1150
Ile Asn Ala Thr Thr Gly Ser Val Glu Val Thr Ala Gln Asn Gly Thr
           1155                1160            1165
Ile Lys Gly Asn Ile Thr Ser Gln Asn Val Thr Val Thr Ala Thr Glu
           1170                1175            1180
Asn Leu Val Thr Thr Glu Asn Ala Val Ile Asn Ala Thr Ser Gly Thr
1185                1190            1195                1200
Val Asn Ile Ser Thr Lys Thr Gly Asp Ile Lys Gly Gly Ile Glu Ser
           1205                1210            1215
Thr Ser Gly Asn Val Asn Ile Thr Ala Ser Gly Asn Thr Leu Lys Val
           1220                1225            1230
Ser Asn Ile Thr Gly Gln Asp Val Thr Val Thr Ala Asp Ala Gly Ala
           1235                1240            1245
Leu Thr Thr Thr Ala Gly Ser Thr Ile Ser Ala Thr Thr Gly Asn Ala
           1250                1255            1260
Asn Ile Thr Thr Lys Thr Gly Asp Ile Asn Gly Lys Val Glu Ser Ser
1265                1270            1275                1280
Ser Gly Ser Val Thr Leu Val Ala Thr Gly Ala Thr Leu Ala Val Gly
           1285                1290            1295
Asn Ile Ser Gly Asn Thr Val Thr Ile Thr Ala Asp Ser Gly Lys Leu
           1300                1305            1310
Thr Ser Thr Val Gly Ser Thr Ile Asn Gly Thr Asn Ser Val Thr Thr
           1315                1320            1325
Ser Ser Gln Ser Gly Asp Ile Glu Gly Thr Ile Ser Gly Asn Thr Val
           1330                1335            1340
Asn Val Thr Ala Ser Thr Gly Asp Leu Thr Ile Gly Asn Ser Ala Lys
1345                1350            1355                1360
Val Glu Ala Lys Asn Gly Ala Ala Thr Leu Thr Ala Glu Ser Gly Lys
           1365                1370            1375
Leu Thr Thr Gln Thr Gly Ser Ser Ile Thr Ser Ser Asn Gly Gln Thr
           1380                1385            1390
Thr Leu Thr Ala Lys Asp Ser Ser Ile Ala Gly Asn Ile Asn Ala Ala
           1395                1400            1405
Asn Val Thr Leu Asn Thr Thr Gly Thr Leu Thr Thr Thr Gly Asp Ser
           1410                1415            1420
Lys Ile Asn Ala Thr Ser Gly Thr Leu Thr Ile Asn Ala Lys Asp Ala
1425                1430            1435                1440
Lys Leu Asp Gly Ala Ala Ser Gly Asp Arg Thr Val Val Asn Ala Thr
           1445                1450            1455
Asn Ala Ser Gly Ser Gly Asn Val Thr Ala Lys Thr Ser Ser Ser Val
           1460                1465            1470
Asn Ile Thr Gly Asp Leu Asn Thr Ile Asn Gly Leu Asn Ile Ile Ser
           1475                1480            1485
```

```
Glu Asn Gly Arg Asn Thr Val Arg Leu Arg Gly Lys Glu Ile Asp Val
    1490                1495                1500

Lys Tyr Ile Gln Pro Gly Val Ala Ser Val Glu Glu Val Ile Glu Ala
1505                1510                1515                1520

Lys Arg Val Leu Glu Lys Val Lys Asp Leu Ser Asp Glu Glu Arg Glu
            1525                1530                1535

Thr Leu Ala Lys Leu Gly Val Ser Ala Val Arg Phe Val Glu Pro Asn
        1540                1545                1550

Asn Ala Ile Thr Val Asn Thr Gln Asn Glu Phe Thr Thr Lys Pro Ser
            1555                1560                1565

Ser Gln Val Thr Ile Ser Glu Gly Lys Ala Cys Phe Ser Ser Gly Asn
        1570                1575                1580

Gly Ala Arg Val Cys Thr Asn Val Ala Asp Asp Gly Gln Gln Pro
1585                1590                1595
```

(2) INFORMATION FOR SEQ ID NO:10:

(i) SEQUENCE CHARACTERISTICS:
        (A) LENGTH: 1600 amino acids
        (B) TYPE: amino acid
        (C) STRANDEDNESS: single
        (D) TOPOLOGY: linear (xi) SEQUENCE DESCRIPTION: SEQ ID NO:10:

```
Met Asn Lys Ile Tyr Arg Leu Lys Phe Ser Lys Arg Leu Asn Ala Leu
1               5                   10                  15

Val Ala Val Ser Glu Leu Thr Arg Gly Cys Asp His Ser Thr Glu Lys
            20                  25                  30

Gly Ser Glu Lys Pro Val Arg Thr Lys Val Arg His Leu Ala Leu Lys
        35                  40                  45

Pro Leu Ser Ala Ile Leu Leu Ser Leu Gly Met Ala Ser Ile Pro Gln
50                  55                  60

Ser Val Leu Ala Ser Gly Leu Gln Gly Met Ser Val Val His Gly Thr
65                  70                  75                  80

Ala Thr Met Gln Val Asp Gly Asn Lys Thr Thr Ile Arg Asn Ser Val
            85                  90                  95

Asn Ala Ile Ile Asn Trp Lys Gln Phe Asn Ile Asp Gln Asn Glu Met
        100                 105                 110

Glu Gln Phe Leu Gln Glu Ser Ser Asn Ser Ala Val Phe Asn Arg Val
    115                 120                 125

Thr Ser Asp Gln Ile Ser Gln Leu Lys Gly Ile Leu Asp Ser Asn Gly
        130                 135                 140

Gln Val Phe Leu Ile Asn Pro Asn Gly Ile Thr Ile Gly Lys Asp Ala
145                 150                 155                 160

Ile Ile Asn Thr Asn Gly Phe Thr Ala Ser Thr Leu Asp Ile Ser Asn
            165                 170                 175

Glu Asn Ile Lys Ala Arg Asn Phe Thr Leu Glu Gln Thr Lys Asp Lys
        180                 185                 190

Ala Leu Ala Glu Ile Val Asn His Gly Leu Ile Thr Val Gly Lys Asp
    195                 200                 205

Gly Ser Val Asn Leu Ile Gly Gly Lys Val Lys Asn Glu Gly Val Ile
        210                 215                 220

Ser Val Asn Gly Gly Ser Ile Ser Leu Leu Ala Gly Gln Lys Ile Thr
225                 230                 235                 240

Ile Ser Asp Ile Ile Asn Pro Thr Ile Thr Tyr Ser Ile Ala Ala Pro
            245                 250                 255
```

-continued

```
Glu Asn Glu Ala Ile Asn Leu Gly Asp Ile Phe Ala Lys Gly Gly Asn
        260                 265                 270

Ile Asn Val Arg Ala Ala Thr Ile Arg Asn Lys Gly Lys Leu Ser Ala
            275                 280                 285

Asp Ser Val Ser Lys Asp Lys Ser Gly Asn Ile Val Leu Ser Ala Lys
290                 295                 300

Glu Gly Glu Ala Glu Ile Gly Gly Val Ile Ser Ala Gln Asn Gln Gln
305                 310                 315                 320

Ala Lys Gly Gly Lys Leu Met Ile Thr Gly Asp Lys Val Thr Leu Lys
                325                 330                 335

Thr Gly Ala Val Ile Asp Leu Ser Gly Lys Glu Gly Glu Thr Tyr
            340                 345                 350

Leu Gly Gly Asp Glu Arg Gly Glu Gly Lys Asn Gly Ile Gln Leu Ala
            355                 360                 365

Lys Lys Thr Thr Leu Glu Lys Gly Ser Thr Ile Asn Val Ser Gly Lys
370                 375                 380

Glu Lys Gly Gly Arg Ala Ile Val Trp Gly Asp Ile Ala Leu Ile Asp
385                 390                 395                 400

Gly Asn Ile Asn Ala Gln Gly Ser Asp Ile Ala Lys Thr Gly Gly Phe
                405                 410                 415

Val Glu Thr Ser Gly His Asp Leu Ser Ile Gly Asp Val Ile Val
            420                 425                 430

Asp Ala Lys Glu Trp Leu Leu Asp Pro Asp Asp Val Ser Ile Glu Thr
            435                 440                 445

Leu Thr Ser Gly Arg Asn Asn Thr Gly Glu Asn Gln Gly Tyr Thr Thr
450                 455                 460

Gly Asp Gly Thr Lys Glu Ser Pro Lys Gly Asn Ser Ile Ser Lys Pro
465                 470                 475                 480

Thr Leu Thr Asn Ser Thr Leu Glu Gln Ile Leu Arg Arg Gly Ser Tyr
                485                 490                 495

Val Asn Ile Thr Ala Asn Asn Arg Ile Tyr Val Asn Ser Ser Ile Asn
            500                 505                 510

Leu Ser Asn Gly Ser Leu Thr Leu His Thr Lys Arg Asp Gly Val Lys
            515                 520                 525

Ile Asn Gly Asp Ile Thr Ser Asn Glu Asn Gly Asn Leu Thr Ile Lys
530                 535                 540

Ala Gly Ser Trp Val Asp Val His Lys Asn Ile Thr Leu Gly Thr Gly
545                 550                 555                 560

Phe Leu Asn Ile Val Ala Gly Asp Ser Val Ala Phe Glu Arg Glu Gly
                565                 570                 575

Asp Lys Ala Arg Asn Ala Thr Asp Ala Gln Ile Thr Ala Gln Gly Thr
            580                 585                 590

Ile Thr Val Asn Lys Asp Asp Lys Gln Phe Arg Phe Asn Asn Val Ser
            595                 600                 605

Leu Asn Gly Thr Gly Lys Gly Leu Lys Phe Ile Ala Asn Gln Asn Asn
610                 615                 620

Phe Thr His Lys Phe Asp Gly Glu Ile Asn Ile Ser Gly Ile Val Thr
625                 630                 635                 640

Ile Asn Gln Thr Thr Lys Lys Asp Val Lys Tyr Trp Asn Ala Ser Lys
                645                 650                 655

Asp Ser Tyr Trp Asn Val Ser Ser Leu Thr Leu Asn Thr Val Gln Lys
            660                 665                 670

Phe Thr Phe Ile Lys Phe Val Asp Ser Gly Ser Asn Gly Gln Asp Leu
            675                 680                 685
```

-continued

```
Arg Ser Ser Arg Arg Ser Phe Ala Gly Val His Phe Asn Gly Ile Gly
    690                 695                 700
Gly Lys Thr Asn Phe Asn Ile Gly Ala Asn Ala Lys Ala Leu Phe Lys
705                 710                 715                 720
Leu Lys Pro Asn Ala Ala Thr Asp Pro Lys Lys Glu Leu Pro Ile Thr
                725                 730                 735
Phe Asn Ala Asn Ile Thr Ala Thr Gly Asn Ser Asp Ser Ser Val Met
            740                 745                 750
Phe Asp Ile His Ala Asn Leu Thr Ser Arg Ala Gly Ile Asn Met
            755                 760                 765
Asp Ser Ile Asn Ile Thr Gly Gly Leu Asp Phe Ser Ile Thr Ser His
    770                 775                 780
Asn Arg Asn Ser Asn Ala Phe Glu Ile Lys Lys Asp Leu Thr Ile Asn
785                 790                 795                 800
Ala Thr Gly Ser Asn Phe Ser Leu Lys Gln Thr Lys Asp Ser Phe Tyr
                805                 810                 815
Asn Glu Tyr Ser Lys His Ala Ile Asn Ser Ser His Asn Leu Thr Ile
            820                 825                 830
Leu Gly Gly Asn Val Thr Leu Gly Gly Glu Asn Ser Ser Ser Ser Ile
    835                 840                 845
Thr Gly Asn Ile Asn Ile Thr Asn Lys Ala Asn Val Thr Leu Gln Ala
    850                 855                 860
Asp Thr Ser Asn Ser Asn Thr Gly Leu Lys Lys Arg Thr Leu Thr Leu
865                 870                 875                 880
Gly Asn Ile Ser Val Glu Gly Asn Leu Ser Leu Thr Gly Ala Asn Ala
                885                 890                 895
Asn Ile Val Gly Asn Leu Ser Ile Ala Glu Asp Ser Thr Phe Lys Gly
            900                 905                 910
Glu Ala Ser Asp Asn Leu Asn Ile Thr Gly Thr Phe Asn Asn Gly
    915                 920                 925
Thr Ala Asn Ile Asn Ile Lys Gly Val Val Lys Leu Gly Asp Ile Asn
    930                 935                 940
Asn Lys Gly Gly Leu Asn Ile Thr Thr Asn Ala Ser Gly Thr Gln Lys
945                 950                 955                 960
Thr Ile Ile Asn Gly Asn Ile Thr Asn Glu Lys Gly Asp Leu Asn Ile
                965                 970                 975
Lys Asn Ile Lys Ala Asp Ala Gly Ile Gln Ile Gly Asn Ile Ser
            980                 985                 990
Gln Lys Glu Gly Asn Leu Thr Ile Ser Ser Asp Lys Val Asn Ile Thr
            995                 1000                1005
Asn Gln Ile Thr Ile Lys Ala Gly Val Glu Gly Gly Arg Ser Asp Ser
    1010                1015                1020
Ser Glu Ala Glu Asn Ala Asn Leu Thr Ile Gln Thr Lys Glu Leu Lys
1025                1030                1035                1040
Leu Ala Gly Asp Leu Asn Ile Ser Gly Phe Asn Lys Ala Glu Ile Thr
                1045                1050                1055
Ala Lys Asn Gly Ser Asp Leu Thr Ile Gly Asn Ala Ser Gly Gly Asn
            1060                1065                1070
Ala Asp Ala Lys Lys Val Thr Phe Asp Lys Val Lys Asp Ser Lys Ile
            1075                1080                1085
Ser Thr Asp Gly His Asn Val Thr Leu Asn Ser Glu Val Lys Thr Ser
    1090                1095                1100
Asn Gly Ser Ser Asn Ala Gly Asn Asp Asn Ser Thr Gly Leu Thr Ile
```

```
             1105                1110                1115                1120
Ser Ala Lys Asp Val Thr Val Asn Asn Val Thr Ser His Lys Thr
                     1125                1130                1135
Ile Asn Ile Ser Ala Ala Ala Gly Asn Val Thr Thr Lys Glu Gly Thr
            1140                1145                1150
Thr Ile Asn Ala Thr Thr Gly Ser Val Glu Val Thr Ala Gln Asn Gly
            1155                1160                1165
Thr Ile Lys Gly Asn Ile Thr Ser Gln Asn Val Thr Val Thr Ala Thr
            1170                1175                1180
Glu Asn Leu Val Thr Thr Glu Asn Ala Val Ile Asn Ala Thr Ser Gly
1185                1190                1195                1200
Thr Val Asn Ile Ser Thr Lys Thr Gly Asp Ile Lys Gly Gly Ile Glu
                1205                1210                1215
Ser Thr Ser Gly Asn Val Asn Ile Thr Ala Ser Gly Asn Thr Leu Lys
                1220                1225                1230
Val Ser Asn Ile Thr Gly Gln Asp Val Thr Val Thr Ala Asp Ala Gly
                1235                1240                1245
Ala Leu Thr Thr Thr Ala Gly Ser Thr Ile Ser Ala Thr Thr Gly Asn
        1250                1255                1260
Ala Asn Ile Thr Thr Lys Thr Gly Asp Ile Asn Gly Lys Val Glu Ser
1265                1270                1275                1280
Ser Ser Gly Ser Val Thr Leu Val Ala Thr Gly Ala Thr Leu Ala Val
                1285                1290                1295
Gly Asn Ile Ser Gly Asn Thr Val Thr Ile Thr Ala Asp Ser Gly Lys
            1300                1305                1310
Leu Thr Ser Thr Val Gly Ser Thr Ile Asn Gly Thr Asn Ser Val Thr
            1315                1320                1325
Thr Ser Ser Gln Ser Gly Asp Ile Glu Gly Thr Ile Ser Gly Asn Thr
            1330                1335                1340
Val Asn Val Thr Ala Ser Thr Gly Asp Leu Thr Ile Gly Asn Ser Ala
1345                1350                1355                1360
Lys Val Glu Ala Lys Asn Gly Ala Ala Thr Leu Thr Ala Glu Ser Gly
                1365                1370                1375
Lys Leu Thr Thr Gln Thr Gly Ser Ser Ile Thr Ser Ser Asn Gly Gln
            1380                1385                1390
Thr Thr Leu Thr Ala Lys Asp Ser Ser Ile Ala Gly Asn Ile Asn Ala
            1395                1400                1405
Ala Asn Val Thr Leu Asn Thr Thr Gly Thr Leu Thr Thr Thr Gly Asp
        1410                1415                1420
Ser Lys Ile Asn Ala Thr Ser Gly Thr Leu Thr Ile Asn Ala Lys Asp
1425                1430                1435                1440
Ala Lys Leu Asp Gly Ala Ala Ser Gly Asp Arg Thr Val Val Asn Ala
                1445                1450                1455
Thr Asn Ala Ser Gly Ser Gly Asn Val Thr Ala Lys Thr Ser Ser Ser
            1460                1465                1470
Val Asn Ile Thr Gly Asp Leu Thr Ile Asn Gly Leu Asn Ile Ile
            1475                1480                1485
Ser Glu Asn Gly Arg Asn Thr Val Arg Leu Arg Gly Lys Glu Ile Asp
        1490                1495                1500
Val Lys Tyr Ile Gln Pro Gly Val Ala Ser Val Glu Glu Val Ile Glu
1505                1510                1515                1520
Ala Lys Arg Val Leu Glu Lys Val Lys Asp Leu Ser Asp Glu Glu Arg
                1525                1530                1535
```

```
Glu Thr Leu Ala Lys Leu Gly Val Ser Ala Val Arg Phe Val Glu Pro
            1540            1545                1550

Asn Asn Ala Ile Thr Val Asn Thr Gln Asn Glu Phe Thr Thr Lys Pro
        1555            1560            1565

Ser Ser Gln Val Thr Ile Ser Glu Gly Lys Ala Cys Phe Ser Ser Gly
    1570            1575            1580

Asn Gly Ala Arg Val Cys Thr Asn Val Ala Asp Asp Gly Gln Gln Pro
1585                1590            1595            1600

(2) INFORMATION FOR SEQ ID NO:11:

(i) SEQUENCE CHARACTERISTICS:
        (A) LENGTH: 29 amino acids
        (B) TYPE: amino acid
        (C) STRANDEDNESS: single
        (D) TOPOLOGY: linear (xi) SEQUENCE DESCRIPTION: SEQ ID NO:11:

Val Asp Glu Val Ile Glu Ala Lys Arg Ile Leu Glu Lys Val Lys Asp
1           5               10              15

Leu Ser Asp Glu Glu Arg Glu Ala Leu Ala Lys Leu Gly
            20              25
```

What I claim is:

1. An isolated and purified nucleic acid molecule encoding a high molecular weight protein (HMW) of a nontypeable Haemophilus strain and having an apparent molecular weight of about 120 to about 130 kDa having the DNA sequence shown in FIG. 8 (SEQ ID No: 7) and encoding protein HMW3 having the derived amino acid sequence of FIG. 10 (SEQ ID No: 9).

2. An isolated and purified nucleic acid molecule encoding a high molecular weight protein (HMW) of a nontypeable Haemophilus strain and having an apparent molecular weight of about 120 to about 130 kDa having the DNA sequence shown in FIG. 9 (SEQ ID No: 8) and encoding protein HMW4 having the derived amino acid sequence of FIG. 10 (SEQ ID No: 10).

3. An isolated and purified nucleic acid molecule encoding a high molecular weight protein (HMW) of a nontypeable Haemophilus strain and having an apparent molecular weight of about 120 to about 130 kDa and having a DNA sequence selected from the group consisting of:

(a) a contiguous DNA sequence as shown in FIGS. 8 and 9 (SEQ ID Nos: 7 and 8); and (b) a contiguous DNA sequence encoding an amino acid sequence as shown in FIG. 10 (SEQ ID Nos: 9 and 10).

4. A vector for transformation of a host comprising the nucleic acid molecule of claims 1,2 or 3.

* * * * *

United States Patent [19]

Barenkamp

[11] Patent Number: 5,977,336
[45] Date of Patent: Nov. 2, 1999

[54] HIGH MOLECULAR WEIGHT SURFACE PROTEINS OF NON-TYPEABLE HAEMOPHILUS

[75] Inventor: Stephen J. Barenkamp, Webster Grove, Mo.

[73] Assignees: St. Louis University; Washington University, both of St. Louis, Mo.

[21] Appl. No.: 08/617,697

[22] Filed: Apr. 1, 1996

Related U.S. Application Data

[63] Continuation-in-part of application No. 08/302,832, Oct. 5, 1994, Pat. No. 5,603,938, which is a continuation of application No. PCT/US93/02166, Mar. 16, 1993.

[51] Int. Cl.$^6$ .................................................. C07H 21/04
[52] U.S. Cl. .................. 536/23.7; 424/256.1; 536/23.1; 435/320.1; 530/350
[58] Field of Search ...................... 424/256.1; 536/23.1, 536/23.7; 435/320.1; 530/350

[56] References Cited

U.S. PATENT DOCUMENTS

| | | | |
|---|---|---|---|
| 4,258,029 | 3/1981 | Moloney et al. | 424/88 |
| 4,855,283 | 8/1989 | Lockhoff et al. | 424/278 |
| 4,952,496 | 8/1990 | Studier et al. | 435/91 |
| 5,194,254 | 3/1993 | Barber et al. | 424/70 |

FOREIGN PATENT DOCUMENTS

WO 92/17167  10/1992  WIPO.

OTHER PUBLICATIONS

Nixon–George et al. (Jun. 15, 1990) The Adjuvant Effect of Stearyl Tyrosine on a Recombinant Subunit Hepatitis B Surface Antigen, J. Immunol. vol. 144:4798–4802.

Weismuller K–H, et al. (1989) Novel low molecular weight synthetic vaccine against foot–and–mouth disease containing a potent B–cell and macrophage activator, Vaccine vol. 7, Feb. 1989, pp. 29–33.

Chang et al., (1978) Nature 275:617–624.

Itakura et al., (1977) Science 198:1056–1063.

Goeddel et al., (1979) Nature 281:544–548.

Goeddel et al., (1980) Nucl. Acids Res. 8:4057–4074.

Pediatric Infectious Disease Journal, vol. 9, No. 5, issued May 1990, S.J. Barenkamp et al., "Development of Serum Bactericidal Activity Following Nontypable *Haemophilus influenzae* Acute Otitis Media", pp. 333–339, see entire document.

Journal of Clinical Microbiology, vol. 29, No. 11, issued Nov. 1991, A.C. Caputa et al., "110 Kilodalton Recombinant Protein which is immunoreactive with Sera from Humans, Dogs, and Horses with Lyme Borreliosis", pp. 2418–2423, see entire document.

Joint Meeting of the American Pediatric Society and the Society for Pediatric Research, May 7–10, 1990, S.J. Barenkamp, "Cloning and Expression of Genes for Nontypable *Haemophilus influenzae* (NTH) High Molecular Weight (HMW) Outer Membrane Proteins which are Targets of Bactericidal Antibody", Abstract 983, Pediatric Research, vol. 27, (4 part 2).

The Journal of Infectious Diseases, vol. 165 (Suppl.), issued Aug. 1992, S.J. Barenkamp, "Outer Membrane Protein and Lipopolysaccharides of Nontypeable *Haemophilus influenzae* ", pp. S181–S184, see entire document.

Infection and Immunity, vol. 60(4), issued Apr. 1992, S.J. Barenkamp et al, Cloning, Expression and DNA Sequence Analysis of Genes Encoding Nontypable *Haemophilus influenzae* High–Molecular–Weight Surface–Exposed Proteins Related to Filamentous Hemagglutinin of *Bordetella pertussis* pp. 1302–1313, see entire document.

Infection and Immunity, vol. 56(1), issued Jan. 1988, E.J. Hansen, Immune Enhancement of Pulmonary Clearance on Nontypable *Haemophilus influenzae,* pp. 182–190, see entire document, especially Figures 3 and 4.

Infection and Immunity, vol. 52(2), issued May 1986, S.J. Barenkamp, "Protection by Serum Antibodies in Experimental Nontypable *Haemophilus influenzae* Otitis Media", pp. 572–578, see Figures 1 and 2.

Proceedings of the National Academy of Sciences USA, vol. 80, issued Mar. 1983, R.A. Young et al, "Efficient Isolation of Genes by Using Antibody Probes", pp. 1194–1198, see entire document.

Infection and Immunity, vol. 45(3), issued Sep. 1984, R. Schneerson et al, "Serum Antibody Responses of Juvenile and Infant Rhesus Monkeys Injected with *Haemophilus influenzae* Type b and Pneumococcus Type 6A Capsular Polysaccharide–Protein Conjugates", pp. 582–591, see entire document.

Journal of Molecular Biology, vol. 157, issued 1982, J. Kyte et al, "A Simple Method for Displaying the Hydropathic Character of a Protein", pp. 105–132, see entire document.

Proceedings of the National Academy of Sciences, vol. 78(6), issued Jun. 1981, T.P. Hopp et al, "Prediction of Protein Antigenic Determinants from Amino Acid Sequences", pp. 3824–3828, see entire document.

Pediatr. Infect. Dis. J., 9:333–339, 1990, Stephen J. Barenkamp and Frank F. Bodor, Development of Serum Bacterial Activity Following Nontypable *Haemophilus influenzae* Acute Otitis Media.

Shakin R.D. et al. Mucosal Immunization with filametous hemagglutinin protects against *Bordetella pertussis* respiratory Infection, Infect. Immun. 60: 1482–1488, 1992.

Giebink G.S. et al. Pneumococcal Capsular Polysaccharide — meningoccocal outer membrane protein complex conjugate vaccines: Immunogenicity and efficacy in experimental pnuemococcal otitis media. J. Infect. Dis. 167:347–355, 1993.

Selected Abstracts from 1993 Interscience Conference on Antimicrobial Agents and Chemotherapy (Annual American Society for Microbiology ICAAC Meeting) in New OrleansO.

Green B.A. et al., Evaluation of mixtures of purified *Haemophilus Influenzae* outer membrance proteins in the chinchilla otitis media model. Infect. Immun. 61: 1950–1957, 1993.

Murphy, T.F. et al., Somatic Antigens of *Haemophilus influenzae* as vaccine components. Pedia. Infect. Dis. J. 8:S66–S68, 1989.

Consensus. Pediatr. Infect. Dis. J.8: S94–S97, 1989.

Makela et al. Pneumococcal Vaccine and Otitis Media, Lancet 2: 547–551, 1990.

Giebink et al. J. Infect. Dis. 140:716–723, 1979.

Giebink, Rev. Infect. Dis. 3:342–352, 1981.

Van Regenmortel, M.H.V., Immunology Today 10(8): 266–272, 1989.

Dick, W.E. et al., Microbiol. Immunol. 10: 48–114, 1989.

Roitt, I.M. et al., Immunology, C.V. Mosby Co. St. Louis, Gower Medical Publishing, London, 1989, pp. 8.3–8.4, 1985.

Boslego, J.W., et al. Vaccine 9: 154–162, Mar. 1991.

Beachey J. Infect. Dis. 143:325–345, 1981.

Barenkamp S.J., St Geme JW III. Genes encoding high molecular weight adhesion proteins of nontypable *Haemophilis influenzae* are part of gene clusters. Infect Immun 62:3320–3328, 1994.

Brunham, R.C., F.A. Plummer, and R.S. Stephens. 1993. Bacterial antigenic variation, host immune response, and pathogen–host coevolution. Infect. Immun. 61:2273–2276.

Green, B.A., T. Quinn–Dey, and G.W. Zlotnick. 1987. Biologic activities of antibody to peptidoglycan–associated lipoprotein of *Haemophilus influenzae* against multiple clinical isolates of *H. influenzae* type b. Infect. Immun. 55:2878–2883.

Green, B.A., B.J. Metcalf, T. Quinn Dey, D.H. Kirkley, S.A. Quataert, and R.A. Deich, 1990. A recombinant non–fatty acylated form of the Hi–PAL (P6) protein of *Haemophilus influenzae* elicits biologically active antibody against both nontypeable and type b.*H. influenzae*. Infect. Immun. 58:3272–3278.

Gnehm, H.E., S.I. Pelton, S. Galati, and P.A. Rice. 1985. Characterization of antigens from nontypable *Haemophilus influenzae* recognized by human bactercidal antibodies: Role of Haemophilus outer membrance proteins. J. Clin. Invest. 75:1645–1658.

Groeneveld, K., L. van Alphen, C, Voorter, P.P. Eijk, H.M. Jansen, and H.C. Zanen. 1989. Antigenic drift of *Haemophilus influenzae* in patients with chronic obstructive pulmonary disease. Infect. Immunol. 57:3038–3044.

Groeneveld, K., L. van Alphen, P.P. Eijk, H.M. Jansen, and H.C. Zanen. 1988. Changes in outer membrane proteins of nontypable *Haemophilus influenzae* in patients with chronic obstructive pulmonary disease. J. Infect. Dis. 1 58:360–365.

Goding, J.W. 1986. Monoclonal antibodies: Principles and practice, p. 59–141. Academic Press Limited, London England.

Hansen, E.J., D.A. Hart, J.L. McGehee, and G.B. Toews. 1988. Immune enhancement of pulmonary clearance of nontypable *Haemophilus influenzae*. Infect. Immun. 56:182–190.

Karasic, R.B., C.E. Trumpp, H. Gnehm, P.A. Rice, and S.I. Pelton. 1985. Modification of otitis media in chinchillas rechallenged with nontypable *Haemophilus influenzae* and serologic response to outer membrane antigens. J. Infect. Dis. 151:273–279.

Kilian, M. 1985. Haemophilus, p. 387–393. In E.H. Lennette, A. Balows, W.J. Hausler, Jr., and H.J. Shadomy (ed.), Manual of clinical microbiology, 4th ed. American Society for Microbiology, Washington, D.C.

Kuklinska, D., and M. Kilian. 1984 Relative proportions of Haemophilus species in the throat of healthy children and adults. Eur. J. Clin. Microbiol. 3:249–252.

Murphy, T.F., L.C. Bartos, P.A. Rice, M.B. Nelson, K.C. Dudas, and M.A. Apicelia. 1986. Identification of a 16,600 dalton outer membrane protein of nontypable *Haemophilus influenzae* as a target for human serum bactericidal antibody. J. Clin. Invest. 78:1020–1027.

Murphy, T.F., and M.A. Apicelia, 1987. Nontypable *Haemophilus influenzae:* A review of clinical aspects, surface antigens, and the human immune response to infection. Rev. Infect. Dis. 9:1–15.

Murphy, T.F., and L.C. Bartos. 1988. Purification and analysis with monoclonal antibodies of P2, the major outer membrane protein of nontypable *Haemophilus influenzae*. Infect. Immun. 56:1084–1089.

Murphy, T.F., and L.C. Bartos. 1988. Human bactericidal antibody response to outer membrane protein P2 of nontypable *Haemophilus influenzae*. Infect. Immun. 56:2673–2679.

Rabinovich, N.R., P. McInnes, D.L. Klein, and B.F. Hall. 1994. Vaccine technologies: View to the future. Science 265:1401–1404.

St. Geme, J.W. III, S. Falkow, and S.J. Barenkamp. 1993. High–molecular–weight proteins of nontypable *Haemophilus influenzae* mediate attachment to human epithelial cells. Proc. Natl . Acad. Sci. USA 90:2875–2879.

Tabor, S., and C.C. Richardson. 1985. A bacteriophage T7 RNA polymerase/promoter system for controlled exclusive expression of specific genes. Proc. Natl. Acad. Sci. USA 82:1074–1078.

Wallace, R.J., Jr., D.M. Musher, E.J. Septimus, J.E. McGowan, Jr., F.J. Quinones, K. Wiss, P.H. Vance, and P.A. Trier. 1981. *Haemophilus influenzae* infection in adults: characterization of strains by serotypes, biotypes, and beta-–lactamase production. J. Infect. Dis. 144:101–106.

Yamanaka, N., and H. Faden. 1993. Antibody response to outer membrane proteins of nontypeable *Haemophilus influenzae* in otis–prone children. J. Pediatr. 122:212–218.

Erwin et al Can. Journ.of Microbiology 34: 723–729, 1988.

Thomas et al Infection & Immunity 58: 1909–1913, 1990.

Barenkamp, Pediatric Research vol. 29, 167A, Abstract 985, 1991.

Barenkamp, Abstract 983, Pediatric Research vol.27.

Young et al, PNAS 80: 1194–1198, 1983.

Houghten et al. Vaccine 86, pp. 21–25.

Abstracts of the 31st Inter science Conferende on Antimicrobial Agents and Chemotherapy, vol.31, Oct. 1991, p. 286 Stem/phen J. Barenkamp Abstract No. 1126.

Thomas et al. Infect & Immun. Jun. 1990. 58(6): 1909–1913.

Barenkanp et al. Apr. 1992. Infect & Immun. 60(4) : 1302–1313.

Barenkanp. Ped. Res. Apr. 29–May 2, 1991, 29(4 pt2.) Abstract 985.

Barenkanp. Ped. Res. May 1990. 27(4 Pt 2). Abstract 983.

*Primary Examiner*—James C. Housel
*Assistant Examiner*—Jennifer Shaver
*Attorney, Agent, or Firm*—Shoemaker and Mattare, Ltd

[57] ABSTRACT

High molecular weight surface proteins of non-typeable *Haemophilus influenzae* which exhibit immunogenic properties and genes encoding the same are described. Specifically, genes coding for two immunodominant high molecular weight proteins, HMW1 and HMW2, have been cloned, expressed and sequenced, while genes coding for high molecular proteins HMW3 and HMW4 have also been cloned, expressed and sequenced.

4 Claims, 81 Drawing Sheets

FIG. 1A. DNA SEQUENCE OF HIGH MOLECULAR WEIGHT PROTEIN I (HMW1)

```
  1  ACAGCGTTCT CTTAATACTA GTACAAACCC ACAATAAAAT ATGACAAACA
 51  ACAATTACAA CACCTTTTTT GCAGTCTATA TGCAAATATT TTAAAAAATA
101  GTATAAATCC GCCATATAAA ATGGTATAAT CTTTCATCTT TCATCTTTCA
151  TCTTTCATCT TTCATCTTTC ATCTTTCATC TTTCATCTTT CATCTTTCAT
201  CTTTCATCTT TCATCTTTCA TCTTTCATCT TTCATCTTTC ACATGCCCTG
251  ATGAACCGAG GGAAGGGAGG GAGGGGCAAG AATGAAGAGG GAGCTGAACG
301  AACGCAAATG ATAAAGTAAT TTAATTGTTC AACTAACCTT AGGAGAAAAT
351  ATGAACAAGC TATATCGTCT CAAATTCAGC AAACGCCTGA ATGCTTTGGT
401  TGCTGTGTCT GAATTGGCAC GGGGTTGTGA CCATTCCACA GAAAAAGGCA
451  GCGAAAAACC TGCTCGCATG AAAGTGCGTC ACTTAGCGTT AAAGCCACTT
501  TCCGCTATGT TACTATCTTT AGGTGTAACA TCTATTCCAC AATCTGTTTT
551  AGCAAGCGGC TTACAAGGAA TGGATGTAGT ACACGGCACA GCCACTATGC
601  AAGTAGATGG TAATAAAACC ATTATCCGCA ACAGTGTTGA CGATATCATT
651  AATTGGAAAC AATTTAACAT CGACCAAAAT GAAATGGTGC AGTTTTTACA
701  AGAAAACAAC AACTCCGCCG TATTCAACCG TGTTACATCT AACCAAATCT
```

FIG. 1B.

```
 751  CCCAATTAAA AGGGATTTTA GATTCTAACG GACAAGTCTT TTTAATCAAC
 801  CCAAATGGTA TCACAATAGG TAAAGACGCA ATTATTAACA CTAATGGCTT
 851  TACGGCTTCT ACGCTAGACA TTTCTAACGA AAACATCAAG GCGCGTAATT
 901  TCACCTTCGA GCAAACCAAA GATAAAGCGC TCGCTGAAAT TGTGAATCAC
 951  GGTTTAATTA CTGTCGGTAA AGACGGCAGT GTAAATCTTA TTGGTGGCAA
1001  AGTGAAAAAC GAGGGTGTGA TTAGCGTAAA TGGTGGCAGC ATTTCTTTAC
1051  TCGCAGGGCA AAAAATCACC ATCAGCGATA TAATAAACCC AACCATTACT
1101  TACAGCATTG CCGCGCCTGA AAATGAAGCG GTCAATCTGG GCGATATTTT
1151  TGCCAAAGGC GGTAACATTA ATGTCCGTGC TGCCACTATT CGAAACCAAG
1201  GTAAACTTTC TGCTGATTCT GTAAGCAAAG ATAAAGCGG  CAATATTGTT
1251  CTTTCCGCCA AAGAGGGTGA AGCGGAAATT GGCGGTGTAA TTTCCGCTCA
1301  AAATCAGCAA GCTAAAGGCG GCAAGCTGAT GATTACAGGC GATAAAGTCA
1351  CATTAAAAAC AGGTGCAGTT ATCGACCTTT CAGGTAAAGA AGGGGGAGAA
1401  ACTTACCTTG GCGGTGACGA GCGCGGGCGAA GGTAAAAAGG GCATTCAATT
1451  AGCAAAGAAA ACCTCTTTAG AAAAAGGCTC AACCATCAAT GTATCAGGCA
1501  AAGAAAAAGG CGGACGCGCT ATTGTGTGGG GCGATATTGC GTTAATTGAC
```

FIG. 1C.

```
1551  GGCAATATTA ACGCTCAAGG TAGTGGTGAT ATCGCTAAAA CCGGTGGTTT
1601  TGTGGAGACG TCGGGGCATG ATTTATTCAT CAAAGACAAT GCAATTGTTG
1651  ACGCCAAAGA GTGGTTGTTA GACCCGGATA ATGTATCTAT TAATGCAGAA
1701  ACAGCAGGAC GCAGCAATAC TTCAGAAGAC GATGAATACA CGGGATCCGG
1751  GAATAGTGCC AGCACCCCAA AACGAAAACAA AGAAAAGACA ACATTAACAA
1801  ACACAACTCT TGAGAGTATA CTAAAAAAAG GTACCTTTGT TAACATCACT
1851  GCTAATCAAC GCATCTATGT CAATAGCTCC ATTAATTTAT CCAATGGCAG
1901  CTTAACTCTT TGGAGTGAGG GTCGGAGCGG TGGCGGCGTT GAGATTAACA
1951  ACGATATTAC CACCGGTGAT GATACCAGAG GTGCAAACTT AACAATTTAC
2001  TCAGGCGGCT GGGTTGATGT TCATAAAAAT ATCTCACTCG GGGCGCAAGG
2051  TAACATAAAC ATTACAGCTA AACAAGATAT CGCCTTTGAG AAAGGAAGCA
2101  ACCAAGTCAT TACAGGTCAA GGGACTATTA CCTCAGGCAA TCAAAAAGGT
2151  TTTAGATTTA ATAATGTCTC TCTAAACGGC ACTGGCAGCG GACTGCAATT
2201  CACCACTAAA AGAACCAATA AATACGCTAT CACAAATAAA TTTGAAGGGA
2251  CTTTAAATAT TTCAGGGAAA GTGAACATCT CAATGGTTTT ACCTAAAAAT
2301  GAAAGTGGAT ATGATAAATT CAAAGGACGC ACTTACTGGA ATTTAACCTC
```

FIG. 1D.

```
2351  CTTAAATGTT TCCGAGAGTG GCGAGTTTAA CCTCACTATT GACTCCAGAG
2401  GAAGCGATAG TGCAGGCACA CTTACCCAGC CTTATAATTT AAACGGTATA
2451  TCATTCAACA AAGACACTAC CTTTAATGTT GAACGAAATG CAAGAGTCAA
2501  CTTTGACATC AAGGCACCAA TAGGGATAAA TAAGTATTCT AGTTTGAATT
2551  ACGCATCATT TAATGGAAAC ATTTCAGTTT CGGGAGGGGG GAGTGTTGAT
2601  TTCACACTTC TCGCCTCATC CTCTAACGTC CAAACCCCCG GTGTAGTTAT
2651  AAATTCTAAA TACTTTAATG TTTCAACAGG GTCAAGTTTA AGATTAAAA
2701  CTTCAGGCTC AACAAAAACT GGCTTCTCAA TAGAGAAAGA TTTAACTTTA
2751  AATGCCACCG GAGGCAACAT AACACTTTTG CAAGTTGAAG GCACCGATGG
2801  AATGATTGGT AAAGGCATTG TAGCCAAAAA AAACATAACC TTTGAAGGAG
2851  GTAACATCAC CTTTGGCTCC AGGAAAGCCG TAACAGAAAT CGAAGGCAAT
2901  GTTACTATCA ATAACAACGC TAACGTCACT CTTATCGGTT CGGATTTTGA
2951  CAACCATCAA AAACCTTTAA CTATTAAAAA AGATGTCATC ATTAATAGCG
3001  GCAACCTTAC CGCTGGAGGC AATATTGTCA ATATAGCCGG AAATCTTACC
3051  GTTGAAAGTA ACGCTAATTT CAAAGCTATC ACAAATTTCA CTTTTAATGT
3101  AGGCGGCTTG TTTGACAACA AAGGCAATTC AAATATTTCC ATTGCCAAAG
3151  GAGGGGCTCG CTTTAAAGAC ATTGATAATT CCAAGAATTT AAGCATCACC
```

FIG. 1E.

```
3201 ACCAACTCCA GCTCCACTTA CCGCACTATT ATAAGCGGCA ATATAACCAA
3251 TAAAAACGGT GATTTAAATA TTACGAACGA AGGTAGTGAT ACTGAAATGC
3301 AAATTGGCGG CGATGTCTCG CAAAAAGAAG GTAATCTCAC GATTCTTCT
3351 GACAAAATCA ATATTACCAA ACAGATAACA ATCAAGGCAG GTGTTGATGG
3401 GGAGAATTCC GATTCAGACG CGACAAACAA TGCCAATCTA ACCATTAAAA
3451 CCAAAGAATT GAAATTAACG CAAGACCTAA ATATTTCAGG TTTCAATAAA
3501 GCAGAGATTA CAGCTAAAGA TGGTAGTGAT TTAACTATTG GTAACACCAA
3551 TAGTGCTGAT GGTACTAATG CCAAAAAAGT AACCTTTAAC CAGGTTAAAG
3601 ATTCAAAAAT CTCTGCTGAC GGTCACAAGG TGACACTACA CAGCAAAGTG
3651 GAAACATCCG GTAGTAATAA CAACACTGAA GATAGCAGTG ACAATAATGC
3701 CGGCTTAACT ATCGATGCAA AAAATGTAAC AGTAAACAAC AATATTACTT
3751 CTCACAAAGC AGTGAGCATC TCTGCGACAA GTGGAGAAAT TACCACTAAA
3801 ACAGGTACAA CCATTAACGC AACCACTGGT AACGTGGAGA TAACCGCTCA
3851 AACAGGTAGT ATCCTAGGTG GAATTGAGTC CAGCTCTGGC TCTGTAACAC
3901 TTACTGCAAC CGAGGGCGCT CTTGCTGTAA GCAATATTTC GGGCAACACC
3951 GTTACTGTTA CTGCAAATAG CGGTGCATTA ACCACTTTGG CAGGCTCTAC
```

FIG. 1F.

```
4001 AATTAAAGGA ACCGAGAGTG TAACCACTTC AAGTCAATCA GGCGATATCG
4051 GCGGTACGAT TTCTGGTGGC ACAGTAGAGG TTAAAGCAAC CGAAAGTTTA
4101 ACCACTCAAT CCAATTCAAA AATTAAAGCA ACAACAGGCG AGGCTAACGT
4151 AACAAGTGCA ACAGGTACAA TTGGTGGTAC GATTTCCGGT AATACGGTAA
4201 ATGTTACGGC AAACGCTGGC GATTTAACAG TTGGGAATGG CGCAGAAATT
4251 AATGCGACAG AAGGAGCTGC AACCTTAACT ACATCATCGG GCAAATTAAC
4301 TACCGAAGCT AGTTCACACA TTACTTCAGC CAAGGGTCAG GTAAATCTTT
4351 CAGCTCAGGA TGGTAGCGTT GCAGGAAGTA TTAATGCCGC CAATGTGACA
4401 CTAAATACTA CAGGCACTTT AACTACCGTG AAGGGTTCAA ACATTAATGC
4451 AACCAGCGGT ACCTTGGTTA TTAACGCAAA AGACGCTGAG CTAAATGGCG
4501 CAGCATTGGG TAACCACACA GTGGTAAATG CAACCAACGC AAATGGCTCC
4551 GGCAGCGTAA TCGCGACAAC CTCAAGCAGA GTGAACATCA CTGGGGATTT
4601 AATCACAATA AATGGATTAA ATATCATTTC AAAAAACGGT ATAAACACCG
4651 TACTGTTAAA AGGCGTTAAA ATTGATGTGA AATACATTCA ACCGGGTATA
4701 GCAAGCGTAG ATGAAGTAAT TGAAGCGAAA CGCATCCCTG AGAAGGTAAA
4751 AGATTTATCT GATGAAGAAA GAGAAGCGTT AGCTAAACTT GGAGTAAGTG
4801 CTGTACGTTT TATTGAGCCA AATAATACAA TTACAGTCGA TACACAAAT
```

FIG. 1G.

```
4851 GAATTTGCAA CCAGACCATT AAGTCGAATA GTGATTTCTG AAGGCAGGGC
4901 GTGTTTCTCA AACAGTGATG GCGCGACGGT GTGCGTTAAT ATCGCTGATA
4951 ACGGGCGGTA GCGGTCAGTA ATTGACAAGG TAGATTTCAT CCTGCAATGA
5001 AGTCATTTTA TTTTCGTATT ATTACTGTG TGGGTTAAAG TTCAGTACGG
5051 GCTTTACCCA TCTTGTAAAA AATTACGGAG AATACAATAA AGTATTTTTA
5101 ACAGGTATT ATTATG
```

FIG. 2A. AMINO ACID SEQUENCE OF HIGH MOLECULAR WEIGHT PROTEIN I

```
  1  MNKIYRLKFS KRLNALVAVS ELARGCDHST EKGSEKPARM KVRHLALKPL
 51  SAMLLSLGVT SIPQSVLASG LQGMDVVHGT ATMQVDGNKT IIRNSVDAII
101  NWKQFNIDQN EMVQFLQENN NSAVFNRVTS NQISQLKGIL DSNGQVFLIN
151  PNGITIGKDA IINTNGFTAS TLDISNENIK ARNFTFEQTK DKALAEIVNH
201  GLITVGKDGS VNLIGGKVKN EGVISVNGGS ISLLAGQKIT ISDIINPTIT
251  YSIAAPENEA VNLGDIFAKG GNINVRAATI RNQGKLSADS VSKDKSGNIV
301  LSAKEGEAEI GGVISAQNQQ AKGGKLMITG DKVTLKTGAV IDLSGKEGGE
351  TYLGGDERGE GKNGIQLAKK TSLEKGSTIN VSGKEKGGRA IVWGDIALID
401  GNINAQGSGD IAKTGGFVET SGHDLFIKDN AIVDAKEWLL DFDNVSINAE
451  TAGRSNTSED DEYTGSGNSA STPKRNKEKT TLTNTTLESI LKKGTFVNIT
501  ANQRIYVNSS INLSNGSLTL WSEGRSGGGV EINNDITTGD DTRGANLTIY
551  SGGWVDVHKN ISLGAQNIN  ITAKQDIAFE KGSNQVITGQ GTITSGNQKG
601  FRFNNVSLNG TGSGLQFTTK RTNKYAITNK FEGTLNISGK VNISMVLPKN
651  ESGYDKFKGR TYWNLTSLNV SESGEFNLTI DSRGSDSAGT LTQPYNLNGI
701  SFNKDTTFNV ERNARVNFDI KAPIGINKYS SLNYASFNGN ISVSGGGSVD
```

FIG. 2B.

```
 751  FTLLASSSNV  QTPGVVINSK  YFNVSTGSSL  RFKTSGSTKT  GFSIEKDLTL
 801  NATGGNITLL  QVEGTDGMIG  KGIVAKKNIT  FEGGNITFGS  RKAVTEIEGN
 851  VTINNNANVT  LIGSDFDNHQ  KPLTIKKDVI  INSGNLTAGG  NIVNIAGNLT
 901  VESNANFKAI  TNFTFNVGGL  FDNKGNSNIS  IAKGGARFKD  IDNSKNLSIT
 951  TNSSSTYRTI  ISGNITNKNG  DLNITNEGSD  TEMQIGGDVS  QKEGNLTISS
1001  DKINITKQIT  IKAGVDGENS  DSDATNNANL  TIKTKELKLT  QDLNISGFNK
1051  AEITAKDGSD  LTIGNTNSAD  GTNAKKVTFN  QVKDSKISAD  GHKVTLHSKV
1101  ETSGSNNNTE  DSSDNNAGLT  IDAKNVTVNN  NITSHKAVSI  SATSGEITTK
1151  TGTTINATTG  NVEITAQTGS  ILGGIESSSG  SVTLTATEGA  LAVSNISGNT
1201  VTVTANSGAL  TTLAGSTIKG  TESVTTSSQS  GDIGGTISGG  TVEVKATESL
1251  TTQSNSKIKA  TGTIGGTISG  SSHITSAKGQ  NTVNVTANAG  DLTVGNGAEI
1301  NATEGAATLT  TSSGKLTTEA  SSHITSAKGQ  VNLSAQDGSV  AGSINAANVT
1351  LNTTGTLTTV  KGSNINATSG  TLVINAKDAE  LNGAALGNHT  VVNATNANGS
1401  GSVIATTSSR  VNITGDLITI  NGLNIISKNG  INTVLLKGVK  IDVKYIQPGI
1451  ASVDEVIEAK  RILEKVKDLS  DEEREALAKL  GVSAVRFIEP  NNTITVDTQN
1501  EFATRPLSRI  VISEGRACFS  NSDGATVCVN  IADNGR
```

FIG. 3A. AMINO ACID SEQUENCE OF HIGH MOLECULAR WEIGHT PROTEIN II (HMW2)

```
  1  TAAATATACA AGATAATAAA AATAAATCAA GATTTTTGTG ATGACAAACA
 51  ACAATTACAA CACCTTTTTT GCAGTCTATA TGCAAATATT TTAAAAAAAT
101  AGTATAAATC CGCCATATAA AATGGTATAA TCTTTCATCT TTCATCTTTA
151  ATCTTTCATC TTTCATCTTT CATCTTTCAT CTTTCATCTT TCATCTTTCA
201  TCTTTCATCT TTCATCTTTC ATCTTTCATC TTTCATCTTT CACATGAAAT
251  GATGAACCGA GGGAAGGGAG GGAGGGGCAA GAATGAAGAG GGAGCTGAAC
301  GAACGCAAAT GATAAAGTAA TTTAATTGTT CAACTAACCT TAGGAGAAAA
351  TATGAACAAG ATATATCGTC TCAAATTCAG CAAACGCCTG AATGCTTTGG
401  TTGCTGTGTC TGAATTGGCA CGGGGTTGTG ACCATTCCAC AGAAAAAGGC
451  TTCCGCTATG TTACTATCTT TAGGTGTAAC CACTTAGCGT TAAAGCCACT
501  TTCCGCTATG TTACTATCTT TAGGTGTAAC ATCTATTCCA CAATCTGTTT
551  TAGCAAGCGG CTTACAAGGA ATGGATGTAG TACACGGCAC AGCCACTATG
601  CAAGTAGATG GTAATAAAAC CATTATCCGC AACAGTGTTG ACGCTATCAT
651  TAATTGGAAA CAATTTAACA TCGACCAAAA TGAAATGGTG CAGTTTTTAC
701  AAGAAAACAA CAACTCCGCC GTATTCAACC GTGTTACATC TAACCAAATC
```

FIG. 3B.

```
 751 TCCCAATTAA AAGGGATTTT AGATTCTAAC GGACAAGTCT TTTTAATCAA
 801 CCCAAATGGT ATCACAATAG GTAAAGACGC AATTATTAAC ACTAATGGCT
 851 TTACGGCTTC TACGCTAGAC ATTTCTAACG AAAACATCAA GGCGCGTAAT
 901 TTCACCTTCG AGCAAACCAA AGATAAAGCG CTCGCTGAAA TTGTGAATCA
 951 CGGTTTAATT ACTGTCGGTA AAGACGGCAG TGTAAATCTT ATTGGTGGCA
1001 AAGTGAAAAA CGAGGGTGTG ATTAGCGTAA ATGGTGGCAG CATTTCTTTA
1051 CTCGCAGGGC AAAAAATCAC CATCAGCGAT ATAATAAACC CAACCATTAC
1101 TTACAGCATT GCCGCGCCTG AAAATGAAGC GGTCAATCTG GGCGATATTT
1151 TTGCCAAAGG CGGTAACATT AATGTCCGTG CTGCCACTAT TCGAAACCAA
1201 GGTAAACTTT CTGCTGATTC TGTAAGCAAA GATAAAAGCG GCAATATTGT
1251 TCTTTCCGCC AAAGAGGGTG AAGCGGAAAT TGGCGGTGTA ATTTCCGCTC
1301 AAAATCAGCA AGCTAAAGGC GGCAAGCTGA TGATTACAGG CGATAAAGTC
1351 ACATTAAAAA CAGGTGCAGT TATCGACCTT TCAGGTAAAG AAGGGGGAGA
1401 AACTTACCTT GGCGGTGACG AGCGCGGCGA AGGTAAAAAC GGCATTCAAT
1451 TAGCAAAGAA AACCTCTTTA GAAAAAGGCT CAACCATCAA TGTATCAGGC
1501 AAAGAAAAAG GCGGACGCGC TATTGTGTGG GGCGATATTG CGTTAATTGA
```

FIG. 3C.

```
1551  CGGCAATATT  AACGCTCAAG  GTAGTGGTGA  TATCGCTAAA  ACCGGTGGTT
1601  TTGTGGAGAC  ATCGGGGCAT  TATTTATCCA  TTGACAGCAA  TGCAATTGTT
1651  AAAACAAAAG  AGTGGTTGCT  AGACCCTGAT  GATGTAACAA  TTGAAGCCGA
1701  AGACCCCCTT  CGCAATAATA  CCGGTATAAA  TGATGAATTC  CCAACAGGCA
1751  CCGGTGAAGC  AAGCGACCCT  AAAAAAAATA  GCGAACTCAA  AACAACGCTA
1801  ACCAATACAA  CTATTTCAAATTATCTGAAA  AACGCCTGGA  CAATGAATAT
1851  AACGGCATCA  AGAAAACTTA  CCGTTAATAG  CTCAATCAAC  ATCGGAAGCA
1901  ACTCCCACTT  AATTCTCCAT  AGTAAAGGTC  AGCGTGGCGG  AGGCGTTCAG
1951  ATTGATGGAG  ATATTACTTC  TAAAGGCGGA  AATTTAACCA  TTTATTCTGG
2001  CGGATGGGTT  GATGTTCATA  AAAATATTAC  GCTTGATCAG  GGTTTTTTAA
2051  ATATTACCGC  CGCTTCCGTA  GCTTTTTGAAG  GTGGAAATAA  CAAAGCACGC
2101  GACGCGGGCAA  ATGCTAAAAT  TGTCGCCCAG  GGCACTGTAA  CCATTACAGG
2151  AGAGGGAAAA  GATTTCAGGG  CTAACAACGT  ATCTTTAAAC  GGAACGGGTA
2201  AAGGTCTGAA  TATCATTTCA  TCAGTGAATA  ATTTAACCCA  CAATCTTAGT
2251  GGCACAATTA  ACATATCTGG  GAATATAACA  ATTAACCAAA  CTACGAGAAA
2301  GAACACCTCG  TATTGGCAAA  CCAGCCATGA  TTCGCACTGG  AACGTCAGTG
2351  CTCTTAATCT  AGAGACAGGC  GCAAATTTTA  CCTTTATTAA  ATACATTTCA
```

FIG. 3D.

```
2401 AGCAATAGCA AAGGCTTAAC AACACAGTAT AGAAGCTCTG CAGGGGTGAA
2451 TTTTAACGGC GTAAATGGCA ACATGTCATT CAATCTCAAA GAAGGAGCGA
2501 AAGTTAATTT CAAATTAAAA CCAAACGAGA ACATGAACAC AAGCAAACCT
2551 TTACCAATTC GGTTTTTAGC CAATATCACA GCCACTGGTG GGGGCTCTGT
2601 TTTTTTTGAT ATATATGCCA ACCATTCTGG CAGAGGGGCT GAGTTAAAAA
2651 TGAGTGAAAT TAATATCTCT AACGGCGCTA ATTTTACCTT AAATTCCCAT
2701 GTTCGCGGCG ATGACGCTTT TAAAATCAAC AAAGACTTAA CCATAAATGC
2751 AACCAATTCA AATTTCAGCC TCAGACAGAC GAAAGATGAT TTTTATGACG
2801 GGTACGCACG CAATGCCATC AATTCAACCT ACAACATATC CATTCTGGGC
2851 GGTAATGTCA CCCTTGGTGG ACAAAACTCA AGCAGCAGCA TTACGGGGAA
2901 TATTACTATC GAGAAAGCAG CAAATGTTAC GCTAGAAGCC AATAACGCCC
2951 CTAATCAGCA AAACATAAGG GATAGAGTTA TAAAACTTGG CAGCTTGCTC
3001 GTTAATGGGA GTTTAAGTTT AACTGGCGAA AATGCAGATA TTAAAGGCAA
3051 TCTCACTATT TCAGAAAGCG CCACTTTTAA AGGAAAGACT AGAGATACCC
3101 TAAATATCAC CGGCAATTTT ACCAATAATG GCACTGCCGA AATTAATATA
3151 ACACAAGGAG TGGTAAAACT TGGCAATGTT ACCAATGATG GTGATTTAAA
```

FIG. 3E.

```
3201 CATTACCACT CACGCTAAAC GCAACCAAAG AAGCATCATC GGCGGAGATA
3251 TAATCAACAA AAAAGGAAGC TTAAATATTA CAGACAGTAA TAATGATGCT
3301 GAAATCCAAA TTGGCGGCAA TATCTCGCAA AAAGAAGGCA ACCTCACGAT
3351 TTCTTCCGAT AAAATTAATA TCACCAAACA GATAACAATC AAAAAGGGTA
3401 TTGATGGAGA GGACTCTAGT TCAGATGCGA CAAGTAATGC CAACCTAACT
3451 ATTAAAACCA AAGAATTGAA ATTGACAGAA GACCTAAGTA TTTCAGGTTT
3501 CAATAAAGCA GAGATTACAG CCAAAGATGG TAGAGATTTA ACTATTGGCA
3551 ACAGTAATGA CGGTAACAGC GGTGCCGAAG CCAAAACAGT AACTTTTAAC
3601 AATGTTAAAG ATTCAAAAAT CTCTGCTGAC GGTCACAATG TGACACTAAA
3651 TAGCAAAGTG AAAACATCTA GCAGCAATGG CGGACGTGAA AGCAATAGCG
3701 ACAACGATAC CGGCTTAACT ATTACTGCAA AAAATGTAGA AGTAAACAAA
3751 GATATTACTT CTCTCAAAAC AGTAAATATC ACCGCGTCGG AAAAGGTTAC
3801 CACCACAGCA GGCTCGACCA TTAACGCAAC AAATGGCAAA GCAAGTATTA
3851 CAACCAAAAC AGGTGATATC AGCGGTACGA TTTCCGGTAA CACGGTAAGT
3901 GTTAGCGCGA CTGGTGATTT AACCACTAAA TCCGCTCAA AAATTGAAGC
3951 GAAATCGGGT GAGGCTAAGT TAACAAGTGC AACAGGTACA ATTGGCGGTA
```

FIG. 3F.

```
4001 CAATTTCCGG TAATACGGTA AATGTTACGG CAAACGCTGG CGATTTAACA
4051 GTTGGGAATG GCGCAGAAAT TAATGCGACA GAAGGAGCTG CAACCTTAAC
4101 CGCAACAGGG AATACCTTGA CTACTGAAGC CGGTTCTAGC ATCACTTCAA
4151 CTAAGGGTCA GGTAGACCTC TTGGCTCAGA ATGGTAGCAT CGCAGGAAGC
4201 ATTAATGCTG CTAATGTGAC ATTAAATACT ACAGGCACCT TAACCACCGT
4251 GGCAGGCTCG GATATTAAAG CAACCAGCGG CACCTTGGTT ATTAACGCAA
4301 AAGATGCTAA GCTAAATGGT GATGCATCAG GTGATAGTAC AGAAGTGAAT
4351 GCAGTCAACG CAAGCGGCTC TGGTAGTGTG ACTGCGGCAA CCTCAAGCAG
4401 TGTGAATATC ACTGGGGATT TAAACACAGT AAATGGGTTA AATATCATTT
4451 CGAAAGATGG TAGAAACACT GTGCGCTTAA GAGGCAAGGA AATTGAGGTG
4501 AAATATATCC AGCCAGTGT AGCAAGTGTA GAAGAAGTAA TTGAAGCGAA
4551 ACGCGTCCTT GAAAAAGTAA AAGATTTATC TGATGAAGAA AGAGAAACAT
4601 TAGCTAAACT TGGTGTAAGT GCTGTACGTT TTGTTGAGCC AAATAATACA
4651 ATTACAGTCA ATACACAAAA TGAATTTACA ACCAGACCGT CAAGTCAAGT
4701 GATAATTTCT GAAGGTAAGG CGTGTTTCTC AAGTGGTAAT GGCGCACGAG
4751 TATGTACCAA TGTTGCTGAC GATGGACAGC CGTAGTCAGT AATTGACAAG
4801 GTAGATTTCA TCCTGCAATG AAGTCATTTT ATTTTCGTAT TATTTACTGT
```

FIG. 3G.

```
4851  GTGGGTAAAA GTTCAGTACG GGCTTTACCC ATCTTGTAAA AAATTACGGA
4901  GAATACAATA AAGTATTTTT AACAGGTTAT TATTATG
```

FIG. 4A. AMINO ACID SEQUENCE OF HIGH MOLECULAR WEIGHT PROTEIN 2

```
  1  MNKIYRLKFS  KRLNALVAVS  ELARGCDHST  EKGSEKPARM  KVRHLALKPL
 51  SAMLLSLGVT  SIPQSVLASG  LQGMDVVHGT  ATMQVDGNKT  IIRNSVDAII
101  NWKQFNIDQN  EMVQFLQENN  NSAVFNRVTS  NQISQLKGIL  DSNGQVFLIN
151  PNGITIGKDA  IINTNGFTAS  TLDISNENIK  ARNFTFEQTK  DKALAEIVNH
201  GLITVGKDGS  VNLIGGKVKN  EGVISVNGGS  ISLLAGQKIT  ISDIINPTIT
251  YSIAAPENEA  VNLGDIFAKG  GNINVRAATI  RNQGKLSADS  VSKDKSGNIV
301  LSAKEGEAEI  GGVISAQNQQ  AKGGKLMITG  DKVTLKTGAV  IDLSGKEGGE
351  TYLGGDERGE  GKNGIQLAKK  TSLEKGSTIN  VSGKEKGGRA  IVWGDIALID
401  GNINAQGSGD  IAKTGGFVET  SGHDLFIKDN  AIVDAKEWLL  DFDNVSINAE
451  DPLRNNTGIN  DEFPTGTGEA  SDPKKNSELK  TTLTNTTISN  YLKNAWTMNI
501  TASRKLTVNS  SINIGSNSHL  ILHSKGQRGG  GVQIDGDITS  KGGNLTIYSG
551  GWVDVHKNIT  LDQGFLNITA  ASVAFEGGNN  KARDAANAKI  VAQGTVTITG
601  EGKDFRANNV  SLNGTGKGLN  IISSVNNLTH  NLSGTINISG  NITINQTTRK
651  NTSYWQTSHD  SHWNVSALNL  ETGANFTFIK  YISSNSKGLT  TQYRSSAGVN
701  FNGVNGNMSF  NLKEGAKVNF  KLKPNENMNT  SKPLPIRFLA  NITATGGGSV
```

FIG. 4B.

```
 751  FFDIYANHSG  RGAELKMSEI  NISNGANFTL  NSHVRGDDAF  KINKDLTINA
 801  TNSNFSLRQT  KDDFYDGYAR  NAINSTYNIS  ILGGNVTLGG  QNSSSSITGN
 851  ITIEKAANVT  LEANNAPNQQ  NIRDRVIKLG  SLLVNGSLSL  TGENADIKGN
 901  LTISESATFK  GKTRDTLNIT  GNFTNNGTAE  INITQGVVKL  GNVTNDGDLN
 951  ITTHAKRNQR  SIGGDIINK   KGSLNITDSN  NDAEIQIGGN  ISQKEGNLTI
1001  SSDKINITKQ  ITIKKGIDGE  DSSSDATSNA  NLTIKTKELK  LTEDLSISGF
1051  NKAEITAKDG  RDLTIGNSND  GNSGAEAKTV  TFNNVKDSKI  SADGHNVTLN
1101  SKVKTSSSNG  GRESNSDNDT  GLTITAKNVE  VNKDITSLKT  VNITASEKVT
1151  TTAGSTINAT  NGKASITTKT  GDISGTISGN  TVSVSATVDL  TTKSGSKIEA
1201  KSGEANVTSA  TGTIGGTISG  NTVNVTANAG  DLTVGNGAEI  NATEGAATLT
1251  ATGNTLTTEA  GSSITSTKGQ  VDLLAQNGSI  AGSINAANVT  LNTTGTLTTV
1301  AGSDIKATSG  TLVINAKDAK  LNGDASGDST  EVNAVNASGS  GSVTAATSSS
1351  VNITGDLNTV  NGLNIISKDG  RNTVRLRGKE  IEVKYIQPGV  ASVEEVIEAK
1401  RVLEKVKDLS  DEERETLAKL  GVSAVRFVEP  NNTITVNTQN  EFTTRPSSQV
1451  IISEGKACFS  SGNGARVCTN  VADDGQP
```

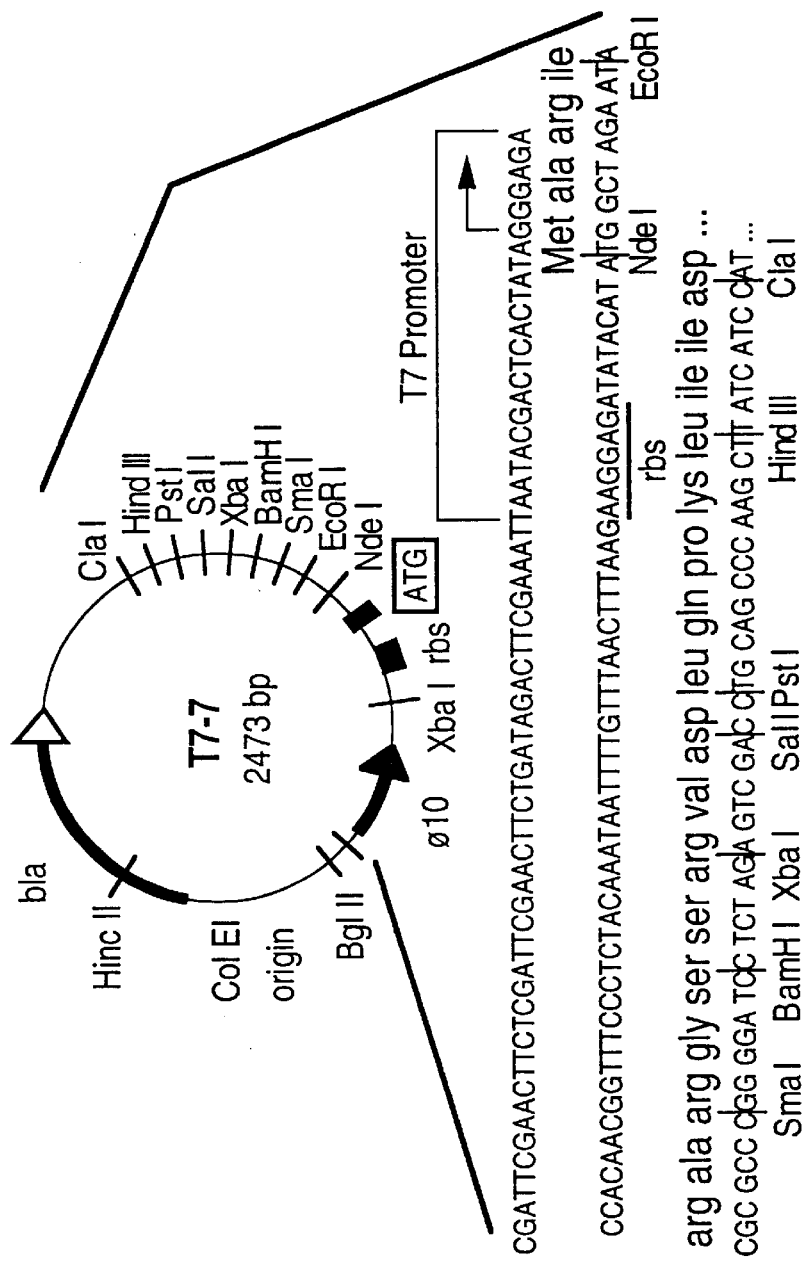

FIG. 5B.

(A) Partial restriction maps of representative HMW1 and HMW2 recombinant phage and of HMW1 plasmid subclones. The shaded boxes indicate the locations of the structural genes. In the recombinant phage, transcription proceeds from left to right for the HMW1 gene and from right to left for the HMW2 gene. The methods used for construction of the plasmids shown are described in the text. (B) Restriction map of the T7 expression vector pT7-7. This vector contains the T7 RNA polymerase promoter φ10, a ribosome - binding site (rbs), and the translational start site for the T7 gene 10 protein upstream from a multiple cloning site (37).

FIG. 6A.

```
  1  ACAGGCGTTCT CTTAATACTA GTACAAACCC ACAATAAAAT ATGACAAACA
 51  ACAATTACAA CACCTTTTTT GCAGTCTATA TGCAAATATT TTAAAAAATA
101  GTATAAATCC GCCATATAAA ATGGTATAAT CTTTCATCTT TCATCTTTCA
151  TCTTTCATCT TTCATCTTTC ATCTTTCATC TTTCATCTTT CATCTTTCAT
201  CTTTCATCTT TCATCTTTCA TCTTTCATCT TTCATCTTTC ACATGAAATG
251  ATGAACCGAG GGAAGGGAGG GAGGGGCAAG AATGAAGAGG GAGCTGAACG
301  AACGCAAATG ATAAAGTAAT TTAATTGTTC AACTAACCTT AGGAGAAAAT
351  ATGAACAAGA TATATCGTCT CAAATTCAGC AAACGCCTGA ATGCTTTGGT
401  TGCTGTGTCT GAATTGGCAC GGGGTTGTGA CCATTCCACA GAAAAAGGCA
451  GCGAAAAACC TGCTCGCATG AAAGTGCGTC ACTTAGCGTT AAAGCCACTT
501  TCCGCTATGT TACTATCTTT AGGTGTAACA TCTATTCCAC AATCTGTTTT
551  AGCAAGCGGC TTACAAGGAA TGGATGTAGT ACACGGCACA GCCACTATGC
601  AAGTAGATGG TAATAAAACC ATTATCCGCA ACAGTGTTGA CGCTATCATT
651  AATTGGAAAC AATTTAACAT CGACCAAAAT GAAATGGTGC AGTTTTTACA
701  AGAAAACAAC AACTCCGCCG TATTCAACCG TGTTACATCT AACCAAATCT
751  CCCAATTAAA AGGGATTTTA GATTCTAACG GACAAGTCTT TTTAATCAAC
```

FIG. 6B.

```
 801  CCAAATGGTA TCACAATAGG TAAAGACGCA ATTATTAACA CTAATGGCTT
 851  TACGGCTTCT ACGCTAGACA TTTCTAACGA AAACATCAAG GCGCGTAATT
 901  TCACCTTCGA GCAAACCAAA GATAAAGCGC TCGCTGAAAT TGTGAATCAC
 951  GGTTTAATTA CTGTCGGTAA AGACGGCAGT GTAAATCTTA TTGGTGGCAA
1001  AGTGAAAAAC GAGGGTGTGA TTAGCGTAAA TGGTGGCAGC ATTTCTTTAC
1051  TCGCAGGGCA AAAAATCACC ATCAGCGATA TAATAAACCC AACCATTACT
1101  TACAGCATTG CCGCGCCTGA AAATGAAGCG GTCAATCTGG GCGATATTTT
1151  TGCCAAAGGC GGTAACATTA ATGTCCGTGC TGCCACTATT CGAAACCAAG
1201  CTTTCCGCCA AAGAGGGTGA AGCGGAAATT GGCGGTGTAA TTTCCGCTCA
1251  AAATCAGCAA GCTAAAGGCG GCAAGCTGAT GATTACAGGC GATAAAGTCA
1301  CATTAAAAAC AGGTGCAGTT ATCGACCTTT CAGGTAAAGA AGGGGAGAA
1351  ACTTACCTTG GCGGTGACGA GCGCGGCGAA GGTAAAAACG GCATTCAATT
1401  AGCAAAGAAA ACCTCTTTAG AAAAAGGCTC AACCATCAAT GTATCAGGCA
1451  AAGAAAAAGG CGGACGCGCT ATTGTGTGGG GCGATATTGC GTTAATTGAC
1501  GGCAATATTA ACGCTCAAGG TAGTGGTGAT ATCGCTAAAA CCGGTGGTTT
1551  TGTGGAGACG TCGGGGCATG ATTTATTCAT CAAAGACAAT GCAATTGTTG
```

FIG. 6C.

```
1651  ACGCCAAAGA  GTGGTTGTTA  GACCCGGATA  ATGTATCTAT  TAATGCAGAA
1701  ACAGCAGGAC  GCAGCAATAC  TTCAGAAGAC  GATGAATACA  CGGGATCCGG
1751  GAATAGTGCC  AGCACCCCAA  AACGAAACAA  AGAAAAGACA  ACATTAACAA
1801  ACACAACTCT  TGAGAGTATA  CTAAAAAAAG  GTACCTTTGT  TAACATCACT
1851  GCTAATCAAC  GCATCTATGT  CAATAGCTCC  ATTAATTTAT  CCAATGGCAG
1901  CTTAACTCTT  TGGAGTGAGG  GTCGGAGCGG  TGGCGGCGTT  GAGATTAACA
1951  ACGATATTAC  CACCGGTGAT  GATACCAGAG  GTGCAAACTT  AACAATTAC
2001  TCAGGCGGCT  GGGTTGATGT  TCATAAAAAT  ATCTCACTCG  GGGCGCAAGG
2051  TAACATAAAC  ATTACAGCTA  AACAAGATAT  CGCCTTTGAG  AAAGGAAGCA
2101  ACCAAGTCAT  TACAGGTCAA  GGGACTATTA  CCTCAGGCAA  TCAAAAAGGT
2151  TTTAGATTTA  ATAATGTCTC  TCTAAACGGC  ACTGGCAGCG  GACTGCAATT
2201  CACCACTAAA  AGAACCAATA  AATACGCTAT  CACAAATAAA  TTTGAAGGGA
2251  CTTTAAATAT  TTCAGGGAAA  GTGAACATCT  CAATGGTTTT  ACCTAAAAAT
2301  GAAAGTGGAT  ATGATAAATT  CAAAGGACGC  ACTTACTGGA  ATTTAACCTC
2351  GAAAGTGGAT  ATGATAAATT  CAAAGGACGC  CCTCACTATT  GACTCCAGAG
2401  GAAGCGATAG  TGCAGGCACA  CTTACCCAGC  CTTATAATTT  AAACGGTATA
2451  TCATTCAACA  AAGACACTAC  CTTTAATGTT  GAACGAAATG  CAAGAGTCAA
```

FIG. 6D.

```
2501  CTTTGACATC  AAGGCACCAA  TAGGGATAAA  TAAGTATTCT  AGTTTGAATT
2551  ACGCATCATT  TAATGGAAAC  ATTTCAGTTT  CGGGAGGGGG  GAGTGTTGAT
2601  TTCACACTTC  TCGCCTCATC  CTCTAACGTC  CAAACCCCCG  GTGTAGTTAT
2651  AAATTCTAAA  TACTTTAATG  TTTCAACAGG  GTCAAGTTTA  AGATTAAAAA
2701  CTTCAGGCTC  AACAAAAACT  GGCTTCTCAA  TAGAGAAAGA  TTTAACTTTA
2751  AATGCCACCG  GAGGCAACAT  AACACTTTTG  CAAGTTGAAG  GCACCGATGG
2801  AATGATTGGT  AAAGGCATTG  TAGCCAAAAA  AAACATAACC  TTTGAAGGAG
2851  GTAAGATGAG  GTTGGCTCC   AGGAAAGCCG  TAACAGAAAT  CGAAGGCAAT
2901  GTTACTATCA  ATAACAACGC  TAACGTCACT  CTTATCGGTT  CGGATTTTGA
2951  CAACCATCAA  AAACCTTTAA  CTATTAAAAA  AGATGTCATC  ATTAATAGCG
3001  GCAACCTTAC  CGCTGGAGGC  AATATTGTCA  ATATAGCCGG  AAATCTTACC
3051  GTTGAAAGTA  ACGCTAATTC  CAAAGCTATC  ACAAATTTCA  CTTTTAATGT
3101  AGGCGGCTTG  TTTGACAACA  AAGGCAATTC  AAATATTTCC  ATTGCCAAAG
3151  GAGGGGCTCG  CTTTAAAGAC  ATTGATAATT  CCAAGAATTT  AAGCATCACC
3201  ACCAACTCCA  GCTCCACTTA  CCGCACTATT  ATAAGCGGCA  ATATAACCAA
3251  TAAAAACGGT  GATTTAAATA  TTACGAACGA  AGGTAGTGAT  ACTGAAATGC
```

FIG. 6E.

```
3301  AAATTGGCGG  CGATGTCTCG  CAAAAAGAAG  GTAATCTCAC  GATTTCTTCT
3351  GACAAAATCA  ATATTACCAA  ACAGATAACA  ATCAAGGCAG  GTGTTGATGG
3401  GGAGAATTCC  GATTCAGACG  CGACAAACAA  TGCCAATCTA  ACCATTAAAA
3451  CCAAAGAATT  GAAATTAACG  CAAGACCTAA  ATATTTCAGG  TTTCAATAAA
3501  GCAGAGATTA  CAGCTAAAGA  TGGTAGTGAT  TTAACTATTG  GTAACACCAA
3551  TAGTGCTGAT  GGTACTAATG  CCAAAAAAGT  AACCTTTAAC  CAGGTTAAAG
3601  ATTCAAAAAT  CTCTGCTGAC  GGTCACAAGG  TGACACTACA  CAGCAAAGTG
3651  GAAACATCCG  GTAGTAATAA  CAACACTGAA  GATAGCAGTG  ACAATAATGC
3701  CGGCTTAACT  ATCGATGCAA  AAAATGTAAC  AGTAAACAAC  AATATTACTT
3751  CTCACAAAGC  AGTGAGCATC  TCTGCGACAA  GTGGAGAAAT  TACCACTAAA
3801  ACAGGTACAA  CCATTAACGC  AACCACTGGT  AACGTGGAGA  TAACCGCTCA
3851  AACAGGTAGT  ATCCTAGGTG  GAATTGAGTC  CAGCTCTGGC  TCTGTAACAC
3901  TTACTGCAAC  CGAGGGCGCT  CTTGCTGTAA  GCAATATTTC  GGGCAACACC
3951  GTTACTGTTA  CTGCAAATAG  CGGTGCATTA  ACCACTTTGG  CAGGCTCTAC
4001  AATTAAAGGA  ACCGAGAGTG  TAACCACTTC  AAGTCAATCA  GGCGATATCG
4051  GCGGTACGAT  TTCTGGTGGC  ACAGTAGAGG  TTAAAGCAAC  CGAAAGTTTA
```

FIG. 6F.

```
4101 ACCACTCAAT CCAATTCAAA AATTAAAGCA ACAACAGGCG AGGCTAACGT
4151 AACAAGTGCA ACAGGTACAA TTGGTGGTAC GATTCCGGT AATACGGTAA
4201 ATGTTACGGC AAACGCTGGC GATTTAACAG TTGGGAATGG CGCAGAAATT
4251 AATGCGACAG AAGGAGCTGC AACCTTAACT ACATCATCGG GCAAATTAAC
4301 TACCGAAGCT AGTTCACACA TTACTTCAGC CAAGGGTCAG GTAAATCTTT
4351 CAGCTCAGGA TGGTAGCGTT GCAGGAAGTA TTAATGCCGC CAATGTGACA
4401 CTAAATACTA CAGGCACTTT AACTACCGTG AAGGGTTCAA ACATTAATGC
4451 AACCAGCGGT ACCTTGGTTA TTAACGCAAA AGACGCTGAG CTAAATGGCG
4501 CAGCATTGGG TAACCACACA GTGGTAAATG CAACCAACGC AAATGGCTCC
4551 GGCAGCGTAA TCGCGACAAC CTCAAGCAGA GTGAACATCA CTGGGGATTT
4601 AATCACAATA AATGGATTAA ATATCATTTC AAAAAACGGT ATAAACACCG
4651 TACTGTTAAA AGGCGTTAAA ATTGATGTGA AATACATTCA ACCGGGTATA
4701 GCAAGCGTAG ATGAAGTAAT TGAAGGCGAAA CGCATCCTTG AGAAGGTAAA
4751 AGATTTATCT GATGAAGAAA GAGAAGCGTT AGCTAAACTT GGCGTAAGTG
4801 CTGTACGTTT TATTGAGCCA AATAATACAA TTACAGTCGA TACACAAAAT
4851 GAATTTGCAA CCAGACCATT AAGTCGAATA GTGATTTCTG AAGGCAGGGC
4901 GTGTTTCTCA AACAGTGATG GCGCGACGGT GTGCGTTAAT ATCGCTGATA
```

FIG. 6G.

```
4951 ACGGGCGGTA GCGGTCAGTA ATTGACAAGG TAGATTTCAT CCTGCAATGA
5001 AGTCATTTTA TTTTCGTATT ATTTACTGTG TGGGTTAAAG TTCAGTACGG
5051 GCTTTACCCA TCTTGTAAAA AATTACGGAG AATACAATAA AGTATTTTTA
5101 ACAGGTTATT ATTATGAAAA ATATAAAAAG CAGATTAAAA CTCAGTGCAA
5151 TATCAGTATT GCTTGGCCTG GCTTCTTCAT CATTGTATGC AGAAGAAGCG
5201 TTTTTAGTAA AAGGCTTTCA GTTATCTGGT GCACTTGAAA CTTTAAGTGA
5251 AGACGCCCAA CTGTCTCTGTAG CAAAATCTTT ATCTAAATAC CAAGGCTCGC
5301 AAACTTTAAC AAACCTAAAA ACAGCACAGC TTGAATTACA GGCTGTGCTA
5351 GATAAGATTG AGCCAAATAA GTTTGATGTG ATATTGCCAC AACAAACCAT
5401 TACGGATGGC AATATTATGT TTGAGCTAGT CTCGAAATCA GCCGCAGAAA
5451 GCCAAGTTTT TTATAAGGCG AGCCAGGGTT ATAGTGAAGA AAATATCGCT
5501 CGTAGCCTGC CATCTTTGAA ACAAGGAAAA GTGTATGAAG ATGGTCGTCA
5551 GTGGTTCGAT TGCCTGAAT TCAATATGGC AAAAGAAAAT CCACTTAAAG
5601 TCACTCGCGT GCATTACGAG TTAAACCCTA AAAACAAAAC CTCTGATTTG
5651 GTAGTTGCAG GTTTTCGCC TTTTGGCAAA ACGCGTAGCT TTGTTTCCTA
5701 TGATAATTTC GGGCAAGGG AGTTAACTA TCAACGTGTA AGTCTAGGTT
```

FIG. 6H.

```
5751  TTGTAAATGC CAATTTGACC GGACATGATG ATGTATTAAA TCTAAACGCA
5801  TTGACCAATG TAAAAGCACC ATCAAAATCT TATGCGGTAG GCATAGGATA
5851  TACTTATCCG TTTTATGATA AACACCAATC CTTAAGTCTT TATACCAGCA
5901  TGAGTTATGC TGATTCTAAT GATATCGACG GCTTACCAAG TGCGATTAAT
5951  CGTAAATTAT CAAAAGGTCA ATCTATCTCT GCGAATCTGA AATGGAGTTA
6001  TTATCTCCCG ACATTTAACC TTGGAATGGA AGACCAGTTT AAAATTAATT
6051  TAGGCTACAA CTACCGCCAT ATTAATCAAA CATCCGAGTT AAACACCCTG
6101  GGTGCAACGA AGAAAAAATT TGCAGTATCA GGCGTAAGTG CAGGCATTGA
6151  TGGACATATC CAATTTACCC CTAAAACAAT CTTTAATATT GATTTAACTC
6201  ATCATTATTA CGCGAGTAAA TTACCAGGCT CTTTTGGAAT GGAGCGCATT
6251  GGCGAAACAT TTAATCGCAG CTATCACATT AGCACAGCCA GTTTAGGGTT
6301  GAGTCAAGAG TTTGCTCAAG GTTGGCATTT TAGCAGTCAA TTATCGGGTC
6351  AGTTTACTCT ACAAGATATA AGTAGCATAG ATTTATTCTC TGTAACAGGT
6401  ACTTATGGCG TCAGAGGCTT TAAATACGGC GGTGCAAGTG GTGAGCGCGG
6451  TCTTGTATGG CGTAATGAAT TAAGTATGCC AAAATACACC CGCTTTCAAA
6501  TCAGCCCTTA TGCGTTTTAT GATGCAGGTC AGTTCCGTTA TAATAGCGAA
6551  AATGCTAAAA CTTACGGCGA AGATATGCAC ACGGTATCCT CTGCGGGTTT
```

FIG. 6I.

```
6601  AGGCATTAAA ACCTCTCCTA CACAAAACTT AAGCTTAGAT GCTTTTGTTG
6651  CTCGTCGCTT TGCAAATGCC AATAGTGACA ATTTGAATGG CAACAAAAAA
6701  CGCACAAGCT CACCTACAAC CTTCTGGGGT AGATTAACAT TCAGTTTCTA
6751  ACCCTGAAAT TTAATCAACT GGTAAGCGTT CCGCCTACCA GTTTATAACT
6801  ATATGCTTTA CCCGCCAATT TACAGTCTAT ACGCAACCCT GTTTTCATCC
6851  TTATATATCA AACAAACTAA GCAAACCAAG CAAACCAAGC AAACCAAGCA
6901  AACCAAGCAA ACCAAGCAAA CCAAGCAAAC CAAGCAAACC AAGCAAACCA
6951  AGCAAACCAA GCAAACCAAG CAAACCAAGC AAACCAAGCA ATGCTAAAAA
7001  ACAATTTATA TGATAAACTA AAACATACTC AAAGTGTTCC CAATACAAGG
7051  GATTTAATAA TATGACAAAA GAAAATTTAC AAAGTGTTCC ACAAAATACG
7101  ACCGCTTCAC TTGTAGAATC AAACAACGAC CAAACTTCCC TGCAAATACT
7151  TAAACAACCA CCCAAACCCA ACCTATTACG CCTGGAACAA CATGTCGCCA
7201  AAAAAGATTA TGAGCTTGCT TGCCGCGAAT TAATGGCGAT TTTGGAAAAA
7251  ATGGACGCTA ATTTTGGAGG CGTTCACGAT ATTGAATTTG ACGCACCTGC
7301  TCAGCTGGCA TATCTACCCG AAAAACTACT AATTCATTTT GCCACTCGTC
7351  TCGCTAATGC AATTACAACA CTCTTTTCCG ACCCCGAATT GGCAATTTCC
```

FIG. 6J.

```
7401 GAAGAAGGGG CATTAAAGAT GATTAGCCTG CAACGCTGGT TGACGCTGAT
7451 TTTGCCTCT  TCCCCCTACG TTAACGCAGA CCATATTCTC AATAAATATA
7501 ATATCAACCC AGATTCCGAA GGTGGCTTTC ATTTAGCAAC AGACAACTCT
7551 TCTATTGCTA AATTCTGTAT TTTTTACTTA CCCGAATCCA ATGTCAATAT
7601 GAGTTTAGAT GCGTTATGGG CAGGGAATCA ACAACTTTGT GCTTCATTGT
7651 GTTTTGCGTT GCAGTCTTCA CGTTTTATTG GTACTGCATC TGCGTTTCAT
7701 AAAAGAGCGG TGGTTTTACA GTGGTTTCCT AAAAAACTCG CCGAAATTGC
7751 TAATTTAGAT GAATTGCCTG CAAATATCCT TCATGATGTA TATATGCACT
7801 GCAGTTATGA TTTAGCAAAA AACAAGCACG ATGTTAAGCG TCCATTAAAC
7851 GAACTTGTCC GCAAGCATAT CCTCACGCAA GGATGGCAAG ACCGCTACCT
7901 TTACACCTTA GGTAAAAAGG ACGGCAAACC TGTGATGATG GTACTGCTTG
7951 AACATTTTAA TTCGGGACAT TCGATTTATC GCACGCATTC AACTTCAATG
8001 ATTGCTGCTC GAGAAAAATT CTATTTAGTC GGCTTAGGCC ATGAGGGCGT
8051 TGATAACATA GGTCGAGAAG TGTTTGACGA GTTCTTTGAA ATCAGTAGCA
8101 ATAATATAAT GGAGAGACTG TTTTTATCC  GTAAACAGTG CGAAACTTTC
8151 CAACCCCGCAG TGTTCTATAT GCCAAGCATT GGCATGGATA TTACCACGAT
```

FIG. 6K.

```
8201  TTTGTGAGC  AACACTCGGC  TTGCCCCTAT  TCAAGCTGTA  GCCTTGGGTC
8251  ATCCTGCCAC  TACGCATTCT  GAATTTATTG  ATTATGTCAT  CGTAGAAGAT
8301  GATTATGTGG  GCAGTGAAGA  TTGTTTAGC   GAAACCCTTT  TACGCTTACC
8351  CAAAGATGCC  CTACCTTATG  TACCATCTGC  ACTCGCCCCA  CAAAAAGTGG
8401  ATTATGTACT  CAGGGAAAAC  CCTGAAGTAG  TCAATATCGG  TATTGCCGCT
8451  ACCACAATGA  AATTAAACCC  TGAATTTTTG  CTAACATTGC  AAGAAATCAG
8501  AAAGTCAAAA  AAAGTCAAAA  TACATTTTCA  TTTCGCACTT  GGACAATCAA
8551  CAGGCTTGAC  ACACCCCTAT  GTCAAATGGT  TTATCGAAAG  CTATTTAGGT
8601  GACGATGCCA  CTGCACATCC  CCACGCACCT  TATCACGATT  ATCTGGCAAT
8651  ATTGCGTGAT  TGCGATATGC  TACTAAATCC  GTTTCCTTTC  GGTAATACTA
8701  ACGGCATAAT  TGATATGGTT  ACATTAGGTT  TAGTTGGTGT  ATGCAAACG
8751  GGGGATGAAG  TACATGAACA  TATTGATGAA  GGTCTGTTTA  AACGCTTAGG
8801  ACTACCAGAA  TGGCTGATAG  CCGACACACG  AGAAACATAT  ATTGAATGTG
8851  CTTTGCGTCT  AGCAGAAAAC  CATCAAGAAC  GCCTTGAACT  CCGTCGTTAC
8901  ATCATAGAAA  ACAACGGCTT  ACAAAAGCTT  TTTACAGGCG  ACCCTCGTCC
8951  ATTGGGCAAA  ATACTGCTTA  AGAAAACAAA  TGAATGGAAG  CGGAAGCACT
9001  TGAGTAAAAA  ATAACGGTTT  TTTAAAGTAA  AAGTGCGGTT  AATTTCAAA
```

FIG. 6L.

```
9051  GCGTTTAAA  AACCTCTCAA  AAATCAACCG  CACTTTTATC  TTTATAACGC
9101  TCCCGCCGC  TGACAGTTTA  TCTCTTTCTT  AAAATACCCA  TAAAATTGTG
9151  GCAATAGTTG  GGTAATCAAA  TTCAATTGTT  GATACGGCAA  ACTAAAGACG
9201  GCGCGTTCTT  CGGCAGTCAT  C
```

FIG. 7A.

```
  1 CGCCACTTCA ATTTTGGATT GTTGAAATTC AACTAACCAA AAAGTGCGGT
 51 TAAAATCTGT GGAGAAAATA GGTTGTAGTG AAGAACGAGG TAATTGTTCA
101 AAAGGATAAA GCTCTCTTAA TTGGGCATTG GTTGGCGTTT CTTTTCGGT
151 TAATAGTAAA TTATATTCTG GACGACTATG CAATCCACCA ACAACTTTAC
201 CGTTGGTTTT AAGCGTTAAT GTAAGTTCTT GCTCTTCTTG GCGAATACGT
251 AATCCCATTT TTTGTTTAGC AAGAAAAATGA TCGGGATAAT CATAATAGGT
301 GTTGCCCAAA AATAAATTTT GATGTTCTAA AATCATAAAT TTTGCAAGAT
351 ATTGTGGCAA TTCAATACCT ATTTGTGGCG AAATCGCCAA TTTTAATTCA
401 ATTTCTTGTA GCATAATATT TCCCACTCAA ATCAACTGGT TAAATATACA
451 AGATAATAAA AATAAATCAA GATTTTTGTG ATGACAAACA ACAATTACAA
501 CACCTTTTTT GCAGTCTATA TGCAAATATT TTAAAAAAAT AGTATAAATC
551 CGCCATATAA AATGGTATAA TCTTTCATCT TTCATCTTTC ATCTTTCATC
601 TTTCATCTTT CATCTTTCAT CTTTCATCTT TTTCATCTTT TCATCTTTCT
651 TTCATCTTTC ATCTTTCATC TTTCATCTTT CACATGAAAT GATGAACCGA
701 GGGAAGGGAG GGAGGGGCAA GAATGAAGAG GGAGCTGAAC GAACGCAAAT
751 GATAAAGTAA TTTAATTGTT CAACTAACCT TAGGAGAAAA TATGAACAAG
```

FIG. 7B.

```
 801  ATATATCGTC  TCAAATTCAG  CAAACGCCTG  AATGCTTTGG  TTGCTGTGTC
 851  TGAATTGGCA  CGGGGTTGTG  ACCATTCCAC  AGAAAAAGGC  AGCGAAAAAC
 901  CTGCTCGCAT  GAAAGTGCGT  CACTTAGCGT  TAAAGCCACT  TTCCGCTATG
 951  TTACTATCTT  TAGGTGTAAC  ATCTATTCCA  CAATCTGTTT  TAGCAAGCGG
1001  CAATTTAACA  TCGACCAAAA  TGAAATGGTG  CAGTTTTTAC  AAGAAAACAA
1051  GTAATAAAAC  CATTATCCGC  AACAGTGTTG  ACGCTATCAT  TAATTGGAAA
1101  CAATTTAACA  TCGACCAAAA  TGAAATGGTG  CAGTTTTTAC  AAGAAAACAA
1151  CAACTCCGCC  GTATTCAACC  GTGTTACATC  TAACCAAATC  TCCCAATTAA
1201  AAGGGATTTT  AGATTCTAAC  GGACAAGTCT  TTTTAATCAA  CCCAAATGGT
1251  ATCACAATAG  GTAAAGACGC  AATTATTAAC  ACTAATGGCT  TTACGGCTTC
1301  TACGCTAGAC  ATTTCTAACG  AAAACATCAA  GGCGCGTAAT  TTCACCTTCG
1351  AGCAAACCAA  AGATAAAGCG  CTCGCTGAAA  TTGTGAATCA  CGGTTTAATT
1401  ACTGTCGGTA  AAGACGGCAG  TGTAAATCTT  ATTGGTGGCA  AAGTGAAAAA
1451  CGAGGGTGTG  ATTAGCGTAA  ATGGTGGCAG  CATTTCTTTA  CTCGCAGGGC
1501  AAAAAATCAC  CATCAGCGAT  ATAATAAACC  CAACCATTAC  TTACAGCATT
1551  GCCGCGCCTG  AAAATGAAGC  GGTCAATCTG  GGCGATATTT  TTGCCAAAGG
```

FIG. 7C.

```
1601  CGGTAACATT  AATGTCCGTG  CTGCCACTAT  TCGAAACCAA  GGTAAACTTT
1651  CTGCTGATTC  TGTAAGCAAA  GATAAAAGCG  GCAATATTGT  TCTTTCCGCC
1701  AAAGAGGGTG  AAGCGGAAAT  TGGCGGTGTA  ATTTCCGCTC  AAAATCAGCA
1751  AGCTAAAGGC  GGCAAGCTGA  TGATTACAGG  CGATAAAGTC  ACATTAAAAA
1801  CAGGTGCAGT  TATCGACCTT  TCAGGTAAAG  AAGGGGGAGA  AACTTACCTT
1851  GGCGGTGACG  AGCGCGGGCA  AGGTAAAAAC  GGCATTCAAT  TAGCAAAGAA
1901  AACCTCTTTA  GAAAAAGGCT  CAACCATCAA  TGTATCAGGC  AAAGAAAAAG
1951  GCGGACGCGC  TATTGTGTGG  GGCGATATTG  CGTTAATTGA  CGGCAATATT
2001  AACGCTCAAG  GTAGTGGTGA  TATCGCTAAA  ACCGGTGGTT  TTGTGGAGAC
2051  ATCGGGGCAT  TATTTATCCA  TTGACAGCAA  TGCAATTGTT  AAAACAAAAG
2101  AGTGGTTGCT  AGACCCTGAT  GATGTAAACAA  TTGAAGCCGA  AGACCCCCTT
2151  CGCAATAATA  CCGGTATAAA  TGATGAATTC  CCAACAGGCA  CCGGTGAAGC
2201  AAGCGACCCT  AAAAAAAATA  GCGAACTCAA  AACAACGCTA  ACCAATACAA
2251  CTATTTCAAA  TTATCTGAAA  AACGCCTGGA  CAATGAATAT  AACGGCATCA
2301  AGAAAACTTA  CCGTTAATAG  CTCAATCAAC  ATCGGAAGCA  ACTCCCACTT
2351  AATTCTCCAT  AGTAAAGGTC  AGCGTGGCGG  AGCGTTCAG   ATTGATGGAG
2401  ATATTACTTC  TAAAGGCGGA  AATTAACCA   TTTATTCTGG  CGGATGGGTT
```

FIG. 7D.

```
2451  GATGTTCATA  AAAATATTAC  GCTTGATCAG  GGTTTTTAA   ATATTACCGC
2501  CGCTTCCGTA  GCTTTTGAAG  GTGGAAATAA  CAAAGCACGC  GACGCGGCAA
2551  ATGCTAAAAT  TGTCGCCCAG  GGCACTGTAA  CCATTACAGG  AGAGGGAAAA
2601  GATTTCAGGG  CTAACAACGT  ATCTTTAAAC  GGAACGGGTA  AAGGTCTGAA
2651  TATCATTTCA  TCAGTGAATA  ATTTAACCCA  CAATCTTAGT  GGCACAATTA
2701  ACATATCTGG  GAATATAACA  ATTAACCAAA  CTACGAGAAA  GAACACCTCG
2751  TATTGGCAAA  CCAGCCATGA  TTCGCACTGG  AACGTCAGTG  CTCTTAATCT
2801  AGAGACAGGC  GCAAATTTTA  CCTTTATTAA  ATACATTTCA  AGCAATAGCA
2851  AAGGCTTAAC  AACACAGTAT  AGAAGCTCTG  CAGGGGTGAA  TTTTAACGGC
2901  GTAAATGGCA  ACATGTCATT  CAATCTCAAA  GAAGGAGCGA  AAGTTAATTT
2951  CAAATTAAAA  CCAAACGAGA  ACATGAACAC  AAGCAAACCT  TTACCAATTC
3001  GGTTTTTAGC  CAATATCACA  GCCACTGGTG  GGGCTCTGT   TTTTTTTGAT
3051  ATATATGCCA  ACCATTCTGG  CAGAGGGGCT  GAGTTAAAAA  TGAGTGAAAT
3101  TAATATCTCT  AACGGCGCTA  ATTTTACCTT  AAATTCCCAT  GTTCGCGGCG
3151  ATGACGCTTT  TAAAATCAAC  AAAGACTTAA  CCATAAATGC  AACCAATTCA
3201  AATTTCAGCC  TCAGACAGAC  GAAAGATGAT  TTTTATGACG  GGTACGCACG
```

FIG. 7E.

```
3251 CAATGCCATC AATTCAACCT ACAACATATC CATTCTGGGC GGTAATGTCA
3301 CCCTTGGTGG ACAAAACTCA AGCAGCAGCA TTACGGGAA  TATTACTATC
3351 GAGAAAGCAG CAAATGTTAC GCTAGAAGCC AATAACGCCC CTAATCAGCA
3401 AAACATAAGG GATAGAGTTA TAAAACTTGG CAGCTTGCTC GTTAATGGGA
3451 GTTTAAGTTT AACTGGCGAA AATGCAGATA TTAAAGGCAA TCTCACTATT
3501 TCAGAAAGCG CCACTTTTAA AGGAAAGACT AGAGATACCC TAAATATCAC
3551 CGGCAATTTT ACCAATAAATG GCACTGCCGA AATTAATATA ACACAAGGAG
3601 TGGTAAAACT TGGCAATGTT ACCAATGATG GTGATTTAAA CATTACCACT
3651 CACGCTAAAC GCAACCAAAG AAGCATCATC GGCGGAGATA TAATCAACAA
3701 AAAAGGAAGC TTAAATATTA CAGACAGTAA TAATGATGCT GAAATCCAAA
3751 TTGGCGGCAA TATCTCGCAA AAAGAAGGCA ACCTCACGAT TTCTTCCGAT
3801 AAAATTAATA TCACCAAACA GATAACAATC AAAAAGGGTA TTGATGGAGA
3851 GGACTCTAGT TCAGATGCGA CAAGTAATGC CAACCTAACT ATTAAAACCA
3901 AAGAATTGAA ATTGACAGAA CAAGTAAGTA TTTCAGTTT  CAATAAAGCA
3951 GAGATTACAG CCAAAGATGG TAGAGATTTA GACCTAAGTA ACAGTAATGA
4001 CGGTAACAGC GGTGCCGAAG CCAAAACAGT AACTATTGGCA AATGTTAAAG
```

FIG. 7F.

```
4051  ATTCAAAAAT CTCTGCTGAC GGTCACAATG TGACACTAAA TAGCAAAGTG
4101  AAAACATCTA GCAGCAATGG CGGACGTGAA AGCAATAGCG ACAACGATAC
4151  CGGCTTAACT ATTACTGCAA AAAATGTAGA AGTAAACAAA GATATTACTT
4201  CTCTCAAAAC AGTAAATATC ACCGCGTCGG AAAAGGTTAC CACCACAGCA
4251  GGCTCGACCA TTAACGCAAC AAATGGCAAA GCAAGTATTA CAACCAAAAC
4301  AGGTGATATC AGCGGTACGA TTTCCGGTAA CACGGTAAGT GTTAGCGCGA
4351  CTGGTGATTT AACCACTAAA TCCGGCTCAA AAATTGAAGC GAAATCGGGT
4401  GAGGCTAATG TAACAAGTGC AACAGGTACA ATTGGCGGTA CAATTTCCGG
4451  TAATACGGTA AATGTTACGG CAAACGCTGG CGATTTAACA GTTGGGAATG
4501  GCGCAGAAAT TAATGCGACA GAAGGAGCTG CAACCTTAAC CGCAACAGGG
4551  AATACCTTGA CTACTGAAGC CGGTTCTAGC ATCACTTCAA CTAAGGGTCA
4601  GGTAGACCTC TTGGCTCAGA ATGGTAGCAT CGCAGGAAGC ATTAATGCTG
4651  CTAATGTGAC ATTAAATACT ACAGGCACCT TAACCACCGT GGCAGGCTCG
4701  GATATTAAAG CAACCAGCGG CACCTTGGTT ATTAACGCAA AAGATGCTAA
4751  GCTAAATGGT GATGCATCAG GTGATAGTAC AGAAGTGAAT GCAGTCAACG
4801  ACTGGGGATT TGGTAGTGTG ACTGCGGCAA CCTCAAGCAG TGTGAATATC
4851  ACTGGGGATT TAAACACAGT AAATGGGTTA AATATCATTT CGAAAGATGG
```

FIG. 7G.

```
4901 TAGAAACACT GTGCGCTTAA GAGGCAAGGA AATTGAGGTG AAATATATCC
4951 AGCCAGGTGT AGCAAGTGTA GAAGAAGTAA TTGAAGCGAA ACGCGTCCTT
5001 GAAAAAGTAA AAGATTTATC TGATGAAGAA AGAGAAACAT TAGCTAAACT
5051 TGGTGTAAGT GCTGTACGTT TTGTTGAGCC AGAGAAACAT ATTACAGTCA
5101 ATACACAAAA TGAATTTACA ACCAGACCGT AAATAATACA GATAATTTCT
5151 GAAGGTAAGG CGTGTTTCTC AAGTGGTAAT CAAGTCAAGT TATGTACCAA
5201 TGTTGCTGAC GATGGACAGC CGTAGTCAGT GGCGCACGAG GTAGATTTCA
5251 TCCTGCAATG AAGTCATTTT ATTTTCGTAT AATTGACAAG GTGGGTTAAA
5301 GTTCAGTACG GGCTTTACCC ATCTTGTAAA TATTTACTGT GAATACAATA
5351 AAGTATTTTT AACAGGTTAT TATTATGAAA AAATTACGGA GCAGATTAAA
5401 ACTCAGTGCA ATATCAGTAT TGCTTGGCCT AATATAAAAA TCATTGTATG
5451 CAGAAGAAGC GTTTTAGTA AAAGGCTTTC GGCTTCTTCA TGCACTTGAA
5501 ACTTTAAGTG AAGACGCCCA ACTGTCTGTA AGTTATCTGG TATCTAAATA
5551 CCAAGGCTCG CAAACTTAA CAAACCTAAA GCAAAATCTT CTTGAATTAC
5601 AGGCTGTGCT AGATAAGATT GAGCCAAATA AACAGCACAG GATATTGCCG
5651 CAACAAACCA TTACGGATGG CAATATCATG AATTTGATGT TCTCGAAATC
```

FIG. 7H.

```
5701  AGCCGCAGAA AGCCAAGTTT TTTATAAGGC GAGCCAGGGT TATAGTGAAG
5751  AAAATATCGC TCGTAGCCTG CCATCTTTGA AACAAGGAAA AGTGTATGAA
5801  GATGGTCGTC AGTGGTTCGA TTTGCGTGAA TTTAATATGG CAAAAGAAAA
5851  CCCGCTTAAG GTTACCCGTG TACATTACGA ACTAAACCCT AAAAACAAAA
5901  CCTCTAATTT GATAATTGCG GGCTTCTCGC CTTTTGGTAA AACGCGTAGC
5951  TTTATTTCTT ATGATAATTT CGGCGCGAGA GAGTTTAACT ACCAACGTGT
6001  AAGCTTGGGT TTTGTTAATG CCAATTTAAC TGGTCATGAT GATGTGTTAA
6151  TTATACCAGT ATGAGTTATG CTGATTCTAA TGATATCGAC GGCTTACCAA
6201  GTGCGATTAA TCGTAAATTA TCAAAAGGTC AATCTATCTC TGCGAATCTG
6251  AAATGGAGTT ATTATCTCCC AACATTTAAC CTTGGCATGG AAGACCAATT
6301  TAAAATTAAT TTAGGCTACA ACTACCGCCA TATTAATCAA ACCTCCCGT
6351  TAAATCGCTT GGGTGAAACG AAGAAAAAT TTGCAGTATC AGCGTAAGT
6401  GCAGGCATTG ATGGACATAT CCAATTTACC CCTAAAAACAA TCTTTAATAT
6451  TGATTTAACT CATCATTATT ACGCGAGTAA ATTACCAGGC TCTTTTGGAA
6501  TGGAGCGCAT TGGCGAAACA TTTAATCGCA GCTATCACAT TAGCACAGCC
6551  AGTTTAGGGT TGAGTCAAGA GTTGCTCAA GGTTGGCATT TTAGCAGTCA
6601  ATTATCAGGT CAATTTACTC TACAAGATAT TAGCAGTATA GATTTATTCT
```

FIG. 7I.

```
6651  CTGTAACAGG  TACTTATGGC  GTCAGAGGCT  TTAAATACGG  CGGTGCAAGT
6701  GGTGAGCGCG  GTCTTGTATG  GCGTAATGAA  TTAAGTATGC  CAAAATACAC
6751  CCGCTTCCAA  ATCAGCCCTT  ATGCGTTTTA  TGATGCAGGT  CAGTTCCGTT
6801  ATAATAGCGA  AAATGCTAAA  ACTTACGGCG  AAGATATGCA  CACGGTATCC
6851  TCTGCGGGTT  TAGGCATTAA  AACCTCTCCT  ACACAAAACT  TAAGCCTAGA
6901  TGCTTTTGTT  GCTCGTCGCT  TTGCAAATGC  CAATAGTGAC  AATTTGAATG
6951  GCAACAAAAA  ACGCACAAGC  TCACCTACAA  CCTTCTGGGG  GAGATTAACA
7001  TTCAGTTTCT  AACCCTGAAA  TTTAATCAAC  TGGTAAGCGT  TCCGCCTACC
7051  AGTTTATAAC  TATATGCTTT  ACCCGCCAAT  TTACAGTCTA  TAGGCAACCC
7101  TGTTTTTACC  CTTATATATC  AAATAAACAA  GCTAAGCTGA  GCTAAGCAAA
7151  CCAAGCAAAC  TCAAGCAAGC  CAAGTAAATAC  TAAAAAAACA  ATTTATATGA
7201  TAAACTAAAG  TATACTCCAT  GCCATGGCGA  TACAAGGGAT  TTAATAAATAT
7251  GACAAAAGAA  AATTTGCAAA  ACGCTCCTCA  AGATGCGACC  GCTTTACTTG
7301  CGGAATTAAG  CAACAATCAA  ACTCCCCTGC  GAATATTTAA  ACAACCACGC
7351  AAGCCCAGCC  TATTACGCTT  GGAACAACAT  ATCGCAAAAA  AAGATTATGA
7401  GTTTGCTTGT  CGTGAATTAA  TGGTGATTCT  GGAAAAAATG  GACGCTAATT
```

FIG. 7J.

```
7451  TTGGAGGCGT  TCACGATATT  GAATTTGACG  CACCCGCTCA  GCTGGCATAT
7501  CTACCCGAAA  AATTACTAAT  TTATTTTGCC  ACTCGTCTCG  CTAATGCAAT
7551  TACAACACTC  TTTTCCGACC  CCGAATTGGC  AATTTCTGAA  GAAGGGGCGT
7601  TAAAGATGAT  TAGCCTGCAA  CGCTGGTTGA  CGCTGATTTT  TGCCTCTTCC
7651  CCCTACGTTA  ACGCAGACCA  TATTCTCAAT  AAATATAATA  TCAACCCAGA
7701  TTCCGAAGGT  GGCTTTCATT  TAGCAACAGA  CAACTCTTCT  ATTGCTAAAT
7751  TCTGTATTTT  TTACTTACCC  GAATCAACA   TCAATATGAG  TTTAGATGCG
7801  TTATGGGCAG  GGAATCAACA  ACTTTGTGCT  TCATTGTGTT  TTGCGTTGCA
7851  GTCTTCACGT  TTTATTGGTA  CCGCATCTGC  GTTTCATAAA  AGAGCGGTGG
7901  TTTTACAGTG  GTTTCCTAAA  AAACTCGCCG  AAATTGCTAA  TTTAGATGAA
7951  TTGCCTGCAA  ATATCCTTCA  TGATGTATAT  ATGCACTGCA  GTTATGATTT
8001  AGCAAAAAAC  AAGCACGATG  TTAAGCGTCC  ATTAAACGAA  CTTGTCCGCA
8051  AGCATATCCT  CACGCAAGGA  TGGCAAGACC  GCTACCTTTA  CACCTTAGGT
8101  AAAAGGACG   GCAAACCTGT  GATGATGGTA  CTGCTTGAAC  ATTTTAATTC
8151  GGGACATTCG  ATTTATCGTA  CACATTCAAC  TTCAATGATT  GCTGCTCGAG
8201  AAAATTCTA   TTTAGTCGGC  TTAGGCCATG  AGGGCGTTGA  TAAATAGGT
```

FIG. 7K.

| | | | | |
|---|---|---|---|---|
| 8251 | CGAGAAGTGT | TTGACGAGTT | CTTTGAAATC | AGTAGCAATA | ATATAATGGA |
| 8301 | GAGACTGTTT | TTTATCCGTA | AACAGTGCGA | AACTTTCCAA | CCCGCAGTGT |
| 8351 | TCTATATGCC | AAGCATTGGC | ATGGATATTA | CCACGATTTT | TGTGAGCAAC |
| 8401 | ACTCGGCTTG | CCCCTATTCA | AGCTGTAGCC | CTGGGTCATC | CTGCCACTAC |
| 8451 | GCATTCTGAA | TTTATTGATT | ATGTCATCGT | AGAAGATGAT | TATGTGGGCA |
| 8501 | GTGAAGATTG | TTTCAGCGAA | ACCCTTTTAC | GCTTACCCAA | AGATGCCCTA |
| 8551 | CCTTATGTAC | CTTCTGCACT | CGCCCCACAA | AAAGTGGATT | ATGTACTCAG |
| 8601 | GGAAAACCCT | GAAGTAGTCA | ATATCGGTAT | TGCCGCTACC | ACAATGAAAT |
| 8651 | TAAACCCTGA | ATTTTGCTA | ACATTGCAAG | AAATCAGAGA | TAAAGCTAAA |
| 8701 | GTCAAAATAC | ATTTTCATTT | CGCACTTGGA | CAATCAACAG | GCTTGACACA |
| 8751 | CCCTTATGTC | AAATGGTTTA | TCGAAAGCTA | TTTAGGTGAC | GATGCCACTG |
| 8801 | CACATCCCCA | CGCACCTTAT | CACGATTATC | TGGCAATATT | GCGTGATTGC |
| 8851 | GATATGCTAC | TAAATCCGTT | TCCTTTCGGT | AATACTAACG | GCATAATTGA |
| 8901 | TATGGTTACA | TTAGGTTTAG | TTGGTGTATG | CAAAACGGGG | GATGAAGTAC |
| 8951 | ATGAACATAT | TGATGAAGGT | CTGTTTAAAC | GCTTAGGACT | ACCAGAATGG |
| 9001 | CTGATAGCCG | ACACACGAGA | AACATATATT | GAATGTGCTT | TGCGTCTAGC |
| 9051 | AGAAAACCAT | CAAGAACGCC | TTGAACTCCG | TCGTTACATC | ATAGAAAACA |

FIG. 7L.

```
9101 ACGGCTTACA AAAGCTTTTT ACAGGGCGACC CTCGTCCATT GGGCAAAATA
9151 CTGCTTAAGA AAACAAATGA ATGGAAGCGG AAGCACTTGA GTAAAAAATA
9201 ACGGTTTTTT AAAGTAAAAG TGCGGGTTAAT TTTCAAAGCG TTTAAAAAC
9251 CTCTCAAAAA TCAACCGCAC TTTTATCTTT ATAACGATCC CGCACGCTGA
9301 CAGTTTATCA GCCTCCCGCC ATAAAACTCC GCCTTTCATG GCGGAGATTT
9351 TAGCCAAAAC TGGCAGAAAT TAAAGGCTAA AATCACCAAA TTGCACCACA
9401 AAATCACCAA TACCCACAAA AAA
```

FIG. 8A.

```
  1  GATCAATCTG GGCGATATTT TTGCCAAAGG TGGTAACATT AATGTCCGCG
 51  CTGCCACTAT TCGCAATAAA GGTAAACTTT CTGCCGACTC TGTAAGCAAA
101  GATAAAAGTG GTAACATTGT TCTCTCTGCC AAAGAAGGTG AAGCGGAAAT
151  TGGCGGTGTA ATTTCCGCTC AAAATCAGCA AGCCAAAGGT GGTAAGTTGA
201  TGATTACAGG CGATAAAGTT ACATTGAAAA CGGGTGCAGT TATCGACCTT
251  TCGGGTAAAG AAGGGGGAGA AACTTATCTT GGCGGTGACG AGCGTGGCGA
301  AGGTAAAAAC GGCATTCAAT TAGCAAAGAA AACCACTTTA GAAAAAGGCT
351  CAACAATTAA TGTGTCAGGT AAAGAAAAAG GTGGGCGCGC TATTGTATGG
401  GGCGATATTG CGTTAATTGA CGGCAATATT AATGCCCAAG GTAAAGATAT
451  CGCTAAAACT GGTGGTTTTG TGGAGACGTC GGGGCATTAC TTATCCATTG
501  ATGATAACGC AATTGTTAAA ACAAAAGAAT GGCTACTAGA CCCAGAGAAT
551  GTGACTATTG AAGCTCCTTC CGCTTCTCGC GTCGAGCTGG GTGCCGATAG
601  GAATTCCCAC TCGGCAGAGG TGATAAAAGT GACCCTAAAA AAAAATAACA
651  CCTCCCTTGA AACACTAACC AATACAACCA TTTCAAATCT TCTGAAAAGT
701  GCCCACGTGG TGAACATAAC GGCAAGGAGA AAACTTACCG TTAATAGCTC
751  TATCAGTATA GAAAGAGGCT CCCACTTAAT TCTCCACAGT GAAGGTCAGG
```

FIG. 8B.

```
 801  GCGGTCAAGG TGTTCAGATT GATAAAGATA TTACTTCTGA AGGCGGAAAT
 851  TTAACCATTT ATTCTGGCGG ATGGGTTGAT GTTCATAAAA ATATTACGCT
 901  TGGTAGCGGC TTTTTAAACA TCACAACTAA AGAAGGAGAT ATCGCCTTCG
 951  AAGACAAGTC TGGACGGAAC AACCTAACCA TTACAGCCCA AGGGACCATC
1001  ACCTCAGGTA ATAGTAACGG CTTTAGATTT AACAACGTCT CTCTAAACAG
1051  CCTTGGCGGA AAGCTGAGCT TTACTGACAG CAGAGAGGAC AGAGGTAGAA
1101  GAACTAAGGG TAATATCTCA AACAAATTTG ACGGAACGTT AAACATTTCC
1151  GGAACTGTAG ATATCTCAAT GAAAGCACCC AAAGTCAGCT GGTTTTACAG
1201  AGACAAAGGA CGCACCTACT GGAACGTAAC CACTTTAAAT GTTACCTCGG
1251  GTAGTAAATT TAACCTCTCC ATTGACAGCA CAGGAAGTGG CTCAACAGGT
1301  CCAAGCATAC GCAATGCAGA ATTAAATGGC ATAACATTTA ATAAAGCCAC
1351  TTTTAATATC GCACAAGGCT CAACAGCTAA CTTTAGCATC AAGGCATCAA
1401  TAATGCCCTT TAAGAGTAAC GCTAACTACG CATTATTTAA TGAAGATATT
1451  TCAGTCTCAG GGGGGGTAG CGTTAATTTC AAACTTAACG CCTCATCTAG
1501  CAACATACAA ACCCCTGGCG TAATTATAAA ATCTCAAAAC TTTAATGTCT
1551  CAGGAGGGTC AACTTTAAAT CTCAAGGCTG AAGGTTCAAC AGAAACCGCT
1601  TTTTCAATAG AAAATGATTT AAACTTAAAC GCCACCGGTG GCAATATAAC
```

FIG. 8C.

```
1651  AATCAGACAA  GTCGAGGGTA  CCGATTCACG  CGTCAACAAA  GGTGTCGCAG
1701  CCAAAAAAAA  CATAACTTTT  AAGGGGGTA   ATATCACCTT  CGGCTCTCAA
1751  AAGCCACAA   CAGAAATCAA  AGGCAATGTT  ACCATCAATA  AAAACACTAA
1801  CGCTACTCTT  CGTGGTGCGA  ATTTTGCCGA  AAACAAATCG  CCTTTAAATA
1851  TAGCAGGAAA  TGTTATTAAT  AATGGCAACC  TTACCACTGC  CGGCTCCATT
1901  ATCAATATAG  CCGGAAATCT  TACTGTTTCA  AAAGGCGCTA  ACCTTCAAGC
1951  TATAACAAAT  TACACTTTTA  ATGTAGCCGG  CTCATTTGAC  AACAATGGCG
2001  CTTCAAACAT  TTCCATTGCC  AGAGGAGGGG  CTAAATTTAA  AGATATCAAT
2051  AACACCAGTA  GCTTAAATAT  TACCACCAAC  TCTGATACCA  CTTACCGCAC
2101  CATTATAAAA  GGCAATATAT  CCAACAAATC  AGGTGATTTG  AATATTATTG
2151  ATAAAAAAAG  CGACGCTGAA  ATCCAAATTG  GCGGCAATAT  CTCACAAAAA
2201  GAAGGCAATC  TCACAATTTC  TTCTGATAAA  GTAAATATTA  CCAATCAGAT
2251  AACAATCAAA  GCAGGCGTTG  AAGGGGGGCG  TTCTGATTCA  AGTGAGGCAG
2301  AAAATGCTAA  CCTAACTATT  CAAACCAAAG  AGTTAAAATT  GGCAGGAGAC
2351  CTAAATATTT  CAGGCTTTAA  TAAAGCAGAA  ATTACAGCTA  AAATGGCAG
2401  TGATTTAACT  ATTGGCAATG  CTAGCGGTGG  TAATGCTGAT  GCTAAAAAAG
```

FIG. 8D.

```
2451  TGACTTTTGA  CAAGGTTAAA  GATTCAAAAA  TCTCGACTGA  CGGTCACAAT
2501  GTAACACTAA  ATAGCGAAGT  GAAAACGTCT  AATGGTAGTA  GCAATGCTGG
2551  TAATGATAAC  AGCACCGGTT  TAACCATTTC  CGCAAAAGAT  GTAACGGTAA
2601  ACAATAACGT  TACCTCCCAC  AAGACAATAA  ATATCTCTGC  CGCAGCAGGA
2651  AATGTAACAA  CCAAAGAAGG  CACAACTATC  AATGCAACCA  CAGGCAGCGT
2701  GGAAGTAACT  GCTCAAAATG  GTACAATTAA  AGGCAACATT  ACCTCGCAAA
2751  ATGTAACAGT  GACAGCAACA  GAAAATCTTG  TTACCACAGA  GAATGCTGTC
2801  ATTAATGCAA  CCAGCGGCAC  AGTAAACATT  AGTACAAAAA  CAGGGATAT
2851  TAAAGGTGGA  ATTGAATCAA  CTTCCGGTAA  TGTAAATATT  ACAGCGAGCG
2901  GCAATACACT  TAAGGTAAGT  AATATCACTG  GTCAAGATGT  AACAGTAACA
2951  GCGGATGCAG  GAGCCTTGAC  AACTACAGCA  GGCTCAACCA  TTAGTGCGAC
3001  AACAGGCAAT  GCAAATATTA  CAACCAAAAC  AGGTGATATC  AACGGTAAAG
3051  TTGAATCCAG  CTCCGGCTCT  GTAACACTTG  TTGCAACTGG  AGCAACTCTT
3101  GCTGTAGGTA  ATATTTCAGG  TAACACTGTT  ACTATTACTG  CGGATAGCGG
3151  TAAATTAACC  TCCACAGTAG  GTTCTACAAT  TAATGGGACT  AATAGTGTAA
3201  CCACCTCAAG  CCAATCAGGC  GATATTGAAG  GTACAATTTC  TGGTAATACA
3251  GTAAATGTTA  CAGCAAGCAC  TGGTGATTTA  ACTATTGGAA  ATAGTGCAAA
```

FIG. 8E.

```
3301  AGTTGAAGCG  AAAAATGGAG  CTGCAACCTT  AACTGCTGAA  TCAGGCAAAT
3351  TAACCACCCA  AACAGGCTCT  AGCATTACCT  CAAGCAATGG  TCAGACAACT
3401  CTTACAGCCA  AGGATAGCAG  TATCGCAGGA  AACATTAATG  CTGCTAATGT
3451  GACGTTAAAT  ACCACAGGCA  CTTTAACTAC  TACAGGGGAT  TCAAAGATTA
3501  ACGCAACCAG  TGGTACCTTA  ACAATCAATG  CAAAAGATGC  CAAATTAGAT
3551  GGTGCTGCAT  CAGGTGACCG  CACAGTAGTA  AATGCAACTA  ACGCAAGTGG
3601  CTCTGGTAAC  GTGACTGCCA  AAACCTCAAG  CAGCGTGAAT  ATCACCGGGG
3651  ATTTAAACAC  AATAAATGGG  TTAAATATCA  TTTCGGAAAA  TGGTAGAAAC
3701  ACTGTGCGCT  TAAGAGGCAA  GGAAATTGAT  GTGAAATATA  TCCAACCAGG
3751  TGTAGCAAGC  GTAGAAGAGG  TAATTGAAGC  GAAACGCGTC  CTTGAGAAGG
3801  TAAAAGATTT  ATCTGATGAA  GAAAGAGAAA  CACTAGCCAA  ACTTGGTGTA
3851  AGTGCTGTAC  GTTTCGTTGA  GCCAAATAAT  GCCATTACGG  TTAATACACA
3901  AAACGAGTTT  ACAACCAAAC  CATCAAGTCA  AGTGACAATT  TCTGAAGGTA
3951  AGGCGTGTTT  CTCAAGTGGT  AATGGCGCAC  GAGTATGTAC  CAATGTTGCT
4001  GACGATGGAC  AGCAGTAGTC  AGTAATTGAC  AAGGTAGATT  TCATCCTGCA
4051  ATGAAGTCAT  TTTATTTTCG  TATTATTTAC  TGTGTGGGTT  AAAGTTCAGT
```

FIG. 8F.

| | | | | | |
|---|---|---|---|---|---|
| 4101 | ACGGGCTTTA | CCCACCTTGT | AAAAAATTAC | GAAAAATACA | ATAAAGTATT |
| 4151 | TTTAACAGGT | TATTATTATG | AAAAACATAA | AAAGCAGATT | AAAACTCAGT |
| 4201 | GCAATATCAA | TATTGCTTGG | CTTGGCTTCT | TCATCGACGT | ATGCAGAAGA |
| 4251 | AGCGTTTTTA | GTAAAAGGCT | TTCAGTTATC | TGGCGCG | |

FIG. 9A.

```
  1  GGGAATGAGC GTCGTACACG GTACAGCAAC CATGCAAGTA GACGGCAATA
 51  AAACCACTAT CCGTAATAGC GTCAATGCTA TCATCAATTG GAAACAATTT
101  AACATTGACC AAAATGAAAT GGAGCAGTTT TTACAAGAAA GCAGCAACTC
151  TGCCGTTTTC AACCGTGTTA CATCTGACCA AATCTCCCAA TTAAAGGGA
201  TTTTAGATTC TAACGGACAA GTCTTTTTAA TCAACCCAAA TGGTATCACA
251  ATAGGTAAAG ACGCAATTAT TAACACTAAT GGCTTTACTG CTTCTACGCT
301  AGACATTTCT AACGAAAACA TCAAGGCGCG TAATTTCACC CTTGAGCAAA
351  CCAAGGATAA AGCACTCGCT GAAATCGTGA ATCACGGTTT AATTACCGTT
401  GGTAAAGACG GTAGCCGTAA ACCTTATTGGT GGCAAAGTGA AAAACGAGGG
451  CGTGATTAGC GTAAATGGCG GTAGTATTTC TTTACTTGCA GGGCAAAAAA
501  TCACCATCAG CGATATAATA AATCCAACCA TCACTTACAG CATTGCTGCA
551  CCTGAAAACG AAGCGATCAA TCTGGGCGAT ATTTTTGCCA AAGGTGGTAA
601  CATTAATGTC CGCGCTGCCA CTATTCGCAA TAAAGGTAAA CTTTCTGCCG
651  ACTCTGTAAG CAAAGATAAA AGTGGTAACA TTGTTCTCTC TGCCAAAGAA
701  GGTGAAGCGG AAATTGGCGG TGTAATTTCC GCTCAAAATC AGCAAGCCAA
751  AGGTGGTAAG TTGATGATTA CAGGTGATAA AGTCACATTA AAAACAGGTG
```

FIG. 9B.

```
 801 CAGTTATCGA CCTTTCAGGT AAAGAAGGGG GAGAGACTTA TCTTGGCGGT
 851 GATGAGCGTG GCGAAGGTAA AAATGGTATT CAATTAGCGA AGAAACCTC
 901 TTTAGAAAAA GGCTCGACAA TTAATGTATC AGGCAAAGAA AAAGGCGGGC
 951 GCGCTATTGT ATGGGGCGAT ATTGCATTAA TTAATGGTAA CATTAATGCT
1001 CAAGGTAGCG ATATTGCTAA AACTGGCGGC TTTGTGGAAA CATCAGGACA
1051 TGACTTATCC ATTGGTGATG ATGTGATTGT TGACGCTAAA GAGTGGTTAT
1101 TAGACCCAGA TGATGTGTCC ATTGAAACTC TTACATCTGG ACGCAATAAT
1151 ACCGGCGAAA ACCAAGGATA TACAACAGGA GATGGGACTA AAGAGTCACC
1201 TAAAGGTAAT AGTATTCTA AACCTACATT AACAAACTCA ACTCTTGAGC
1251 AAATCCTAAG AAGAGGTTCT TATGTTAATA TCACTGCTAA TAATAGAATT
1301 TATGTTAATA GCTCCATCAA CTTATCTAAT GGCAGTTTAA CACTTCACAC
1351 TAAACGAGAT GGAGTTAAAA TTAACGGTGA TATTACCTCA AACGAAAATG
1401 GTAATTTAAC CATTAAAGCA GGCTCTTGGG TTGATGTTCA TAAAAACATC
1451 ACGCTTGGTA CGGGTTTTTT GAATATTGTC GCTGGGGATT CTGTAGCTTT
1501 TGAGAGAGAG GGCGATAAAG CACGTAACGC AACAGATGCT CAAATTACCG
1551 CACAAGGGAC GATAACCGTC AATAAAGATG ATAAACAATT TAGATTCAAT
1601 AATGTATCTA TTAACGGGAC GGGCAAGGGT TTAAAGTTTA TTGCAAATCA
```

FIG. 9C.

```
1651 AAATAAATTTC ACTCATAAAT TTGATGGCGA AATTAACATA TCTGGAATAG
1701 TAACAATTAA CCAAACCACG AAAAAAGATG TTAAATACTG GAATGCATCA
1751 AAAGACTCTT ACTGGAATGT TTCTTCTCTT ACTTTGAATA CGGTGCAAAA
1801 ATTTACCTTT ATAAAATTCG TTGATAGCGG CTCAAATTCC CAAGATTTGA
1851 GGTCATCACG TAGAAGTTTT GCAGGCGTAC ATTTTAACGG CATCGGAGGC
1901 AAAACAAACT TCAACATCGG AGCTAACGCA AAAGCCTTAT TTAAATTAAA
1951 ACCAAACGCC GCTACAGACC CAAAAAAAGA ATTACCTATT ACTTTTAACG
2001 CCAACATTAC AGCTACCGGT AACAGTGATA GCTCTGTGAT GTTTGACATA
2051 CACGCCAATC TTACCTCTAG AGCTGCCGGC ATAAACATGG ATTCAATTAA
2101 CATTACCGGC GGGCTTGACT TTTCCATAAC ATCCCATAAT CGCAATAGTA
2151 ATGCTTTTGA AATCAAAAAA GACTTAACTA TAAATGCAAC TGGCTCGAAT
2201 TTTAGTCTTA AGCAAACGAA AGATTCTTTT TATAATGAAT ACAGCAAACA
2251 CGCCATTAAC TCAAGTCATA ATCTAACCAT TCTTGGCGGC AATGTCACTC
2301 TAGGTGGGGA AAATTCAAGC AGTAGCATTA CGGGCAATAT CAATATCACC
2351 AATAAAGCAA ATGTTACATT ACAAGCTGAC ACCAGCAACA GCAACACAGG
2401 CTTGAAGAAA AGAACTCTAA CTCTTGGCAA TATATCTGTT GAGGGAATT
```

FIG. 9D.

```
2451 TAAGCCTAAC TGGTGCAAAT GCAAACATTG TCGGCAATCT TTCTATTGCA
2501 GAAGATTCCA CATTTAAAGG AGAAGCCAGT GACAACCTAA ACATCACCGG
2551 CACCTTTACC AACAACGGTA CCGCCAACAT TAATATAAAA CAAGGAGTGG
2601 TAAAACTCCA AGGCGATATT ATCAATAAAG GTGGTTTAAA TATCACTACT
2651 AACGCCTCAG GCACTCAAAA AACCATTATT AACGGAAATA TAACTAACGA
2701 AAAAGGCGAC TTAAACATCA AGAATATTAA AGCCGACGCC GAAATCCAAA
2751 TTGGCGGGCAA TATCTCACAA AAAGAAGGCA ATCTCACAAT TTCTTCTGAT
2801 AAAGTAAAATA TTACCAATCA GATAACAATC AAAGCAGGCG TTGAAGGGGG
2851 GCGTTCTGAT TCAAGTGAGG CAGAAAATGC TAACCTAACT ATTCAAACCA
2901 AAGAGTTAAA ATTGGCAGGA GACCTAAATA TTTCAGGCTT TAATAAAGCA
2951 GAAATTACAG CTAAAAAATGG CAGTGATTTA ACTATTGGCA ATGCTAGCGG
3001 TGGTAATGCT GATGCTAAAA AAGTGACTTT TGACAAGGTT AAAGATTCAA
3051 AAATCTCGAC TGACGGTCAC AATGTAACAC TAAATAGCGA AGTGAAAACG
3101 TCTAATGGTA GTAGCAATGC TGGTAATGAT AACAGCACCG GTTTAACCAT
3151 TTCCGCAAAA GATGTAACGG TAAACAATAA CGTTACCTCC CACAAGACAA
3201 TAAATATCTC TGCCGCAGCA GGAAATGTAA CAACCAAAGA AGGCACAACT
3251 ATCAATGCAA CCACAGGCAG CGTGGAAGTA ACTGCTCAAA ATGGTACAAT
```

FIG. 9E.

```
3301  TAAAGGCAAC  ATTACCTCGC  AAAATGTAAC  AGTGACAGCA  ACAGAAAATC
3351  TTGTTACCAC  AGAGAATGCT  GTCATTAATG  CAACCAGCGG  CACAGTAAAC
3401  ATTAGTACAA  AAACAGGGGA  TATTAAAGGT  GGAATTGAAT  CAACTTCCGG
3451  TAATGTAAAT  ATTACAGCGA  GCGGCAATAC  ACTTAAGGTA  AGTAATATCA
3501  CTGGTCAAGA  TGTAACAGTA  ACAGCGGATG  CAGGAGCCTT  GACAACTACA
3551  GCAGGCTCAA  CCATTAGTGC  GACAACAGGC  AATGCAAATA  TTACAACCAA
3601  AACAGGTGAT  ATCAACGGTA  AAGTTGAATC  CAGCTCCGGC  TCTGTAACAC
3651  TTGTTGCAAC  TGGAGCAACT  CTTGCTGTAG  GTAATATTTC  AGGTAACACT
3701  GTTACTATTA  CTGCCGGATAG  CGGTAAATTA  ACCTCCACAG  TAGGTTCTAC
3751  AATTAATGGG  ACTAATAGTG  TAACCACCTC  AAGCCAATCA  GGCGATATTG
3801  AAGGTACAAT  TTCTGGTAAT  ACAGTAAATG  TTACAGCAAG  CACTGGTGAT
3851  TTAACTATTG  GAAATAGTGC  AAAAGTTGAA  GCGAAAAATG  GAGCTGCAAC
3901  CTTAACTGCT  GAATCAGGCA  AATTAACCAC  CCAAACAGGC  TCTAGCATTA
3951  CCTCAAGCAA  TGGTCAGACA  ACTCTTACAG  CCAAGGATAG  CAGTATCGCA
4001  GGAAACATTA  ATGCTGCTAA  TGTGACGTTA  AATACCACAG  GCACTTTAAC
4051  TACTACAGGG  GATTCAAAGA  TTAACGCAAC  CAGTGGTACC  TTAACAATCA
```

FIG. 9F.

```
4101  ATGCAAAAGA TGCCAAATTA GATGGTGCTG CATCAGGTGA CCGCACAGTA
4151  GTAAATGCAA CTAACGCAAG TGGCTCTGGT AACGTGACTG CGAAACCTC
4201  AAGCAGCGTG AATATCACCG GGGATTTAAA CACAATAAAT GGGTAAAATA
4251  TCATTTCGGA AAATGGTAGA AACACTGTGC GCTTAAGAGG CAAGGAAATT
4301  GATGTGAAAT ATATCCAACC AGGTGTAGCA AGCGTAGAAG AGGTAATTGA
4351  AGCGAAACGC GTCCTTGAGA AGGTAAAAGA TTTATCTGAT GAAGAAAGAG
4401  AAACACTAGC CAAACTTGGT GTAAGTGCTG TACGTTTCGT TGAGCCAAAT
4451  AATGCCATTA CGGTTAATAC ACAAAACGAG TTTACAACCA AACCATCAAG
4501  TCAAGTGACA ATTTCTGAAG GTAAGGCGTG TTTCTCAAGT GGTAATGGCG
4551  CACGAGTATG TACCAATGTT GCTGACGATG GACAGCAGTA GTCAGTAATT
4601  GACAAGGTAG ATTTCATCCT GCAATGAAGT CATTTTATTT TCGTATTATT
4651  TACTGTGTGG GTTAAAGTTC AGTACGGGCT TTACCCACCT TGTAAAAAAT
4701  TA
```

FIG. 10A. COMPARISON OF DERIVED AMINO ACID SEQUENCE

```
              1                                                                    50
Hmw3com       ..........  ..........  ..........  ..........  ..........
Hmw4com       ..........  ..........  ..........  ..........  ..........
Hmw1com       MNKIYRLKFS  KRLNALVAVS  ELARGCDHST  EKGSEKPARM  KVRHLALKPL
Hmw2com       MNKIYRLKFS  KRLNALVAVS  ELARGCDHST  EKGSEKPARM  KVRHLALKPL 51                                                                  100
Hmw3com       ..........  ..........  ..........  ..........  ..........
Hmw4com       ..........  ..........  ..GMSVVHGT  ATMQVDGNKT  TIRNSVNAII
Hmw1com       SAMLLSLGVT  SIPQSVLASG  LQGMSVVHGT  ATMQVDGNKT  TIRNSVNAII
Hmw2com       SAMLLSLGVT  SIPQSVLASG  LQGMSVVHGT  ATMQVDGNKT  TIRNSVNAII 101                                                                 150
Hmw3com       ..........  ..........  ..........  ..........  ..........
Hmw4com       NWKQFNIDQN  EMEQFLQESS  NSAVFNRVTS  DQISQLKGIL  DSNGQVFLIN
```

FIG. 10B.

```
Hmw1com   NWKQFNIDQN  EMVQFLQENN  NSAVFNRVTS  NQISQLKGIL  DSNGQVFLIN
Hmw2com   NWKQFNIDQN  EMVQFLQENN  NSAVFNRVTS  NQISQLKGIL  DSNGQVFLIN
                                                                 200
Hmw3com   ..........  ..........  ..........  ..........  ..........
          151
Hmw4com   PNGITIGKDA  IINTNGFTAS  TLDISNENIK  ARNFTLEQTK  DKALAEIVNH
Hmw1com   PNGITIGKDA  IINTNGFTAS  TLDISNENIK  ARNFTLEQTK  DKALAEIVNH
Hmw2com   PNGITIGKDA  IINTNGFTAS  TLDISNENIK  ARNFTLEQTK  DKALAEIVNH
                                                                 250
Hmw3com   ..........  ..........  ..........  ..........  ..........
          201
Hmw4com   GLITVGKDGS  VNLIGGKVKN  EGVISVNGGS  ISLLAGQKIT  ISDIINPTIT
Hmw1com   GLITVGKDGS  VNLIGGKVKN  EGVISVNGGS  ISLLAGQKIT  ISDIINPTIT
Hmw2com   GLITVGKDGS  VNLIGGKVKN  EGVISVNGGS  ISLLAGQKIT  ISDIINPTIT
                                                                 300
Hmw3com   ..........  INLGDIFAKG  GNINVRAATI  RNKGKLSADS  VSKDKSGNIV
          251
```

FIG. 10C.

```
Hmw4com  YSIAAPENEA  INLGDIFAKG  GNINVRAATI  RNKGKLSADS  VSKDKSGNIV
Hmw1com  YSIAAPENEA  VNLGDIFAKG  GNINVRAATI  RNKGKLSADS  VSKDKSGNIV
Hmw2com  YSIAAPENEA  VNLGDIFAKG  GNINVRAATI  RNKGKLSADS  VSKDKSGNIV
         301                                                   350
Hmw3com  LSAKEGEAEI  GGVISAQNQQ  AKGGKLMITG  DKVTLKTGAV  IDLSGKEGGE
Hmw4com  LSAKEGEAEI  GGVISAQNQQ  AKGGKLMITG  DKVTLKTGAV  IDLSGKEGGE
Hmw1com  LSAKEGEAEI  GGVISAQNQQ  AKGGKLMITG  DKVTLKTGAV  IDLSGKEGGE
Hmw2com  LSAKEGEAEI  GGVISAQNQQ  AKGGKLMITG  DKVTLKTGAV  IDLSGKEGGE
         351                                                   400
Hmw3com  TYLGGDERGE  GKNGIQLAKK  TTLEKGSTIN  VSGKEKGGRA  IVWGDIALID
Hmw4com  TYLGGDERGE  GKNGIQLAKK  TTLEKGSTIN  VSGKEKGGRA  IVWGDIALID
Hmw1com  TYLGGDERGE  GKNGIQLAKK  TTLEKGSTIN  VSGKEKGGRA  IVWGDIALID
Hmw2com  TYLGGDERGE  GKNGIQLAKK  TTLEKGSTIN  VSGKEKGGRA  IVWGDIALID
```

FIG. 10D.

```
        401                                                              450
Hmw3com  GNINAQGK.D  IAKTGGFVET  SGHYLSIDDN  AIVKTKEWLL  DPENVTIEAP
Hmw4com  GNINAQGS..D IAKTGGFVET  SGHDLSIGDD  VIVDAKEWLL  DPDDVSIETL
Hmw1com  GNINAQGSGD  IAKTGGFVET  SGHDLFIKDN  AIVDAKEWLL  DPDNVTINAE
Hmw2com  GNINAQGSGD  IAKTGGFVET  SGHYLSIESN  AIVKTKEWLL  DPDDVTIEAE 451                                                              500
Hmw3com  SASRVELGAD  RNSHSAEVIK  VTLKKNNTSL  TTLTNTTISN  LLKSAHVVNI
Hmw4com  TSGRNNTGEN  QGYTTGDGTK  ESPKGNSISK  PTLTNSTLEQ  ILRRGSYVNI
Hmw1com  TAGRSNTSED  DEYTGSGNSA  STPKRNKE.K  TTLTNTTLES  ILKKGTFVNI
Hmw2com  DPLRNNTGIN  DEFPTGTGEA  SDPKKNSELK  TTLTNTTISN  YLKNAWTMNI 501                                                              550
Hmw3com  TARRKLTVNS  SISIERGSHL  ILHSEGQGGQ  GVQIDKDITS  .E...GGNLT
Hmw4com  TANNRIYVNS  SINLSNGS.L  TLHTK...RD  GVKINGDITS  NE...NGNLT
Hmw1com  TANQRIYVNS  SINL.SNGSL  TLWSEGRSGG  GVEINNDITT  GDDTRGANLT
Hmw2com  TASRKLTVNS  SINGSNGSHL  ILHSKGQRGG  GVQIDGDIT.  ...SKGGNLT
```

FIG. 10E.

```
        551                                                         600
Hmw3com IYSGGWVDVH KNITLGS.GF LNITTKEGDI AFEDKSGR.. ..NNLTITAQ
Hmw4com IKAGSWVDVH KNITLGT.GF LNIVAGDS.V AFEREGDKAR NATDAQITAQ
Hmw1com IYSGGWVDVH KNISLGAQGN INITAKQD.I AFEKGSNQV. ......ITGQ
Hmw2com IYSGGWVDVH KNITLD.QGF LNITA.AS.V AFEGGNNKAR DANNLTITAQ 601                                                         650
Hmw3com GTITSG.NSN GFRFNNVSLN SLGGKLSFTD SREDRGRRTK GNISNKFDGT
Hmw4com GTITVNKDDK QFRFNNVSIN GTGKGLKFIA NQN....... .NFTHKFDGE
Hmw1com GTIT.SGNQK GFRFNNVSLN GTGSGLQFTT KRTN......K YAITNKFEGT
Hmw2com GTVTITGEGK DFRANNVSLN GTGKGLNIIS SVNN...... ..LTHNLSGT 651                                                         700
Hmw3com LNISGTVDIS MKAPKVSWFY RD.KGRTYWN VTTLNVTSGS KFNLSIDSTG
Hmw4com INISGIVTIN QTTKKDVKYW NA.SKDSYWN VSSLTLNTVQ KFTF.IKFVD
Hmw1com LNISGKVNIS MVLPKNESGY DKFKGRTYWN LTSLNVSESG EFNLTIDSRG
```

FIG. 10F.

```
Hmw2com  INISGNITIN QTTRKNTSYW QTSHD.SHWN VSALNLETGA NFTF.IKYIS
                                                              750
         701
Hmw3com  SGSTG...PS IRNA..ELNG ITFN....KA TFNIAQGSTA NFSIKASIMP
Hmw4com  SGSNS...QD LRSSRRSFAG VHFNGIGGKT NFNIGANAKA LFKLKPNAAT
Hmw1com  SDSAGTLTQ. ....PYNLNG ISFN....KDT TFNVERNARV NFDIKAPIGI
Hmw2com  SNSKGLTTQY RSSAGVNFNG V..N...GNM SFNLKEGAKV NFKLKPNENM 751                                                  800
Hmw3com  FKSNANYAL. FNEDISVSG. .GGSVNFKLN ASSSNIQTPG VIIKSQNFNV
Hmw4com  DPKKELPIT. FNANITATGN SDSSVMFDIH A....NLTSRA AGINMDSINI
Hmw1com  NKYSSLNYAS FNGNISVSG. .GGSVDFTLL ASSSNVQTPG VVINSKYFNV
Hmw2com  NTSKPLPI.R FLANITATG. .GGSVFFDIY ANHS...GRG AELKMSEINI 801                                                  850
Hmw3com  SGGSTLNLKA EGSTETAFSI ENDLNLNATG GNITIRQVEG T..DSRVNKG
Hmw4com  TGGLDFSITS HNRNSNAFEI KKDLTINATG SNFSLKQTKD SFYNEYSKHA
```

FIG. 10G.

```
Hmw1com  STGSSLRFKT SGSTKTGFSI EKDLTLNATG GNITLLQVEG T..DGMIGKG
Hmw2com  SNGANFTLNS HVRGDDAFKI NKDLTINATN SNFSLRQTKD DFYDGYARNA
         851                                                900

Hmw3com  VAAKKNITFK GGNITFGSQK ATTEIKGNVT INKNTNATLR GANFAEN...
Hmw4com  INSSHNLTIL GGNVTLGGEN SSSSITGNIN ITNKANVTLQ ADTSNSNTGL
Hmw1com  IVAKKNITFE GGNITFGSRK AVTEIEGNVT INNNANVTLI GSDFDNHQ..
Hmw2com  INSTYNISIL GGNVTLGGQN SSSSITGNIT IEKAANVTLE ANNAPNQQNI
         901                                                950

Hmw3com  KSPLNIAGNV INNGNLTTAG SIINIAGNLT VSKGANLQAI TNYTFNVAGS
Hmw4com  KKRTLTLGNI SVEGNLSLTG ANANIVGNLS IAEDSTFKGE ASDNLNITGT
Hmw1com  KPLTIKKDVI INSGNLTAGG NIVNIAGNLT VESNANFKAI TNFTFNVGGL
Hmw2com  RDRVIKLGSL LVNGSLSLTG ENADIKGNLT ISESATFKGK TRDTLNITGN
         951                                               1000
```

FIG. 10H.

```
Hmw3com  FDNNGASNIS  IARGGAKFK.  DINNTSSLNI  TTNSDTTYRT  IIKGNISNKS
Hmw4com  FTNNGTANIN  IKQGVVKLQG  DINNKGGLNI  TTNASGTQKT  IINGNITNEK
Hmw1com  FDNKGNSNIS  IAKGGARFK.  DIDNSKNLSI  TTNSSSTYRT  IISGNITNKN
Hmw2com  FTNNGTAEIN  ITQGVVKLG.  NVTNDGDLNI  TTHAKRNQRS  IIGGDIINNK
                                                        1001      1050

Hmw3com  GDLNIIDKKS  DAEIQIGGNI  SQKEGNLTIS  SDKVNITNQI  TIKAGVEGGR
Hmw4com  GDLNIKNIKA  DAEIQIGGNI  SQKEGNLTIS  SDKVNITNQI  TIKAGVEGGR
Hmw1com  GDLNITNEGS  DTEMQIGGDI  SQKEGNLTIS  SDKINITKQI  TIKAGVDGEN
Hmw2com  GSLNITDSNN  DAEIQIGGNI  SQKEGNLTIS  SDKINITKQI  TIKKGIDGED
                                                        1051      1100

Hmw3com  SDSSEAEANAN  LTIQTKELKL  AGDLNISGFN  KAEITAKNGS  DLTIGNASGG
Hmw4com  SDSSEAENAN  LTIQTKELKL  AGDLNISGFN  KAEITAKNGS  DLTIGNASGG
Hmw1com  SDSDATNNAN  LTIKTKELKL  TQDLNISGFN  KAEITAKDGS  DLTIGNTNSA
Hmw2com  SSSDATSNAN  LTIKTKELKL  TEDLSISGFN  KAEITAKDGR  DLTIGNSNDG
```

FIG. 10I.

```
         1101                                                                    1150
Hmw3com  N..ADAKKVT  FDKVKDSKIS  TDGHNVTLNS  EVKT..SNGS  SNAGNDNSTG
Hmw4com  N..ADAKKVT  FDKVKDSKIS  TDGHNVTLNS  EVKT..SNGS  SNAGNDNSTG
Hmw1com  D.GTNAKKVT  FNQVKDSKIS  ADGHKVTLHS  KVETSGSNNN  TEDSSDNNAG
Hmw2com  NSGAEAKKVT  FNNVKDSKIS  ADGHNVTLNS  KVKTSSSNGG  RESNSDNDTG 1151                                                                    1200
Hmw3com  LTISAKDVTV  NNNVTSHKTI  NISAAAGNVT  TKEGTTINAT  TGSVEVTAQN
Hmw4com  LTISAKDVTV  NNNVTSHKTI  NISAAAGNVT  TKEGTTINAT  TGSVEVTAQN
Hmw1com  LTIDAKNVTV  NNNITSHKAV  SISATSGEIT  TKTGTTINAT  TGNVEIT....
Hmw2com  LTITAKNVEV  NKDVTSLKTV  NITA.SEKVT  TTAGSTINAT  NGKASIT....

1201                                                                    1250
Hmw3com  GTIKGNITSQ  NVTVTATENL  VTTENAVINA  TSGTVNISTK  TGDIKGGIES
Hmw4com  GTIKGNITSQ  NVTVTATENL  VTTENAVINA  TSGTVNISTK  TGDIKGGIES
Hmw1com  ..........  ..........  ..........  .........AQ  TGDIKGGIES
```

FIG. 10J.

```
                                                                                              1300
Hmw2com  ..........  ..........  ..........  ..........  ..........  .......TK  T.........

1251
Hmw3com  TSGNVNITAS  GNTLKVSNIT  GQDVTVTADA  GALTTTAGST  ISATTGNANI
Hmw4com  TSGNVNITAS  GNTLKVSNIT  GQDVTVTADA  GALTTTAGST  ISATTGNANI
Hmw1com  SSGSVTLTAT  EGALAVSNIS  GNTVTVTANS  GALTTLAGST  IKG.TESVTT
Hmw2com  ..........  ..........  ..........  ..........  ..........

1350
Hmw3com  TTKTGDINGK  VESSSGSVTL  VATGATLAVG  NISGNTVTIT  ADSGKLTSTV
Hmw4com  TTKTGDINGK  VESSSGSVTL  VATGATLAVG  NISGNTVTIT  ADSGKLTSTV
Hmw1com  SSQSGDIG..  ..........  .........G  TISGGTVEVK  ATESLTTQSN
Hmw2com  ....GDIS..  ..........  .........G  TISGNTVSVS  ATVDLTTKSG 1351                                                                                 1400
Hmw3com  GSTINGTNSV  TTSSQSGDIE  GTISGNTVNV  TASTGDLTIG  NSAKVEAKNG
Hmw4com  GSTINGTNSV  TTSSQSGDIE  GTISGNTVNV  TASTGDLTIG  NSAKVEAKNG
```

FIG. 10K.

```
Hmw1com  SKIKATTGEA NVTSATGTIG GTISGNTVNV TANAGDLTVG NGAEINATEG
Hmw2com  SKIEAKSGEA NVTSATGTIG GTISGNTVNV TANAGDLTVG NGAEINATEG
         1401                                              1450

Hmw3com  AATLTAESGK LTTQTGSSIT SSNGQTTLTA KDSSIAGNIN AANVTLNTTG
Hmw4com  AATLTAESGK LTTQTGSSIT SSNGQTTLTA KDSSIAGNIN AANVTLNTTG
Hmw1com  AATLTTSSGK LTTEASSHIT SAKGQVNLSA QDSSVAGSIN AANVTLNTTG
Hmw2com  AATLTATGNT LTTEAGSSIT STKGQVDLLA QNSSIAGNIN AANVTLNTTG
         1451                                              1500

Hmw3com  TLTTTGDSKI NATSGTLTIN AKDAKLDGAA SGDRTVVNAT NASGSGNVTA
Hmw4com  TLTTTGDSKI NATSGTLTIN AKDAKLDGAA SGDRTVVNAT NASGSGNVTA
Hmw1com  TLTTVKGSNI NATSGTLTIN AKDAELNGAA LGNHTVVNAT NANGSGSVIA
Hmw2com  TLTTVAGSDI KATSGTLTIN AKDAKLNGDA SGDSTEVNAV NASGSGVTA
         1501                                              1550
```

FIG. 10L.

```
Hmw3com  KTSSSVNITG  DLNTINGLNI  ISENGRNTVR  LRGKEIDVKY  IQPGVASVEE
Hmw4com  KTSSSVNITG  DLNTINGLNI  ISENGRNTVR  LRGKEIDVKY  IQPGVASVEE
Hmw1com  TTSSRVNITG  DLITINGLNI  ISKNGINTVL  LKGVKIDVKY  IQPGIASVDE
Hmw2com  ATSSSVNITG  DLNTVNGLNI  ISKDGRNTVR  LRGKEIEVKY  IQPGVASVEE
         1551                                                 1600

Hmw3com  VIEAKRVLEK  VKDLSDEERE  TLAKLGVSAV  RFVEPNNAIT  VNTQNEFTTK
Hmw4com  VIEAKRVLEK  VKDLSDEERE  TLAKLGVSAV  RFVEPNNAIT  VNTQNEFTTK
Hmw1com  VIEAKRILEK  VKDLSDEERE  ALAKLGVSAV  RFIEPNNTIT  VDTQNEFATR
Hmw2com  VIEAKRVLEK  VKDLSDEERE  TLAKLGVSAV  RFVEPNNTIT  VNTQNEFTTR
         1601                                                 1632

Hmw3com  PSSQVTISEG  KACFSSGNGA  RVCTNVADDG  QQ
Hmw4com  PSSQVTISEG  KACFSSGNGA  RVCTNVADDG  QQ
Hmw1com  PLSRIVISEG  RACFSNSDGA  TVCVNIADNG  R.
Hmw2com  PSSQVIISEG  KACFSSGNGA  RVCTNVADDG  QP
```

WESTERN IMMUNOBLOT ASSAY OF PHAGE LYSATES CONTAINING EITHER THE HMW1 OR HMW2 RECOMBINANT PROTEINS. LYSATES WERE PROBED WITH AN *E. COLI*-ABSORBED ADULT SERUM SAMPLE WITH HIGH-TITER ANTIBODY AGAINST HIGH-MOLECULAR-WEIGHT PROTEINS. THE ARROWS INDICATE THE MAJOR IMMUNOREACTIVE PROTEIN BANDS OF 125 AND 120 kDa IN THE HMW1 AND HMW2 LYSATES, RESPECTIVELY.

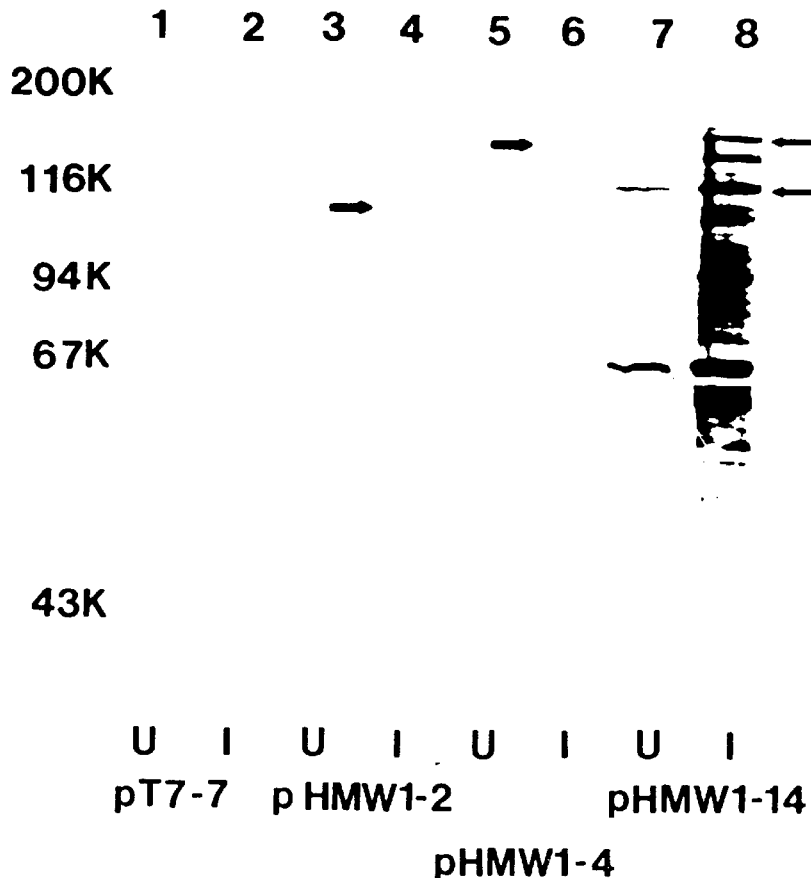

FIG. 12

WESTERN IMMUNOBLOT ASSAY OF CELL SONICATES PREPARED FROM E. COLI TRANSFORMED WITH PLASMID pT7-7 ( LANES 1 AND 2 ) pHMW1-2 (LANES 3 AND 4), pHMW1-4 ( LANES 5 AND 6), OR pHMW1-14 ( LANES 7 AND 8 ). THE SONICATES WERE PROBED WITH AN E. COLI-ABSORBED ADULT SERUM SAMPLE WITH HIGH -TITER ANTIBODY AGAINST HIGH - MOLECULAR -WEIGHT PROTEINS. LANES LABELED U AND I REPRESENT SONICATES PREPARED BEFORE AND AFTER INDUCTION OF THE GROWING SAMPLES WITH IPTG, RESPECTIVELY. THE ARROWS INDICATE PROTEIN BANDS OF INTEREST AS DESCRIBED IN THE TEXT.

FIG. 13

ELISA WITH rHMW1 ANTISERUM ASSAYED AGAINST PURIFIED FILAMENTOUS HEMAGLUTININ OF B. *PERTUSSIS*. Ab, ANTIBODY.

WESTERN IMMUNOBLOT ASSAY OF CELL SONICATES FROM A PANEL OF EPIDEMIOLOGICALLY UNRELATED NONTYPEABLE *H. INFLUENZAE* STRAINS. THE SONICATES WERE PROBED WITH RABBIT ANTISERUM PREPARED AGAINST HMW1-4 RECOMBINANT PROTEIN. THE STRAIN DESIGNATIONS ARE INDICATED BY THE NUMBERS BELOW EACH LANE.

200K

116K

94K

67K

43K

5    7   12  14  15  16  17  18

WESTERN IMMUNOBLOT ASSAY OF CELL SONICATES FROM A PANEL OF EPIDEMIOLOGICALLY UNRELATED NONTYPEABLE H. INFLUENZAE STRAINS. THE SONICATES WERE PROBED WITH MONOCLONAL ANTIBODY X3C, A MURINE IgG ANTIBODY WHICH RECOGNIZES THE FILAMENTOUS HEMAGGLUTININ OF B. PERTUSSIS (13). THE STRAIN DESIGNATIONS ARE INDICATED BY THE NUMBERS BELOW EACH LANE.

IMMUNOBLOT ASSAY OF CELL SONICATES OF NONTYPABLE *H. INFLUENZAE* STRAIN 12 DERIVATIVES. THE SONICATES WERE PROBED WITH RABBIT ANTISERUM PREPARED AGAINST HMW-1 RECOMBINANT PROTEIN. LANES: 1, WILD-TYPE STRAIN; 2, HMW-2⁻ MUTANT; 3, HMW-1⁻ MUTANT; 4, HMW-1⁻ / HMW-2⁻ DOUBLE MUTANT.

IMMUNOELECTRON MICROSCOPY WITH Mab AD6

WESTERN IMMUNOBLOT ASSAY WITH Mab AD6 AND HMW1A OR HMW2A RECOMBINANT PROTEINS

WESTERN IMMUNOBLOT ASSAY WITH Mab 10C5 AND HMW1A OR HMW2A RECOMBINANT PROTEINS

WESTERN IMMUNOBLOT ASSAY WITH Mab AD6 AND TEN UNRELATED NONTYPABLE *HAEMOPHILUS INFLUENZAE*

HIGH MOLECULAR WEIGHT SURFACE PROTEINS OF NON-TYPEABLE HAEMOPHILUS

REFERENCE TO RELATED APPLICATION

This application is a continuation-in-part of U.S. patent application Ser. No. 08/302,832 filed Oct. 5, 1994, now U.S. Pat. No. 5,603,938, which is a continuation of PCT/US93/02166 filed Mar. 16, 1993.

FIELD OF INVENTION

This invention relates to high molecular weight proteins of non-typeable haemophilus.

BACKGROUND TO THE INVENTION

Non-typeable *Haemophilus influenzae* are non-encapsulated organisms that are defined by their lack of reactivity with antisera against known *H. influenzae* capsular antigens.

These organisms commonly inhabit the upper respiratory tract of humans and are frequently responsible for a variety of common mucosal surface infections, such as otitis media, sinusitis, conjunctivitis, chronic bronchitis and pneumonia. Otitis media remains an important health problem for children and most children have had at least one episode of otitis by their third birthday and approximately one-third of children have had three or more episodes. Non-typeable *Haemophilus influenzae* generally accounts for about 20 to 25% of acute otitis media and for a larger percentage of cases of chronic otitis media with effusion.

A critical first step in the pathogenesis of these infections is colonization of the respiratory tract mucosa. Bacterial surface molecules which mediate adherence, therefore, are of particular interest as possible vaccine candidates.

Since the non-typeable organisms do not have a polysaccharide capsule, they are not controlled by the present *Haemophilus influenzae* type b (Hib) vaccines, which are directed towards Hib bacterial capsular polysaccharides. The non-typeable strains, however, do produce surface antigens that can elicit bactericidal antibodies. Two of the major outer membrane proteins, P2 and P6, have been identified as targets of human serum bactericidal activity. However, it has been shown that the P2 protein sequence is variable, in particular in the non-typeable Haemophilus strains. Thus, a P2-based vaccine would not protect against all strains of the organism.

There have previously been identified by Barenkamp et al (*Pediatr. Infect. Dis. J.*, 9:333–339, 1990) a group of high-molecular-weight (HMW) proteins of non-typeable *Haemophilus influenzae* that appeared to be major targets of antibodies present in human convalescent sera. Examination of a series of middle ear isolates revealed the presence of one or two such proteins in most strains. However, prior to the present invention, the structures of these proteins and their encoding nucleic acid sequences were unknown as were pure isolates of such proteins. In addition, the identification of surface accessible epitopes of such proteins was unknown.

SUMMARY OF INVENTION

The inventor, in an effort to further characterize the high molecular weight (HMW) non-typeable Haemophilus proteins, has cloned, expressed and sequenced the genes coding for two immunodominant HMW proteins (designated HMW1 and HMW2) from a prototype non-typeable Haemophilus strain and has cloned, expressed and sequenced the genes coding for two additional immunodominant HMW proteins (designated HMW3 and HMW4) from another non-typeable Haemophilus strain.

In accordance with one aspect of the present invention, therefore, there is provided an isolated and purified nucleic acid molecule coding for a high molecular weight protein of a non-typeable Haemophilus strain, particularly a nucleic acid molecule coding for protein HMW1, HMW2, HMW3 or HMW4, as well as any variant or fragment of such protein which retains the immunological ability to protect against disease caused by a non-typeable Haemophilus strain.

The nucleic acid molecule may have a DNA sequence shown in FIG. 1 (SEQ ID No: 1) and encoding HMW1 for strain 12 having the derived amino acid sequence of FIG. 2 (SEQ ID No: 2). The nucleic acid molecule may have the DNA sequence shown in FIG. 3 (SEQ ID No: 3) and encoding protein HMW2 for strain 12 having the derived amino acid sequence of FIG. 4 (SEQ ID No: 4). The nucleic acid molecule may have the DNA sequence shown in FIG. 8 (SEQ ID No: 7) and encoding HMW3 for strain 5 having the derived amino acid sequence of FIG. 10 (SEQ ID No: 9). The nucleic acid molecule may have a DNA sequence shown in FIG. 9 (SEQ ID No: 8) and encoding protein HMW4 for strain 5 having the derived amino acid sequence of FIG. 10 (SEQ ID No: 10).

In another aspect of the invention, there is provided an isolated and purified nucleic acid molecule encoding a high molecular weight protein of a non-typeable Haemophilus strain, which is selected from the group consisting of:

(a) a DNA sequence as shown in any one of FIGS. 1, 3, 8 and 9 (SEQ ID Nos: 1, 3, 7 and 8);

(b) a DNA sequence encoding an amino acid sequence as shown in any one of FIGS. 2, 4 and 10 (SEQ ID Nos: 2, 4, 9 and 10); and (c) a DNA sequence which hybridizes under stringent conditions to any one of the sequences of (a) and (b).

A DNA sequence according to (c) may be one having at least about 90% identity of sequence to the DNA sequences (a) or (b).

The inventor has further found correct processing of the HMW protein requires the presence of additional downstream nucleic acid sequences. Accordingly, a further aspect of the present invention provides an isolated and purified gene cluster comprising a first nucleotide sequence encoding a high molecular weight protein of a non-typeable Haemophilus strain and at least one downstream nucleotide sequence for effecting expression of a gene product of the first nucleotide sequence fully encoded by the structural gene.

The gene cluster may comprise a DNA sequence encoding high molecular weight protein HMW1 or HMW2 and two downstream accessory genes. The gene cluster may have the DNA sequence shown in FIG. 6 (SEQ ID No: 5) or FIG. 7 (SEQ ID No. 6).

In an additional aspect, the present invention includes a vector adapted for transformation of a host, comprising a nucleic acid molecule as provided herein, particularly the gene cluster provided herein. The vector may be an expression vector or a plasmid adapted for expression of the encoded high molecular weight protein, fragments or analogs thereof, in a heterologous or homologous host and comprising expression means operatively coupled to the nucleic acid molecule. The expression means may include a nucleic acid portion encoding a leader sequence for secretion from the host of the high molecular weight protein. The expression means may include a nucleic acid portion encoding a lipidation signal for expression from the host of a lipidated form of the high molecular weight protein. The host may be selected from, for example, *E. coli*, Bacillus, Haemophilus, fungi, yeast, baculovirus and Semliki Forest Virus expression systems. The invention further includes a recombinant high molecular weight protein of non-typeable Haemophilus or fragment or analog thereof producible by the transformed host.

In another aspect, the invention provides an isolated and purified high molecular weight protein of non-typeable *Haemophilus influenzae* which is encoded by a nucleic acid molecule as provided herein. Such high molecular weight proteins may be produced recombinantly to be devoid of non-high molecular weight proteins of non-typeable *Haemophilus influenzae* or from natural sources.

Such protein may be characterized by at least one surface-exposed B-cell epitope which is recognized by monoclonal antibody AD6. Such protein may be HMW1 encoded by the DNA sequence shown in FIG. 1 (SEQ ID No: 1) and having the derived amino acid sequence of FIG. 2 (SEQ ID No: 2) and having an apparent molecular weight of 125 kDa. Such protein may be HMW2 encoded by the DNA sequence shown in FIG. 3 (SEQ ID No: 3) and having the derived amino acid sequence of FIG. 4 (SEQ ID No: 4) and having an apparent molecular weight of 120 kDA. Such protein may be HMW3 encoded by the DNA sequence shown in FIG. 8 (SEQ ID No: 7) and having the derived amino acid sequence of FIG. 10 (SEQ ID No: 9) and having an apparent molecular weight of 125 kDa. Such protein may be HMW4 encoded by the DNA sequence shown in FIG. 9 (SEQ ID No: 8) and having the derived amino acid sequence shown in FIG. 10 (SEQ ID No: 10) and having the apparent molecular weight of 123 kDa.

A further aspect of the invention provides an isolated and purified high molecular weight protein of non-typeable *Haemophilus influenzae* which is antigenically related to the filamentous hemagglutinin surface protein of *Bordetella pertussis*, particularly HMW1, HMW2, HMW3 or HMW4.

The novel high molecular weight proteins of non-typeable Haemophilus may be used as carrier molecules by linking to an antigen, hapten or polysaccharide for eliciting an immune response to the antigen, hapten or polysaccharide. An example of such polysaccharide is a protective polysaccharide against *Haemophilus influenzae* type b.

In a further aspect of the invention, there is provided a synthetic peptide having an amino acid sequence containing at least six amino acids and no more than 150 amino acids and corresponding to at least one protective epitope of a high molecular weight protein of non-typeable *Haemophilus influenzae*, specifically HMW1, HMW2, HMW3 or HMW4. The epitope may be one recognized by at least one of the monoclonal antibodies AD6 (ATCC) and 10C5. Specifically, the epitope may be located within 75 amino acids of the carboxy terminus of the HMW1 or HMW2 protein and recognized by the monoclonal antibody AD6.

The present invention also provides an immunogenic composition comprising an immunoeffective amount of an active component, which may be the novel high molecular weight protein or synthetic peptide provided herein, which may be formulated along with a pharmaceutically acceptable carrier therefor. The immunogenic composition may be formulated as a vaccine for in vivo administration to a host.

The immunogenic composition may be formulated as a microparticle, capsule, ISCOM or liposome preparation. The immunogenic composition may be used in combination with a targeting molecule for delivery to specific cells of the immune system or to mucosal surfaces. Some targeting molecules include vitamin B12 and fragments of bacterial toxins, as described in WO 92/17167 (Biotech Australia Pty. Ltd.), and monoclonal antibodies, as described in U.S. Pat. No. 5,194,254 (Barber et al). The immunogenic compositions of the invention (including vaccines) may further comprise at least one other immunogenic or immunostimulating material and the immunostimulating material may be at least one adjuvant.

Suitable adjuvants for use in the present invention include, (but are not limited to) aluminum phosphate, aluminum hydroxide, QS21, Quil A, derivatives and components thereof, ISCOM matrix, calcium phosphate, calcium hydroxide, zinc hydroxide, a glycolipid analog, an octadecyl ester of an amino acid, a muramyl dipeptide polyphosphazare, ISCOPRP, DC-chol, DDBA and a lipoprotein and other adjuvants to induce a Th1 response. Advantageous combinations of adjuvants are described in copending U.S. patent application Ser. No. 08/261,194 filed Jun. 16, 1994, assigned to Connaught Laboratories Limited and the disclosure of which is incorporated herein by reference.

In a further aspect of the invention, there is provided a method of generating an immune response in a host, comprising administering thereto an immuno-effective amount of the immunogenic composition as provided herein. The immune response may be a humoral or a cell-mediated immune response. Hosts in which protection against disease may be conferred include primates including humans.

The present invention additionally provides a method of producing antibodies specific for a high molecular weight protein of non-typeable *Haemophilus influenzae*, comprising:

(a) administering the high molecular weight protein or epitope containing peptide provided herein to at least one mouse to produce at least one immunized mouse;

(b) removing B-lymphocytes from the at least one immunized mouse;

(c) fusing the B-lymphocytes from the at least one immunized mouse with myeloma cells, thereby producing hybridomas;

(d) cloning the hybridomas;

(e) selecting clones which produce anti-high molecular weight protein antibody;

(f) culturing the anti-high molecular weight protein antibody-producing clones; and then (g) isolating anti-high molecular weight protein antibodies from the cultures.

Additional aspects of the present invention include monoclonal antibody AD6 and monoclonal antibody 10C5.

The present invention provides, in an additional aspect thereof, a method for producing an immunogenic composition, comprising administering the immunogenic composition provided herein to a first test host to determine an amount and a frequency of administration thereof to elicit a selected immune response against a high molecular weight protein of non-typeable *Haemophilus influenzae;* and formulating the immunogenic composition in a form suitable for administration to a second host in accordance with the determined amount and frequency of administration. The second host may be a human.

The novel envelope protein provided herein is useful in diagnostic procedures and kits for detecting antibodies to high molecular weight proteins of non-typeable *Haemophilus influenzae*. Further monoclonal antibodies specific for the high molecular protein or epitopes thereof are useful in diagnostic procedure and kits for detecting the presence of the high molecular weight protein.

Accordingly, a further aspect of the invention provides a method of determining the presence in a sample, of antibodies specifically reactive with a high molecular weight protein of *Haemophilus influenzae* comprising the steps of:

(a) contacting the sample with the high molecular weight protein or epitope-containing peptide as provided herein to produce complexes comprising the protein and any said antibodies present in the sample specifically reactive therewith; and (b) determining production of the complexes.

In a further aspect of the invention, there is provided a method of determining the presence, in a sample, of a high molecular weight protein of *Haemophilus influenzae* or an epitope-containing peptide, comprising the steps of:

(a) immunizing a host with the protein or peptide as provided herein, to produce antibodies specific for the protein or peptide;

(b) contacting the sample with the antibodies to produce complexes comprising any high molecular weight protein or epitope-containing peptide present in the sample and said specific antibodies; and (c) determining production of the complexes.

A further aspect of the invention provides a diagnostic kit for determining the presence of antibodies in a sample specifically reactive with a high molecular weight protein of non-typeable *Haemophilus influenzae* or epitope-containing peptide, comprising:

(a) the high molecular weight protein or epitope-containing peptide as provided herein;

(b) means for contacting the protein or peptide with the sample to produce complexes comprising the protein or peptide and any said antibodies present in the sample; and (c) means for determining production of the complexes.

The invention also provides a diagnostic kit for detecting the presence, in a sample, of a high molecular weight protein of *Haemophilus influenzae* or epitope-containing peptide, comprising:

(a) an antibody specific for the novel envelope protein as provided herein;

(b) means for contacting the antibody with the sample to produce a complex comprising the protein or peptide and protein-specific antibody; and (c) means for determining production of the complex.

In this application, the term "high molecular weight protein" is used to define a family of high molecular weight proteins of *Haemophilus influenzae*, generally having an apparent molecular weight of from about 120 to about 130 kDa and includes proteins having variations in their amino acid sequences. In this application, a first protein or peptide is a "functional analog" of a second protein or peptide if the first protein or peptide is immunologically related to and/or has the same function as the second protein or peptide. The functional analog may be, for example, a fragment of the protein or a substitution, addition or deletion mutant thereof. The invention also extends to such functional analogs.

Advantages of the present invention include:

an isolated and purified envelope high molecular weight protein of *Haemophilus influenzae* produced recombinantly to be devoid of non-high molecular weight proteins of *Haemophilus influenzae* or from natural sources as well as nucleic acid molecules encoding the same;

high molecular weight protein specific human monoclonal antibodies which recognize conserved epitopes in such protein; and diagnostic kits and immunological reagents for specific identification of hosts infected by *Haemophilus influenzae*.

BRIEF DESCRIPTION OF DRAWINGS

FIGS. 1A to 1G contain the DNA sequence of a gene coding for protein HMW1 (SEQ ID No: 1). The hmw1A open reading frame extends from nucleotides 351 to 4958;

FIGS. 2A and 2B contain the derived amino acid sequence of protein HMW1 (SEQ ID No: 2);

FIGS. 3A to 3G contain the DNA sequence of a gene coding for protein HMW2 (SEQ ID No: 3). The open hmw2A open reading frame extends from nucleotides 382 to 4782;

FIGS. 4A and 4B contain the derived amino acid sequence of HMW2 (SEQ ID No: 4);

FIG. 5A shows restriction maps of representative recombinant phages which contained the HMW1 or HMW2 structural genes and of HMW1 plasmid subclones. The shaded boxes indicate the location of the structural genes. In the recombinant phage, transcription proceeds from left to right for the HMW1 gene and from right to left for the HMW2 gene;

FIG. 5B shows the restriction map of the T7 expression vector pT7-7. This vector contains the T7 RNA polymerase promoter $\Phi10$, a ribosomal binding site (rbs) and the translational start site for the T7 gene 10 protein upstream from a multiple cloning site;

FIGS. 6A to 6L contain the DNA sequence of a gene cluster for the hmw1 gene (SEQ ID NO: 5), comprising nucleotides 351 to 4958 (ORF a) (as in FIG. 1), as well as two additional downstream genes in the 3' flanking region, comprising ORFs b, nucleotides 5114 to 6748 and c nucleotides 7062 to 9011;

FIGS. 7A to 7L contain the DNA sequence of a gene cluster for the hmw2 gene (SEQ ID NO: 6), comprising nucleotides 792 to 5222 (ORF a) (as in FIG. 3), as well as two additional downstream genes in the 3' flanking region, comprising ORFs b, nucleotides 5375 to 7009, and c, nucleotides 7249 to 9198;

FIGS. 8A–8F contain the DNA sequence of a gene coding for protein HMW3 (SEQ ID NO: 7);

FIGS. 9A–9F contain the DNA sequence of a gene coding for protein HMW4 (SEQ ID NO: 8);

FIGS. 10A to 10L contain a comparison table for the derived amino acid sequence for proteins HMW1 (SEQ ID No: 2), HMW2 (SEQ ID No: 4), HMW3 (SEQ ID No: 9) and HMW4 (SEQ ID No: 10);

FIG. 11 illustrates a Western immunoblot assay of phage lysates containing either the HMW1 or HMW2 recombinant proteins. Lysates were probed with an *E. coli*-absorbed adult serum sample with high-titer antibody against high molecular weight proteins. The arrows indicate the major immunoreactive bands of 125 and 120 kDa in the HMW1 and HMW2 lysates respectively;

FIG. 12 is a Western immunoblot assay of cell sonicates prepared from *E. coli* transformed with plasmid pT7-7 (lanes 1 and 2), pHMW1-2 (lanes 3 and 4), pHMW1-4 (lanes 5 and 6) or pHMW1-14 (lanes 7 and 8). The sonicates were probed with an *E. coli*-absorbed adult serum sample with high-titer antibody against high-molecular weight proteins.

Lanes labelled U and I sequence sonicates prepared before and after indication of the growing samples with IPTG, respectively. The arrows indicate protein bands of interest as discussed below;

FIG. 13 is a graphical illustration of an ELISA with rHMW1 antiserum assayed against purified filamentous haemagglutinin of *B. pertussis*. Ab=antibody;

FIG. 14 is a Western immunoblot assay of cell sonicates from a panel of epidemiologically unrelated non-typeable *H. influenzae* strains. The sonicates were probed with rabbit antiserum prepared against HMW1-4 recombinant protein. The strain designations are indicated by the numbers below each line;

FIG. 15 is a Western immunoblot assay of cell sonicates from a panel of epidemiologically unrelated non-typeable *H. influenzae* strains. The sonicates were probed with monoclonal antibody X3C, a murine 1gG antibody which recognizes the filamentous hemagglutinin of *B. pertussis*. The strain designations are indicated by the numbers below each line;

FIG. 16 shows an immunoblot assay of cell sonicates of non-typeable *H. influenzae* strain 12 derivatives. The sonicates were probed with rabbit antiserum prepared against HMW-1 recombinant protein. Lanes: 1, wild-type strain; 2, HMW2$^-$ mutant; 3, HMW1$^-$ mutant; 4. HMW1$^-$ HMW2$^-$ double mutant;

FIG. 17 shows middle ear bacterial counts in PBS-immunized control animals (left panel) and HMW1/HMW2-immunized animals (right panel) seven days after middle ear inoculation with non-typeable *Haemophilus influenzae* strain 12. Data are log-transformed and the horizontal lanes indicate the means and standard deviations of middle ear fluid bacterial counts for only the infected animals in each group;

FIG. 18 is a schematic diagram of pGEMEX®-hmw1 recombinant plasmids. The restriction enzymes are B-BamHI, E-EcoRI, C-ClaI, RV-EcoRV, Bst-BstEII and H-HindIII;

FIG. 19 is a schematic diagram of pGEMEX®-hmw2 recombinant plasmids. The restriction enzymes are E-EcoRI, H-HindIII, Hc-HincII, M-MluI and X-XhoI;

FIG. 20 is an immunoelectron micrograph of representative non-typeable *Haemophilus influenzae* strains after incubation with monoclonal antibody AD6 followed by incubation with goat anti-mouse IgG conjugated with 10-nm colloidal gold particles. Strains are: upper left panel-strain 12; upper right panel-strain 12 mutant deficient in expression of the high molecular weight proteins; lower left panel-strain 5; lower right panel-strain 15;

FIG. 21 is a Western immunoblot assay with Mab AD6 and HMW1 or HMW2 recombinant proteins. The upper left panel indicates the segments of hmw1A or hmw2A structural genes which are being expressed in the recombinant proteins. The lane numbers correspond to the indicated segments;

FIG. 22 is a Western immunoblot assay with MAb 10C5 and HMW1 or HMW2 recombinant proteins. The upper panel indicates the segments of the hmw1A or hmw2A structural genes which are being expressed in the recombinant proteins. The lane numbers correspond to the indicated segments; and FIG. 23 is a Western immunoblot assay with MAb AD6 and a panel of unrelated non-typeable *Haemophilus influenzae* strains which express HMW1/HMW-2 like protein. Cell sonicates were prepared from freshly grown samples of each strain prior to analysis in the Western blot.

GENERAL DESCRIPTION OF INVENTION

The DNA sequences of the genes coding for the HMW1 and HMW2 proteins of non-typeable *Haemophilus influenzae* strain 12, shown in FIGS. 1 and 3 respectively, were shown to be about 80% identical, with the first 1259 base pairs of the genes being identical. The open reading frame extend from nucleotides 351 to 4958 and from nucleotide 382 to 4782 respectively. The derived amino acid sequences of the two HMW proteins, shown in FIGS. 2 and 4 respectively, are about 70% identical. Furthermore, the encoded proteins are antigenically related to the filamentous hemagglutinin surface protein of *Bordetella pertussis*. A monoclonal antibody prepared against filamentous hemagglutinin (FHA) of *Bordetella pertussis* was found to recognize both of the high molecular weight proteins. This data suggests that the HMW and FHA proteins may serve similar biological functions. The derived amino acid sequences of the HMW1 and HMW2 proteins show sequence similarity to that for the FHA protein. It has further been shown that these antigenically-related proteins are produced by the majority of the non-typeable strains of Haemophilus. Antisera raised against the protein expressed by the HMW1 gene recognizes both the HMW2 protein and the *B. pertussis* FHA. The present invention includes an isolated and purified high molecular weight protein of non-typeable haemophilus which is antigenically related to the *B. pertussis* FHA and which may be obtained from natural sources or produced recombinantly.

A phage genomic library of a known strain of non-typeable Haemophilus was prepared by standard methods and the library was screened for clones expressing high molecular weight proteins, using a high titre antiserum against HMW's. A number of strongly reactive DNA clones were plaque-purified and sub-cloned into a T7 expression plasmid. It was found that they all expressed either one or the other of the two high-molecular-weight proteins designated HMW1 and HMW2, with apparent molecular weights of 125 and 120 kDa, respectively, encoded by open reading frames of 4.6 kb and 4.4 kb, respectively.

Representative clones expressing either HMW1 or HMW2 were further characterized and the genes isolated, purified and sequenced. The DNA sequence of HMW1 is shown in FIG. 1 and the corresponding derived amino acid sequence in FIG. 2. Similarly, the DNA sequence of HMW2 is shown in FIG. 3 and the corresponding derived amino acid sequence in FIG. 4. Partial purification of the isolated proteins and N-terminal sequence analysis indicated that the expressed proteins are truncated since their sequence starts at residue number 442 of both full length HMW1 and HMW2 gene products.

Subcloning studies with respect to the hmw1 and hmw2 genes indicated that correct processing of the HMW proteins required the products of additional downstream genes. It has been found that both the hmw1 and hmw2 genes are flanked by two additional downstream open reading frames (ORFs), designated b and c, respectively, (see FIGS. 6 and 7).

The b ORFs are 1635 bp in length, extending from nucleotides 5114 to 6748 in the case of hmw1 and nucleotides 5375 to 7009 in the case of hmw2, with their derived amino acid sequences being 99% identical. The derived amino acid sequences demonstrate similarity with the derived amino acid sequences of two genes which encode proteins required for secretion and activation of hemolysins of *P. mirabilis* and *S. marcescens*.

The c ORFs are 1950 bp in length, extending from nucleotides 7062 to 9011 in the case of hmw1 and nucleotides 7249 to 9198 in the case of hmw2, with their derived amino acid sequences 96% identical. The hmw1c ORF is preceded by a series of 9 bp direct tandem repeats. In plasmid subclones, interruption of the hmw1 b or c ORF results in defective processing and secretion of the hmw1 structural gene product.

The two high molecular weight proteins HMW1 and HMW2 have been isolated and purified by the procedures described below in the Examples and shown to be protective against otitis media in chinchillas and to function as adhesins. These results indicate the potential for use of such high molecular proteins and structurally-related proteins of other non-typeable strains of Haemophilus influenzae as components in immunogenic compositions for protecting a susceptible host, such as a human infant, against disease caused by infection with non-typeable Haemophilus influenzae.

Since the proteins provided herein are good cross-reactive antigens and are present in the majority of non-typeable Haemophilus strains, it is evident that these HMW proteins may become integral constituents of a universal Haemophilus vaccine. Indeed, these proteins may be used not only as protective antigens against otitis, sinusitis and bronchitis caused by the non-typeable Haemophilus strains, but also may be used as carriers for the protective Hib polysaccharides in a conjugate vaccine against meningitis. The proteins also may be used as carriers for other antigens, haptens and polysaccharides from other organisms, so as to induce immunity to such antigens, haptens and polysaccharides.

The nucleotide sequences encoding two high molecular weight proteins of a different non-typeable Haemophilus strain (designated HMW3 and HMW4), namely strain 5 have been elucidated, and are presented in FIGS. 8 and 9 (SEQ ID Nos: 7 and 8). HMW3 has an apparent molecular weight of 125 kDa while HMW4 has an apparent molecular weight of 123 kDa. These high molecular weight proteins are antigenically related to the HMW1 and HMW2 proteins and to FHA. FIG. 10 contains a multiple sequence comparison of the derived amino acid sequences for the four high molecular weight proteins identified herein (HMW1, SEQ ID No: 2; HMW2, SEQ ID No: 4; HMW3, SEQ ID No: 9; HMW4, SEQ ID No. 10). As may be seen from this comparison, stretches of identical amino acid sequence may be found throughout the length of the comparison, with HMW3 more closely resembling HMW1 and HMW4 more closely resembling HMW2. This information is highly suggestive of a considerable sequence homology between high molecular weight proteins from various non-typeable Haemophilus strains. This information is also suggestive that the HMW3 and HMW4 proteins will have the same immunological properties as the HMW1 and HMW2 proteins and that corresponding HMW proteins from other non-typeable Haemophilus strains will have the same immunological properties as the HMW1 and HMW2 proteins.

In addition, mutants of non-typeable H. influenzae strains that are deficient in expression of HMW1 or HMW2 or both have been constructed and examined for their capacity to adhere to cultured human epithelial cells. The hmw1 and hmw2 gene clusters have been expressed in E. coli and have been examined for in vitro adherence. The results of such experimentation, described below, demonstrate that both HMW1 and HMW2 mediate attachment and hence are adhesins and that this function is present even in the absence of other H. influenzae surface structures. The ability of a bacterial surface protein to function as an adhesin provides strong in vitro evidence for its potential role as a protective antigen. In view of the considerable sequence homology between the HMW3 and HMW4 proteins and the HMW1 and HMW2 proteins, these results indicate that HMW3 and HMW4 also are likely to function as adhesins and that other HMW proteins of other strains of non-typeable Haemophilus influenzae similarly are likely to function as adhesins. This expectation is borne out by the results described in the Examples below.

With the isolation and purification of the high molecular weight proteins, the inventor is able to determine the major protective epitopes of the proteins by conventional epitope mapping and synthesizing peptides corresponding to these determinants for incorporation into fully synthetic or recombinant vaccines. Accordingly, the invention also comprises a synthetic peptide having at least six and no more than 150 amino acids and having an amino acid sequence corresponding to at least one protective epitope of a high molecular weight protein of a non-typeable Haemophilus influenzae. Such peptides are of varying length that constitute portions of the high molecular weight proteins, that can be used to induce immunity, either directly or as part of a conjugate, against the respective organisms and thus constitute active components of immunogenic compositions for protection against the corresponding diseases.

In particular, the applicant has sought to identify regions of the high molecular weight proteins which are demonstrated experimentally to be surface-exposed B-cell epitopes and which are common to all or at least a large number of non-typeable strains of Haemophilus influenzae. The strategy which has been adopted by the inventor has been to:
(a) generate a panel of monoclonal antibodies reactive with the high molecular weight proteins;
(b) screen those monoclonal antibodies for reactivity with surface epitopes of intact bacteria using immunoelectron microscopy or other suitable screening technique;
(c) map the epitopes recognized by the monoclonal antibody by determining the reactivity of the monoclonals with a panel of recombinant fusion proteins; and
(d) determining the reactivity of the monoclonal antibodies with heterologous non-typable Haemophilus influenzae strains using standard Western blot assays.

Using this approach, the inventor has identified one monoclonal antibody, designated AD6, which recognized a surface-exposed B-cell epitope common to all non-typeable H. influenzae which express the HMW1 and HMW2 proteins. The epitope recognized by this antibody was mapped to a 75 amino acid sequence at the carboxy termini of both HMW1 and HMW2 proteins. The ability to identify shared surface-exposed epitopes on the high molecular weight adhesion proteins suggests that it would be possible to develop recombinant or synthetic peptide based vaccines which would be protective against disease caused by the majority of non-typeable Haemophilus influenzae.

The present invention also provides any variant or fragment of the proteins that retains the potential immunological ability to protect against disease caused by non-typeable Haemophilus strains. The variants may be constructed by partial deletions or mutations of the genes and expression of the resulting modified genes to give the protein variants.

It is clearly apparent to one skilled in the art, that the various embodiments of the present invention have many applications in the fields of vaccination, diagnosis, treatment of bacterial infections and the generation of immunological reagents. A further non-limiting discussion of such uses is further presented below.

1. Vaccine Preparation and Use

Immunogenic compositions, suitable to be used as vaccines, may be prepared from the high molecular weight proteins of *Haemophilus influenzae*, as well as analogs and fragments thereof, and synthetic peptides containing epitopes of the protein, as disclosed herein. The immunogenic composition elicits an immune response which produces antibodies, including anti-high molecular weight protein antibodies and antibodies that are opsonizing or bactericidal.

Immunogenic compositions, including vaccines, may be prepared as injectables, as liquid solutions or emulsions. The active component may be mixed with pharmaceutically acceptable excipients which are compatible therewith. Such excipients may include, water, saline, dextrose, glycerol, ethanol, and combinations thereof. The immunogenic compositions and vaccines may further contain auxiliary substances, such as wetting or emulsifying agents, pH buffering agents, or adjuvants to enhance the effectiveness thereof. Immunogenic compositions and vaccines may be administered parenterally, by injection subcutaneously or intramuscularly. Alternatively, the immunogenic compositions formed according to the present invention, may be formulated and delivered in a manner to evoke an immune response at mucosal surfaces. Thus, the immunogenic composition may be administered to mucosal surfaces by, for example, the nasal or oral (intragastric) routes. Alternatively, other modes of administration including suppositories and oral formulations may be desirable. For suppositories, binders and carriers may include, for example, polyalkalene glycols or triglycerides. Oral formulations may include normally employed incipients such as, for example, pharmaceutical grades of saccharine, cellulose and magnesium carbonate. These compositions can take the form of solutions, suspensions, tablets, pills, capsules, sustained release formulations or powders and contain about 1 to 95% of the active component. The immunogenic preparations and vaccines are administered in a manner compatible with the dosage formulation, and in such amount as will be therapeutically effective, protective and immunogenic. The quantity to be administered depends on the subject to be treated, including, for example, the capacity of the individual's immune system to synthesize antibodies, and if needed, to produce a cell-mediated immune response. Precise amounts of active ingredient required to be administered depend on the judgment of the practitioner. However, suitable dosage ranges are readily determinable by one skilled in the art and may be of the order of micrograms of the HMW proteins. Suitable regimes for initial administration and booster doses are also variable, but may include an initial administration followed by subsequent administrations. The dosage may also depend on the route of administration and will vary according to the size of the host.

The concentration of the active component in an immunogenic composition according to the invention is in general about 1 to 95%. A vaccine which contains antigenic material of only one pathogen is a monovalent vaccine. Vaccines which contain antigenic material of several pathogens are combined vaccines and also belong to the present invention. Such combined vaccines contain, for example, material from various pathogens or from various strains of the same pathogen, or from combinations of various pathogens.

Immunogenicity can be significantly improved if the antigens are co-administered with adjuvants, commonly used as 0.05 to 0.1 percent solution in phosphate-buffered saline. Adjuvants enhance the immunogenicity of an antigen but are not necessarily immunogenic themselves. Adjuvants may act by retaining the antigen locally near the site of administration to produce a depot effect facilitating a slow, sustained release of antigen to cells of the immune system. Adjuvants can also attract cells of the immune system to an antigen depot and stimulate such cells to elicit immune responses.

Immunostimulatory agents or adjuvants have been used for many years to improve the host immune responses to, for example, vaccines. Intrinsic adjuvants, such as lipopolysaccharides, normally are the components of the killed or attenuated bacteria used as vaccines. Extrinsic adjuvants are immunomodulators which are typically non-covalently linked to antigens and are formulated to enhance the host immune responses. Thus, adjuvants have been identified that enhance the immune response to antigens delivered parenterally. Some of these adjuvants are toxic, however, and can cause undesirable side-effects, making them unsuitable for use in humans and many animals. Indeed, only aluminum hydroxide and aluminum phosphate (collectively commonly referred to as alum) are routinely used as adjuvants in human and veterinary vaccines. The efficacy of alum in increasing antibody responses to diphtheria and tetanus toxoids is well established and a HBsAg vaccine has been adjuvanted with alum. While the usefulness of alum is well established for some applications, it has limitations. For example, alum is ineffective for influenza vaccination and inconsistently elicits a cell mediated immune response. The antibodies elicited by alum-adjuvanted antigens are mainly of the IgG1 isotype in the mouse, which may not be optimal for protection by some vaccinal agents.

A wide range of extrinsic adjuvants can provoke potent immune responses to antigens. These include saponins complexed to membrane protein antigens (immune stimulating complexes), pluronic polymers with mineral oil, killed mycobacteria in mineral oil, Freund's complete adjuvant, bacterial products, such as muramyl dipeptide (MDP) and lipopolysaccharide (LPS), as well as lipid A, and liposomes.

To efficiently induce humoral immune responses (HIR) and cell-mediated immunity (CMI), immunogens are often emulsified in adjuvants. Many adjuvants are toxic, inducing granulomas, acute and chronic inflammations (Freund's complete adjuvant, FCA), cytolysis (saponins and Pluronic polymers) and pyrogenicity, arthritis and anterior uveitis (LPS and MDP). Although FCA is an excellent adjuvant and widely used in research, it is not licensed for use in human or veterinary vaccines because of its toxicity.

Desirable characteristics of ideal adjuvants include:
(1) lack of toxicity;
(2) ability to stimulate a long-lasting immune response;
(3) simplicity of manufacture and stability in long-term storage;
(4) ability to elicit both CMI and HIR to antigens administered by various routes, if required;
(5) synergy with other adjuvants;
(6) capability of selectively interacting with populations of antigen presenting cells (APC);
(7) ability to specifically elicit appropriate $T_H1$ or $T_H2$ cell-specific immune responses; and
(8) ability to selectively increase appropriate antibody isotype levels (for example, IgA) against antigens.

U.S. Pat. No. 4,855,283 granted to Lockhoff et al on Aug. 8, 1989 which is incorporated herein by reference thereto teaches glycolipid analogues including N-glycosylamides, N-glycosylureas and N-glycosylcarbamates, each of which is substituted in the sugar residue by an amino acid, as immuno-modulators or adjuvants. Thus, Lockhoff et al. (U.S. Pat. No. 4,855,283 and ref. 29) reported that N-glycolipid analogs displaying structural similarities to the naturally-occurring glycolipids, such as glycosphingolipids and glycoglycerolipids, are capable of eliciting strong immune responses in both herpes simplex virus vaccine and pseudorabies virus vaccine. Some glycolipids have been synthesized from long chain-alkylamines and fatty acids that are linked directly with the sugars through the anomeric carbon atom, to mimic the functions of the naturally occurring lipid residues.

U.S. Pat. No. 4,258,029 granted to Moloney, incorporated herein by reference thereto, teaches that octadecyl tyrosine hydrochloride (OTH) functioned as an adjuvant when complexed with tetanus toxoid and formalin inactivated type I, II and III poliomyelitis virus vaccine. Also, Nixon-George et al. (ref. 30), reported that octadecyl esters of aromatic amino acids complexed with a recombinant hepatitis B surface antigen, enhanced the host immune responses against hepatitis B virus.

Lipidation of synthetic peptides has also been used to increase their immunogenicity. Thus, Wiesmuller 1989, describes a peptide with a sequence homologous to a foot-and-mouth disease viral protein coupled to an adjuvant tripalmityl-s-glyceryl-cysteinylserylserine, being a synthetic analogue of the N-terminal part of the lipoprotein from Gram negative bacteria. Furthermore, Deres et al. 1989, reported in vivo priming of virus-specific cytotoxic T lymphocytes with synthetic lipopeptide vaccine which comprised of modified synthetic peptides derived from influenza virus nucleoprotein by linkage to a lipopeptide, N-palmityl-s-[2,3-bis(palmitylxy)-(2RS)-propyl-[R]-cysteine (TPC).

2. Immunoassays

The high molecular weight protein of *Haemophilus influenzae* of the present invention is useful as an immunogen for the generation of anti-protein antibodies, as an antigen in immunoassays including enzyme-linked immunosorbent assays (ELISA), RIAs and other non-enzyme linked antibody binding assays or procedures known in the art for the detection of antibodies. In ELISA assays, the protein is immobilized onto a selected surface, for example, a surface capable of binding proteins, such as the wells of a polystyrene microtiter plate. After washing to remove incompletely adsorbed protein, a nonspecific protein, such as a solution of bovine serum albumin (BSA) that is known to be antigenically neutral with regard to the test sample, may be bound to the selected surface. This allows for blocking of nonspecific adsorption sites on the immobilizing surface and thus reduces the background caused by nonspecific bindings of antisera onto the surface.

The immobilizing surface is then contacted with a sample, such as clinical or biological materials, to be tested in a manner conducive to immune complex (antigen/antibody) formation. This may include diluting the sample with diluents, such as solutions of BSA, bovine gamma globulin (BGG) and/or phosphate buffered saline (PBS)/Tween. The sample is then allowed to incubate for from about 2 to 4 hours, at temperatures such as of the order of about 25° to 37° C. Following incubation, the sample-contacted surface is washed to remove non-immunocomplexed material. The washing procedure may include washing with a solution, such as PBS/Tween or a borate buffer. Following formation of specific immunocomplexes between the test sample and the bound protein, and subsequent washing, the occurrence, and even amount, of immunocomplex formation may be determined by subjecting the immunocomplex to a second antibody having specificity for the first antibody. If the test sample is of human origin, the second antibody is an antibody having specificity for human immunoglobulins and in general IgG. To provide detecting means, the second antibody may have an associated activity such as an enzymatic activity that will generate, for example, a colour development upon incubating with an appropriate chromogenic substrate. Quantification may then be achieved by measuring the degree of colour generation using, for example, a visible spectra spectrophotometer.

3. Use of sequences as Hybridization Probes

The nucleotide sequences of the present invention, comprising the sequences of the genes encoding the high molecular weight proteins of specific strains of non-typeable *Haemophilus influenzae*, now allow for the identification and cloning of the genes from any species of non-typeable Haemophilus and other strains of non-typeable *Haemophilus influenzae.*

The nucleotide sequences comprising the sequences of the genes of the present invention are useful for their ability to selectively form duplex molecules with complementary stretches of other genes of high molecular weight proteins of non-typeable Haemophilus. Depending on the application, a variety of hybridization conditions may be employed to achieve varying degrees of selectivity of the probe toward the other genes. For a high degree of selectivity, relatively stringent conditions are used to form the duplexes, such as low salt and/or high temperature conditions, such as provided by 0.02 M to 0.15 M NaCl at temperatures of between about 50° C. to 70C. For some applications, less stringent hybridization conditions are required such as 0.15 M to 0.9 M salt, at temperatures ranging from between about 20° C. to 55° C. Hybridization conditions can also be rendered more stringent by the addition of increasing amounts of formamide, to destabilize the hybrid duplex. Thus, particular hybridization conditions can be readily manipulated, and will generally be a method of choice depending on the desired results. In general, convenient hybridization temperatures in the presence of 50% formamide are: 42° C. for a probe which is 95 to 100% homologous to the target fragment, 37° C. for 90 to 95% homology and 32° C. for 85 to 90% homology.

In a clinical diagnostic embodiment, the nucleic acid sequences of the genes of the present invention may be used in combination with an appropriate means, such as a label, for determining hybridization. A wide variety of appropriate indicator means are known in the art, including radioactive, enzymatic or other ligands, such as avidin/biotin, which are capable of providing a detectable signal. In some diagnostic embodiments, an enzyme tag such as urease, alkaline phosphatase or peroxidase, instead of a radioactive tag may be used. In the case of enzyme tags, calorimetric indicator substrates are known which can be employed to provide a means visible to the human eye or spectrophotometrically, to identify specific hybridization with samples containing gene sequences encoding high molecular weight proteins of non-typeable Haemophilus.

The nucleic acid sequences of genes of the present invention are useful as hybridization probes in solution hybridizations and in embodiments employing solid-phase procedures. In embodiments involving solid-phase procedures, the test DNA (or RNA) from samples, such as clinical samples, including exudates, body fluids (e. g., serum, amniotic fluid, middle ear effusion, sputum, bronchoalveolar lavage fluid) or even tissues, is adsorbed or otherwise affixed to a selected matrix or surface. The fixed, single-stranded nucleic acid is then subjected to specific hybridization with selected probes comprising the nucleic acid sequences of the genes or fragments thereof of the present invention under desired conditions. The selected conditions will depend on the particular circumstances based on the particular criteria required depending on, for example, the G+C contents, type of target nucleic acid, source of nucleic acid, size of hybridization probe etc. Following washing of the hybridization surface so as to remove non-specifically bound probe molecules, specific hybridization is detected, or even quantified, by means of the label. As with the selection of peptides, it is preferred to select nucleic acid sequence portions which are conserved among species of non-typeable Haemophilus. The selected probe may be at least about 18 bp and may be in the range of about 30 bp to about 90 bp long.

4. Expression of the High Molecular Weight Protein Genes

Plasmid vectors containing replicon and control sequences which are derived from species compatible with the host cell may be used for the expression of the genes encoding high molecular weight proteins of non-typeable Haemophilus in expression systems. The vector ordinarily carries a replication site, as well as marking sequences which are capable of providing phenotypic selection in transformed cells. For example, E. coli may be transformed using pBR322 which contains genes for ampicillin and tetracycline resistance and thus provides easy means for identifying transformed cells. The pBR322 plasmid, or other microbial plasmid or phage must also contain, or be modified to contain, promoters which can be used by the host cell for expression of its own proteins.

In addition, phage vectors containing replicon and control sequences that are compatible with the host can be used as a transforming vector in connection with these hosts. For example, the phage in lambda GEM™-11 may be utilized in making recombinant phage vectors which can be used to transform host cells, such as E. coli LE392.

Promoters commonly used in recombinant DNA construction include the β-lactamase (penicillinase) and lactose promoter systems (Chang et al., 1978: Itakura et al., 1977 Goeddel et al., 1979; Goeddel et al., 1980) and other microbial promoters such as the T7 promoter system (U.S. Pat. No. 4,952,496). Details concerning the nucleotide sequences of promoters are known, enabling a skilled worker to ligate them functionally with genes. The particular promoter used will generally be a matter of choice depending upon the desired results. Hosts that are appropriate for expression of the genes encoding the high molecular weight proteins, fragment analogs or variants thereof, include E. coli, Bacillus species, Haemophilus, fungi, yeast or the baculovirus expression system may be used.

In accordance with this invention, it is preferred to make the high molecular weight proteins by recombinant methods, particularly since the naturally occurring high molecular weight protein as purified from a culture of a species of non-typeable Haemophilus may include trace amounts of toxic materials or other contaminants. This problem can be avoided by using recombinantly produced proteins in heterologous systems which can be isolated from the host in a manner to minimize comtaminants in the purified material. Particularly desirable hosts for expression in this regard include Gram positive bacteria which do not have LPS and are, therefore, endotoxin free. Such hosts include species of Bacillus and may be particularly useful for the production of non-pyrogenic high molecular weight protein, fragments or analogs thereof. Furthermore, recombinant methods of production permit the manufacture of HMW1, HMW2, HMW3 or HMW4, and corresponding HMW proteins from other non-typeable *Haemophilus influenzae* strains, or fragments thereof, separate from one another and devoid of non-HMW protein of non-typeable *Haemophilus influenzae*.

Biological Deposits

Certain hybridomas producing monoclonal antibodies specific for high molecular weight protein of *Haemophilus influenzae* according to aspects of the present invention that are described and referred to herein have been deposited with the American Type Culture Collection (ATCC) located at 12301 Parklawn Drive, Rockville, Md., USA, 20852, pursuant to the Budapest Treaty and prior to the filing of this application. Samples of the deposited hybridomas will become available to the public upon grant of a patent based upon this United States patent application. The invention described and claimed herein is not to be limited in scope by the hybridomas deposited, since the deposited embodiment is intended only as an illustration of the invention. Any equivalent or similar hybridomas that produce similar or equivalent antibodies as described in this application are within the scope of the invention.

EXAMPLES

The above disclosure generally describes the present invention. A more complete understanding can be obtained by reference to the following specific Examples. These Examples are described solely for purposes of illustration and are not intended to limit the scope of the invention. Changes in form and substitution of equivalents are contemplated as circumstances may suggest or render expedient. Although specific terms have been employed herein, such terms are intended in a descriptive sense and not for purposes of limitations.

Methods of molecular genetics, protein biochemistry, and immunology used but not explicitly described in this disclosure and these Examples are amply reported in the scientific literature and are well within the ability of those skilled in the art.

Example 1

This Example describes the isolation of DNA encoding HMW1 and HMW2 proteins, cloning and expression of such proteins, and sequencing and sequence analysis of the DNA molecules encoding the HMW1 and HMW2 proteins.

Non-typeable *H.influenzae* strains 5 and 12 were isolated in pure culture from the middle ear fluid of children with acute otitis media. Chromosomal DNA from strain 12, providing genes encoding proteins HMW1 and HMW2, was prepared by preparing Sau3A partial restriction digests of chromosomal DNA and fractionating on sucrose gradients. Fractions containing DNA fragments in the 9 to 20 kbp range were pooled and a library was prepared by ligation into λEMBL3 arms. Ligation mixtures were packaged in vitro and plate-amplified in a P2 lysogen of E. coli LE392.

For plasmid subcloning studies, DNA from a representative recombinant phage was subcloned into the T7 expression plasmid pT7-7, containing the T7 RNA polymerase promoter Φ10, a ribosome-binding site and the translational start site for the T7 gene 10 protein upstream from a multiple cloning site (see FIG. 5B).

DNA sequence analysis was performed by the dideoxy method and both strands of the HMW1 gene and a single strand of the HMW2 gene were sequenced.

Western immunoblot analysis was performed to identify the recombinant proteins being produced by reactive phage clones (FIG. 11). Phage lysates grown in LE392 cells or plaques picked directly from a lawn of LE392 cells on YT plates were solubilized in gel electrophoresis sample buffer prior to electrophoresis. Sodium dodecyl sulfate polyacrylamide gel electrophoresis (SDS-PAGE) was performed on 7.5% or 11% polyacrylamide modified Laemmli gels. After transfer of the proteins to nitrocellulose sheets, the sheets were probed sequentially with an *E. coli*-absorbed human serum sample containing high-titer antibody to the high-molecular-weight proteins and then with alkaline phosphatase-conjugated goat anti-human immunoglobulin G (IgG) second antibody. Sera from healthy adults contains high-titer antibody directed against surface-exposed high-molecular-weight proteins of non-typeable *H. influenzae*. One such serum sample was used as the screening antiserum after having been extensively absorbed with LE392 cells.

To identify recombinant proteins being produced by *E. coli* transformed with recombinant plasmids, the plasmids of interest were used to transform *E. coli* BL21 (DE3)/pLysS. The transformed strains were grown to an $A_{600}$ of 0.5 in L broth containing 50 μg of ampicillin per ml. IPTG was then added to 1 mM. One hour later, cells were harvested, and a sonicate of the cells was prepared. The protein concentrations of the samples were determined by the bicinchoninic acid method. Cell sonicates containing 100 μg of total protein were solubilized in electrophoresis sample buffer, subjected to SDS-polyacrylamide gel electrophoresis, and transferred to nitrocellulose. The nitrocellulose was then probed sequentially with the *E. coli*-absorbed adult serum sample and then with alkaline phosphatase-conjugated goat anti-human IgG second antibody.

Western immunoblot analysis also was performed to determine whether homologous and heterologous non-typeable *H. influenzae* strains expressed high-molecular-weight proteins antigenically related to the protein encoded by the cloned HMW1 gene (rHMW1). Cell sonicates of bacterial cells were solubilized in electrophoresis sample buffer, subjected to SDS-polyacrylamide gel electrophoresis, and transferred to nitrocellulose. Nitrocellulose was probed sequentially with polyclonal rabbit rHMW1 antiserum and then with alkaline phosphatase-conjugated goat anti-rabbit IgG second antibody.

Finally, Western immunoblot analysis was performed to determine whether non-typeable Haemophilus strains expressed proteins antigenically related to the filamentous hemagglutinin protein of *Bordetella pertussis*. Monoclonal antibody X3C, a murine immunoglobulin G (IgG) antibody which recognizes filamentous hemagglutinin, was used to probe cell sonicates by Western blot. An alkaline phosphatase-conjugated goat anti-mouse IgG second antibody was used for detection.

To generate recombinant protein antiserum, *E. coli* BL21 (DE3)/pLysS was transformed with pHMW1-4, and expression of recombinant protein was induced with IPTG, as described above. A cell sonicate of the bacterial cells was prepared and separated into a supernatant and pellet fraction by centrifugation at 10,000×g for 30 min. The recombinant protein fractionated with the pellet fraction. A rabbit was subcutaneously immunized on biweekly schedule with 1 mg of protein from the pellet fraction, the first dose given with Freund's complete adjuvant and subsequent doses with Freund's incomplete adjuvant. Following the fourth injection, the rabbit was bled. Prior to use in the Western blot assay, the antiserum was absorbed extensively with sonicates of the host *E. coli* strain transformed with cloning vector alone.

To assess the sharing of antigenic determinants between HMW1 and filamentous hemagglutinin, enzyme-linked immunosorbent assay (ELISA) plates (Costar, Cambridge, Mass.) were coated with 60 μl of a 4-μg/ml solution of filamentous hemagglutinin in Dulbecco's phosphate-buffered saline per well for 2 h at room temperature. Wells were blocked for 1 h with 1% bovine serum albumin in Dulbecco's phosphate-buffered saline prior to addition of serum dilutions. rHMW1 antiserum was serially diluted in 0.1% Brij (Sigma, St. Louis, Mo.) in Dulbecco's phosphate-buffered saline and incubated for 3 h at room temperature. After being washed, the plates were incubated with peroxidase-conjugated goat anti-rabbit IgG antibody (Bio-Rad) for 2 h at room temperature and subsequently developed with 2,2'-azino-bis(3-ethylbenzthiazoline-6-sulfonic acid) (Sigma) at a concentration of 0.54 in mg/ml in 0.1 M sodium citrate buffer, pH 4.2, containing 0.03% $H_2O_2$. Absorbances were read on an automated ELISA reader.

Recombinant phage expressing HMW1 or HMW2 were recovered as follows. The non-typeable *H. influenzae* strain 12 genomic library was screened for clones expressing high-molecular-weight proteins with an *E. coli*-absorbed human serum sample containing a high titer of antibodies directed against the high-molecular-weight proteins.

Numerous strongly reactive clones were identified along with more weakly reactive ones. Twenty strongly reactive clones were plaque-purified and examined by Western blot for expression of recombinant proteins. Each of the strongly reactive clones expressed one of two types of high-molecular-weight proteins, designated HMW1 and HMW2. The major immunoreactive protein bands in the HMW1 and HMW2 lysates migrated with apparent molecular masses of 125 and 120 kDa, respectively. In addition to the major bands, each lysate contained minor protein bands of higher apparent molecular weight. Protein bands seen in the HMW2 lysates at molecular masses of less than 120 kDa were not regularly observed and presumably represent proteolytic degradation products. Lysates of LE392 infected with the XEMBL3 cloning vector alone were non-reactive when immunologically screened with the same serum sample. Thus, the observed activity was not due to cross-reactive *E. coli* proteins or XEMBL3-encoded proteins. Furthermore, the recombinant proteins were not simply binding immunoglobulin nonspecifically, since the proteins were not reactive with the goat anti-human IgG conjugate alone, with normal rabbit sera, or with serum from a number of healthy young infants.

Representative clones expressing either the HMW1 or HMW2 recombinant proteins were characterized further. The restriction maps of the two phage types were different from each other, including the regions encoding the HMW1 and HMW2 structural genes. FIG. 5A shows restriction maps of representative recombinant phage which contained the HMW1 or HMW2 structural genes. The locations of the structural genes are indicated by the shaded bars.

HMW1 plasmid subclones were constructed by using the T7 expression plasmid T7-7 (FIG. 5A and B). HMW2 plasmid subclones also were constructed, and the results with these latter subclones were similar to those observed with the HMW1 constructs.

The approximate location and direction of transcription of the HMW1 structure gene were initially determined by using plasmid pHMW1 (FIG. 5A). This plasmid was constructed by inserting the 8.5-kb BamHI-SalI fragment from λHMW1 into BamHI- and SalI-cut pT7-7. *E. coli* transformed with pHMW1 expressed an immunoreactive recombinant protein with an apparent molecular mass of 115 kDa, which was strongly inducible with IPTG. This protein was significantly smaller than the 125-kDa major protein expressed by the parent phage, indicating that it either was being expressed as a fusion protein or was truncated at the carboxy terminus.

To more precisely localize the 3' end of the structural gene, additional plasmids were constructed with progressive deletions from the 3' end of the pHMW1 construct. Plasmid pHMW1-1 was constructed by digestion of pHMW1 with PstI, isolation of the resulting 8.8-kb fragment, and religation. Plasmid pHMW1-2 was constructed by digestion of pHMW1 with HindIII, isolation of the resulting 7.5-kb fragment, and religation. E. coli transformed with either plasmid pHMW1-1 or pHMW1-2 also expressed an immunoreactive recombinant protein with an apparent molecular mass of 115 kDa. These results indicated that the 3' end of the structural gene was 5' of the HindIII site. FIG. 12 demonstrates the Western blot results with pHMW1-2 transformed cells before and after IPTG indicates (lanes 3 and 4, respectively). The 115 kDa recombinant protein is indicated by the arrow. Transformants also demonstrated cross-reactive bands of lower apparent molecular weight, and probably represent partial degradation products. Shown for comparison and the results for E. coli transformed with the pT7-7 cloning vector alone (FIG. 12, lanes 1 and 2).

To more precisely localize the 5' end of the gene, plasmids pHMW1-4 and pHMW1-7 were constructed. Plasmid pHMW1-4 was constructed by cloning the 5.1-kb BamHI-HindIII fragment from λHMW1 into a pT7-7-derived plasmid containing the upstream 3.8-kb EcoRI-BamHI fragment. E. coli transformed with pHMW1-4 expressed an immunoreactive protein with an apparent molecular mass of approximately 160 kDa (FIG. 12, lane 6). Although protein production was inducible with IPTG, the levels of protein production in these transformants were substantially lower than those with the pHMW1-2 transformants described above. Plasmid pHMW1-7 was constructed by digesting pHMW1-4 with NdeI and SpeI. The 9.0-kbp fragment generated by this double digestion was isolated, blunt ended, and religated. E. coli transformed with pHMW1-7 also expressed an immunoreactive protein with an apparent molecular mass of 160 kDa, a protein identical in size to that expressed by the pHMW1-4 transformants. The result indicated that the initiation codon for the HMW1 structural gene was 3' of the SpeI site. DNA sequence analysis (described below) confirmed this conclusion.

As noted above, the λHMW1 phage clones expressed a major immunoreactive band of 125 kDa, whereas the HMW1 plasmid clones pHMW1-4 and pHMW1-7, which contained what was believed to be the full-length gene, expressed an immunoreactive protein of approximately 160 kDa. This size discrepancy was disconcerting. One possible explanation was that an additional gene or genes necessary for correct processing of the HMW1 gene product were deleted in the process of subcloning. To address this possibility, plasmid pHMW1-14 was constructed. This construct was generated by digesting pHMW1 with NdeI and MluI and inserting the 7.6-kbp NdeI-MluI fragment isolated from pHMW1-4. Such a construct would contain the full-length HMW1 gene as well as the DNA 3' of the HMW1 gene which was present in the original HMW1 phage. E. coli transformed with this plasmid expressed major immunoreactive proteins with apparent molecular masses of 125 and 160 kDa as well as additional degradation products (FIG. 12, lanes 7 and 8). The 125- and 160-kDa bands were identical to the major and minor immunoreactive bands detected in the HMW1 phage lysates. Interestingly, the pHMW1-14 construct also expressed significant amounts of protein in the uninduced condition, a situation not observed with the earlier constructs.

The relationship between the 125- and 160-kDa proteins remains somewhat unclear. Sequence analysis, described below, reveals that the HMW1 gene would be predicted to encode a protein of 159 kDa. It is believed that the 160-kDa protein is a precursor form of the mature 125-kDa protein, with the conversion from one protein to the other being dependent on the products of the two downstream genes.

Sequence analysis of the HMW1 gene (FIG. 1) revealed a 4,608-bp open reading frame (ORF), beginning with an ATG codon at nucleotide 351 and ending with a TAG stop codon at nucleotide 4959. A putative ribosome-binding site with the sequence AGGAG begins 10 bp up-stream of the putative initiation codon. Five other in-frame ATG codons are located within 250 bp of the beginning of the ORF, but none of these is preceded by a typical ribosome-binding site. The 5'-flanking region of the ORF contains a series of direct tandem repeats, with the 7-bp sequence ATCTTTC repeated 16 times. These tandem repeats stop 100 bp 5' of the putative initiation codon. An 8-bp inverted repeat characteristic of a rho-independent transcriptional terminator is present, beginning at nucleotide 4983, 25 bp 3' of the presumed translational stop. Multiple termination codons are present in all three reading frames both upstream and downstream of the ORF. The derived amino acid sequence of the protein encoded by the HMW1 gene (FIG. 2) has a molecular weight of 159,000, in good agreement with the apparent molecular weights of the proteins expressed by the HMW1-4 and HMW1-7 transformants. The derived amino acid sequence of the amino terminus does not demonstrate the characteristics of a typical signal sequence. The BamHI site used in generation of pHMW1 comprises bp 1743 through 1748 of the nucleotide sequence. The ORF downstream of the BamHI site would be predicted to encode a protein of 111 kDa, in good agreement with the 115 kDa estimated for the apparent molecular mass of the pHMW1-encoded fusion protein.

The sequence of the HMW2 gene (FIG. 3) consists of a 4,431-bp ORF, beginning with an ATG codon at nucleotide 352 and ending with a TAG stop codon at nucleotide 4783. The first 1,259 bp of the ORF of the HMW2 gene are identical to those of the HMW1 gene. Thereafter, the sequences begin to diverge but are 80% identical overall. With the exception of a single base addition at nucleotide 93 of the HMW2 sequence, the 5'-flanking regions of the HMW1 and HMW2 genes are identical for 310 bp upstream from the respective initiation codons. Thus, the HMW2 gene is preceded by the same set of tandem repeats and the same putative ribosome-binding site which lies 5' of the HMW1 gene. A putative transcriptional terminator identical to that identified 3' of the HMW1 ORF is noted, beginning at nucleotide 4804. The discrepancy in the lengths of the two genes is principally accounted for by a 186-bp gap in the HMW2 sequence, beginning at nucleotide position 3839. The derived amino acid sequence of the protein encoded by the HMW2 gene (FIG. 4) has a molecular weight of 155,000 and is 71% identical with the derived amino acid sequence of the HMW1 gene.

The derived amino acid sequences of both the HMW1 and HMW2 genes (FIGS. 2 and 4) demonstrated sequence similarity with the derived amino acid sequence of filamentous hemagglutinin of Bordetella pertussis, a surface-associated protein of this organism. The initial and optimized TFASTA scores for the HMW1-filamentous hemagglutinin sequence comparison were 87 and 186, respectively, with a word size of 2. The z score for the comparison was 45.8. The initial and optimized TFASTA scores for the HMW2-filamentous hemagglutinin sequence comparison were 68 and 196, respectively. The z score for the latter comparison was 48.7. The magnitudes of the initial and optimized TFASTA scores and the z scores suggested that a biologically significant relationship existed between the HMW1 and HMW2 gene products and filamentous hemagglutinin. When the derived amino acid sequences of HMW1, HMW2, and filamentous hemagglutinin genes were aligned and compared, the similarities were most notable at the amino-terminal ends of the three sequences. Twelve of the first 22 amino acids in the predicted peptide sequences were identical. In addition, the sequences demonstrated a common five-amino-acid stretch, Asn-Pro-Asn-Gly-Ile, and several shorter stretches of sequence identity within the first 200 amino acids.

Example 2

This Example describes the relationship of filamentous hemagglutinin and the HMW1 protein.

To further explore the HMW1-filamentous hemagglutinin relationship, the ability of antiserum prepared against the HMW1-4 recombinant protein (rHMW1) to recognize purified filamentous hemagglutinin was assessed (FIG. 13). The rHMW1 antiserum demonstrated ELISA reactivity with filamentous hemagglutinin in a dose-dependent manner. Preimmune rabbit serum had minimal reactivity in this assay. The rHMW1 antiserum also was examined in a Western blot assay and demonstrated weak but positive reactivity with purified filamentous hemagglutinin in this system also.

To identify the native Haemophilus protein corresponding to the HMW1 gene product and to determine the extent to which proteins antigenically related to the HMW1 cloned gene product were common among other non-typeable *H. influenzae* strains, a panel of Haemophilus strains was screened by Western blot with the rHMW1 antiserum. The antiserum recognized both a 125- and a 120-kDa protein band in the homologous strain 12 (FIG. 14), the putative mature protein products of the HMW1 and HMW2 genes, respectively. The 120-kDa protein appears as a single band in FIG. 14, wherein it appeared as a doublet in the HMW2 phage lysates (FIG. 11).

When used to screen heterologous non-typeable *H. influenzae* strains, rHMW1 antiserum recognized high-molecular-weight proteins in 75% of 125 epidemiologically unrelated strains. In general, the antiserum reacted with one or two protein bands in the 100- to 150-kDa range in each of the heterologous strains in a pattern similar but not identical to that seen in the homologous strain (FIG. 14).

Monoclonal antibody X3C is a murine IgG antibody directed against the filamentous hemagglutinin protein of *B. pertussis*. This antibody can inhibit the binding of *B. pertussis* cells to Chinese hamster ovary cells and HeLa cells in culture and will inhibit hemagglutination of erythrocytes by purified filamentous hemagglutinin. A Western blot assay was performed in which this monoclonal antibody was screened against the same panel of non-typeable *H. influenzae* strains discussed above (FIG. 14). Monoclonal antibody X3C recognized both the high-molecular-weight proteins in non-typeable *H. influenzae* strain 12 which were recognized by the recombinant-protein antiserum (FIG. 15). In addition, the monoclonal antibody recognized protein bands in a subset of heterologous non-typeable *H. influenzae* strains which were identical to those recognized by the recombinant-protein antiserum, as may be seen by comparison of FIGS. 14 and 15. On occasion, the filamentous hemagglutinin monoclonal antibody appeared to recognize only one of the two bands which had been recognized by the recombinant-protein antiserum (compare strain lane 18 in FIGS. 14 and 15, for example). Overall, monoclonal antibody X3C recognized high-molecular-weight protein bands identical to those recognized by the rHMW1 antiserum in approximately 35% of our collection of non-typeable *H. influenzae* strains.

Example 3

This Example describes the adhesin properties of the HMW1 and HMW2 proteins.

Mutants deficient in expression of HMW1, HMW2 or both proteins were constructed to examine the role of these proteins in bacterial adherence. The following strategy was employed. pHMW1-14 (see Example 1, FIG. 5A) was digested with BamHI and then ligated to a kanamycin cassette isolated on a 1.3-kb BamHl fragment from pUC4K. The resultant plasmid (pHMW1-17) was linearized by digestion with XbaI and transformed into non-typeable *H. influenzae* strain 12, followed by selection for kanamycin resistant colonies. Southern analysis of a series of these colonies demonstrated two populations of transformants, one with an insertion in the HMW1 structural gene and the other with an insertion in the HMW2 structural gene. One mutant from each of these classes was selected for further studies.

Mutants deficient in expression of both proteins were recovered using the following protocol. After deletion of the 2.1-kb fragment of DNA between two EcoRI sites spanning the 3'-portion of the HMW1 structural gene and the 5'-portion of a downstream gene encoding an accessory processing protein in pHMW-15, the kanamycin cassette from pUC4K was inserted as a 1.3-kb EcoRl fragment. The resulting plasmid (pHMW1-16) was linearized by digestion with XbaI and transformed into strain 12, followed again by selection for kanamycin resistant colonies. Southern analysis of a representative sampling of these colonies demonstrated that in seven of eight cases, insertion into both the HMW1 and HMW2 loci had occurred. One such mutant was selected for further studies.

To confirm the intended phenotypes, the mutant strains were examined by Western blot analysis with a polyclonal antiserum against recombinant HMW1 protein. The parental strain expressed both the 125-kD HMW1 and the 120-kD HMW2 protein (FIG. 16). In contrast, the HMW2⁻ mutant failed to express the 120-kD protein, and the HMW1 mutant failed to express the 125-kD protein. The double mutant lacked expression of either protein. On the basis of whole cell lysates, outer membrane profiles, and colony morphology, the wild type strain and the mutants were otherwise identical with one another. Transmission electron microscopy demonstrated that none of the four strains expressed pili.

The capacity of wild type strain 12 to adhere to Chang epithelial cells was examined. In such assays, bacteria were inoculated into broth and allowed to grow to a density of ~$2 \times 10^9$ cfu/ml. Approximately $2 \times 10^7$ cfu were inoculated onto epithelial cell monolayers, and plates were gently centrifuged at 165×g for 5 minutes to facilitate contact between bacteria and the epithelial surface. After incubation for 30 minutes at 37° C. in 5% $CO_2$, monolayers were rinsed 5 times with PBS to remove nonadherent organisms and were treated with trypsin-EDTA (0.05% trypsin, 0.5% EDTA) in PBS to release them from the plastic support. Well contents were agitated, and dilutions were plated on solid medium to yield the number of adherent bacteria per monolayer. Percent adherence was calculated by dividing the number of adherent cfu per monolayer by the number of inoculated cfu.

As depicted in Table 1 below (the Tables appear at the end of the descriptive text), this strain adhered quite efficiently, with nearly 90% of the inoculum binding to the monolayer. Adherence by the mutant expressing HMW1 but not HMW2 (HMW2-) was also quite efficient and comparable to that by the wild type strain. In contrast, attachment by the strain expressing HMW2 but deficient in expression of HMW1 (HMW1⁻) was decreased about 15-fold relative to the wild type. Adherence by the double mutant (HMW1⁻/HMW2⁻) was decreased even further, approximately 50-fold compared with the wild type and approximately 3-fold compared with the HMW1 mutant. Considered together, these results suggest that both the HMW1 protein and the, HMW2 protein influence attachment to Chang epithelial cells. Interestingly, optimal adherence to this cell line appears to require HMW1 but not HMW2.

Example 4

This Example illustrates the preparation and expression of HMW3 and HMW4 proteins and their function as adhesins.

Using the plasmids pHMW1-16 and pHMW1-17 (see Example 3) and following a scheme similar to that employed with strain 12 as described in Example 3, three non-typeable Haemophilus strain 5 mutants were isolated, including one with the kanamycin gene inserted into the hmw1-like (designated hmw3) locus, a second with an insertion in the hmw2-like (designated hmw4) locus, and a third with insertions in both loci. As predicted, Western immunoblot analysis demonstrated that the mutant with insertion of the kanamycin cassette into the hmw1-like locus had lost expression of the HMW3 125-kD protein, while the mutant with insertion into the hmw2-like locus failed to express the HMW4 123-kD protein. The mutant with a double insertion was unable to express either of the high molecular weight proteins.

As shown in Table 1 below, wild type strain 5 demonstrated high level adherence, with almost 80% of the inoculum adhering per monolayer. Adherence by the mutant deficient in expression of the HMW2-like protein (i.e. HMW4 protein) was also quite high. In contrast, adherence by the mutant unable to express the HMW1-like protein (i.e. HMW3 protein) was reduced about 5-fold relative to the wild type, and attachment by the double mutant was diminished even further (approximately 25-fold). Examination of Giemsa-stained samples confirmed these observations (not shown). Thus, the results with strain 5 for proteins HMW3 and HMW4 corroborate the findings with strain 12 and the HMW1 and HMW2 proteins.

Example 5

This Example contains additional data concerning the adhesin properties of the HMW1 and HMW2 proteins.

To confirm an adherence function for the HMW1 and HMW2 proteins and to examine the effect of HMW1 and HMW2 independently of other *H. influenzae* surface structures, the hmw1 and the hmw2 gene clusters were introduced into *E. coli* DH5α, using plasmids pHMW1-14 and pHMW2-21, respectively. As a control, the cloning vector, pT7-7, was also transformed into *E. coli* DH5α. Western blot analysis demonstrated that *E. coli* DH5α containing the hmw1 genes expressed a 125 kDa protein, while the same strain harboring the hmw2 genes expressed a 120-kDa protein. *E. coli* DH5α containing pT7-7 failed to react with antiserum against recombinant HMW1. Transmission electron microscopy revealed no pili or other surface appendages on any of the *E. coli* strains.

Adherence by the *E. coli* strains was quantitated and compared with adherence by wild type non-typeable *H. influenzae* strain 12. As shown in Table 2 below, adherence by *E. coli* DH5α containing vector alone was less than 1% of that for strain 12. In contrast, *E. coli* DH5α harboring the hmw1 gene cluster demonstrated adherence levels comparable to those for strain 12. Adherence by *E. coli* DH5α containing the hmw2 genes was approximately 6-fold lower than attachment by strain 12 but was increased 20-fold over adherence by *E. coli* DH5α with pT7-7 alone. These results indicate that the HMW1 and HMW2 proteins are capable of independently mediating attachment to Chang conjunctival cells. These results are consistent with the results with the *H. influenzae* mutants reported in Examples 3 and 4, providing further evidence that, with Chang epithelial cells, HMW1 is a more efficient adhesin than is HMW2.

Experiments with *E. coli* HB101 harboring pT7-7, pHMW1-14, or pHMW2-21 confirmed the results obtained with the DH5α derivatives (see Table 2).

Example 6

This Example illustrates the copurification of HMW1 and HMW2 proteins from wild-type non-typeable *H. influenzae* strain.

HMW1 and HMW2 were isolated and purified from non-typeable *H. influenzae* (NTHI) strain 12 in the following manner. Non-typeable Haemophilus bacteria from frozen stock culture were streaked onto a chocolate plate and grown overnight at 37° C. in an incubator with 5% $CO_2$. 50 ml starter culture of brain heart infusion (BHI) broth, supplemented with 10 μg/ml each of hemin and NAD was inoculated with growth on chocolate plate. The starter culture was grown until the optical density (O.D.-600 nm) reached 0.6 to 0.8 and then the bacteria in the starter culture was used to inoculate six 500 ml flasks of supplemented BHI using 8 to 10 ml per flask. The bacteria were grown in 500 ml flasks for an additional 5 to 6 hours at which time the O.D. was 1.5 or greater. Cultures were centrifuged at 10,000 rpm for 10 minutes.

Bacterial pellets were resuspended in a total volume of 250 ml of an extraction solution comprising 0.5 M NaCl, 0.01 M $Na_2EDTA$, 0.01 M Tris 50 μM 1,10-phenanthroline, pH 7.5. The cells were not sonicated or otherwise disrupted. The resuspended cells were allowed to sit on ice at 0° C. for 60 minutes. The resuspended cells were centrifuged at 10,000 rpm for 10 minutes at 4° C. to remove the majority of intact cells and cellular debris. The supernatant was collected and centrifuged at 100,000×g for 60 minutes at 4° C. The supernatant again was collected and dialyzed overnight at 4° C. against 0.01 M sodium phosphate, pH 6.0.

The sample was centrifuged at 10,000 rpm for 10 minutes at 4° C. to remove insoluble debris precipitated from solution during dialysis. The supernatant was applied to a 10 ml CM Sepharose column which has been pre-equilibrated with 0.01 M sodium phosphate, pH 6. Following application to this column, the column was washed with 0.01 M sodium phosphate. Proteins were elevated from the column with a 0–0.5M KCl gradient in 0.01 M Na phosphate, pH 6 and fractions were collected for gel examination. Coomassie gels of column fractions were carried out to identify those fractions containing high molecular weight proteins. The fractions containing high molecular weight proteins were pooled and concentrated to a 1 to 3 ml volume in preparation for application of sample to gel filtration column.

A Sepharose CL-4B gel filtration column was equilibrated with phosphate-buffered saline, pH 7.5. The concentrated high molecular weight protein sample was applied to the gel filtration column and column fractions were collected. Coomassie gels were performed on the column fractions to identify those containing high molecular weight proteins. The column fractions containing high molecular weight proteins were pooled.

Example 7

This Example illustrates the use of specified HMW1 and HMW2 proteins in immunization studies.

The copurified HMW1 and HMW2 proteins prepared as described in Example 6 were tested to determine whether they would protect against experimental otitis media caused by the homologous strain.

Healthy adult chinchillas, 1 to 2 years of age with weights of 350 to 500 g, received three monthly subcutaneous injections with 40 µg of an HMW1-HMW2 protein mixture in Freund's adjuvant. Control animals received phosphate-buffered saline in Freunds' adjuvant. one month after the last injection, the animals were challenged by intrabullar inoculation with 300 cfu of NTHI strain 12.

Middle ear infection developed in 5 of 5 control animals versus 5 of 10 immunized animals. Although only 5 of 10 chinchillas were protected in this test, the test conditions are very stringent, requiring bacteria to be injected directly into the middle ear space and to proliferate in what is in essence a small abscess cavity. As seen from the additional data below, complete protection of chinchillas can be achieved.

The five HMW1/HMW2-immunized animals that did not develop otitis media demonstrated no signs of middle ear inflammation when examined by otoscopy nor were middle ear effusions detectable.

Among the five HMW1/HMW2-immunized animals that became infected, the total duration of middle ear infection as assessed by the persistence of culture-positive middle ear fluid was not different from controls. However, the degree of inflammation of the tympanic membranes was subjectively less than in the HMW1/HMW2-immunized animals. When quantitative bacterial counts were performed on the middle ear fluid specimens recovered from infected animals, notable differences were apparent between the HMW1/HMW2-immunized and PBS-immunized animals (FIG. 17). Shown in FIG. 17 are quantitative middle ear fluid bacterial counts from animals on day 7 post-challenge, a time point associated with the maximum colony counts in middle ear fluid. The data were log-transformed for purpose of statistical comparison. The data from the control animals are shown on the left and data from the high molecular weight protein immunized animals on the right. The two horizontal lines indicate the respective means and standard derivations of middle ear fluid colony counts for only the infected animals in each group. As can be seen from this Figure, the HMW1/HMW2-immunized animals had significantly lower middle ear fluid bacterial counts than the PBS-immunized controls, geometric means of $7.4 \times 10^6$ and $1.3 \times 10^5$, respectively ($p=0.02$, Students' t-test)

Serum antibody titres following immunization were comparable in uninfected and infected animals. However, infection in immunized animals was uniformly associated with the appearance of bacteria down-regulated in expression of the HMW proteins, suggesting bacterial selection in response to immunologic pressure.

Although this data shows that protection following immunization was not complete, this data suggests the HMW adhesin proteins are potentially important protective antigens which may comprise one component of a multi-component NTHI vaccine.

In addition, complete protection has been achieved in the chinchilla model at lower dosage challenge, as set forth in Table 3 below.

Groups of five animals were immunized with 20 µg of the HMW1-HMW2 mixture prepared as described in Example 6 on days 1, 28 and 42 in the presence of alum. Blood samples were collected on day 53 to monitor the antibody response. On day 56, the left ear of animals was challenged with about 10 cfu of *H. influenzae* strain 12. Ear infection was monitored on day 4. Four animals in Group 3 were infected previously by *H. influenzae* strain 12 and were recovered completely for at least one month before the second challenge.

Example 8

This Example illustrates the provision of synthetic peptides corresponding to a portion only of the HMW1 protein.

A number of synthetic peptides were derived from HMW1. Antisera then were raised to these peptides. The anti-peptide antisera to peptide HMW1-P5 was shown to recognize HMW1. Peptide HMW1-P5 covers amino acids 1453 to 1481 of HMW1, has the sequence VDEVIEAKRILEKVKDLSDEEREALAKLG (SEQ ID No: 11), and represents bases 1498 to 1576 in FIG. 10.

This finding demonstrates that the DNA sequence and the derived protein is being interpreted in the correct reading frame and that peptides derived from the sequence can be produced which will be immunogenic.

Example 9

This Example describes the generation of monoclonal antibodies to the high molecular weight proteins of non-typeable *H. influenzae*.

Monoclonal antibodies were generated using standard techniques. In brief, female BALB/c mice (4 to 6 weeks old) were immunized by intraperitoneal injection with high molecular weight proteins purified from nontypable Haemophilus strain 5 or strain 12, as described in Example 6. The first injection of 40 to 50 µg of protein was administered with Freund's complete adjuvant and the second dose, received four to five weeks after the first, was administered with phosphate-buffered saline. Three days following the second injection, the mice were sacrificed and splenic lymphocytes were fused with SP2/0-Agl4 plasmacytoma cells.

Two weeks following fusion, hybridoma supernatants were screened for the presence of high molecular weight protein specific antibodies by a dot-blot assay. Purified high molecular weight proteins at a concentration of 10 µg per ml in TRIS-buffered saline (TBS), were used to sensitize nitrocellulose sheets (Bio-Rad Laboratories, Richmond, Calif.) by soaking for 20 minutes. Following a blocking step with TBS-3% gelatin, the nitrocellulose was incubated for 60 minutes at room temperature with individual hybridoma supernatants, at a 1:5 dilution in TBS-0.1% Tween, using a 96-well Bio-Dot micro-filtration apparatus (Bio-Rad). After washing, the sheets were incubated for one hour with alkaline-phosphatase-conjugated affinity isolated goat-anti (mouse IgG+IgM) antibodies (Tago, Inc., Burlingame, Calif.). Following additional washes, positive supernatants were identified by incubation of the nitrocellulose sheet in alkaline phosphatase buffer (0.10 M TRIS, 0.10 M NaCl, 0.005 M $MgCl_2$) containing nitroblue tetrazolium (0.1 mg/ml) and 5-bromo-4-chloro-3-indoyl phosphate (BCIP) (0.05 mg/ml).

For the antibody isotyping and immunoelectron microscopy studies to be described below, the monoclonal antibodies were purified from hybridoma supernatants. The antibodies recovered in this work were all of the IgG class.

To purify the monoclonal antibodies, the hybridoma supernatants were first subjected to ammonium sulfate precipitation (50% final concentration at 0° C.). Following overnight incubation, the precipitate was recovered by centrifugation and resolubilized in phosphate buffered saline. The solution was then dialyzed overnight against 0.01 M sodium phosphate buffer, pH 6.0. The following day the sample was applied to a DEAE-Sephacel column preequilibrated with the same phosphate buffer and the proteins were subsequently eluted with a KCl gradient. Column fractions containing the monoclonal antibodies were identified by examination of samples on Coomassie gels for protein bands typical of light and heavy chains.

The isotype of each monoclonal antibody was determined by immunodiffusion using the Ouchterlony method. Immunodiffusion plates were prepared on glass slides with 10 ml of 1% DNA-grade agarose (FMC Bioproducts, Rockland, Me.) in phospate-buffered saline. After the agarose solidified, 5-mm wells were punched into the agarose in a circular pattern. The center well contained a concentrated preparation of the monoclonal antibody being evaluated and the surrounding wells contained goat anti-mouse subclass-specific antibodies (Tago). The plates were incubated for 48 hours in a humid chamber at 4° C. and then examined for white lines of immunoprecipitation.

Hybridoma supernatants which were reactive in the dot-blot assay described above were examined by Western blot analysis, both to confirm the reactivity with the high molecular weight proteins of the homologous nontypable Haemophilus strain and to examine the cross-reactivity with similar proteins in heterologous strains. Nontypable *Haemophilus influenzae* cell sonicates containing 100 μg of total protein were solubilized in electrophoresis sample buffer, subjected to SDS-polyacrylamide gel electrophoresis on 7.5% acrylamide gels, and transferred to nitrocellulose using a Genie electrophoretic blotter (Idea Scientific Company, Corvallis, Oreg.) for 45 min at 24 V. After transfer, the nitrocellulose sheet was blocked and then probed sequentially with the hybridoma supernatant, with alkaline phosphatase-conjugated goat-anti(mouse IgG+IgM) second antibody, and finally bound antibodies were detected by incubation with nitroblue tetrazolium/BCIP solution. This same assay was employed to examine the reactivity of the monoclonals with recombinant fusion proteins expressed in *E. coli* (see below).

In preparation for immunoelectronmicroscopy, bacteria were grown overnight on supplemented chocolate agar and several colonies were suspended in phosphate-buffered-saline containing 1% albumin. A 20-μl drop of this bacterial suspension was then applied to a carbon-coated grid and incubated for 2 min. Excess fluid was removed and the specimen was then incubated for 5 min with the purified high molecular weight protein-specific monoclonal antibody being analyzed. Following removal of excess liquid and a wash with phosphatebuffered saline, the specimen was incubated with anti-mouse IgG conjugated to 10-nm colloidal gold particles. Following final washes with phosphate-buffered saline, the sample was rinsed with distilled water. Staining of the bacterial cells was performed with 0.5% uranyl acetate for 1 min. Samples were then examined in a Phillips 201c electron microscope.

Fourteen different hybridomas were recovered which produced monoclonal antibodies reactive with the purified HMW1 and HMW2 proteins of nontypable Haemophilus strain 12 in the immunoblot screening assay. Of the monoclonals screened by immunoelectron microscopy to date, as described below, two were demonstrated to bind surface epitopes on prototype strain 12. These two monoclonal antibodies, designated AD6 and 10C5 were both of the IgG1 subclass.

Example 10

This Example describes the identification of surface-exposed B-cell epitopes of high molecular weight proteins of non-typeable *H. influenzae*.

To map epitopes recognized by the monoclonal antibodies, their reactivity with a panel of recombinant fusion proteins expressed by pGEMEX® recombinant plasmids was examined. These plasmids were constructed by cloning various segments of the hmw1a or hmw2A structural genes into T7 expression vectors pGEMEX®-1 and GEMEX®-2 (Promega Corporation, Madison, Wis.). Shown in FIGS. 18 and 19 are the schematic diagrams depicting the segments derived from the hmw1 and hmw2 gene clusters cloned into the pGEMEX® expression plasmids. These segments were inserted such that in-frame fusions were created at each junction site. Thus, these plasmids encode recombinant fusion proteins containing pGEMEX®-encoded T7 gene 10 amino acids in the regions indicated by the hatched bars and hmw1a or hmw2A encoded amino acids in the regions indicated by the black bars in these Figures. A stop codon is present at the junction of the black and white segments of each bar.

Four discrete sites within the hmw1A structural gene were selected as the 5' ends of the hmw1 inserts. For each 5' end, a series of progressively smaller inserts was created by taking advantage of convenient downstream restriction sites. The first recombinant plasmid depicted in FIG. 18 was constructed by isolating a 4.9 kbp BamHI-HindIII fragment from pHMW1-14 (Example 1, FIG. 5A), which contains the entire hmw1 gene cluster and inserting it into BamHI-HindIII digested pGEMEX®-1. The second recombinant plasmid in this set was constructed by digesting the "parent" plasmid with BstEII-HindIII, recovering the 6.8 kbp larger fragment, blunt-ending with Klenow DNA polymerase, and religating. The third recombinant plasmid in this set was constructed by digesting the "parent" plasmid with ClaI-HindIII, recovering the 6.0 kbp larger fragment, blunt-ending, and religating. The next set of four hmw1 recombinant plasmids was derived from a "parent" plasmid constructed by ligating a 2.2 kbp EcoRI fragment from the hmw1 gene cluster into EcoRI-digested pGEMEX®-2. The other three recombinant plasmids in this second set were constructed by digesting at downstream BstEII, EcoRV, and ClaI sites, respectively, using techniques similar to those just described. The third set of three recombinant plasmids depicted was derived from a "parent" plasmid constructed by double-digesting the first recombinant plasmid described above (i.e. the one containing the 4.9 kbp BamHI-HindIII fragment) with BamHI and ClaI, blunt-ending, and religating. This resulted in a construct encoding a recombinant protein with an in-frame fusion at the ClaI site of the hmw1A gene. The remaining two plasmids in this third set were constructed by digesting at downstream BstEII and EcoRV sites, respectively. Finally, the fourth set of two recombinant plasmids was derived from a "parent" plasmid constructed by double-digesting the original BamHI-HindIII construct with HincII and EcoRV, then religating. This resulted in a construct encoding a recombinant protein with an in-frame fusion at the EcoRV site of the hmw1A gene. The remaining plasmid in this fourth set was constructed by digesting at the downstream BstEII site.

Three discrete sites with the hmw2A structural gene were selected as the 5' ends of the hmw2 inserts. The first recombinant plasmid depicted in FIG. 19 was constructed by isolating a 6.0 kbp EcoRI-XhoI fragment from pHMW2-21, which contains the entire hmw2 gene cluster, and inserting it into EcoRI-SalI digested pGEMEX®-1. The second recombinant plasmid in this set was constructed by digesting at an MluI site near the 3' end of the hmw2A gene. The second set of two hmw2 recombinant plasmids was derived from a "parent" plasmid constructed by isolating a 2.3 kbp HindIII fragment from pHMW2-21 and inserting it into HindIII-digested PGEMEX®-2. The remaining plasmid in this second set was constructed by digesting at the downstream MluI site. Finally, the last plasmid depicted was constructed by isolating a 1.2 kbp HincII-HindIII fragment from the indicated location in the hmw2 gene cluster and inserting it into HincII-HindIII digested pGEMEX®-1.

Each of the recombinant plasmids was used to transform E. coli strain JM101. The resulting transformants were used to generate the recombinant fusion proteins employed in the mapping studies. To prepare recombinant proteins, the transformed E. coli strains were grown to an A6 of 0.5 in L broth containing 50 μg of ampicillin per ml. IPTG was then added to 1 mM and mGP1-2, the M13 phage containing the T7 RNA polymerase gene, was added at multiplicity of infection of 10. One hour later, cells were harvested, and a sonicate of the cells was prepared. The protein concentrations of the samples were determined and cell sonicates containing 100 μg of total protein were solubilized in electrophoresis sample buffer, subjected to SDS-polyacrylamide gel electrophoresis, and examined on Coomassie gels to assess the expression level of recombinant fusion proteins. Once high levels of expression of the recombinant fusion proteins were confirmed, the cell sonicates were used in the Western blot analyses described above.

Shown in FIG. 20 is an electron micrograph demonstrating surface binding of Mab AD6 to representative nontypable *Haemophilus influenzae* strains. In the upper left panel of the Figure is nontypable Haemophilus strain 12 and in the upper right panel is a strain 12 derivative which no longer expressed the high molecular weight proteins. As can be seen, colloidal gold particles decorate the surface of strain 12, indicating bound AD6 antibody on the surface. In contrast, no gold particles are evident on the surface of the strain 12 mutant which no longer expresses the high molecular weight proteins. These results indicate that monoclonal antibody AD6 is recognizing a surface-exposed epitope on the high molecular weight proteins of strain 12. Analogous studies were performed with monoclonal antibody 10C5 demonstrating it too bound to surface-accessible epitopes on the high molecular weight HMW1 and HMW2 proteins of strain 12.

Having identified two surface-binding monoclonals, the epitope which each monoclonal recognized was mapped. To accomplish this task, the two sets of recombinant plasmids containing various portions of either the hmw1 a or hmw2A structural genes (FIGS. 18 and 19) were employed. With these complementary sets of recombinant plasmids, the epitopes recognized by the monoclonal antibodies were mapped to relatively small regions of the very large HMW1 and HMW2 proteins.

To localize epitopes recognized by Mab AD6, the pattern of reactivity of this monoclonal antibody with a large set of recombinant fusion protein was examined. FIG. 21 is a Western blot which demonstrates the pattern of reactivity of Mab AD6 with five recombinant fusion proteins, a relevant subset of the larger number originally examined. From analysis of the pattern of reactivity of Mab AD6 with this set of proteins, one is able to map the epitope it recognizes to a very short segment of the HMW1 and HMW2 proteins. A brief summary of this analysis follows. For reference, the relevant portions of the hmw1A or hmw2A structural genes which were expressed in the recombinant proteins being examined are indicated in the diagram at the top of the figure. As shown in lane 1, Mab AD6 recognizes an epitope encoded by fragment 1, a fragment which encompasses the distal one-fourth of the hmw1A gene. Reactivity is lost when only the portion of the gene comprising fragment 2 is expressed. This observation localizes the AD6 epitope somewhere within the last 180 amino acids at the carboxy-terminal end of the HMW1 protein. Mab AD6 also recognizes an epitope encoded by fragment 3, derived from the hmw2A structural gene. This is a rather large fragment which encompasses nearly one-third of the gene. Reactivity is lost when fragment 4 is expressed. The only difference between fragments 3 and 4 is that the last 225 base pairs at the 3' end of the hmw2A structural gene were deleted in the latter construct. This observation indicates that the AD6 epitope is encoded by this short terminal segment of the hmw2A gene. Strong support for this idea is provided by the demonstrated binding of Mab AD6 to the recombinant protein encoded by fragment 5, a fragment encompassing the distal one-tenth of the hmw2A structural gene. Taken together, these data identify the AD6 epitope as common to both the HMW1 and HMW2 proteins and place its location with 75 amino acids of the carboxy termini of the two proteins.

FIG. 22 is a Western blot demonstrating the pattern of reactivity of Mab 10C5 with the same five recombinant fusion proteins examined in FIG. 21. As shown in lane 1, Mab 10C5 recognizes an epitope encoded by fragment 1. In contrast to Mab AD6, Mab 10C5 also recognizes an epitope encoded by fragment 2. Also in contrast to Mab AD6, Mab 10C5 does not recognize any of the hmw2A-derived recombinant fusion proteins. Thus, these data identify the 10C5 epitope as being unique to the HMW1 protein and as being encoded by the fragment designated as fragment 2 in this figure. This fragment corresponds to a 155-amino acid segment encoded by the EcoRV-BstEII segment of the hmw1A structural gene.

Having identified the approximate locations of the epitopes on HMW1 and HMW2 recognized by the two monoclonals, the extent to which these epitopes were shared by the high molecular weight proteins of heterologous nontypable Haemophilus strains was next determined. When examined in Western blot assays with bacterial cell sonicates, Mab AD6 was reactive with epitopes expressed on the high molecular weight proteins of 75% of the inventor's collection of more than 125 nontypable *Haemophilus influenzae* strains. In fact, this monoclonal appeared to recognize epitopes expressed on high molecular weight proteins in virtually all nontypable Haemophilus strains which we previously identified as expressing HMW1/HMW2-like proteins. FIG. 23 is an example of a Western blot demonstrating the reactivity of Mab AD6 with a representative panel of such heterologous strains. As can be seen, the monoclonal antibody recognizes one or two bands in the 100 to 150 kDa range in each of these strains. For reference, the strain shown in lane 1 is prototype strain 12 and the two bands visualized represent HMW1 and HMW2 as the upper and lower immunoreactive bands, respectively.

In contrast to the broad cross-reactivity observed with Mab AD6, Mab 10C5 was much more limited in its ability to recognize high molecular weight proteins in heterologous strains. Mab 10C5 recognized high molecular weight proteins in approximately 40% of the strains which expressed HMW1/HMW2-like proteins. As was the case with Mab AD6, Mab 10C5 did not recognize proteins in any the nontypable Haemophilus strains which did not express HMW1/HMW2-like proteins.

In a limited fashion, the reactivity of Mab AD6 with surface-exposed epitopes on the heterologous strains has been examined. In the bottom two panels of FIG. 20 are electron micrographs demonstrating the reactivity of Mab AD6 with surface-accessible epitopes on nontypable Haemophilus strains 5 and 15. As can be seen, abundant colloidal-gold particles are evident on the surfaces of each of these strains, confirming their surface expression of the AD6 epitope. Although limited in scope, these data suggest that the AD6 epitope may be a common surface-accessible epitope on the high molecular weight adhesion proteins of most nontypable *Haemophilus influenzae* which express HMW1/HMW2-like proteins.

SUMMARY OF DISCLOSURE

In summary of this disclosure, the present invention provides high molecular weight proteins of non-typeable Haemophilus, genes coding for the same and vaccines incorporating such proteins. Modifications are possible within the scope of this invention.

TABLE 1

Effect of mutation of high molecular weight proteins on adherence to change epithelial cells by nontypable *H. influenzae*.

| Strain | ADHERENCE % * | |
|---|---|---|
| | % Inoculation | Relative to wild Type† |
| Strain 12 derivatives wild type | 87.76 ± 5.9 | 100.0 ± 6.7 |
| HMW1 mutant | 6.0 ± 0.9 | 6.8 ± 1.0 |
| HMW2 mutant | 89.9 ± 10.8 | 102.5 ± 12.3 |
| HMW1/HMW2 mutant | 2.0 ± 0.3 | 2.3 ± 0.3 |
| Strain 5 derivatives wild type | 78.7 ± 3.2 | 100.0 ± 4.1 |
| HMW1-like mutant | 15.7 ± 2.6 | 19.9 ± 3.3 |
| HMW2-like mutant | 103.7 ± 14.0 | 131.7 ± 17.8 |
| double mutant | 3.5 ± 0.6 | 4.4 ± 0.8 |

*Numbers represent mean (± standard error of the mean) of measurements in triplicate or quadruplicate from representative experiments.
†Adherence values for strain 12 derivatives are relative to strain 12 wild type; values for strain 5 derivatives are relative to strain 5 wild type.

TABLE 2

Adherence by *E. coli* DH5α and HB101 harboring *hmw1* or *hmw2* gene clusters.

| Strain* | Adherence relative to *H. influenzae* strain 12† |
|---|---|
| DH5α (pT7-7) | 0.7 ± 0.02 |
| DH5α (pHMW1-14) | 114.2 ± 15.9 |
| DH5α (pHMW2-21) | 14.0 ± 3.7 |
| HB101 (pT7-7) | 1.2 ± 0.5 |
| HB101 (pHMW1-14) | 93.6 ± 15.8 |
| HB101 (pHMW2-21) | 3.6 ± 0.9 |

*The plasmid PHMW1-14 contains the *hmw1* gene cluster,' while pHMW2-21 contains the *hmw2* gene cluster; pT7-7 is the cloning vector used in these constructs.
†Numbers represent the mean (± standard error of the mean) of measurements made in triplicate from representative experiments.

TABLE 3

Protective ability of HMW protein against non-typeable *H. influenzae* challenge in chinchilla model

| | | | Number of Animals Showed Positive Ear Infection | | |
|---|---|---|---|---|---|
| Group (#) | Antigens | Total Animals | Tympano-gram | Otoscopic Examination | cfu of Bacteria/ 10µL |
| 1 | HMW | 5 | 0 | 0 | 0 |
| 2 | None | 5 | 5 | 5 | 850–3200 (4/5) |
| 3 | Convalescent | 4 | 0 | 0 | 0 |

---

SEQUENCE LISTING (1) GENERAL INFORMATION:

(iii) NUMBER OF SEQUENCES: 11

(2) INFORMATION FOR SEQ ID NO:1:

(i) SEQUENCE CHARACTERISTICS:
      (A) LENGTH: 5116 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO:1:

```
ACAGCGTTCT CTTAATACTA GTACAAACCC ACAATAAAAT ATGACAAACA ACAATTACAA      60

CACCTTTTTT GCAGTCTATA TGCAAATATT TTAAAAAATA GTATAAATCC GCCATATAAA     120

ATGGTATAAT CTTTCATCTT TCATCTTTCA TCTTTCATCT TTCATCTTTC ATCTTTCATC     180

TTTCATCTTT CATCTTTCAT CTTTCATCTT TCATCTTTCA TCTTTCATCT TTCATCTTTC     240

ACATGCCCTG ATGAACCGAG GGAAGGGAGG GAGGGGCAAG AATGAAGAGG GAGCTGAACG     300

AACGCAAATG ATAAAGTAAT TTAATTGTTC AACTAACCTT AGGAGAAAAT ATGAACAAGC     360

TATATCGTCT CAAATTCAGC AAACGCCTGA ATGCTTTGGT TGCTGTGTCT GAATTGGCAC     420

GGGGTTGTGA CCATTCCACA GAAAAAGGCA GCGAAAAACC TGCTCGCATG AAAGTGCGTC     480

ACTTAGCGTT AAAGCCACTT TCCGCTATGT TACTATCTTT AGGTGTAACA TCTATTCCAC     540

AATCTGTTTT AGCAAGCGGC TTACAAGGAA TGGATGTAGT ACACGGCACA GCCACTATGC     600

AAGTAGATGG TAATAAAACC ATTATCCGCA ACAGTGTTGA CGATATCATT AATTGGAAAC     660

AATTTAACAT CGACCAAAAT GAAATGGTGC AGTTTTTACA AGAAAACAAC AACTCCGCCG     720

TATTCAACCG TGTTACATCT AACCAAATCT CCCAATTAAA AGGGATTTTA GATTCTAACG     780

GACAAGTCTT TTTAATCAAC CCAAATGGTA TCACAATAGG TAAAGACGCA ATTATTAACA     840

CTAATGGCTT TACGGCTTCT ACGCTAGACA TTTCTAACGA AAACATCAAG GCGCGTAATT     900

TCACCTTCGA GCAAACCAAA GATAAAGCGC TCGCTGAAAT TGTGAATCAC GGTTTAATTA     960

CTGTCGGTAA AGACGGCAGT GTAAATCTTA TTGGTGGCAA AGTGAAAAAC GAGGGTGTGA    1020

TTAGCGTAAA TGGTGGCAGC ATTTCTTTAC TCGCAGGGCA AAAAATCACC ATCAGCGATA    1080

TAATAAACCC AACCATTACT TACAGCATTG CCGCGCCTGA AAATGAAGCG GTCAATCTGG    1140

GCGATATTTT TGCCAAAGGC GGTAACATTA ATGTCCGTGC TGCCACTATT CGAAACCAAG    1200

GTAAACTTTC TGCTGATTCT GTAAGCAAAG ATAAAAGCGG CAATATTGTT CTTTCCGCCA    1260

AAGAGGGTGA AGCGGAAATT GGCGGTGTAA TTTCCGCTCA AAATCAGCAA GCTAAAGGCG    1320

GCAAGCTGAT GATTACAGGC GATAAAGTCA CATTAAAAAC AGGTGCAGTT ATCGACCTTT    1380

CAGGTAAAGA AGGGGGAGAA ACTTACCTTG GCGGTGACGA GCGCGGCGAA GGTAAAAAGG    1440

GCATTCAATT AGCAAAGAAA ACCTCTTTAG AAAAAGGCTC AACCATCAAT GTATCAGGCA    1500

AAGAAAAAGG CGGACGCGCT ATTGTGTGGG GCGATATTGC GTTAATTGAC GGCAATATTA    1560

ACGCTCAAGG TAGTGGTGAT ATCGCTAAAA CCGGTGGTTT TGTGGAGACG TCGGGGCATG    1620

ATTTATTCAT CAAAGACAAT GCAATTGTTG ACGCCAAAGA GTGGTTGTTA GACCCGGATA    1680

ATGTATCTAT TAATGCAGAA ACAGCAGGAC GCAGCAATAC TTCAGAAGAC GATGAATACA    1740

CGGGATCCGG GAATAGTGCC AGCACCCCAA AACGAAACAA AGAAAAGACA ACATTAACAA    1800

ACACAACTCT TGAGAGTATA CTAAAAAAAG GTACCTTTGT TAACATCACT GCTAATCAAC    1860

GCATCTATGT CAATAGCTCC ATTAATTTAT CCAATGGCAG CTTAACTCTT TGGAGTGAGG    1920

GTCGGAGCGG TGGCGGCGTT GAGATTAACA ACGATATTAC CACCGGTGAT GATACCAGAG    1980

GTGCAAACTT AACAATTTAC TCAGGCGGCT GGGTTGATGT TCATAAAAAT ATCTCACTCG    2040

GGGCGCAAGG TAACATAAAC ATTACAGCTA ACAAGATAT CGCCTTTGAG AAAGGAAGCA    2100

ACCAAGTCAT TACAGGTCAA GGGACTATTA CCTCAGGCAA TCAAAAAGGT TTTAGATTTA    2160

ATAATGTCTC TCTAAACGGC ACTGGCAGCG GACTGCAATT CACCACTAAA AGAACCAATA    2220

AATACGCTAT CACAAATAAA TTTGAAGGGA CTTTAAATAT TTCAGGGAAA GTGAACATCT    2280

CAATGGTTTT ACCTAAAAAT GAAAGTGGAT ATGATAAATT CAAAGGACGC ACTTACTGGA    2340
```

```
ATTTAACCTC CTTAAATGTT TCCGAGAGTG GCGAGTTTAA CCTCACTATT GACTCCAGAG    2400

GAAGCGATAG TGCAGGCACA CTTACCCAGC CTTATAATTT AAACGGTATA TCATTCAACA    2460

AAGACACTAC CTTTAATGTT GAACGAAATG CAAGAGTCAA CTTTGACATC AAGGCACCAA    2520

TAGGGATAAA TAAGTATTCT AGTTTGAATT ACGCATCATT TAATGGAAAC ATTTCAGTTT    2580

CGGGAGGGGG GAGTGTTGAT TTCACACTTC TCGCCTCATC CTCTAACGTC CAAACCCCCG    2640

GTGTAGTTAT AAATTCTAAA TACTTTAATG TTTCAACAGG GTCAAGTTTA AGATTTAAAA    2700

CTTCAGGCTC AACAAAAACT GGCTTCTCAA TAGAGAAAGA TTTAACTTTA AATGCCACCG    2760

GAGGCAACAT AACACTTTTG CAAGTTGAAG GCACCGATGG AATGATTGGT AAAGGCATTG    2820

TAGCCAAAAA AAACATAACC TTTGAAGGAG GTAACATCAC CTTTGGCTCC AGGAAAGCCG    2880

TAACAGAAAT CGAAGGCAAT GTTACTATCA ATAACAACGC TAACGTCACT CTTATCGGTT    2940

CGGATTTTGA CAACCATCAA AAACCTTTAA CTATTAAAAA AGATGTCATC ATTAATAGCG    3000

GCAACCTTAC CGCTGGAGGC AATATTGTCA ATATAGCCGG AAATCTTACC GTTGAAAGTA    3060

ACGCTAATTT CAAAGCTATC ACAAATTTCA CTTTTAATGT AGGCGGCTTG TTTGACAACA    3120

AAGGCAATTC AAATATTTCC ATTGCCAAAG GAGGGGCTCG CTTTAAAGAC ATTGATAATT    3180

CCAAGAATTT AAGCATCACC ACCAACTCCA GCTCCACTTA CCGCACTATT ATAAGCGGCA    3240

ATATAACCAA TAAAAACGGT GATTTAAATA TTACGAACGA AGGTAGTGAT ACTGAAATGC    3300

AAATTGGCGG CGATGTCTCG CAAAAAGAAG GTAATCTCAC GATTTCTTCT GACAAAATCA    3360

ATATTACCAA ACAGATAACA ATCAAGGCAG GTGTTGATGG GGAGAATTCC GATTCAGACG    3420

CGACAAACAA TGCCAATCTA ACCATTAAAA CCAAAGAATT GAAATTAACG CAAGACCTAA    3480

ATATTTCAGG TTTCAATAAA GCAGAGATTA CAGCTAAAGA TGGTAGTGAT TTAACTATTG    3540

GTAACACCAA TAGTGCTGAT GGTACTAATG CCAAAAAAGT AACCTTTAAC CAGGTTAAAG    3600

ATTCAAAAAT CTCTGCTGAC GGTCACAAGG TGACACTACA CAGCAAAGTG GAAACATCCG    3660

GTAGTAATAA CAACACTGAA GATAGCAGTG ACAATAATGC CGGCTTAACT ATCGATGCAA    3720

AAAATGTAAC AGTAAACAAC AATATTACTT CTCACAAAGC AGTGAGCATC TCTGCGACAA    3780

GTGGAGAAAT TACCACTAAA ACAGGTACAA CCATTAACGC AACCACTGGT AACGTGGAGA    3840

TAACCGCTCA AACAGGTAGT ATCCTAGGTG GAATTGAGTC CAGCTCTGGC TCTGTAACAC    3900

TTACTGCAAC CGAGGGCGCT CTTGCTGTAA GCAATATTTC GGGCAACACC GTTACTGTTA    3960

CTGCAAATAG CGGTGCATTA ACCACTTTGG CAGGCTCTAC AATTAAAGGA ACCGAGAGTG    4020

TAACCACTTC AAGTCAATCA GGCGATATCG GCGGTACGAT TTCTGGTGGC ACAGTAGAGG    4080

TTAAAGCAAC CGAAAGTTTA ACCACTCAAT CCAATTCAAA AATTAAAGCA ACAACAGGCG    4140

AGGCTAACGT AACAAGTGCA ACAGGTACAA TTGGTGGTAC GATTTCCGGT AATACGGTAA    4200

ATGTTACGGC AAACGCTGGC GATTTAACAG TTGGGAATGG CGCAGAAATT AATGCGACAG    4260

AAGGAGCTGC AACCTTAACT ACATCATCGG GCAAATTAAC TACCGAAGCT AGTTCACACA    4320

TTACTTCAGC CAAGGGTCAG GTAAATCTTT CAGCTCAGGA TGGTAGCGTT GCAGGAAGTA    4380

TTAATGCCGC CAATGTGACA CTAAATACTA CAGGCACTTT AACTACCGTG AAGGGTTCAA    4440

ACATTAATGC AACCAGCGGT ACCTTGGTTA TTAACGCAAA AGACGCTGAG CTAAATGGCG    4500

CAGCATTGGG TAACCACACA GTGGTAAATG CAACCAACGC AAATGGCTCC GGCAGCGTAA    4560

TCGCGACAAC CTCAAGCAGA GTGAACATCA CTGGGGATTT AATCACAATA AATGGATTAA    4620

ATATCATTTC AAAAAACGGT ATAAACACCG TACTGTTAAA AGGCGTTAAA ATTGATGTGA    4680

AATACATTCA ACCGGGTATA GCAAGCGTAG ATGAAGTAAT TGAAGCGAAA CGCATCCTTG    4740
```

-continued

```
AGAAGGTAAA AGATTTATCT GATGAAGAAA GAGAAGCGTT AGCTAAACTT GGAGTAAGTG     4800

CTGTACGTTT TATTGAGCCA AATAATACAA TTACAGTCGA TACACAAAAT GAATTTGCAA     4860

CCAGACCATT AAGTCGAATA GTGATTTCTG AAGGCAGGGC GTGTTTCTCA AACAGTGATG     4920

GCGCGACGGT GTGCGTTAAT ATCGCTGATA ACGGGCGGTA GCGGTCAGTA ATTGACAAGG     4980

TAGATTTCAT CCTGCAATGA AGTCATTTTA TTTTCGTATT ATTTACTGTG TGGGTTAAAG     5040

TTCAGTACGG GCTTTACCCA TCTTGTAAAA AATTACGGAG AATACAATAA AGTATTTTTA     5100

ACAGGTTATT ATTATG                                                    5116
```

(2) INFORMATION FOR SEQ ID NO:2:

(i) SEQUENCE CHARACTERISTICS:
       (A) LENGTH: 1536 amino acids
       (B) TYPE: amino acid
       (C) STRANDEDNESS: single
       (D) TOPOLOGY: linear (ii) MOLECULE TYPE: DNA (genomic)

(xi) SEQUENCE DESCRIPTION: SEQ ID NO:2:

```
Met Asn Lys Ile Tyr Arg Leu Lys Phe Ser Lys Arg Leu Asn Ala Leu
1               5                   10                  15

Val Ala Val Ser Glu Leu Ala Arg Gly Cys Asp His Ser Thr Glu Lys
            20                  25                  30

Gly Ser Glu Lys Pro Ala Arg Met Lys Val Arg His Leu Ala Leu Lys
        35                  40                  45

Pro Leu Ser Ala Met Leu Leu Ser Leu Gly Val Thr Ser Ile Pro Gln
    50                  55                  60

Ser Val Leu Ala Ser Gly Leu Gln Gly Met Asp Val Val His Gly Thr
65                  70                  75                  80

Ala Thr Met Gln Val Asp Gly Asn Lys Thr Ile Ile Arg Asn Ser Val
                85                  90                  95

Asp Ala Ile Ile Asn Trp Lys Gln Phe Asn Ile Asp Gln Asn Glu Met
            100                 105                 110

Val Gln Phe Leu Gln Glu Asn Asn Ser Ala Val Phe Asn Arg Val
        115                 120                 125

Thr Ser Asn Gln Ile Ser Gln Leu Lys Gly Ile Leu Asp Ser Asn Gly
    130                 135                 140

Gln Val Phe Leu Ile Asn Pro Asn Gly Ile Thr Ile Gly Lys Asp Ala
145                 150                 155                 160

Ile Ile Asn Thr Asn Gly Phe Thr Ala Ser Thr Leu Asp Ile Ser Asn
                165                 170                 175

Glu Asn Ile Lys Ala Arg Asn Phe Thr Phe Glu Gln Thr Lys Asp Lys
            180                 185                 190

Ala Leu Ala Glu Ile Val Asn His Gly Leu Ile Thr Val Gly Lys Asp
        195                 200                 205

Gly Ser Val Asn Leu Ile Gly Gly Lys Val Lys Asn Glu Gly Val Ile
    210                 215                 220

Ser Val Asn Gly Gly Ser Ile Ser Leu Leu Ala Gly Gln Lys Ile Thr
225                 230                 235                 240

Ile Ser Asp Ile Ile Asn Pro Thr Ile Thr Tyr Ser Ile Ala Ala Pro
                245                 250                 255

Glu Asn Glu Ala Val Asn Leu Gly Asp Ile Phe Ala Lys Gly Gly Asn
            260                 265                 270

Ile Asn Val Arg Ala Ala Thr Ile Arg Asn Gln Gly Lys Leu Ser Ala
        275                 280                 285
```

-continued

```
Asp Ser Val Ser Lys Asp Lys Ser Gly Asn Ile Val Leu Ser Ala Lys
    290                 295                 300
Glu Gly Glu Ala Glu Ile Gly Val Ile Ser Ala Gln Asn Gln Gln
305                 310                 315                 320
Ala Lys Gly Gly Lys Leu Met Ile Thr Gly Asp Lys Val Thr Leu Lys
                325                 330                 335
Thr Gly Ala Val Ile Asp Leu Ser Gly Lys Glu Gly Glu Thr Tyr
            340                 345                 350
Leu Gly Gly Asp Glu Arg Gly Gly Lys Asn Gly Ile Gln Leu Ala
        355                 360                 365
Lys Lys Thr Ser Leu Glu Lys Gly Ser Thr Ile Asn Val Ser Gly Lys
    370                 375                 380
Glu Lys Gly Gly Arg Ala Ile Val Trp Gly Asp Ile Ala Leu Ile Asp
385                 390                 395                 400
Gly Asn Ile Asn Ala Gln Gly Ser Gly Asp Ile Ala Lys Thr Gly Gly
                405                 410                 415
Phe Val Glu Thr Ser Gly His Asp Leu Phe Ile Lys Asp Asn Ala Ile
            420                 425                 430
Val Asp Ala Lys Glu Trp Leu Leu Asp Phe Asp Asn Val Ser Ile Asn
        435                 440                 445
Ala Glu Thr Ala Gly Arg Ser Asn Thr Ser Glu Asp Asp Glu Tyr Thr
    450                 455                 460
Gly Ser Gly Asn Ser Ala Ser Thr Pro Lys Arg Asn Lys Glu Lys Thr
465                 470                 475                 480
Thr Leu Thr Asn Thr Thr Leu Glu Ser Ile Leu Lys Lys Gly Thr Phe
                485                 490                 495
Val Asn Ile Thr Ala Asn Gln Arg Ile Tyr Val Asn Ser Ser Ile Asn
            500                 505                 510
Leu Ser Asn Gly Ser Leu Thr Leu Trp Ser Glu Gly Arg Ser Gly Gly
        515                 520                 525
Gly Val Glu Ile Asn Asn Asp Ile Thr Thr Gly Asp Asp Thr Arg Gly
    530                 535                 540
Ala Asn Leu Thr Ile Tyr Ser Gly Gly Trp Val Asp Val His Lys Asn
545                 550                 555                 560
Ile Ser Leu Gly Ala Gln Gly Asn Ile Asn Ile Thr Ala Lys Gln Asp
                565                 570                 575
Ile Ala Phe Glu Lys Gly Ser Asn Gln Val Ile Thr Gly Gln Gly Thr
            580                 585                 590
Ile Thr Ser Gly Asn Gln Lys Gly Phe Arg Phe Asn Asn Val Ser Leu
        595                 600                 605
Asn Gly Thr Gly Ser Gly Leu Gln Phe Thr Thr Lys Arg Thr Asn Lys
    610                 615                 620
Tyr Ala Ile Thr Asn Lys Phe Glu Gly Thr Leu Asn Ile Ser Gly Lys
625                 630                 635                 640
Val Asn Ile Ser Met Val Leu Pro Lys Asn Glu Ser Gly Tyr Asp Lys
                645                 650                 655
Phe Lys Gly Arg Thr Tyr Trp Asn Leu Thr Ser Leu Asn Val Ser Glu
            660                 665                 670
Ser Gly Glu Phe Asn Leu Thr Ile Asp Ser Arg Gly Ser Asp Ser Ala
        675                 680                 685
Gly Thr Leu Thr Gln Pro Tyr Asn Leu Asn Gly Ile Ser Phe Asn Lys
    690                 695                 700
Asp Thr Thr Phe Asn Val Glu Arg Asn Ala Arg Val Asn Phe Asp Ile
```

```
705                 710                 715                 720
Lys Ala Pro Ile Gly Ile Asn Lys Tyr Ser Leu Asn Tyr Ala Ser
                725                 730                 735
Phe Asn Gly Asn Ile Ser Val Ser Gly Gly Ser Val Asp Phe Thr
                740                 745                 750
Leu Leu Ala Ser Ser Ser Asn Val Gln Thr Pro Gly Val Val Ile Asn
                755                 760                 765
Ser Lys Tyr Phe Asn Val Ser Thr Gly Ser Ser Leu Arg Phe Lys Thr
770                 775                 780
Ser Gly Ser Thr Lys Thr Gly Phe Ser Ile Glu Lys Asp Leu Thr Leu
785                 790                 795                 800
Asn Ala Thr Gly Gly Asn Ile Thr Leu Leu Gln Val Glu Gly Thr Asp
                805                 810                 815
Gly Met Ile Gly Lys Gly Ile Val Ala Lys Lys Asn Ile Thr Phe Glu
                820                 825                 830
Gly Gly Asn Ile Thr Phe Gly Ser Arg Lys Ala Val Thr Glu Ile Glu
                835                 840                 845
Gly Asn Val Thr Ile Asn Asn Asn Ala Asn Val Thr Leu Ile Gly Ser
                850                 855                 860
Asp Phe Asp Asn His Gln Lys Pro Leu Thr Ile Lys Lys Asp Val Ile
865                 870                 875                 880
Ile Asn Ser Gly Asn Leu Thr Ala Gly Gly Asn Ile Val Asn Ile Ala
                885                 890                 895
Gly Asn Leu Thr Val Glu Ser Asn Ala Asn Phe Lys Ala Ile Thr Asn
                900                 905                 910
Phe Thr Phe Asn Val Gly Gly Leu Phe Asp Asn Lys Gly Asn Ser Asn
                915                 920                 925
Ile Ser Ile Ala Lys Gly Gly Ala Arg Phe Lys Asp Ile Asp Asn Ser
                930                 935                 940
Lys Asn Leu Ser Ile Thr Thr Asn Ser Ser Ser Thr Tyr Arg Thr Ile
945                 950                 955                 960
Ile Ser Gly Asn Ile Thr Asn Lys Asn Gly Asp Leu Asn Ile Thr Asn
                965                 970                 975
Glu Gly Ser Asp Thr Glu Met Gln Ile Gly Gly Asp Val Ser Gln Lys
                980                 985                 990
Glu Gly Asn Leu Thr Ile Ser Ser Asp Lys Ile Asn Ile Thr Lys Gln
                995                 1000                1005
Ile Thr Ile Lys Ala Gly Val Asp Gly Glu Asn Ser Asp Ser Asp Ala
                1010                1015                1020
Thr Asn Asn Ala Asn Leu Thr Ile Lys Thr Lys Glu Leu Lys Leu Thr
1025                1030                1035                1040
Gln Asp Leu Asn Ile Ser Gly Phe Asn Lys Ala Glu Ile Thr Ala Lys
                1045                1050                1055
Asp Gly Ser Asp Leu Thr Ile Gly Asn Thr Asn Ser Ala Asp Gly Thr
                1060                1065                1070
Asn Ala Lys Lys Val Thr Phe Asn Gln Val Lys Asp Ser Lys Ile Ser
                1075                1080                1085
Ala Asp Gly His Lys Val Thr Leu His Ser Lys Val Glu Thr Ser Gly
                1090                1095                1100
Ser Asn Asn Asn Thr Glu Asp Ser Ser Asp Asn Asn Ala Gly Leu Thr
1105                1110                1115                1120
Ile Asp Ala Lys Asn Val Thr Val Asn Asn Asn Ile Thr Ser His Lys
                1125                1130                1135
```

```
Ala Val Ser Ile Ser Ala Thr Ser Gly Glu Ile Thr Thr Lys Thr Gly
            1140                1145                1150

Thr Thr Ile Asn Ala Thr Thr Gly Asn Val Glu Ile Thr Ala Gln Thr
            1155                1160            1165

Gly Ser Ile Leu Gly Gly Ile Glu Ser Ser Gly Ser Val Thr Leu
        1170                1175                1180

Thr Ala Thr Glu Gly Ala Leu Ala Val Ser Asn Ile Ser Gly Asn Thr
1185                1190                1195                1200

Val Thr Val Thr Ala Asn Ser Gly Ala Leu Thr Thr Leu Ala Gly Ser
            1205                1210                1215

Thr Ile Lys Gly Thr Glu Ser Val Thr Thr Ser Gln Ser Gly Asp
            1220                1225            1230

Ile Gly Gly Thr Ile Ser Gly Gly Thr Val Glu Val Lys Ala Thr Glu
        1235                1240                1245

Ser Leu Thr Thr Gln Ser Asn Ser Lys Ile Lys Ala Thr Thr Gly Glu
        1250                1255            1260

Ala Asn Val Thr Ser Ala Thr Gly Thr Ile Gly Gly Thr Ile Ser Gly
1265                1270                1275                1280

Asn Thr Val Asn Val Thr Ala Asn Ala Gly Asp Leu Thr Val Gly Asn
            1285                1290                1295

Gly Ala Glu Ile Asn Ala Thr Glu Gly Ala Ala Thr Leu Thr Thr Ser
            1300                1305                1310

Ser Gly Lys Leu Thr Thr Glu Ala Ser Ser His Ile Thr Ser Ala Lys
            1315                1320            1325

Gly Gln Val Asn Leu Ser Ala Gln Asp Gly Ser Val Ala Gly Ser Ile
            1330                1335            1340

Asn Ala Ala Asn Val Thr Leu Asn Thr Thr Gly Thr Leu Thr Thr Val
1345                1350                1355                1360

Lys Gly Ser Asn Ile Asn Ala Thr Ser Gly Thr Leu Val Ile Asn Ala
            1365                1370                1375

Lys Asp Ala Glu Leu Asn Gly Ala Ala Leu Gly Asn His Thr Val Val
            1380                1385                1390

Asn Ala Thr Asn Ala Asn Gly Ser Gly Ser Val Ile Ala Thr Thr Ser
            1395                1400                1405

Ser Arg Val Asn Ile Thr Gly Asp Leu Ile Thr Ile Asn Gly Leu Asn
            1410                1415                1420

Ile Ile Ser Lys Asn Gly Ile Asn Thr Val Leu Leu Lys Gly Val Lys
1425                1430                1435                1440

Ile Asp Val Lys Tyr Ile Gln Pro Gly Ile Ala Ser Val Asp Glu Val
                    1445                1450                1455

Ile Glu Ala Lys Arg Ile Leu Glu Lys Val Lys Asp Leu Ser Asp Glu
            1460                1465                1470

Glu Arg Glu Ala Leu Ala Lys Leu Gly Val Ser Ala Val Arg Phe Ile
            1475                1480                1485

Glu Pro Asn Asn Thr Ile Thr Val Asp Thr Gln Asn Glu Phe Ala Thr
            1490                1495            1500

Arg Pro Leu Ser Arg Ile Val Ile Ser Glu Gly Arg Ala Cys Phe Ser
1505                1510                1515                1520

Asn Ser Asp Gly Ala Thr Val Cys Val Asn Ile Ala Asp Asn Gly Arg
            1525                1530                1535

(2) INFORMATION FOR SEQ ID NO:3:

(i) SEQUENCE CHARACTERISTICS:
        (A) LENGTH: 4937 base pairs
```

(B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:3:

```
TAAATATACA AGATAATAAA AATAAATCAA GATTTTGTG ATGACAAACA ACAATTACAA      60

CACCTTTTTT GCAGTCTATA TGCAAATATT TTAAAAAAAT AGTATAAATC CGCCATATAA     120

AATGGTATAA TCTTTCATCT TTCATCTTTA ATCTTTCATC TTTCATCTTT CATCTTTCAT     180

CTTTCATCTT TCATCTTTCA TCTTTCATCT TTCATCTTTC ATCTTTCATC TTTCATCTTT     240

CACATGAAAT GATGAACCGA GGGAAGGGAG GGAGGGGCAA GAATGAAGAG GGAGCTGAAC     300

GAACGCAAAT GATAAAGTAA TTTAATTGTT CAACTAACCT TAGGAGAAAA TATGAACAAG     360

ATATATCGTC TCAAATTCAG CAAACGCCTG AATGCTTTGG TTGCTGTGTC TGAATTGGCA     420

CGGGGTTGTG ACCATTCCAC AGAAAAAGGC TTCCGCTATG TTACTATCTT TAGGTGTAAC     480

CACTTAGCGT TAAAGCCACT TTCCGCTATG TTACTATCTT TAGGTGTAAC ATCTATTCCA     540

CAATCTGTTT TAGCAAGCGG CTTACAAGGA ATGGATGTAG TACACGGCAC AGCCACTATG     600

CAAGTAGATG GTAATAAAAC CATTATCCGC AACAGTGTTG ACGCTATCAT TAATTGGAAA     660

CAATTTAACA TCGACCAAAA TGAAATGGTG CAGTTTTTAC AAGAAAACAA CAACTCCGCC     720

GTATTCAACC GTGTTACATC TAACCAAATC TCCCAATTAA AAGGGATTTT AGATTCTAAC     780

GGACAAGTCT TTTTAATCAA CCCAAATGGT ATCACAATAG GTAAAGACGC AATTATTAAC     840

ACTAATGGCT TTACGGCTTC TACGCTAGAC ATTTCTAACG AAAACATCAA GGCGCGTAAT     900

TTCACCTTCG AGCAAACCAA AGATAAAGCG CTCGCTGAAA TTGTGAATCA CGGTTTAATT     960

ACTGTCGGTA AAGACGGCAG TGTAAATCTT ATTGGTGGCA AAGTGAAAAA CGAGGGTGTG    1020

ATTAGCGTAA ATGGTGGCAG CATTTCTTTA CTCGCAGGGC AAAAAATCAC CATCAGCGAT    1080

ATAATAAACC CAACCATTAC TTACAGCATT GCCGCGCCTG AAAATGAAGC GGTCAATCTG    1140

GGCGATATTT TTGCCAAAGG CGGTAACATT AATGTCCGTG CTGCCACTAT TCGAAACCAA    1200

GGTAAACTTT CTGCTGATTC TGTAAGCAAA GATAAAGCG GCAATATTGT TCTTTCCGCC     1260

AAAGAGGGTG AAGCGGAAAT TGGCGGTGTA ATTTCCGCTC AAAATCAGCA AGCTAAAGGC    1320

GGCAAGCTGA TGATTACAGG CGATAAAGTC ACATTAAAAA CAGGTGCAGT TATCGACCTT    1380

TCAGGTAAAG AAGGGGGAGA AACTTACCTT GGCGGTGACG AGCGCGGCGA AGGTAAAAAC    1440

GGCATTCAAT TAGCAAAGAA AACCTCTTTA GAAAAAGGCT CAACCATCAA TGTATCAGGC    1500

AAAGAAAAAG GCGGACGCGC TATTGTGTGG GGCGATATTG CGTTAATTGA CGGCAATATT    1560

AACGCTCAAG GTAGTGGTGA TATCGCTAAA ACCGGTGGTT TTGTGGAGAC ATCGGGGCAT    1620

TATTTATCCA TTGACAGCAA TGCAATTGTT AAAACAAAAG AGTGGTTGCT AGACCCTGAT    1680

GATGTAACAA TTGAAGCCGA AGACCCCCTT CGCAATAATA CCGGTATAAA TGATGAATTC    1740

CCAACAGGCA CCGGTGAAGC AAGCGACCCT AAAAAAAATA GCGAACTCAA AACAACGCTA    1800

ACCAATACAA CTATTTCAAA TTATCTGAAA AACGCCTGGA CAATGAATAT AACGGCATCA    1860

AGAAAACTTA CCGTTAATAG CTCAATCAAC ATCGGAAGCA ACTCCCACTT AATTCTCCAT    1920

AGTAAAGGTC AGCGTGGCGG AGGCGTTCAG ATTGATGGAG ATATTACTTC TAAAGGCGGA    1980

AATTTAACCA TTTATTCTGG CGGATGGGTT GATGTTCATA AAAATATTAC GCTTGATCAG    2040

GGTTTTTTAA ATATTACCGC CGCTTCCGTA GCTTTTGAAG GTGGAAATAA CAAAGCACGC    2100

GACGCGGCAA ATGCTAAAAT TGTCGCCCAG GGCACTGTAA CCATTACAGG AGAGGGAAAA    2160
```

```
GATTTCAGGG CTAACAACGT ATCTTTAAAC GGAACGGGTA AAGGTCTGAA TATCATTTCA    2220

TCAGTGAATA ATTTAACCCA CAATCTTAGT GGCACAATTA ACATATCTGG AATATAACA     2280

ATTAACCAAA CTACGAGAAA GAACACCTCG TATTGGCAAA CCAGCCATGA TTCGCACTGG    2340

AACGTCAGTG CTCTTAATCT AGAGACAGGC GCAAATTTTA CCTTTATTAA ATACATTTCA    2400

AGCAATAGCA AAGGCTTAAC AACACAGTAT AGAAGCTCTG CAGGGGTGAA TTTTAACGGC    2460

GTAAATGGCA ACATGTCATT CAATCTCAAA GAAGGAGCGA AAGTTAATTT CAAATTAAAA    2520

CCAAACGAGA ACATGAACAC AAGCAAACCT TTACCAATTC GGTTTTTAGC CAATATCACA    2580

GCCACTGGTG GGGGCTCTGT TTTTTTTGAT ATATATGCCA ACCATTCTGG CAGAGGGGCT    2640

GAGTTAAAAA TGAGTGAAAT TAATATCTCT AACGGCGCTA ATTTTACCTT AAATTCCCAT    2700

GTTCGCGGCG ATGACGCTTT TAAAATCAAC AAAGACTTAA CCATAAATGC AACCAATTCA    2760

AATTTCAGCC TCAGACAGAC GAAAGATGAT TTTTATGACG GGTACGCACG CAATGCCATC    2820

AATTCAACCT ACAACATATC CATTCTGGGC GGTAATGTCA CCCTTGGTGG ACAAAACTCA    2880

AGCAGCAGCA TTACGGGGAA TATTACTATC GAGAAAGCAG CAAATGTTAC GCTAGAAGCC    2940

AATAACGCCC CTAATCAGCA AAACATAAGG GATAGAGTTA TAAAACTTGG CAGCTTGCTC    3000

GTTAATGGGA GTTTAAGTTT AACTGGCGAA AATGCAGATA TTAAAGGCAA TCTCACTATT    3060

TCAGAAAGCG CCACTTTTAA AGGAAAGACT AGAGATACCC TAAATATCAC CGGCAATTTT    3120

ACCAATAATG GCACTGCCGA AATTAATATA ACACAAGGAG TGGTAAAACT TGGCAATGTT    3180

ACCAATGATG GTGATTTAAA CATTACCACT CACGCTAAAC GCAACCAAAG AAGCATCATC    3240

GGCGGAGATA TAATCAACAA AAAAGGAAGC TTAAATATTA CAGACAGTAA TAATGATGCT    3300

GAAATCCAAA TTGGCGGCAA TATCTCGCAA AAAGAAGGCA ACCTCACGAT TTCTTCCGAT    3360

AAAATTAATA TCACCAAACA GATAACAATC AAAAAGGGTA TTGATGGAGA GGACTCTAGT    3420

TCAGATGCGA CAAGTAATGC CAACCTAACT ATTAAAACCA AGAATTGAA ATTGACAGAA     3480

GACCTAAGTA TTTCAGGTTT CAATAAAGCA GAGATTACAG CCAAAGATGG TAGAGATTTA    3540

ACTATTGGCA ACAGTAATGA CGGTAACAGC GGTGCCGAAG CCAAAACAGT AACTTTTAAC    3600

AATGTTAAAG ATTCAAAAAT CTCTGCTGAC GGTCACAATG TGACACTAAA TAGCAAAGTG    3660

AAAACATCTA GCAGCAATGG CGGACGTGAA AGCAATAGCG ACAACGATAC CGGCTTAACT    3720

ATTACTGCAA AAAATGTAGA AGTAAACAAA GATATTACTT CTCTCAAAAC AGTAAATATC    3780

ACCGCGTCGG AAAAGGTTAC CACCCACAGCA GGCTCGACCA TTAACGCAAC AAATGGCAAA    3840

GCAAGTATTA CAACCAAAAC AGGTGATATC AGCGGTACGA TTTCCGGTAA CACGGTAAGT    3900

GTTAGCGCGA CTGGTGATTT AACCACTAAA TCCGGCTCAA AAATTGAAGC GAAATCGGGT    3960

GAGGCTAATG TAACAAGTGC AACAGGTACA ATTGGCGGTA CAATTTCCGG TAATACGGTA    4020

AATGTTACGG CAAACGCTGG CGATTTAACA GTTGGGAATG GCGCAGAAAT TAATGCGACA    4080

GAAGGAGCTG CAACCTTAAC CGCAACAGGG AATACCTTGA CTACTGAAGC CGGTTCTAGC    4140

ATCACTTCAA CTAAGGGTCA GGTAGACCTC TTGGCTCAGA ATGGTAGCAT CGCAGGAAGC    4200

ATTAATGCTG CTAATGTGAC ATTAAATACT ACAGGCACCT TAACCACCGT GGCAGGCTCG    4260

GATATTAAAG CAACCAGCGG CACCTTGGTT ATTAACGCAA AAGATGCTAA GCTAAATGGT    4320

GATGCATCAG GTGATAGTAC AGAAGTGAAT GCAGTCAACG CAAGCGGCTC TGGTAGTGTG    4380

ACTGCGGCAA CCTCAAGCAG TGTGAATATC ACTGGGGATT TAAACACAGT AAATGGGTTA    4440

AATATCATTT CGAAAGATGG TAGAAACACT GTGCGCTTAA GAGGCAAGGA AATTGAGGTG    4500

AAATATATCC AGCCAGGTGT AGCAAGTGTA GAAGAAGTAA TTGAAGCGAA ACGCGTCCTT    4560
```

```
GAAAAAGTAA AAGATTTATC TGATGAAGAA AGAGAAACAT TAGCTAAACT TGGTGTAAGT    4620

GCTGTACGTT TTGTTGAGCC AAATAATACA ATTACAGTCA ATACACAAAA TGAATTTACA    4680

ACCAGACCGT CAAGTCAAGT GATAATTTCT GAAGGTAAGG CGTGTTTCTC AAGTGGTAAT    4740

GGCGCACGAG TATGTACCAA TGTTGCTGAC GATGGACAGC CGTAGTCAGT AATTGACAAG    4800

GTAGATTTCA TCCTGCAATG AAGTCATTTT ATTTTCGTAT TATTTACTGT GTGGGTAAA    4860

GTTCAGTACG GGCTTTACCC ATCTTGTAAA AAATTACGGA GAATACAATA AAGTATTTTT    4920

AACAGGTTAT TATTATG                                                   4937

(2) INFORMATION FOR SEQ ID NO:4:

(i) SEQUENCE CHARACTERISTICS:
        (A) LENGTH: 1477 amino acids
        (B) TYPE: amino acid
        (C) STRANDEDNESS: single
        (D) TOPOLOGY: linear (xi) SEQUENCE DESCRIPTION: SEQ ID NO:4:

Met Asn Lys Ile Tyr Arg Leu Lys Phe Ser Lys Arg Leu Asn Ala Leu
1               5                   10                  15

Val Ala Val Ser Glu Leu Ala Arg Gly Cys Asp His Ser Thr Glu Lys
            20                  25                  30

Gly Ser Glu Lys Pro Ala Arg Met Lys Val Arg His Leu Ala Leu Lys
        35                  40                  45

Pro Leu Ser Ala Met Leu Leu Ser Leu Gly Val Thr Ser Ile Pro Gln
    50                  55                  60

Ser Val Leu Ala Ser Gly Leu Gln Gly Met Asp Val Val His Gly Thr
65                  70                  75                  80

Ala Thr Met Gln Val Asp Gly Asn Lys Thr Ile Ile Arg Asn Ser Val
                85                  90                  95

Asp Ala Ile Ile Asn Trp Lys Gln Phe Asn Ile Asp Gln Asn Glu Met
            100                 105                 110

Val Gln Phe Leu Gln Glu Asn Asn Ser Ala Val Phe Asn Arg Val
        115                 120                 125

Thr Ser Asn Gln Ile Ser Gln Leu Lys Gly Ile Leu Asp Ser Asn Gly
    130                 135                 140

Gln Val Phe Leu Ile Asn Pro Asn Gly Ile Thr Ile Gly Lys Asp Ala
145                 150                 155                 160

Ile Ile Asn Thr Asn Gly Phe Thr Ala Ser Thr Leu Asp Ile Ser Asn
                165                 170                 175

Glu Asn Ile Lys Ala Arg Asn Phe Thr Phe Glu Gln Thr Lys Asp Lys
            180                 185                 190

Ala Leu Ala Glu Ile Val Asn His Gly Leu Ile Thr Val Gly Lys Asp
        195                 200                 205

Gly Ser Val Asn Leu Ile Gly Gly Lys Val Lys Asn Glu Gly Val Ile
    210                 215                 220

Ser Val Asn Gly Gly Ser Ile Ser Leu Leu Ala Gly Gln Lys Ile Thr
225                 230                 235                 240

Ile Ser Asp Ile Ile Asn Pro Thr Ile Thr Tyr Ser Ile Ala Ala Pro
                245                 250                 255

Glu Asn Glu Ala Val Asn Leu Gly Asp Ile Phe Ala Lys Gly Gly Asn
            260                 265                 270

Ile Asn Val Arg Ala Ala Thr Ile Arg Asn Gln Gly Lys Leu Ser Ala
        275                 280                 285

Asp Ser Val Ser Lys Asp Lys Ser Gly Asn Ile Val Leu Ser Ala Lys
```

```
                    290                 295                 300
Glu Gly Glu Ala Glu Ile Gly Val Ile Ser Ala Gln Asn Gln Gln
305                 310                 315                 320

Ala Lys Gly Gly Lys Leu Met Ile Thr Gly Asp Lys Val Thr Leu Lys
                325                 330                 335

Thr Gly Ala Val Ile Asp Leu Ser Gly Lys Glu Gly Gly Glu Thr Tyr
                340                 345                 350

Leu Gly Gly Asp Glu Arg Gly Glu Gly Lys Asn Gly Ile Gln Leu Ala
                355                 360                 365

Lys Lys Thr Ser Leu Glu Lys Gly Ser Thr Ile Asn Val Ser Gly Lys
    370                 375                 380

Glu Lys Gly Gly Phe Ala Ile Val Trp Gly Asp Ile Ala Leu Ile Asp
385                 390                 395                 400

Gly Asn Ile Asn Ala Gln Gly Ser Gly Asp Ile Ala Lys Thr Gly Gly
                405                 410                 415

Phe Val Glu Thr Ser Gly His Asp Leu Phe Ile Lys Asp Asn Ala Ile
                420                 425                 430

Val Asp Ala Lys Glu Trp Leu Leu Asp Phe Asp Asn Val Ser Ile Asn
                435                 440                 445

Ala Glu Asp Pro Leu Phe Asn Asn Thr Gly Ile Asn Asp Glu Phe Pro
450                 455                 460

Thr Gly Thr Gly Glu Ala Ser Asp Pro Lys Lys Asn Ser Glu Leu Lys
465                 470                 475                 480

Thr Thr Leu Thr Asn Thr Thr Ile Ser Asn Tyr Leu Lys Asn Ala Trp
                485                 490                 495

Thr Met Asn Ile Thr Ala Ser Arg Lys Leu Thr Val Asn Ser Ser Ile
                500                 505                 510

Asn Ile Gly Ser Asn Ser His Leu Ile Leu His Ser Lys Gly Gln Arg
                515                 520                 525

Gly Gly Gly Val Gln Ile Asp Gly Asp Ile Thr Ser Lys Gly Gly Asn
                530                 535                 540

Leu Thr Ile Tyr Ser Gly Gly Trp Val Asp Val His Lys Asn Ile Thr
545                 550                 555                 560

Leu Asp Gln Gly Phe Leu Asn Ile Thr Ala Ala Ser Val Ala Phe Glu
                565                 570                 575

Gly Gly Asn Asn Lys Ala Arg Asp Ala Ala Asn Ala Lys Ile Val Ala
                580                 585                 590

Gln Gly Thr Val Thr Ile Thr Gly Glu Gly Lys Asp Phe Arg Ala Asn
                595                 600                 605

Asn Val Ser Leu Asn Gly Thr Gly Lys Gly Leu Asn Ile Ile Ser Ser
                610                 615                 620

Val Asn Asn Leu Thr His Asn Leu Ser Gly Thr Ile Asn Ile Ser Gly
625                 630                 635                 640

Asn Ile Thr Ile Asn Gln Thr Thr Arg Lys Asn Thr Ser Tyr Trp Gln
                645                 650                 655

Thr Ser His Asp Ser His Trp Asn Val Ser Ala Leu Asn Leu Glu Thr
                660                 665                 670

Gly Ala Asn Phe Thr Phe Ile Lys Tyr Ile Ser Ser Asn Ser Lys Gly
                675                 680                 685

Leu Thr Thr Gln Tyr Arg Ser Ser Ala Gly Val Asn Phe Asn Gly Val
    690                 695                 700

Asn Gly Asn Met Ser Phe Asn Leu Lys Glu Gly Ala Lys Val Asn Phe
705                 710                 715                 720
```

-continued

```
Lys Leu Lys Pro Asn Glu Asn Met Asn Thr Ser Lys Pro Leu Pro Ile
            725                 730                 735

Arg Phe Leu Ala Asn Ile Thr Ala Thr Gly Gly Ser Val Phe Phe
        740                 745                 750

Asp Ile Tyr Ala Asn His Ser Gly Arg Gly Ala Glu Leu Lys Met Ser
            755                 760                 765

Glu Ile Asn Ile Ser Asn Gly Ala Asn Phe Thr Leu Asn Ser His Val
            770                 775                 780

Arg Gly Asp Asp Ala Phe Lys Ile Asn Lys Asp Leu Thr Ile Asn Ala
785                 790                 795                 800

Thr Asn Ser Asn Phe Ser Leu Arg Gln Thr Lys Asp Phe Tyr Asp
                805                 810                 815

Gly Tyr Ala Arg Asn Ala Ile Asn Ser Thr Tyr Asn Ile Ser Ile Leu
            820                 825                 830

Gly Gly Asn Val Thr Leu Gly Gly Gln Asn Ser Ser Ser Ile Thr
            835                 840                 845

Gly Asn Ile Thr Ile Glu Lys Ala Ala Asn Val Thr Leu Glu Ala Asn
            850                 855                 860

Asn Ala Pro Asn Gln Gln Asn Ile Arg Asp Arg Val Ile Lys Leu Gly
865                 870                 875                 880

Ser Leu Leu Val Asn Gly Ser Leu Ser Leu Thr Gly Glu Asn Ala Asp
                885                 890                 895

Ile Lys Gly Asn Leu Thr Ile Ser Glu Ser Ala Thr Phe Lys Gly Lys
                900                 905                 910

Thr Arg Asp Thr Leu Asn Ile Thr Gly Asn Phe Thr Asn Asn Gly Thr
            915                 920                 925

Ala Glu Ile Asn Ile Thr Gln Gly Val Val Lys Leu Gly Asn Val Thr
            930                 935                 940

Asn Asp Gly Asp Leu Asn Ile Thr Thr His Ala Lys Arg Asn Gln Arg
945                 950                 955                 960

Ser Ile Ile Gly Gly Asp Ile Asn Lys Lys Gly Ser Leu Asn Ile
                965                 970                 975

Thr Asp Ser Asn Asn Asp Ala Glu Ile Gln Ile Gly Gly Asn Ile Ser
            980                 985                 990

Gln Lys Glu Gly Asn Leu Thr Ile Ser Ser Asp Lys Ile Asn Ile Thr
            995                 1000                1005

Lys Gln Ile Thr Ile Lys Lys Gly Ile Asp Gly Glu Asp Ser Ser Ser
    1010                1015                1020

Asp Ala Thr Ser Asn Ala Asn Leu Thr Ile Lys Thr Lys Glu Leu Lys
1025                1030                1035                1040

Leu Thr Glu Asp Leu Ser Ile Ser Gly Phe Asn Lys Ala Glu Ile Thr
                1045                1050                1055

Ala Lys Asp Gly Arg Asp Leu Thr Ile Gly Asn Ser Asn Asp Gly Asn
            1060                1065                1070

Ser Gly Ala Glu Ala Lys Thr Val Thr Phe Asn Asn Val Lys Asp Ser
            1075                1080                1085

Lys Ile Ser Ala Asp Gly His Asn Val Thr Leu Asn Ser Lys Val Lys
    1090                1095                1100

Thr Ser Ser Ser Asn Gly Gly Arg Glu Ser Asn Ser Asp Asn Asp Thr
1105                1110                1115                1120

Gly Leu Thr Ile Thr Ala Lys Asn Val Glu Val Asn Lys Asp Ile Thr
            1125                1130                1135

Ser Leu Lys Thr Val Asn Ile Thr Ala Ser Glu Lys Val Thr Thr Thr
            1140                1145                1150
```

```
Ala Gly Ser Thr Ile Asn Ala Thr Asn Gly Lys Ala Ser Ile Thr Thr
        1155                1160                1165
Lys Thr Gly Asp Ile Ser Gly Thr Ile Ser Gly Asn Thr Val Ser Val
    1170                1175                1180
Ser Ala Thr Val Asp Leu Thr Thr Lys Ser Gly Ser Lys Ile Glu Ala
1185                1190                1195                1200
Lys Ser Gly Glu Ala Asn Val Thr Ser Ala Thr Gly Thr Ile Gly Gly
            1205                1210                1215
Thr Ile Ser Gly Asn Thr Val Asn Val Thr Ala Asn Ala Gly Asp Leu
        1220                1225                1230
Thr Val Gly Asn Gly Ala Glu Ile Asn Ala Thr Glu Gly Ala Ala Thr
        1235                1240                1245
Leu Thr Ala Thr Gly Asn Thr Leu Thr Thr Glu Ala Gly Ser Ser Ile
        1250                1255                1260
Thr Ser Thr Lys Gly Gln Val Asp Leu Leu Ala Gln Asn Gly Ser Ile
1265                1270                1275                1280
Ala Gly Ser Ile Asn Ala Ala Asn Val Thr Leu Asn Thr Thr Gly Thr
            1285                1290                1295
Leu Thr Thr Val Ala Gly Ser Asp Ile Lys Ala Thr Ser Gly Thr Leu
        1300                1305                1310
Val Ile Asn Ala Lys Asp Ala Lys Leu Asn Gly Asp Ala Ser Gly Asp
        1315                1320                1325
Ser Thr Glu Val Asn Ala Val Asn Ala Ser Gly Ser Gly Ser Val Thr
        1330                1335                1340
Ala Ala Thr Ser Ser Ser Val Asn Ile Thr Gly Asp Leu Asn Thr Val
1345                1350                1355                1360
Asn Gly Leu Asn Ile Ile Ser Lys Asp Gly Arg Asn Thr Val Arg Leu
            1365                1370                1375
Arg Gly Lys Glu Ile Glu Val Lys Tyr Ile Gln Pro Gly Val Ala Ser
        1380                1385                1390
Val Glu Glu Val Ile Glu Ala Lys Arg Val Leu Glu Lys Val Lys Asp
        1395                1400                1405
Leu Ser Asp Glu Glu Arg Glu Thr Leu Ala Lys Leu Gly Val Ser Ala
    1410                1415                1420
Val Arg Phe Val Glu Pro Asn Asn Thr Ile Thr Val Asn Thr Gln Asn
1425                1430                1435                1440
Glu Phe Thr Thr Arg Pro Ser Ser Gln Val Ile Ile Ser Glu Gly Lys
            1445                1450                1455
Ala Cys Phe Ser Ser Gly Asn Gly Ala Arg Val Cys Thr Asn Val Ala
            1460                1465                1470
Asp Asp Gly Gln Pro
        1475

(2) INFORMATION FOR SEQ ID NO:5:

(i) SEQUENCE CHARACTERISTICS:
        (A) LENGTH: 9171 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:5:

ACAGCGTTCT CTTAATACTA GTACAAACCC ACAATAAAAT ATGACAAACA ACAATTACAA      60

CACCTTTTTT GCAGTCTATA TGCAAATATT TTAAAAAATA GTATAAATCC GCCATATAAA    120
```

-continued

```
ATGGTATAAT CTTTCATCTT TCATCTTTCA TCTTTCATCT TTCATCTTTC ATCTTTCATC    180

TTTCATCTTT CATCTTTCAT CTTTCATCTT TCATCTTTCA TCTTTCATCT TTCATCTTTC    240

ACATGAAATG ATGAACCGAG GGAAGGGAGG GAGGGGCAAG AATGAAGAGG GAGCTGAACG    300

AACGCAAATG ATAAAGTAAT TTAATTGTTC AACTAACCTT AGGAGAAAAT ATGAACAAGA    360

TATATCGTCT CAAATTCAGC AAACGCCTGA ATGCTTTGGT TGCTGTGTCT GAATTGGCAC    420

GGGGTTGTGA CCATTCCACA GAAAAAGGCA GCGAAAAACC TGCTCGCATG AAAGTGCGTC    480

ACTTAGCGTT AAAGCCACTT TCCGCTATGT TACTATCTTT AGGTGTAACA TCTATTCCAC    540

AATCTGTTTT AGCAAGCGGC TTACAAGGAA TGGATGTAGT ACACGGCACA GCCACTATGC    600

AAGTAGATGG TAATAAAACC ATTATCCGCA ACAGTGTTGA CGCTATCATT AATTGGAAAC    660

AATTTAACAT CGACCAAAAT GAAATGGTGC AGTTTTTACA AGAAAACAAC AACTCCGCCG    720

TATTCAACCG TGTTACATCT AACCAAATCT CCCAATTAAA AGGGATTTTA GATTCTAACG    780

GACAAGTCTT TTTAATCAAC CCAAATGGTA TCACAATAGG TAAAGACGCA ATTATTAACA    840

CTAATGGCTT TACGGCTTCT ACGCTAGACA TTTCTAACGA AAACATCAAG GCGCGTAATT    900

TCACCTTCGA GCAAACCAAA GATAAAGCGC TCGCTGAAAT TGTGAATCAC GGTTTAATTA    960

CTGTCGGTAA AGACGGCAGT GTAAATCTTA TTGGTGGCAA AGTGAAAAAC GAGGGTGTGA   1020

TTAGCGTAAA TGGTGGCAGC ATTTCTTTAC TCGCAGGGCA AAAAATCACC ATCAGCGATA   1080

TAATAAACCC AACCATTACT TACAGCATTG CCGCGCCTGA AAATGAAGCG GTCAATCTGG   1140

GCGATATTTT TGCCAAAGGC GGTAACATTA ATGTCCGTGC TGCCACTATT CGAAACCAAG   1200

CTTTCCGCCA AAGAGGGTGA AGCGGAAATT GGCGGTGTAA TTTCCGCTCA AAATCAGCAA   1260

GCTAAAGGCG GCAAGCTGAT GATTACAGGC GATAAAGTCA CATTAAAAAC AGGTGCAGTT   1320

ATCGACCTTT CAGGTAAAGA AGGGGAGAA ACTTACCTTG GCGGTGACGA GCGCGGCGAA   1380

GGTAAAAACG GCATTCAATT AGCAAAGAAA ACCTCTTTAG AAAAAGGCTC AACCATCAAT   1440

GTATCAGGCA AAGAAAAAGG CGGACGCGCT ATTGTGTGGG GCGATATTGC GTTAATTGAC   1500

GGCAATATTA ACGCTCAAGG TAGTGGTGAT ATCGCTAAAA CCGGTGGTTT TGTGGAGACG   1560

TCGGGGCATG ATTTATTCAT CAAAGACAAT GCAATTGTTG ACGCCAAAGA GTGGTTGTTA   1620

GACCCGGATA ATGTATCTAT TAATGCAGAA ACAGCAGGAC GCAGCAATAC TTCAGAAGAC   1680

GATGAATACA CGGGATCCGG GAATAGTGCC AGCACCCCAA AACGAAACAA AGAAAAGACA   1740

ACATTAACAA ACACAACTCT TGAGAGTATA CTAAAAAAAG GTACCTTTGT TAACATCACT   1800

GCTAATCAAC GCATCTATGT CAATAGCTCC ATTAATTTAT CCAATGGCAG CTTAACTCTT   1860

TGGAGTGAGG GTCGGAGCGG TGGCGGCGTT GAGATTAACA ACGATATTAC CACCGGTGAT   1920

GATACCAGAG GTGCAAACTT AACAATTTAC TCAGGCGGCT GGGTTGATGT TCATAAAAAT   1980

ATCTCACTCG GGGCGCAAGG TAACATAAAC ATTACAGCTA ACAAGATAT CGCCTTTGAG    2040

AAAGGAAGCA ACCAAGTCAT TACAGGTCAA GGGACTATTA CCTCAGGCAA TCAAAAAGGT   2100

TTTAGATTTA ATAATGTCTC TCTAAACGGC ACTGGCAGCG GACTGCAATT CACCACTAAA   2160

AGAACCAATA AATACGCTAT CACAAATAAA TTTGAAGGGA CTTTAAATAT TTCAGGGAAA   2220

GTGAACATCT CAATGGTTTT ACCTAAAAAT GAAAGTGGAT ATGATAAATT CAAAGGACGC   2280

ACTTACTGGA ATTTAACCTC GAAAGTGGAT ATGATAAATT CAAAGGACGC CCTCACTATT   2340

GACTCCAGAG GAAGCGATAG TGCAGGCACA CTTACCCAGC CTTATAATTT AAACGGTATA   2400

TCATTCAACA AAGACACTAC CTTTAATGTT GAACGAAATG CAAGAGTCAA CTTTGACATC   2460

AAGGCACCAA TAGGGATAAA TAAGTATTCT AGTTTGAATT ACGCATCATT TAATGGAAAC   2520
```

-continued

```
ATTTCAGTTT CGGGAGGGGG GAGTGTTGAT TTCACACTTC TCGCCTCATC CTCTAACGTC    2580

CAAACCCCCG GTGTAGTTAT AAATTCTAAA TACTTTAATG TTTCAACAGG GTCAAGTTTA    2640

AGATTTAAAA CTTCAGGCTC AACAAAAACT GGCTTCTCAA TAGAGAAAGA TTTAACTTTA    2700

AATGCCACCG GAGGCAACAT AACACTTTTG CAAGTTGAAG GCACCGATGG AATGATTGGT    2760

AAAGGCATTG TAGCCAAAAA AAACATAACC TTTGAAGGAG GTAAGATGAG GTTTGGCTCC    2820

AGGAAAGCCG TAACAGAAAT CGAAGGCAAT GTTACTATCA ATAACAACGC TAACGTCACT    2880

CTTATCGGTT CGGATTTTGA CAACCATCAA AAACCTTTAA CTATTAAAAA AGATGTCATC    2940

ATTAATAGCG GCAACCTTAC CGCTGGAGGC AATATTGTCA ATATAGCCGG AAATCTTACC    3000

GTTGAAAGTA ACGCTAATTT CAAAGCTATC ACAAATTTCA CTTTTAATGT AGGCGGCTTG    3060

TTTGACAACA AAGGCAATTC AAATATTTCC ATTGCCAAAG GAGGGGCTCG CTTTAAAGAC    3120

ATTGATAATT CCAAGAATTT AAGCATCACC ACCAACTCCA GCTCCACTTA CCGCACTATT    3180

ATAAGCGGCA ATATAACCAA TAAAAACGGT GATTTAAATA TTACGAACGA AGGTAGTGAT    3240

ACTGAAATGC AAATTGGCGG CGATGTCTCG CAAAAAGAAG GTAATCTCAC GATTTCTTCT    3300

GACAAAATCA ATATTACCAA ACAGATAACA ATCAAGGCAG GTGTTGATGG GGAGAATTCC    3360

GATTCAGACG CGACAAACAA TGCCAATCTA ACCATTAAAA CCAAAGAATT GAAATTAACG    3420

CAAGACCTAA ATATTTCAGG TTTCAATAAA GCAGAGATTA CAGCTAAAGA TGGTAGTGAT    3480

TTAACTATTG GTAACACCAA TAGTGCTGAT GGTACTAATG CCAAAAAAGT AACCTTTAAC    3540

CAGGTTAAAG ATTCAAAAAT CTCTGCTGAC GGTCACAAGG TGACACTACA CAGCAAAGTG    3600

GAAACATCCG GTAGTAATAA CAACACTGAA GATAGCAGTG ACAATAATGC CGGCTTAACT    3660

ATCGATGCAA AAAATGTAAC AGTAAACAAC AATATTACTT CTCACAAAGC AGTGAGCATC    3720

TCTGCGACAA GTGGAGAAAT TACCACTAAA ACAGGTACAA CCATTAACGC AACCACTGGT    3780

AACGTGGAGA TAACCGCTCA AACAGGTAGT ATCCTAGGTG GAATTGAGTC CAGCTCTGGC    3840

TCTGTAACAC TTACTGCAAC CGAGGGCGCT CTTGCTGTAA GCAATATTTC GGGCAACACC    3900

GTTACTGTTA CTGCAAATAG CGGTGCATTA ACCACTTTGG CAGGCTCTAC AATTAAAGGA    3960

ACCGAGAGTG TAACCACTTC AAGTCAATCA GGCGATATCG GCGGTACGAT TTCTGGTGGC    4020

ACAGTAGAGG TTAAAGCAAC CGAAAGTTTA ACCACTCAAT CCAATTCAAA AATTAAAGCA    4080

ACAACAGGCG AGGCTAACGT AACAAGTGCA ACAGGTACAA TTGGTGGTAC GATTTCCGGT    4140

AATACGGTAA ATGTTACGGC AAACGCTGGC GATTTAACAG TTGGGAATGG CGCAGAAATT    4200

AATGCGACAG AAGGAGCTGC AACCTTAACT ACATCATCGG GCAAATTAAC TACCGAAGCT    4260

AGTTCACACA TTACTTCAGC CAAGGGTCAG GTAAATCTTT CAGCTCAGGA TGGTAGCGTT    4320

GCAGGAAGTA TTAATGCCGC CAATGTGACA CTAAATACTA CAGGCACTTT AACTACCGTG    4380

AAGGGTTCAA ACATTAATGC AACCAGCGGT ACCTTGGTTA TTAACGCAAA AGACGCTGAG    4440

CTAAATGGCG CAGCATTGGG TAACCACACA GTGGTAAATG CAACCAACGC AAATGGCTCC    4500

GGCAGCGTAA TCGCGACAAC CTCAAGCAGA GTGAACATCA CTGGGGATTT AATCACAATA    4560

AATGGATTAA ATATCATTTC AAAAAACGGT ATAAACACCG TACTGTTAAA AGGCGTTAAA    4620

ATTGATGTGA AATACATTCA ACCGGGTATA GCAAGCTAG ATGAAGTAAT TGAAGCGAAA    4680

CGCATCCTTG AGAAGGTAAA AGATTTATCT GATGAAGAAA GAGAAGCGTT AGCTAAACTT    4740

GGCGTAAGTG CTGTACGTTT TATTGAGCCA AATAATACAA TTACAGTCGA TACACAAAAT    4800

GAATTTGCAA CCAGACCATT AAGTCGAATA GTGATTTCTG AAGGCAGGGC GTGTTTCTCA    4860

AACAGTGATG GCGCGACGGT GTGCGTTAAT ATCGCTGATA ACGGGCGGTA GCGGTCAGTA    4920
```

```
ATTGACAAGG TAGATTTCAT CCTGCAATGA AGTCATTTTA TTTTCGTATT ATTTACTGTG    4980

TGGGTTAAAG TTCAGTACGG GCTTTACCCA TCTTGTAAAA AATTACGGAG AATACAATAA    5040

AGTATTTTTA ACAGGTTATT ATTATGAAAA ATATAAAAAG CAGATTAAAA CTCAGTGCAA    5100

TATCAGTATT GCTTGGCCTG GCTTCTTCAT CATTGTATGC AGAAGAAGCG TTTTTAGTAA    5160

AAGGCTTTCA GTTATCTGGT GCACTTGAAA CTTTAAGTGA AGACGCCCAA CTGTCTGTAG    5220

CAAAATCTTT ATCTAAATAC CAAGGCTCGC AAACTTTAAC AAACCTAAAA ACAGCACAGC    5280

TTGAATTACA GGCTGTGCTA GATAAGATTG AGCCAAATAA GTTTGATGTG ATATTGCCAC    5340

AACAAACCAT TACGGATGGC AATATTATGT TTGAGCTAGT CTCGAAATCA GCCGCAGAAA    5400

GCCAAGTTTT TTATAAGGCG AGCCAGGGTT ATAGTGAAGA AAATATCGCT CGTAGCCTGC    5460

CATCTTTGAA ACAAGGAAAA GTGTATGAAG ATGGTCGTCA GTGGTTCGAT TTGCGTGAAT    5520

TCAATATGGC AAAAGAAAAT CCACTTAAAG TCACTCGCGT GCATTACGAG TTAAACCCTA    5580

AAAACAAAAC CTCTGATTTG GTAGTTGCAG GTTTTTCGCC TTTTGGCAAA ACGCGTAGCT    5640

TTGTTTCCTA TGATAATTTC GGCGCAAGGG AGTTTAACTA TCAACGTGTA AGTCTAGGTT    5700

TTGTAAATGC CAATTTGACC GGACATGATG ATGTATTAAA TCTAAACGCA TTGACCAATG    5760

TAAAAGCACC ATCAAAATCT TATGCGGTAG GCATAGGATA TACTTATCCG TTTTATGATA    5820

AACACCAATC CTTAAGTCTT TATACCAGCA TGAGTTATGC TGATTCTAAT GATATCGACG    5880

GCTTACCAAG TGCGATTAAT CGTAAATTAT CAAAAGGTCA ATCTATCTCT GCAATCTGA    5940

AATGGAGTTA TTATCTCCCG ACATTTAACC TTGGAATGGA AGACCAGTTT AAAATTAATT    6000

TAGGCTACAA CTACCGCCAT ATTAATCAAA CATCCGAGTT AAACACCCTG GGTGCAACGA    6060

AGAAAAAATT TGCAGTATCA GGCGTAAGTG CAGGCATTGA TGGACATATC CAATTTACCC    6120

CTAAAACAAT CTTTAATATT GATTTAACTC ATCATTATTA CGCGAGTAAA TTACCAGGCT    6180

CTTTTGGAAT GGAGCGCATT GGCGAAACAT TTAATCGCAG CTATCACATT AGCACAGCCA    6240

GTTTAGGGTT GAGTCAAGAG TTTGCTCAAG GTTGGCATTT TAGCAGTCAA TTATCGGGTC    6300

AGTTTACTCT ACAAGATATA AGTAGCATAG ATTTATTCTC TGTAACAGGT ACTTATGGCG    6360

TCAGAGGCTT TAAATACGGC GGTGCAAGTG GTGAGCGCGG TCTTGTATGG CGTAATGAAT    6420

TAAGTATGCC AAAATACACC CGCTTTCAAA TCAGCCCTTA TGCGTTTTAT GATGCAGGTC    6480

AGTTCCGTTA TAATAGCGAA AATGCTAAAA CTTACGGCGA AGATATGCAC ACGGTATCCT    6540

CTGCGGGTTT AGGCATTAAA ACCTCTCCTA CACAAAACTT AAGCTTAGAT GCTTTTGTTG    6600

CTCGTCGCTT TGCAAATGCC AATAGTGACA ATTTGAATGG CAACAAAAAA CGCACAAGCT    6660

CACCTACAAC CTTCTGGGGT AGATTAACAT TCAGTTTCTA ACCCTGAAAT TTAATCAACT    6720

GGTAAGCGTT CCGCCTACCA GTTTATAACT ATATGCTTTA CCCGCCAATT TACAGTCTAT    6780

ACGCAACCCT GTTTTCATCC TTATATATCA AACAAACTAA GCAAACCAAG CAAACCAAGC    6840

AAACCAAGCA AACCAAGCAA ACCAAGCAAA CCAAGCAAAC CAAGCAAACC AAGCAAACCA    6900

AGCAAACCAA GCAAACCAAG CAAACCAAGC AAACCAAGCA ATGCTAAAAA CAATTTATA    6960

TGATAAACTA AAACATACTC CATACCATGG CAATACAAGG GATTTAATAA TATGACAAAA    7020

GAAAATTTAC AAAGTGTTCC ACAAAATACG ACCGCTTCAC TTGTAGAATC AAACAACGAC    7080

CAAACTTCCC TGCAAATACT TAAACAACCA CCCAAACCCA ACCTATTACG CCTGGAACAA    7140

CATGTCGCCA AAAAGATTA TGAGCTTGCT TGCCGCGAAT AATGGCGAT TTTGAAAAA    7200

ATGGACGCTA ATTTTGGAGG CGTTCACGAT ATTGAATTTG ACGCACCTGC TCAGCTGGCA    7260

TATCTACCCG AAAAACTACT AATTCATTTT GCCACTCGTC TCGCTAATGC AATTACAACA    7320
```

```
CTCTTTTCCG ACCCCGAATT GGCAATTTCC GAAGAAGGGG CATTAAAGAT GATTAGCCTG    7380

CAACGCTGGT TGACGCTGAT TTTTGCCTCT TCCCCCTACG TTAACGCAGA CCATATTCTC    7440

AATAAATATA ATATCAACCC AGATTCCGAA GGTGGCTTTC ATTTAGCAAC AGACAACTCT    7500

TCTATTGCTA AATTCTGTAT TTTTTACTTA CCCGAATCCA ATGTCAATAT GAGTTTAGAT    7560

GCGTTATGGG CAGGGAATCA ACAACTTTGT GCTTCATTGT GTTTTGCGTT GCAGTCTTCA    7620

CGTTTTATTG GTACTGCATC TGCGTTTCAT AAAAGAGCGG TGGTTTTACA GTGGTTTCCT    7680

AAAAAACTCG CCGAAATTGC TAATTTAGAT GAATTGCCTG CAAATATCCT TCATGATGTA    7740

TATATGCACT GCAGTTATGA TTTAGCAAAA AACAAGCACG ATGTTAAGCG TCCATTAAAC    7800

GAACTTGTCC GCAAGCATAT CCTCACGCAA GGATGGCAAG ACCGCTACCT TTACACCTTA    7860

GGTAAAAAGG ACGGCAAACC TGTGATGATG GTACTGCTTG AACATTTTAA TTCGGGACAT    7920

TCGATTTATC GCACGCATTC AACTTCAATG ATTGCTGCTC GAGAAAAATT CTATTTAGTC    7980

GGCTTAGGCC ATGAGGGCGT TGATAACATA GGTCGAGAAG TGTTTGACGA GTTCTTTGAA    8040

ATCAGTAGCA ATAATATAAT GGAGAGACTG TTTTTTATCC GTAAACAGTG CGAAACTTTC    8100

CAACCCGCAG TGTTCTATAT GCCAAGCATT GGCATGGATA TTACCACGAT TTTTGTGAGC    8160

AACACTCGGC TTGCCCCTAT TCAAGCTGTA GCCTTGGGTC ATCCTGCCAC TACGCATTCT    8220

GAATTTATTG ATTATGTCAT CGTAGAAGAT GATTATGTGG GCAGTGAAGA TTGTTTTAGC    8280

GAAACCCTTT TACGCTTACC CAAAGATGCC CTACCTTATG TACCATCTGC ACTCGCCCCA    8340

CAAAAGTGG ATTATGTACT CAGGGAAAAC CCTGAAGTAG TCAATATCGG TATTGCCGCT     8400

ACCACAATGA AATTAAACCC TGAATTTTTG CTAACATTGC AAGAAATCAG AGATAAAGCT    8460

AAAGTCAAAA TACATTTTCA TTTCGCACTT GGACAATCAA CAGGCTTGAC ACACCCTTAT    8520

GTCAAATGGT TTATCGAAAG CTATTTAGGT GACGATGCCA CTGCACATCC CCACGCACCT    8580

TATCACGATT ATCTGGCAAT ATTGCGTGAT TGCGATATGC TACTAAATCC GTTTCCTTTC    8640

GGTAATACTA ACGGCATAAT TGATATGGTT ACATTAGGTT TAGTTGGTGT ATGCAAAACG    8700

GGGGATGAAG TACATGAACA TATTGATGAA GGTCTGTTTA AACGCTTAGG ACTACCAGAA    8760

TGGCTGATAG CCGACACACG AGAAACATAT ATTGAATGTG CTTTGCGTCT AGCAGAAAAC    8820

CATCAAGAAC GCCTTGAACT CCGTCGTTAC ATCATAGAAA ACAACGGCTT ACAAAAGCTT    8880

TTTACAGGCG ACCCTCGTCC ATTGGGCAAA ATACTGCTTA AGAAAACAAA TGAATGGAAG    8940

CGGAAGCACT TGAGTAAAAA ATAACGGTTT TTTAAAGTAA AAGTGCGGTT AATTTTCAAA    9000

GCGTTTTAAA AACCTCTCAA AAATCAACCG CACTTTTATC TTTATAACGC TCCCGCGCGC    9060

TGACAGTTTA TCTCTTTCTT AAAATACCCA TAAAATTGTG GCAATAGTTG GGTAATCAAA    9120

TTCAATTGTT GATACGGCAA ACTAAAGACG GCGCGTTCTT CGGCAGTCAT C             9171
```

(2) INFORMATION FOR SEQ ID NO:6:

(i) SEQUENCE CHARACTERISTICS:
        (A) LENGTH: 9323 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:6:

```
CGCCACTTCA ATTTTGGATT GTTGAAATTC AACTAACCAA AAAGTGCGGT TAAAATCTGT      60

GGAGAAAATA GGTTGTAGTG AAGAACGAGG TAATTGTTCA AAAGGATAAA GCTCTCTTAA     120
```

| | |
|---|---|
| TTGGGCATTG GTTGGCGTTT CTTTTTCGGT TAATAGTAAA TTATATTCTG GACGACTATG | 180 |
| CAATCCACCA ACAACTTTAC CGTTGGTTTT AAGCGTTAAT GTAAGTTCTT GCTCTTCTTG | 240 |
| GCGAATACGT AATCCCATTT TTTGTTTAGC AAGAAAATGA TCGGGATAAT CATAATAGGT | 300 |
| GTTGCCCAAA AATAAATTTT GATGTTCTAA AATCATAAAT TTTGCAAGAT ATTGTGGCAA | 360 |
| TTCAATACCT ATTTGTGGCG AAATCGCCAA TTTTAATTCA ATTTCTTGTA GCATAATATT | 420 |
| TCCCACTCAA ATCAACTGGT TAAATATACA AGATAATAAA AATAAATCAA GATTTTTGTG | 480 |
| ATGACAAACA ACAATTACAA CACCTTTTTT GCAGTCTATA TGCAAATATT TTAAAAAAAT | 540 |
| AGTATAAATC CGCCATATAA AATGGTATAA TCTTTCATCT TTCATCTTTC ATCTTTCATC | 600 |
| TTTCATCTTT CATCTTTCAT CTTTCATCTT TCATCTTTCA TCTTTCATCT TTCATCTTTC | 660 |
| ATCTTTCATC TTTCATCTTT CACATGAAAT GATGAACCGA GGGAAGGGAG GGAGGGGCAA | 720 |
| GAATGAAGAG GGAGCTGAAC GAACGCAAAT GATAAAGTAA TTTAATTGTT CAACTAACCT | 780 |
| TAGGAGAAAA TATGAACAAG ATATATCGTC TCAAATTCAG CAAACGCCTG AATGCTTTGG | 840 |
| TTGCTGTGTC TGAATTGGCA CGGGGTTGTG ACCATTCCAC AGAAAAGGC AGCGAAAAAC | 900 |
| CTGCTCGCAT GAAAGTGCGT CACTTAGCGT TAAAGCCACT TTCCGCTATG TTACTATCTT | 960 |
| TAGGTGTAAC ATCTATTCCA CAATCTGTTT TAGCAAGCGG CAATTTAACA TCGACCAAAA | 1020 |
| TGAAATGGTG CAGTTTTTAC AAGAAAACAA GTAATAAAAC CATTATCCGC AACAGTGTTG | 1080 |
| ACGCTATCAT TAATTGGAAA CAATTTAACA TCGACCAAAA TGAAATGGTG CAGTTTTTAC | 1140 |
| AAGAAAACAA CAACTCCGCC GTATTCAACC GTGTTACATC TAACCAAATC TCCCAATTAA | 1200 |
| AAGGGATTTT AGATTCTAAC GGACAAGTCT TTTTAATCAA CCCAAATGGT ATCACAATAG | 1260 |
| GTAAAGACGC AATTATTAAC ACTAATGGCT TTACGGCTTC TACGCTAGAC ATTTCTAACG | 1320 |
| AAAACATCAA GGCGCGTAAT TTCACCTTCG AGCAAACCAA AGATAAAGCG CTCGCTGAAA | 1380 |
| TTGTGAATCA CGGTTTAATT ACTGTCGGTA AAGACGGCA TGTAAATCTT ATTGGTGGCA | 1440 |
| AAGTGAAAAA CGAGGGTGTG ATTAGCGTAA ATGGTGGCAG CATTTCTTTA CTCGCAGGGC | 1500 |
| AAAAAATCAC CATCAGCGAT ATAATAAACC CAACCATTAC TTACAGCATT GCCGCGCCTG | 1560 |
| AAAATGAAGC GGTCAATCTG GCGATATTT TTGCCAAAGG CGGTAACATT AATGTCCGTG | 1620 |
| CTGCCACTAT TCGAAACCAA GGTAAACTTT CTGCTGATTC TGTAAGCAAA GATAAAAGCG | 1680 |
| GCAATATTGT TCTTTCCGCC AAAGAGGGTG AAGCGGAAAT TGGCGGTGTA ATTTCCGCTC | 1740 |
| AAAATCAGCA AGCTAAAGGC GGCAAGCTGA TGATAAAGTC CGATAAAGTC ACATTAAAAA | 1800 |
| CAGGTGCAGT TATCGACCTT TCAGGTAAAG AAGGGGGAGA AACTTACCTT GGCGGTGACG | 1860 |
| AGCGCGGCGA AGGTAAAAAC GGCATTCAAT TAGCAAAGAA AACCTCTTTA GAAAAAGGCT | 1920 |
| CAACCATCAA TGTATCAGGC AAAGAAAAAG GCGGACGCGC TATTGTGTGG GGCGATATTG | 1980 |
| CGTTAATTGA CGGCAATATT AACGCTCAAG GTAGTGGTGA TATCGCTAAA ACCGGTGGTT | 2040 |
| TTGTGGAGAC ATCGGGCAT TATTTATCCA TTGACAGCAA TGCAATTGTT AAAACAAAAG | 2100 |
| AGTGGTTGCT AGACCCTGAT GATGTAACAA TTGAAGCCGA AGACCCCCTT CGCAATAATA | 2160 |
| CCGGTATAAA TGATGAATTC CCAACAGGCA CCGGTGAAGC AAGCGACCCT AAAAAAAATA | 2220 |
| GCGAACTCAA AACAACGCTA ACCAATACAA CTATTTCAAA TTATCTGAAA AACGCCTGGA | 2280 |
| CAATGAATAT AACGGCATCA AGAAAACTTA CCGTTAATAG CTCAATCAAC ATCGGAAGCA | 2340 |
| ACTCCCACTT AATTCTCCAT AGTAAAGGTC AGCGTGGCGG AGGCGTTCAG ATTGATGGAG | 2400 |
| ATATTACTTC TAAAGGCGGA AATTTAACCA TTTATTCTGG CGGATGGGTT GATGTTCATA | 2460 |
| AAAATATTAC GCTTGATCAG GGTTTTTTAA ATATTACCGC CGCTTCCGTA GCTTTTGAAG | 2520 |

```
GTGGAAATAA CAAAGCACGC GACGCGGCAA ATGCTAAAAT TGTCGCCCAG GGCACTGTAA    2580

CCATTACAGG AGAGGGAAAA GATTTCAGGG CTAACAACGT ATCTTTAAAC GGAACGGGTA    2640

AAGGTCTGAA TATCATTTCA TCAGTGAATA ATTTAACCCA CAATCTTAGT GGCACAATTA    2700

ACATATCTGG GAATATAACA ATTAACCAAA CTACGAGAAA GAACACCTCG TATTGGCAAA    2760

CCAGCCATGA TTCGCACTGG AACGTCAGTG CTCTTAATCT AGAGACAGGC GCAAATTTTA    2820

CCTTTATTAA ATACATTTCA AGCAATAGCA AAGGCTTAAC AACACAGTAT AGAAGCTCTG    2880

CAGGGGTGAA TTTTAACGGC GTAAATGGCA ACATGTCATT CAATCTCAAA GAAGGAGCGA    2940

AAGTTAATTT CAAATTAAAA CCAAACGAGA ACATGAACAC AAGCAAACCT TTACCAATTC    3000

GGTTTTTAGC CAATATCACA GCCACTGGTG GGGGCTCTGT TTTTTTTGAT ATATATGCCA    3060

ACCATTCTGG CAGAGGGGCT GAGTTAAAAA TGAGTGAAAT TAATATCTCT AACGGCGCTA    3120

ATTTTACCTT AAATTCCCAT GTTCGCGGCG ATGACGCTTT TAAAATCAAC AAAGACTTAA    3180

CCATAAATGC AACCAATTCA AATTTCAGCC TCAGACAGAC GAAAGATGAT TTTTATGACG    3240

GGTACGCACG CAATGCCATC AATTCAACCT ACAACATATC CATTCTGGGC GGTAATGTCA    3300

CCCTTGGTGG ACAAAACTCA AGCAGCAGCA TTACGGGAA TATTACTATC GAGAAAGCAG    3360

CAAATGTTAC GCTAGAAGCC AATAACGCCC CTAATCAGCA AAACATAAGG GATAGAGTTA    3420

TAAAACTTGG CAGCTTGCTC GTTAATGGGA GTTTAAGTTT AACTGGCGAA AATGCAGATA    3480

TTAAAGGCAA TCTCACTATT TCAGAAAGCG CCACTTTTAA AGGAAAGACT AGAGATACCC    3540

TAAATATCAC CGGCAATTTT ACCAATAATG GCACTGCCGA AATTAATATA ACACAAGGAG    3600

TGGTAAAACT TGGCAATGTT ACCAATGATG GTGATTTAAA CATTACCACT CACGCTAAAC    3660

GCAACCAAAG AAGCATCATC GGCGGAGATA TAATCAACAA AAAAGGAAGC TTAAATATTA    3720

CAGACAGTAA TAATGATGCT GAAATCCAAA TTGGCGGCAA TATCTCGCAA AAAGAAGGCA    3780

ACCTCACGAT TTCTTCCGAT AAAATTAATA TCACCAAACA GATAACAATC AAAAAGGGTA    3840

TTGATGGAGA GGACTCTAGT TCAGATGCGA CAAGTAATGC CAACCTAACT ATTAAAACCA    3900

AAGAATTGAA ATTGACAGAA GACCTAAGTA TTTCAGGTTT CAATAAAGCA GAGATTACAG    3960

CCAAAGATGG TAGAGATTTA ACTATTGGCA ACAGTAATGA CGGTAACAGC GGTGCCGAAG    4020

CCAAAACAGT AACTTTTAAC AATGTTAAAG ATTCAAAAAT CTCTGCTGAC GGTCACAATG    4080

TGACACTAAA TAGCAAAGTG AAAACATCTA GCAGCAATGG CGGACGTGAA AGCAATAGCG    4140

ACAACGTAC CGGCTTAACT ATTACTGCAA AAAATGTAGA AGTAAACAAA GATATTACTT    4200

CTCTCAAAAC AGTAAATATC ACCGCGTCGG AAAAGGTTAC CACCACAGCA GGCTCGACCA    4260

TTAACGCAAC AAATGGCAAA GCAAGTATTA CAACCAAAAC AGGTGATATC AGCGGTACGA    4320

TTTCCGGTAA CACGGTAAGT GTTAGCGCGA CTGGTGATTT AACCACTAAA TCCGGCTCAA    4380

AAATTGAAGC GAAATCGGGT GAGGCTAATG TAACAAGTGC AACAGGTACA ATTGGCGGTA    4440

CAATTTCCGG TAATACGGTA AATGTTACGG CAAACGCTGG CGATTTAACA GTTGGGAATG    4500

GCGCAGAAAT TAATGCGACA GAAGGAGCTG CAACCTTAAC CGCAACAGGG AATACCTTGA    4560

CTACTGAAGC CGGTTCTAGC ATCACTTCAA CTAAGGGTCA GGTAGACCTC TTGGCTCAGA    4620

ATGGTAGCAT CGCAGGAAGC ATTAATGCTG CTAATGTGAC ATTAAATACT ACAGGCACCT    4680

TAACCACCGT GGCAGGCTCG GATATTAAAG CAACCAGCGG CACCTTGGTT ATTAACGCAA    4740

AAGATGCTAA GCTAAATGGT GATGCATCAG GTGATAGTAC AGAAGTGAAT GCAGTCAACG    4800

ACTGGGGATT TGGTAGTGTG ACTGCGGCAA CCTCAAGCAG TGTGAATATC ACTGGGGATT    4860

TAAACACAGT AAATGGGTTA AATATCATTT CGAAAGATGG TAGAAACACT GTGCGCTTAA    4920
```

```
GAGGCAAGGA AATTGAGGTG AAATATATCC AGCCAGGTGT AGCAAGTGTA GAAGAAGTAA    4980

TTGAAGCGAA ACGCGTCCTT GAAAAAGTAA AAGATTTATC TGATGAAGAA AGAGAAACAT    5040

TAGCTAAACT TGGTGTAAGT GCTGTACGTT TTGTTGAGCC AAATAATACA ATTACAGTCA    5100

ATACACAAAA TGAATTTACA ACCAGACCGT CAAGTCAAGT GATAATTTCT GAAGGTAAGG    5160

CGTGTTTCTC AAGTGGTAAT GGCGCACGAG TATGTACCAA TGTTGCTGAC GATGGACAGC    5220

CGTAGTCAGT AATTGACAAG GTAGATTTCA TCCTGCAATG AAGTCATTTT ATTTTCGTAT    5280

TATTTACTGT GTGGGTTAAA GTTCAGTACG GGCTTTACCC ATCTTGTAAA AAATTACGGA    5340

GAATACAATA AAGTATTTTT AACAGGTTAT TATTATGAAA AATATAAAAA GCAGATTAAA    5400

ACTCAGTGCA ATATCAGTAT TGCTTGGCCT GGCTTCTTCA TCATTGTATG CAGAAGAAGC    5460

GTTTTTAGTA AAAGGCTTTC AGTTATCTGG TGCACTTGAA ACTTTAAGTG AAGACGCCCA    5520

ACTGTCTGTA GCAAAATCTT TATCTAAATA CCAAGGCTCG CAAACTTTAA CAAACCTAAA    5580

AACAGCACAG CTTGAATTAC AGGCTGTGCT AGATAAGATT GAGCCAAATA AATTTGATGT    5640

GATATTGCCG CAACAAACCA TTACGGATGG CAATATCATG TTTGAGCTAG TCTCGAAATC    5700

AGCCGCAGAA AGCCAAGTTT TTTATAAGGC GAGCCAGGGT TATAGTGAAG AAAATATCGC    5760

TCGTAGCCTG CCATCTTTGA AACAAGGAAA AGTGTATGAA GATGGTCGTC AGTGGTTCGA    5820

TTTGCGTGAA TTTAATATGG CAAAAGAAAA CCCGCTTAAG GTTACCCGTG TACATTACGA    5880

ACTAAACCCT AAAAACAAAA CCTCTAATTT GATAATTGCG GGCTTCTCGC CTTTTGGTAA    5940

AACGCGTAGC TTTATTTCTT ATGATAATTT CGGCGCGAGA GAGTTAACT ACCAACGTGT    6000

AAGCTTGGGT TTTGTTAATG CCAATTTAAC TGGTCATGAT GATGTGTTAA TTATACCAGT    6060

ATGAGTTATG CTGATTCTAA TGATATCGAC GGCTTACCAA GTGCGATTAA TCGTAAATTA    6120

TCAAAAGGTC AATCTATCTC TGCGAATCTG AAATGGAGTT ATTATCTCCC AACATTTAAC    6180

CTTGGCATGG AAGACCAATT TAAAATTAAT TTAGGCTACA ACTACCGCCA TATTAATCAA    6240

ACCTCCGCGT TAAATCGCTT GGGTGAAACG AAGAAAAAAT TTGCAGTATC AGGCGTAAGT    6300

GCAGGCATTG ATGGACATAT CCAATTTACC CCTAAAACAA TCTTTAATAT TGATTTAACT    6360

CATCATTATT ACGCGAGTAA ATTACCAGGC TCTTTTGGAA TGGAGCGCAT TGGCGAAACA    6420

TTTAATCGCA GCTATCACAT TAGCACAGCC AGTTTAGGGT TGAGTCAAGA GTTTGCTCAA    6480

GGTTGGCATT TTAGCAGTCA ATTATCAGGT CAATTTACTC TACAAGATAT TAGCAGTATA    6540

GATTTATTCT CTGTAACAGG TACTTATGGC GTCAGAGGCT TTAAATACGG CGGTGCAAGT    6600

GGTGAGCGCG GTCTTGTATG GCGTAATGAA TTAAGTATGC CAAAATACAC CCGCTTCCAA    6660

ATCAGCCCTT ATGCGTTTTA TGATGCAGGT CAGTTCCGTT ATAATAGCGA AAATGCTAAA    6720

ACTTACGGCG AAGATATGCA CACGGTATCC TCTGCGGGTT TAGGCATTAA AACCTCTCCT    6780

ACACAAAACT TAAGCCTAGA TGCTTTTGTT GCTCGTCGCT TTGCAAATGC CAATAGTGAC    6840

AATTTGAATG GCAACAAAAA ACGCACAAGC TCACCTACAA CCTTCTGGGG GAGATTAACA    6900

TTCAGTTTCT AACCCTGAAA TTTAATCAAC TGGTAAGCGT TCCGCCTACC AGTTTATAAC    6960

TATATGCTTT ACCCGCCAAT TTACAGTCTA TAGGCAACCC TGTTTTTACC CTTATATATC    7020

AAATAAACAA GCTAAGCTGA GCTAAGCAAA CCAGCAAAC TCAAGCAAGC CAAGTAATAC    7080

TAAAAAAACA ATTTATATGA TAAACTAAAG TATACTCCAT GCCATGGCGA TACAAGGGAT    7140

TTAATAATAT GACAAAAGAA AATTTGCAAA ACGCTCCTCA AGATGCGACC GCTTTACTTG    7200

CGGAATTAAG CAACAATCAA ACTCCCCTGC GAATATTTAA ACAACCACGC AAGCCCAGCC    7260

TATTACGCTT GGAACAACAT ATCGCAAAAA AAGATTATGA GTTTGCTTGT CGTGAATTAA    7320
```

| | |
|---|---|
| TGGTGATTCT GGAAAAAATG GACGCTAATT TTGGAGGCGT TCACGATATT GAATTTGACG | 7380 |
| CACCCGCTCA GCTGGCATAT CTACCCGAAA AATTACTAAT TTATTTTGCC ACTCGTCTCG | 7440 |
| CTAATGCAAT TACAACACTC TTTTCCGACC CCGAATTGGC AATTTCTGAA GAAGGGGCGT | 7500 |
| TAAAGATGAT TAGCCTGCAA CGCTGGTTGA CGCTGATTTT TGCCTCTTCC CCCTACGTTA | 7560 |
| ACGCAGACCA TATTCTCAAT AAATATAATA TCAACCCAGA TTCCGAAGGT GGCTTTCATT | 7620 |
| TAGCAACAGA CAACTCTTCT ATTGCTAAAT TCTGTATTTT TTACTTACCC GAATCCAATG | 7680 |
| TCAATATGAG TTTAGATGCG TTATGGGCAG GGAATCAACA ACTTTGTGCT TCATTGTGTT | 7740 |
| TTGCGTTGCA GTCTTCACGT TTTATTGGTA CCGCATCTGC GTTTCATAAA AGAGCGGTGG | 7800 |
| TTTTACAGTG GTTTCCTAAA AAACTCGCCG AAATTGCTAA TTTAGATGAA TTGCCTGCAA | 7860 |
| ATATCCTTCA TGATGTATAT ATGCACTGCA GTTATGATTT AGCAAAAAAC AAGCACGATG | 7920 |
| TTAAGCGTCC ATTAAACGAA CTTGTCCGCA AGCATATCCT CACGCAAGGA TGGCAAGACC | 7980 |
| GCTACCTTTA CACCTTAGGT AAAAAGGACG GCAAACCTGT GATGATGGTA CTGCTTGAAC | 8040 |
| ATTTTAATTC GGGACATTCG ATTTATCGTA CACATTCAAC TTCAATGATT GCTGCTCGAG | 8100 |
| AAAAATTCTA TTTAGTCGGC TTAGGCCATG AGGGCGTTGA TAAAATAGGT CGAGAAGTGT | 8160 |
| TTGACGAGTT CTTTGAAATC AGTAGCAATA ATATAATGGA GAGACTGTTT TTTATCCGTA | 8220 |
| AACAGTGCGA AACTTTCCAA CCCGCAGTGT TCTATATGCC AAGCATTGGC ATGGATATTA | 8280 |
| CCACGATTTT TGTGAGCAAC ACTCGGCTTG CCCCTATTCA AGCTGTAGCC CTGGGTCATC | 8340 |
| CTGCCACTAC GCATTCTGAA TTTATTGATT ATGTCATCGT AGAAGATGAT TATGTGGGCA | 8400 |
| GTGAAGATTG TTTCAGCGAA ACCCTTTTAC GCTTACCCAA AGATGCCCTA CCTTATGTAC | 8460 |
| CTTCTGCACT CGCCCCACAA AAAGTGGATT ATGTACTCAG GGAAAACCCT GAAGTAGTCA | 8520 |
| ATATCGGTAT TGCCGCTACC ACAATGAAAT TAAACCCTGA ATTTTTGCTA ACATTGCAAG | 8580 |
| AAATCAGAGA TAAAGCTAAA GTCAAAATAC ATTTTCATTT CGCACTTGGA CAATCAACAG | 8640 |
| GCTTGACACA CCCTTATGTC AAATGGTTTA TCGAAAGCTA TTTAGGTGAC GATGCCACTG | 8700 |
| CACATCCCCA CGCACCTTAT CACGATTATC TGGCAATATT GCGTGATTGC GATATGCTAC | 8760 |
| TAAATCCGTT TCCTTTCGGT AATACTAACG GCATAATTGA TATGGTTACA TTAGGTTTAG | 8820 |
| TTGGTGTATG CAAAACGGGG GATGAAGTAC ATGAACATAT TGATGAAGGT CTGTTTAAAC | 8880 |
| GCTTAGGACT ACCAGAATGG CTGATAGCCG ACACACGAGA AACATATATT GAATGTGCTT | 8940 |
| TGCGTCTAGC AGAAAACCAT CAAGAACGCC TTGAACTCCG TCGTTACATC ATAGAAAACA | 9000 |
| ACGGCTTACA AAAGCTTTTT ACAGGCGACC CTCGTCCATT GGGCAAAATA CTGCTTAAGA | 9060 |
| AAACAAATGA ATGGAAGCGG AAGCACTTGA GTAAAAAATA ACGTTTTTTT AAAGTAAAAG | 9120 |
| TGCGGTTAAT TTTCAAAGCG TTTTAAAAAC CTCTCAAAAA TCAACCGCAC TTTTATCTTT | 9180 |
| ATAACGATCC CGCACGCTGA CAGTTTATCA GCCTCCCGCC ATAAAACTCC GCCTTTCATG | 9240 |
| GCGGAGATTT TAGCCAAAAC TGGCAGAAAT TAAAGGCTAA AATCACCAAA TTGCACCACA | 9300 |
| AAATCACCAA TACCCACAAA AAA | 9323 |

(2) INFORMATION FOR SEQ ID NO:7:

(i) SEQUENCE CHARACTERISTICS:
        (A) LENGTH: 4794 base pairs
        (B) TYPE: nucleic acid
        (C) STRANDEDNESS: single
        (D) TOPOLOGY: linear (xi) SEQUENCE DESCRIPTION: SEQ ID NO:7:

| | |
|---|---|
| ATGAACAAGA TATATCGTCT CAAATTCAGC AAACGCCTGA ATGCTTTGGT TGCTGTGTCT | 60 |

-continued

```
GAATTGACAC GGGGTTGTGA CCATTCCACA GAAAAAGGCA GTGAAAAACC TGTTCGTACG      120
AAAGTACGCC ACTTGGCGTT AAAGCCACTT TCCGCTATAT TGCTATCTTT GGGCATGGCA      180
TCCATTCCGC AATCTGTTTT AGCGAGCGGT TTACAGGGAA TGAGCGTCGT ACACGGTACA      240
GCAACCATGC AAGTAGACGG CAATAAAACC ACTATCCGTA ATAGCGTCAA TGCTATCATC      300
AATTGGAAAC AATTTAACAT TGACCAAAAT GAAATGGTGC AGTTTTTACA AGAAAGCAGC      360
AACTCTGCCG TTTTCAACCG TGTTACATCT GACCAAATCT CCCAATTAAA AGGGATTTTA      420
GATTCTAACG GACAAGTCTT TTTAATCAAC CCAAATGGTA TCACAATAGG TAAAGACGCA      480
ATTATTAACA CTAATGGCTT TACTGCTTCT ACGCTAGACA TTTCTAACGA AAACATCAAG      540
GCGCGTAATT TCACCCTTGA GCAAACCAAG GATAAAGCAC TCGCTGAAAT CGTGAATCAC      600
GGTTTAATTA CCGTTGGTAA AGACGGTAGC GTAAACCTTA TTGGTGGCAA AGTGAAAAAC      660
GAGGGCGTGA TTAGCGTAAA TGGCGGTAGT ATTTCTTTAC TTGCAGGGCA AAAAATCACC      720
ATCAGCGATA TAATAAATCC AACCATCACT TACAGCATTG CTGCACCTGA AAACGAAGCG      780
ATCAATCTGG GCGATATTTT TGCCAAAGGT GGTAACATTA ATGTCCGCGC TGCCACTATT      840
CGCAATAAAG GTAAACTTTC TGCCGACTCT GTAAGCAAAG ATAAAAGTGG TAACATTGTT      900
CTCTCTGCCA AAGAAGGTGA AGCGGAAATT GGCGGTGTAA TTTCCGCTCA AAATCAGCAA      960
GCCAAAGGTG GTAAGTTGAT GATTACAGGC GATAAAGTTA CATTGAAAAC GGGTGCAGTT     1020
ATCGACCTTT CGGGTAAAGA AGGGGGAGAA ACTTATCTTG GCGGTGACGA GCGTGGCGAA     1080
GGTAAAAACG GCATTCAATT AGCAAAGAAA ACCACTTTAG AAAAAGGCTC AACAATTAAT     1140
GTGTCAGGTA AAGAAAAAGG TGGGCGCGCT ATTGTATGGG GCGATATTGC GTTAATTGAC     1200
GGCAATATTA ATGCCCAAGG TAAAGATATC GCTAAAACTG GTGGTTTTGT GGAGACGTCG     1260
GGGCATTACT TATCCATTGA TGATAACGCA ATTGTTAAAA CAAAGAATG GCTACTAGAC      1320
CCAGAGAATG TGACTATTGA AGCTCCTTCC GCTTCTCGCG TCGAGCTGGG TGCCGATAGG     1380
AATTCCCACT CGGCAGAGGT GATAAAAGTG ACCCTAAAAA AAAATAACAC CTCCTTGACA     1440
ACACTAACCA ATACAACCAT TTCAAATCTT CTGAAAAGTG CCCACGTGGT GAACATAACG     1500
GCAAGGAGAA AACTTACCGT TAATAGCTCT ATCAGTATAG AAAGAGGCTC CCACTTAATT     1560
CTCCACAGTG AAGGTCAGGG CGGTCAAGGT GTTCAGATTG ATAAAGATAT TACTTCTGAA     1620
GGCGGAAATT TAACCATTTA TTCTGGCGGA TGGGTTGATG TTCATAAAAA TATTACGCTT     1680
GGTAGCGGCT TTTAAACAT CACAACTAAA GAAGGAGATA TCGCCTTCGA AGACAAGTCT      1740
GGACGGAACA ACCTAACCAT TACAGCCCAA GGGACCATCA CCTCAGGTAA TAGTAACGGC     1800
TTTAGATTTA ACAACGTCTC TCTAAACAGC CTTGGCGGAA AGCTGAGCTT TACTGACAGC     1860
AGAGAGGACA GAGGTAGAAG AACTAAGGGT AATATCTCAA ACAAATTTGA CGGAACGTTA     1920
AACATTTCCG GAACTGTAGA TATCTCAATG AAAGCACCCA AAGTCAGCTG GTTTTACAGA     1980
GACAAAGGAC GCACCTACTG GAACGTAACC ACTTTAAATG TTACCTCGGG TAGTAAATTT     2040
AACCTCTCCA TTGACAGCAC AGGAAGTGGC TCAACAGGTC CAAGCATACG CAATGCAGAA     2100
TTAAATGGCA TAACATTTAA TAAAGCCACT TTTAATATCG CACAAGGCTC AACAGCTAAC     2160
TTTAGCATCA AGGCATCAAT AATGCCCTTT AAGAGTAACG CTAACTACGC ATTATTTAAT     2220
GAAGATATTT CAGTCTCAGG GGGGGGTAGC CTTAATTTCA AACTTAACGC CTCATCTAGC     2280
AACATACAAA CCCCTGGCGT AATTATAAAA TCTCAAAACT TTAATGTCTC AGGAGGGTCA     2340
ACTTTAAATC TCAAGGCTGA AGGTTCAACA GAAACCGCTT TTTCAATAGA AAATGATTTA     2400
AACTTAAACG CCACCGGTGG CAATATAACA ATCAGACAAG TCGAGGGTAC CGATTCACGC     2460
```

-continued

```
GTCAACAAAG GTGTCGCAGC CAAAAAAAAC ATAACTTTTA AAGGGGGTAA TATCACCTTC    2520

GGCTCTCAAA AAGCCACAAC AGAAATCAAA GGCAATGTTA CCATCAATAA AAACACTAAC    2580

GCTACTCTTT GTGGTGCGAA TTTTGCCGAA AACAAATCGC CTTTAAATAT AGCAGGAAAT    2640

GTTATTAATA ATGGCAACCT TACCACTGCC GGCTCCATTA TCAATATAGC CGGAAATCTT    2700

ACTGTTTCAA AAGGCGCTAA CCTTCAAGCT ATAACAAATT ACACTTTTAA TGTAGCCGGC    2760

TCATTTGACA ACAATGGCGC TTCAAACATT TCCATTGCCA GAGGAGGGGC TAAATTTAAA    2820

GATATCAATA ACACCAGTAG CTTAAATATT ACCACCAACT CTGATACCAC TTACCGCACC    2880

ATTATAAAAG GCAATATATC CAACAAATCA GGTGATTTGA ATATTATTGA TAAAAAAAGC    2940

GACGCTGAAA TCCAAATTGG CGGCAATATC TCACAAAAAG AAGGCAATCT CACAATTTCT    3000

TCTGATAAAG TAAATATTAC CAATCAGATA ACAATCAAAG CAGGCGTTGA AGGGGGGCGT    3060

TCTGATTCAA GTGAGGCAGA AAATGCTAAC CTAACTATTC AAACCAAAGA GTTAAAATTG    3120

GCAGGAGACC TAAATATTTC AGGCTTTAAT AAAGCAGAAA TTACAGCTAA AAATGGCAGT    3180

GATTTAACTA TTGGCAATGC TAGCGGTGGT AATGCTGATG CTAAAAAAGT GACTTTTGAC    3240

AAGGTTAAAG ATTCAAAAAT CTCGACTGAC GGTCACAATG TAACACTAAA TAGCGAAGTG    3300

AAAACGTCTA ATGGTAGTAG CAATGCTGGT AATGATAACA GCACCGGTTT AACCATTTCC    3360

GCAAAAGATG TAACGGTAAA CAATAACGTT ACCTCCCACA AGACAATAAA TATCTCTGCC    3420

GCAGCAGGAA ATGTAACAAC CAAAGAAGGC ACAACTATCA ATGCAACCAC AGGCAGCGTG    3480

GAAGTAACTG CTCAAAATGG TACAATTAAA GGCAACATTA CCTCGCAAAA TGTAACAGTG    3540

ACAGCAACAG AAAATCTTGT TACCACAGAG AATGCTGTCA TTAATGCAAC CAGCGGCACA    3600

GTAAACATTA GTACAAAAAC AGGGGATATT AAAGGTGGAA TTGAATCAAC TTCCGGTAAT    3660

GTAAATATTA CAGCGAGCGG CAATACACTT AAGGTAAGTA ATATCACTGG TCAAGATGTA    3720

ACAGTAACAG CGGATGCAGG AGCCTTGACA ACTACAGCAG GCTCAACCAT TAGTGCGACA    3780

ACAGGCAATG CAAATATTAC AACCAAAACA GGTGATATCA ACGGTAAAGT TGAATCCAGC    3840

TCCGGCTCTG TAACACTTGT TGCAACTGGA GCAACTCTTG CTGTAGGTAA TATTTCAGGT    3900

AACACTGTTA CTATTACTGC GGATAGCGGT AAATTAACCT CCACAGTAGG TTCTACAATT    3960

AATGGGACTA ATAGTGTAAC CACCTCAAGC CAATCAGGCG ATATTGAAGG TACAATTTCT    4020

GGTAATACAG TAAATGTTAC AGCAAGCACT GGTGATTTAA CTATTGGAAA TAGTGCAAAA    4080

GTTGAAGCGA AAAATGGAGC TGCAACCTTA ACTGCTGAAT CAGGCAAATT AACCACCCAA    4140

ACAGGCTCTA GCATTACCTC AAGCAATGGT CAGACAACTC TTACAGCCAA GGATAGCAGT    4200

ATCGCAGGAA ACATTAATGC TGCTAATGTG ACGTTAAATA CCACAGGCAC TTTAACTACT    4260

ACAGGGGATT CAAAGATTAA CGCAACCAGT GGTACCTTAA CAATCAATGC AAAAGATGCC    4320

AAATTAGATG GTGCTGCATC AGGTGACCGC ACAGTAGTAA ATGCAACTAA CGCAAGTGGC    4380

TCTGGTAACG TGACTGCGAA AACCTCAAGC AGCGTGAATA TCACCGGGGA TTTAAACACA    4440

ATAAATGGGT TAAATATCAT TTCGGAAAAT GGTAGAAACA CTGTGCGCTT AAGAGGCAAG    4500

GAAATTGATG TGAAATATAT CCAACCAGGT GTAGCAAGCG TAGAAGAGGT AATTGAAGCG    4560

AAACGCGTCC TTGAGAAGGT AAAAGATTTA TCTGATGAAG AAAGAGAAAC ACTAGCCAAA    4620

CTTGGTGTAA GTGCTGTACG TTTCGTTGAG CCAAATAATG CCATTACGGT TAATACACAA    4680

AACGAGTTTA CAACCAAACC ATCAAGTCAA GTGACAATTT CTGAAGGTAA GGCGTGTTTC    4740

TCAAGTGGTA ATGGCGCACG AGTATGTACC AATGTTGCTG ACGATGGACA GCAG         4794
```

(2) INFORMATION FOR SEQ ID NO:8:

(i) SEQUENCE CHARACTERISTICS:
        (A) LENGTH: 4803 base pairs
        (B) TYPE: nucleic acid
        (C) STRANDEDNESS: single
        (D) TOPOLOGY: linear (xi) SEQUENCE DESCRIPTION: SEQ ID NO:8:

```
ATGAACAAGA TATATCGTCT CAAATTCAGC AAACGCCTGA ATGCTTTGGT TGCTGTGTCT      60
GAATTGACAC GGGGTTGTGA CCATTCCACA GAAAAAGGCA GTGAAAAACC TGTTCGTACG     120
AAAGTACGCC ACTTGGCGTT AAAGCCACTT TCCGCTATAT TGCTATCTTT GGGCATGGCA     180
TCCATTCCGC AATCTGTTTT AGCGAGCGGT TTACAGGGAA TGAGCGTCGT ACACGGTACA     240
GCAACCATGC AAGTAGACGG CAATAAAACC ACTATCCGTA ATAGCGTCAA TGCTATCATC     300
AATTGGAAAC AATTTAACAT TGACCAAAAT GAAATGGTGC AGTTTTTACA AGAAAGCAGC     360
AACTCTGCCG TTTTCAACCG TGTTACATCT GACCAAATCT CCCAATTAAA AGGGATTTTA     420
GATTCTAACG ACAAGTCTT TTTAATCAAC CCAAATGGTA TCACAATAGG TAAAGACGCA     480
ATTATTAACA CTAATGGCTT TACTGCTTCT ACGCTAGACA TTTCTAACGA AACATCAAG     540
GCGCGTAATT TCACCCTTGA GCAAACCAAG GATAAAGCAC TCGCTGAAAT CGTGAATCAC     600
GGTTTAATTA CCGTTGGTAA AGACGGTAGC GTAAACCTTA TTGGTGGCAA AGTGAAAAAC     660
GAGGGCGTGA TTAGCGTAAA TGGCGGTAGT ATTTCTTTAC TTGCAGGGCA AAAAATCACC     720
ATCAGCGATA TAATAAATCC AACCATCACT TACAGCATTG CTGCACCTGA AAACGAAGCG     780
ATCAATCTGG GCGATATTTT TGCCAAAGGT GGTAACATTA ATGTCCGCGC TGCCACTATT     840
CGCAATAAAG GTAAACTTTC TGCCGACTCT GTAAGCAAAG ATAAAAGTGG TAACATTGTT     900
CTCTCTGCCA AGAAGGTGA AGCGGAAATT GGCGGTGTAA TTTCCGCTCA AAATCAGCAA     960
GCCAAAGGTG GTAAGTTGAT GATTACAGGT GATAAAGTCA CATTAAAAAC AGGTGCAGTT    1020
ATCGACCTTT CAGGTAAAGA AGGGGGAGAG ACTTATCTTG GCGGTGATGA GCGTGGCGAA    1080
GGTAAAAATG GTATTCAATT AGCGAAGAAA ACCTCTTTAG AAAAAGGCTC GACAATTAAT    1140
GTATCAGGCA AGAAAAAGG CGGGCGCGCT ATTGTATGGG GCGATATTGC ATTAATTAAT    1200
GGTAACATTA TGCTCAAGG TAGCGATATT GCTAAAACTG GCGGCTTTGT GGAAACATCA    1260
GGACATGACT TATCCATTGG TGATGATGTG ATTGTTGACG CTAAAGAGTG GTTATTAGAC    1320
CCAGATGATG TGTCCATTGA AACTCTTACA TCTGGACGCA ATAATACCGG CGAAAACCAA    1380
GGATATACAA CAGGAGATGG GACTAAAGAG TCACCTAAAG GTAATAGTAT TTCTAAACCT    1440
ACATTAACAA ACTCAACTCT TGAGCAAATC CTAAGAAGAG GTTCTTATGT TAATATCACT    1500
GCTAATAATA GAATTTATGT TAATAGCTCC ATCAACTTAT CTAATGGCAG TTTAACACTT    1560
CACACTAAAC GAGATGGAGT TAAAATTAAC GGTGATATTA CCTCAAACGA AAATGGTAAT    1620
TTAACCATTA AAGCAGGCTC TTGGGTTGAT GTTCATAAAA ACATCACGCT TGGTACGGGT    1680
TTTTTGAATA TTGTCGCTGG GGATTCTGTA GCTTTTGAGA GAGAGGGCGA TAAAGCACGT    1740
AACGCAACAG ATGCTCAAAT TACCGCACAA GGGACGATAA CCGTCAATAA AGATGATAAA    1800
CAATTTAGAT TCAATAATGT ATCTATTAAC GGGACGGGCA AGGGTTTAAA GTTTATTGCA    1860
AATCAAAATA ATTTCACTCA TAAATTTGAT GGCGAAATTA ACATATCTGG AATAGTAACA    1920
ATTAACCAAA CCACGAAAAA AGATGTTAAA TACTGGAATG CATCAAAAGA CTCTTACTGG    1980
AATGTTTCTT CTCTTACTTT GAATACGGTG CAAAAATTTA CCTTTATAAA ATTCGTTGAT    2040
AGCGGCTCAA ATTCCCAAGA TTTGAGGTCA TCACGTAGAA GTTTTGCAGG CGTACATTTT    2100
```

```
AACGGCATCG GAGGCAAAAC AAACTTCAAC ATCGGAGCTA ACGCAAAAGC CTTATTTAAA     2160

TTAAAACCAA ACGCCGCTAC AGACCCAAAA AAAGAATTAC CTATTACTTT TAACGCCAAC     2220

ATTACAGCTA CCGGTAACAG TGATAGCTCT GTGATGTTTG ACATACACGC CAATCTTACC     2280

TCTAGAGCTG CCGGCATAAA CATGGATTCA ATTAACATTA CCGGCGGGCT TGACTTTTCC     2340

ATAACATCCC ATAATCGCAA TAGTAATGCT TTTGAAATCA AAAAAGACTT AACTATAAAT     2400

GCAACTGGCT CGAATTTTAG TCTTAAGCAA ACGAAAGATT CTTTTTATAA TGAATACAGC     2460

AAACACGCCA TTAACTCAAG TCATAATCTA ACCATTCTTG GCGGCAATGT CACTCTAGGT     2520

GGGGAAAATT CAAGCAGTAG CATTACGGGC AATATCAATA TCACCAATAA AGCAAATGTT     2580

ACATTACAAG CTGACACCAG CAACAGCAAC ACAGGCTTGA AGAAAAGAAC TCTAACTCTT     2640

GGCAATATAT CTGTTGAGGG GAATTTAAGC CTAACTGGTG CAAATGCAAA CATTGTCGGC     2700

AATCTTTCTA TTGCAGAAGA TTCCACATTT AAAGGAGAAG CCAGTGACAA CCTAAACATC     2760

ACCGGCACCT TTACCAACAA CGGTACCGCC AACATTAATA TAAAACAAGG AGTGGTAAAA     2820

CTCCAAGGCG ATATTATCAA TAAAGGTGGT TTAAATATCA CTACTAACGC CTCAGGCACT     2880

CAAAAAACCA TTATTAACGG AAATATAACT AACGAAAAAG GCGACTTAAA CATCAAGAAT     2940

ATTAAAGCCG ACGCCGAAAT CCAAATTGGC GGCAATATCT CACAAAAAGA AGGCAATCTC     3000

ACAATTTCTT CTGATAAAGT AAATATTACC AATCAGATAA CAATCAAAGC AGGCGTTGAA     3060

GGGGGGCGTT CTGATTCAAG TGAGGCAGAA AATGCTAACC TAACTATTCA AACCAAAGAG     3120

TTAAAATTGG CAGGAGACCT AAATATTTCA GGCTTTAATA AGCAGAAAT TACAGCTAAA      3180

AATGGCAGTG ATTTAACTAT TGGCAATGCT AGCGGTGGTA ATGCTGATGC TAAAAAAGTG     3240

ACTTTTGACA AGGTTAAAGA TTCAAAAATC TCGACTGACG GTCACAATGT AACACTAAAT     3300

AGCGAAGTGA AAACGTCTAA TGGTAGTAGC AATGCTGGTA ATGATAACAG CACCGGTTTA     3360

ACCATTTCCG CAAAAGATGT AACGGTAAAC AATAACGTTA CCTCCCACAA GACAATAAAT     3420

ATCTCTGCCG CAGCAGGAAA TGTAACAACC AAAGAAGGCA CAACTATCAA TGCAACCACA     3480

GGCAGCGTGG AAGTAACTGC TCAAAATGGT ACAATTAAAG GCAACATTAC CTCGCAAAAT     3540

GTAACAGTGA CAGCAACAGA AAATCTTGTT ACCACAGAGA ATGCTGTCAT TAATGCAACC     3600

AGCGGCACAG TAAACATTAG TACAAAAACA GGGGATATTA AAGTGGAAT TGAATCAACT      3660

TCCGGTAATG TAAATATTAC AGCGAGCGGC AATACACTTA AGGTAAGTAA TATCACTGGT     3720

CAAGATGTAA CAGTAACAGC GGATGCAGGA GCCTTGACAA CTACAGCAGG CTCAACCATT     3780

AGTGCGACAA CAGGCAATGC AAATATTACA ACCAAAACAG GTGATATCAA CGGTAAAGTT     3840

GAATCCAGCT CCGGCTCTGT AACACTTGTT GCAACTGGAG CAACTCTTGC TGTAGGTAAT     3900

ATTTCAGGTA ACACTGTTAC TATTACTGCG GATAGCGGTA AATTAACCTC CACAGTAGGT     3960

TCTACAATTA ATGGGACTAA TAGTGTAACC ACCTCAAGCC AATCAGGCGA TATTGAAGGT     4020

ACAATTTCTG GTAATACAGT AAATGTTACA GCAAGCACTG GTGATTTAAC TATTGGAAAT     4080

AGTGCAAAAG TTGAAGCGAA AAATGGAGCT GCAACCTTAA CTGCTGAATC AGGCAAATTA     4140

ACCACCCAAA CAGGCTCTAG CATTACCTCA AGCAATGGTC AGACAACTCT TACAGCCAAG     4200

GATAGCAGTA TCGCAGGAAA CATTAATGCT GCTAATGTGA CGTTAAATAC CACAGGCACT     4260

TTAACTACTA CAGGGGATTC AAAGATTAAC GCAACCAGTG GTACCTTAAC AATCAATGCA     4320

AAAGATGCCA AATTAGATGG TGCTGCATCA GGTGACCGCA CAGTAGTAAA TGCAACTAAC     4380

GCAAGTGGCT CTGGTAACGT GACTGCGAAA ACCTCAAGCA GCGTGAATAT CACCGGGGAT     4440

TTAAACACAA TAAATGGGTT AAATATCATT TCGGAAAATG GTAGAAACAC TGTGCGCTTA     4500
```

-continued

```
AGAGGCAAGG AAATTGATGT GAAATATATC CAACCAGGTG TAGCAAGCGT AGAAGAGGTA    4560

ATTGAAGCGA AACGCGTCCT TGAGAAGGTA AAAGATTTAT CTGATGAAGA AAGAGAAACA    4620

CTAGCCAAAC TTGGTGTAAG TGCTGTACGT TTCGTTGAGC CAAATAATGC CATTACGGTT    4680

AATACACAAA ACGAGTTTAC AACCAAACCA TCAAGTCAAG TGACAATTTC TGAAGGTAAG    4740

GCGTGTTTCT CAAGTGGTAA TGGCGCACGA GTATGTACCA ATGTTGCTGA CGATGGACAG    4800

CAG                                                                 4803
```

(2) INFORMATION FOR SEQ ID NO:9:

(i) SEQUENCE CHARACTERISTICS:
        (A) LENGTH: 1599 amino acids
        (B) TYPE: amino acid
        (C) STRANDEDNESS: single
        (D) TOPOLOGY: linear (xi) SEQUENCE DESCRIPTION: SEQ ID NO:9:

```
Met Asn Lys Ile Tyr Arg Leu Lys Phe Ser Lys Arg Leu Asn Ala Leu
1               5                   10                  15

Val Ala Val Ser Glu Leu Thr Arg Gly Cys Asp His Ser Thr Glu Lys
            20                  25                  30

Gly Ser Glu Lys Pro Val Arg Thr Lys Val Arg His Leu Ala Leu Lys
        35                  40                  45

Pro Leu Ser Ala Ile Leu Leu Ser Leu Gly Met Ala Ser Ile Pro Gln
    50                  55                  60

Ser Val Leu Ala Ser Gly Leu Gln Gly Met Ser Val Val His Gly Thr
65                  70                  75                  80

Ala Thr Met Gln Val Asp Gly Asn Lys Thr Thr Ile Arg Asn Ser Val
                85                  90                  95

Asn Ala Ile Ile Asn Trp Lys Gln Phe Asn Ile Asp Gln Asn Glu Met
            100                 105                 110

Glu Gln Phe Leu Gln Glu Ser Ser Asn Ser Ala Val Phe Asn Arg Val
        115                 120                 125

Thr Ser Asp Gln Ile Ser Gln Leu Lys Gly Ile Leu Asp Ser Asn Gly
    130                 135                 140

Gln Val Phe Leu Ile Asn Pro Asn Gly Ile Thr Ile Gly Lys Asp Ala
145                 150                 155                 160

Ile Ile Asn Thr Asn Gly Phe Thr Ala Ser Thr Leu Asp Ile Ser Asn
                165                 170                 175

Glu Asn Ile Lys Ala Arg Asn Phe Thr Leu Glu Gln Thr Lys Asp Lys
            180                 185                 190

Ala Leu Ala Glu Ile Val Asn His Gly Leu Ile Thr Val Gly Lys Asp
        195                 200                 205

Gly Ser Val Asn Leu Ile Gly Gly Lys Val Lys Asn Glu Gly Val Ile
    210                 215                 220

Ser Val Asn Gly Gly Ser Ile Ser Leu Leu Ala Gly Gln Lys Ile Thr
225                 230                 235                 240

Ile Ser Asp Ile Ile Asn Pro Thr Ile Thr Tyr Ser Ile Ala Ala Pro
                245                 250                 255

Glu Asn Glu Ala Ile Asn Leu Gly Asp Ile Phe Ala Lys Gly Gly Asn
            260                 265                 270

Ile Asn Val Arg Ala Ala Thr Ile Arg Asn Lys Gly Lys Leu Ser Ala
        275                 280                 285

Asp Ser Val Ser Lys Asp Lys Ser Gly Asn Ile Val Leu Ser Ala Lys
    290                 295                 300
```

-continued

```
Glu Gly Glu Ala Glu Ile Gly Val Ile Ser Ala Gln Asn Gln Gln
305                 310                 315                 320

Ala Lys Gly Gly Lys Leu Met Ile Thr Gly Asp Lys Val Thr Leu Lys
            325                 330                 335

Thr Gly Ala Val Ile Asp Leu Ser Gly Lys Glu Gly Gly Glu Thr Tyr
                340                 345                 350

Leu Gly Gly Asp Glu Arg Gly Glu Gly Lys Asn Gly Ile Gln Leu Ala
            355                 360                 365

Lys Lys Thr Thr Leu Glu Lys Gly Ser Thr Ile Asn Val Ser Gly Lys
370                 375                 380

Glu Lys Gly Gly Arg Ala Ile Val Trp Gly Asp Ile Ala Leu Ile Asp
385                 390                 395                 400

Gly Asn Ile Asn Ala Gln Gly Lys Asp Ile Ala Lys Thr Gly Gly Phe
                405                 410                 415

Val Glu Thr Ser Gly His Tyr Leu Ser Ile Asp Asp Asn Ala Ile Val
                420                 425                 430

Lys Thr Lys Glu Trp Leu Leu Asp Pro Glu Asn Val Thr Ile Glu Ala
            435                 440                 445

Pro Ser Ala Ser Arg Val Glu Leu Gly Ala Asp Arg Asn Ser His Ser
450                 455                 460

Ala Glu Val Ile Lys Val Thr Leu Lys Lys Asn Asn Thr Ser Leu Thr
465                 470                 475                 480

Thr Leu Thr Asn Thr Thr Ile Ser Asn Leu Leu Lys Ser Ala His Val
                485                 490                 495

Val Asn Ile Thr Ala Arg Arg Lys Leu Thr Val Asn Ser Ser Ile Ser
            500                 505                 510

Ile Glu Arg Gly Ser His Leu Ile Leu His Ser Glu Gly Gln Gly Gly
        515                 520                 525

Gln Gly Val Gln Ile Asp Lys Asp Ile Thr Ser Glu Gly Gly Asn Leu
    530                 535                 540

Thr Ile Tyr Ser Gly Gly Trp Val Asp Val His Lys Asn Ile Thr Leu
545                 550                 555                 560

Gly Ser Gly Phe Leu Asn Ile Thr Thr Lys Glu Gly Asp Ile Ala Phe
                565                 570                 575

Glu Asp Lys Ser Gly Arg Asn Asn Leu Thr Ile Thr Ala Gln Gly Thr
            580                 585                 590

Ile Thr Ser Gly Asn Ser Asn Gly Phe Arg Phe Asn Asn Val Ser Leu
        595                 600                 605

Asn Ser Leu Gly Gly Lys Leu Ser Phe Thr Asp Ser Arg Glu Asp Arg
610                 615                 620

Gly Arg Arg Thr Lys Gly Asn Ile Ser Asn Lys Phe Asp Gly Thr Leu
625                 630                 635                 640

Asn Ile Ser Gly Thr Val Asp Ile Ser Met Lys Ala Pro Lys Val Ser
                645                 650                 655

Trp Phe Tyr Arg Asp Lys Gly Arg Thr Tyr Trp Asn Val Thr Thr Leu
                660                 665                 670

Asn Val Thr Ser Gly Ser Lys Phe Asn Leu Ser Ile Asp Ser Thr Gly
            675                 680                 685

Ser Gly Ser Thr Gly Pro Ser Ile Arg Asn Ala Glu Leu Asn Gly Ile
690                 695                 700

Thr Phe Asn Lys Ala Thr Phe Asn Ile Ala Gln Gly Ser Thr Ala Asn
705                 710                 715                 720

Phe Ser Ile Lys Ala Ser Ile Met Pro Phe Lys Ser Asn Ala Asn Tyr
                725                 730                 735
```

```
Ala Leu Phe Asn Glu Asp Ile Ser Val Ser Gly Gly Ser Val Asn
            740                 745                 750
Phe Lys Leu Asn Ala Ser Ser Asn Ile Gln Thr Pro Gly Val Ile
            755                 760                 765
Ile Lys Ser Gln Asn Phe Asn Val Ser Gly Gly Ser Thr Leu Asn Leu
            770                 775                 780
Lys Ala Glu Gly Ser Thr Glu Thr Ala Phe Ser Ile Glu Asn Asp Leu
785                 790                 795                 800
Asn Leu Asn Ala Thr Gly Gly Asn Ile Thr Ile Arg Gln Val Glu Gly
                805                 810                 815
Thr Asp Ser Arg Val Asn Lys Gly Val Ala Ala Lys Lys Asn Ile Thr
                820                 825                 830
Phe Lys Gly Gly Asn Ile Thr Phe Gly Ser Gln Lys Ala Thr Thr Glu
                835                 840                 845
Ile Lys Gly Asn Val Thr Ile Asn Lys Asn Thr Asn Ala Thr Leu Arg
            850                 855                 860
Gly Ala Asn Phe Ala Glu Asn Lys Ser Pro Leu Asn Ile Ala Gly Asn
865                 870                 875                 880
Val Ile Asn Asn Gly Asn Leu Thr Thr Ala Gly Ser Ile Ile Asn Ile
                885                 890                 895
Ala Gly Asn Leu Thr Val Ser Lys Gly Ala Asn Leu Gln Ala Ile Thr
                900                 905                 910
Asn Tyr Thr Phe Asn Val Ala Gly Ser Phe Asp Asn Asn Gly Ala Ser
                915                 920                 925
Asn Ile Ser Ile Ala Arg Gly Gly Ala Lys Phe Lys Asp Ile Asn Asn
            930                 935                 940
Thr Ser Ser Leu Asn Ile Thr Thr Asn Ser Asp Thr Thr Tyr Arg Thr
945                 950                 955                 960
Ile Ile Lys Gly Asn Ile Ser Asn Lys Ser Gly Asp Leu Asn Ile Ile
                965                 970                 975
Asp Lys Lys Ser Asp Ala Glu Ile Gln Ile Gly Gly Asn Ile Ser Gln
                980                 985                 990
Lys Glu Gly Asn Leu Thr Ile Ser Ser Asp Lys Val Asn Ile Thr Asn
            995                 1000                1005
Gln Ile Thr Ile Lys Ala Gly Val Glu Gly Gly Arg Ser Asp Ser Ser
1010                1015                1020
Glu Ala Glu Asn Ala Asn Leu Thr Ile Gln Thr Lys Glu Leu Lys Leu
1025                1030                1035                1040
Ala Gly Asp Leu Asn Ile Ser Gly Phe Asn Lys Ala Glu Ile Thr Ala
                1045                1050                1055
Lys Asn Gly Ser Asp Leu Thr Ile Gly Asn Ala Ser Gly Gly Asn Ala
                1060                1065                1070
Asp Ala Lys Lys Val Thr Phe Asp Lys Val Lys Asp Ser Lys Ile Ser
            1075                1080                1085
Thr Asp Gly His Asn Val Thr Leu Asn Ser Glu Val Lys Thr Ser Asn
            1090                1095                1100
Gly Ser Ser Asn Ala Gly Asn Asp Asn Ser Thr Gly Leu Thr Ile Ser
1105                1110                1115                1120
Ala Lys Asp Val Thr Val Asn Asn Val Thr Ser His Lys Thr Ile
            1125                1130                1135
Asn Ile Ser Ala Ala Ala Gly Asn Val Thr Thr Lys Glu Gly Thr Thr
            1140                1145                1150
Ile Asn Ala Thr Thr Gly Ser Val Glu Val Thr Ala Gln Asn Gly Thr
```

-continued

```
             1155                1160                1165
Ile Lys Gly Asn Ile Thr Ser Gln Asn Val Thr Val Thr Ala Thr Glu
    1170                1175                1180
Asn Leu Val Thr Thr Glu Asn Ala Val Ile Asn Ala Thr Ser Gly Thr
1185                1190                1195                1200
Val Asn Ile Ser Thr Lys Thr Gly Asp Ile Lys Gly Gly Ile Glu Ser
                1205                1210                1215
Thr Ser Gly Asn Val Asn Ile Thr Ala Ser Gly Asn Thr Leu Lys Val
                1220                1225                1230
Ser Asn Ile Thr Gly Gln Asp Val Thr Val Thr Ala Asp Ala Gly Ala
        1235                1240                1245
Leu Thr Thr Thr Ala Gly Ser Thr Ile Ser Ala Thr Thr Gly Asn Ala
        1250                1255                1260
Asn Ile Thr Thr Lys Thr Gly Asp Ile Asn Gly Lys Val Glu Ser Ser
1265                1270                1275                1280
Ser Gly Ser Val Thr Leu Val Ala Thr Gly Ala Thr Leu Ala Val Gly
                1285                1290                1295
Asn Ile Ser Gly Asn Thr Val Thr Ile Thr Ala Asp Ser Gly Lys Leu
                1300                1305                1310
Thr Ser Thr Val Gly Ser Thr Ile Asn Gly Thr Asn Ser Val Thr Thr
        1315                1320                1325
Ser Ser Gln Ser Gly Asp Ile Glu Gly Thr Ile Ser Gly Asn Thr Val
    1330                1335                1340
Asn Val Thr Ala Ser Thr Gly Asp Leu Thr Ile Gly Asn Ser Ala Lys
1345                1350                1355                1360
Val Glu Ala Lys Asn Gly Ala Ala Thr Leu Thr Ala Glu Ser Gly Lys
                1365                1370                1375
Leu Thr Thr Gln Thr Gly Ser Ser Ile Thr Ser Ser Asn Gly Gln Thr
                1380                1385                1390
Thr Leu Thr Ala Lys Asp Ser Ser Ile Ala Gly Asn Ile Asn Ala Ala
            1395                1400                1405
Asn Val Thr Leu Asn Thr Thr Gly Thr Leu Thr Thr Thr Gly Asp Ser
    1410                1415                1420
Lys Ile Asn Ala Thr Ser Gly Thr Leu Thr Ile Asn Ala Lys Asp Ala
1425                1430                1435                1440
Lys Leu Asp Gly Ala Ala Ser Gly Asp Arg Thr Val Val Asn Ala Thr
                1445                1450                1455
Asn Ala Ser Gly Ser Gly Asn Val Thr Ala Lys Thr Ser Ser Ser Val
                1460                1465                1470
Asn Ile Thr Gly Asp Leu Asn Thr Ile Asn Gly Leu Asn Ile Ile Ser
        1475                1480                1485
Glu Asn Gly Arg Asn Thr Val Arg Leu Arg Gly Lys Glu Ile Asp Val
    1490                1495                1500
Lys Tyr Ile Gln Pro Gly Val Ala Ser Val Glu Glu Val Ile Glu Ala
1505                1510                1515                1520
Lys Arg Val Leu Glu Lys Val Lys Asp Leu Ser Asp Glu Glu Arg Glu
                1525                1530                1535
Thr Leu Ala Lys Leu Gly Val Ser Ala Val Arg Phe Val Glu Pro Asn
            1540                1545                1550
Asn Ala Ile Thr Val Asn Thr Gln Asn Glu Phe Thr Thr Lys Pro Ser
        1555                1560                1565
Ser Gln Val Thr Ile Ser Glu Gly Lys Ala Cys Phe Ser Ser Gly Asn
        1570                1575                1580
```

```
Gly Ala Arg Val Cys Thr Asn Val Ala Asp Asp Gly Gln Gln Pro
1585                1590                1595
```

(2) INFORMATION FOR SEQ ID NO:10:

(i) SEQUENCE CHARACTERISTICS:
        (A) LENGTH: 1600 amino acids
        (B) TYPE: amino acid
        (C) STRANDEDNESS: single
        (D) TOPOLOGY: linear (xi) SEQUENCE DESCRIPTION: SEQ ID NO:10:

```
Met Asn Lys Ile Tyr Arg Leu Lys Phe Ser Lys Arg Leu Asn Ala Leu
1               5                   10                  15

Val Ala Val Ser Glu Leu Thr Arg Gly Cys Asp His Ser Thr Glu Lys
                20                  25                  30

Gly Ser Glu Lys Pro Val Arg Thr Lys Val Arg His Leu Ala Leu Lys
            35                  40                  45

Pro Leu Ser Ala Ile Leu Leu Ser Leu Gly Met Ala Ser Ile Pro Gln
50                  55                  60

Ser Val Leu Ala Ser Gly Leu Gln Gly Met Ser Val Val His Gly Thr
65                  70                  75                  80

Ala Thr Met Gln Val Asp Gly Asn Lys Thr Thr Ile Arg Asn Ser Val
                85                  90                  95

Asn Ala Ile Ile Asn Trp Lys Gln Phe Asn Ile Asp Gln Asn Glu Met
                100                 105                 110

Glu Gln Phe Leu Gln Glu Ser Ser Asn Ser Ala Val Phe Asn Arg Val
            115                 120                 125

Thr Ser Asp Gln Ile Ser Gln Leu Lys Gly Ile Leu Asp Ser Asn Gly
130                 135                 140

Gln Val Phe Leu Ile Asn Pro Asn Gly Ile Thr Ile Gly Lys Asp Ala
145                 150                 155                 160

Ile Ile Asn Thr Asn Gly Phe Thr Ala Ser Thr Leu Asp Ile Ser Asn
                165                 170                 175

Glu Asn Ile Lys Ala Arg Asn Phe Thr Leu Glu Gln Thr Lys Asp Lys
                180                 185                 190

Ala Leu Ala Glu Ile Val Asn His Gly Leu Ile Thr Val Gly Lys Asp
            195                 200                 205

Gly Ser Val Asn Leu Ile Gly Gly Lys Val Lys Asn Glu Gly Val Ile
210                 215                 220

Ser Val Asn Gly Gly Ser Ile Ser Leu Leu Ala Gly Gln Lys Ile Thr
225                 230                 235                 240

Ile Ser Asp Ile Ile Asn Pro Thr Ile Thr Tyr Ser Ile Ala Ala Pro
                245                 250                 255

Glu Asn Glu Ala Ile Asn Leu Gly Asp Ile Phe Ala Lys Gly Gly Asn
                260                 265                 270

Ile Asn Val Arg Ala Ala Thr Ile Arg Asn Lys Gly Lys Leu Ser Ala
            275                 280                 285

Asp Ser Val Ser Lys Asp Lys Ser Gly Asn Ile Val Leu Ser Ala Lys
290                 295                 300

Glu Gly Glu Ala Glu Ile Gly Gly Val Ile Ser Ala Gln Asn Gln Gln
305                 310                 315                 320

Ala Lys Gly Gly Lys Leu Met Ile Thr Gly Asp Lys Val Thr Leu Lys
                325                 330                 335

Thr Gly Ala Val Ile Asp Leu Ser Gly Lys Glu Gly Gly Glu Thr Tyr
                340                 345                 350
```

-continued

```
Leu Gly Gly Asp Glu Arg Gly Glu Gly Lys Asn Gly Ile Gln Leu Ala
            355                 360                 365

Lys Lys Thr Thr Leu Glu Lys Gly Ser Thr Ile Asn Val Ser Gly Lys
370                 375                 380

Glu Lys Gly Gly Arg Ala Ile Val Trp Gly Asp Ile Ala Leu Ile Asp
385                 390                 395                 400

Gly Asn Ile Asn Ala Gln Gly Ser Asp Ile Ala Lys Thr Gly Gly Phe
                405                 410                 415

Val Glu Thr Ser Gly His Asp Leu Ser Ile Gly Asp Val Ile Val
                420                 425                 430

Asp Ala Lys Glu Trp Leu Leu Asp Pro Asp Val Ser Ile Glu Thr
            435                 440                 445

Leu Thr Ser Gly Arg Asn Asn Thr Gly Glu Asn Gln Gly Tyr Thr Thr
450                 455                 460

Gly Asp Gly Thr Lys Glu Ser Pro Lys Gly Asn Ser Ile Ser Lys Pro
465                 470                 475                 480

Thr Leu Thr Asn Ser Thr Leu Glu Gln Ile Leu Arg Arg Gly Ser Tyr
                485                 490                 495

Val Asn Ile Thr Ala Asn Asn Arg Ile Tyr Val Asn Ser Ser Ile Asn
                500                 505                 510

Leu Ser Asn Gly Ser Leu Thr Leu His Thr Lys Arg Asp Gly Val Lys
            515                 520                 525

Ile Asn Gly Asp Ile Thr Ser Asn Glu Asn Gly Asn Leu Thr Ile Lys
530                 535                 540

Ala Gly Ser Trp Val Asp Val His Lys Asn Ile Thr Leu Gly Thr Gly
545                 550                 555                 560

Phe Leu Asn Ile Val Ala Gly Asp Ser Val Ala Phe Glu Arg Glu Gly
                565                 570                 575

Asp Lys Ala Arg Asn Ala Thr Asp Ala Gln Ile Thr Ala Gln Gly Thr
            580                 585                 590

Ile Thr Val Asn Lys Asp Asp Lys Gln Phe Arg Phe Asn Asn Val Ser
                595                 600                 605

Leu Asn Gly Thr Gly Lys Gly Leu Lys Phe Ile Ala Asn Gln Asn Asn
610                 615                 620

Phe Thr His Lys Phe Asp Gly Glu Ile Asn Ile Ser Gly Ile Val Thr
625                 630                 635                 640

Ile Asn Gln Thr Thr Lys Lys Asp Val Lys Tyr Trp Asn Ala Ser Lys
                645                 650                 655

Asp Ser Tyr Trp Asn Val Ser Ser Leu Thr Leu Asn Thr Val Gln Lys
                660                 665                 670

Phe Thr Phe Ile Lys Phe Val Asp Ser Gly Ser Asn Gly Gln Asp Leu
            675                 680                 685

Arg Ser Ser Arg Arg Ser Phe Ala Gly Val His Phe Asn Gly Ile Gly
690                 695                 700

Gly Lys Thr Asn Phe Asn Ile Gly Ala Asn Ala Lys Ala Leu Phe Lys
705                 710                 715                 720

Leu Lys Pro Asn Ala Ala Thr Asp Pro Lys Lys Glu Leu Pro Ile Thr
                725                 730                 735

Phe Asn Ala Asn Ile Thr Ala Thr Gly Asn Ser Asp Ser Ser Val Met
                740                 745                 750

Phe Asp Ile His Ala Asn Leu Thr Ser Arg Ala Ala Gly Ile Asn Met
            755                 760                 765

Asp Ser Ile Asn Ile Thr Gly Gly Leu Asp Phe Ser Ile Thr Ser His
770                 775                 780
```

-continued

```
Asn Arg Asn Ser Asn Ala Phe Glu Ile Lys Lys Asp Leu Thr Ile Asn
785                 790                 795                 800

Ala Thr Gly Ser Asn Phe Ser Leu Lys Gln Thr Lys Asp Ser Phe Tyr
                805                 810                 815

Asn Glu Tyr Ser Lys His Ala Ile Asn Ser Ser His Asn Leu Thr Ile
                820                 825                 830

Leu Gly Gly Asn Val Thr Leu Gly Gly Glu Asn Ser Ser Ser Ile
                835                 840                 845

Thr Gly Asn Ile Asn Ile Thr Asn Lys Ala Asn Val Thr Leu Gln Ala
850                 855                 860

Asp Thr Ser Asn Ser Asn Thr Gly Leu Lys Lys Arg Thr Leu Thr Leu
865                 870                 875                 880

Gly Asn Ile Ser Val Glu Gly Asn Leu Ser Leu Thr Gly Ala Asn Ala
                885                 890                 895

Asn Ile Val Gly Asn Leu Ser Ile Ala Glu Asp Ser Thr Phe Lys Gly
                900                 905                 910

Glu Ala Ser Asp Asn Leu Asn Ile Thr Gly Thr Phe Thr Asn Asn Gly
                915                 920                 925

Thr Ala Asn Ile Asn Ile Lys Gly Val Val Lys Leu Gly Asp Ile Asn
930                 935                 940

Asn Lys Gly Gly Leu Asn Ile Thr Thr Asn Ala Ser Gly Thr Gln Lys
945                 950                 955                 960

Thr Ile Ile Asn Gly Asn Ile Thr Asn Glu Lys Gly Asp Leu Asn Ile
                965                 970                 975

Lys Asn Ile Lys Ala Asp Ala Glu Ile Gln Ile Gly Gly Asn Ile Ser
                980                 985                 990

Gln Lys Glu Gly Asn Leu Thr Ile Ser Ser Asp Lys Val Asn Ile Thr
                995                 1000                1005

Asn Gln Ile Thr Ile Lys Ala Gly Val Glu Gly Gly Arg Ser Asp Ser
            1010                1015                1020

Ser Glu Ala Glu Asn Ala Asn Leu Thr Ile Gln Thr Lys Glu Leu Lys
1025                1030                1035                1040

Leu Ala Gly Asp Leu Asn Ile Ser Gly Phe Asn Lys Ala Glu Ile Thr
                1045                1050                1055

Ala Lys Asn Gly Ser Asp Leu Thr Ile Gly Asn Ala Ser Gly Gly Asn
                1060                1065                1070

Ala Asp Ala Lys Lys Val Thr Phe Asp Lys Val Lys Asp Ser Lys Ile
                1075                1080                1085

Ser Thr Asp Gly His Asn Val Thr Leu Asn Ser Glu Val Lys Thr Ser
                1090                1095                1100

Asn Gly Ser Ser Asn Ala Gly Asn Asp Asn Ser Thr Gly Leu Thr Ile
1105                1110                1115                1120

Ser Ala Lys Asp Val Thr Val Asn Asn Val Thr Ser His Lys Thr
                1125                1130                1135

Ile Asn Ile Ser Ala Ala Gly Asn Val Thr Thr Lys Glu Gly Thr
                1140                1145                1150

Thr Ile Asn Ala Thr Thr Gly Ser Val Glu Val Thr Ala Gln Asn Gly
                1155                1160                1165

Thr Ile Lys Gly Asn Ile Thr Ser Gln Asn Val Thr Val Thr Ala Thr
                1170                1175                1180

Glu Asn Leu Val Thr Thr Glu Asn Ala Val Ile Asn Ala Thr Ser Gly
1185                1190                1195                1200

Thr Val Asn Ile Ser Thr Lys Thr Gly Asp Ile Lys Gly Gly Ile Glu
```

1205                1210                1215

Ser Thr Ser Gly Asn Val Asn Ile Thr Ala Ser Gly Asn Thr Leu Lys
                1220                1225                1230

Val Ser Asn Ile Thr Gly Gln Asp Val Thr Val Thr Ala Asp Ala Gly
            1235                1240                1245

Ala Leu Thr Thr Thr Ala Gly Ser Thr Ile Ser Ala Thr Thr Gly Asn
        1250                1255                1260

Ala Asn Ile Thr Thr Lys Thr Gly Asp Ile Asn Gly Lys Val Glu Ser
1265                1270                1275                1280

Ser Ser Gly Ser Val Thr Leu Val Ala Thr Gly Ala Thr Leu Ala Val
                1285                1290                1295

Gly Asn Ile Ser Gly Asn Thr Val Thr Ile Thr Ala Asp Ser Gly Lys
            1300                1305                1310

Leu Thr Ser Thr Val Gly Ser Thr Ile Asn Gly Thr Asn Ser Val Thr
        1315                1320                1325

Thr Ser Ser Gln Ser Gly Asp Ile Glu Gly Thr Ile Ser Gly Asn Thr
    1330                1335                1340

Val Asn Val Thr Ala Ser Thr Gly Asp Leu Thr Ile Gly Asn Ser Ala
1345                1350                1355                1360

Lys Val Glu Ala Lys Asn Gly Ala Ala Thr Leu Thr Ala Glu Ser Gly
                1365                1370                1375

Lys Leu Thr Thr Gln Thr Gly Ser Ser Ile Thr Ser Ser Asn Gly Gln
            1380                1385                1390

Thr Thr Leu Thr Ala Lys Asp Ser Ser Ile Ala Gly Asn Ile Asn Ala
        1395                1400                1405

Ala Asn Val Thr Leu Asn Thr Thr Gly Thr Leu Thr Thr Thr Gly Asp
    1410                1415                1420

Ser Lys Ile Asn Ala Thr Ser Gly Thr Leu Thr Ile Asn Ala Lys Asp
1425                1430                1435                1440

Ala Lys Leu Asp Gly Ala Ala Ser Gly Asp Arg Thr Val Val Asn Ala
                1445                1450                1455

Thr Asn Ala Ser Gly Ser Gly Asn Val Thr Ala Lys Thr Ser Ser Ser
            1460                1465                1470

Val Asn Ile Thr Gly Asp Leu Asn Thr Ile Asn Gly Leu Asn Ile Ile
        1475                1480                1485

Ser Glu Asn Gly Arg Asn Thr Val Arg Leu Arg Gly Lys Glu Ile Asp
    1490                1495                1500

Val Lys Tyr Ile Gln Pro Gly Val Ala Ser Glu Glu Val Ile Glu
1505                1510                1515                1520

Ala Lys Arg Val Leu Glu Lys Val Lys Asp Leu Ser Asp Glu Glu Arg
                1525                1530                1535

Glu Thr Leu Ala Lys Leu Gly Val Ser Ala Val Arg Phe Val Glu Pro
            1540                1545                1550

Asn Asn Ala Ile Thr Val Asn Thr Gln Asn Glu Phe Thr Thr Lys Pro
        1555                1560                1565

Ser Ser Gln Val Thr Ile Ser Glu Gly Lys Ala Cys Phe Ser Ser Gly
    1570                1575                1580

Asn Gly Ala Arg Val Cys Thr Asn Val Ala Asp Asp Gly Gln Gln Pro
1585                1590                1595                1600

(2) INFORMATION FOR SEQ ID NO:11:

(i) SEQUENCE CHARACTERISTICS:
        (A) LENGTH: 29 amino acids
        (B) TYPE: amino acid -continued

```
         (C) STRANDEDNESS: single
         (D) TOPOLOGY: linear (xi) SEQUENCE DESCRIPTION: SEQ ID NO:11:

Val Asp Glu Val Ile Glu Ala Lys Arg Ile Leu Glu Lys Val Lys Asp
1               5                   10                  15

Leu Ser Asp Glu Glu Arg Glu Ala Leu Ala Lys Leu Gly
            20                  25
```

What I claim is:

1. An isolated and purified nucleic acid molecule encoding a high molecular weight protein (HMW) of a non-typeable Haemophilus strain and having an apparent molecular weight of about 120 to about 130 kDa having the DNA sequence shown in FIG. 8 (SEQ ID No: 7) and encoding protein HMW3 having the derived amino acid sequence of FIG. 10 (SEQ ID No: 9).

2. An isolated and purified nucleic acid molecule encoding a high molecular weight protein (HMW) of a non-typeable Haemophilus strain and having an apparent molecular weight of about 120 to about 130 kDa having the DNA sequence shown in FIG. 9 (SEQ ID No: 8) and encoding protein HMW4 having the derived amino acid sequence of FIG. 10 (SEQ ID No: 10).

3. An isolated and purified nucleic acid molecule encoding a high molecular weight protein (HMW) of a non-typeable Haemophilus strain and having an apparent molecular weight of about 120 to about 130 kDa and having a DNA sequence selected from the group consisting of:

(a) a contiguous DNA sequence as shown in FIGS. 8 and 9 (SEQ ID Nos: 7 and 8); and (b) a contiguous DNA sequence encoding an amino acid sequence as shown in FIG. 10 (SEQ ID Nos: 9 and 10).

4. A vector for transformation of a host comprising the nucleic acid molecule of claims 1,2 or 3.

* * * * *